United States Patent
Jung et al.

(10) Patent No.: US 10,199,584 B2
(45) Date of Patent: Feb. 5, 2019

(54) ORGANOMETALLIC COMPOUND AND ORGANIC LIGHT-EMITTING DEVICE INCLUDING THE SAME

(71) Applicants: SAMSUNG ELECTRONICS CO., LTD., Suwon-si, Gyeonggi-do (KR); Samsung SDI Co., Ltd., Yongin-si, Gyeonggi-do (KR)

(72) Inventors: Yongsik Jung, Yongin-si (KR); Dalho Huh, Suwon-si (KR); Jhunmo Son, Yongin-si (KR); Eunsuk Kwon, Suwon-si (KR); Sangmo Kim, Hwaseong-si (KR); Saeyoun Lee, Suwon-si (KR); Soonok Jeon, Seoul (KR); Yeonsook Chung, Seoul (KR); Joonghyuk Kim, Seoul (KR); Myungsun Sim, Suwon-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 61 days.

(21) Appl. No.: 15/400,253

(22) Filed: Jan. 6, 2017

(65) Prior Publication Data
US 2018/0047919 A1 Feb. 15, 2018

(30) Foreign Application Priority Data
Aug. 10, 2016 (KR) .................. 10-2016-0101886

(51) Int. Cl.
*H01L 51/50* (2006.01)
*H01L 51/00* (2006.01)
*C07F 7/08* (2006.01)
*C09K 11/02* (2006.01)
*C09K 11/06* (2006.01)

(52) U.S. Cl.
CPC ........ *H01L 51/0094* (2013.01); *C07F 7/0812* (2013.01); *C07F 7/0814* (2013.01);
(Continued)

(58) Field of Classification Search
None
See application file for complete search history.

(56) References Cited

U.S. PATENT DOCUMENTS

| 8,652,656 B2 | 2/2014 | Zeng et al. |
| 8,748,012 B2 | 6/2014 | Zeng et al. |
| 2006/0228582 A1* | 10/2006 | Ragini ............... C07F 15/0033 428/690 |
| 2015/0162553 A1 | 6/2015 | Kim et al. |
| 2015/0218441 A1 | 8/2015 | Cho et al. |
| 2016/0079545 A1 | 3/2016 | Fukuzaki |

FOREIGN PATENT DOCUMENTS

| DE | 102012220691 A1 | 5/2013 |
| JP | 5457907 B2 | 4/2014 |

(Continued)

*Primary Examiner* — Gregory D Clark
(74) *Attorney, Agent, or Firm* — Cantor Colburn LLP

(57) ABSTRACT

A silyl group-containing compound represented by Formula 1:

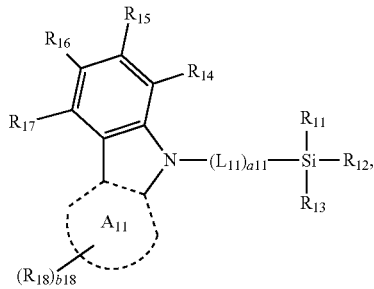

Formula 1 wherein, in Formula 1, groups and variables are the same as described in the specification.

19 Claims, 1 Drawing Sheet

(52) U.S. Cl.
CPC ............ *C09K 11/025* (2013.01); *C09K 11/06* (2013.01); *H01L 51/008* (2013.01); *H01L 51/009* (2013.01); *H01L 51/0072* (2013.01); *H01L 51/0074* (2013.01); *C09K 2211/1007* (2013.01); *C09K 2211/1022* (2013.01); *C09K 2211/1029* (2013.01); *C09K 2211/1044* (2013.01); *C09K 2211/185* (2013.01); *H01L 51/0085* (2013.01); *H01L 51/506* (2013.01); *H01L 51/5016* (2013.01); *H01L 51/5096* (2013.01)

(56) References Cited

FOREIGN PATENT DOCUMENTS

| KR | 10-2011-0011578 A | 2/2011 | | |
|----|----|----|----|----|
| KR | 10-2012-0065214 A | 6/2012 | | |
| KR | 10-2014-0006711 A | 1/2014 | | |
| KR | 10-2014-0079595 A | 6/2014 | | |
| KR | 10-1502316 B1 | 3/2015 | | |
| KR | 10-2015-0034333 A | 4/2015 | | |
| KR | 10-1511072 B1 | 4/2015 | | |
| WO | 2012-162325 A1 | 11/2012 | | |
| WO | 2014-038867 A1 | 3/2014 | | |
| WO | WO 2014/050588 | * | 3/2014 | ............ C09K 11/06 |
| WO | 2014-081131 A1 | 5/2014 | | |
| WO | 2015-046916 A1 | 4/2015 | | |
| WO | 2015-076599 A1 | 5/2015 | | |

* cited by examiner

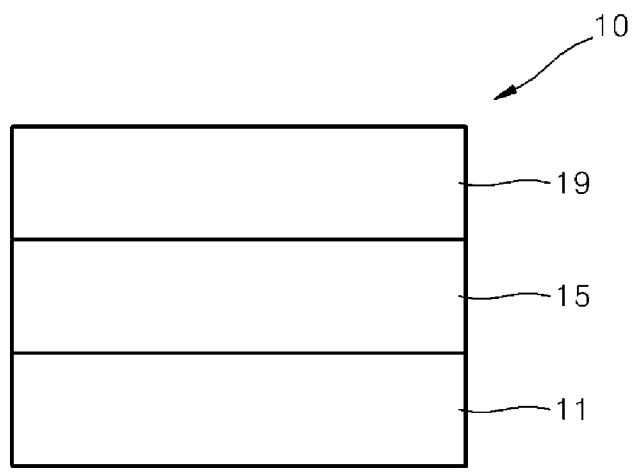

ORGANOMETALLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2016-0101886, filed on Aug. 10, 2016, in the Korean Intellectual Property Office, and all the benefits accruing therefrom under 35 U.S.C. § 119, the content of which is incorporated herein in its entirety by reference.

BACKGROUND

1. Field

One or more exemplary embodiments relate to a silyl group-containing compound and an organic light-emitting device including the same.

2. Description of the Related Art

Organic light-emitting devices (OLEDs) are self-emission devices that produce full-color images and have wide viewing angles, high contrast ratios, and short response times, as well as excellent brightness, driving voltage, and response speed characteristics.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transition from an excited state to a ground state, thereby generating light.

SUMMARY

One or more exemplary embodiments include a silyl group-containing compound and an organic light-emitting device including the same.

Additional aspects will be set forth in part in the description which follows and, in part, will be apparent from the description, or may be learned by practice of the presented exemplary embodiments.

According to one or more exemplary embodiments, a silyl group-containing compound is represented by Formula 1:

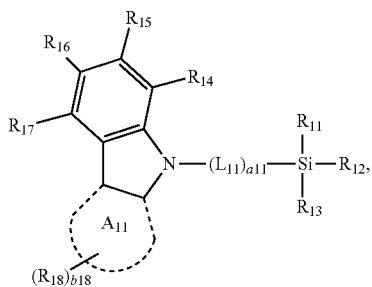

Formula 1 wherein, in Formula 1, $A_{11}$ may be selected from a carbazole group, a fluorene group, a dibenzofuran group, and a dibenzothiophene group, $R_{11}$ to $R_{13}$ may each independently be selected from groups represented by Formulae 2-1 to 2-6, provided that at least one selected from $R_{11}$ to $R_{13}$ is selected from groups represented by Formulae 2-1 to 2-5;

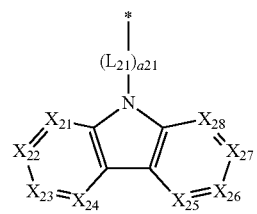

2-1

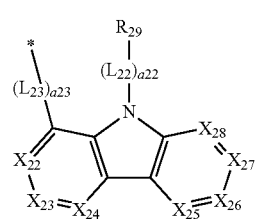

2-2

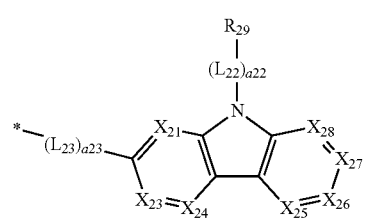

2-3

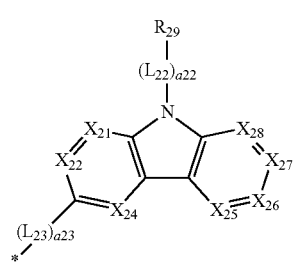

2-4

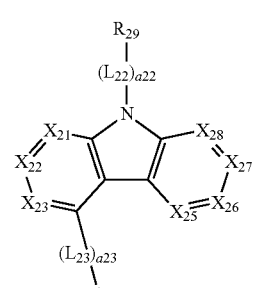

2-5

$$*-(L_{24})_{a24}-R_{30},$$ 2-6

$X_{21}$ may be selected from N and $CR_{21}$, $X_{22}$ may be selected from N and $CR_{22}$, $X_{23}$ may be selected from N and $CR_{23}$, $X_{24}$ may be selected from N and $CR_{24}$, $X_{25}$ may be selected from N and $CR_{25}$, $X_{26}$ may be selected from N and $CR_{26}$, $X_{27}$ may be selected from N and $CR_{27}$, and $X_{28}$ may be selected from N and $CR_{28}$, $L_{11}$ and $L_{21}$ to $L_{24}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 and a21 may each independently be selected from 1, 2, 3, and 4, a22 to a24 may each independently be selected from 0, 1, 2, 3, and 4, $R_{14}$ to $R_{18}$ and $R_{21}$ to $R_{29}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_1)(Q_2)$, and —B$(Q_1)(Q_2)$, $R_{30}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b18 may be an integer selected from 1, 2, 3, 4, 5, 6, 7, 8, 9, and 10, $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

In one or more exemplary embodiments, an organic light-emitting device includes:

a first electrode, a second electrode, and an organic layer disposed between the first electrode and the second electrode, wherein the organic layer includes an emission layer, and wherein the organic layer includes at least one of the silyl group-containing compounds represented by Formula 1.

BRIEF DESCRIPTION OF THE DRAWING

These and/or other aspects will become apparent and more readily appreciated from the following description of the exemplary embodiments, taken in conjunction with FIG. 1 which is a schematic view of an organic light-emitting device according to an exemplary embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Hereinafter, with reference to attached drawings, a silyl group-containing compound and an organic light-emitting device including the same according to an exemplary embodiment will be described in detail. However, these are for illustrative purposes only and are not intended to limit the scope of this disclosure.

A silyl group-containing compound according to an exemplary embodiment may be represented by Formula 1:

Formula 1

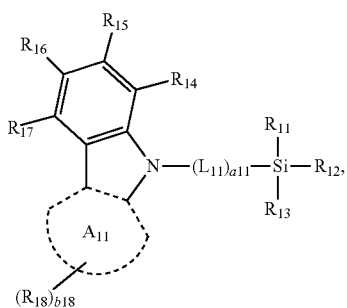

wherein $A_{11}$ in Formula 1 may be selected from a carbazole group, a fluorene group, a dibenzofuran group, and a dibenzothiophene group.

In one or more exemplary embodiments, the silyl group-containing compound represented by Formula 1 may be represented by one of Formulae 1-1 to 1-6, but exemplary embodiments of the present disclosure are not limited thereto:

1-1

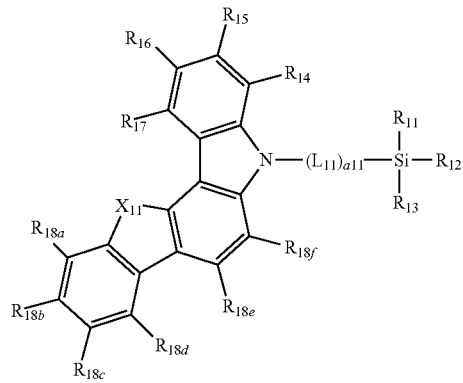

1-2

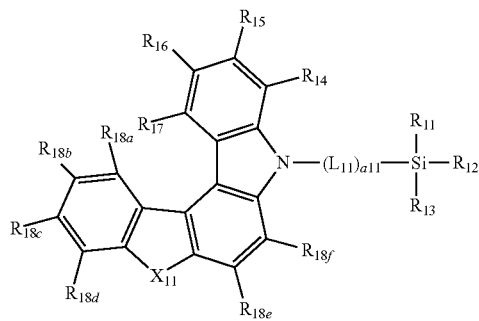

1-3

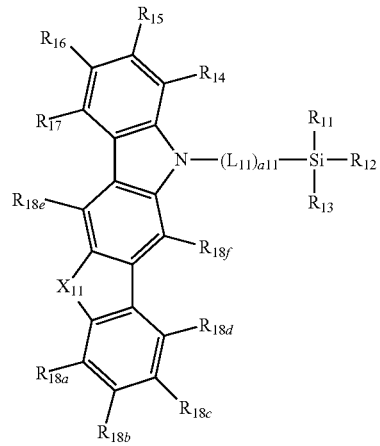

1-4

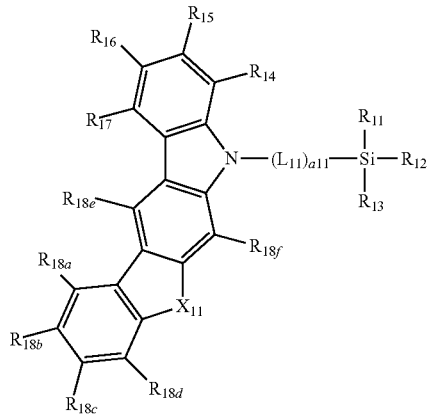

-continued 1-5

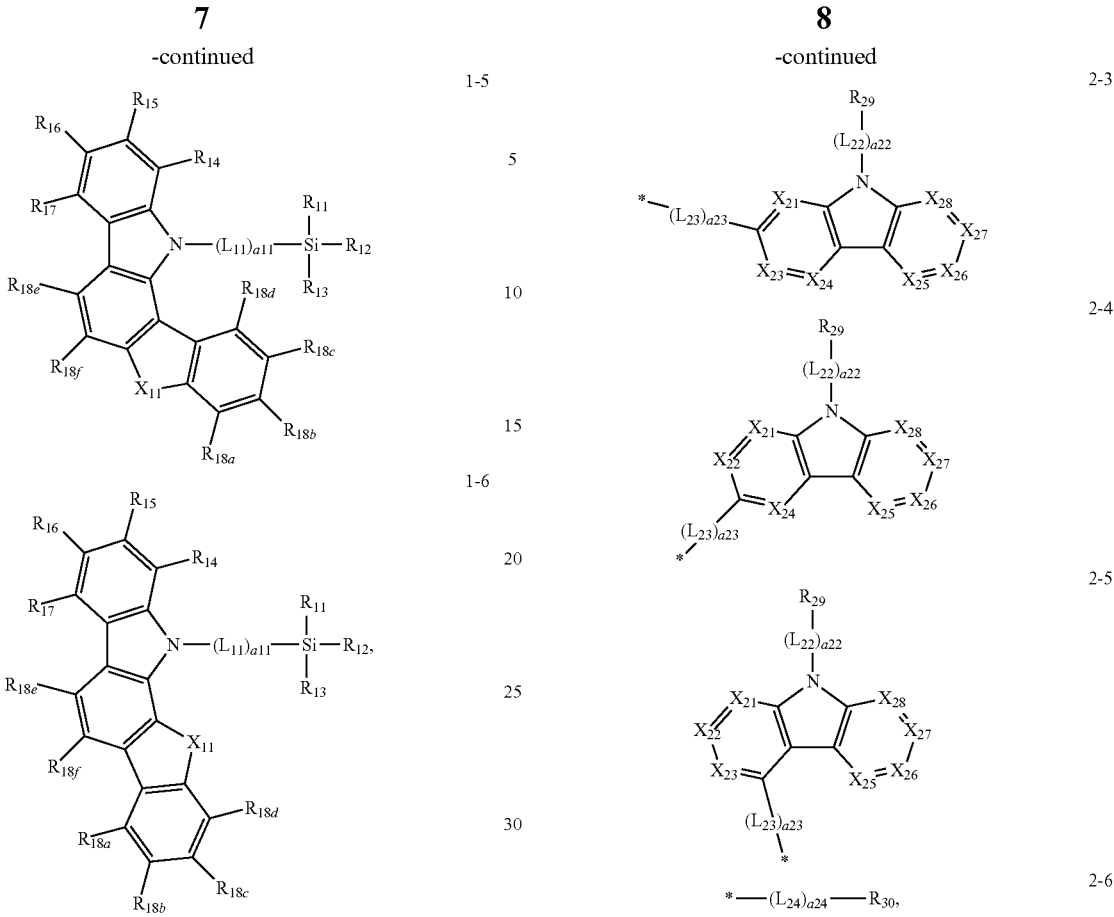

1-6

2-3

2-4

2-5

2-6 wherein, in Formulae 1-1 to 1-6, $X_{11}$ may be selected from O, S, $N(R_{18g})$, and $C(R_{18g})(R_{18h})$, $R_{11}$ to $R_{17}$, $L_{11}$, and a11 are the same as described below, and $R_{18a}$ to $R_{18h}$ are each independently the same as described below in connection with $R_{18}$.

$R_{11}$ to $R_{13}$ in Formula 1 may each independently be selected from groups represented by Formulae 2-1 to 2-6, provided that at least one selected from $R_{11}$ to $R_{13}$ is selected from groups represented by Formulae 2-1 to 2-5:

2-1

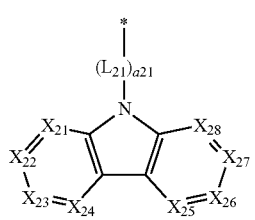

2-2

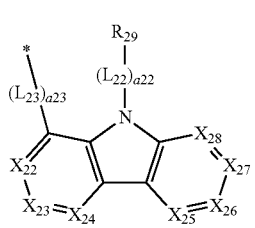

wherein, in Formulae 2-1 to 2-6, $X_{21}$ to $X_{28}$, $L_{21}$ to $L_{24}$, a21 to a24, $R_{29}$, and $R_{30}$ are the same as described below, and

* indicates a binding site to a neighboring atom.

In one or more exemplary embodiments, in Formula 1, $R_{11} \neq R_{12} \neq R_{13}$;
$R_{11}=R_{12}$ and $R_{12} \neq R_{13}$;
$R_{12}=R_{13}$ and $R_{11} \neq R_{12}$;
$R_{13}=R_{11}$ and $R_{12} \neq R_{13}$; or
$R_{11}=R_{12}=R_{13}$, but exemplary embodiments of the present disclosure are not limited thereto.

In one or more exemplary embodiments, in Formula 1, $R_{11}=R_{12}$ and $R_{12} \neq R_{13}$; or
$R_{11} \neq R_{12}$ and $R_{12}=R_{13}$, but exemplary embodiments of the present disclosure are not limited thereto.

In Formulae 2-1 to 2-5, $X_{21}$ may be selected from N and $CR_{21}$, $X_{22}$ may be selected from N and $CR_{22}$, $X_{23}$ may be selected from N and $CR_{23}$, $X_{24}$ may be selected from N and $CR_{24}$, $X_{25}$ may be selected from N and $CR_{25}$, $X_{26}$ may be selected from N and $CR_{26}$, $X_{27}$ may be selected from N and $CR_{27}$, $X_{28}$ may be selected from N and $CR_{28}$, and $R_{21}$ to $R_{28}$ are the same as described below.

In one or more exemplary embodiments, in Formula 2-1, $X_{21}$ may be $CR_{21}$, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formula 2-2, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formula 2-3, $X_{21}$ may be $CR_{21}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formula 2-4, $X_{21}$ may be $CR_{21}$, $X_{22}$ may be $CR_{22}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formula 2-5, $X_{21}$ may be $CR_{21}$, $X_{22}$ may be $CR_{22}$, $X_{23}$ may be $CR_{23}$, $X_{25}$ may be $CR_{25}$, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formulae 2-1 to 2-5, one, two, or three of $X_{21}$, $X_{22}$, $X_{23}$, $X_{24}$, $X_{25}$, $X_{26}$, $X_{27}$, and $X_{28}$ in Formula 2-1 may be N;

one, two, or three of $X_{22}$, $X_{23}$, $X_{24}$, $X_{25}$, $X_{26}$, $X_{27}$, and $X_{28}$ in Formula 2-2 may be N;

one, two, or three of $X_{21}$, $X_{23}$, $X_{24}$, $X_{25}$, $X_{26}$, $X_{27}$, and $X_{28}$ in Formula 2-3 may be N;

one, two, or three of $X_{21}$, $X_{22}$, $X_{24}$, $X_{25}$, $X_{26}$, $X_{27}$, and $X_{28}$ in Formula 2-4 may be N; or one, two, or three of $X_{21}$, $X_{22}$, $X_{23}$, $X_{25}$, $X_{26}$, $X_{27}$, and $X_{28}$ in Formula 2-5 may be N, but exemplary embodiments of the present disclosure are not limited thereto.

In one or more exemplary embodiments, in Formula 2-1, $X_{21}$ may be N, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be N, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be N, $X_{22}$ may be $CR_{22}$, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be N, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be N, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be N, $X_{26}$ may be $CR_{26}$, $X_{27}$ may be $CR_{27}$, and $X_{28}$ may be N;

$X_{21}$ may be N, $X_{22}$ may be $CR_{22}$, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be N, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be $CR_{28}$;

$X_{21}$ may be $CR_{21}$, $X_{22}$ may be $CR_{22}$, $X_{23}$ may be N, $X_{24}$ may be N, $X_{25}$ may be $CR_{25}$, $X_{26}$ may be $CR_{26}$, $X_{27}$ may be $CR_{27}$, and $X_{28}$ may be $CR_{28}$; or $X_{21}$ may be $CR_{21}$, $X_{22}$ may be $CR_{22}$, $X_{23}$ may be $CR_{23}$, $X_{24}$ may be N, $X_{25}$ may be N, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formula 2-2, $X_{22}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{22}$ may be $CR_{22}$, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{22}$ may be $CR_{22}$, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{22}$ may be $CR_{22}$, $X_{23}$ may be $CR_{23}$, $X_{24}$ may be $CR_{24}$, $X_{25}$ may be N, $X_{26}$ may be $CR_{26}$, $X_{27}$ may be $CR_{27}$, and $X_{28}$ may be $CR_{28}$;

$X_{22}$ may be $CR_{22}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be $CR_{28}$;

$X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{22}$ may be N, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{22}$ may be $CR_{22}$, $X_{23}$ may be $CR_{23}$, $X_{24}$ may be $CR_{24}$, $X_{25}$ may be N, $X_{26}$ may be $CR_{26}$, $X_{27}$ may be N, and $X_{28}$ may be $CR_{28}$;

$X_{22}$ may be $CR_{22}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be N;

$X_{22}$ may be $CR_{22}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be N;

$X_{22}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{22}$ may be $CR_{22}$, $X_{23}$ may be N, $X_{24}$ may be $CR_{24}$, $X_{25}$ may be $CR_{25}$, $X_{26}$ may be N, $X_{27}$ may be $CR_{27}$, and $X_{28}$ may be $CR_{28}$; or $X_{22}$ may be $CR_{22}$, $X_{23}$ may be $CR_{23}$, $X_{24}$ may be N, $X_{25}$ may be N, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formula 2-3, $X_{21}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{23}$ may be $CR_{23}$, $X_{24}$ may be $CR_{24}$, $X_{25}$ may be N, $X_{26}$ may be $CR_{26}$, $X_{27}$ may be $CR_{27}$, and $X_{28}$ may be $CR_{28}$;

$X_{21}$ may be $CR_{21}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be $CR_{28}$;

$X_{21}$ may be $CR_{21}$, $X_{23}$ may be $CR_{23}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{21}$ may be $CR_{21}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be N, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{23}$ may be $CR_{23}$, $X_{24}$ may be $CR_{24}$, $X_{25}$ may be N, $X_{26}$ may be $CR_{26}$, $X_{27}$ may be N, and $X_{28}$ may be $CR_{28}$;

$X_{21}$ may be $CR_{21}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be N;

$X_{21}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{23}$ may be N, $X_{24}$ may be $CR_{24}$, $X_{25}$ may be $CR_{25}$, $X_{26}$ may be N, $X_{27}$ may be $CR_{27}$, and $X_{28}$ may be $CR_{28}$; or $X_{21}$ may be $CR_{21}$, $X_{23}$ may be $CR_{23}$, $X_{24}$ may be N, $X_{25}$ may be N, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formula 2-4, $X_{21}$ may be N, $X_{22}$ may be $CR_{22}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{24}$ may be $CR_{24}$, $X_{25}$ may be N, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{24}$ may be $CR_{24}$, $X_{25}$ may be $CR_{25}$, $X_{26}$ may be N, $X_{27}$ may be $CR_{27}$, and $X_{28}$ may be $CR_{28}$;

$X_{21}$ may be $CR_{21}$, $X_{22}$ may be $CR_{22}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{22}$ may be N, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{24}$ may be $CR_{24}$, $X_{25}$ may be N, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{24}$ may be $CR_{24}$, $X_{25}$ may be $CR_{25}$, $X_{26}$ may be N, $X_{27}$ may be $CR_{27}$, and $X_{28}$ may be N;

$X_{21}$ may be N, $X_{22}$ may be $CR_{22}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{22}$ may be $CR_{22}$, $X_{24}$ may be N, $X_{25}$ may be N, $X_{26}$ may be $CR_{26}$, $X_{27}$ may be $CR_{27}$, and $X_{28}$ may be $CR_{28}$; or $X_{21}$ may be $CR_{21}$, $X_{22}$ may be $CR_{22}$, $X_{24}$ may be N, $X_{25}$ may be N, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formula 2-5, $X_{21}$ may be N, $X_{22}$ may be $CR_{22}$, $X_{23}$ may be $CR_{23}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be N, $X_{23}$ may be $CR_{23}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{25}$ may be N, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{25}$ may be $CR_{25}$, $X_{26}$ may be N, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{25}$ may be $CR_{25}$, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{23}$ may be $CR_{23}$, $X_{25}$ may be $CR_{25}$, $X_{26}$ may be $CR_{26}$, $X_{27}$ may be $CR_{27}$, and $X_{28}$ may be N;

$X_{21}$ may be N, $X_{22}$ may be $CR_{22}$, $X_{23}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{25}$ may be N, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{23}$ may be $CR_{23}$, $X_{25}$ may be $CR_{25}$, $X_{26}$ may be N, $X_{27}$ may be $CR_{27}$, and $X_{28}$ may be N;

$X_{21}$ may be N, $X_{22}$ may be $CR_{22}$, $X_{23}$ may be $CR_{23}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{22}$ may be N, $X_{23}$ may be $CR_{23}$, $X_{25}$ may be $CR_{25}$, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{23}$ may be N, $X_{25}$ may be $CR_{25}$, $X_{26}$ may be N, $X_{27}$ may be $CR_{27}$, and $X_{28}$ may be $CR_{28}$, but exemplary embodiments of the present disclosure are not limited thereto.

In one or more exemplary embodiments, groups represented by one of Formulae 2-1 to 2-5 may be represented by one of Formulae 2-11 to 2-19, 2-21 to 2-28, 2-31 to 2-38, 2-41 to 2-48, and 2-51 to 2-58, but exemplary embodiments of the present disclosure are not limited thereto:

2-11

2-12 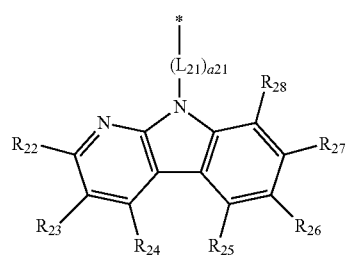
2-13 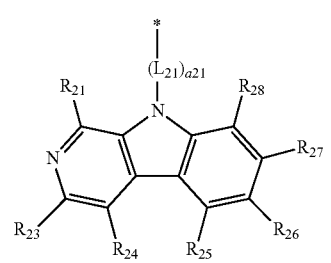
2-14 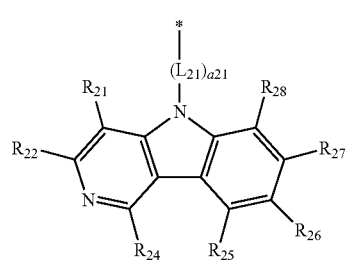
2-15 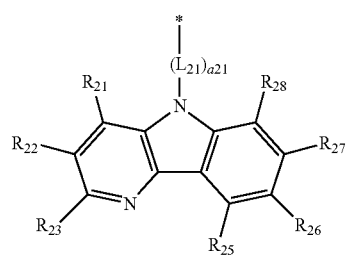
2-16 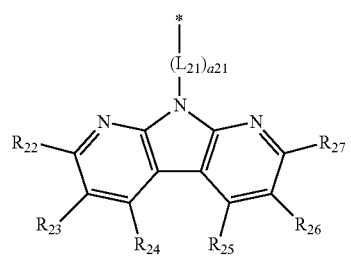
2-17 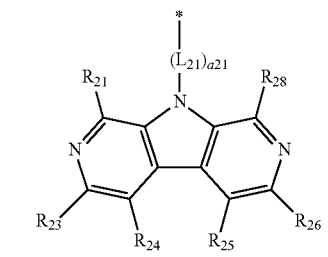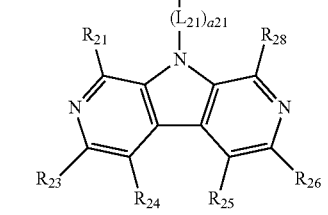
2-18 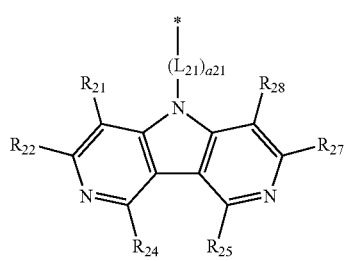
2-19 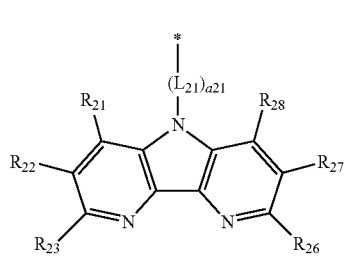
2-21 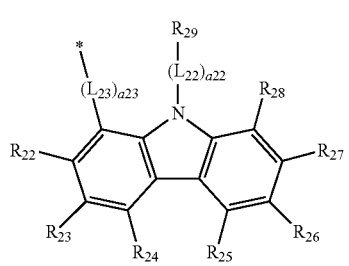
2-22 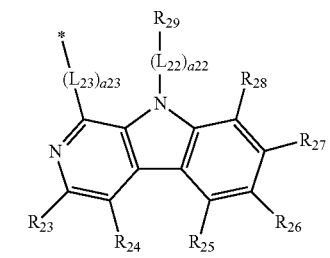
2-23 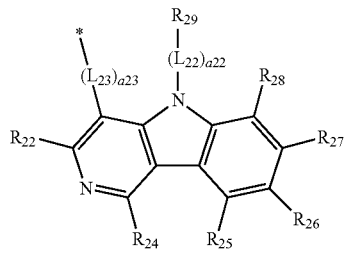
2-24 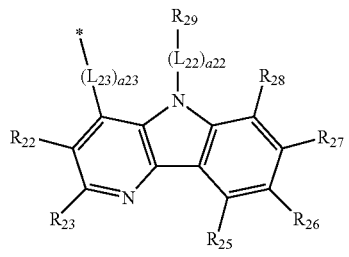

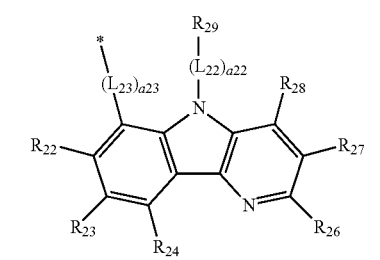 2-25
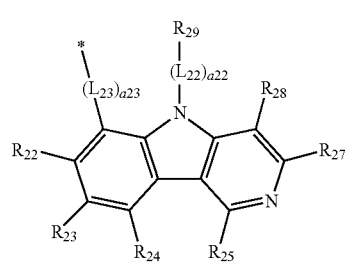 2-26
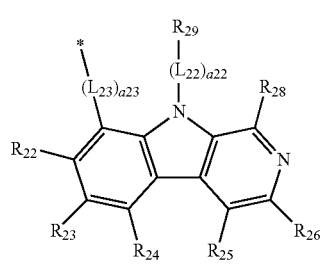 2-27
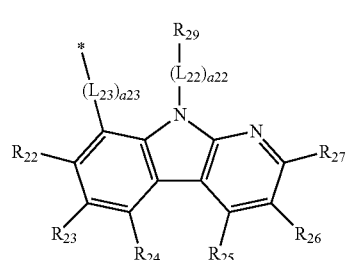 2-28
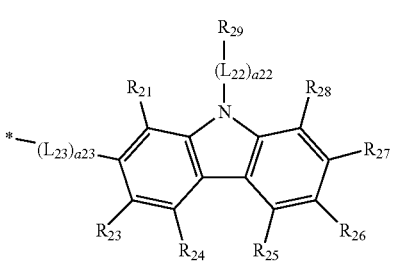 2-31
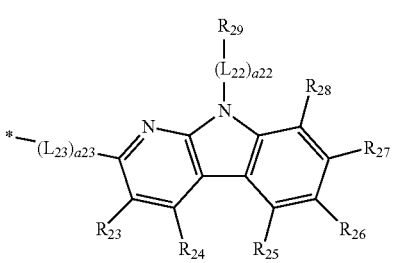 2-32
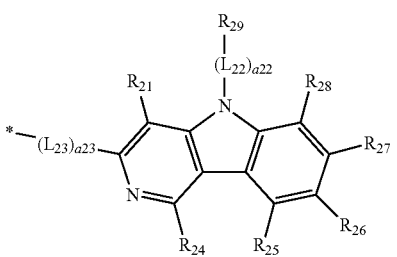 2-33
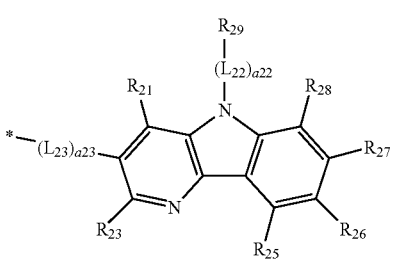 2-34
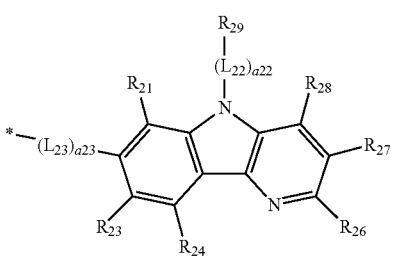 2-35
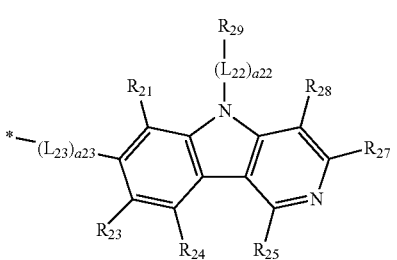 2-36
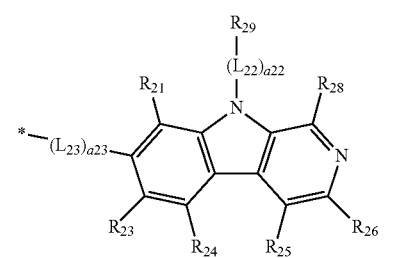 2-37
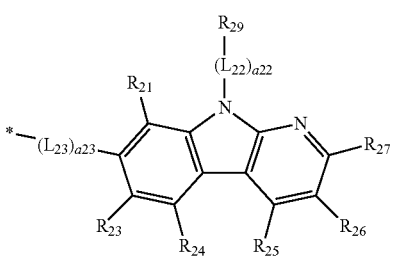 2-38

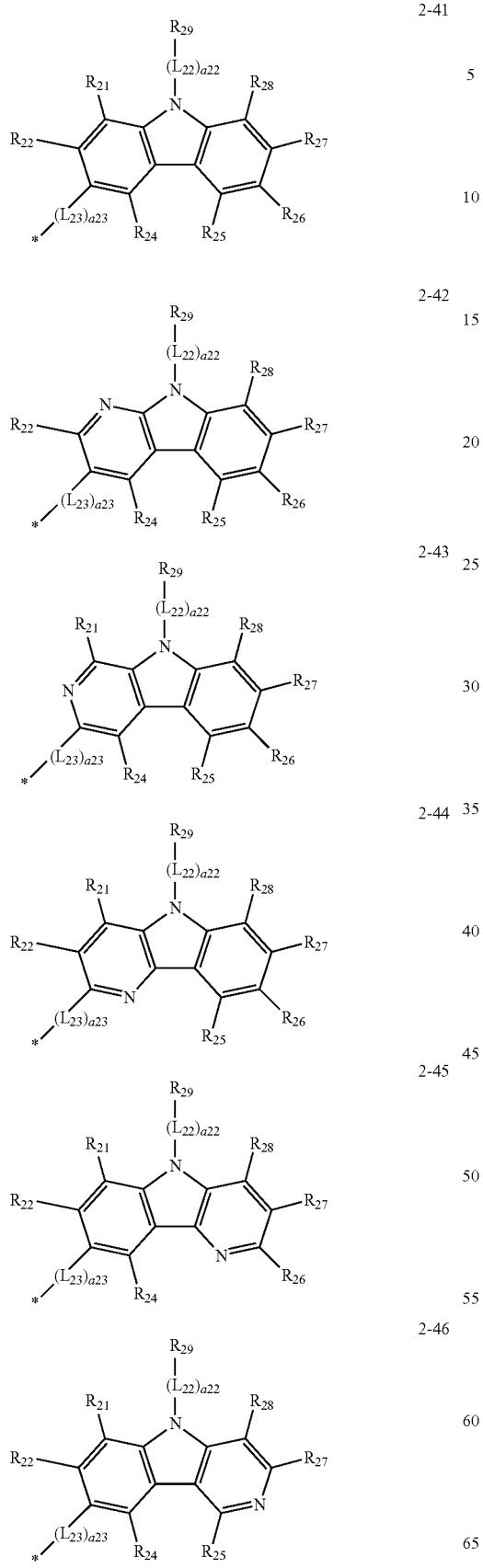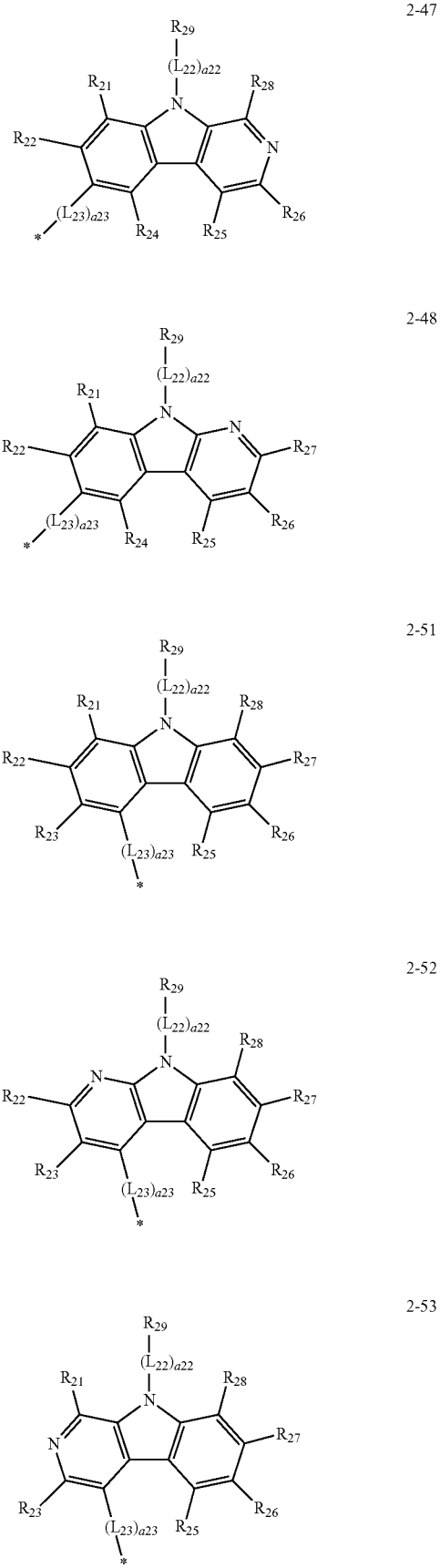

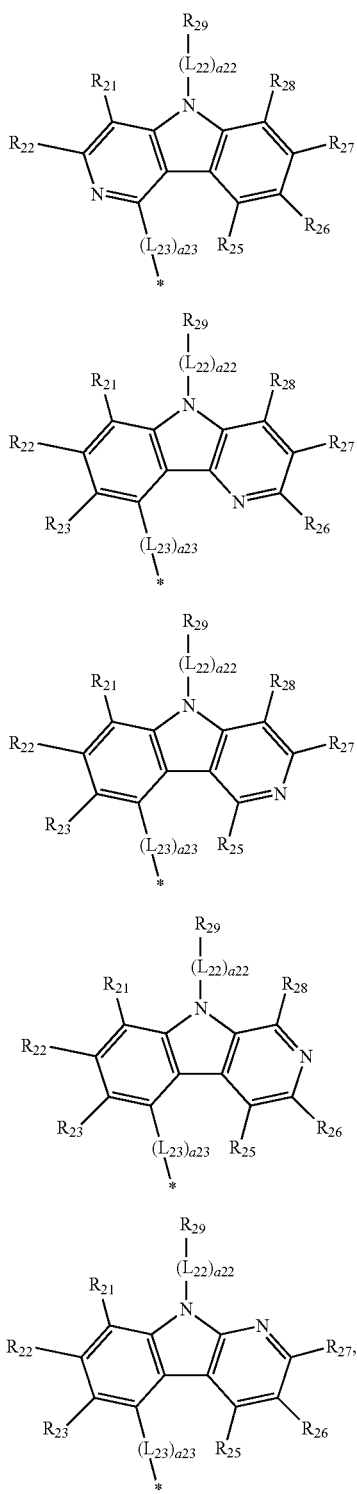

wherein, in Formulae 2-11 to 2-19, 2-21 to 2-28, 2-31 to 2-38, 2-41 to 2-48, and 2-51 to 2-58, $L_{21}$ to $L_{23}$, a21 to a23, and $R_{21}$ to $R_{29}$ are the same as described above in connection with Formulae 2-1 to 2-5, and * indicates a binding site to a neighboring atom.

$L_{11}$ and $L_{21}$ to $L_{24}$ in Formulae 1 and 2-1 to 2-6 may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In one or more exemplary embodiments, $L_{11}$ and $L_{21}$ to $L_{24}$ in Formulae 1 and 2-1 to 2-6 may each independently be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, but exemplary embodiments of the present disclosure are not limited thereto.

In one or more exemplary embodiments, $L_{11}$ and $L_{21}$ to $L_{24}$ in Formulae 1 and 2-1 to 2-6 may each independently be selected from:

a phenylene group, a naphthylene group, a fluorenylene group, a phenanthrenylene group, an anthracenylene group, a triphenylenylene group, a pyrenylene group, a chrysenylene group, a pyridinylene group, a pyrazinylene group, a pyrimidinylene group, and a triazinylene group; and a phenylene group, a naphthylene group, a fluorenylene group, a phenanthrenylene group, an anthracenylene group, a triphenylenylene group, a pyrenylene group, a chrysenylene group, a pyridinylene group, a pyrazinylene group, a pyrimidinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a triphenylenyl group, a pyrenyl group, a chrysenyl group, a pyridinyl group, a pyrazinyl group, a pyrimidinyl group, and a triazinyl group, but exemplary embodiments of the present disclosure are not limited thereto.

In one or more exemplary embodiments, $L_{11}$ and $L_{21}$ to $L_{24}$ in Formulae 1 and 2-1 to 2-6 may each independently be selected from:

a phenylene group, a naphthylene group, a pyridinylene group, a pyrazinylene group, a pyrimidinylene group, and a triazinylene group; and a phenylene group, a naphthylene group, a pyridinylene group, a pyrazinylene group, a pyrimidinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group, but exemplary embodiments of the present disclosure are not limited thereto.

In one or more exemplary embodiments, $L_{11}$ and $L_{21}$ to $L_{24}$ in Formulae 1 and 2-1 to 2-6 may each independently be selected from groups represented by Formulae 3-1 to 3-28, but exemplary embodiments of the present disclosure are not limited thereto:

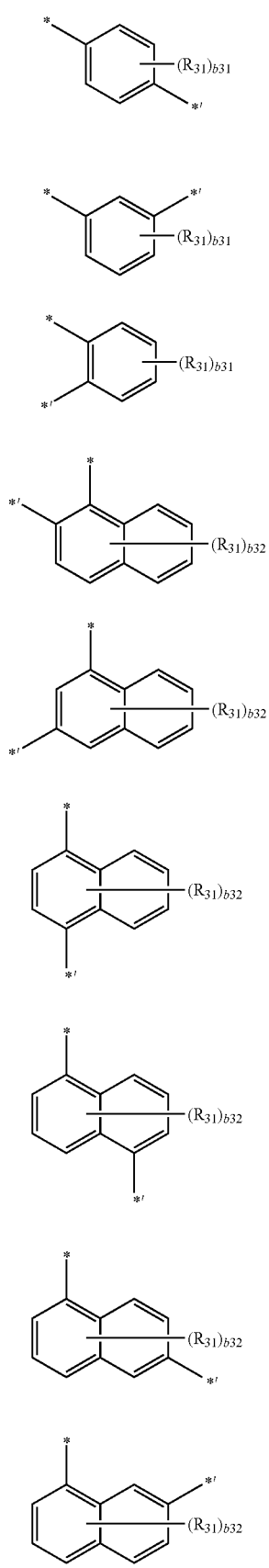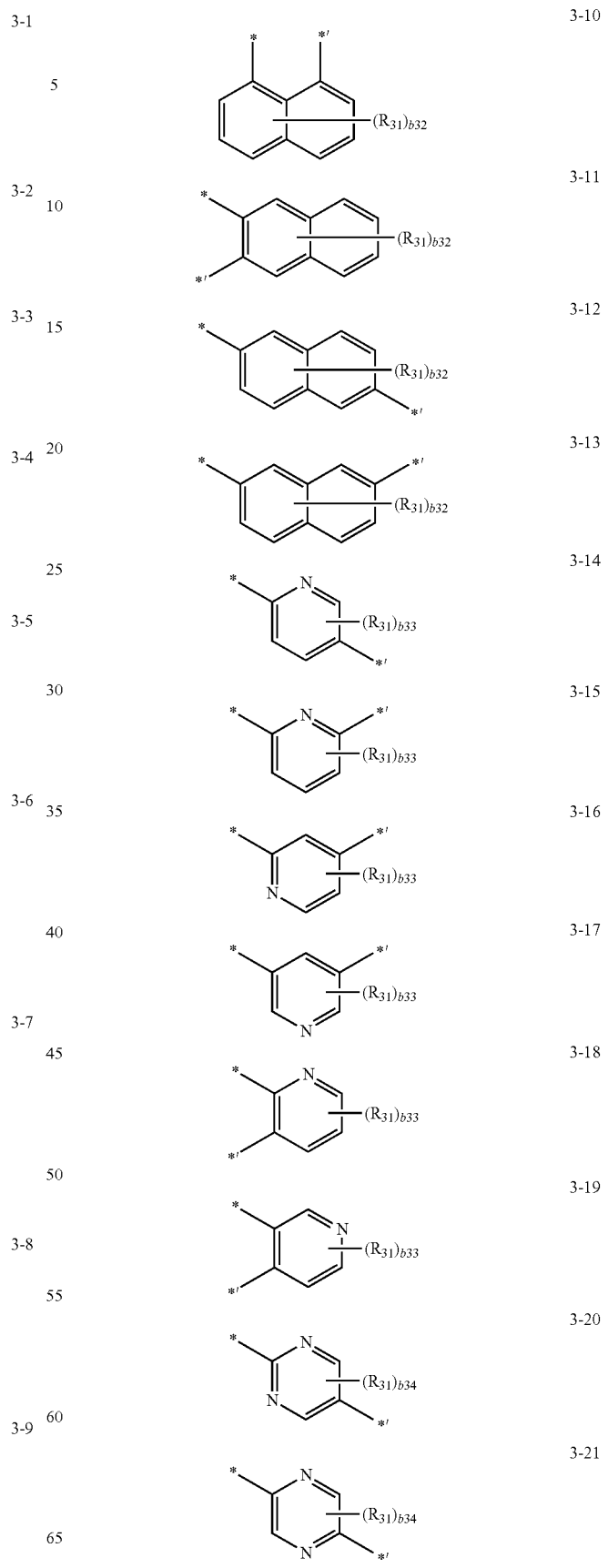

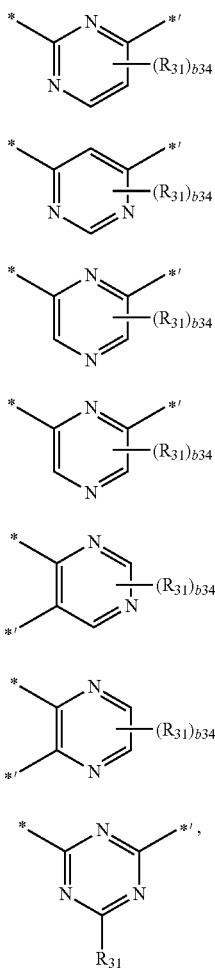

3-22

3-23

3-24

3-25

3-26

3-27

3-28 wherein, in Formulae 3-1 to 3-28, $R_{31}$ may be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group, b31 may be an integer selected from 1, 2, 3, and 4,
b32 may be an integer selected from 1, 2, 3, 4, 5, and 6,
b33 may be an integer selected from 1, 2, and 3,
b34 may be an integer selected from 1 and 2, and
* and *' each indicate a binding site to a neighboring atom.

In one or more exemplary embodiments, $L_{11}$ and $L_{21}$ to $L_{24}$ in Formulae 1 and 2-1 to 2-6 may each independently be selected from groups represented by Formulae 4-1 to 4-22, but exemplary embodiments of the present disclosure are not limited thereto:

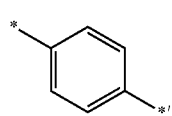

4-1

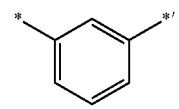

4-2

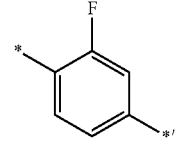

4-3

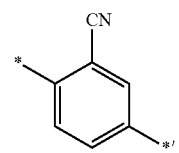

4-4

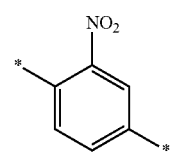

4-5

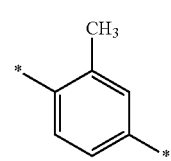

4-6

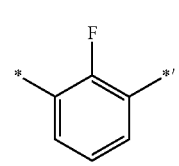

4-7

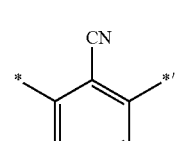

4-8

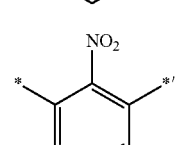

4-9

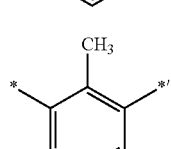

4-10

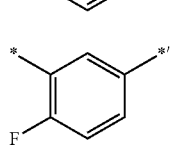

4-11

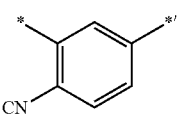

4-12

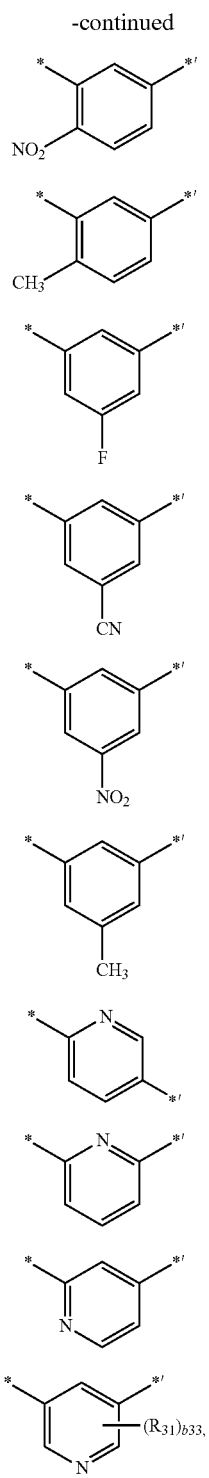

wherein, in Formulae 4-1 to 4-22,

* and *' each indicate a binding site to a neighboring atom.

a11 in Formula 1 indicates the repeating number of groups $L_{11}$ and may be selected from 1, 2, 3, and 4. When a11 is two or more, two or more groups $L_{11}$ may be identical to or different from each other.

a21 in Formula 2-1 indicates the repeating number of groups $L_{21}$ and may be selected from 1, 2, 3, and 4. When a21 is two or more, two or more groups $L_{21}$ may be identical to or different from each other.

In one or more exemplary embodiments, a11 and a21 in Formulae 1 and 2-1 may be 1, but exemplary embodiments of the present disclosure are not limited thereto.

a22, a23, and a24 in Formulae 2-2 to 2-6 respectively indicate the repeating number of groups $L_{22}$, $L_{23}$, and $L_{24}$ and may be selected from 0, 1, 2, 3, and 4. When a22 is zero, $(L_{22})_{a22}$ means a single bond. When a22 is two or more, two or more groups $L_{22}$ may be identical to or different from each other. When a23 is zero, $(L_{23})_{a23}$ means a single bond. When a23 is two or more, two or more groups $L_{23}$ may be identical to or different from each other. When a24 is two or more, two or more groups $L_{24}$ may be identical to or different from each other. When a24 is zero, $(L_{24})_{a24}$ means a single bond.

In one or more exemplary embodiments, a22 to a24 in Formulae 2-2 to 2-6 may each independently be selected from 0 and 1, but exemplary embodiments of the present disclosure are not limited thereto.

$R_{14}$ to $R_{18}$ and $R_{21}$ to $R_{29}$ in Formulae 1 and 2-1 to 2-5 may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —N(Q$_1$)(Q$_2$), and —B(Q$_1$)(Q$_2$), wherein $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, but exemplary embodiments of the present disclosure are not limited thereto.

In one or more exemplary embodiments, $R_{14}$ to $R_{18}$ and $R_{21}$ to $R_{29}$ in Formulae 1 and 2-1 to 2-5 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a pyridinyl group, a pyrimidinyl group, and a triazinyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, a dibenzothiophenyl group, —Si($Q_{31}$)($Q_{32}$)($Q_{33}$), —N($Q_{31}$)($Q_{32}$), and —B($Q_{31}$)($Q_{32}$); and —Si($Q_1$)($Q_2$)($Q_3$), —N($Q_1$)($Q_2$), and —B($Q_1$)($Q_2$), wherein $Q_1$ to $Q_3$ and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, but exemplary embodiments of the present disclosure are not limited thereto.

In one or more exemplary embodiments, $R_{14}$ to $R_{18}$ and $R_{21}$ to $R_{29}$ in Formulae 1 and 2-1 to 2-5 may each independently be selected from hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a pyridinyl group, and a pyrimidinyl group, but exemplary embodiments of the present disclosure are not limited thereto.

$R_{30}$ in Formula 2-6 may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one or more exemplary embodiments, $R_{30}$ in Formula 2-6 may be selected from:

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a dibenzosilolyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a carbazolyl group, a benzocarbazolyl group, a dibenzocarbazolyl group, an imidazopyridimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group; and a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a dibenzosilolyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a carbazolyl group, a benzocarbazolyl group, a dibenzocarbazolyl group, an imidazopyridimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{31}$)($Q_{32}$), and —B($Q_{31}$)($Q_{32}$), wherein $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, but exemplary embodiments of the present disclosure are not limited thereto.

In one or more exemplary embodiments, $R_{30}$ in Formula 2-6 may be selected from:

a cyclohexyl group, a piperidinyl group, a tetrahydro-2H-pyranyl group, a tetrahydro-2H-thiopyranyl group, a phenyl group, a biphenyl group, a terphenyl group, a naphthyl group, a fluorenyl group, a dibenzosilolyl group, a pyrrolyl group, a pyridinyl group, a pyrazinyl group, a pyrimidinyl group, a pyridazinyl group, a furanyl group, a thiophenyl group, a triazinyl group, a carbazolyl group, a dibenzofuranyl group, and a dibenzothiophenyl group; and a cyclohexyl group, a piperidinyl group, a tetrahydro-2H-pyranyl group, a tetrahydro-2H-thiopyranyl group, a phenyl group, a biphenyl group, a terphenyl group, a naphthyl group, a fluorenyl group, a dibenzosilolyl group, a pyrrolyl group, a pyridinyl group, a pyrazinyl group, a pyrimidinyl group, a pyridazinyl group, a furanyl group, a thiophenyl group, a triazinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a fluorenyl group, a carbazolyl group, a pyridinyl group, a pyrimidinyl group, a pyrazinyl group, a pyridazinyl group, and a triazinyl group, but exemplary embodiments of the present disclosure are not limited thereto.

In one or more exemplary embodiments, $R_{30}$ in Formula 2-6 may be one of the groups represented by Formulae 5-1 to 5-15, but exemplary embodiments of the present disclosure are not limited thereto:

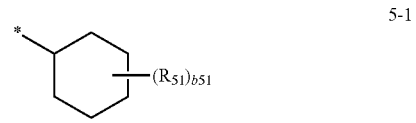

5-1

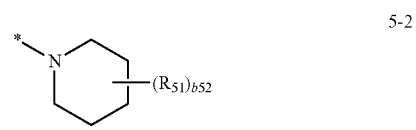

5-2

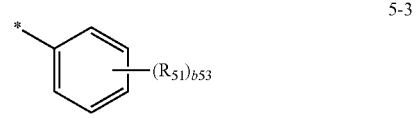

5-3

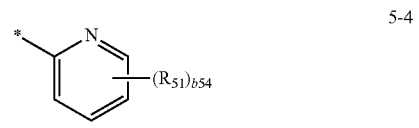

5-4

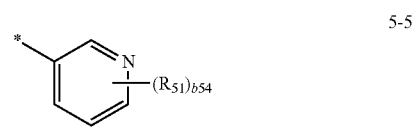

5-5

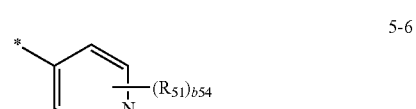

5-6

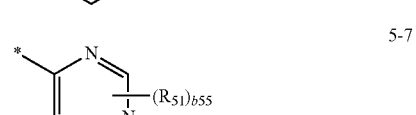

5-7

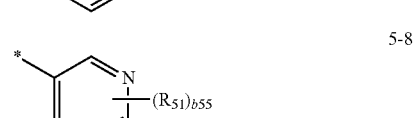

5-8


5-9

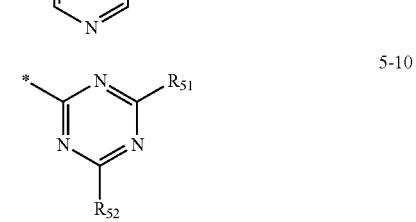

5-10

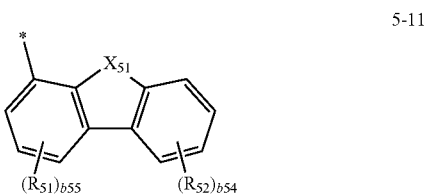

5-11

-continued

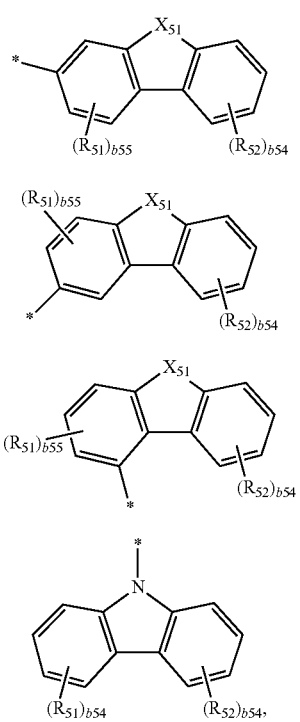

wherein, in Formulae 5-1 to 5-15, $X_{51}$ may be selected from $C(R_{53})(R_{54})$, $Si(R_{53})(R_{54})$, $N(R_{53})$, O, and S, $R_{51}$ to $R_{54}$ may each independently be selected from hydrogen, deuterium, —F, —Cl, —Br, —I, a hydroxyl group, a cyano group, a nitro group, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, and a triazinyl group, b51 may be an integer selected from 1, 2, 3, 4, 5, 6, 7, 8, 9, 10, and 11, b52 may be an integer selected from 1, 2, 3, 4, 5, 6, 7, 8, 9, and 10, b53 may be an integer selected from 1, 2, 3, 4, and 5, b54 may be an integer selected from 1, 2, 3, and 4, b55 may be an integer selected from 1, 2, and 3, and

* indicates a binding site to a neighboring atom.

In one or more exemplary embodiments, $R_{30}$ in Formula 2-6 may be one of the groups represented by Formulae 6-1 to 6-35, but exemplary embodiments of the present disclosure are not limited thereto:

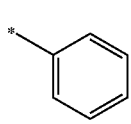

6-1

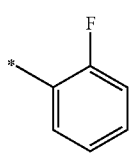

6-2

-continued

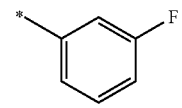

6-3

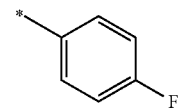

6-4

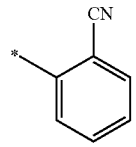

6-5

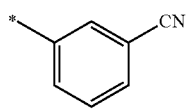

6-6

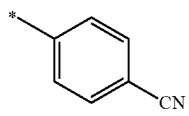

6-7

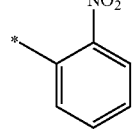

6-8

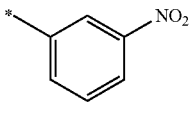

6-9

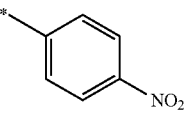

6-10

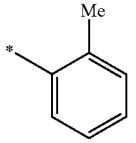

6-11

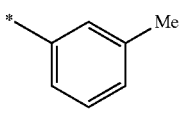

6-12

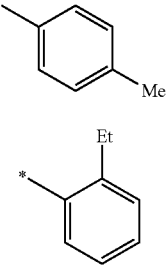

6-13

6-14

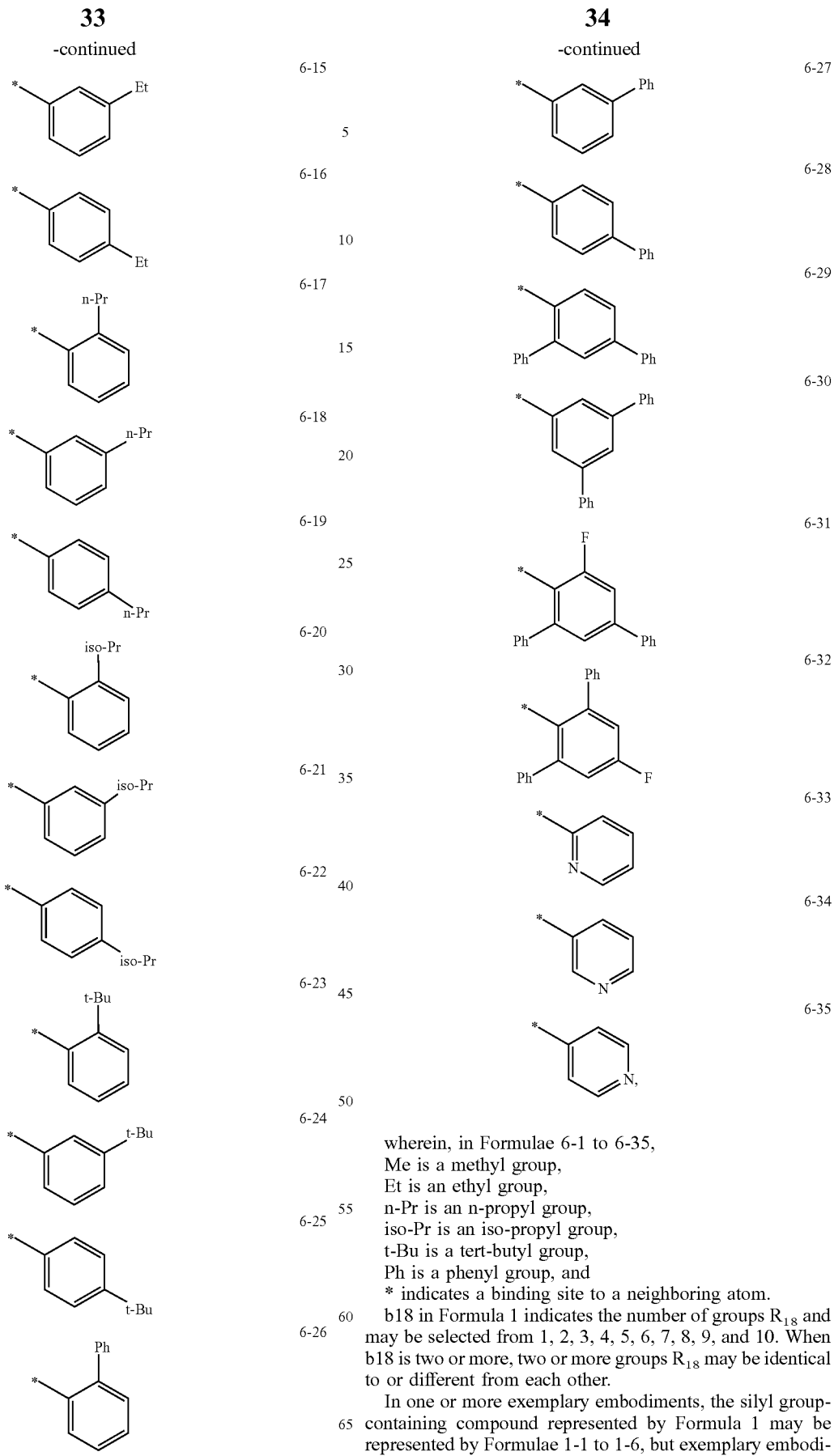

wherein, in Formulae 6-1 to 6-35,
Me is a methyl group,
Et is an ethyl group,
n-Pr is an n-propyl group,
iso-Pr is an iso-propyl group,
t-Bu is a tert-butyl group,
Ph is a phenyl group, and
* indicates a binding site to a neighboring atom.

b18 in Formula 1 indicates the number of groups $R_{18}$ and may be selected from 1, 2, 3, 4, 5, 6, 7, 8, 9, and 10. When b18 is two or more, two or more groups $R_{18}$ may be identical to or different from each other.

In one or more exemplary embodiments, the silyl group-containing compound represented by Formula 1 may be represented by Formulae 1-1 to 1-6, but exemplary embodiments of the present disclosure are not limited thereto:

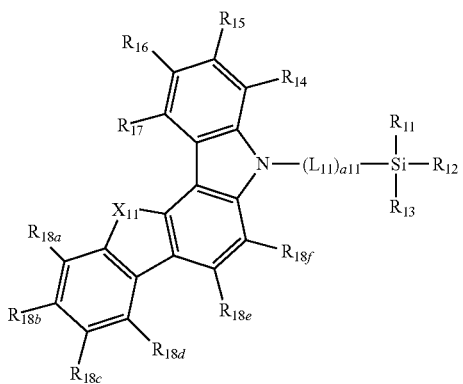

1-1

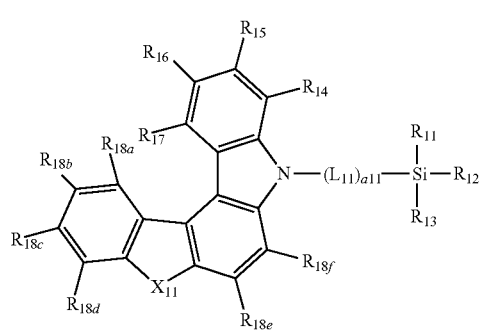

1-2

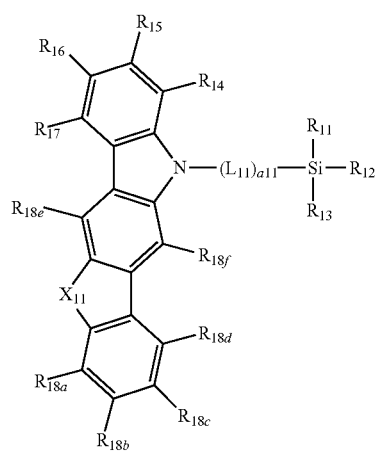

1-3

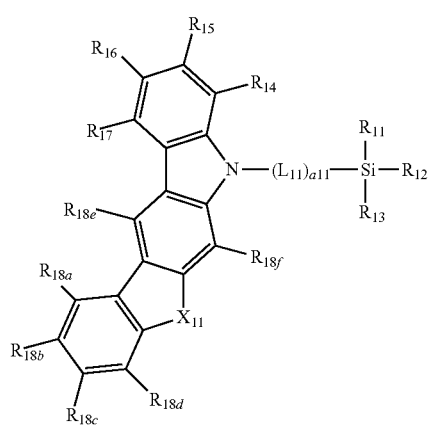

1-4

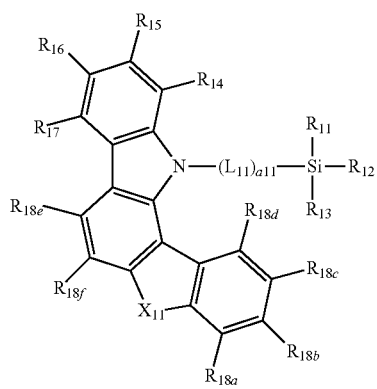

1-5

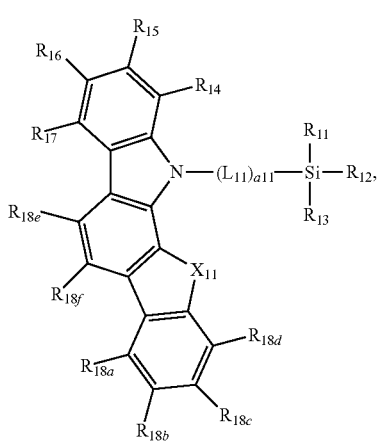

1-6 wherein, in Formulae 1-1 to 1-6, $R_{11}$ to $R_{13}$ may each independently be selected from groups represented by Formulae 2-11 to 2-19, 2-21 to 2-28, 2-31 to 2-38, 2-41 to 2-48, 2-51 to 2-58, and 2-6, provided that at least one selected from $R_{11}$ to $R_{13}$ is selected from groups represented by Formulae 2-11 to 2-19, 2-21 to 2-28, 2-31 to 2-38, 2-41 to 2-48, and 2-51 to 2-58, $X_{11}$ may be selected from O, S, N($R_{18g}$), and C($R_{18g}$)($R_{18h}$), $R_{11}$ to $R_{17}$, $L_{11}$, and a11 are the same as described above in connection with Formula 1, and $R_{18a}$ to $R_{18h}$ are each independently the same as described above in connection with $R_{18}$ in Formula 1:

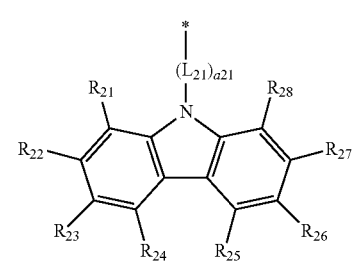

2-11

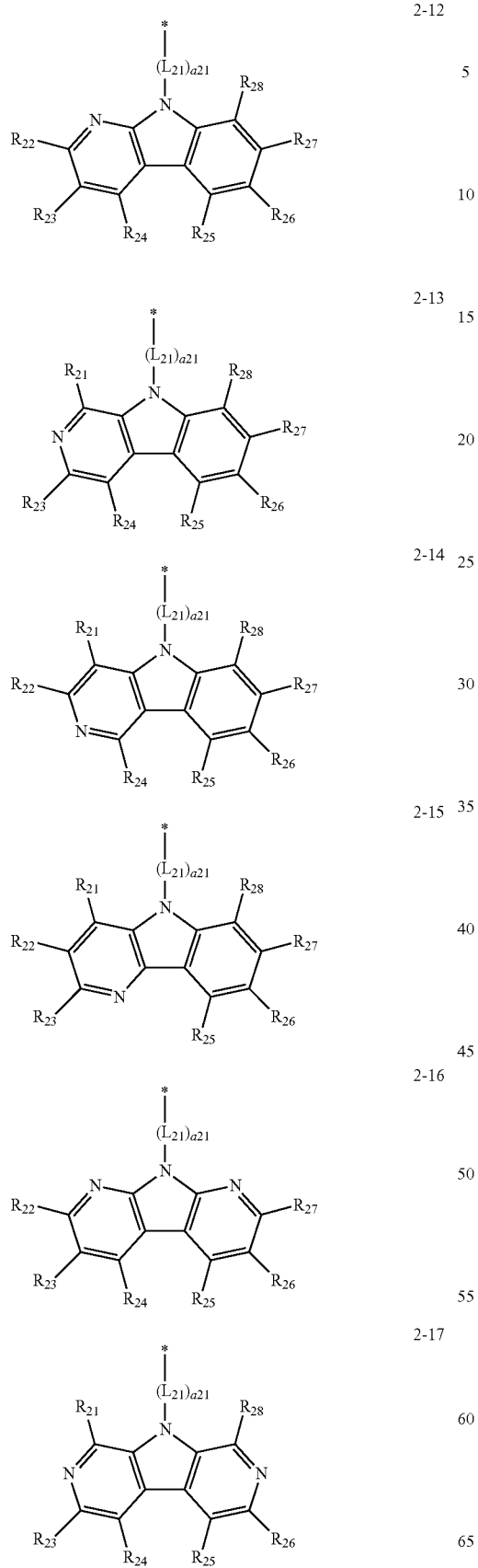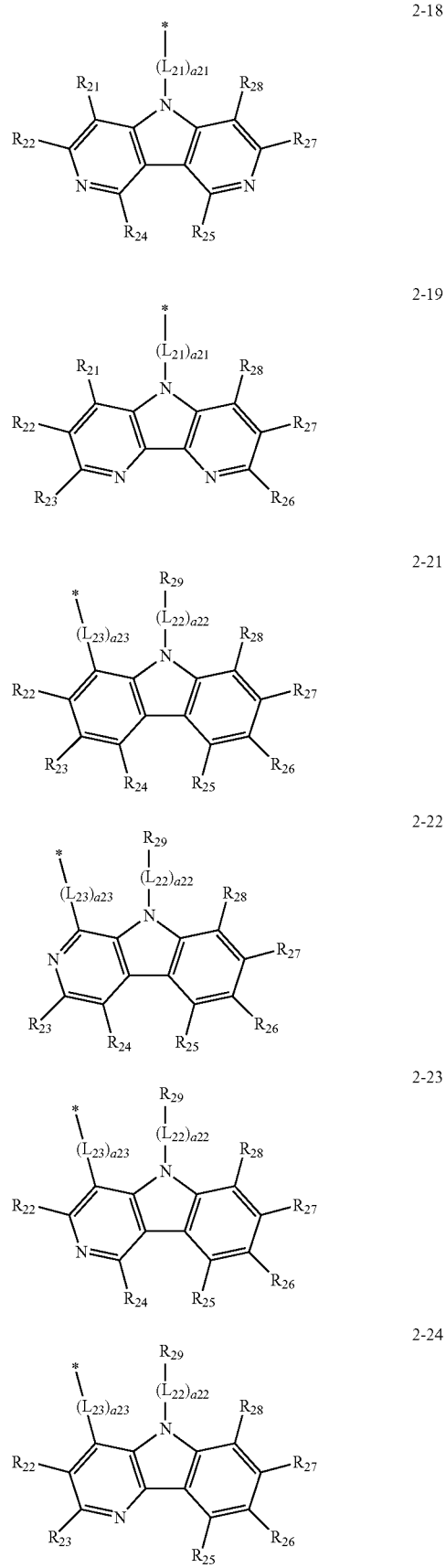

2-25
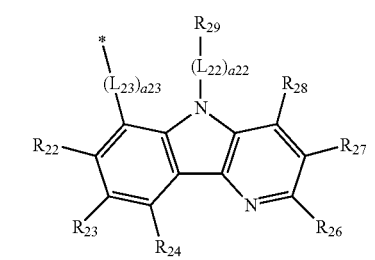
2-26
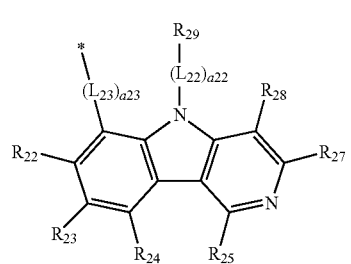
2-27
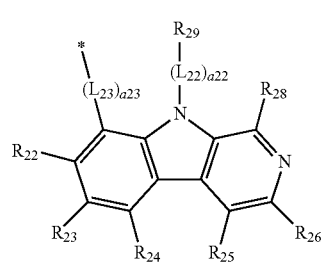
2-28
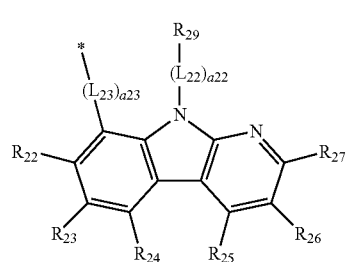
2-31
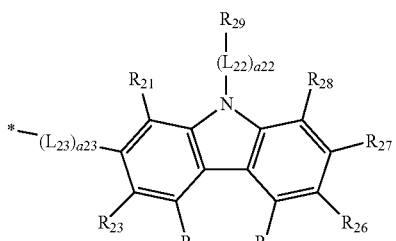
2-32
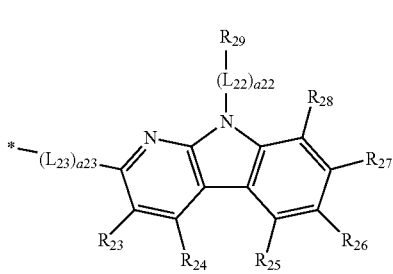
2-33
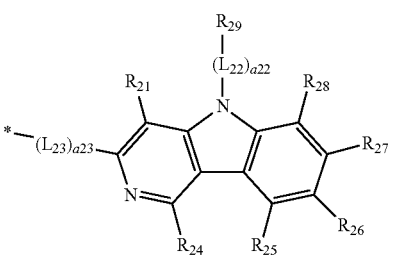
2-34
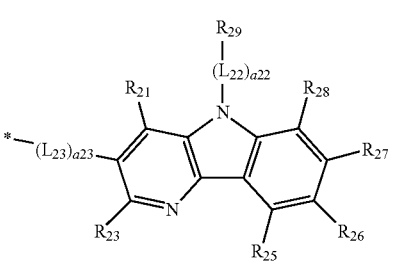
2-35
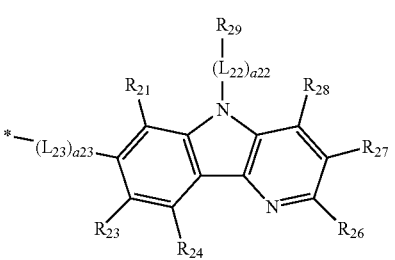
2-36
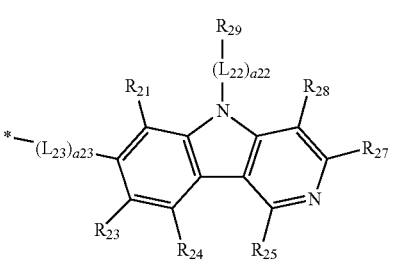
2-37
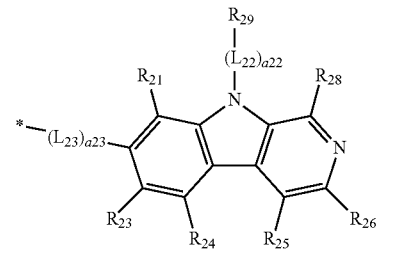
2-38
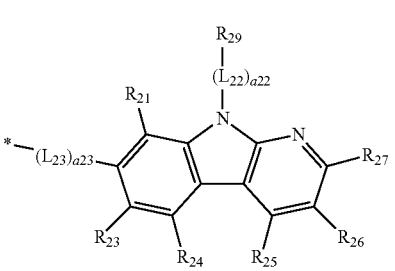

2-41

2-42

2-43

2-44

2-45

2-46

2-47

2-48

2-51

2-52

2-53

2-54

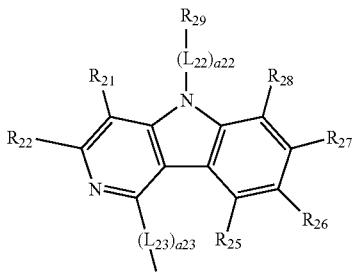

2-55

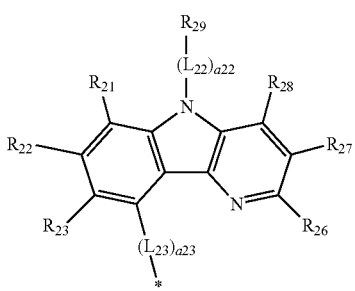

2-56

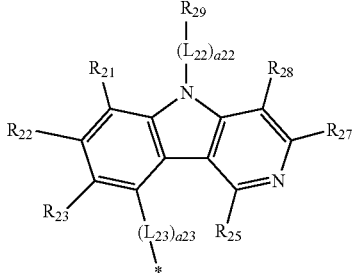

2-57

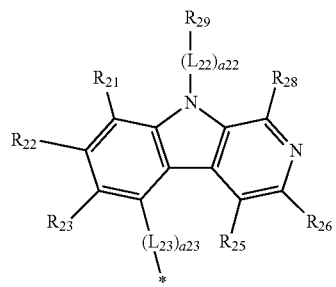

2-58

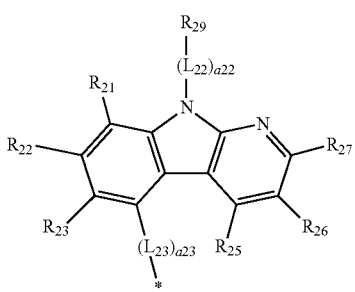

2-6

*—(L$_{24}$)$_{a24}$—R$_{30}$, wherein, in Formulae 2-11 to 2-19, 2-21 to 2-28, 2-31 to 2-38, 2-41 to 2-48, 2-51 to 2-58, and 2-6, L$_{21}$ to L$_{24}$, a21 to a24, and R$_{21}$ to R$_{30}$ are the same as described above in connection with Formulae 2-1 to 2-6, and

* indicates a binding site to a neighboring atom.

In one or more exemplary embodiments, R$_{11}$ to R$_{13}$ in Formulae 1-1 to 1-6 may each independently be selected from groups represented by Formulae 2-11 to 2-19, 2-21 to 2-28, 2-31 to 2-38, 2-41 to 2-48, 2-51 to 2-58, and 2-6, provided that one or two of R$_{11}$ to R$_{13}$ are selected from groups represented by Formulae 2-11 to 2-19, 2-21 to 2-28, 2-31 to 2-38, 2-41 to 2-48, and 2-51 to 2-58, but exemplary embodiments of the present disclosure are not limited thereto.

In one or more exemplary embodiments, the silyl group-containing compound represented by Formula 1 may be represented by one of Formulae 1-11 to 1-40, but exemplary embodiments of the present disclosure are not limited thereto:

1-11

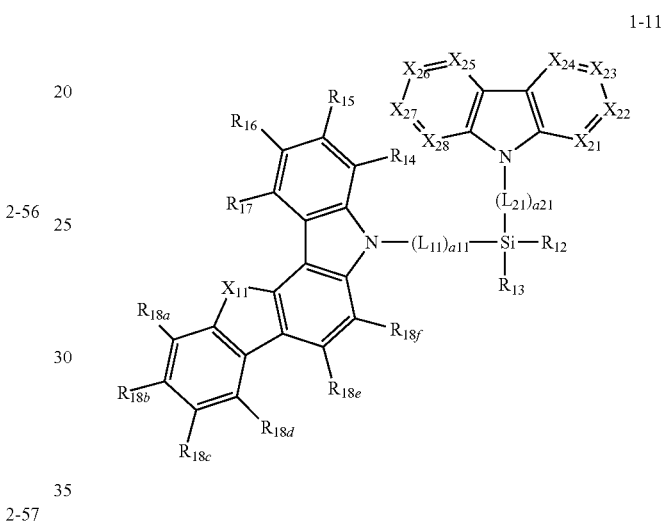

1-12

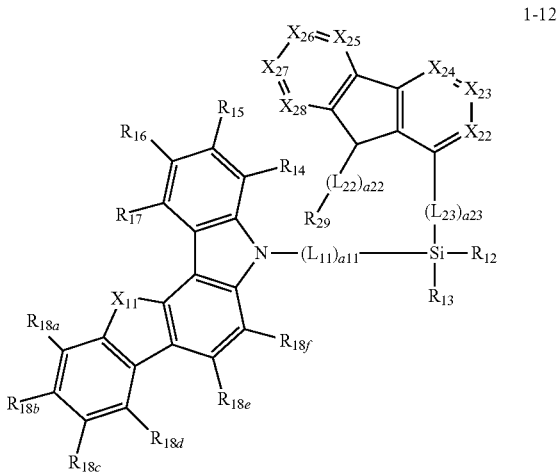

1-13
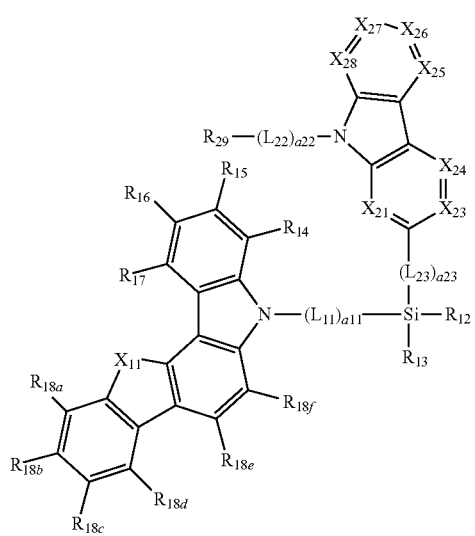
1-14
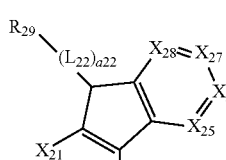
1-15
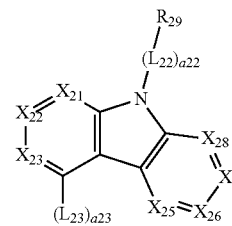
1-16
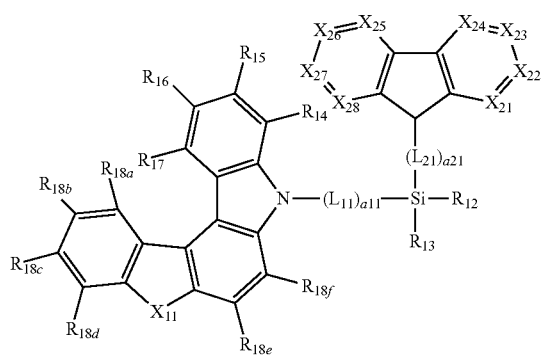
1-17
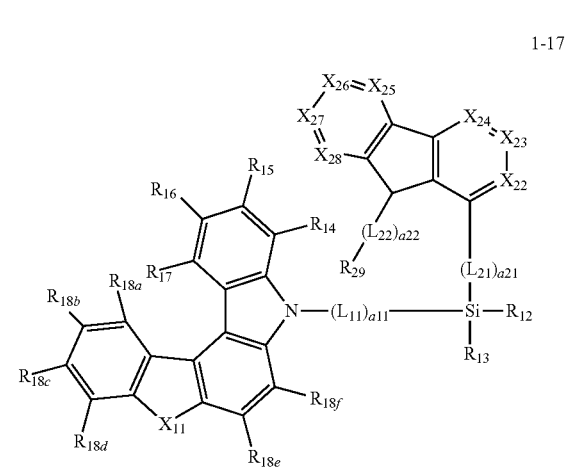
1-18
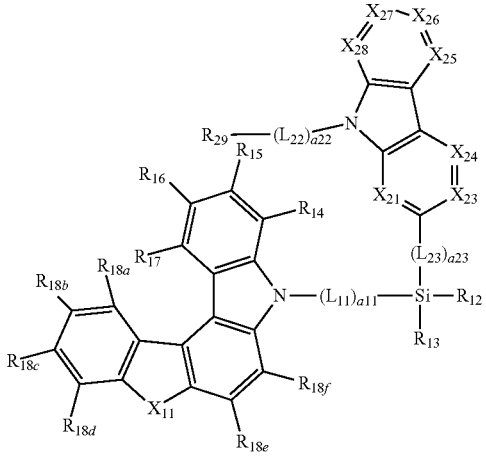

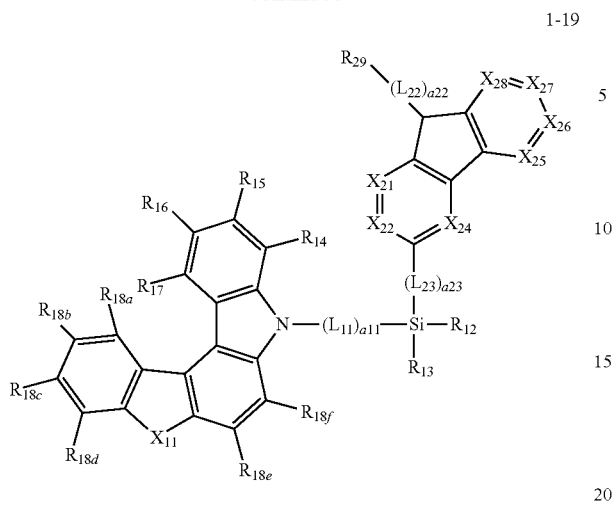
1-19
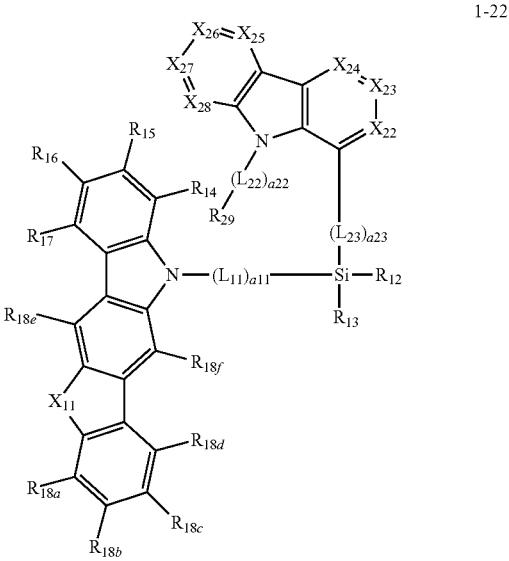
1-22
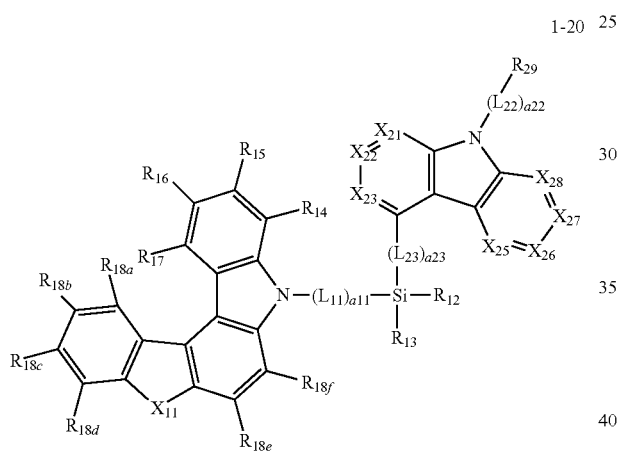
1-20
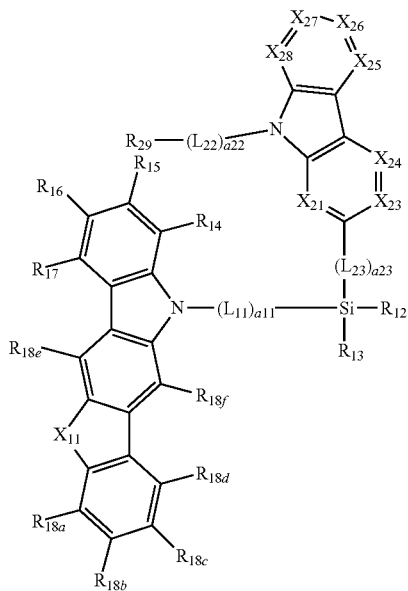
1-21
1-23

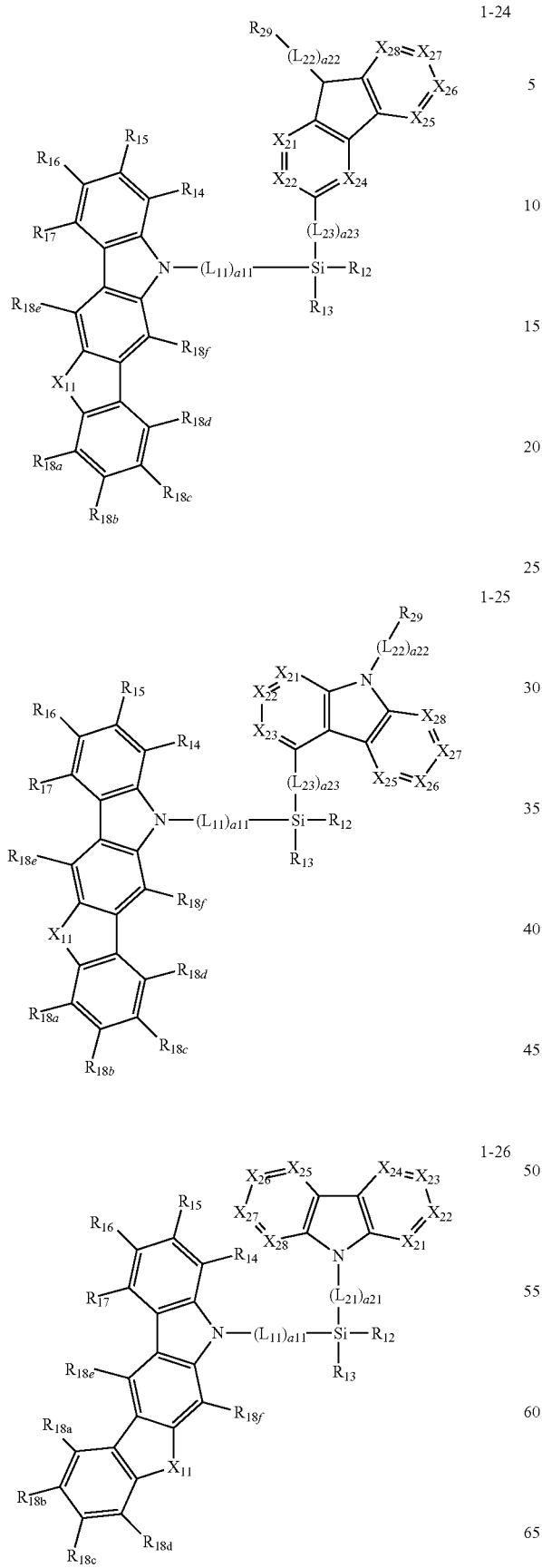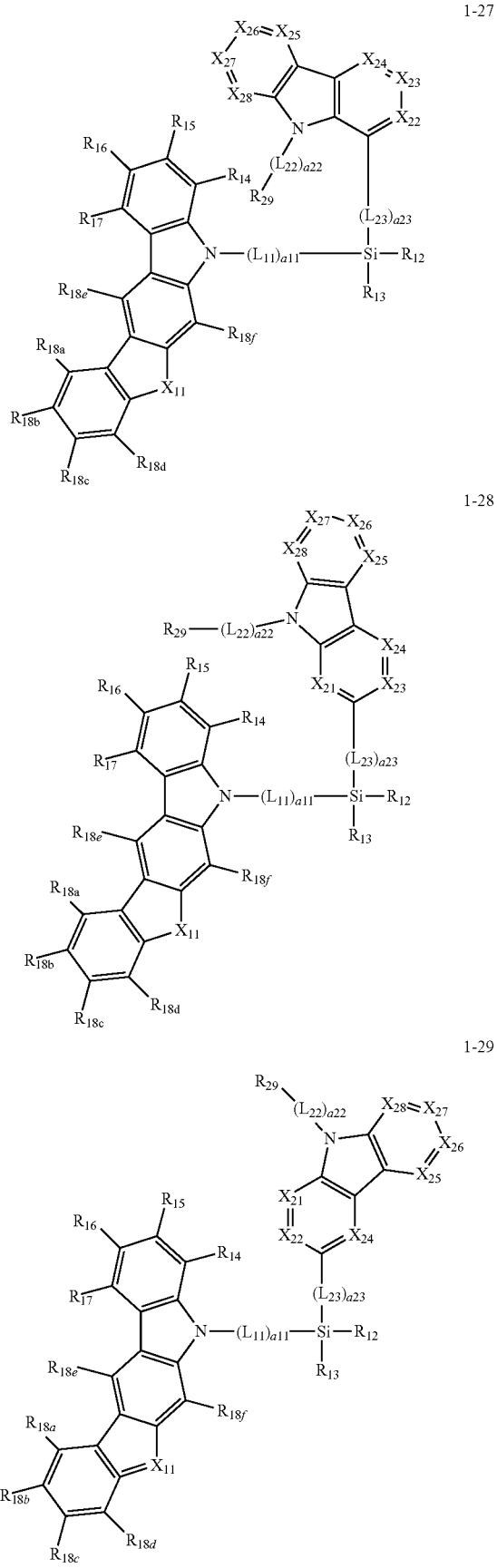

-continued
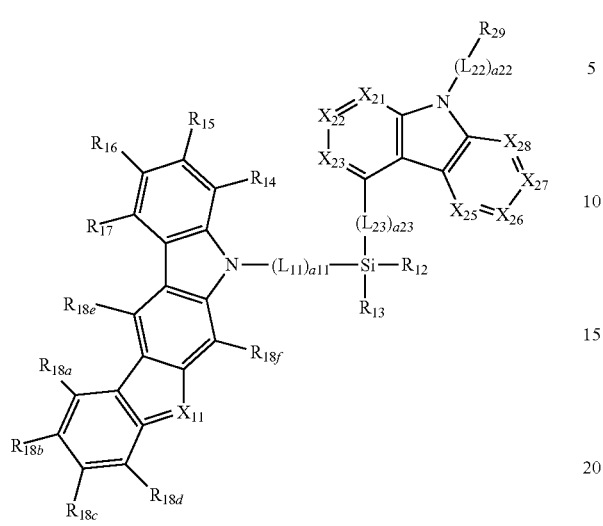
1-30
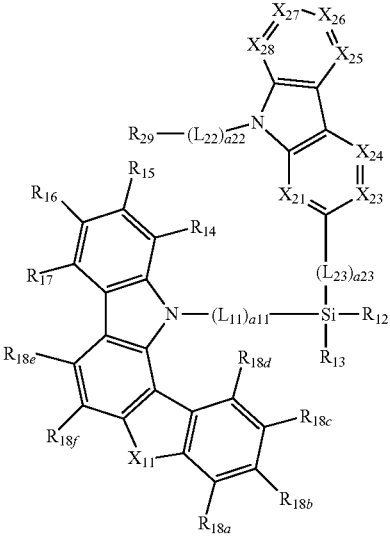
1-33
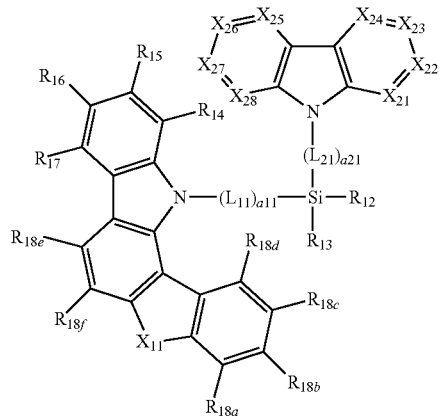
1-31
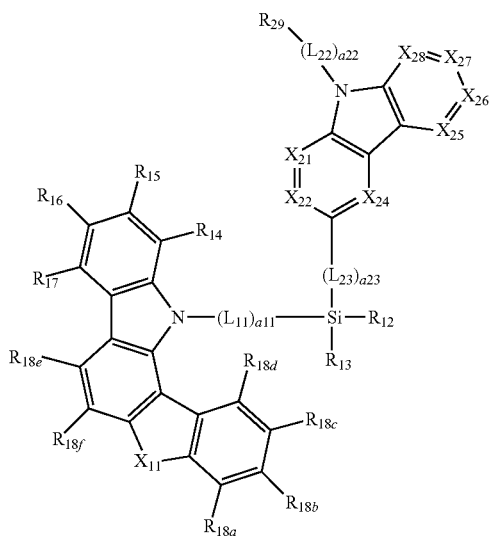
1-34
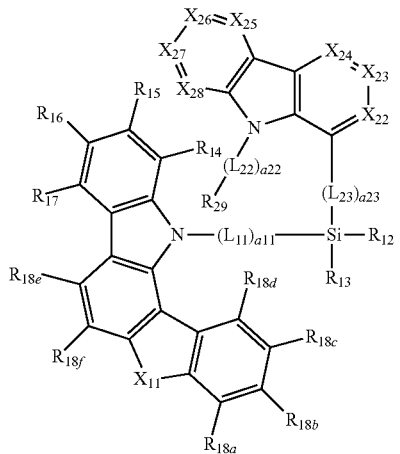
1-32
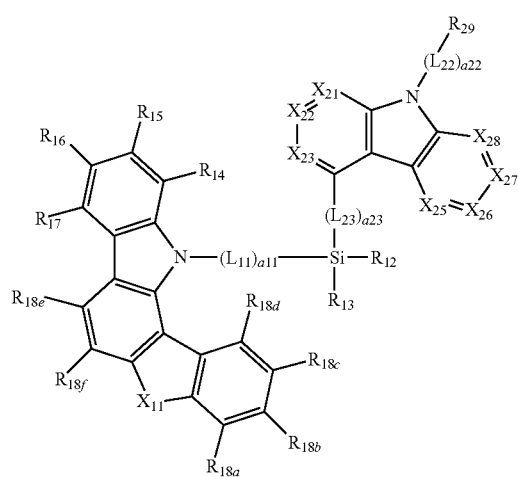
1-35

1-36
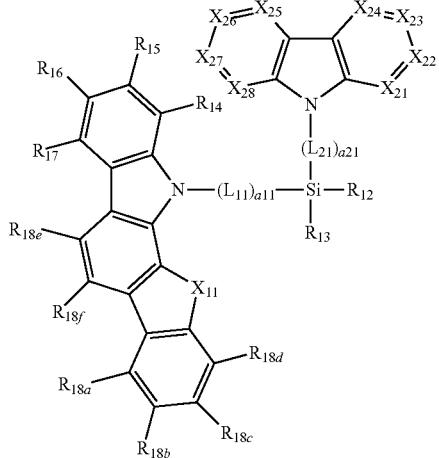

1-37
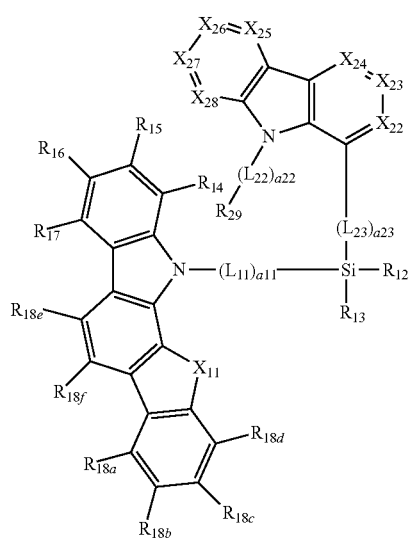

1-38
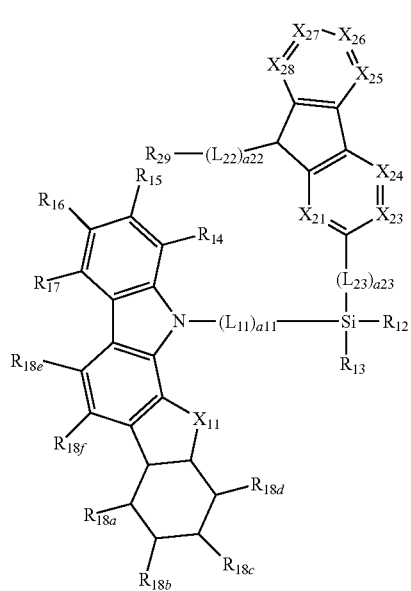

1-39
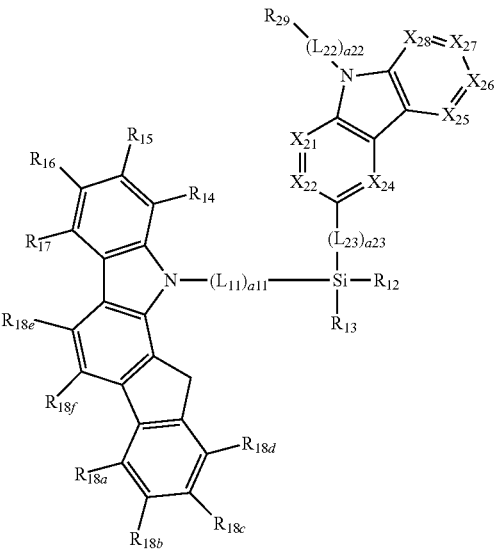

1-40
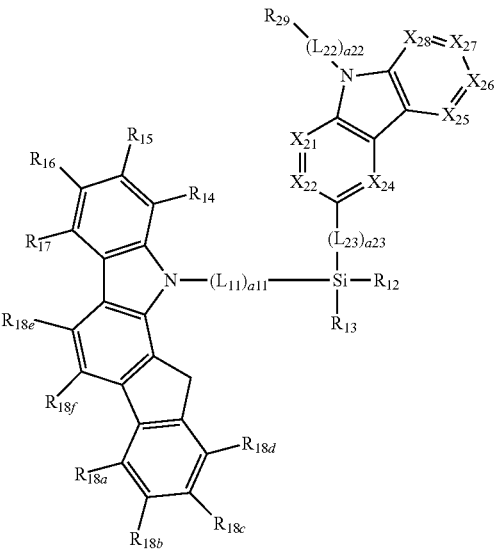

wherein, in Formulae 1-11 to 1-40, $X_{11}$ may be selected from O, S, $N(R_{18g})$, and $C(R_{18g})(R_{18h})$, $R_{12}$ to $R_{17}$, $L_{11}$, and a11 are the same as described above in connection with Formula 1, $X_{21}$ to $X_{28}$, $L_{21}$ to $L_{23}$, a21 to a23, and $R_{29}$ are the same as described above in connection with Formulae 2-1 to 2-6, and $R_{18a}$ to $R_{18h}$ are each independently the same as described above in connection with $R_{18}$ in Formula 1.

In one or more exemplary embodiments, in Formulae 1-11 to 1-40, $R_{12}=R_{13}$ or $R_{12}\neq R_{13}$, but exemplary embodiments of the present disclosure are not limited thereto.

In one or more exemplary embodiments, in Formulae 1-11, 1-16, 1-21, 1-26, 1-31, and 1-36, for example, in Formula 2-1, $X_{21}$ may be $CR_{21}$, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be N, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be N, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be N, $X_{22}$ may be $CR_{22}$, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be N, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be N, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be N;

$X_{21}$ may be N, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{22}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{22}$ may be $CR_{22}$, $X_{23}$ may be N, $X_{24}$ may be $CR_{24}$, $X_{25}$ may be $CR_{25}$, $X_{26}$ may be N, $X_{27}$ may be $CR_{27}$, and $X_{28}$ may be $CR_{28}$; or $X_{21}$ may be $CR_{21}$, $X_{22}$ may be $CR_{22}$, $X_{23}$ may be $CR_{23}$, $X_{24}$ may be N, $X_{25}$ may be N, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formulae 1-12, 1-17, 1-22, 1-27, 1-32, and 1-37, $X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{22}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{22}$ may be $CR_{22}$, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{22}$ may be $CR_{22}$, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{22}$ may be $CR_{22}$, $X_{23}$ may be $CR_{23}$, $X_{24}$ may be $CR_{24}$, $X_{25}$ may be N, $X_{26}$ may be $CR_{26}$, $X_{27}$ may be $CR_{27}$, and $X_{28}$ may be $CR_{28}$;

$X_{22}$ may be $CR_{22}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be $CR_{28}$;

$X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{22}$ may be N, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{22}$ may be $CR_{22}$, $X_{23}$ may be $CR_{23}$, $X_{24}$ may be $CR_{24}$, $X_{25}$ may be N, $X_{26}$ may be $CR_{26}$, $X_{27}$ may be N, and $X_{28}$ may be $CR_{28}$;

$X_{22}$ may be $CR_{22}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be N;

$X_{22}$ may be $CR_{22}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{22}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{22}$ may be $CR_{22}$, $X_{23}$ may be N, $X_{24}$ may be $CR_{24}$, $X_{25}$ may be $CR_{25}$, $X_{26}$ may be N, $X_{27}$ may be $CR_{27}$, and $X_{28}$ may be $CR_{28}$; or $X_{22}$ may be $CR_{22}$, $X_{23}$ may be $CR_{23}$, $X_{24}$ may be N, $X_{25}$ may be N, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formulae 1-13, 1-18, 1-23, 1-28, 1-33, and 1-38, $X_{21}$ may be $CR_{21}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{23}$ may be $CR_{23}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{23}$ may be $CR_{23}$, $X_{24}$ may be $CR_{24}$, $X_{25}$ may be N, $X_{26}$ may be $CR_{26}$, $X_{27}$ may be $CR_{27}$, and $X_{28}$ may be $CR_{28}$;

$X_{21}$ may be $CR_{21}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be $CR_{28}$;

$X_{21}$ may be $CR_{21}$, $X_{23}$ may be $CR_{23}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{21}$ may be $CR_{21}$, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be N, $X_{23}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{23}$ may be $CR_{23}$, $X_{24}$ may be $CR_{24}$, $X_{25}$ may be N, $X_{26}$ may be $CR_{26}$, $X_{27}$ may be N, and $X_{28}$ may be $CR_{28}$;

$X_{21}$ may be $CR_{21}$, $X_{23}$ may be $CR_{23}$, $X_{24}$ may be $CR_{24}$, $X_{25}$ may be $CR_{25}$, $X_{26}$ may be N, $X_{27}$ may be $CR_{27}$, and $X_{28}$ may be N;

$X_{21}$ may be N, $X_{23}$ may be $CR_{23}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{23}$ may be N, $X_{24}$ may be $CR_{24}$, $X_{25}$ may be $CR_{25}$, $X_{26}$ may be N, $X_{27}$ may be $CR_{27}$, and $X_{28}$ may be $CR_{28}$; or $X_{21}$ may be $CR_{21}$, $X_{23}$ may be $CR_{23}$, $X_{24}$ may be N, $X_{25}$ may be N, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formulae 1-14, 1-19, 1-24, 1-29, 1-34, and 1-39, $X_{21}$ may be $CR_{21}$, $X_{22}$ may be $CR_{22}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be N, $X_{22}$ may be $CR_{22}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be N, $X_{24}$ may be $CR_{24}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{24}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{24}$ may be $CR_{24}$, $X_{25}$ may be N, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{24}$ may be $CR_{24}$, $X_{25}$ may be $CR_{25}$, $X_{26}$ may be N, $X_{27}$ may be $CR_{27}$, and $X_{28}$ may be $CR_{28}$;

$X_{21}$ may be $CR_{21}$, $X_{22}$ may be $CR_{22}$, $X_{24}$ may be $CR_{24}$, $X_{25}$ may be $CR_{25}$, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{22}$ may be N, $X_{24}$ may be N, $X_{25}$ may be $CR_{25}$, $X_{26}$ may be $CR_{26}$, $X_{27}$ may be $CR_{27}$, and $X_{28}$ may be $CR_{26}$;

$X_{21}$ may be $CR_{21}$, $X_{22}$ may be $CR_{22}$, $X_{24}$ may be $CR_{24}$, $X_{25}$ may be N, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{24}$ may be $CR_{24}$, $X_{25}$ may be $CR_{25}$, $X_{26}$ may be N, $X_{27}$ may be $CR_{27}$, and $X_{28}$ may be N;

$X_{21}$ may be N, $X_{22}$ may be $CR_{22}$, $X_{24}$ may be $CR_{24}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{22}$ may be N, $X_{24}$ may be $CR_{24}$, $X_{25}$ may be $CR_{25}$, $X_{26}$ may be $CR_{26}$, $X_{27}$ may be N, and $X_{28}$ may be $CR_{28}$; or $X_{21}$ may be $CR_{21}$, $X_{22}$ may be $CR_{22}$, $X_{24}$ may be N, $X_{25}$ may be N, $X_{26}$ may be $CR_{26}$, $X_{27}$ may be $CR_{27}$, and $X_{28}$ may be $CR_{28}$, but exemplary embodiments of the present disclosure are not limited thereto.

In one or more exemplary embodiments, in Formulae 1-15, 1-20, 1-25, 1-30, 1-35, and 1-40, $X_{21}$ may be $CR_{21}$, $X_{22}$ may be $CR_{22}$, $X_{23}$ may be $CR_{23}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be N, $X_{22}$ may be $CR_{22}$, $X_{23}$ may be $CR_{23}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be N, $X_{23}$ may be $CR_{23}$, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{25}$ may be N, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{25}$ may be $CR_{25}$, $X_{26}$ may be N, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{25}$ may be $CR_{25}$, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{23}$ may be $CR_{23}$, $X_{25}$ may be $CR_{25}$, $X_{26}$ may be $CR_{26}$, $X_{27}$ may be $CR_{27}$, and $X_{28}$ may be N;

$X_{21}$ may be N, $X_{22}$ may be $CR_{22}$, $X_{23}$ may be N, $X_{25}$ may be $CR_{25}$, $X_{26}$ may be $CR_{26}$, $X_{27}$ may be $CR_{27}$, and $X_{28}$ may be $CR_{28}$;

$X_{21}$ may be $CR_{21}$, $X_{22}$ may be $CR_{22}$, $X_{23}$ may be $CR_{23}$, $X_{25}$ may be N, $X_{26}$ may be $CR_{26}$, $X_{27}$ may be N, and $X_{28}$ may be $CR_{28}$;

$X_{21}$ may be $CR_{21}$, $X_{22}$ may be $CR_{22}$, $X_{23}$ may be $CR_{23}$, $X_{25}$ may be $CR_{25}$, $X_{26}$ may be N, $X_{27}$ may be $CR_{27}$, and $X_{28}$ may be N;

$X_{21}$ may be N, $X_{22}$ may be $CR_{22}$, $X_{23}$ may be $CR_{23}$, $X_{25}$ may be $CR_{25}$, $X_{26}$ may be $CR_{26}$, $X_{27}$ may be $CR_{27}$, and $X_{28}$ may be N;

$X_{21}$ may be $CR_{21}$, $X_{22}$ may be $CR_{22}$, $X_{23}$ may be N, $X_{25}$ may be $CR_{25}$, $X_{26}$ may be $CR_{26}$, $X_{27}$ may be N, and $X_{28}$ may be $CR_{28}$; or $X_{21}$ may be $CR_{21}$, $X_{22}$ may be $CR_{22}$, $X_{23}$ may be N, $X_{25}$ may be $CR_{25}$, $X_{26}$ may be N, $X_{27}$ may be $CR_{27}$, and $X_{28}$ may be $CR_{28}$, but exemplary embodiments of the present disclosure are not limited thereto.

The silyl group-containing compound represented by Formula 1 may be selected from Compounds 1 to 432, but exemplary embodiments of the present disclosure are not limited thereto:

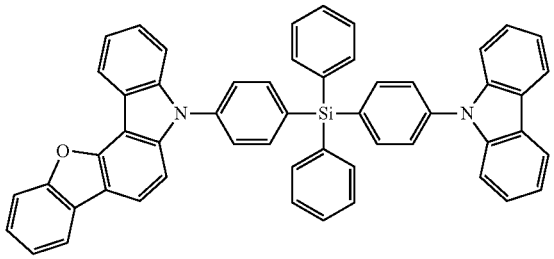

1

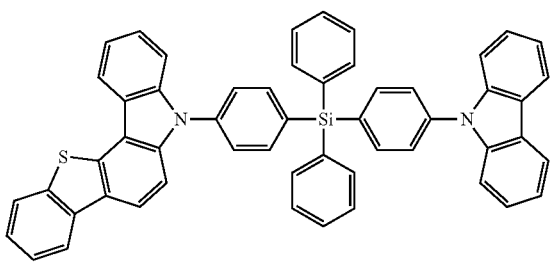

2

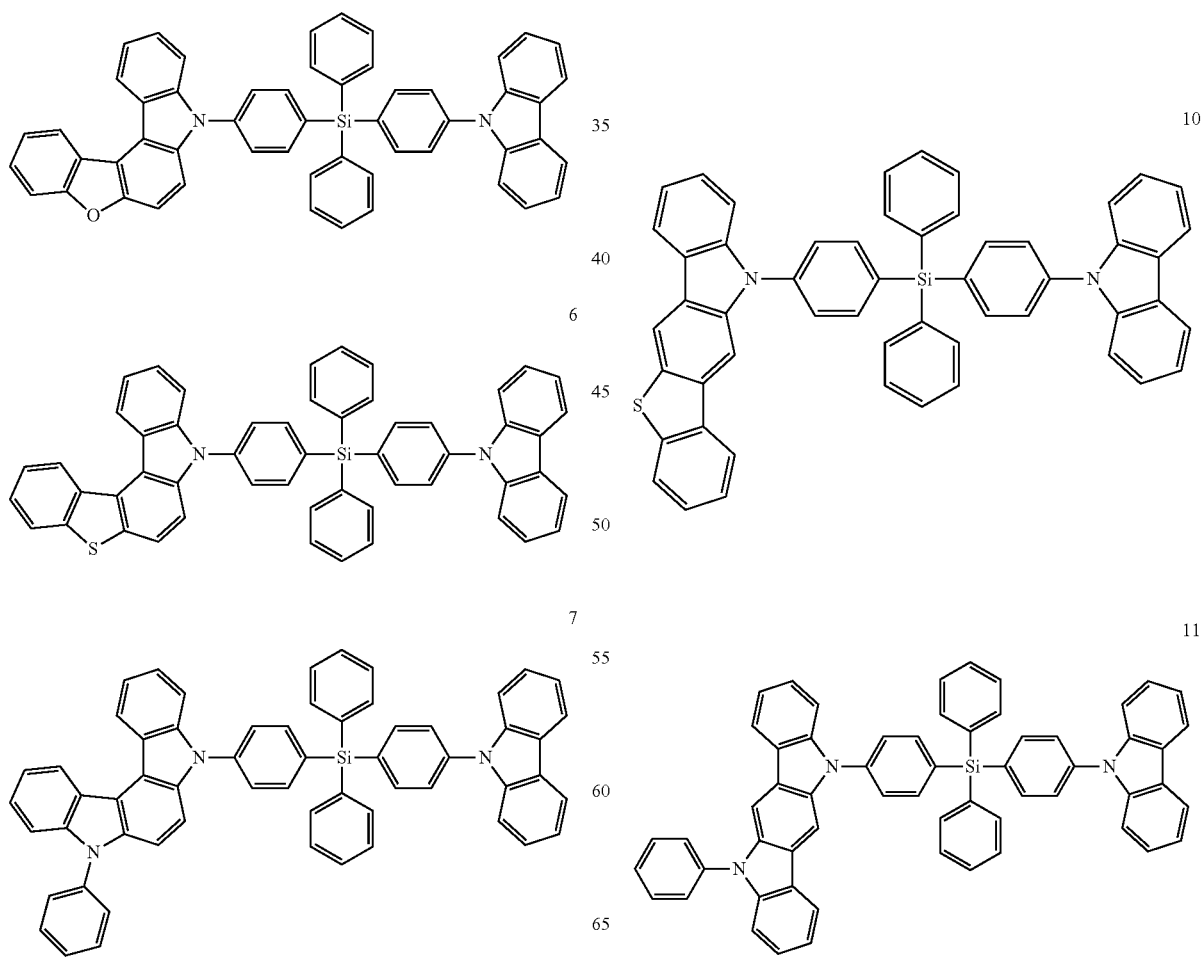

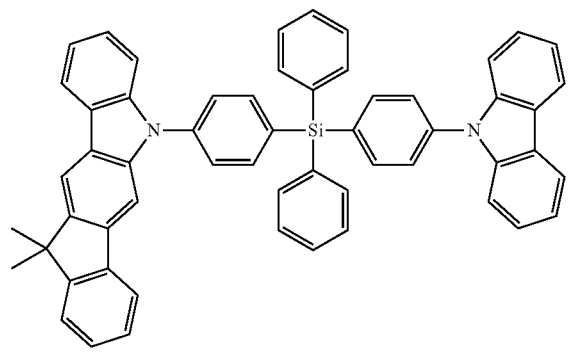
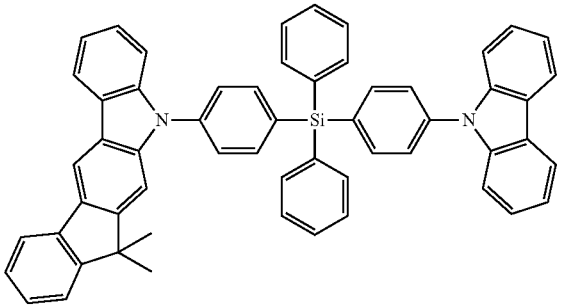
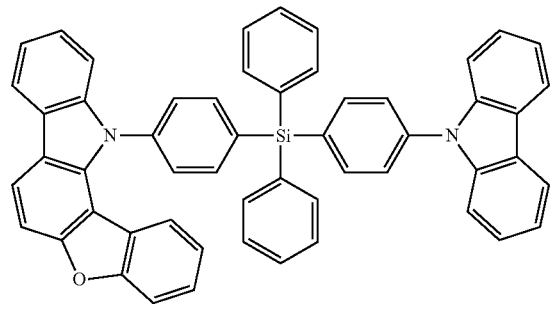
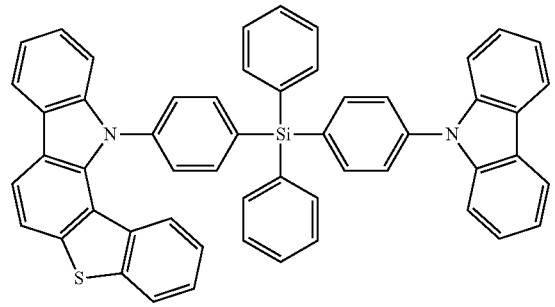
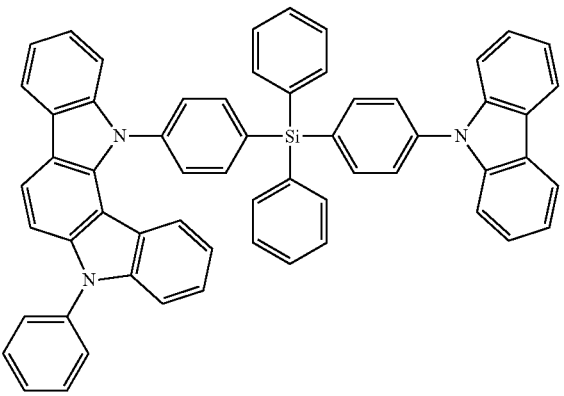

20
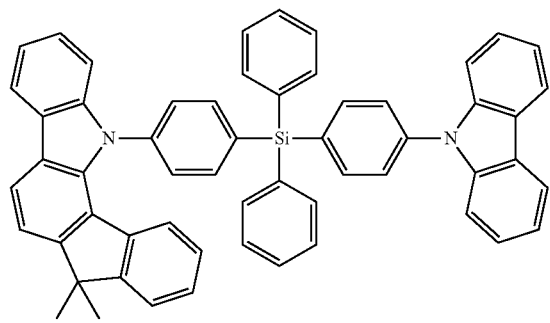
21
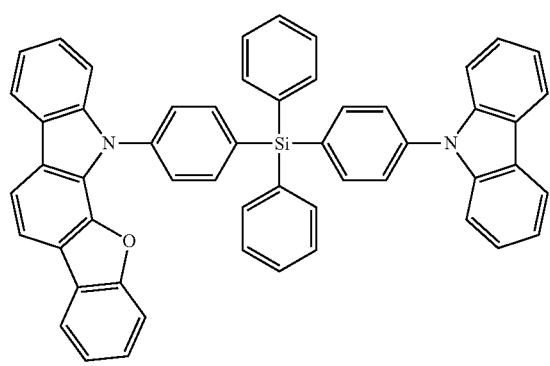
22
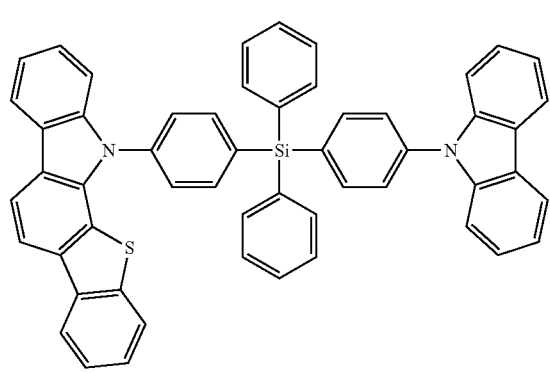
23
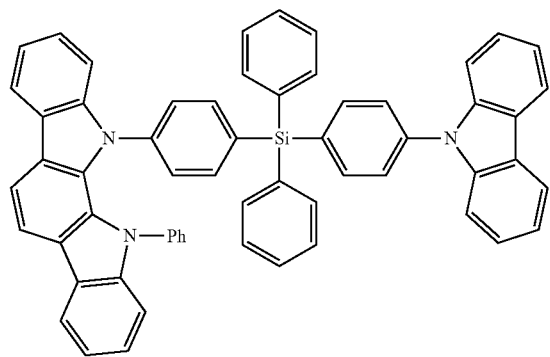
24
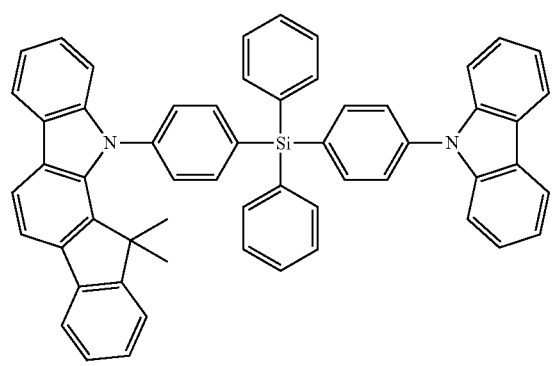
25
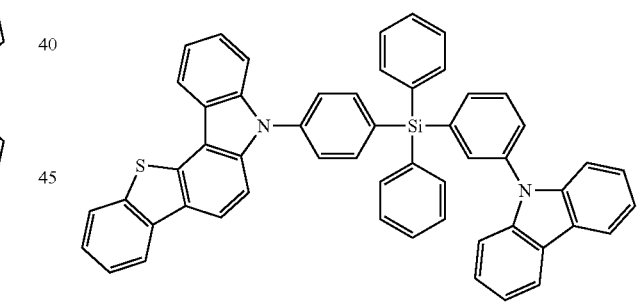
26
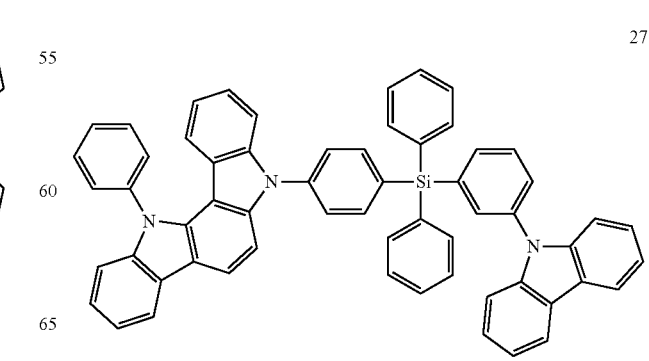
27

28
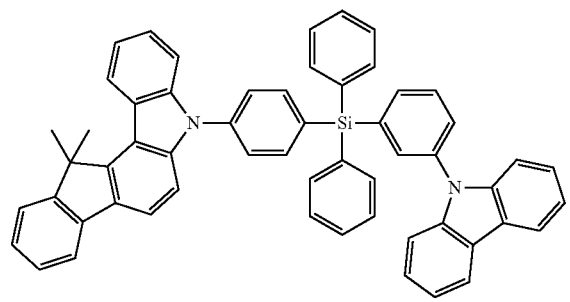
29
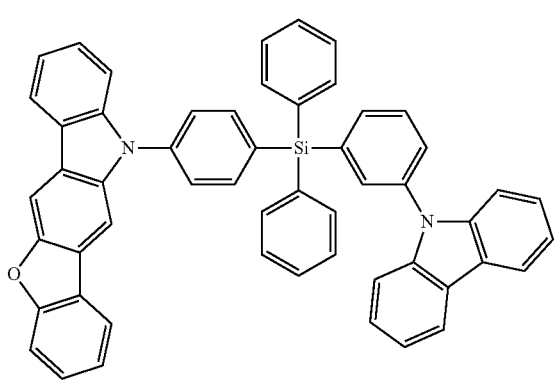
33
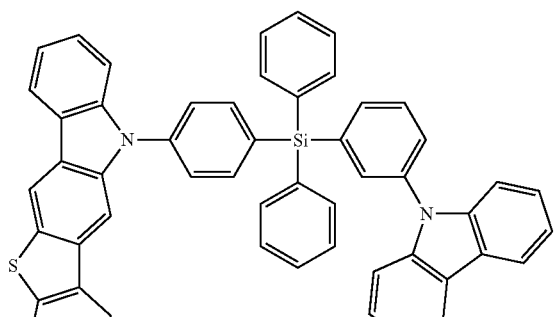
34
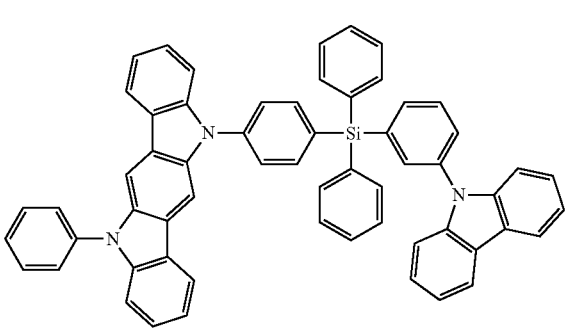
30
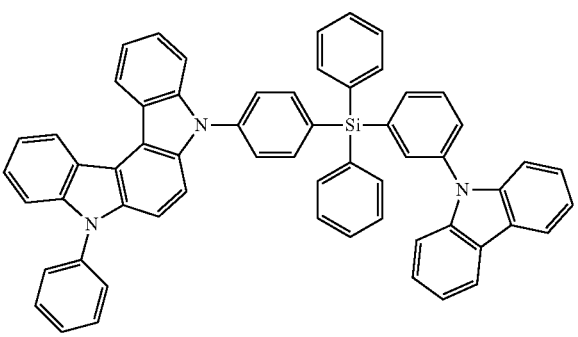
31
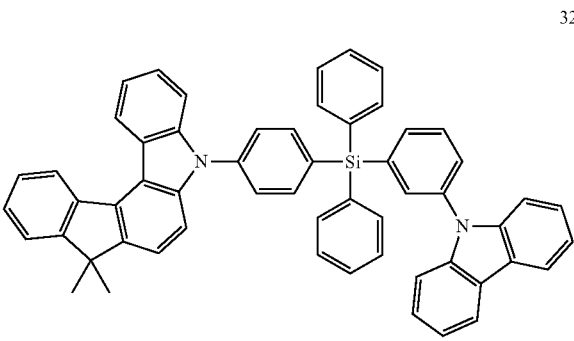
35
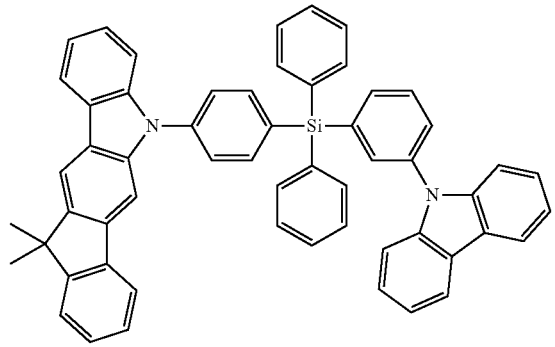
32
36

37
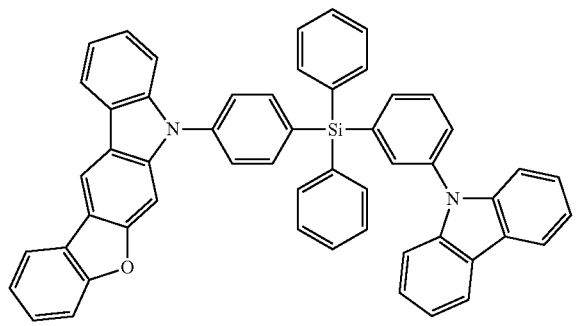
38
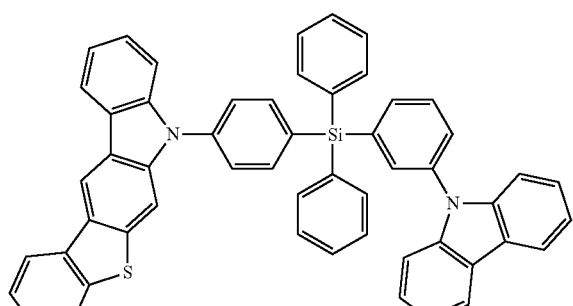
39
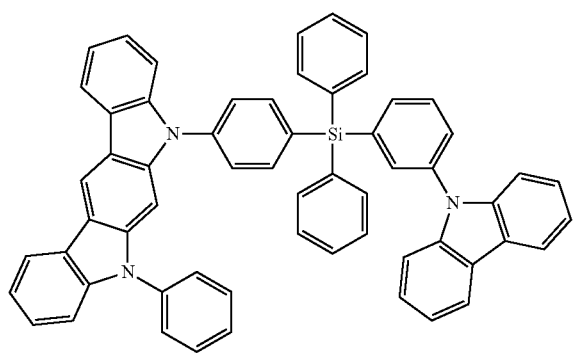
40
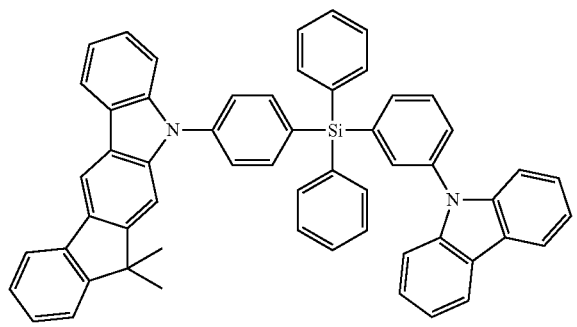
41
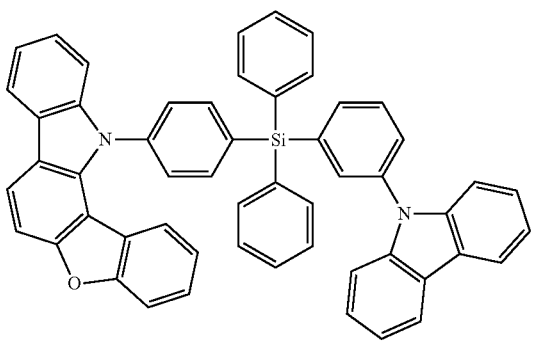
42
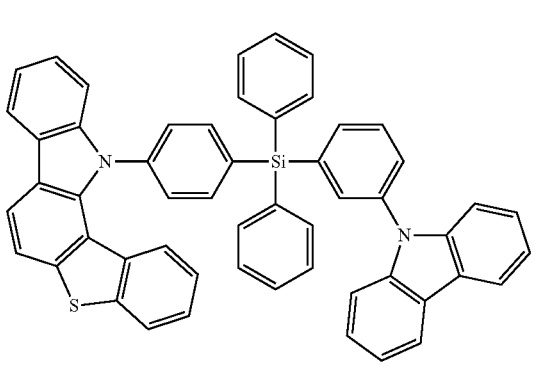
43
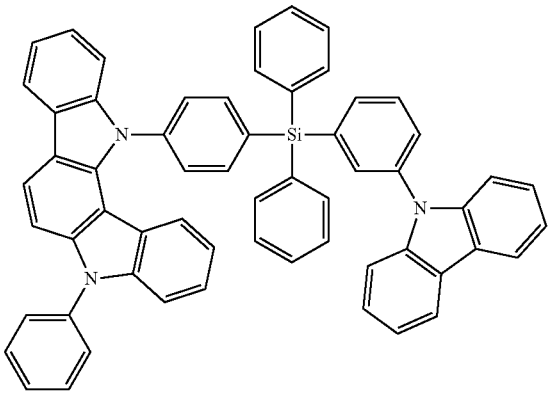
44
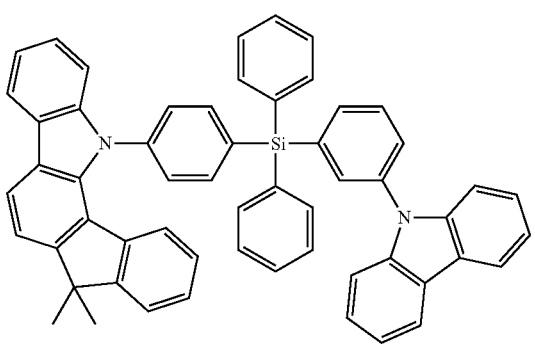

45
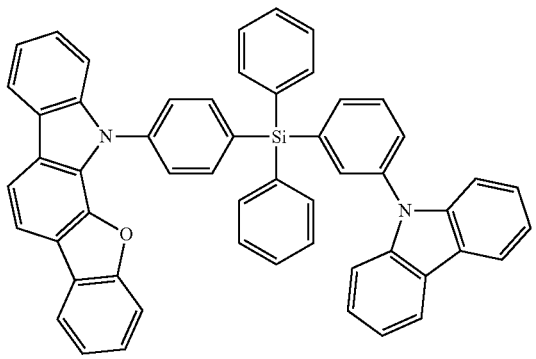
46
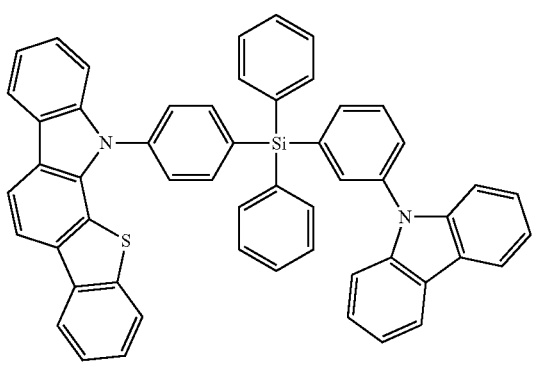
47
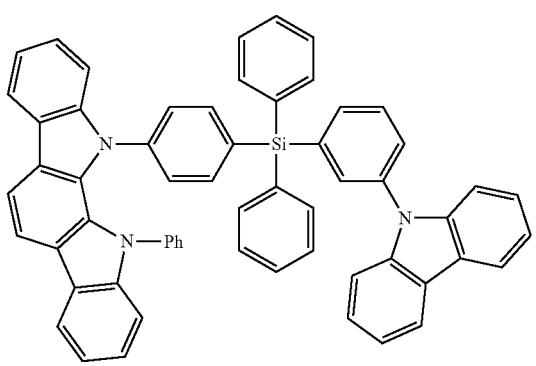
48
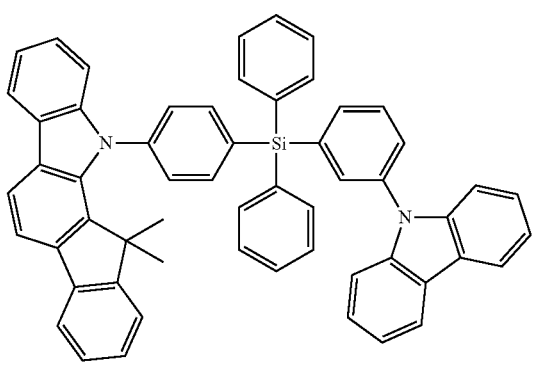
49
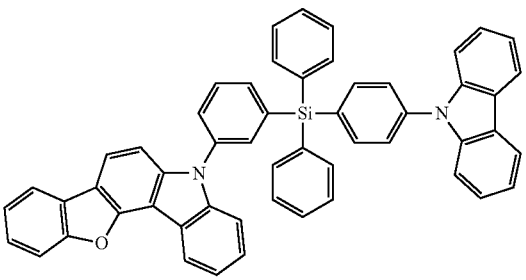
50
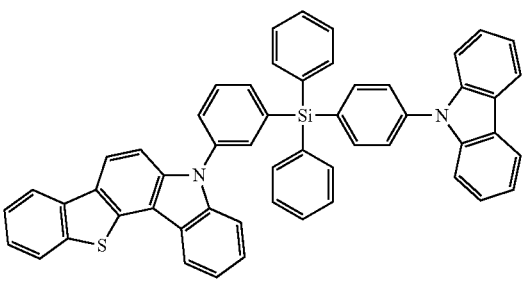
51
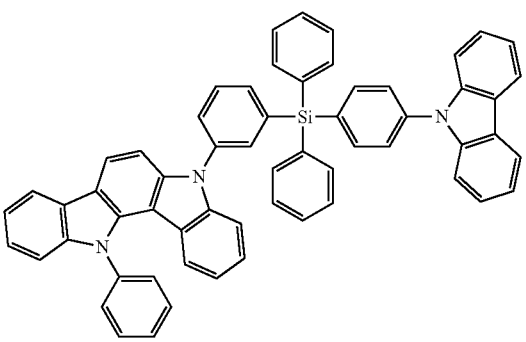
52
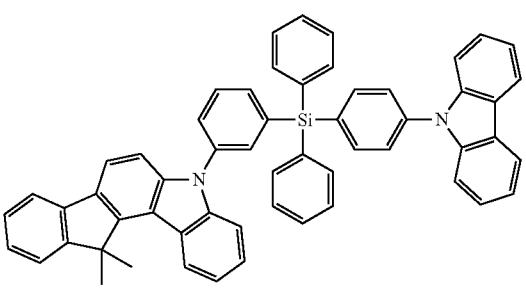
53
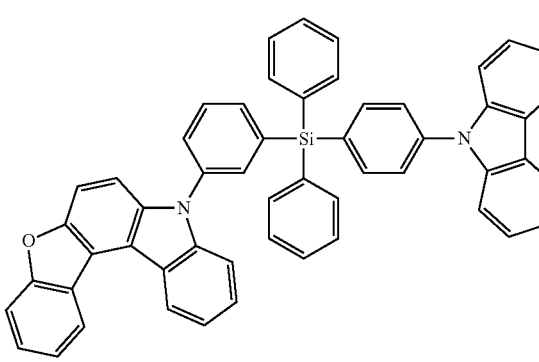

-continued
54
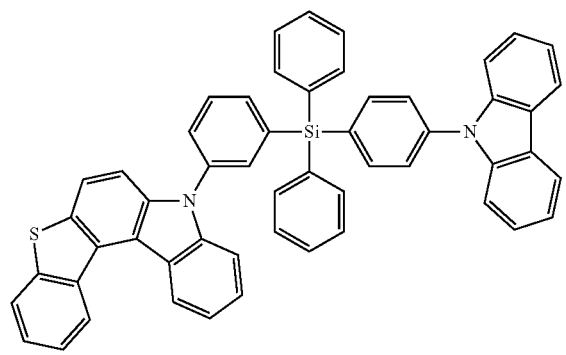
55
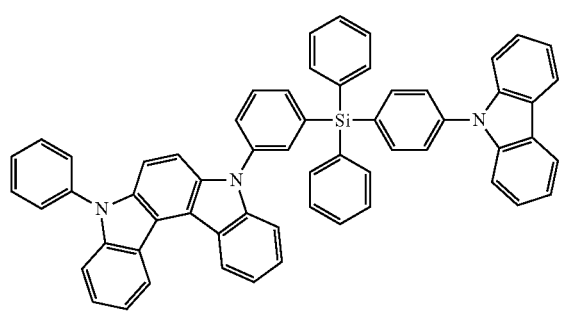
56
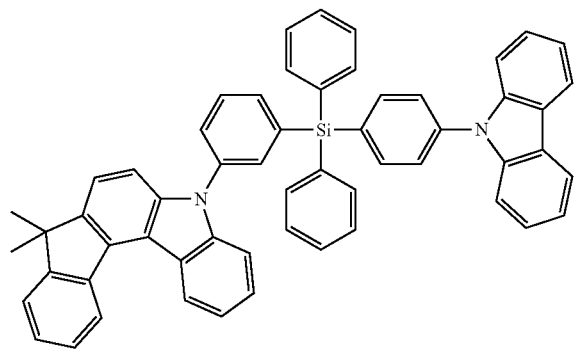
57
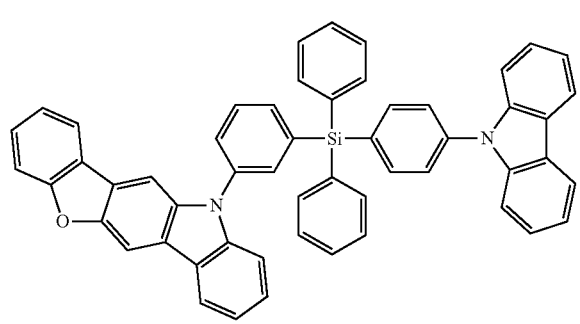
-continued
58
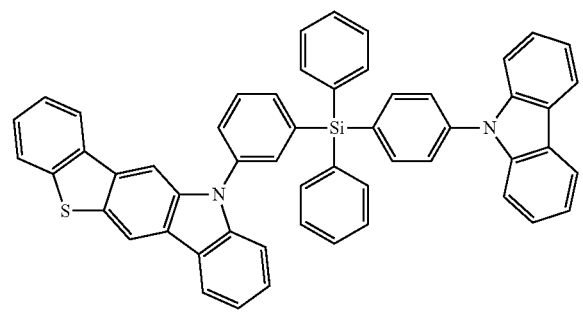
59
60
61
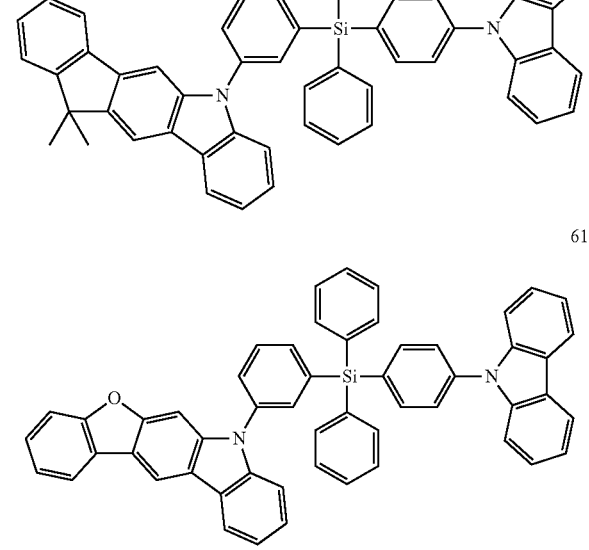
62
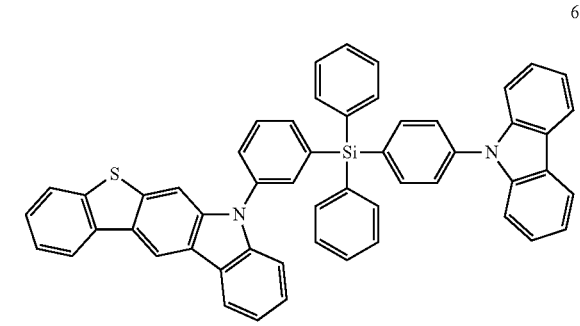

73
-continued
63
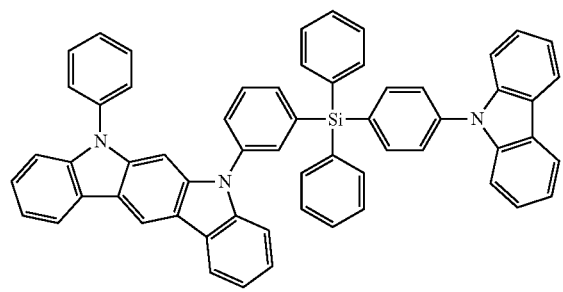
64
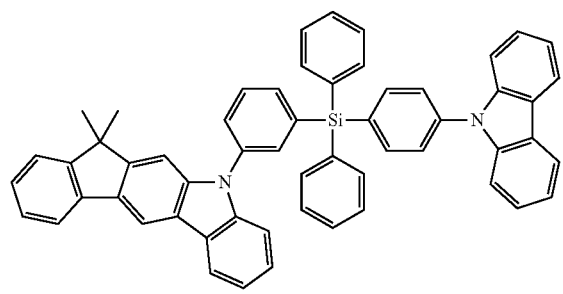
65
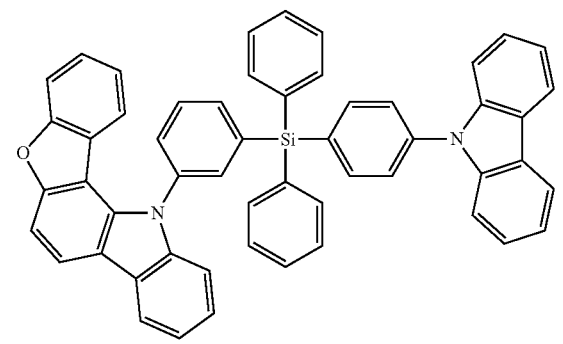
66
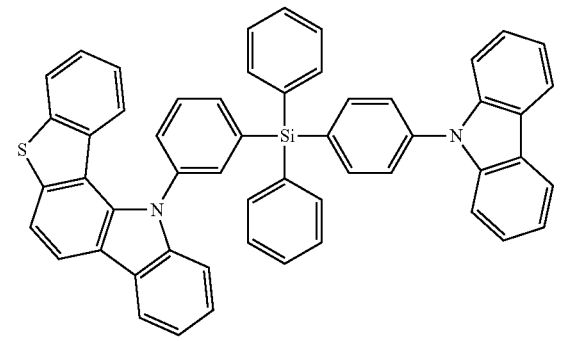
74
-continued
67
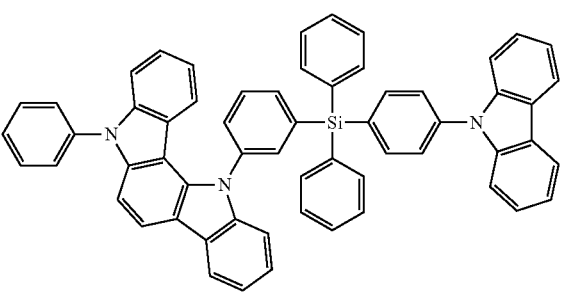
68
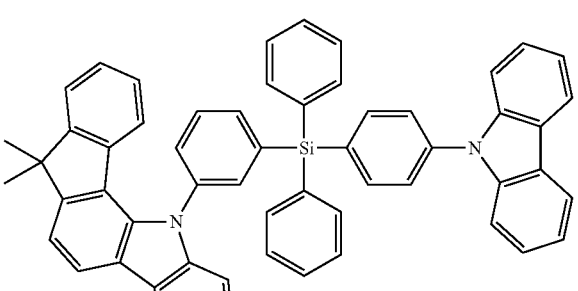
69
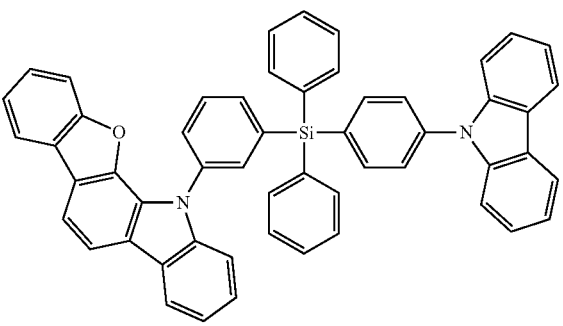
70
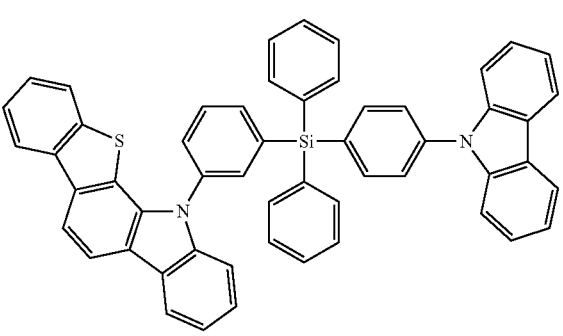

-continued

71

72

73

74

-continued

75

76

77

78

79
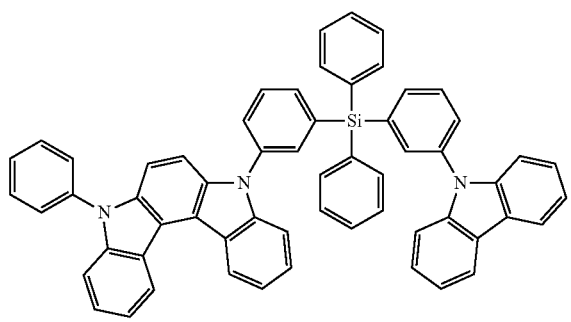
80
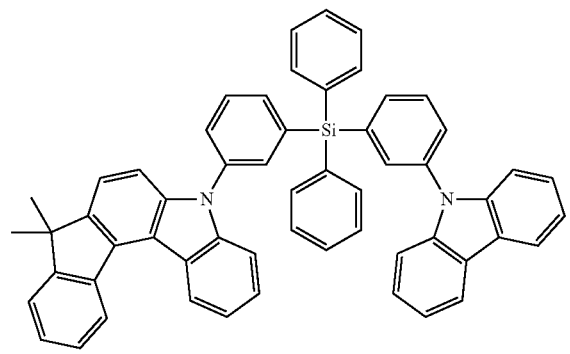
81
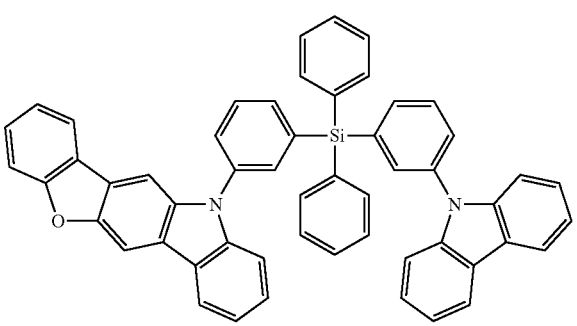
82
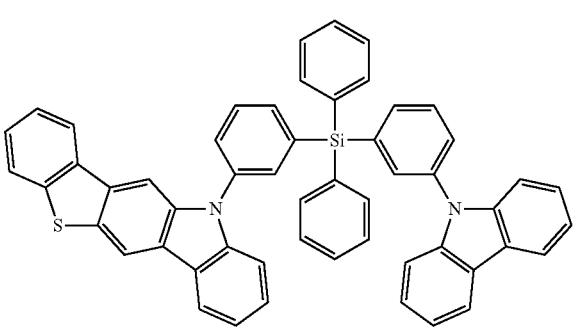
83
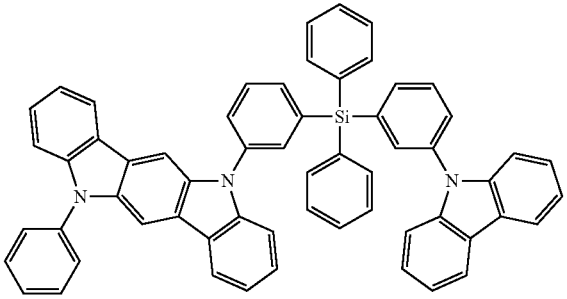
84
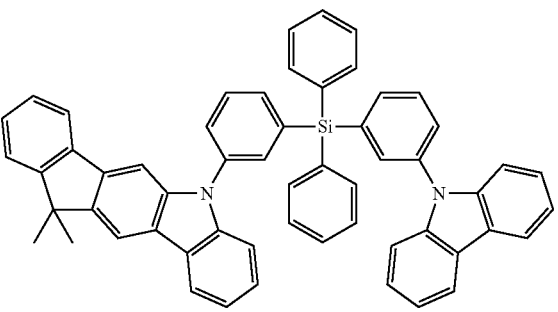
85
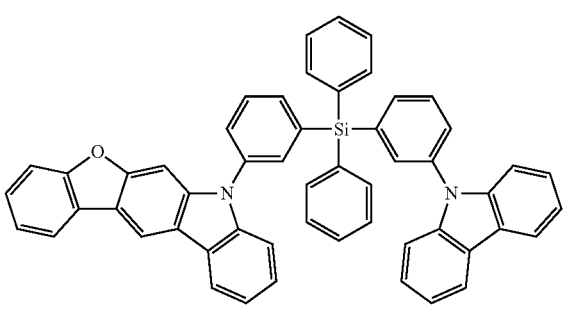
86
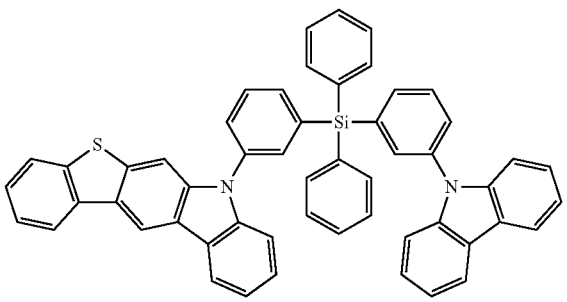
87
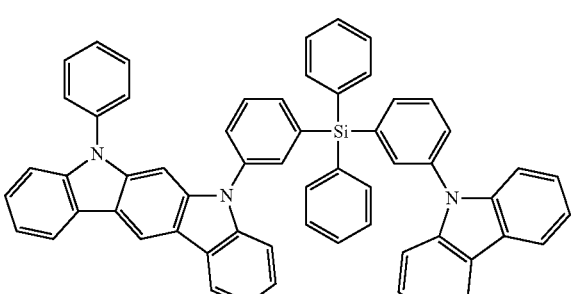

88
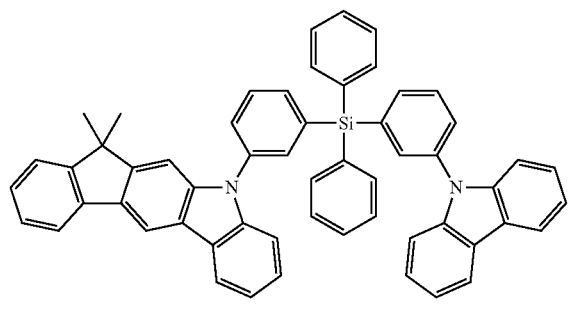
89
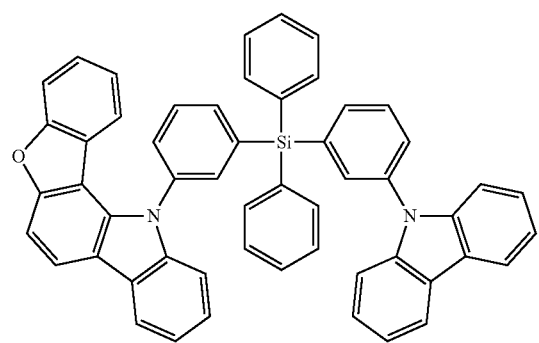
90
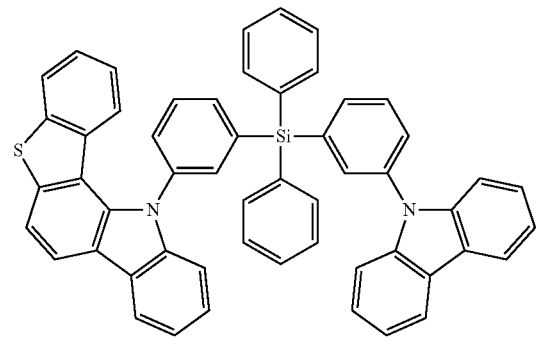
91
92
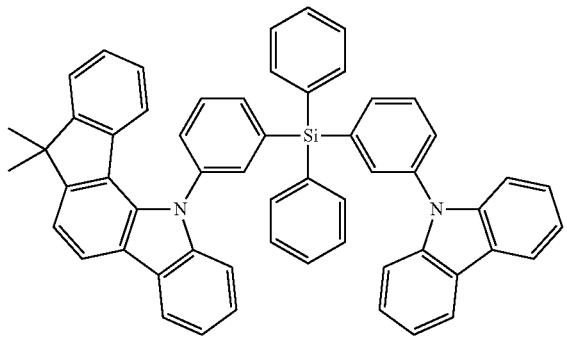
93
94
95
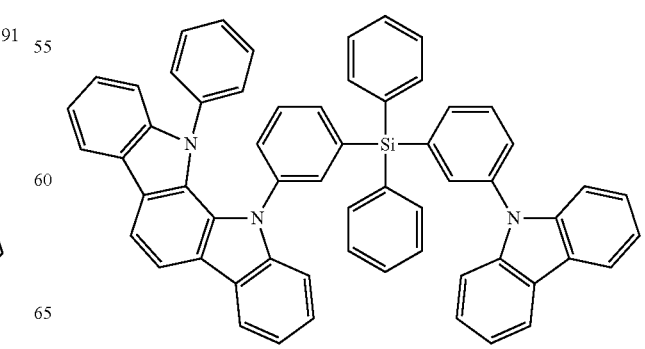

96
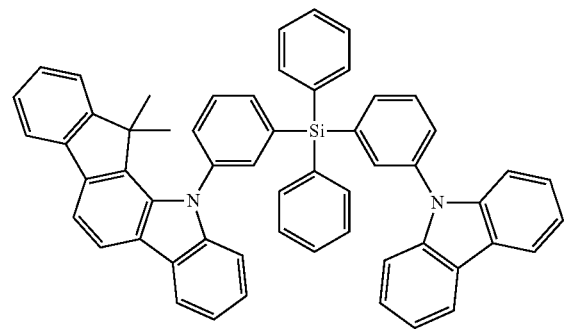
97
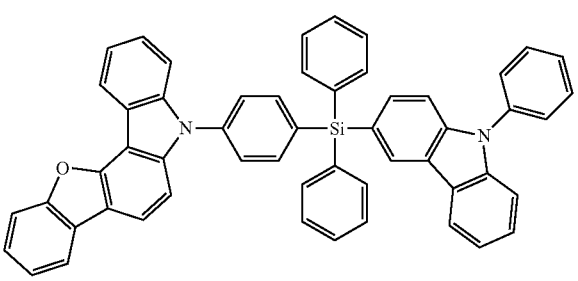
98
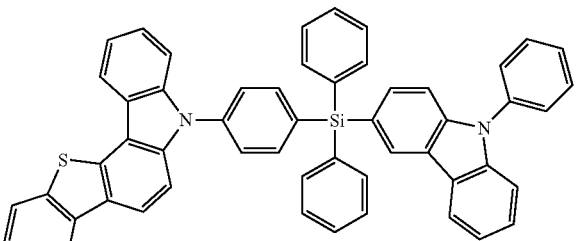
99
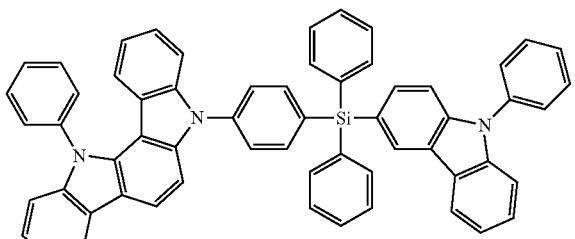
100
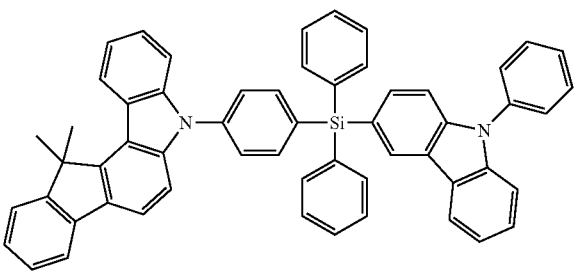
101
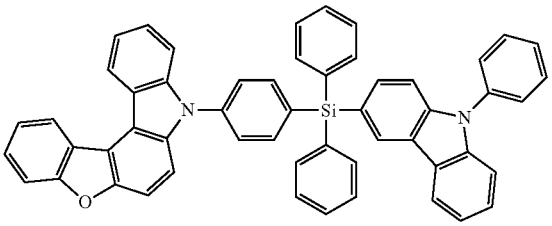
102
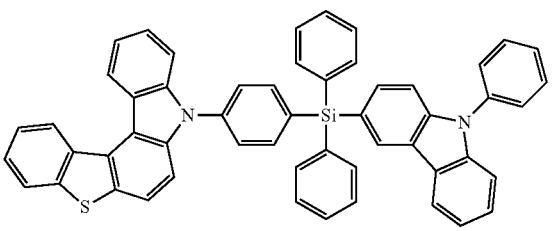
103
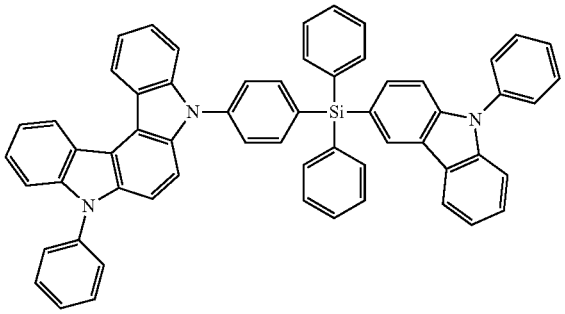
104
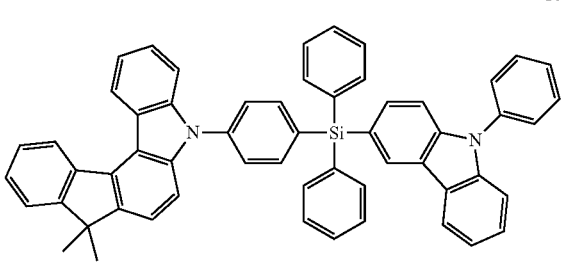
105
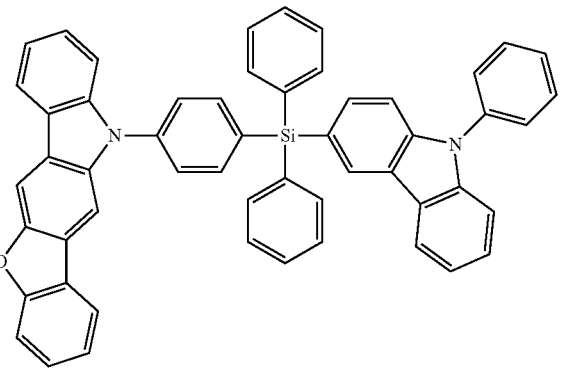

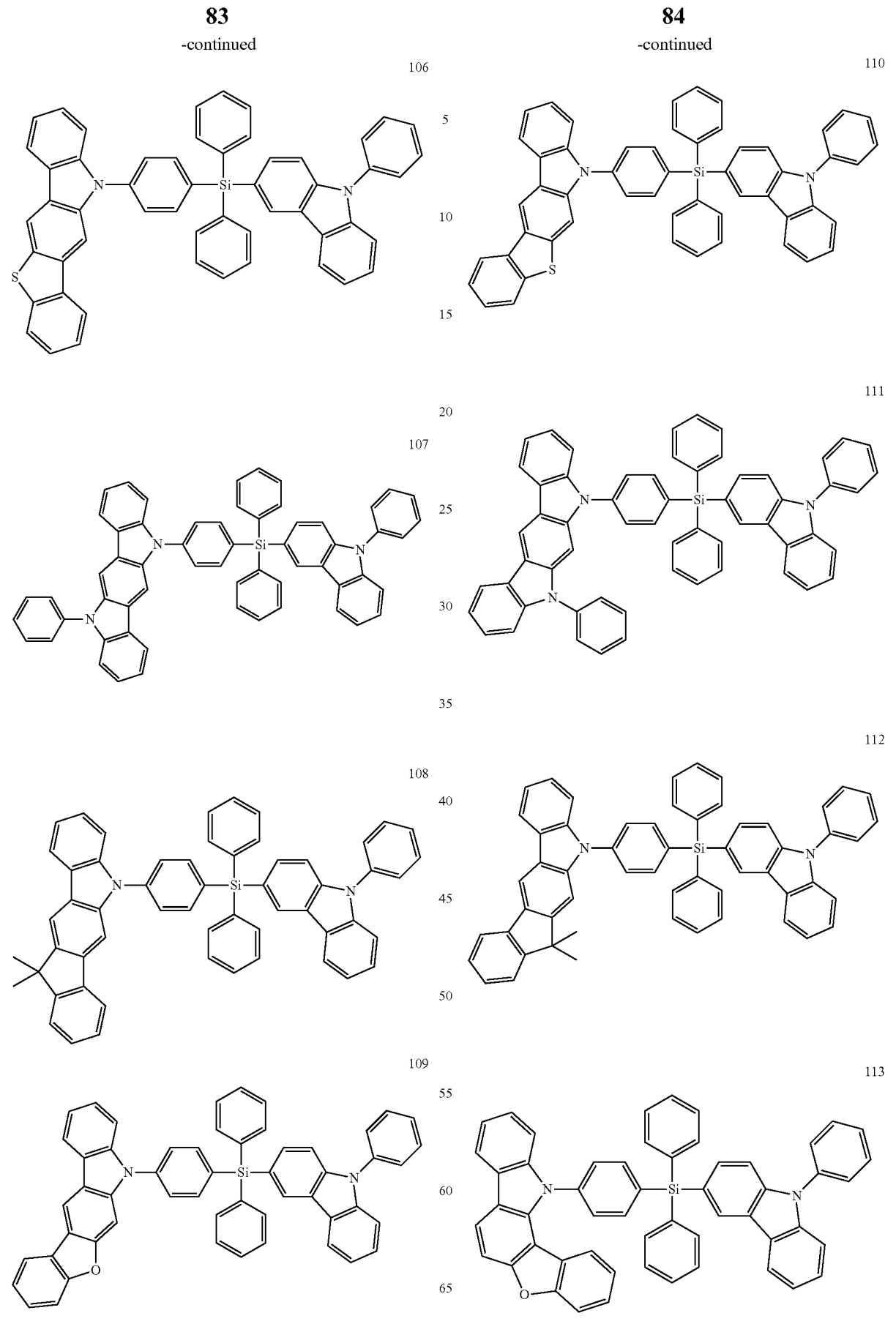

-continued

114
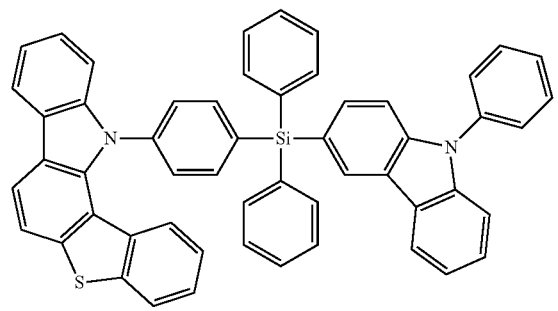
115
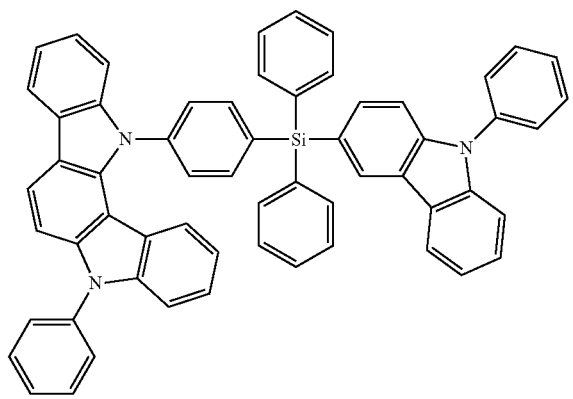
116
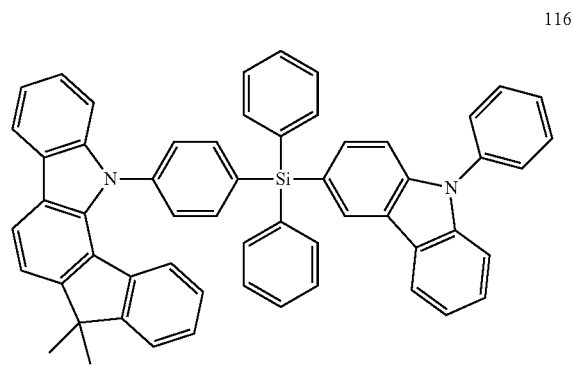
117
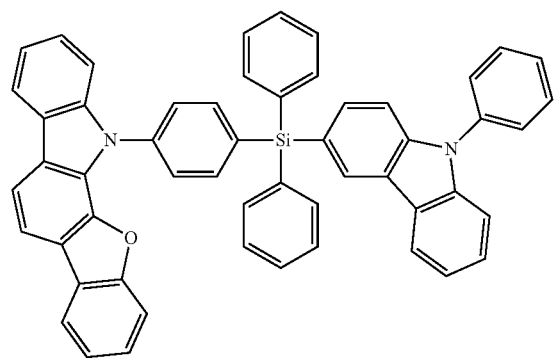
118
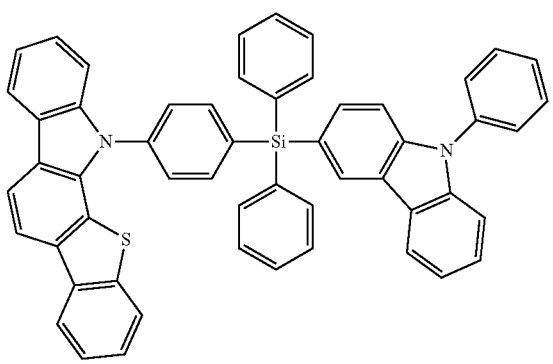
119
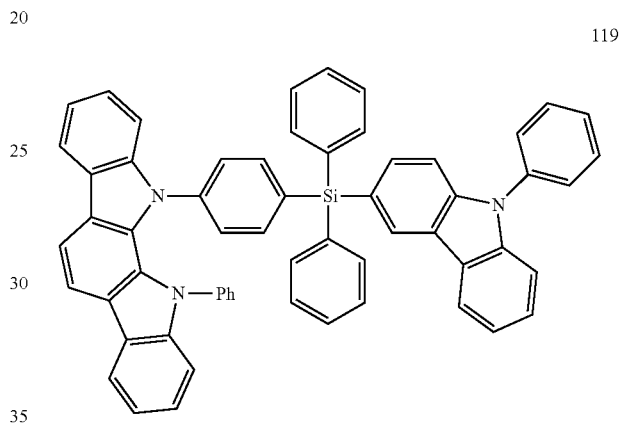
120
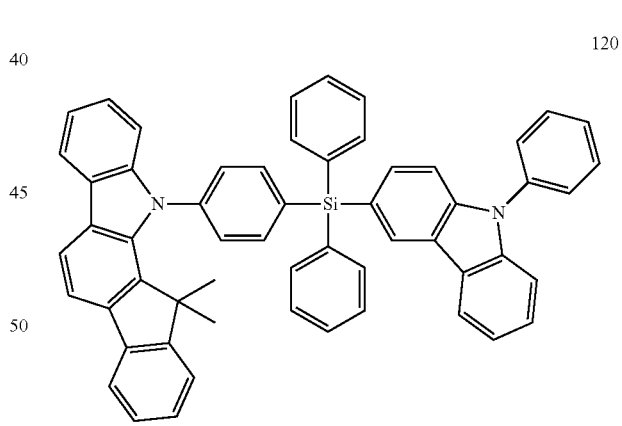
121
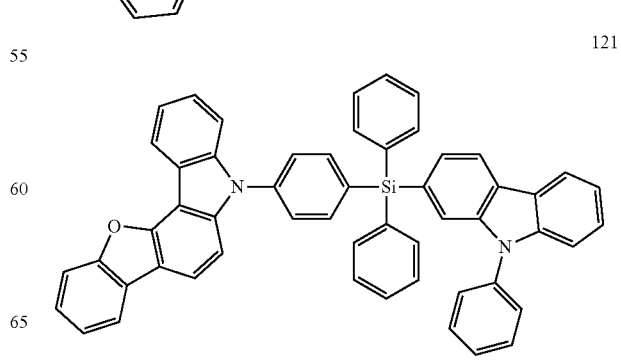

122
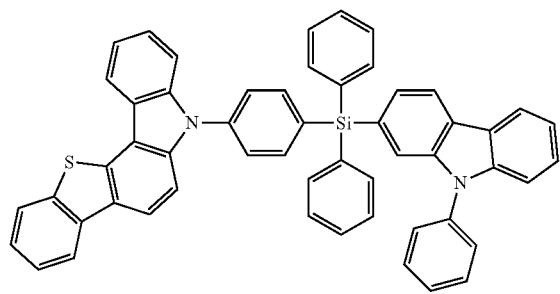
123
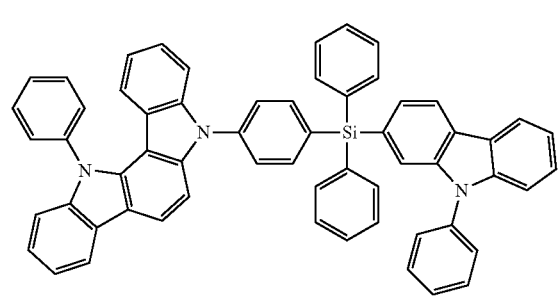
124
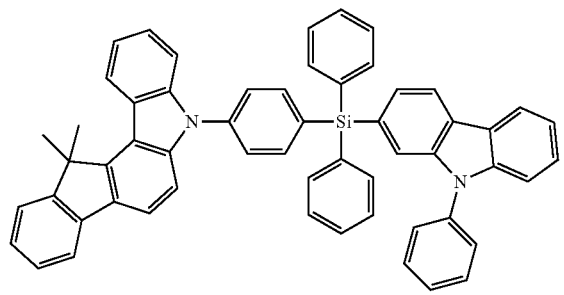
125
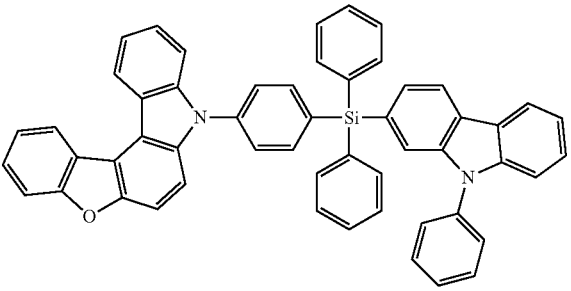
126
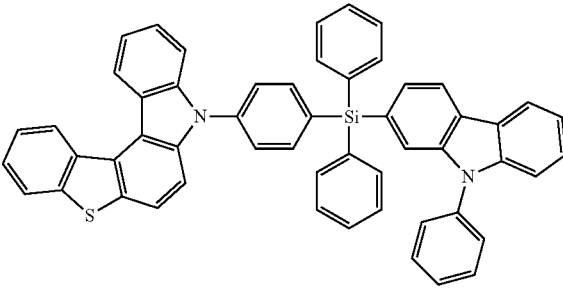
127
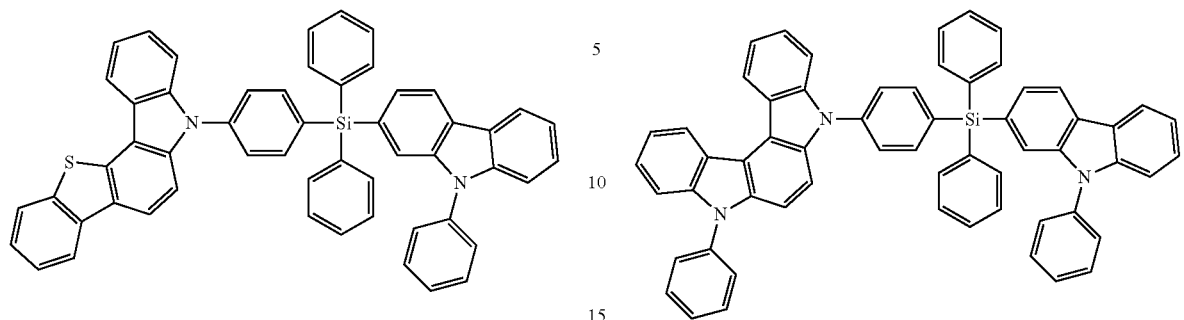
128
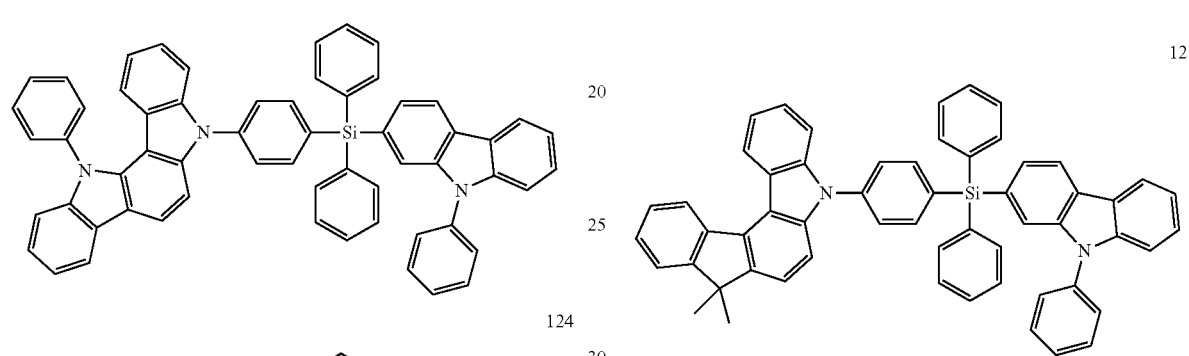
129
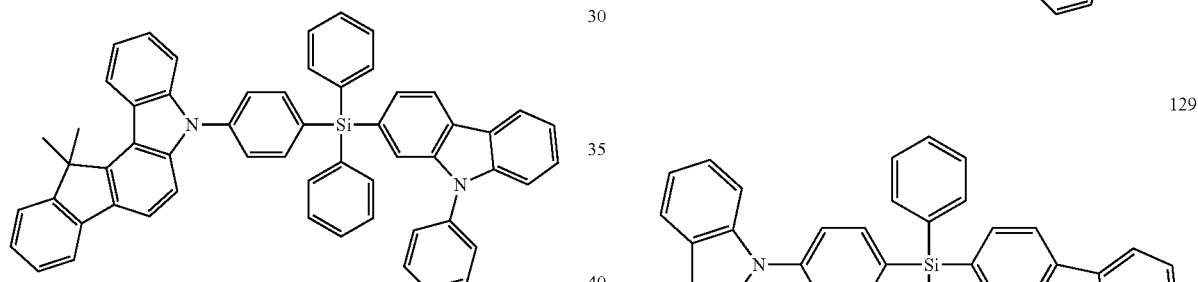
130
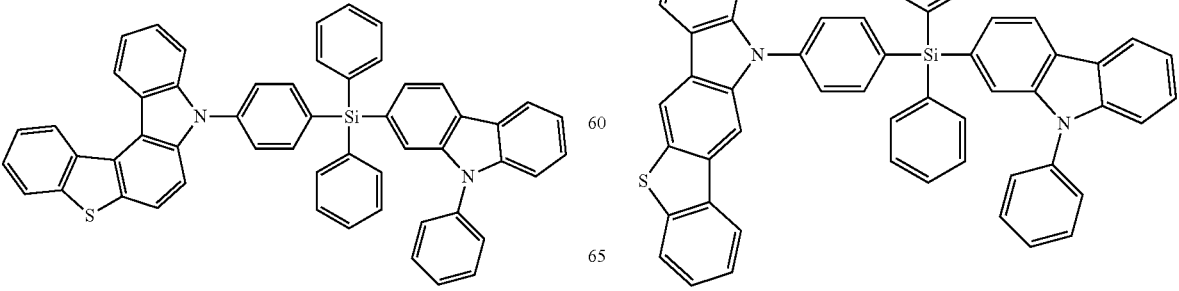

131
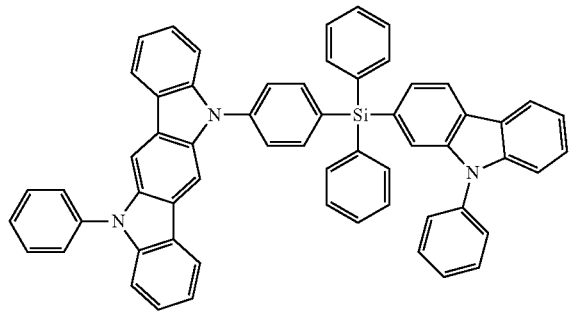
135
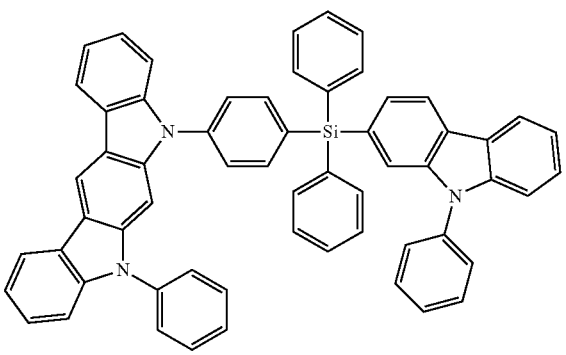
132
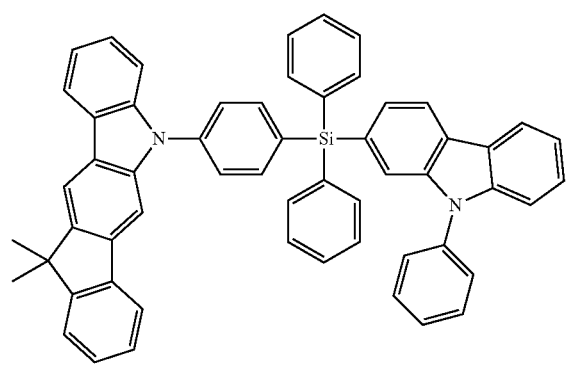
136
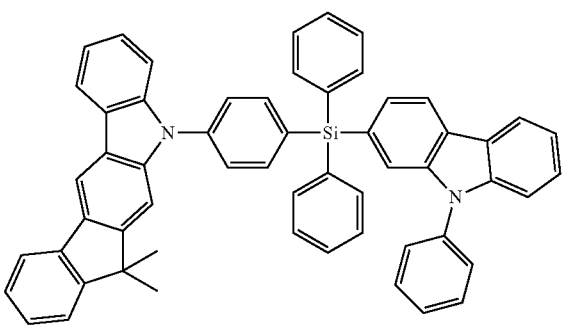
133
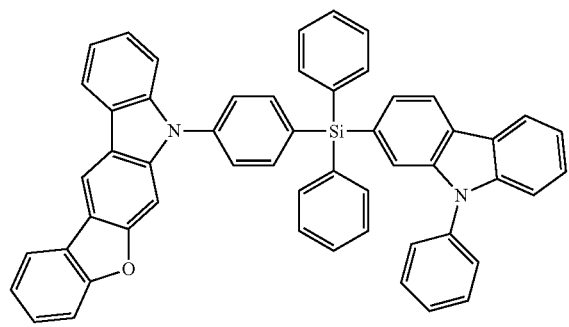
137
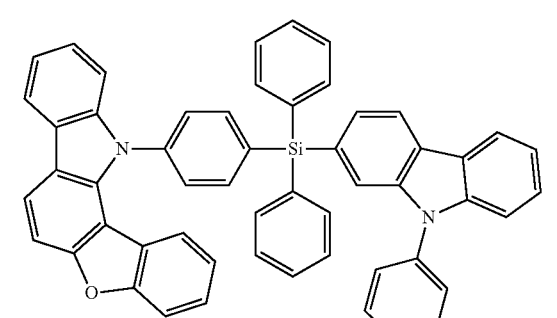
134
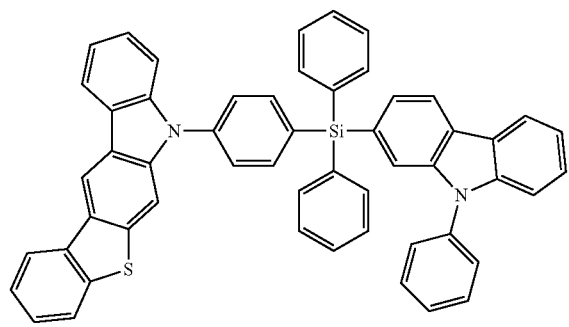
138
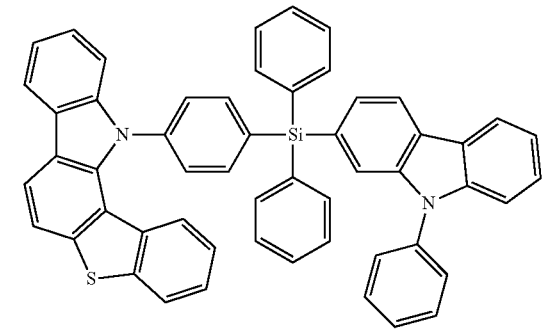

-continued
139
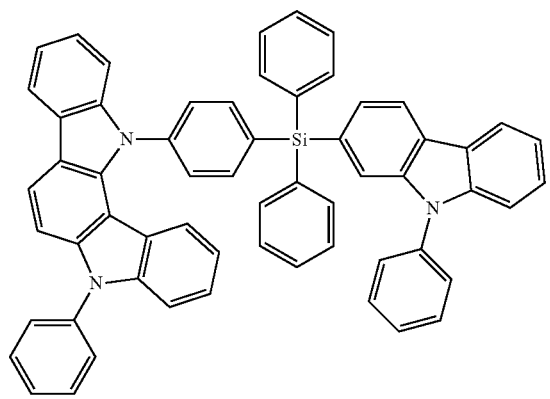
140
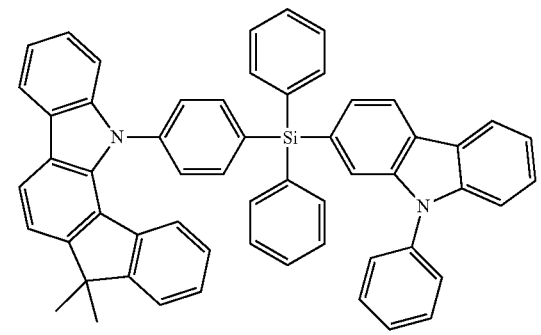
141
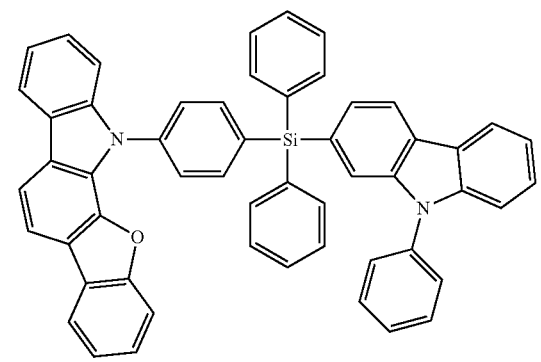
142
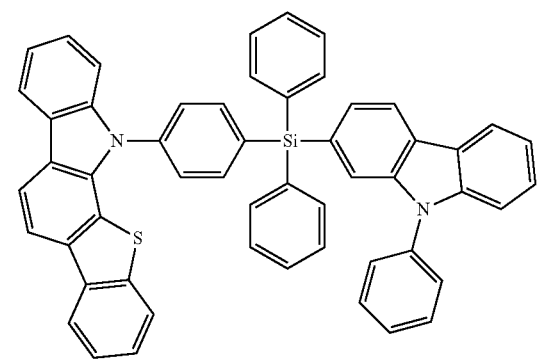
-continued
143
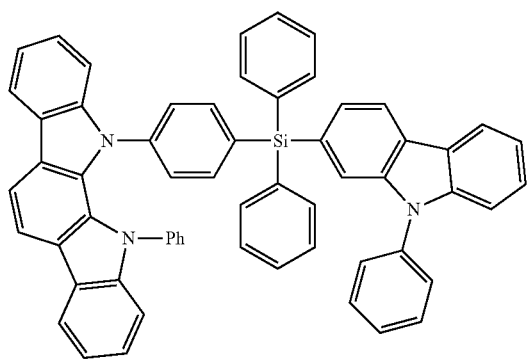
144
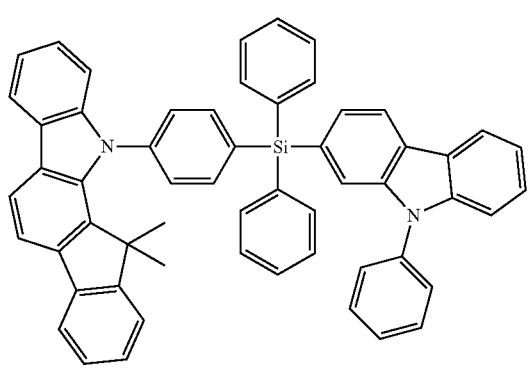
145
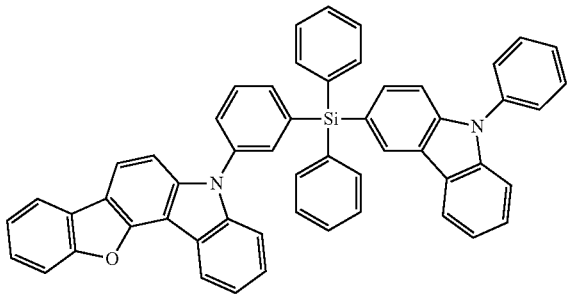
146
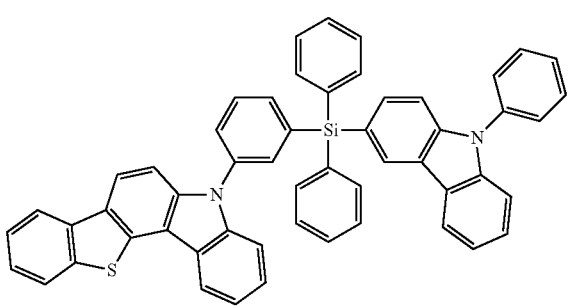

147
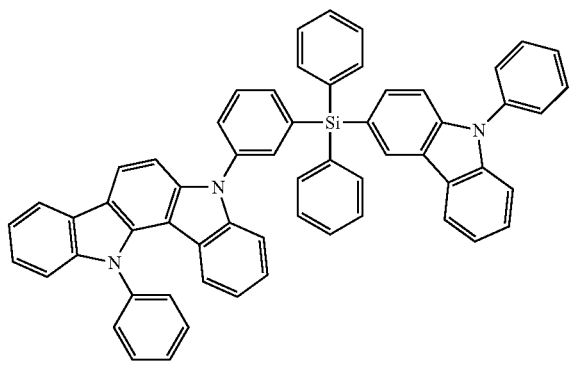
148
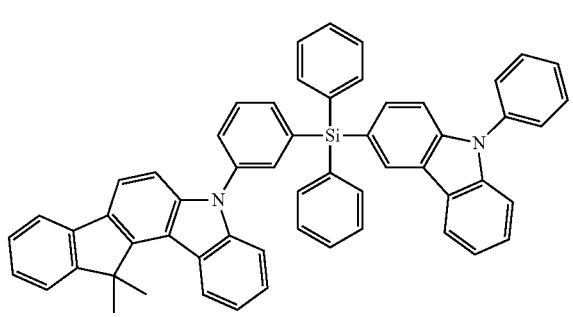
149
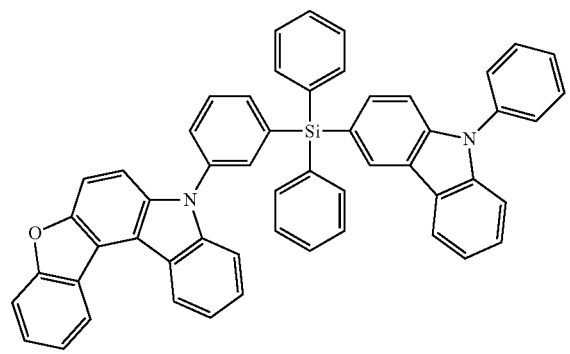
150
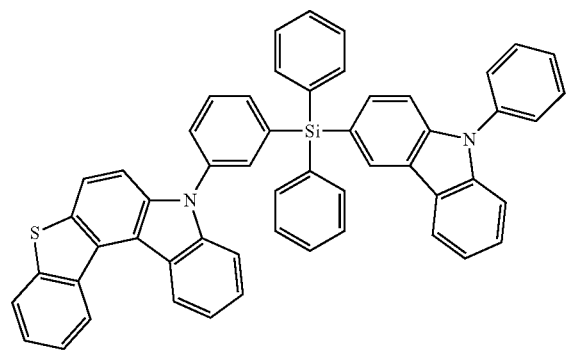
151
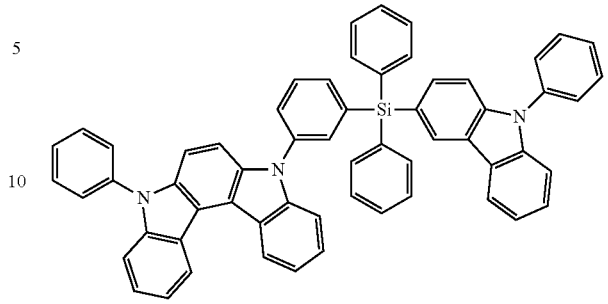
152
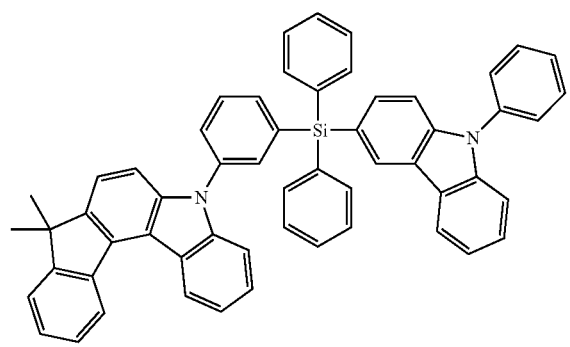
153
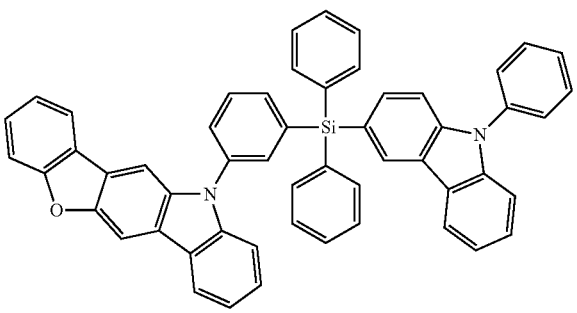
154
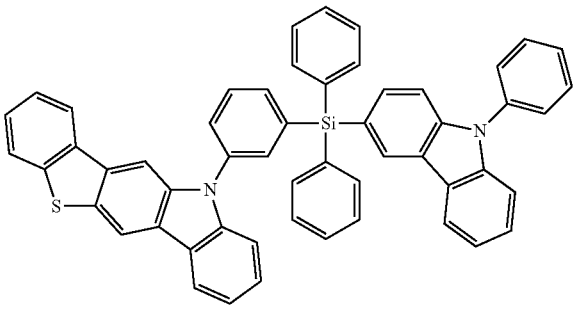

155
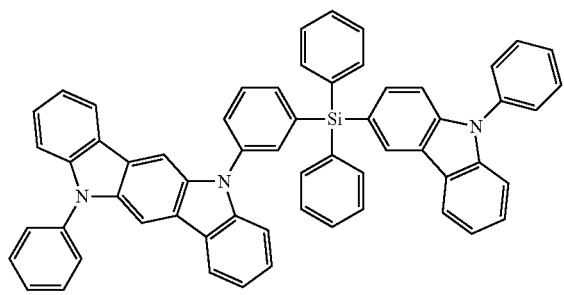
156
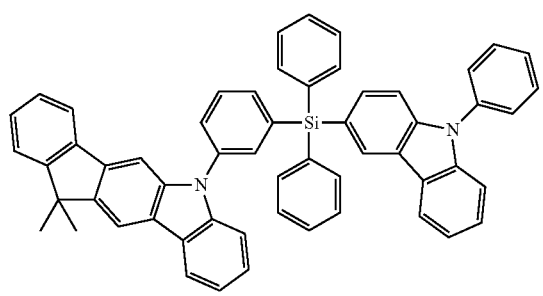
157
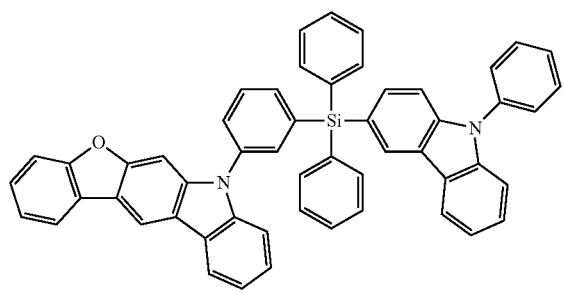
158
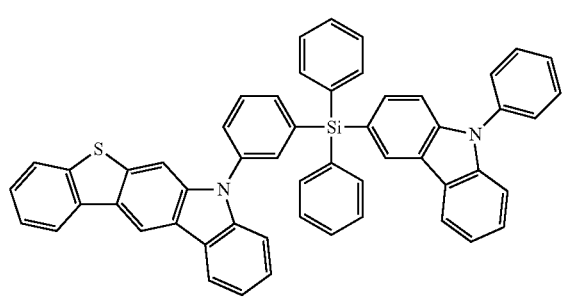
159
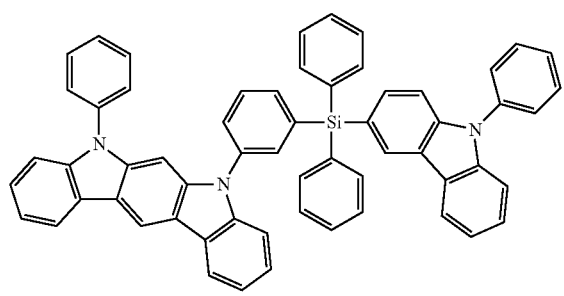
160
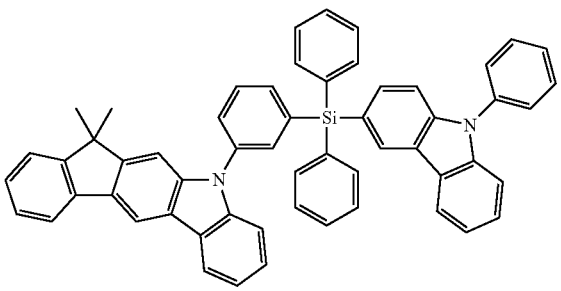
161
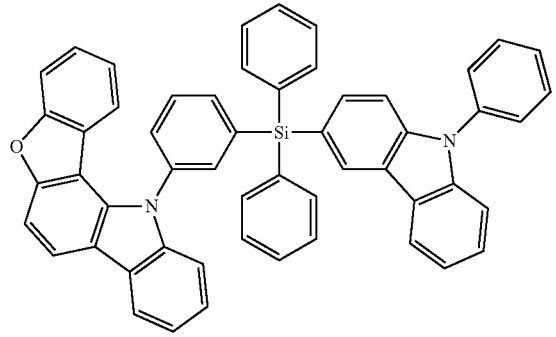
162
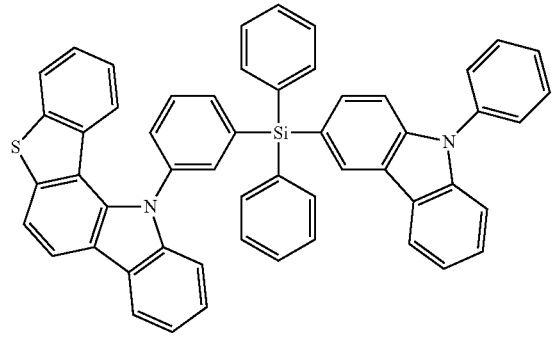
163
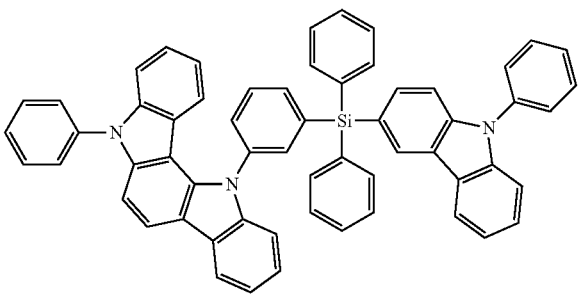

164
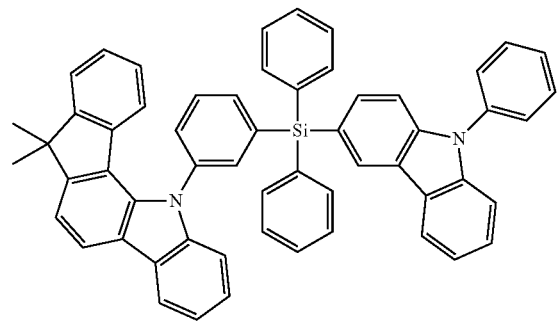
165
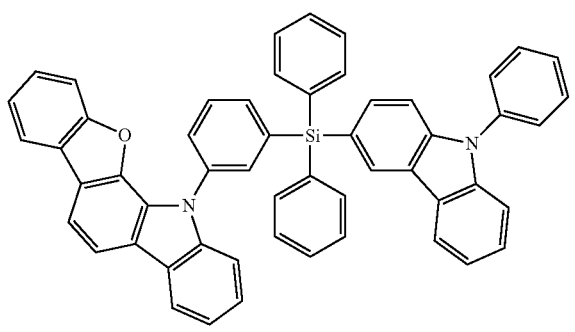
166
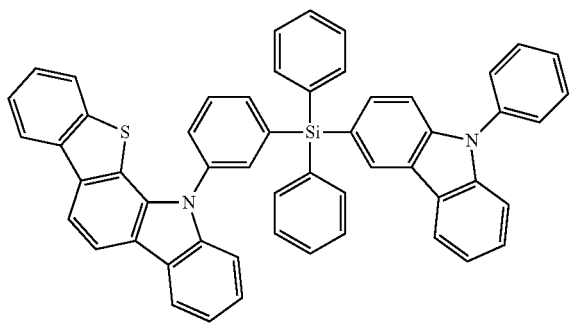
167
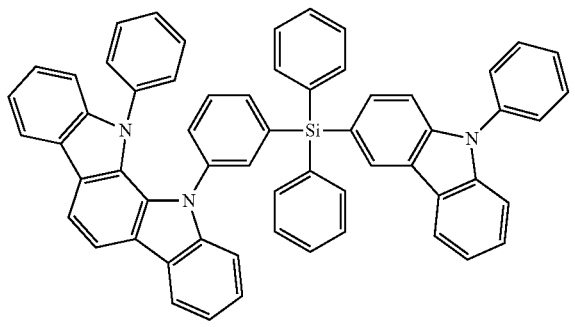
168
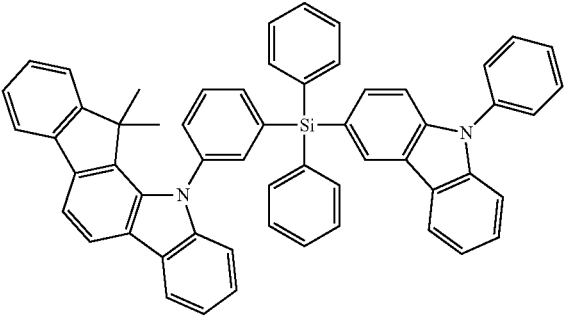
169
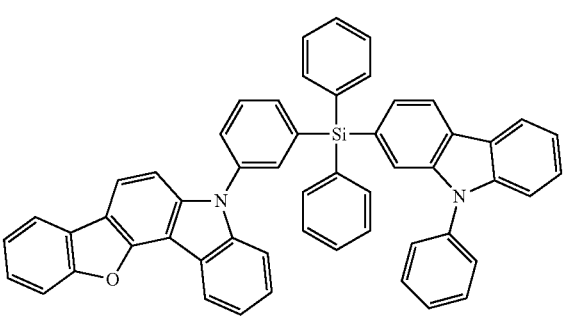
170
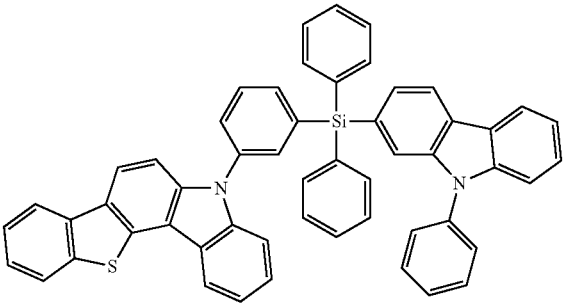
171
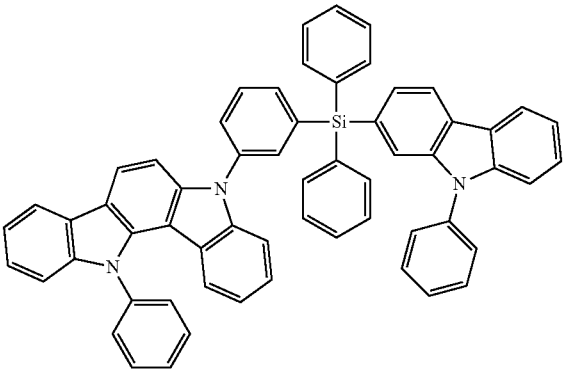

172
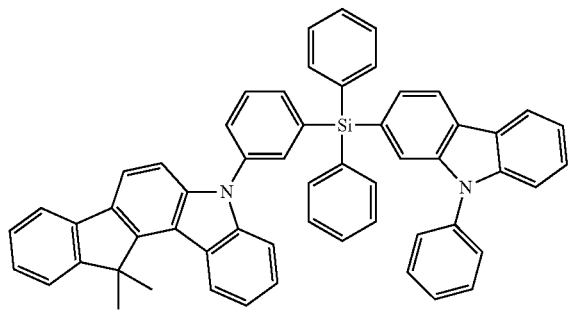
173
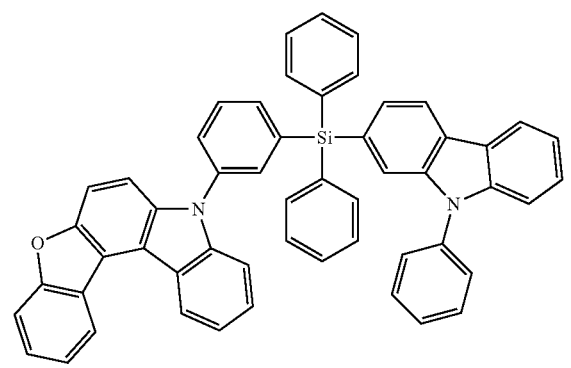
174
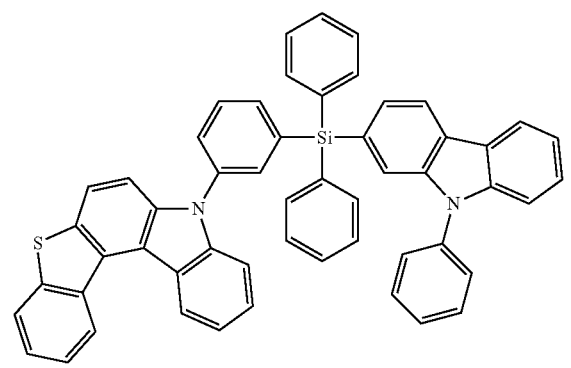
175
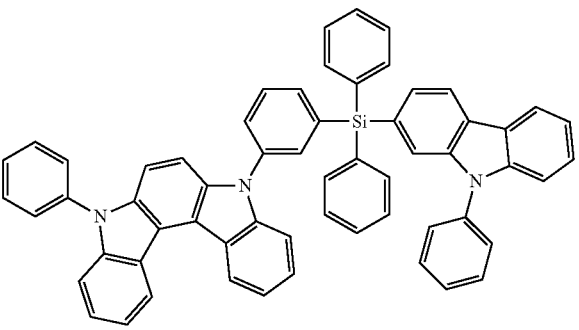
176
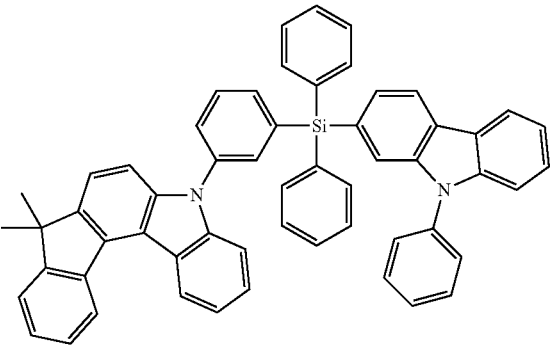
177
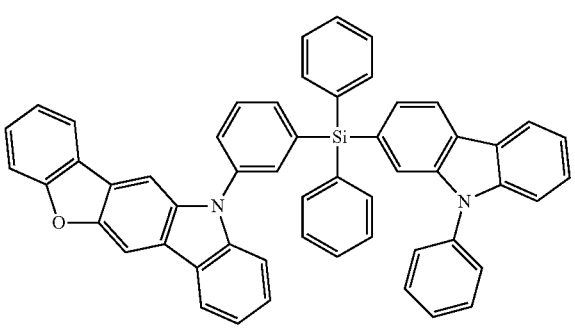
178
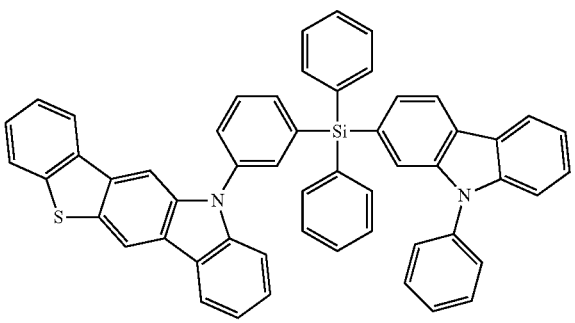
179
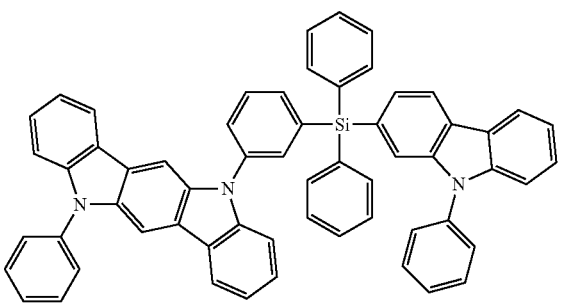

180
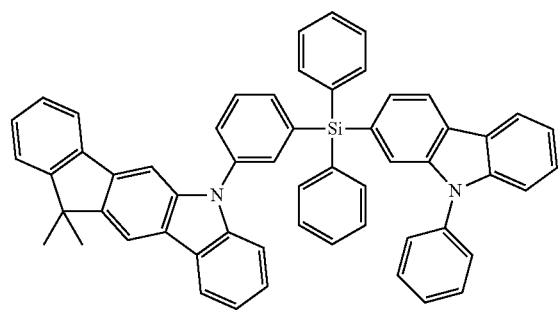
181
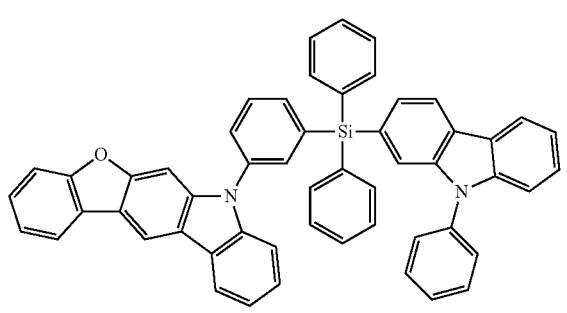
182
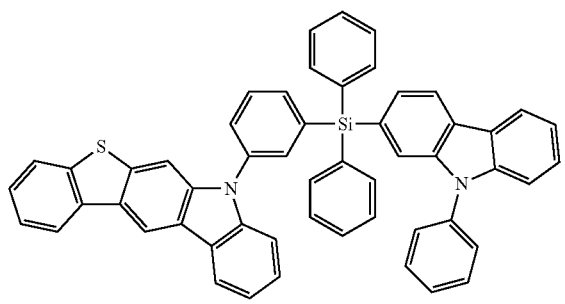
183
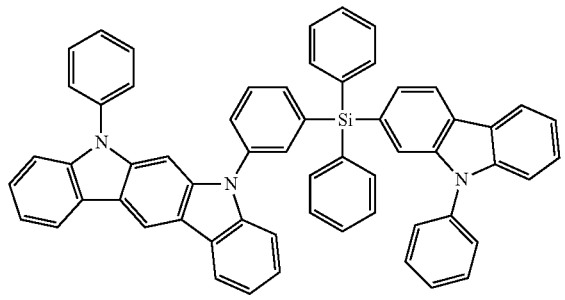
184
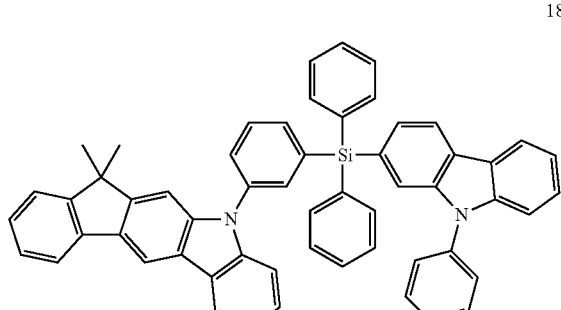
185
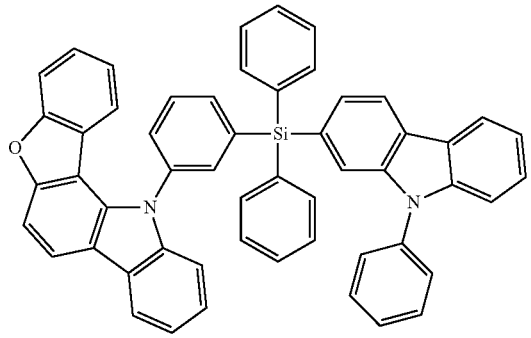
186
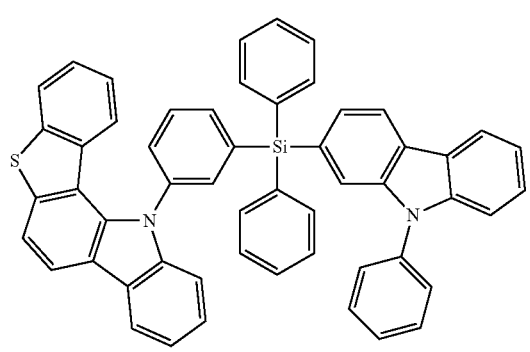
187
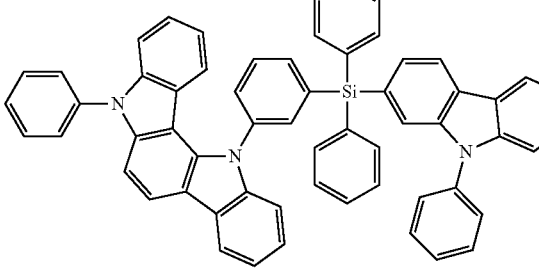
188
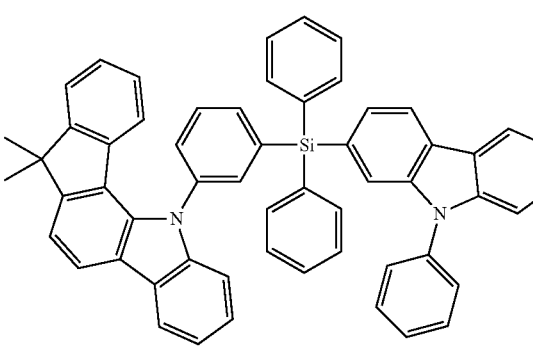

189
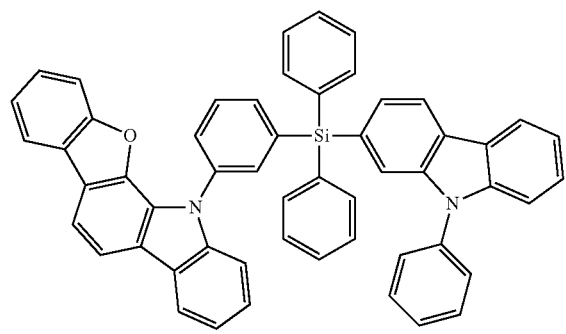
193
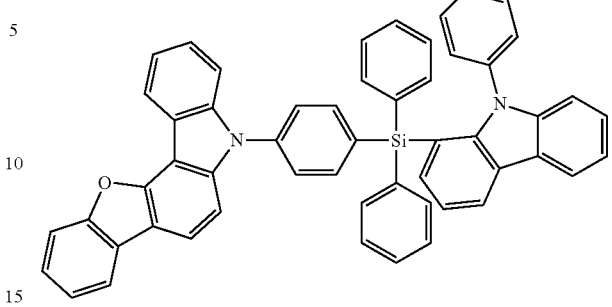
190
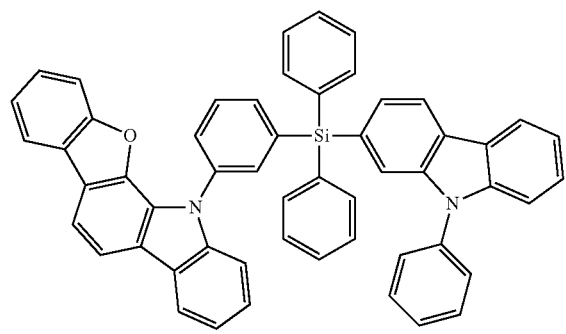
194
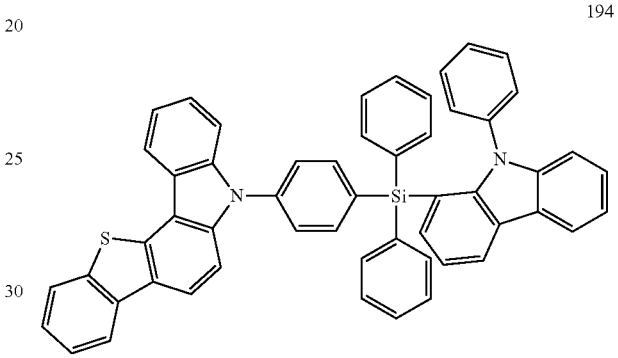
191
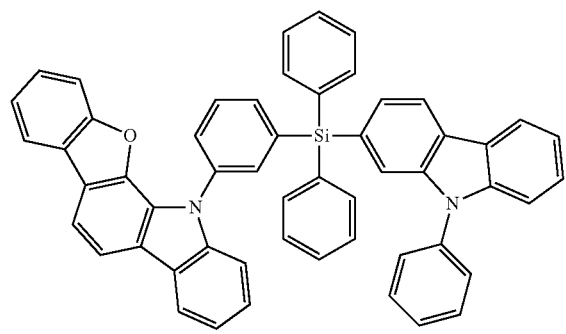
195
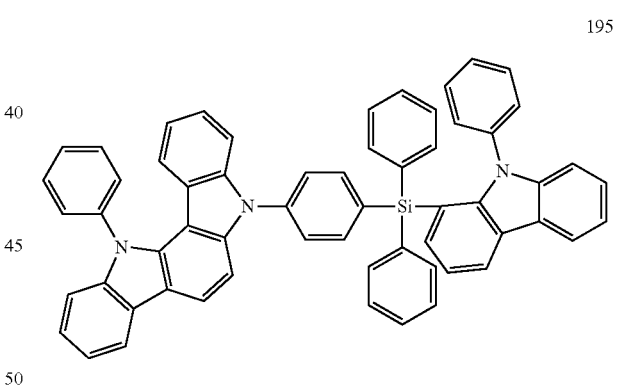
192
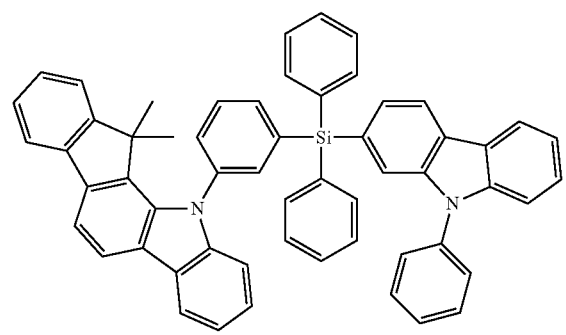
196
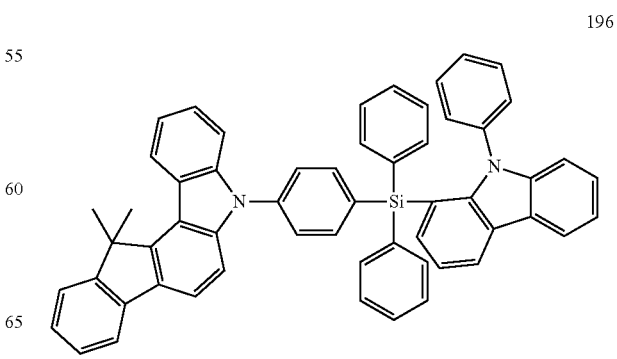

105
-continued
197
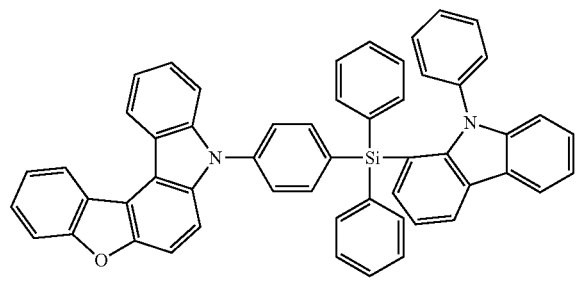
198
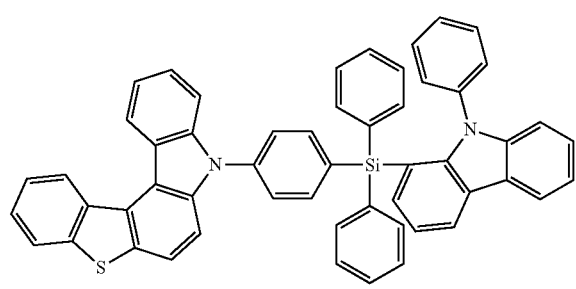
199
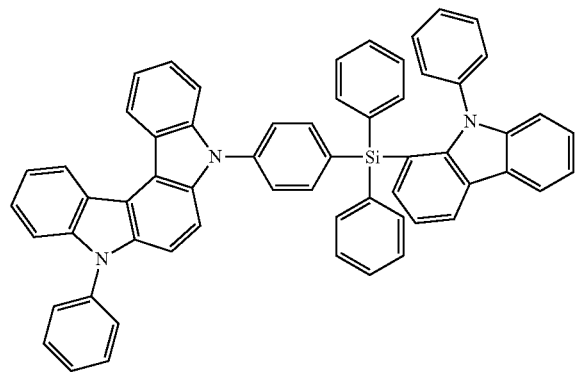
106
-continued
201
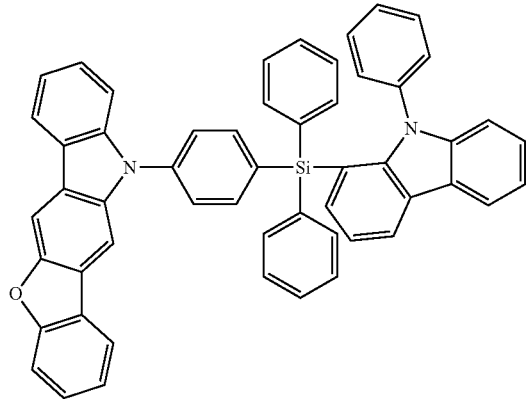
202
203
204
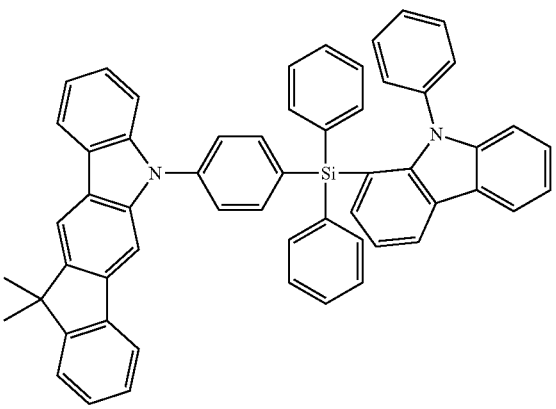
200

205
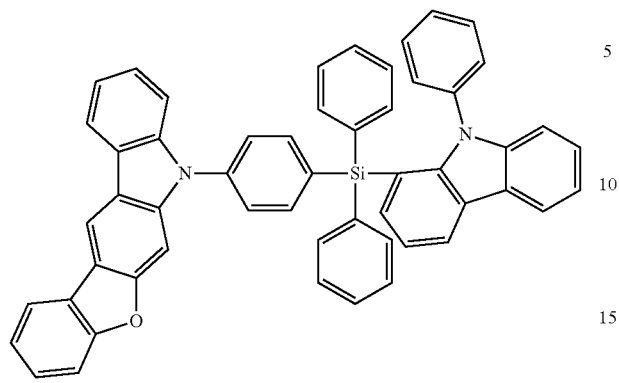
206
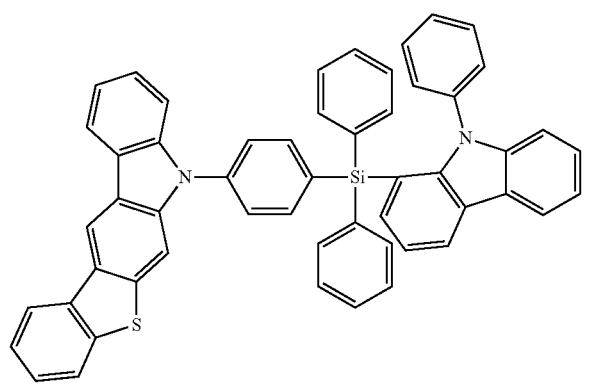
207
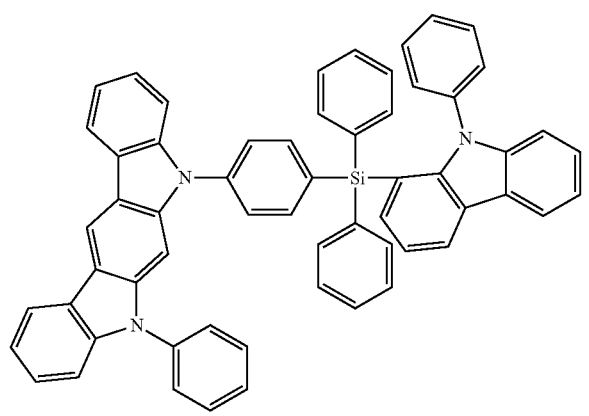
208
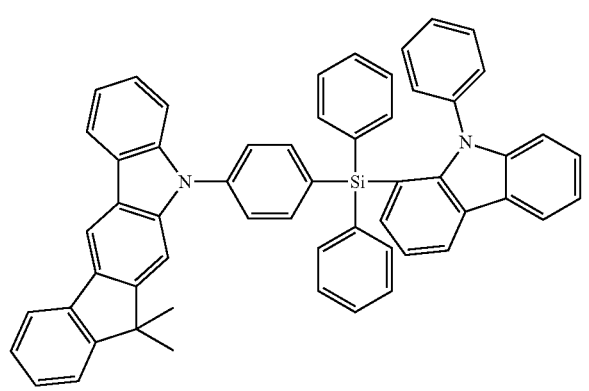
209
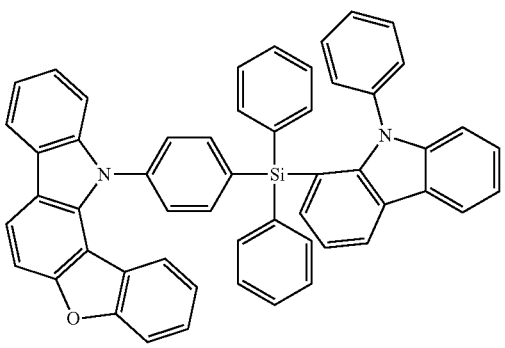
210
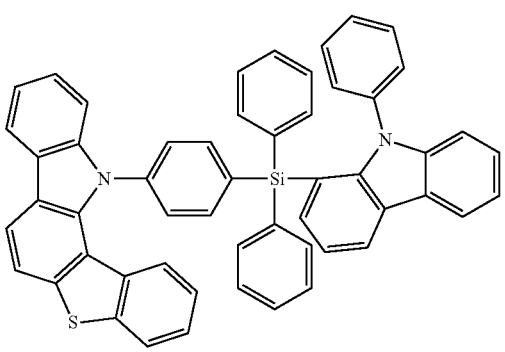
211
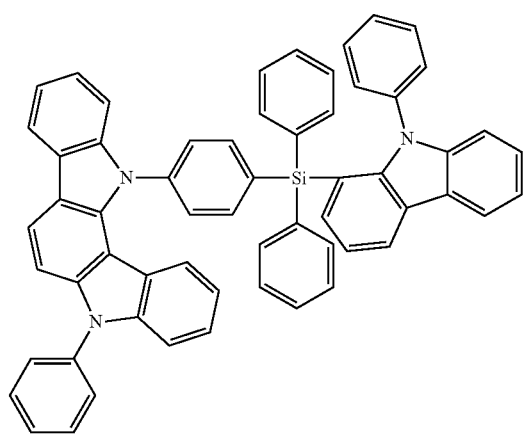
212
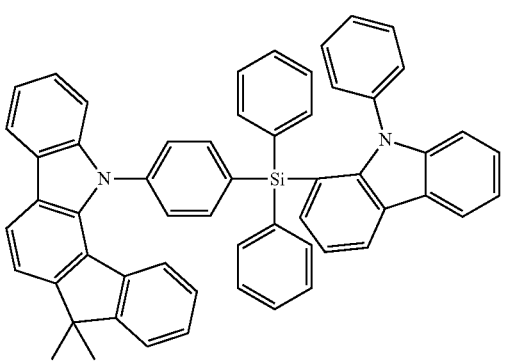

213
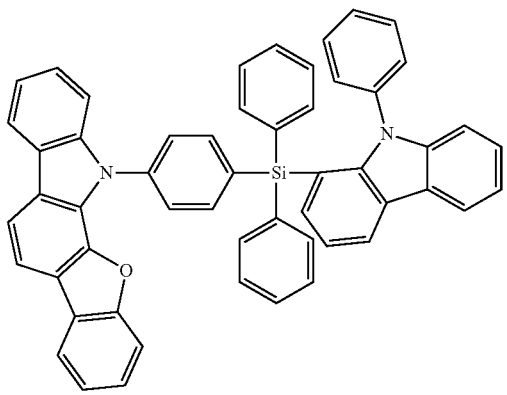
214
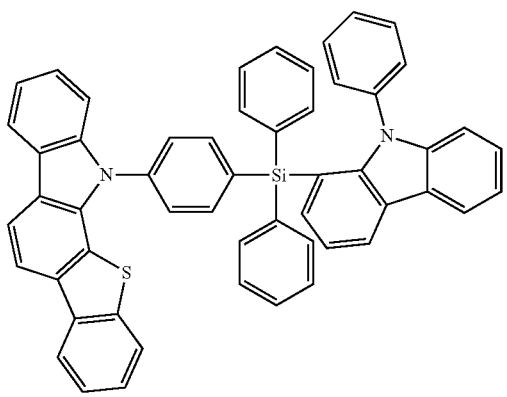
215
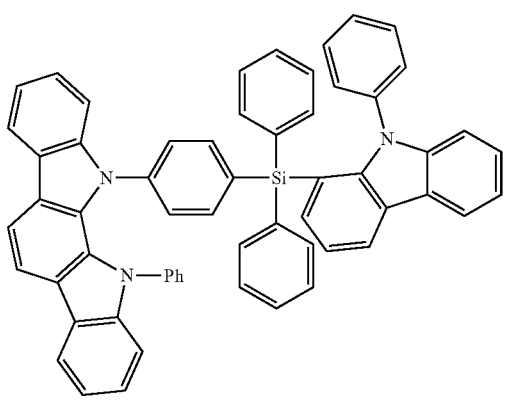
216
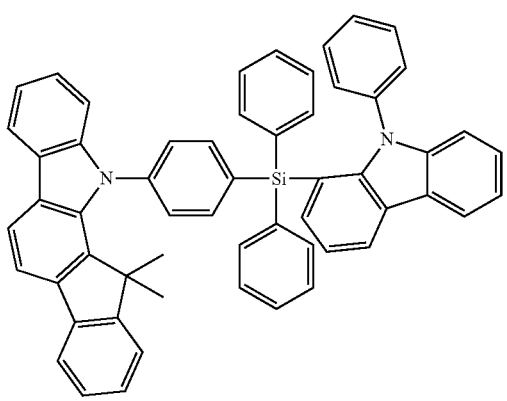
217
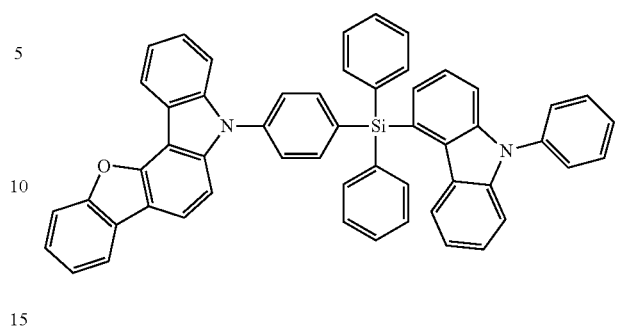
218
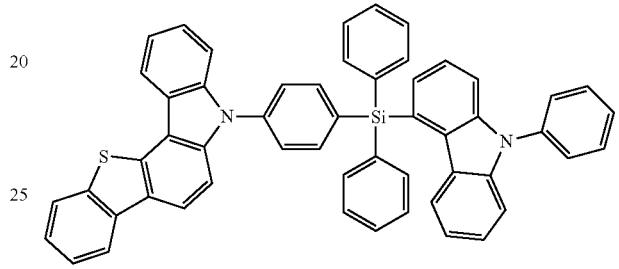
219
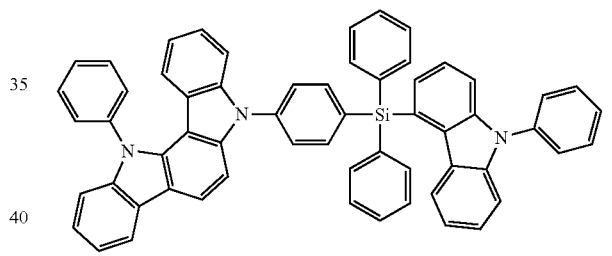
220
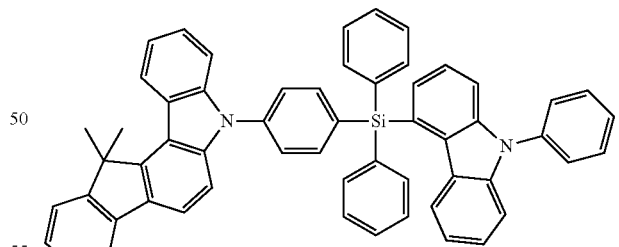
221
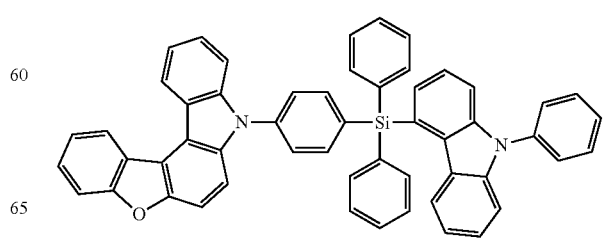

-continued
222
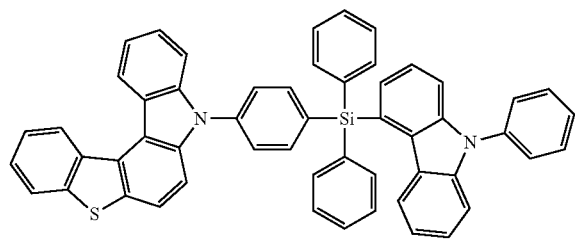
223
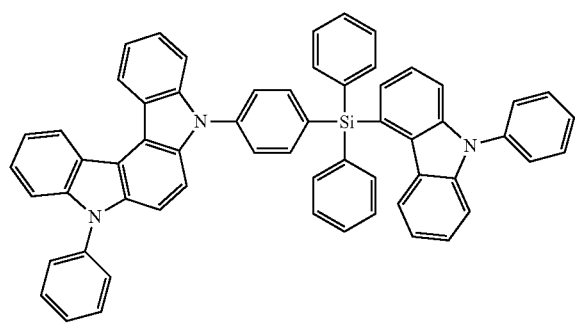
224
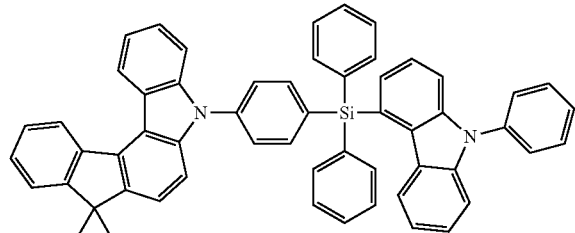
225
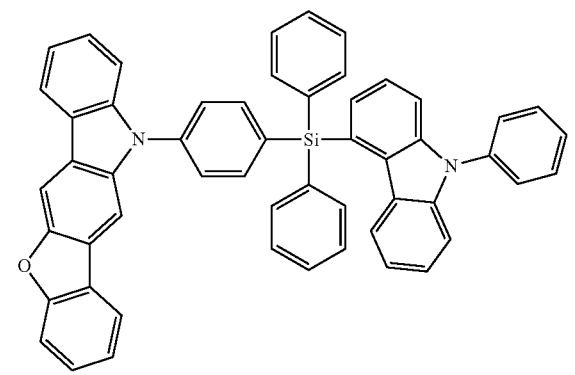
-continued
226
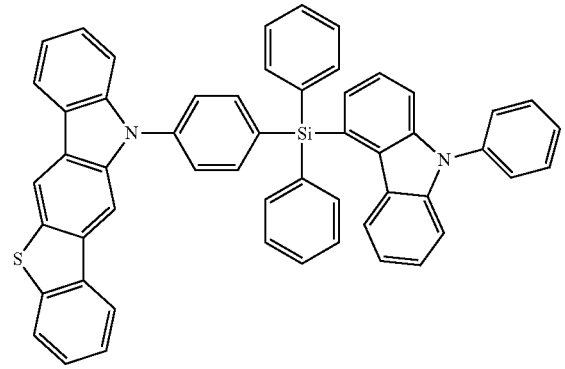
227
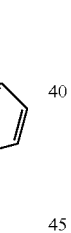
228
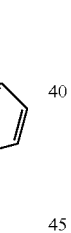
229
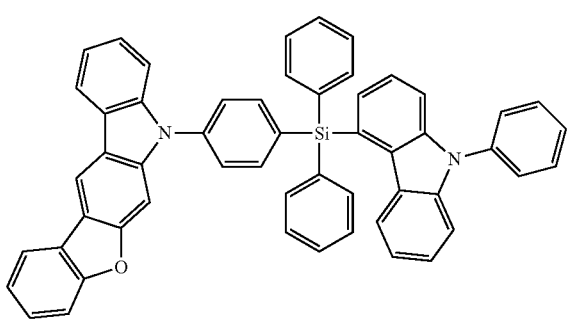

230
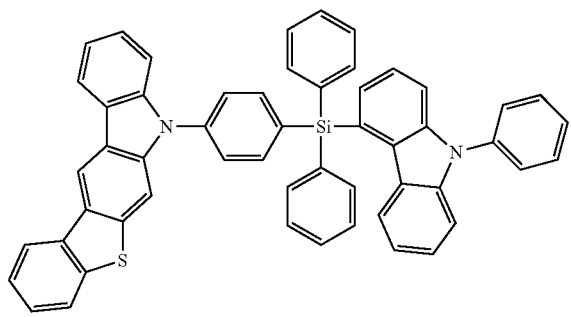
231
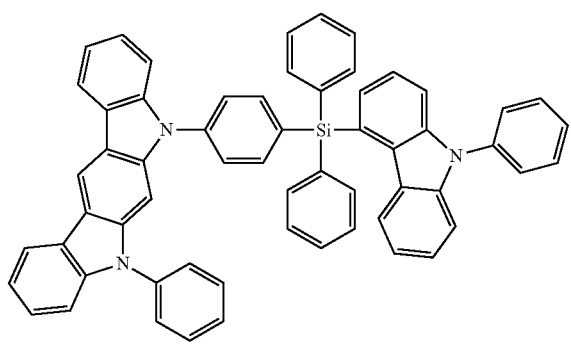
232
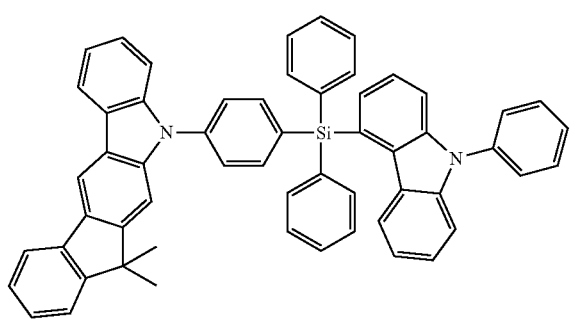
233
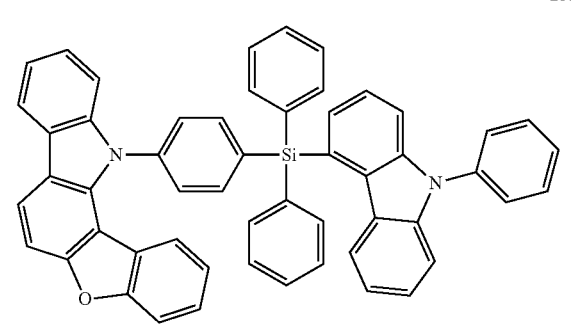
234
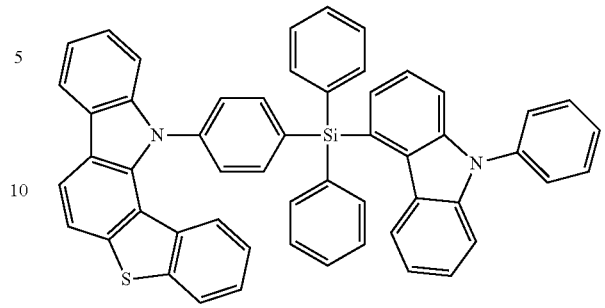
235
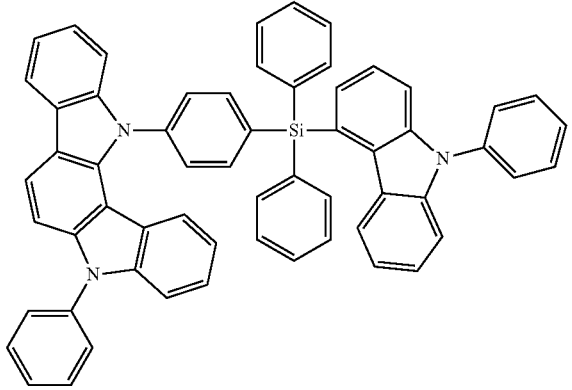
236
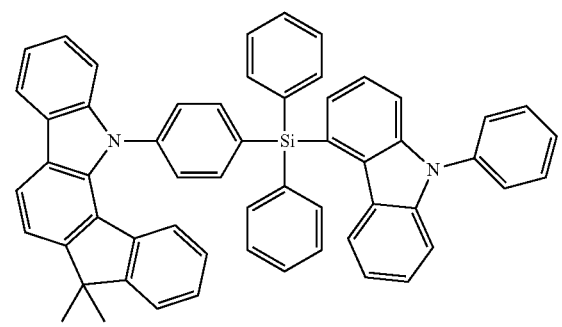
237
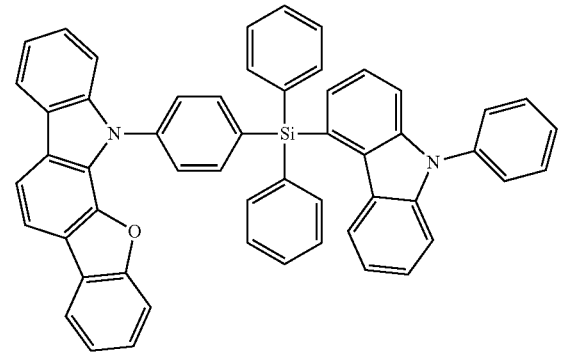

238
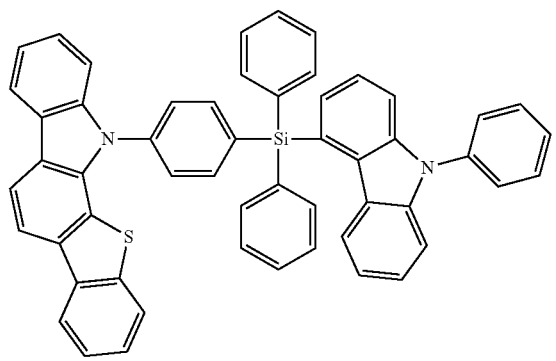
239
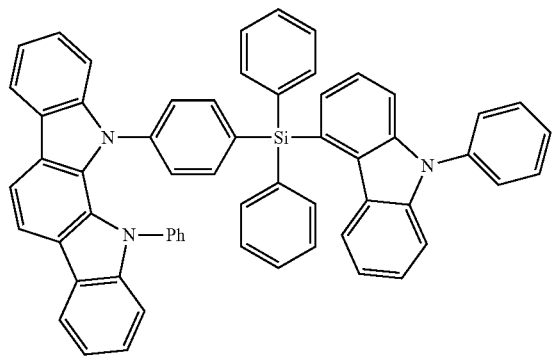
240
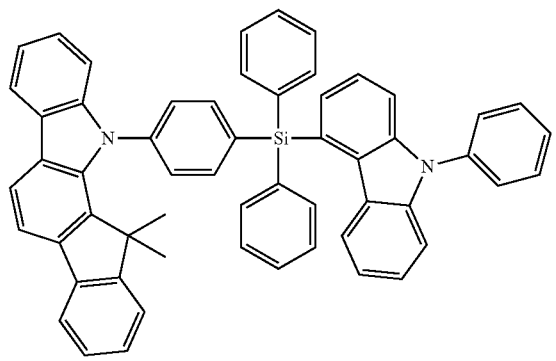
241
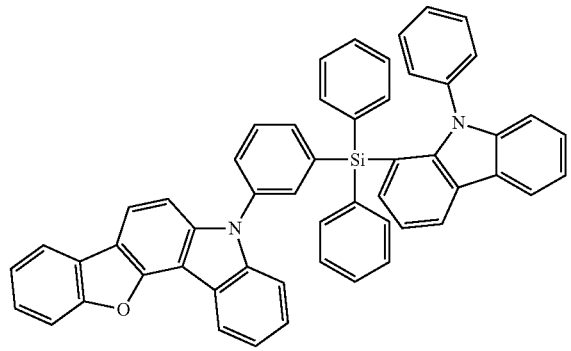
242
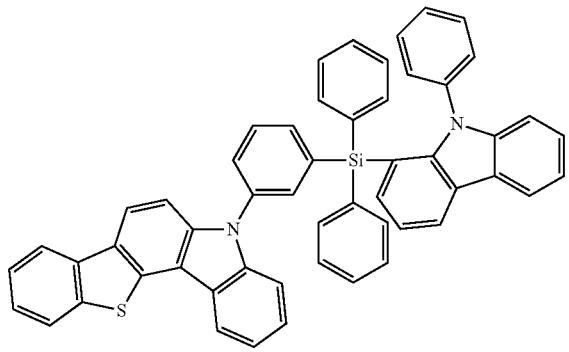
243
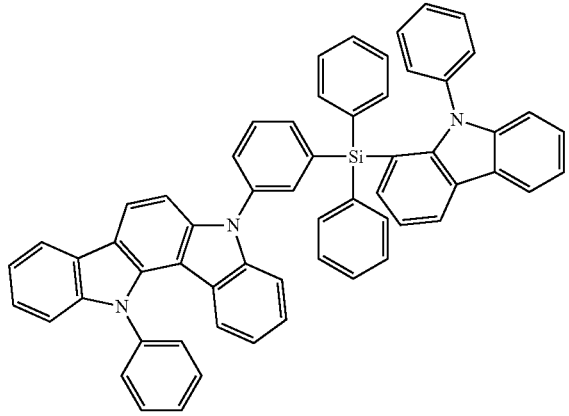
244
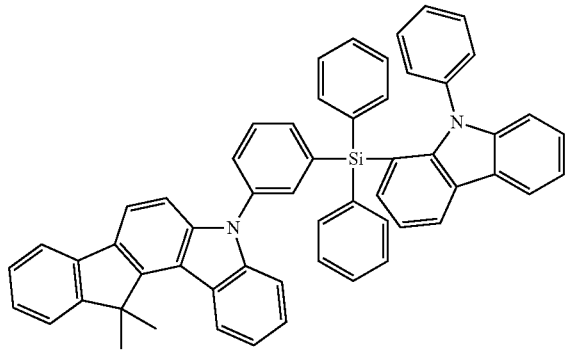
245
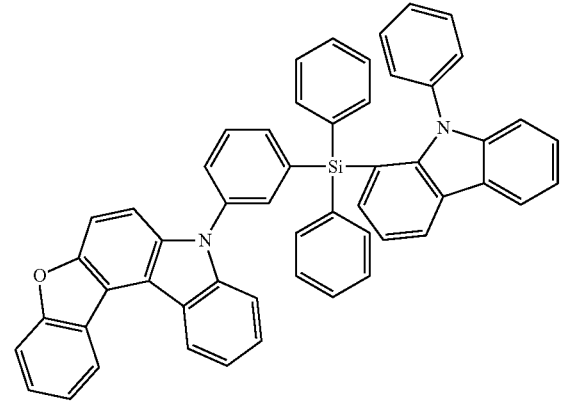

246
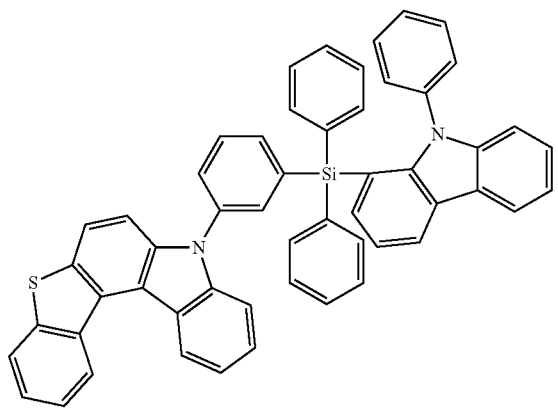
250
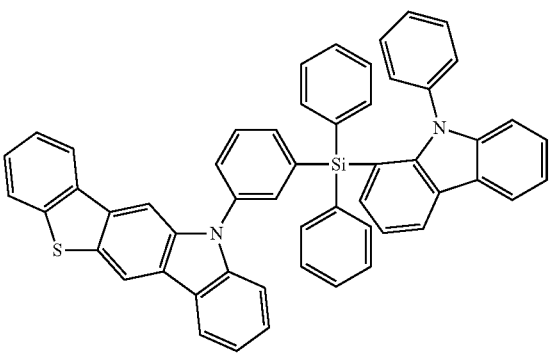
247
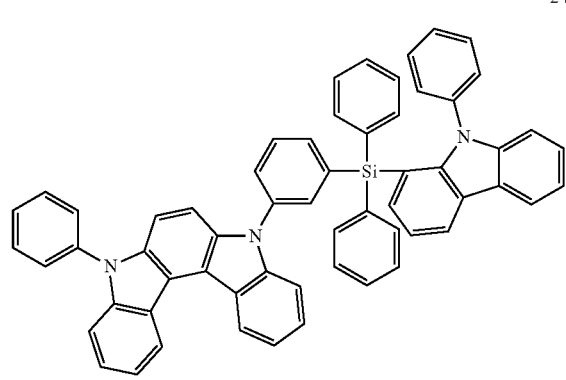
251
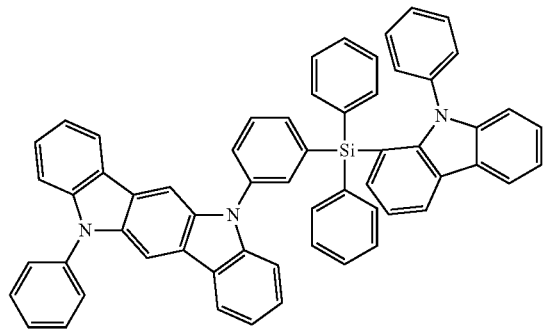
248
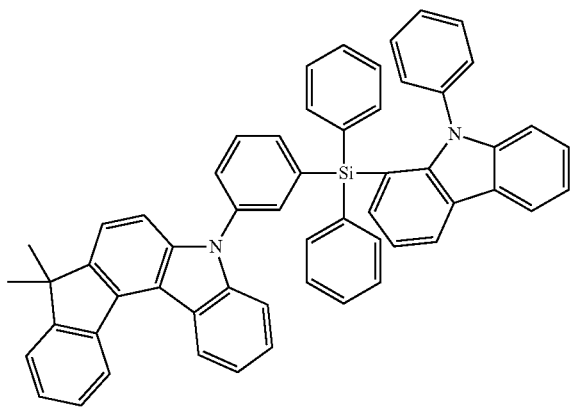
252
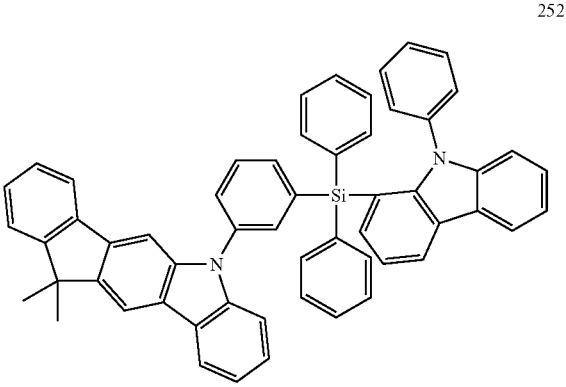
249
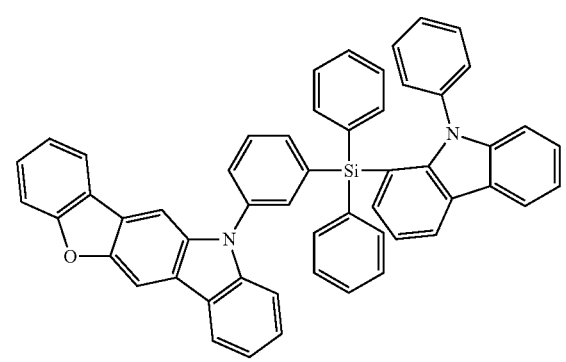
253
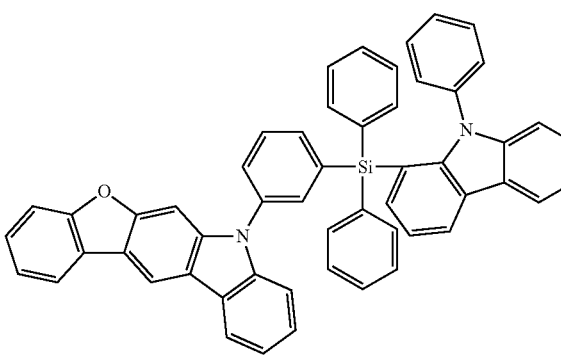

254
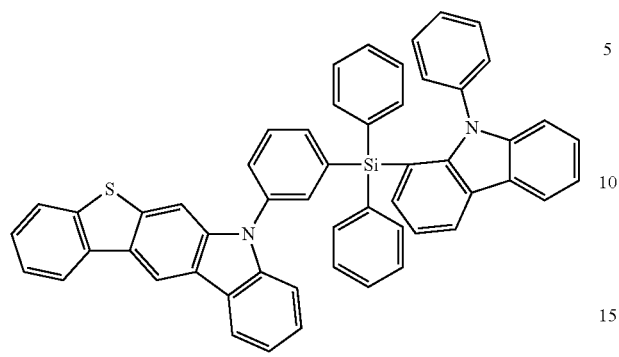
258
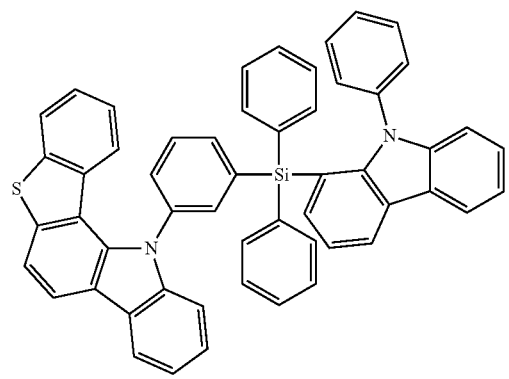
255
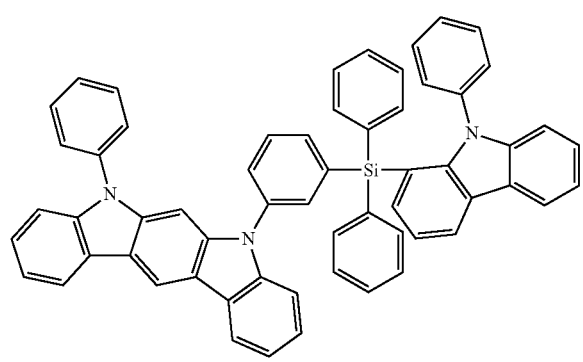
259
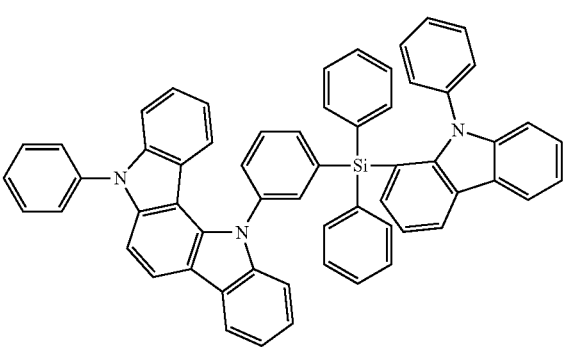
256
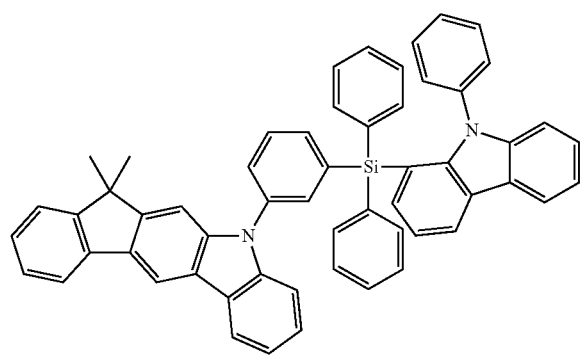
260
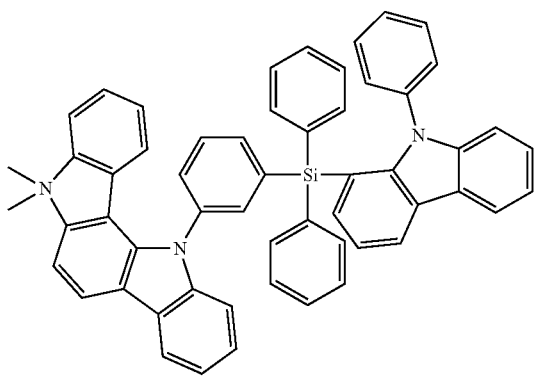
257
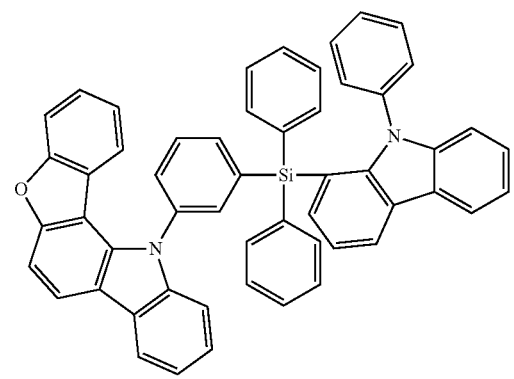
261
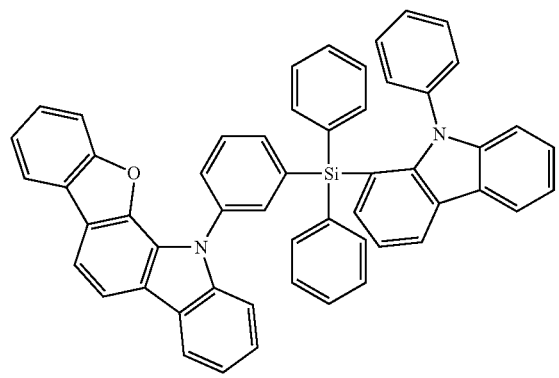

262
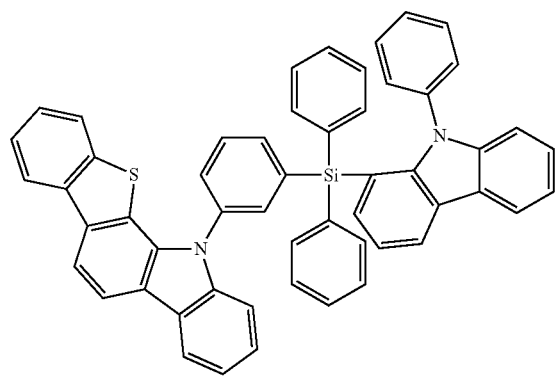
263
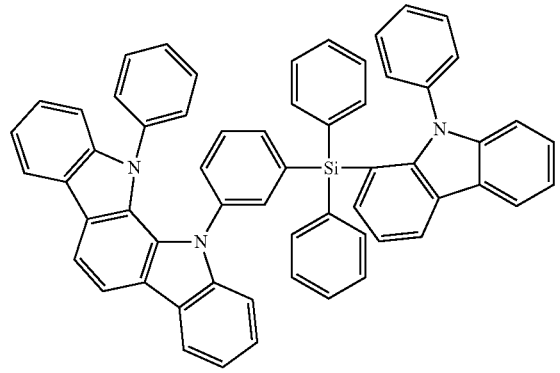
264
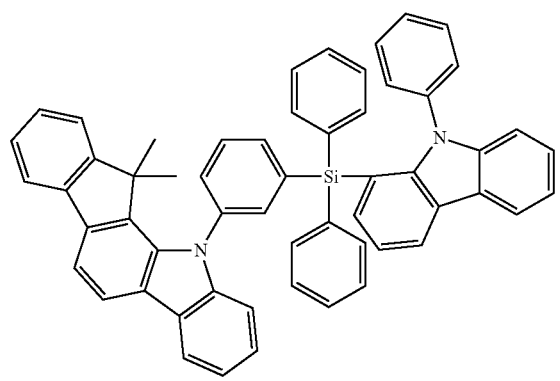
265
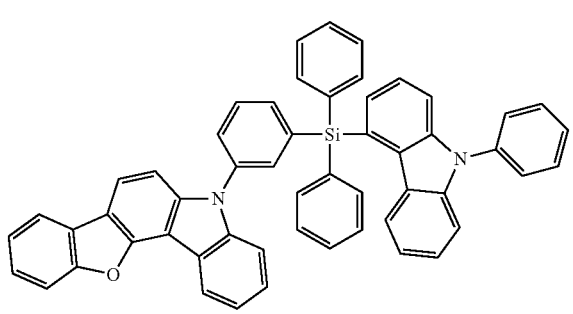
266
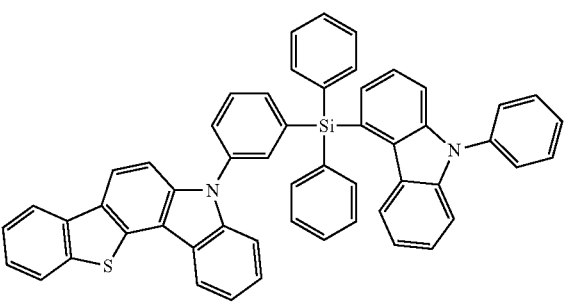
267
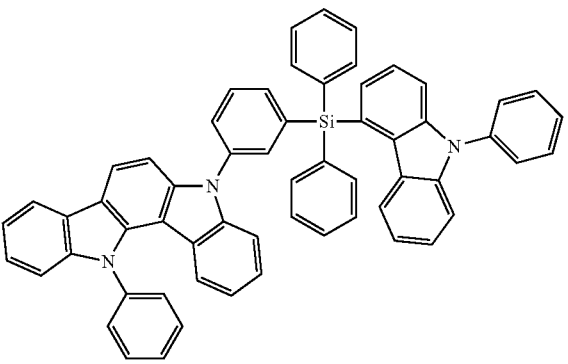
268
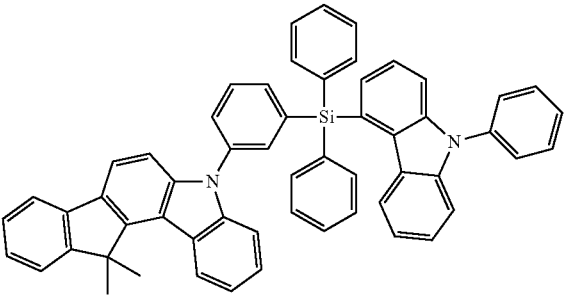
269
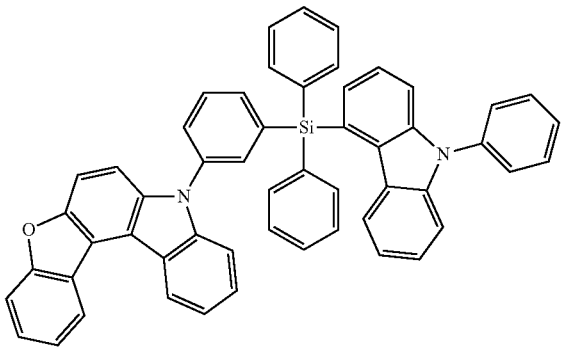

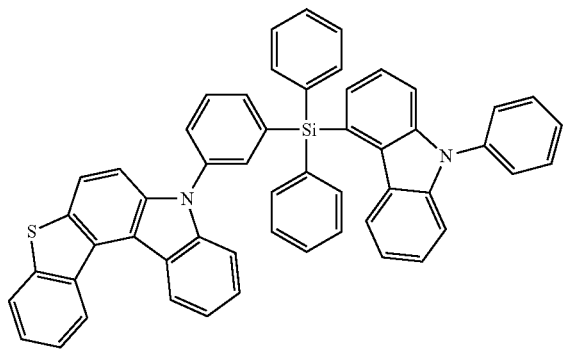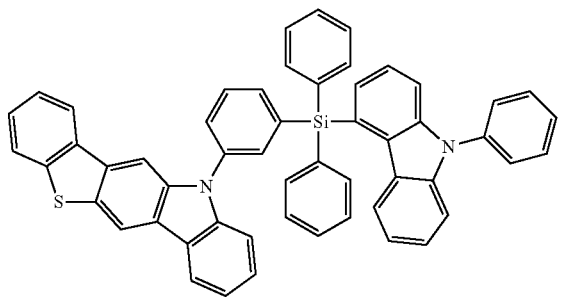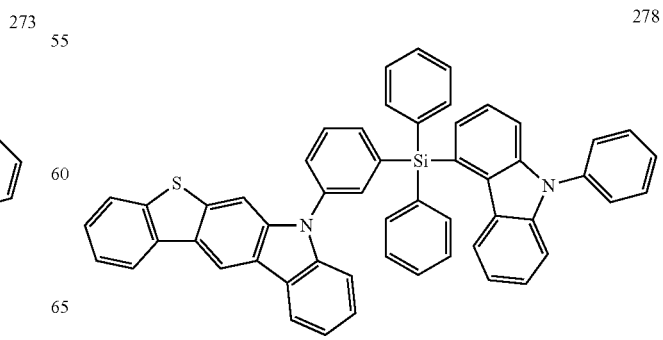

-continued
279
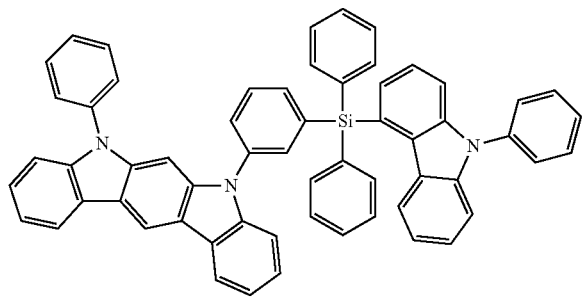
280
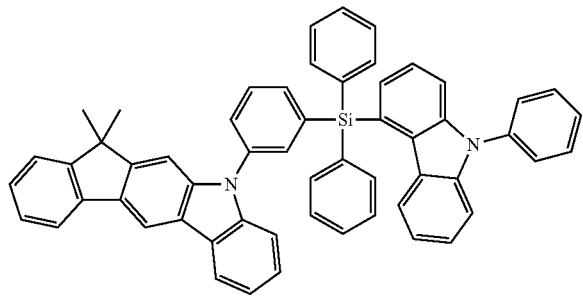
281
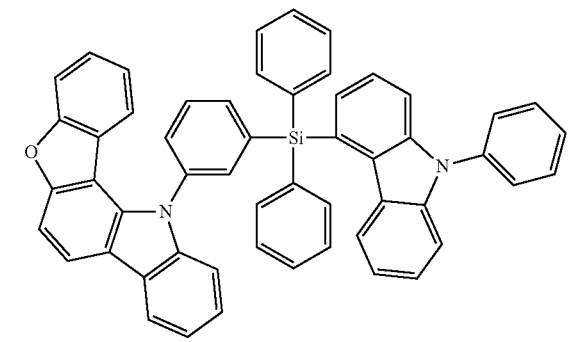
282
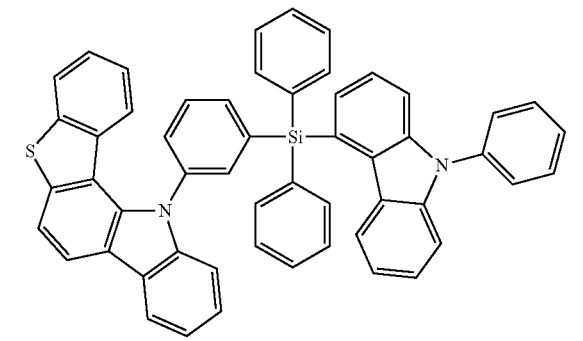
-continued
283
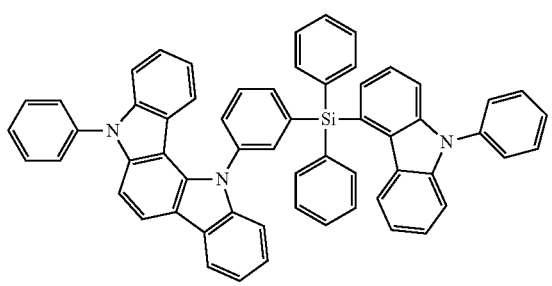
284
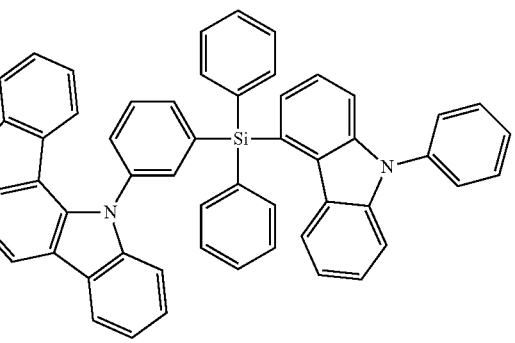
285
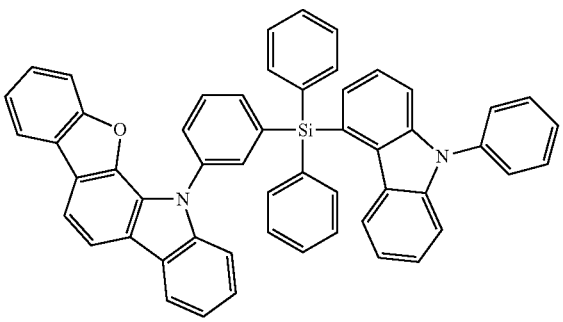
286
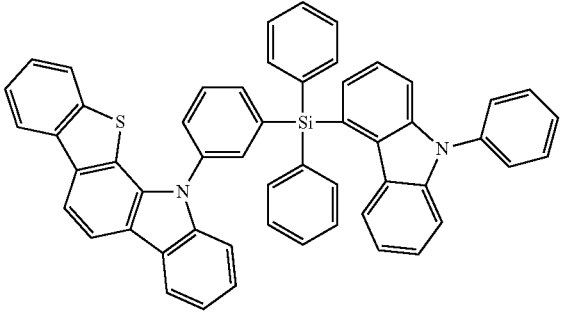

287
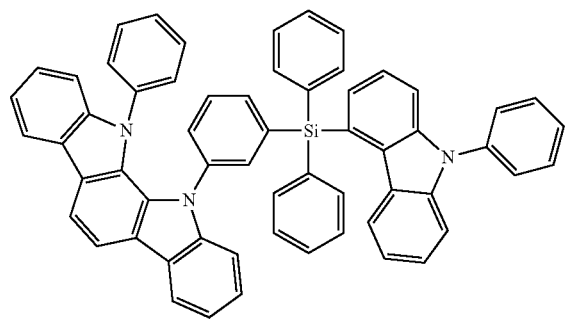
288
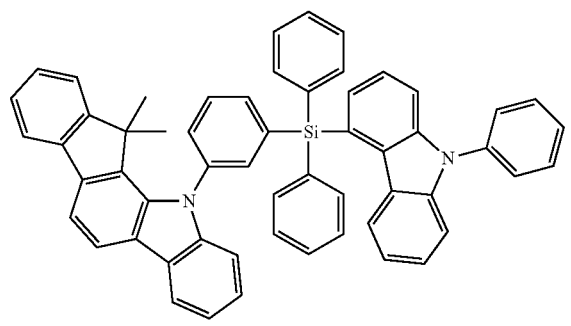
289
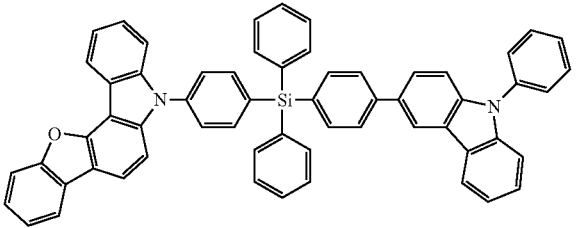
290
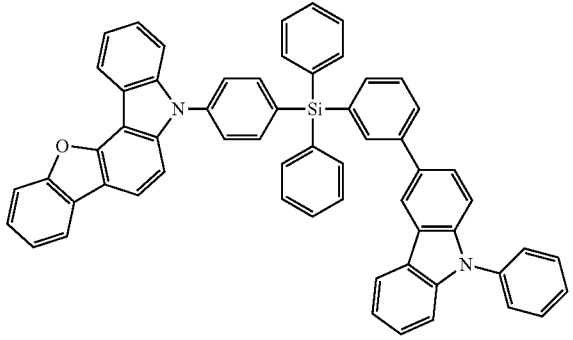
291
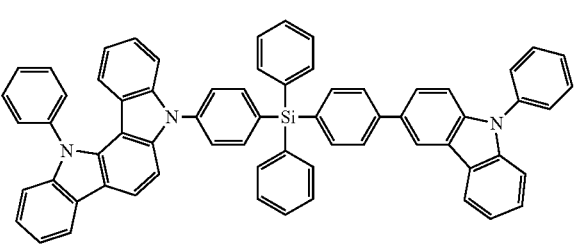
292
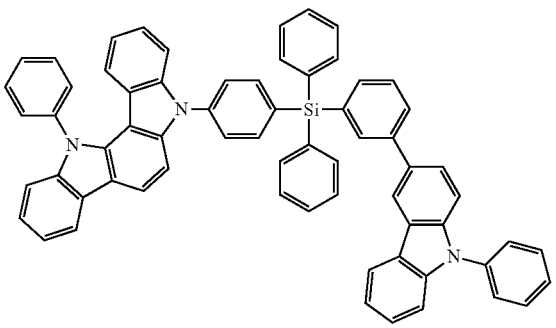
293
294
295
296
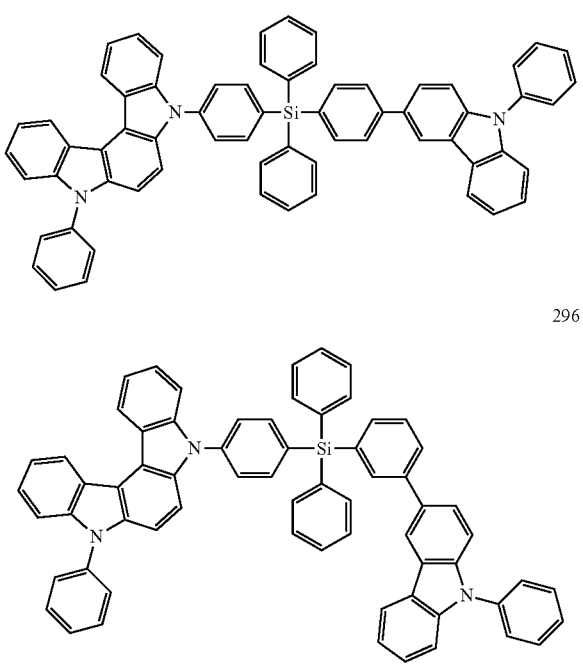

297
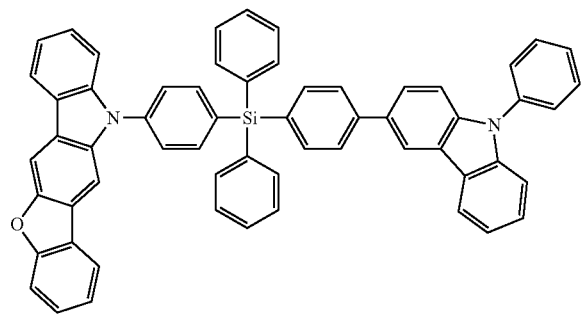
298
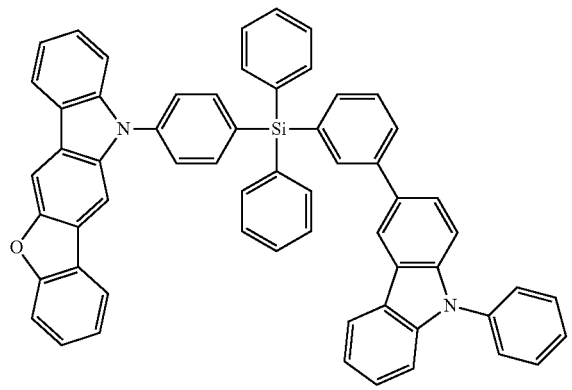
299
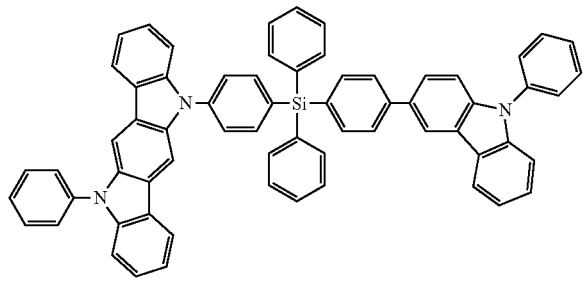
300
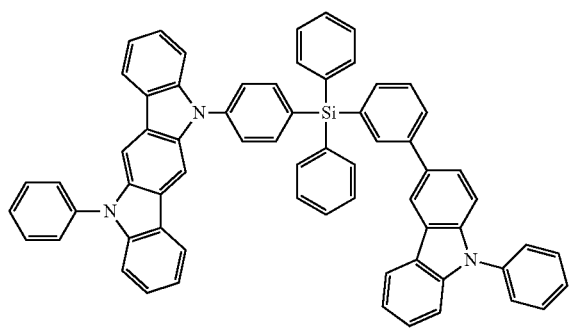
301
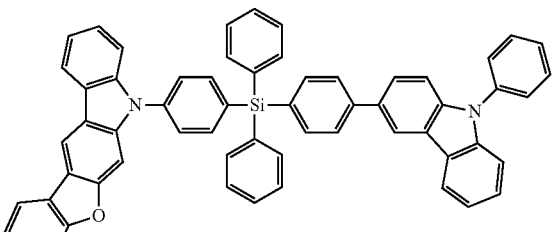
302
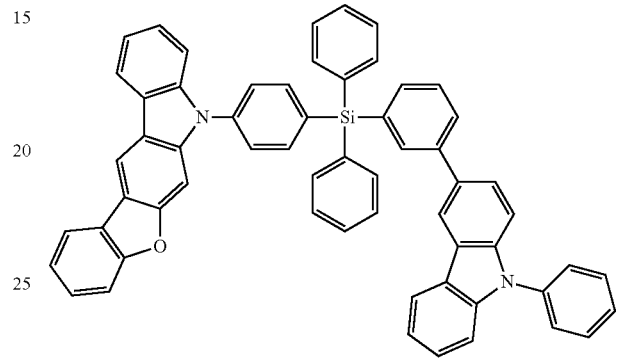
303
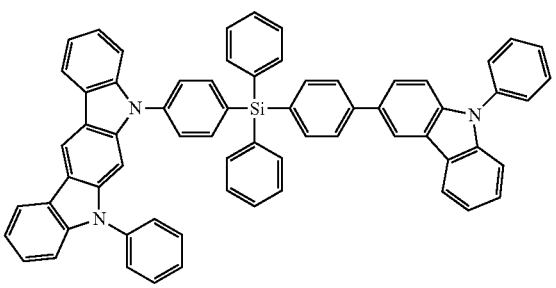
304
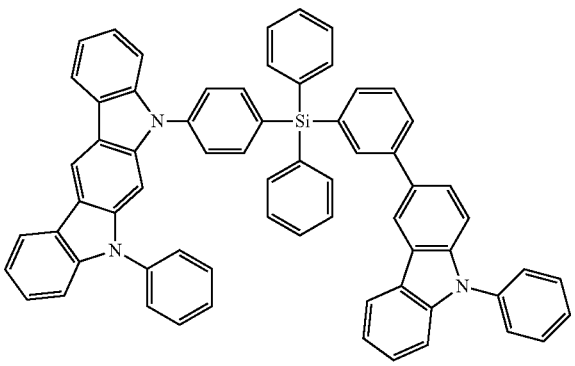
305
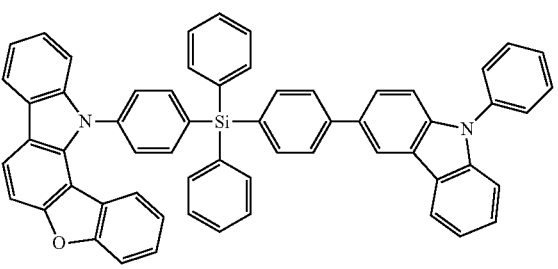

306
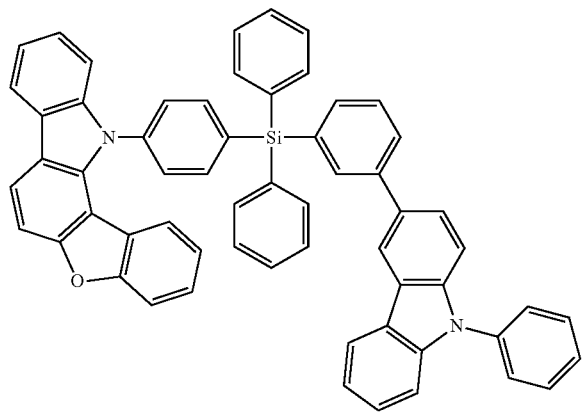
307
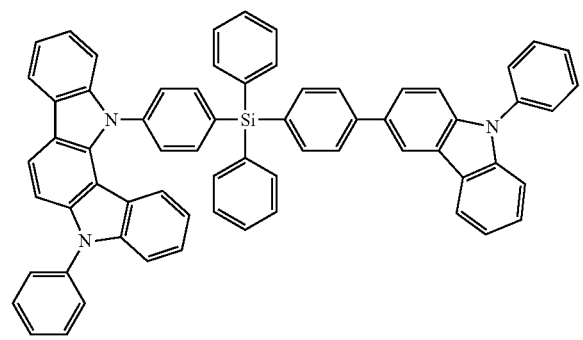
308
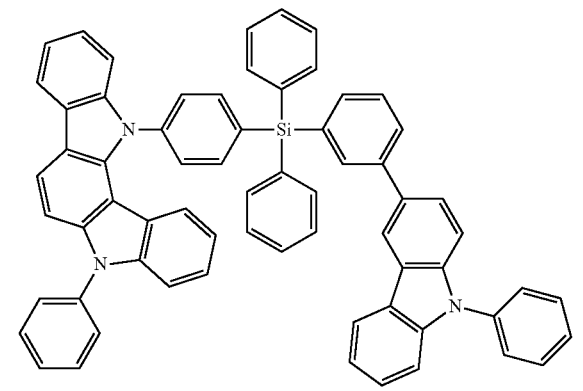
309
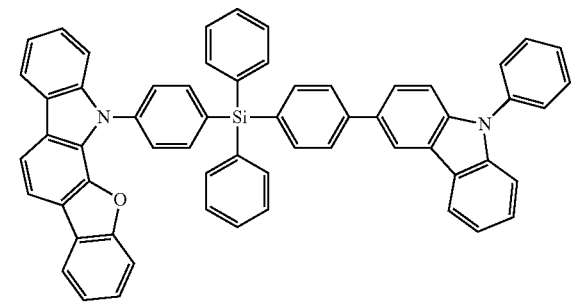
310
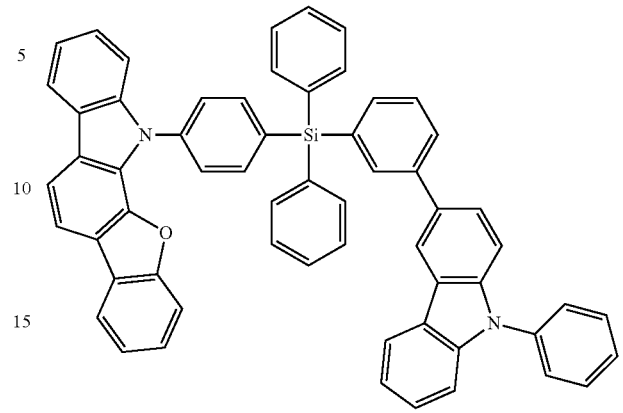
311
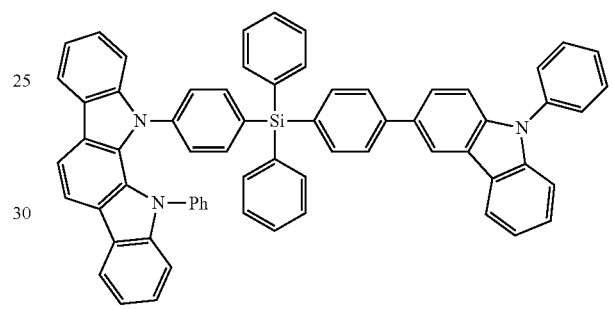
312
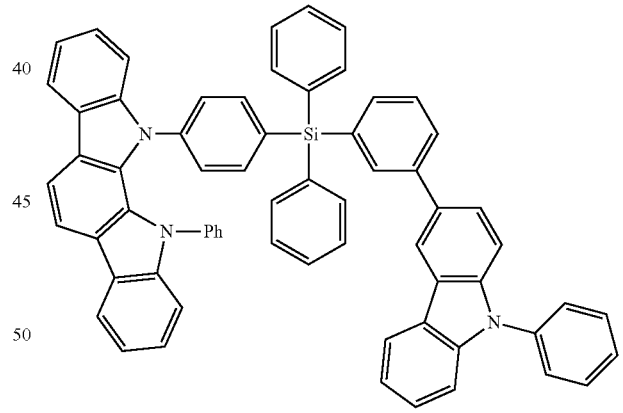
313
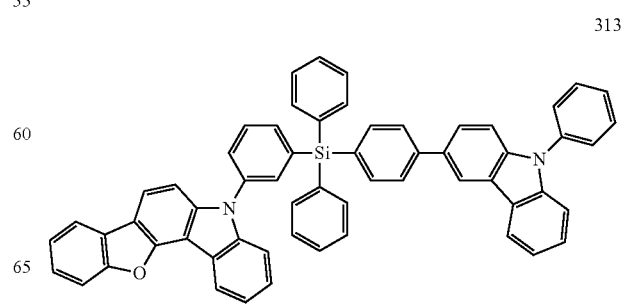

314
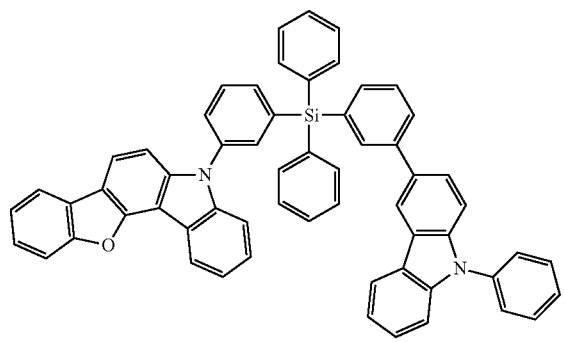
318
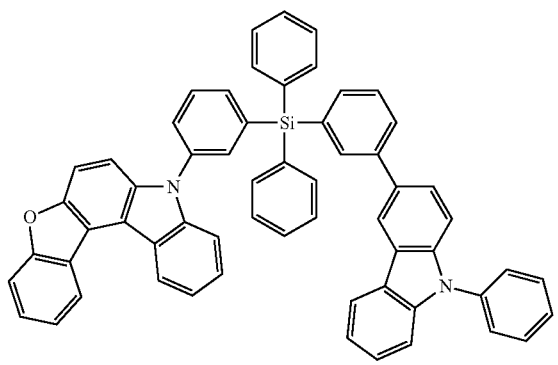
315
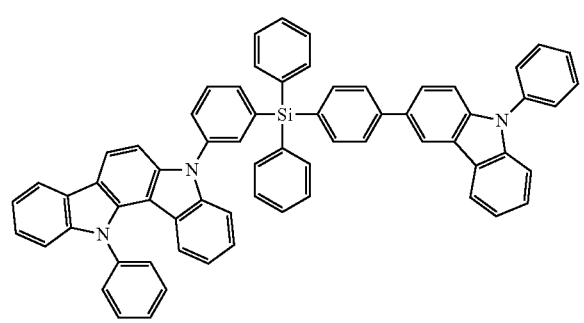
319
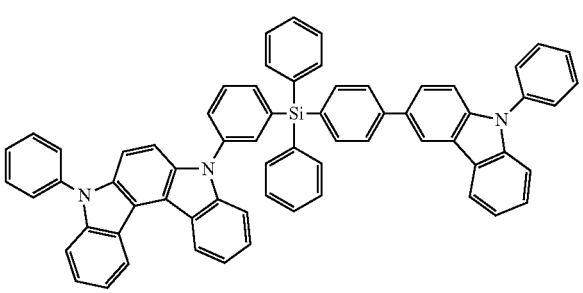
316
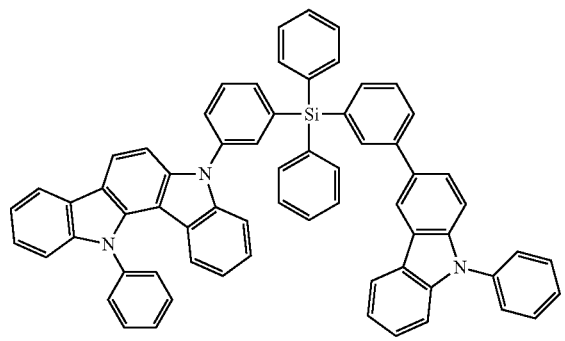
320
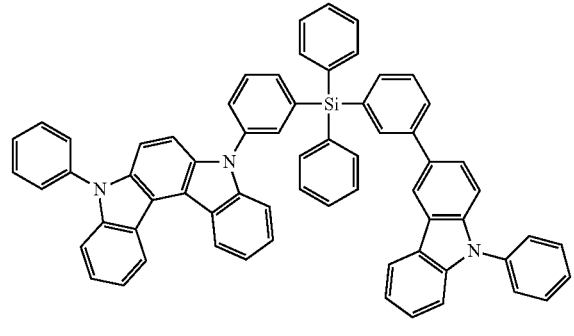
317
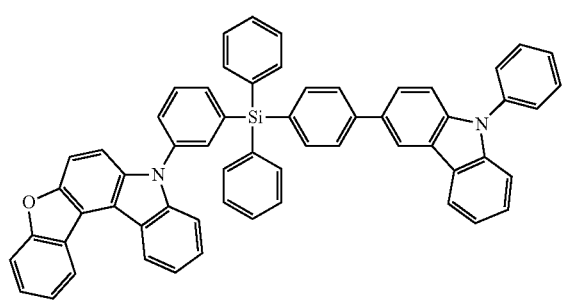
321
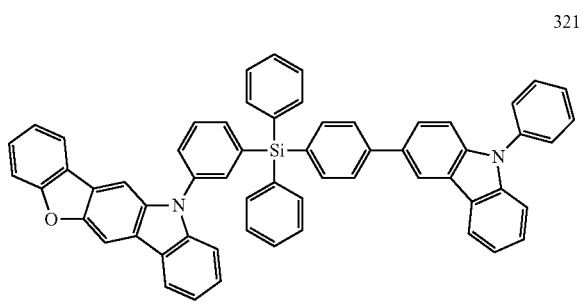

322
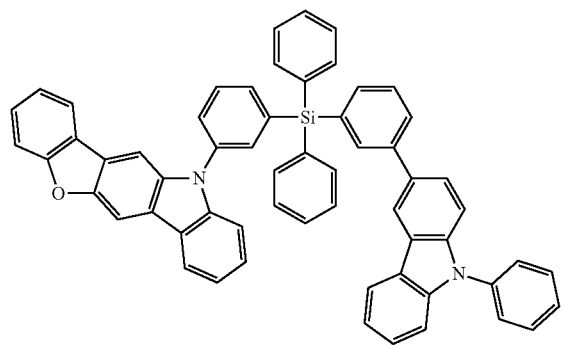
326
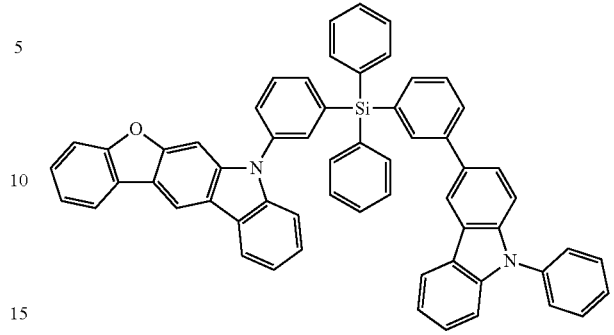
323
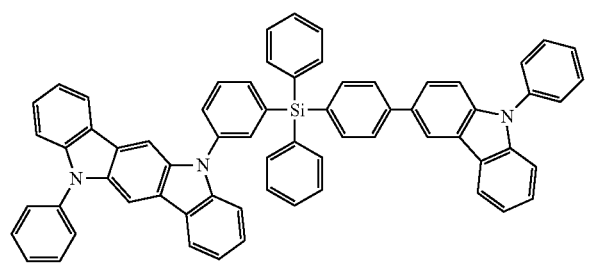
327
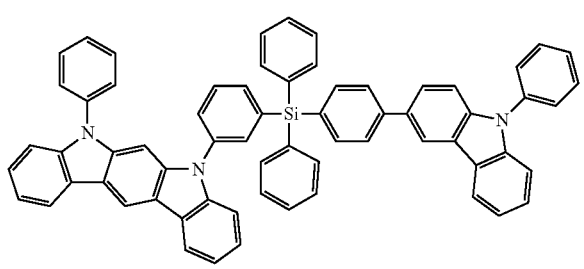
324
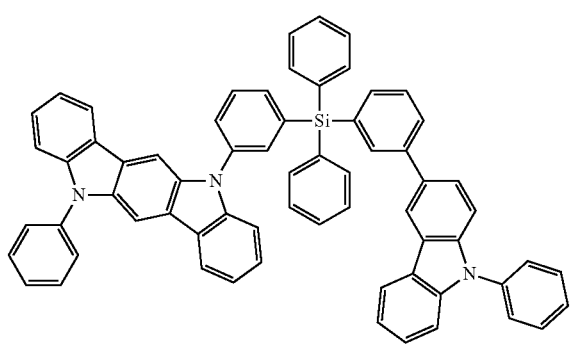
328
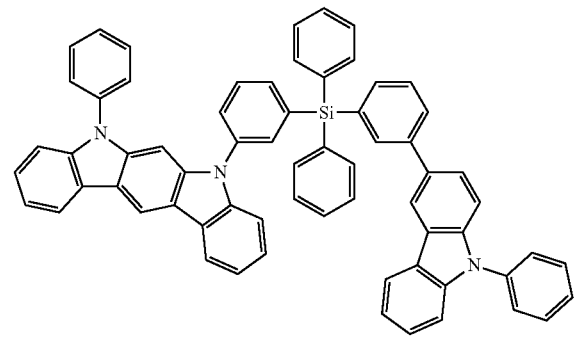
325
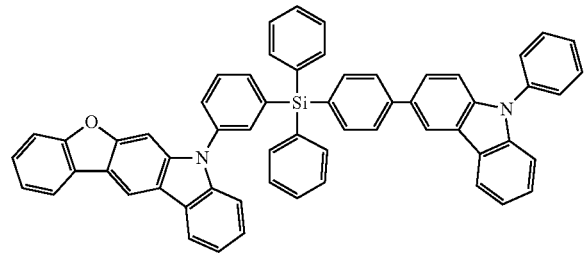
329
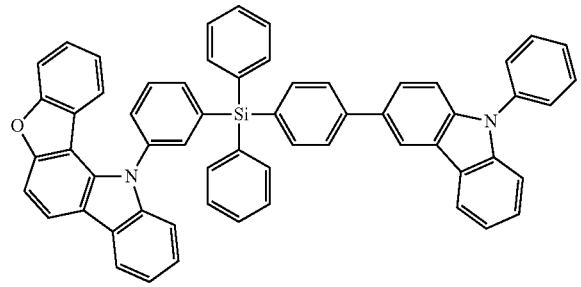

330
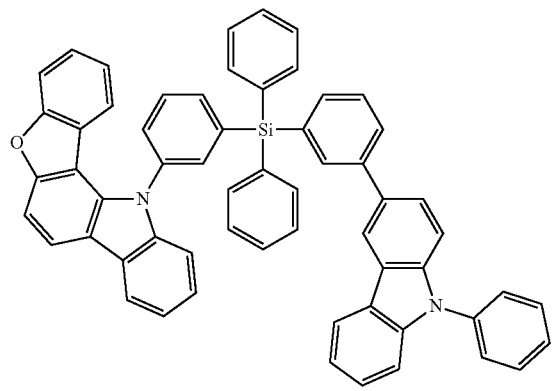
331
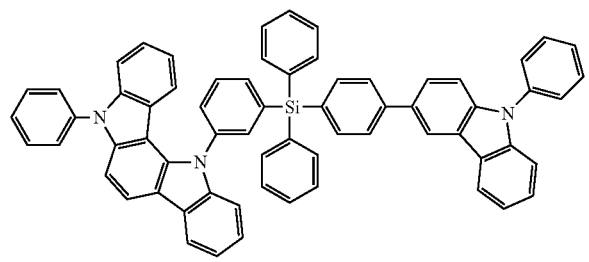
332
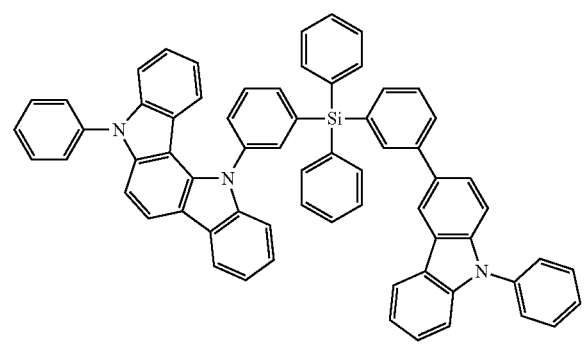
333
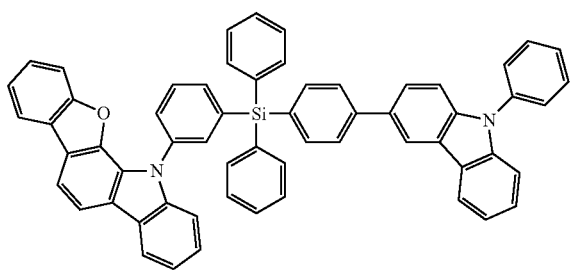
334
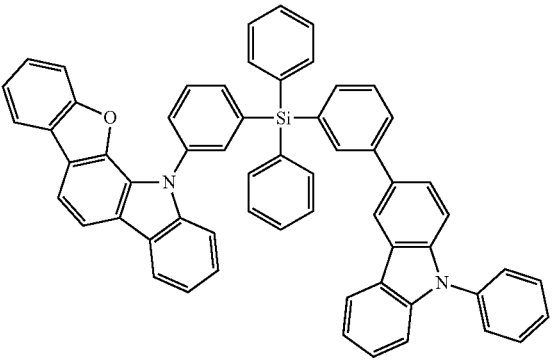
335
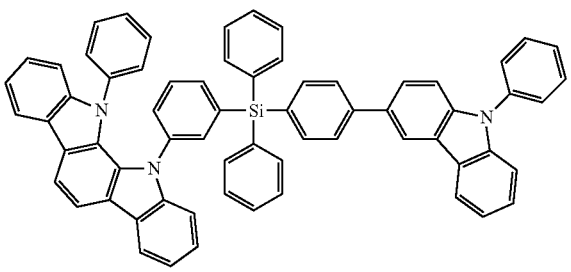
336
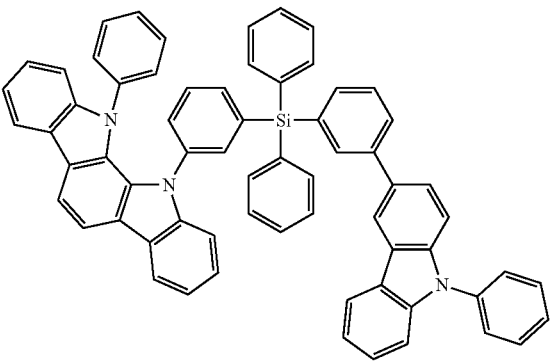
337
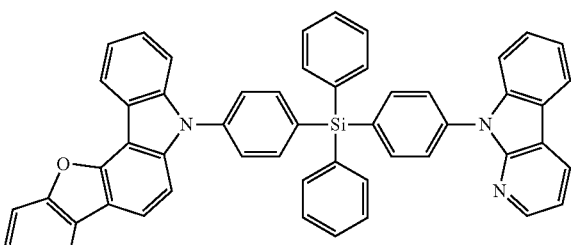
338
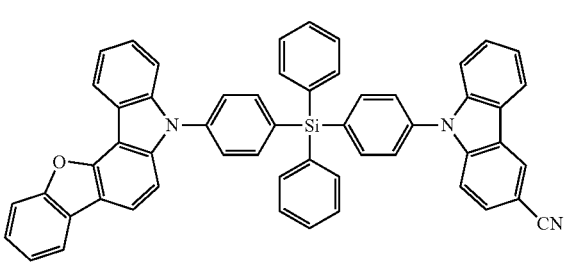

139
-continued

339

340

341

342

343

344

140
-continued

345

346

347

348

141
-continued
349
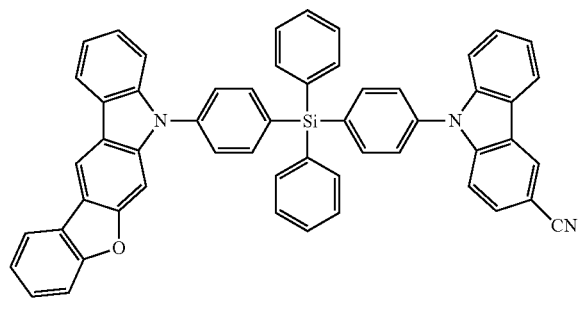
350
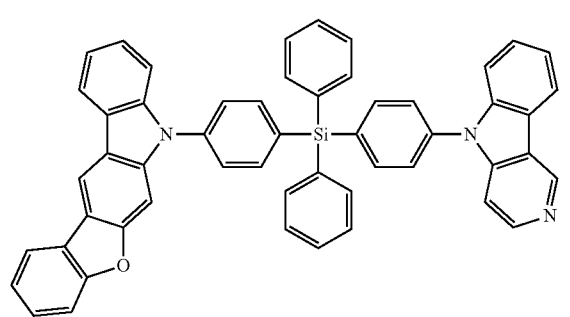
351
352
142
-continued
353
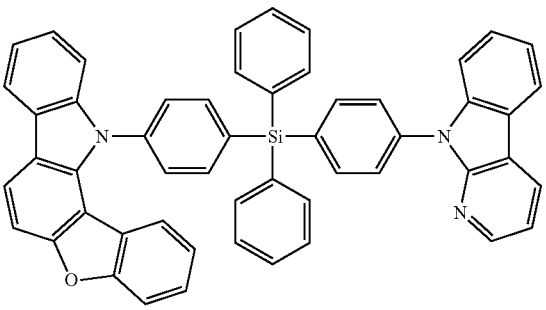
354
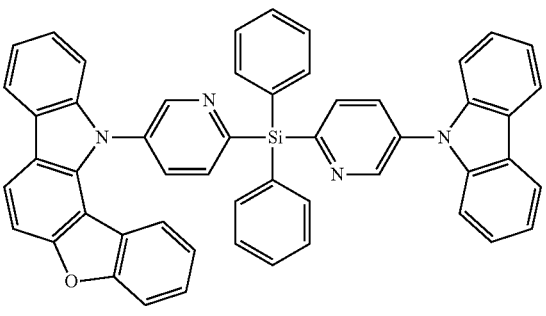
355
356
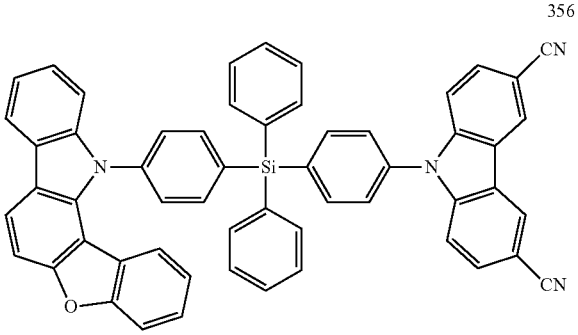

357
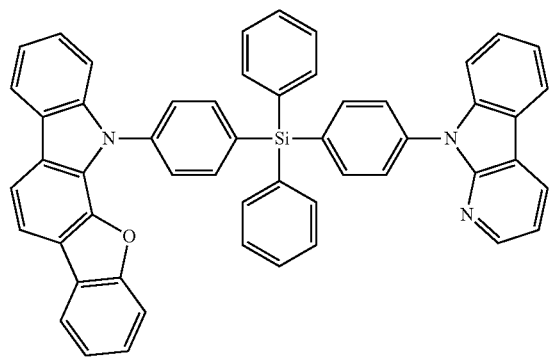
358
359
360
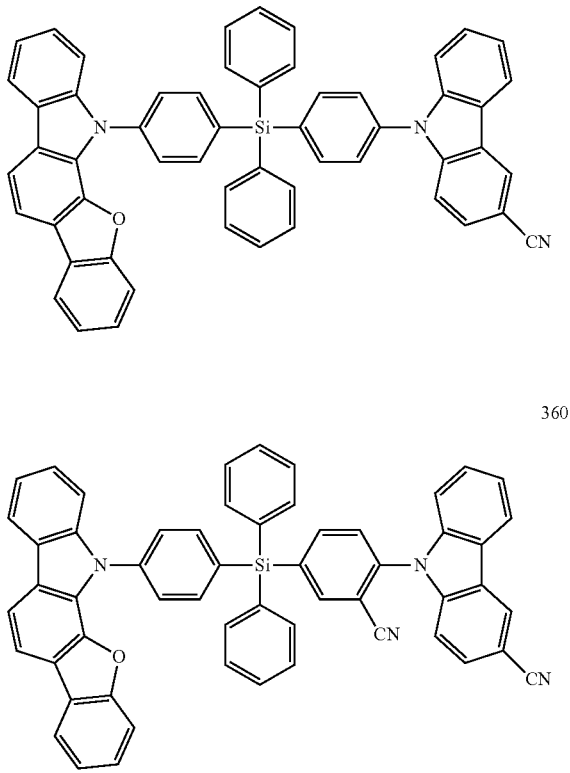
361
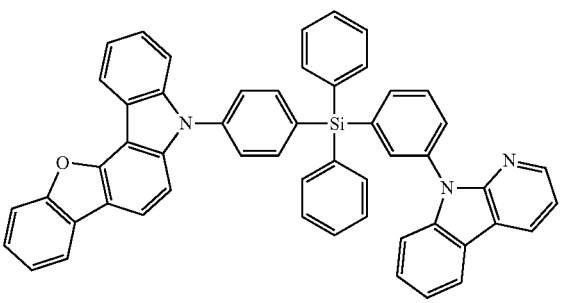
362
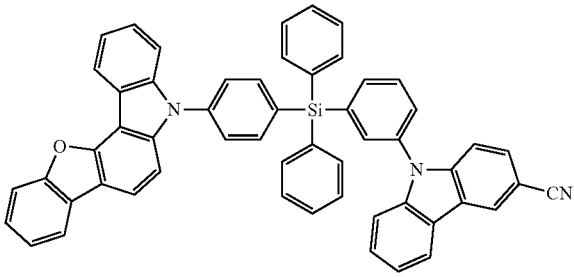
363
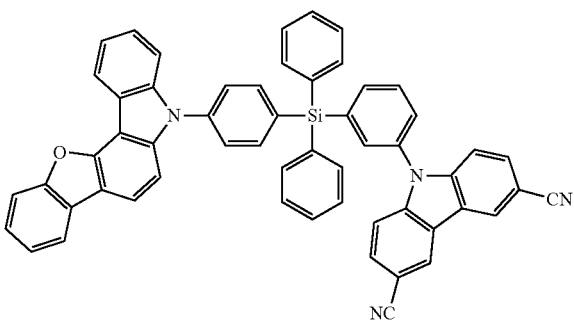
364
365
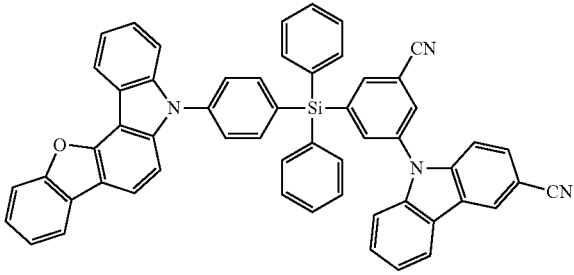

366
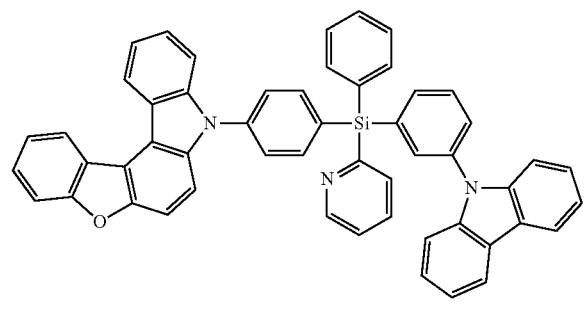
370
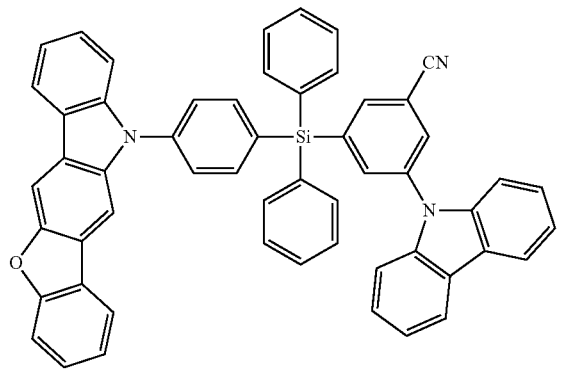
367
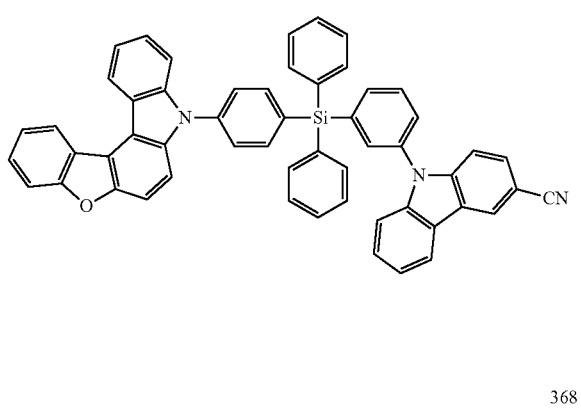
371
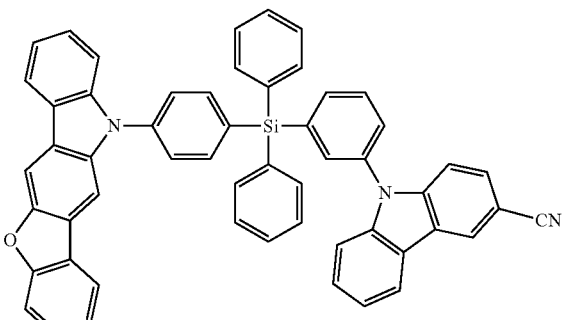
368
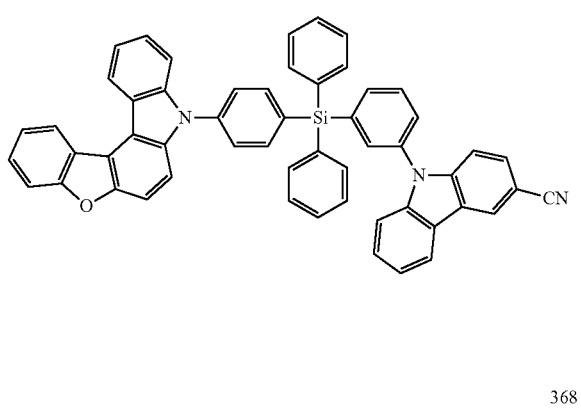
372
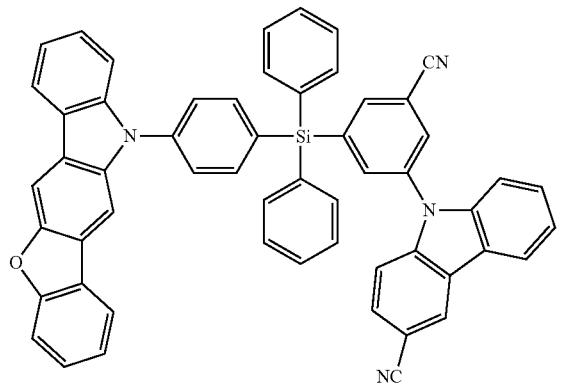
369
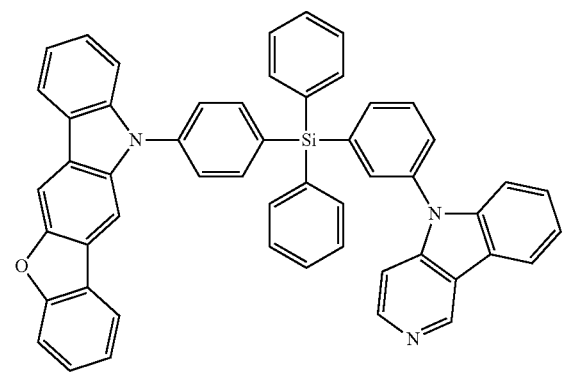
373
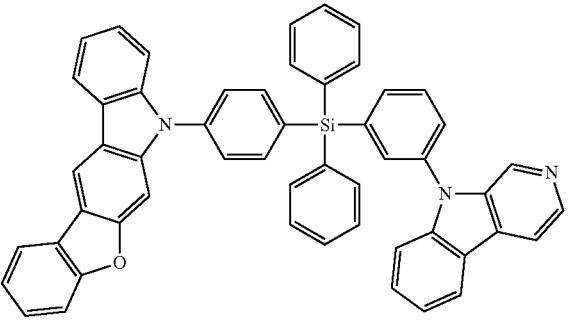

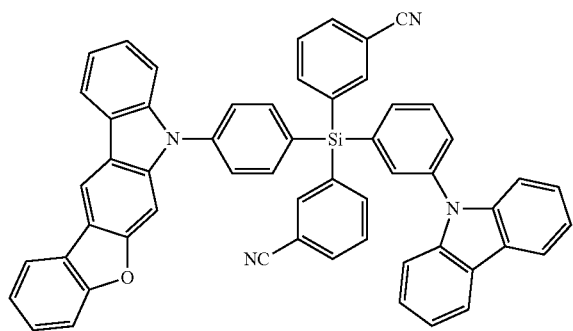
374
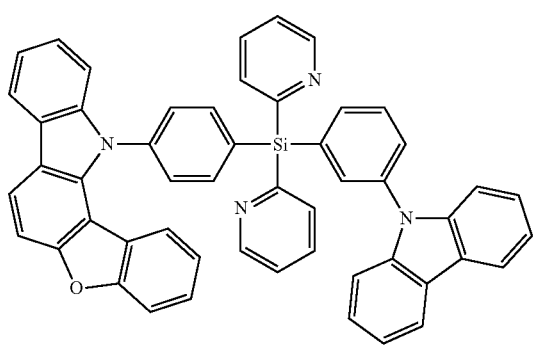
378
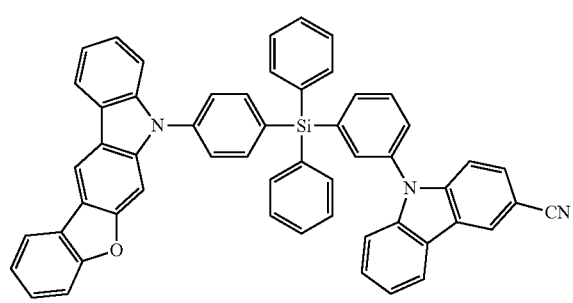
375
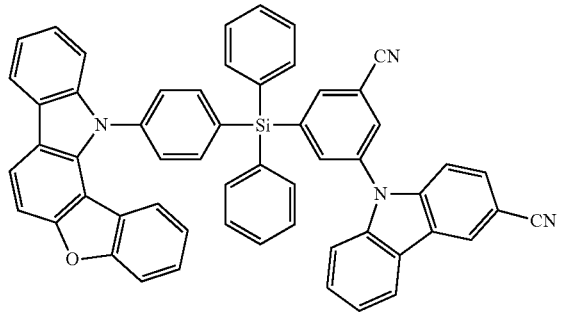
379
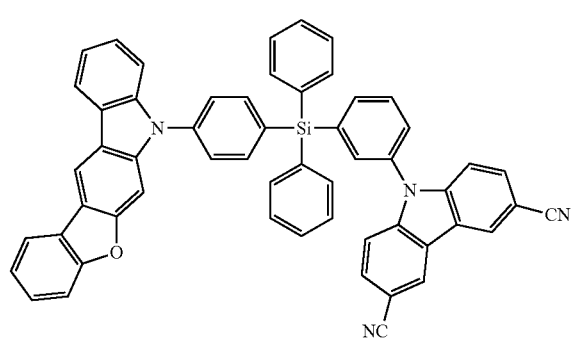
376
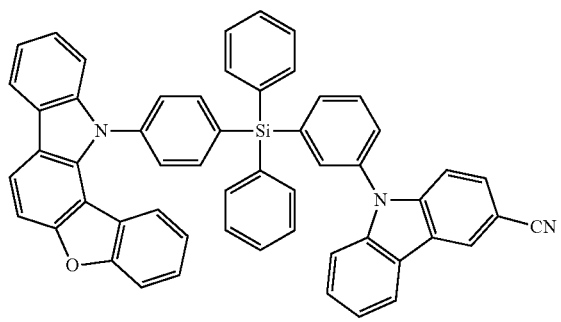
380
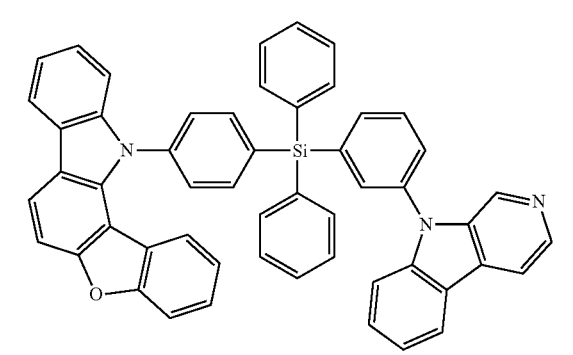
377
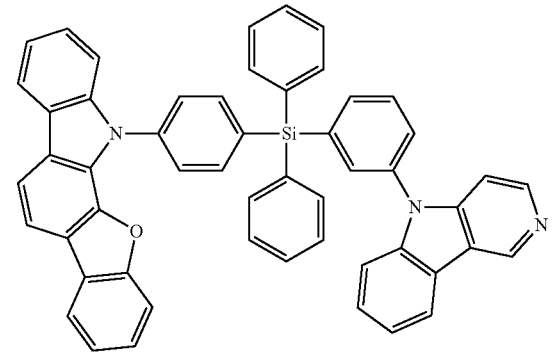
381

-continued
382
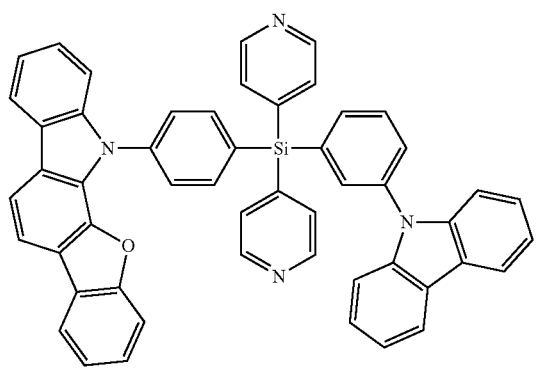
383
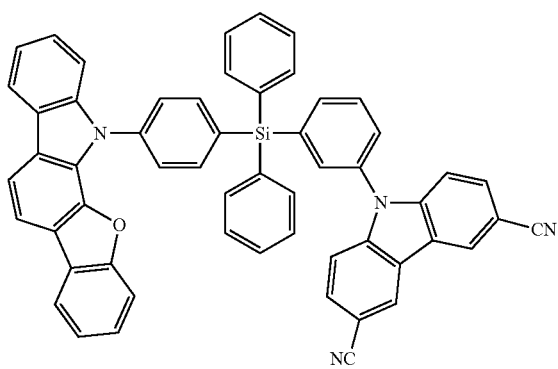
384
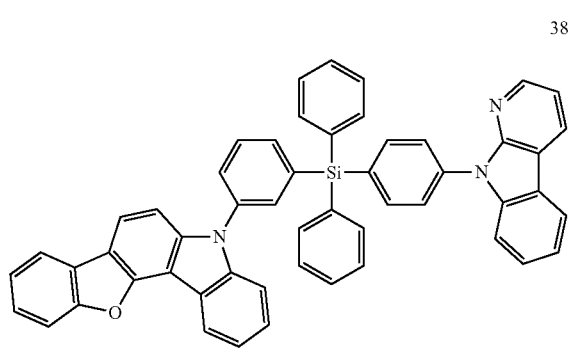
385
-continued
386
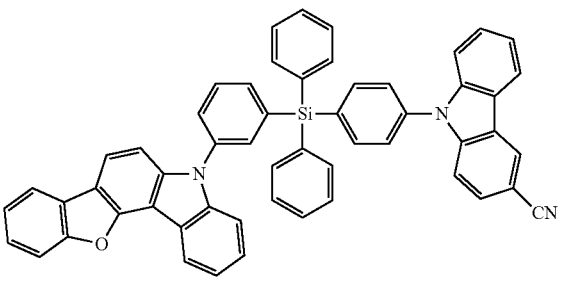
387
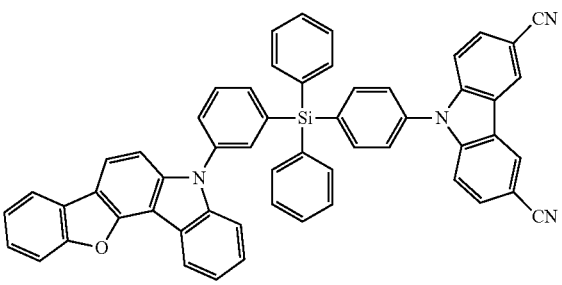
388
389

-continued
390
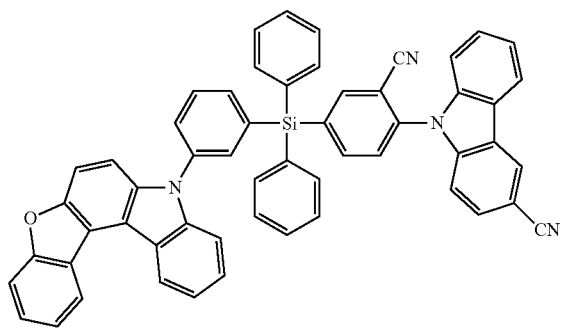
391
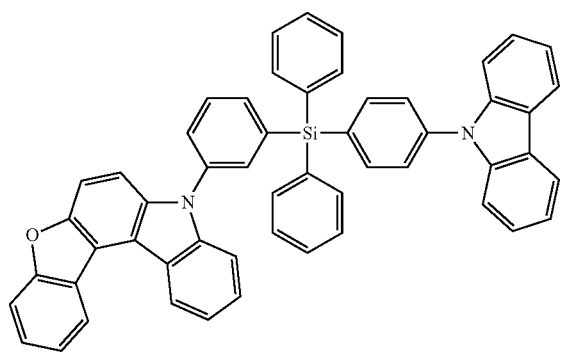
392
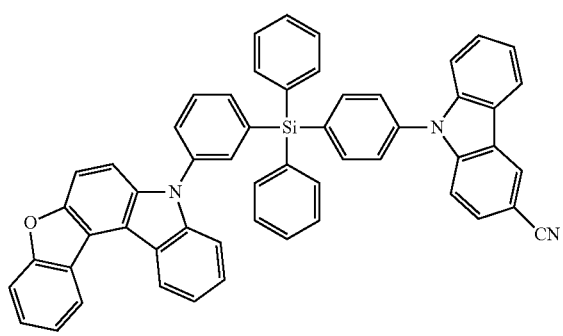
393
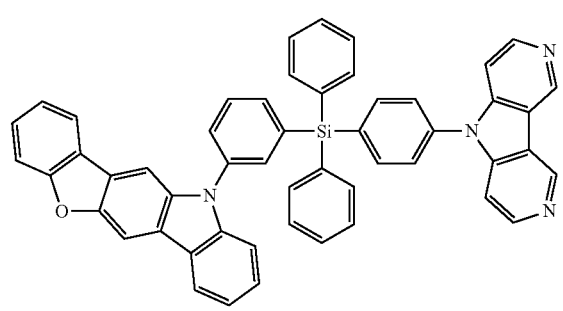
-continued
394
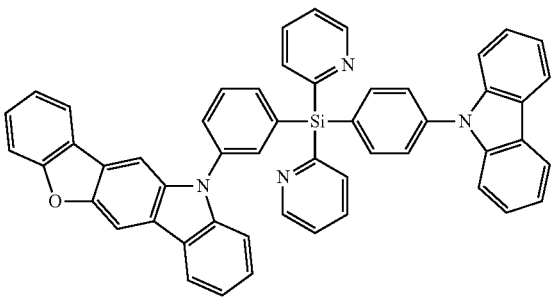
395
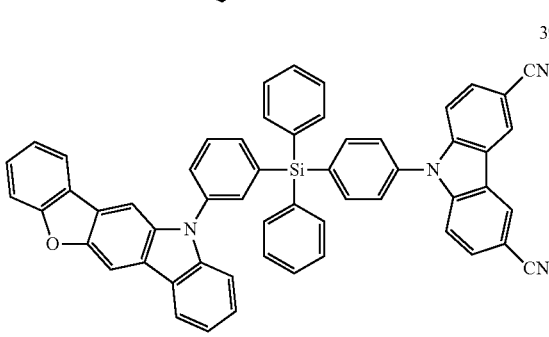
396
397
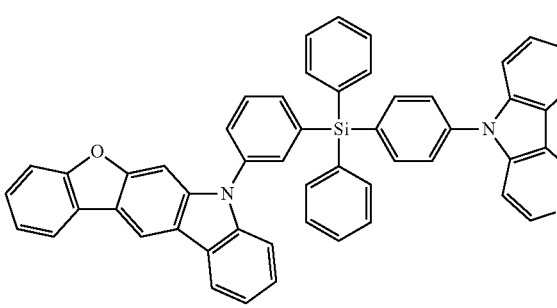
398

399
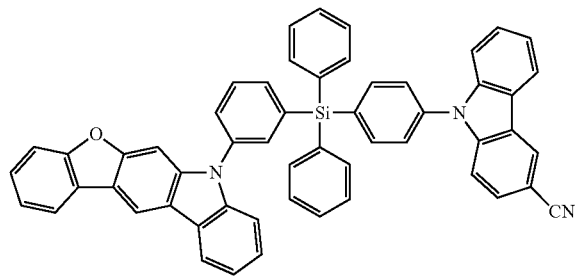
400
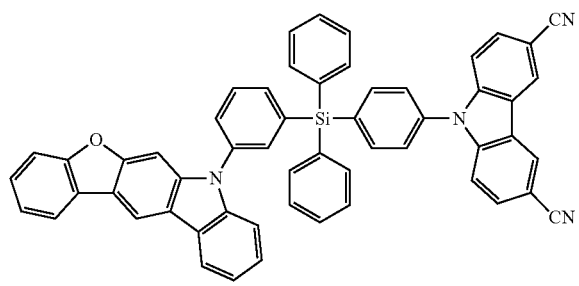
401
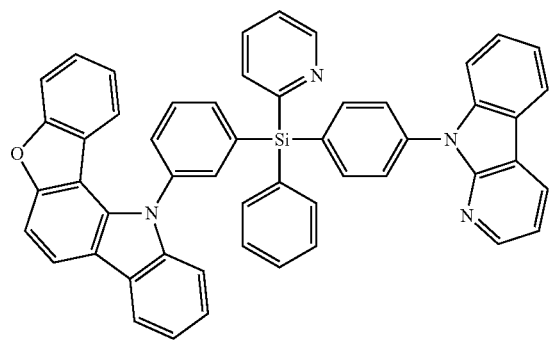
402
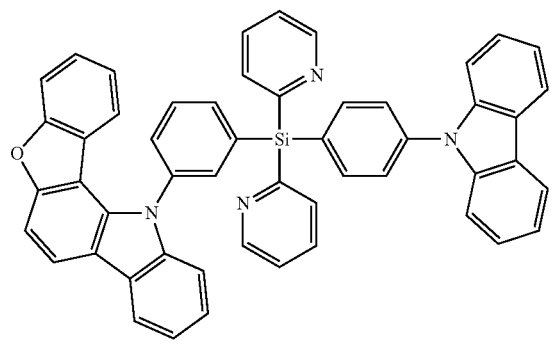
403
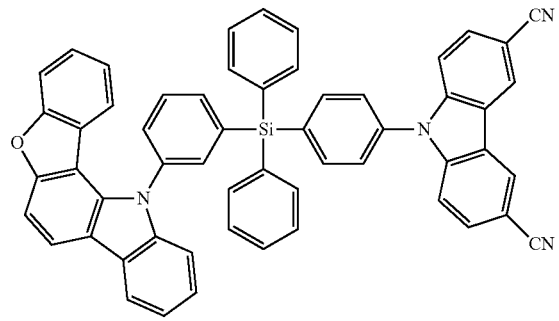
404
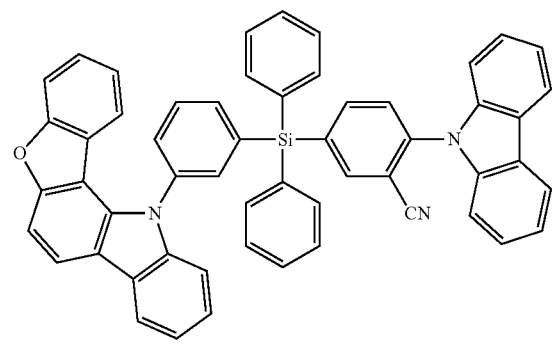
405
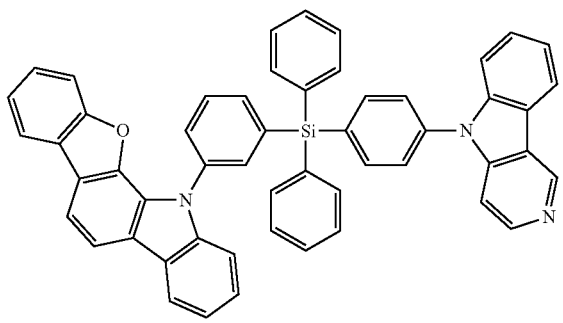
406
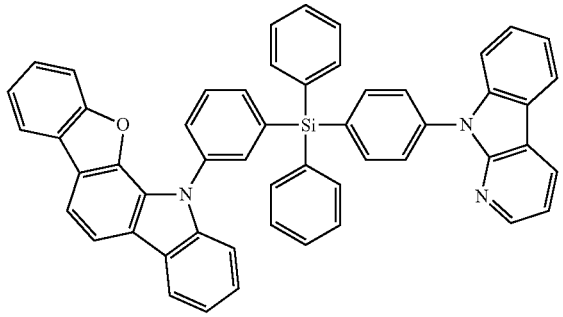

-continued
407
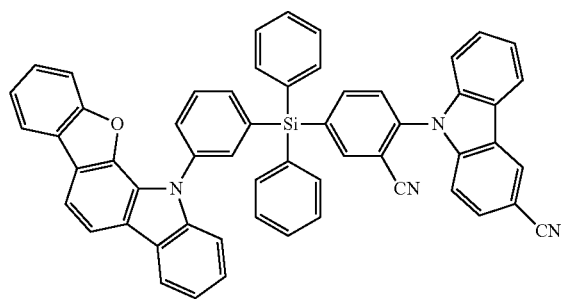
408
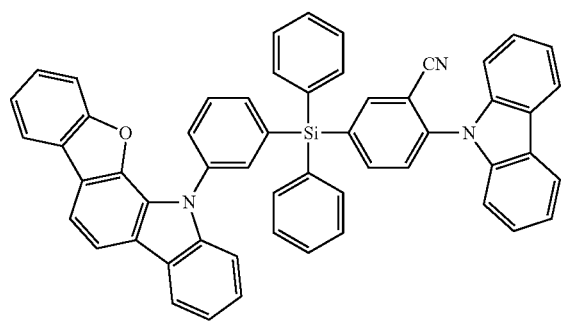
409
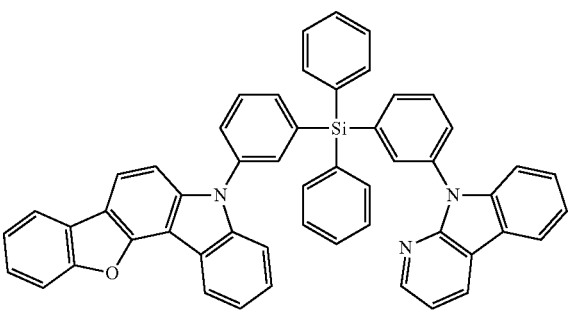
410
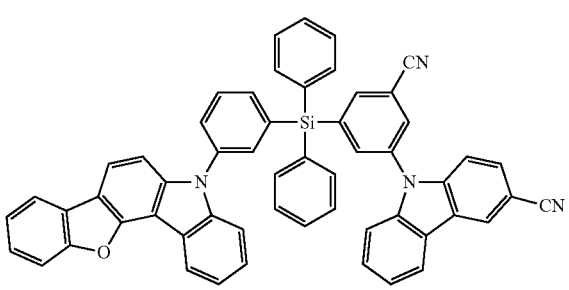
411
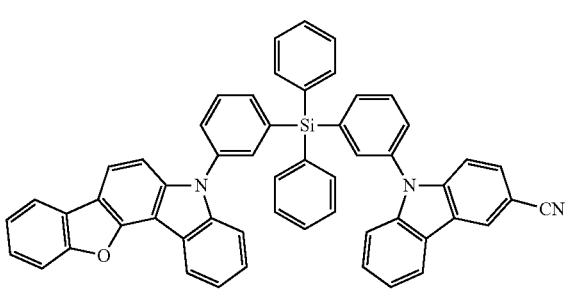
-continued
412
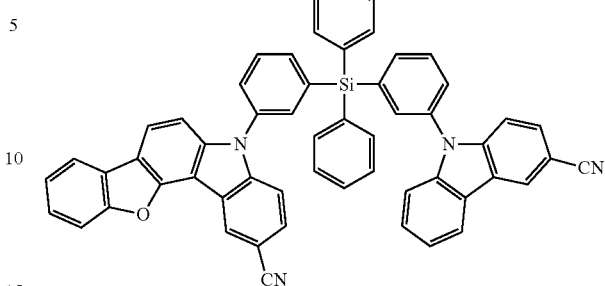
413
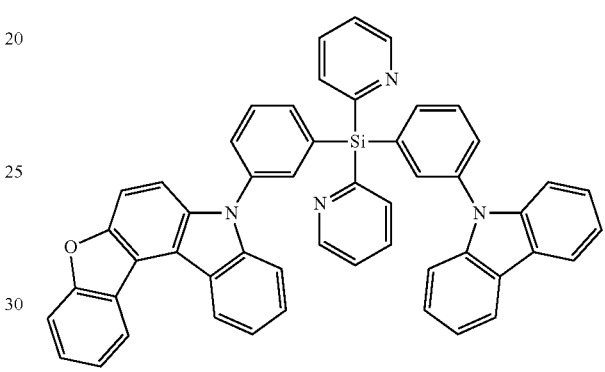
414
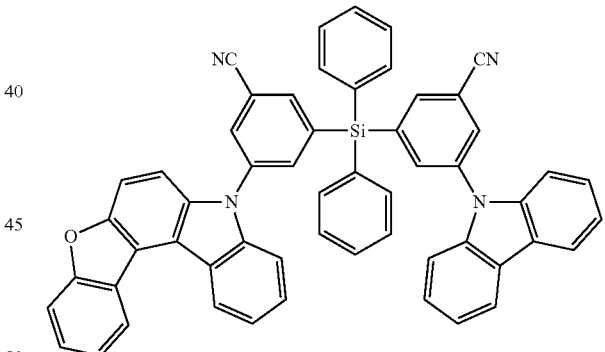
415
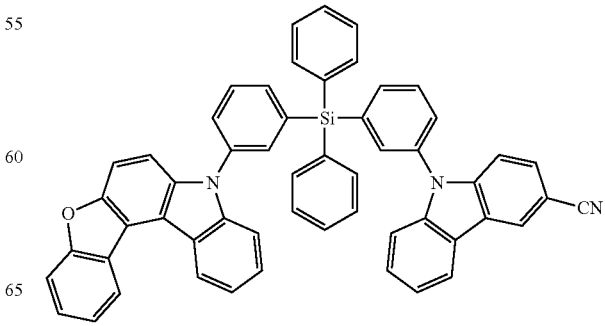

-continued
416
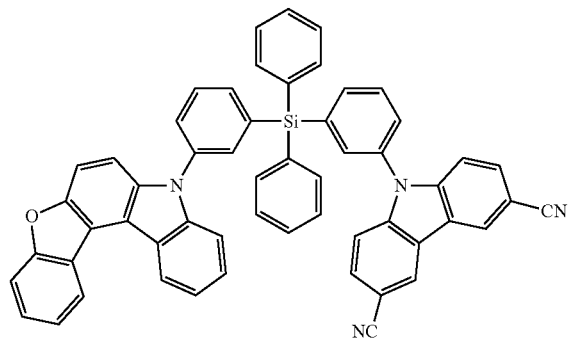
417
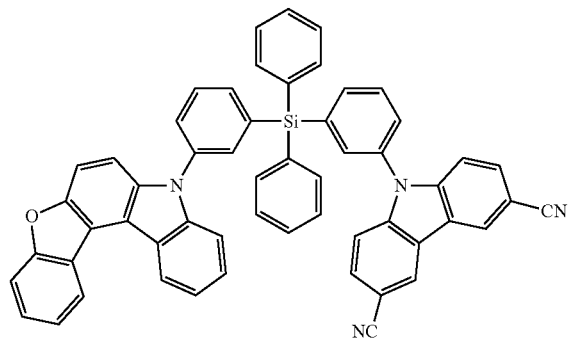
418
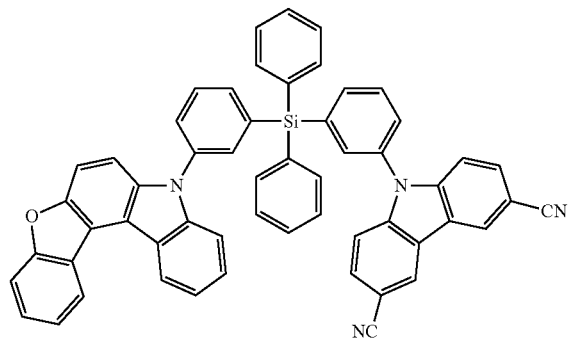
419
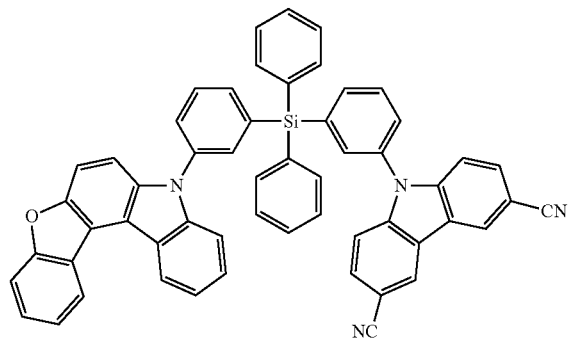
420
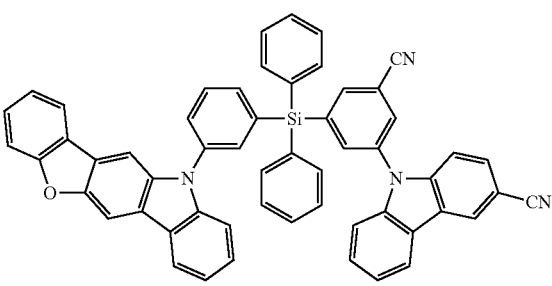
421
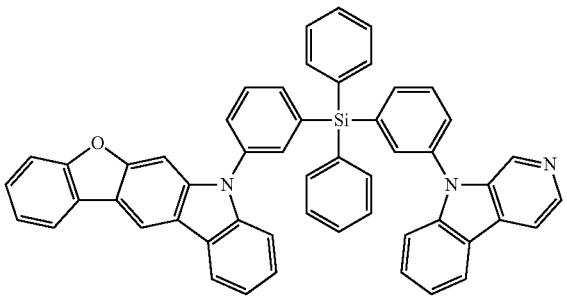
422
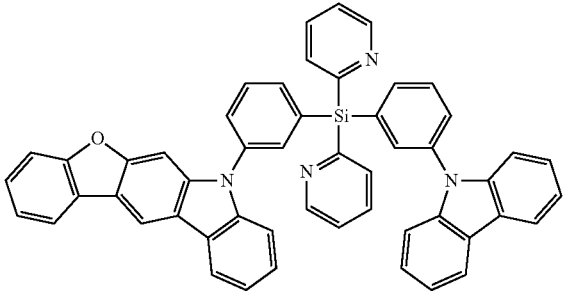
423
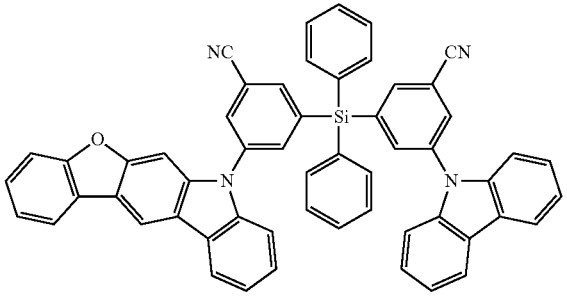
424
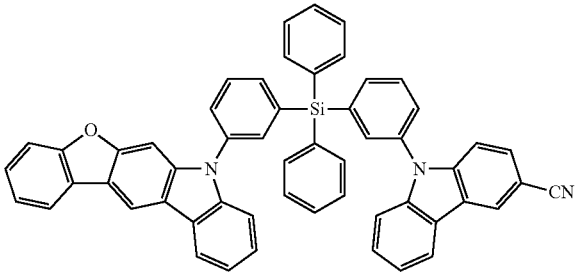

425

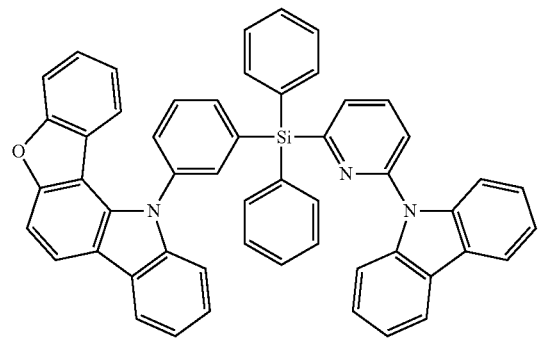

426

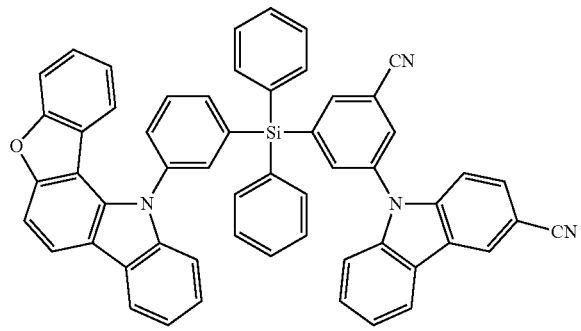

427

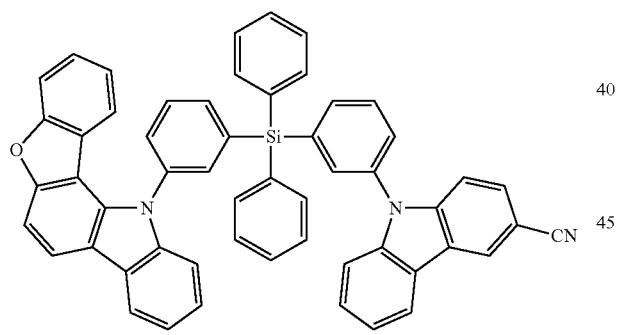

428

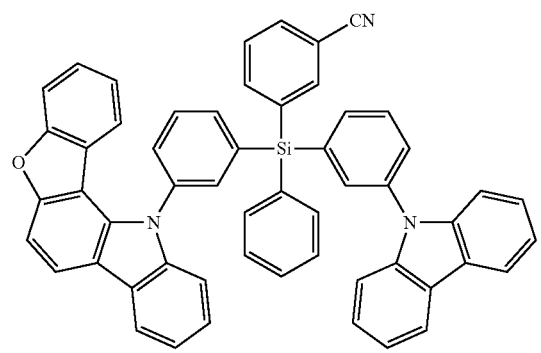

429

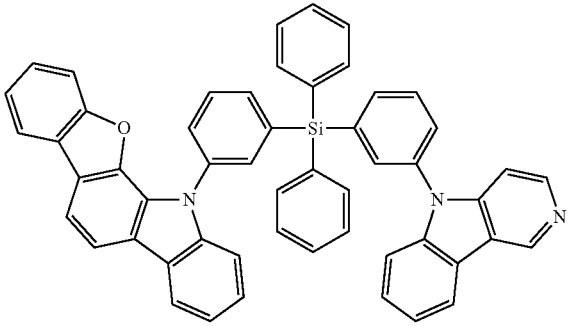

430

431

432 wherein, in Compounds 1 to 432,
Ph is a phenyl group.

The silyl group-containing compound represented by Formula 1 essentially includes "Si". Thus, a conjugation length of the silyl group-containing compound represented by Formula 1 may be adjusted and may have a high minimum excitation triplet energy level accordingly. For example, the silyl group-containing compound may have a minimum excitation triplet energy level of 2.8 electron volts (eV) or higher. Therefore, the silyl group-containing compound represented by Formula 1 may have high efficiency and a long lifespan.

Since the silyl group-containing compound represented by Formula 1 essentially includes a "condensed ring

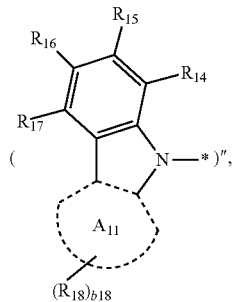

such as an indenocarbazole or an indolocarbazole, the silyl group-containing compound may have high thermal stability and high charge mobility. Therefore, the silyl group-containing compound represented by Formula 1 may have high efficiency and a long lifespan.

Since the silyl group-containing compound represented by Formula 1 may introduce various substituents into $R_{11}$ to $R_{13}$, it may allow to adjust the lowest unoccupied molecular orbital (LUMO) energy level and the highest occupied molecular orbital (HOMO) energy level of the silyl group-containing compound represented by Formula 1. Therefore, an organic light-emitting device including the silyl group-containing compound represented by Formula 1 may have high efficiency and a long lifespan.

Furthermore, since the silyl group-containing compound represented by Formula 1 essentially includes at least one "carbazole", the silyl group-containing compound represented by Formula 1 may have improved hole mobility characteristics. Also, since the silyl group-containing compound represented by Formula 1 includes a "condensed ring

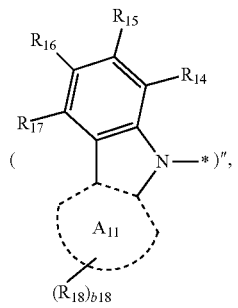

and a substituent, the silyl group-containing compound represented by Formula 1 may have improved electron mobility characteristics. That is, the silyl group-containing compound represented by Formula 1 may have improved hole mobility characteristics and may have bipolar characteristics. Therefore, an organic light-emitting device including the silyl group-containing compound represented by Formula 1 may have high efficiency and a long lifespan.

A HOMO energy level, a LUMO energy level, a minimum excitation triplet energy level ($T_1$), and a minimum excitation singlet energy level ($S_1$) of Compounds 1, 2, 17, 19, 21, 25, 26, 41, 43, 45, 49, 65, 69, 73, 97, 98, 113, 115, 117, 121, 338, 362, 386, A, and B were evaluated by a density functional theory (DFT) method of a Gaussian program (the structure was optimized at B3LYP/6-31G(d,p) level). Results thereof are shown in Table 1.

TABLE 1

| Compound No. | HOMO (eV) | LUMO (eV) | $T_1$ (eV) | $S_1$ (eV) |
| --- | --- | --- | --- | --- |
| 1 | −5.265 | −0.987 | 3.002 | 3.743 |
| 2 | −5.310 | −0.999 | 2.968 | 3.764 |
| 17 | −5.388 | −1.015 | 2.981 | 3.777 |
| 19 | −5.052 | −0.903 | 2.963 | 3.652 |
| 21 | −5.362 | −1.062 | 2.958 | 3.757 |
| 25 | −5.267 | −0.982 | 3.003 | 3.740 |
| 26 | −5.312 | −0.992 | 2.968 | 3.764 |
| 41 | −5.382 | −1.010 | 2.981 | 3.768 |
| 43 | −5.063 | −0.883 | 2.963 | 3.653 |
| 45 | −5.328 | −1.069 | 2.958 | 3.757 |
| 49 | −5.228 | −0.972 | 3.005 | 3.748 |
| 65 | −5.369 | −1.015 | 2.978 | 3.786 |
| 69 | −5.345 | −1.019 | 2.960 | 3.766 |
| 73 | −5.231 | −0.946 | 3.005 | 3.773 |
| 97 | −5.179 | −0.897 | 3.003 | 3.783 |
| 98 | −5.230 | −0.876 | 2.969 | 3.796 |
| 113 | −5.298 | −0.918 | 2.980 | 3.828 |
| 115 | −4.972 | −0.838 | 2.963 | 3.688 |
| 117 | −5.289 | −0.974 | 2.961 | 3.757 |
| 121 | −5.280 | −0.946 | 3.004 | 3.805 |
| 338 | −5.345 | −1.225 | 3.002 | 3.700 |
| 362 | −5.298 | −1.190 | 3.002 | 3.681 |
| 386 | −5.318 | −1.238 | 3.005 | 3.679 |
| A | −5.231 | −1.065 | 2.972 | 3.792 |
| B | −5.236 | −0.852 | 2.971 | 3.810 |

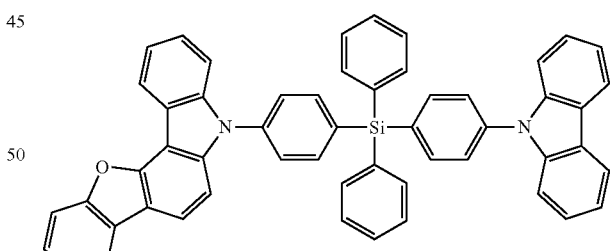

1

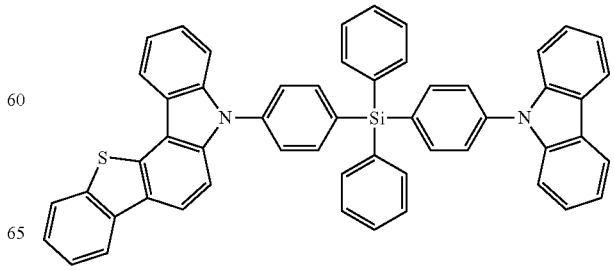

2

17
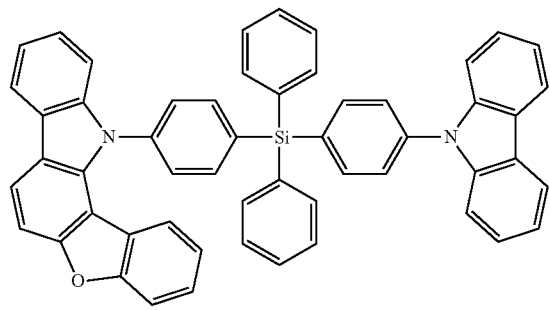
26
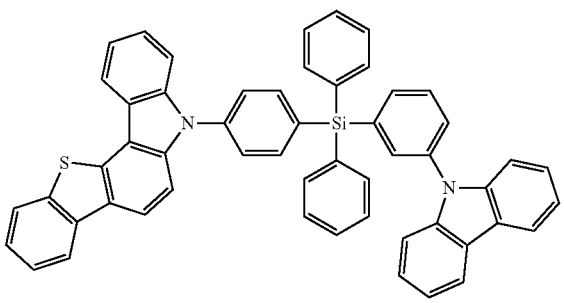
19
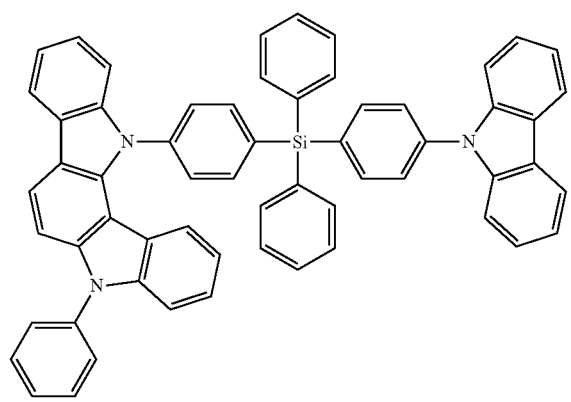
41
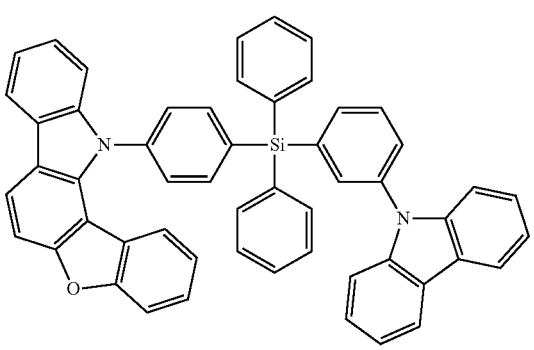
21
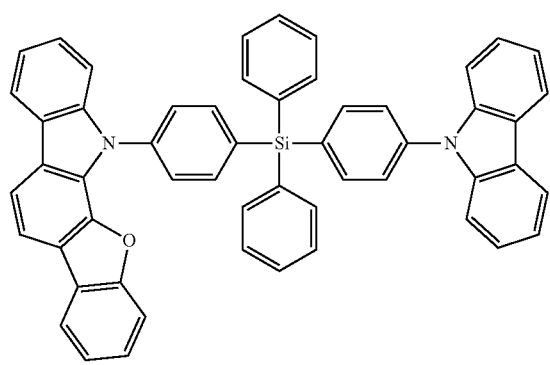
43
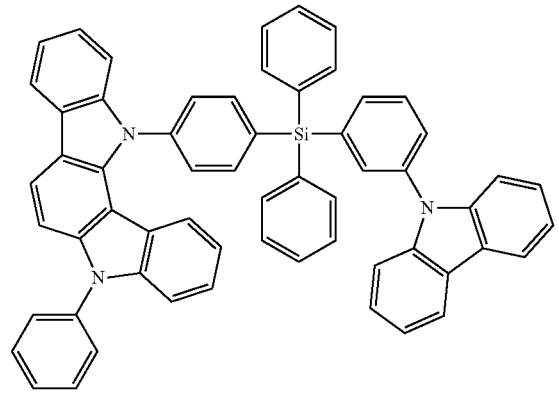
25
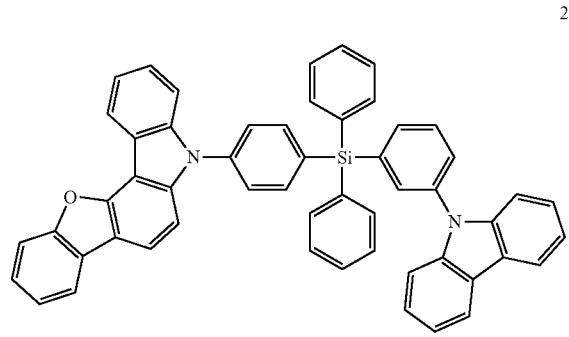
45
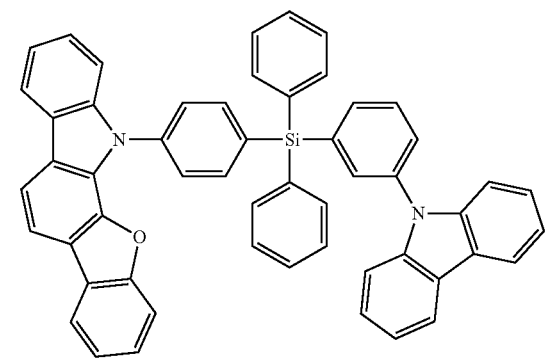

49
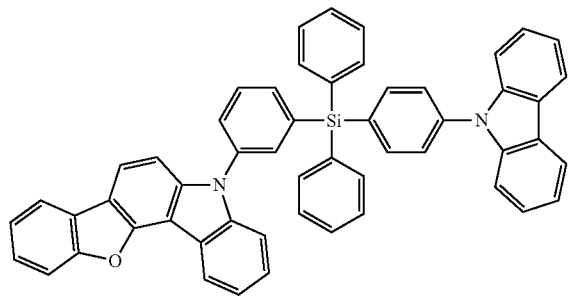
65
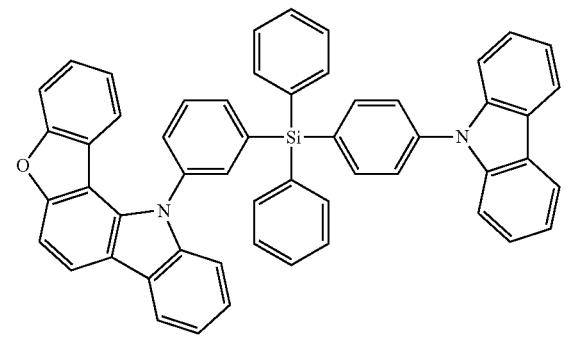
69
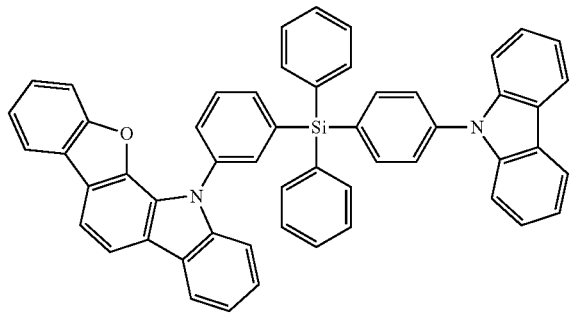
73
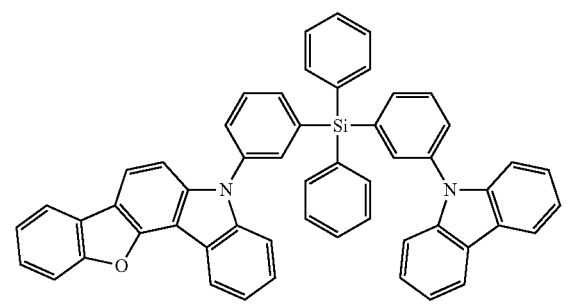
97
98
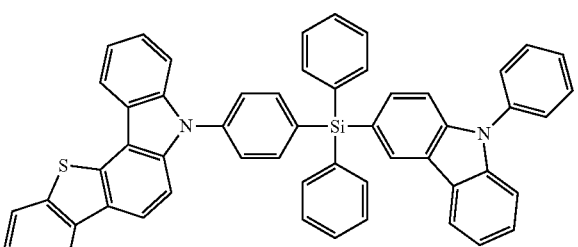
113
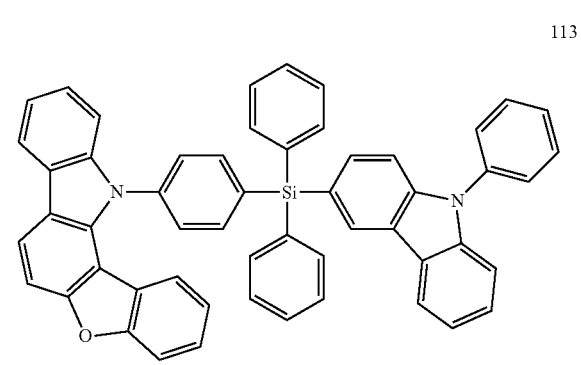
115
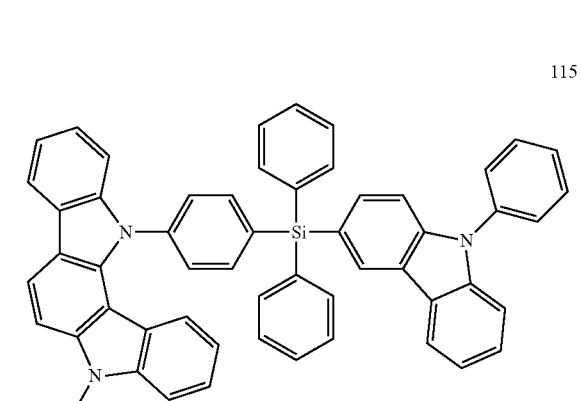
117
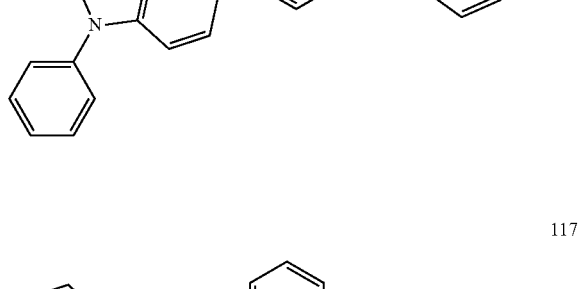

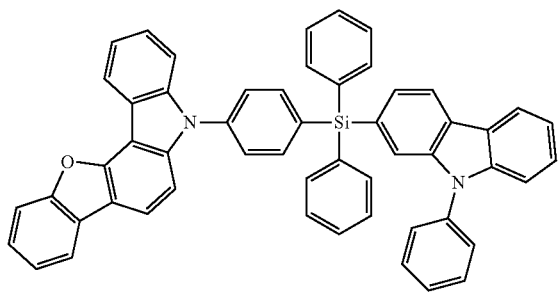

121

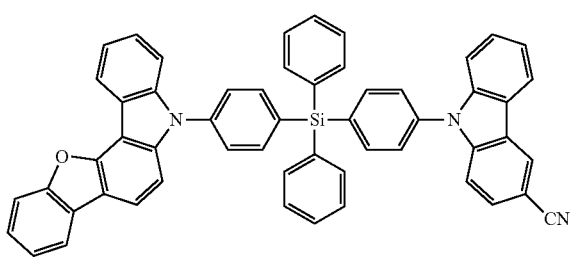

338

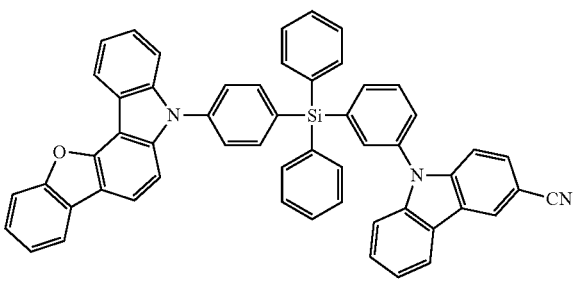

362

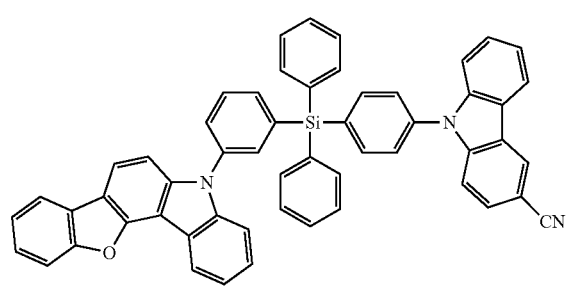

386

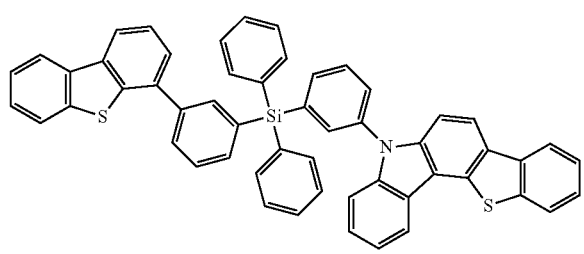

A

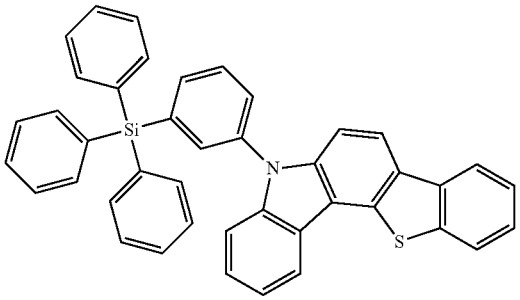

B

Synthesis methods of the silyl group-containing compound represented by Formula 1 may be recognizable by one of ordinary skill in the art by Synthesis Examples provided below.

Therefore, the silyl group-containing compound represented by Formula 1 is suitable for use in an organic layer of an organic light-emitting device, for example, for use as a material for a host or a hole transport region of an emission layer in the organic layer.

According to one or more exemplary embodiments, an organic light-emitting device may include:

a first electrode;
a second electrode; and
an organic layer disposed between the first electrode and the second electrode, wherein the organic layer includes an emission layer, and
wherein the organic layer includes at least one of the silyl group-containing compounds represented by Formula 1.

The organic light-emitting device may have, due to the inclusion of an organic layer including the silyl group-containing compound represented by Formula 1, a low driving voltage, high efficiency, high luminance, high quantum emission efficiency, and a long lifespan.

The silyl group-containing compound represented by Formula 1 may be used between a pair of electrodes of the organic light-emitting device. For example, the silyl group-containing compound may be included in at least one of the emission layer, the hole transport region disposed between the first electrode and the emission layer (for example, the hole injection layer, the hole transport layer, the electron blocking layer, or any combination thereof), and the electron transport region disposed between the emission layer and the second electrode (for example, the hole blocking layer, the electron transport layer, the electron injection layer, or any combination thereof).

For example, the silyl group-containing compound represented by Formula 1 may be included in the emission layer. In this regard, the silyl group-containing compound included in the emission layer may act as a host, and the emission layer may further include a dopant (a fluorescent dopant or a phosphorescent dopant). The emission layer may be a blue emission layer that emits blue light.

In one or more exemplary embodiments, the silyl group-containing compound represented by Formula 1 may be included in the emission layer, the emission layer may further include a phosphorescent dopant, and the emission layer may emit blue light.

In one or more exemplary embodiments, the emission layer may include a host and a dopant, and the host may include the silyl group-containing compound represented by Formula 1. An amount of the host is larger than an amount of the dopant.

In one or more exemplary embodiments, the silyl group-containing compound represented by Formula 1 may be included in the hole transport region.

In one or more exemplary embodiments, the hole transport region may include a hole transport layer, and the hole transport layer may include the silyl group-containing compound.

In one or more exemplary embodiments, the hole transport region may include a hole transport layer and an electron blocking layer, the electron blocking layer may be disposed between the hole transport layer and the emission layer, and the electron blocking layer may include the silyl group-containing compound represented by Formula 1.

In one or more exemplary embodiments, the hole transport region may include a hole transport layer and an electron blocking layer. The electron blocking layer may be disposed between the hole transport layer and the emission layer. Each of the electron blocking layer and the emission layer may include the silyl group-containing compound represented by Formula 1. The silyl group-containing compound represented by Formula 1 and included in the electron blocking layer, and the silyl group-containing compound represented by Formula 1 and included in the emission layer, may be identical to or different from each other.

The expression "(an organic layer) may include at least one of the silyl group-containing compounds" as used herein may include an embodiment in which (an organic layer) includes identical silyl group-containing compounds represented by Formula 1 and an embodiment in which (an organic layer) includes two or more different silyl group-containing compounds represented by Formula 1.

For example, the organic layer may include only Compound 1 as the silyl group-containing compound. In this regard, Compound 1 may be included only in the emission layer of the organic light-emitting device. In one or more exemplary embodiments, the organic layer may include, as the silyl group-containing compound, Compound 1 and Compound 2. In this regard, Compound 1 and Compound 2 may be included in an identical layer (for example, Compound 1 and Compound 2 all may be included in an emission layer), or may be included in different layers (for example, Compound 1 may be included in an emission layer and Compound 2 may be included in an electron blocking layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

For example, the first electrode may be an anode, and the second electrode may be a cathode, and the organic layer may include: i) a hole transport region disposed between the first electrode and the emission layer, wherein the hole transport region may include at least one selected from a hole injection layer, a hole transport layer, and an electron blocking layer, and ii) an electron transport region disposed between the emission layer and the second electrode, wherein the electron transport region may include at least one selected from a hole blocking layer, an electron transport layer, and an electron injection layer.

The term "organic layer" as used herein refers to a single layer and/or a plurality of layers disposed between the first electrode and the second electrode of the organic light-emitting device. The "organic layer" may include, in addition to an organic compound, an organometallic complex including metal.

FIG. 1 is a schematic view of an organic light-emitting device 10 according to an exemplary embodiment. Hereinafter, the structure of an organic light-emitting device according to an exemplary embodiment and a method of manufacturing an organic light-emitting device according to an exemplary embodiment will be described in connection with FIG. 1. The organic light-emitting device 10 includes a first electrode 11, an organic layer 15, and a second electrode 19, which are sequentially stacked in this stated order.

A substrate may be additionally disposed under the first electrode 11 or over the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

In one or more exemplary embodiments, the first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be an indium tin oxide (ITO), an indium zinc oxide (IZO), tin oxide ($SnO_2$), or zinc oxide (ZnO). In one or more exemplary embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 may be disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or a combination thereof.

The hole transport region may include only either a hole injection layer or a hole transport layer. In one or more exemplary embodiments, the hole transport region may have a hole injection layer/hole transport layer structure or a hole injection layer/hole transport layer/electron blocking layer structure, or a hole transport layer/electron blocking layer structure, wherein, in each structure, constituting layers are sequentially stacked in this stated order from the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary depending on a material used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec. However, the deposition conditions are not limited thereto.

When the hole injection layer is formed using spin coating, coating conditions may vary depending on the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202:

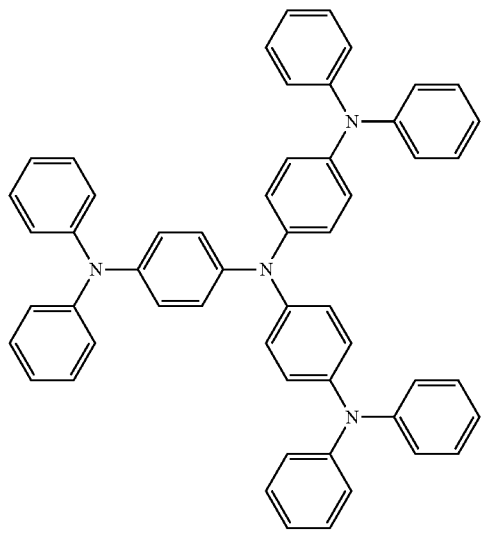

TDATA

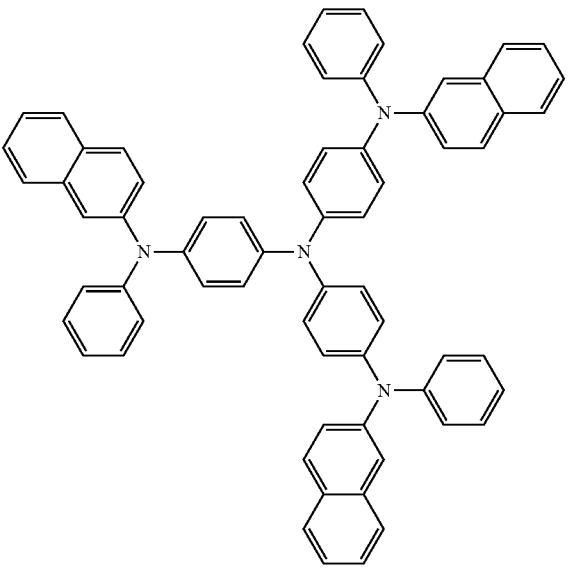

2-TNATA

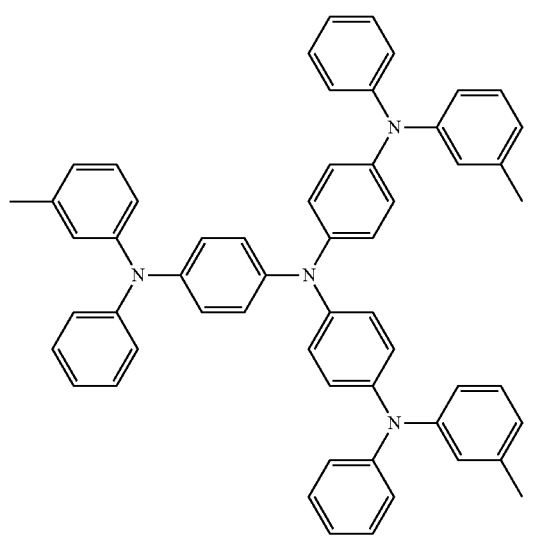

m-MTDATA

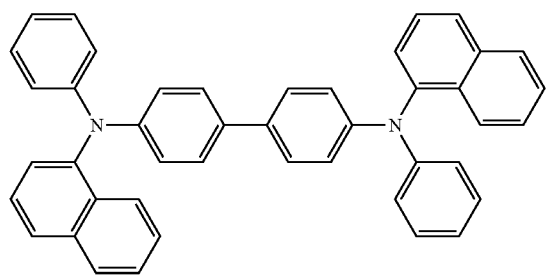

NPB

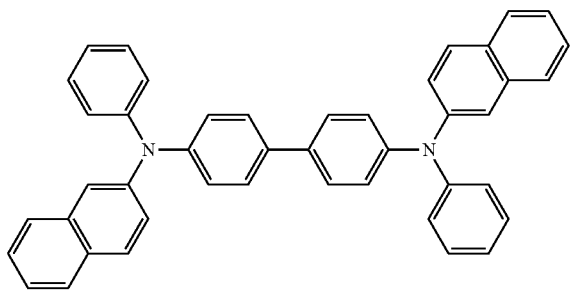

β-NPB

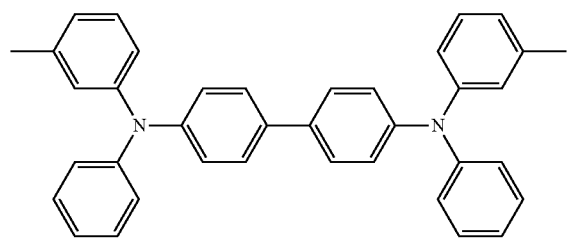

TPD

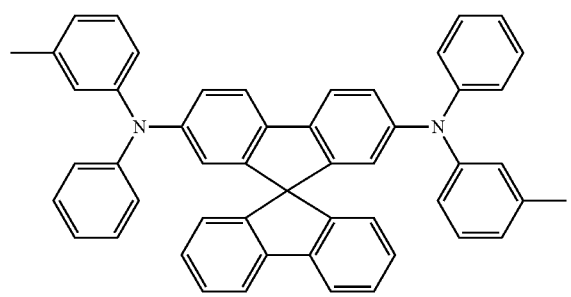

Spiro-TPD

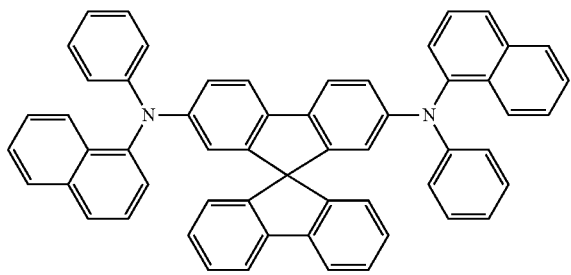

Spiro-NPB

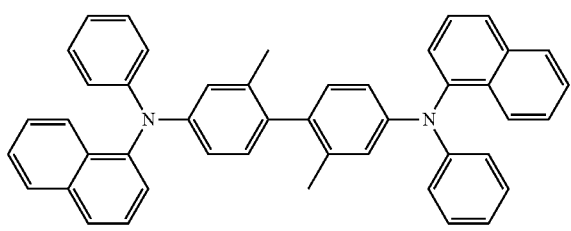

methylated NPB

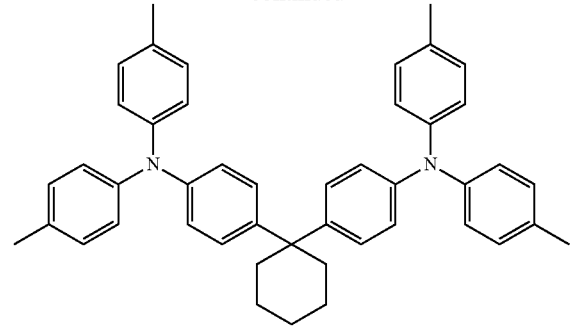

TAPC

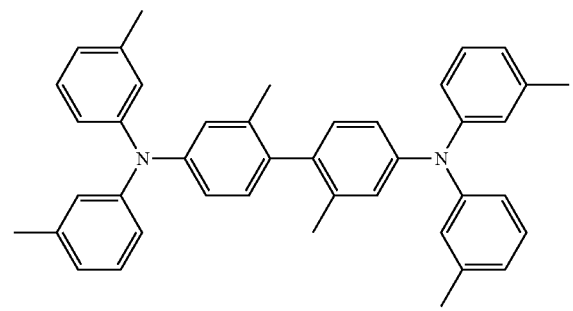

HMTPD

Formula 201

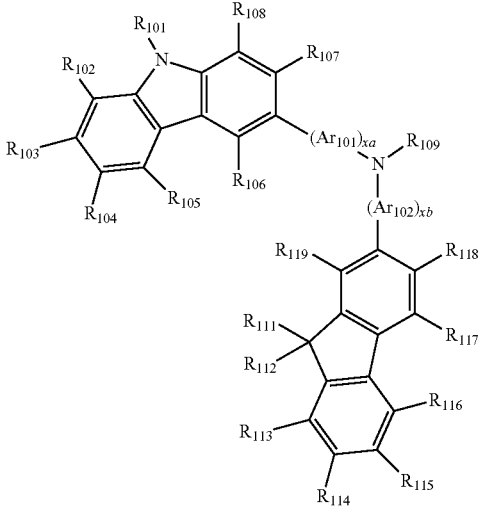

Formula 202

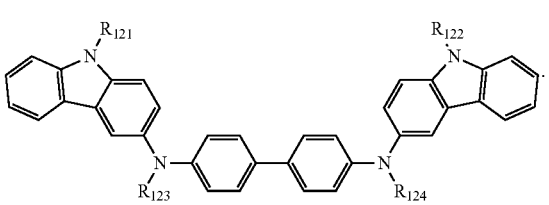

$Ar_{101}$ and $Ar_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

xa and xb in Formula 201 may each independently be an integer selected from 0 to 5, or 0, 1, or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but exemplary embodiments are not limited thereto.

$R_{109}$ in Formula 201 may be selected from:
a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an exemplary embodiment, the compound represented by Formula 201 may be represented by Formula 201A below, but is not limited thereto:

Formula 201A

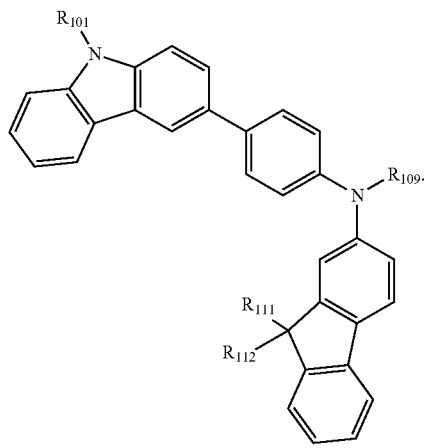

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

HT1

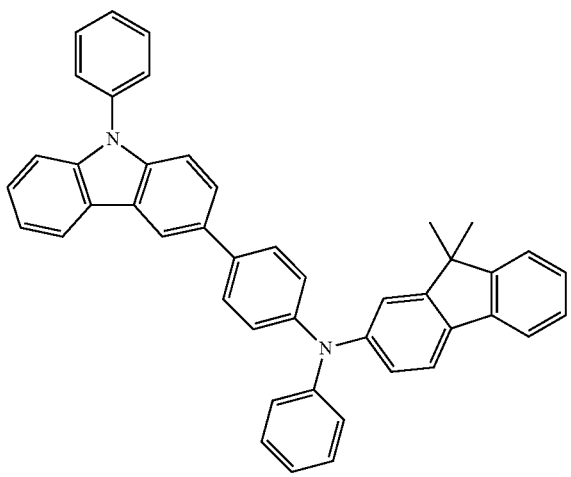

177
-continued
HT2
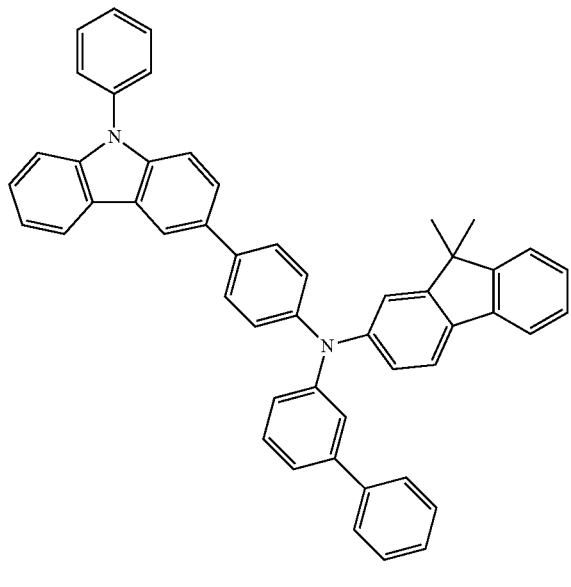
178
-continued
HT4
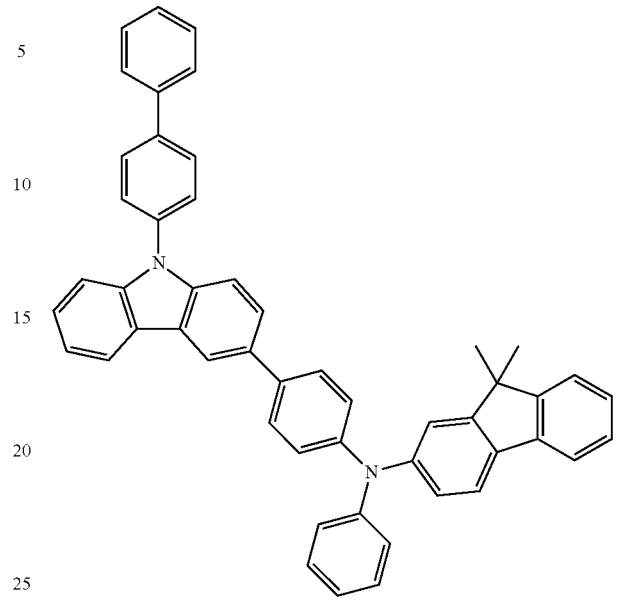
HT3
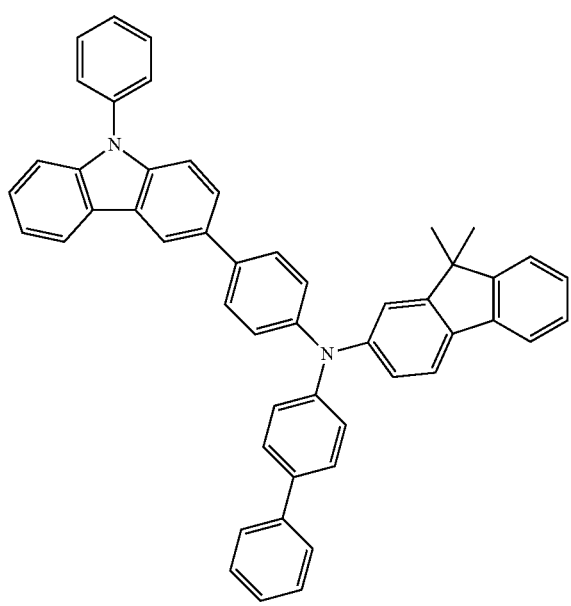
HT5
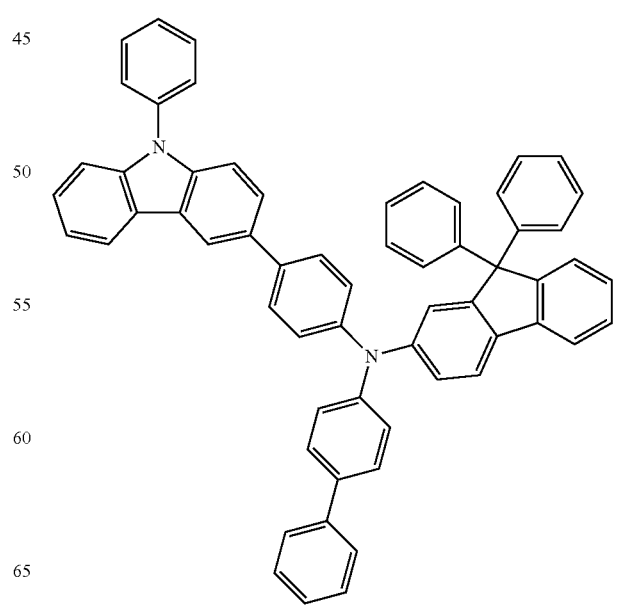

HT6
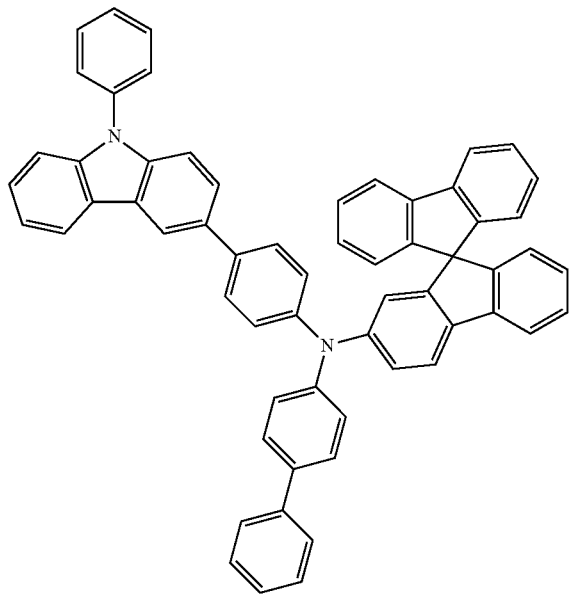
HT7
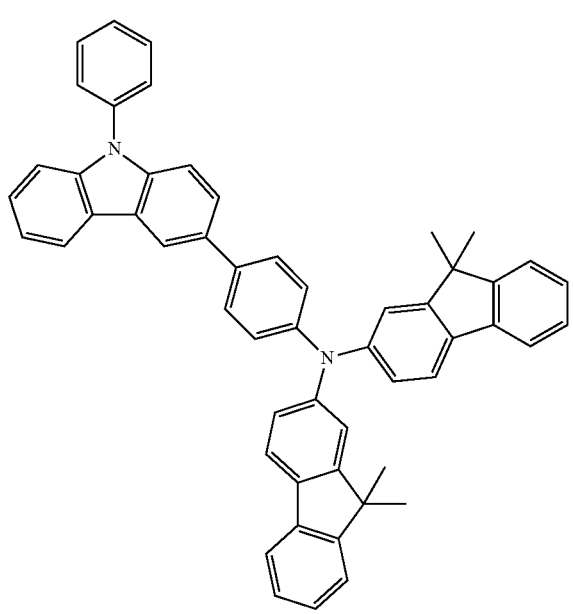
HT8
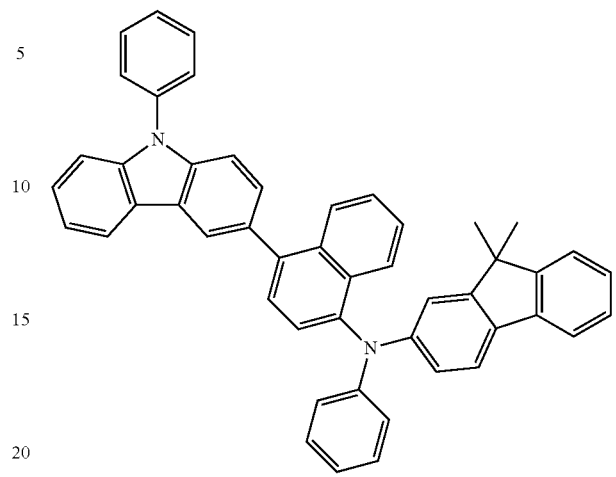
HT9
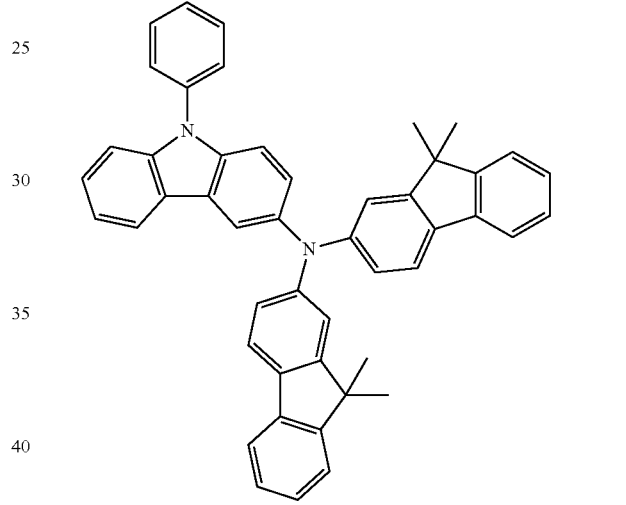
HT10
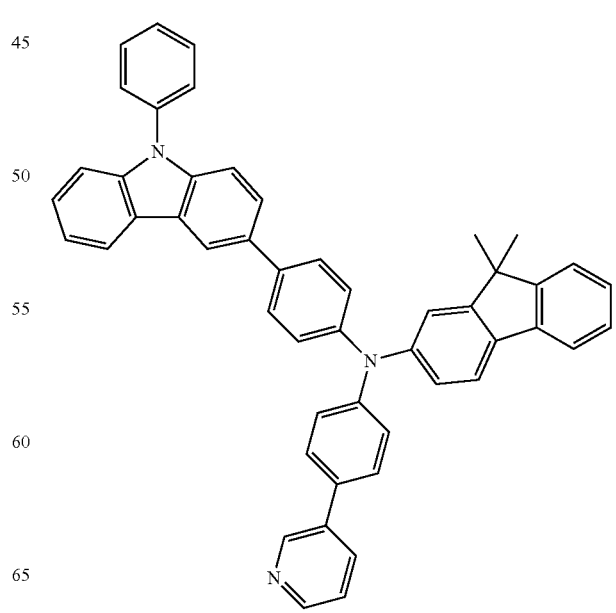

HT11
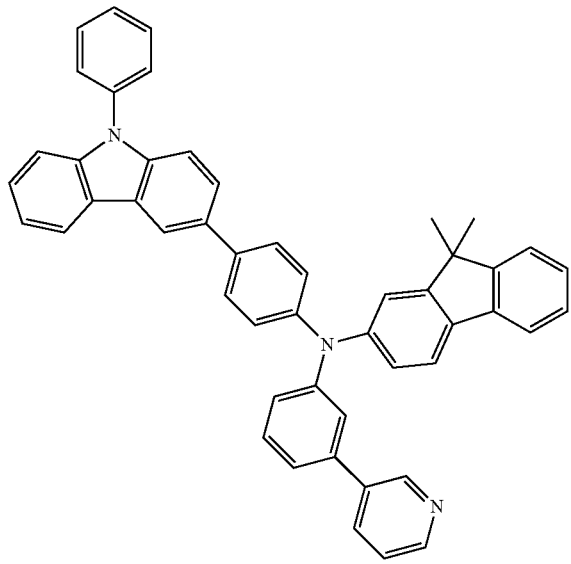
HT12
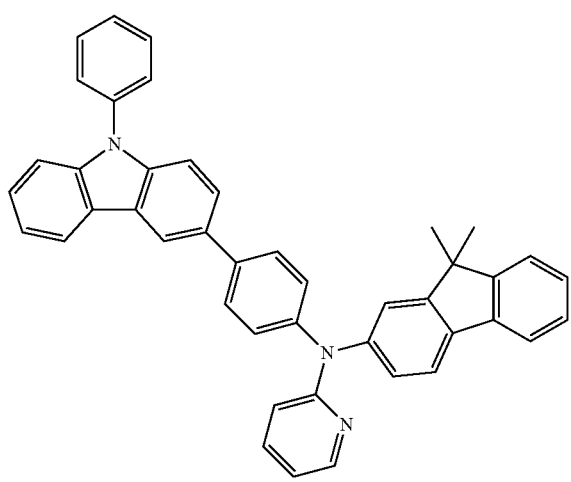
HT13
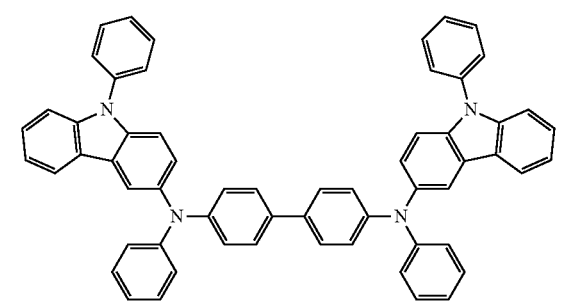
HT14
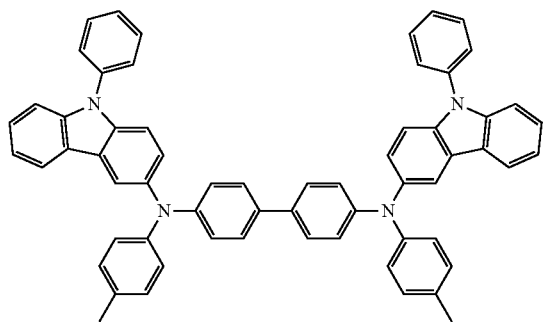
HT15
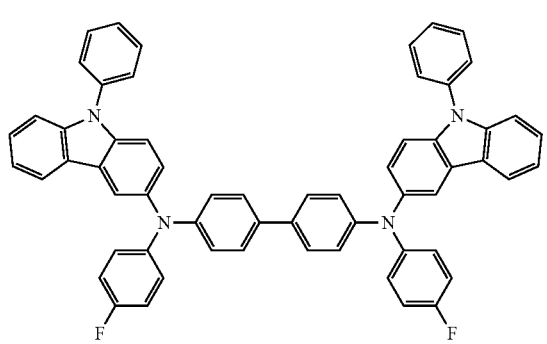
HT16
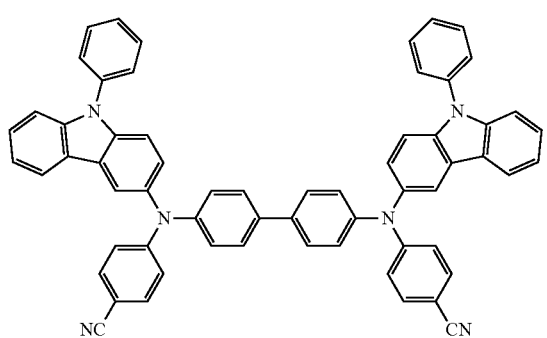
HT17
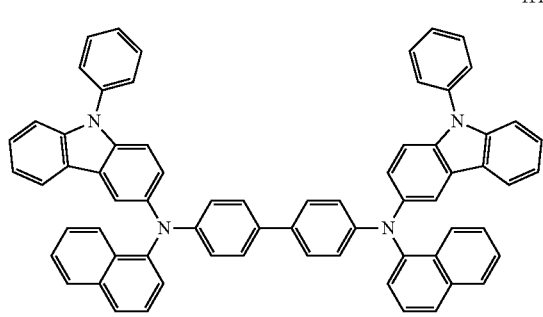

-continued

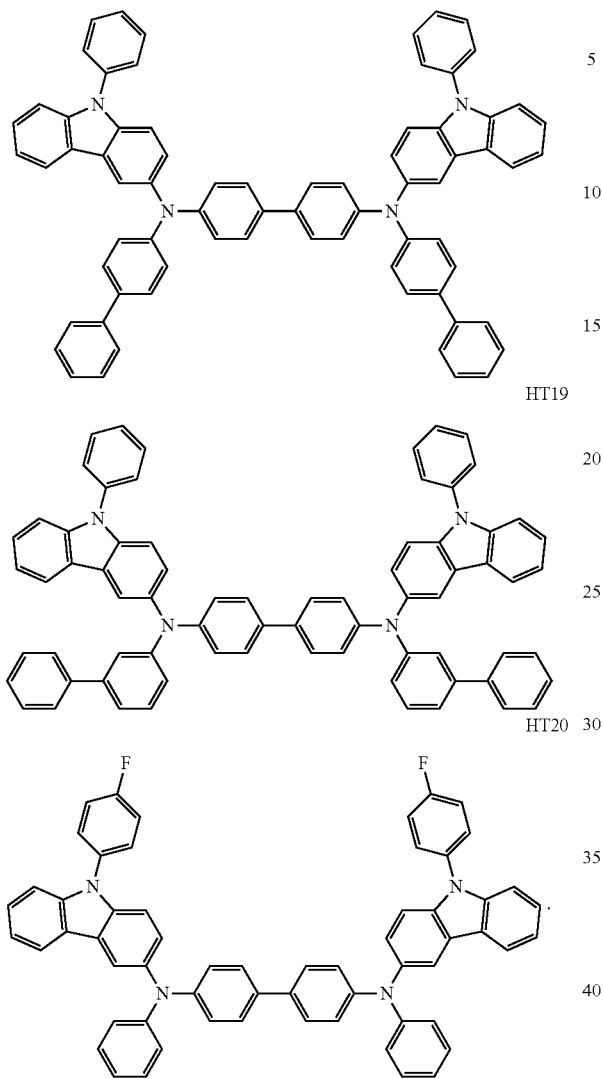

HT18

HT19

HT20

A thickness of the hole transport region may be in a range of about 100 Angstroms (Å) to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for improving conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but exemplary embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or HP-1, but are not limited thereto.

Compound HT-D1

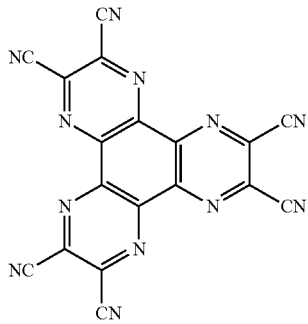

F4-TCNQ

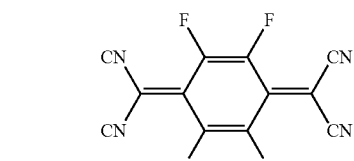

HP-1

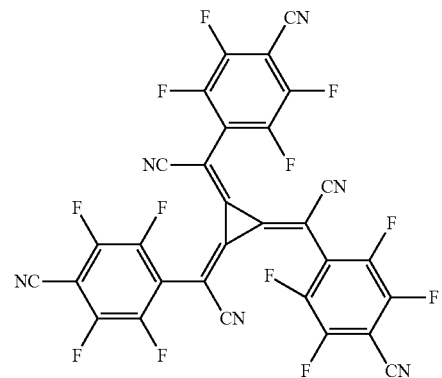

The hole transport region may include a buffer layer.

The buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer, although the deposition or coating conditions may vary according to the material that is used to form the emission layer.

The electron transport region may further include an electron blocking layer. The electron blocking layer may include, for example, mCP, but a material included in the electron blocking layer is not limited thereto.

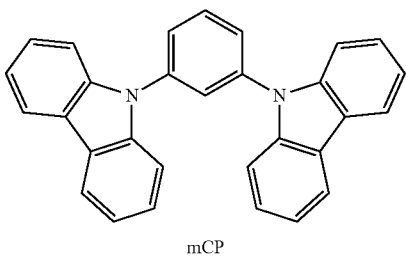 [SMILES: c1cc(-n2c3ccccc3c3ccccc32)cc(-n2c3ccccc3c3ccccc32)c1]

mCP

In one or more exemplary embodiments, the electron blocking layer may include the silyl group-containing compound represented by Formula 1, but exemplary embodiments of the present disclosure are not limited thereto.

When the organic light-emitting device is a full color organic light-emitting device, the emission layer may be patterned into a red emission layer, a green emission layer, and a blue emission layer. In one or more exemplary embodiments, due to a stack structure including a red emission layer, a green emission layer, and/or a blue emission layer, the emission layer may emit white light.

The emission layer may include the silyl group-containing compound represented by Formula 1. The emission layer may include a dopant. The dopant may include at least one selected from a phosphorescent dopant and a fluorescent dopant.

For example, a host in the emission layer may include the silyl group-containing compound represented by Formula 1.

In one or more exemplary embodiments, the host in the emission layer may include a first host and a second host, and the first host may be the silyl group-containing compound represented by Formula 1. In this regard, the first host may be different from the second host.

A dopant in the emission layer may be a fluorescent dopant that emits light according to a fluorescent emission mechanism or a phosphorescent dopant that emits light according to a phosphorescent emission mechanism.

In one or more exemplary embodiment, the dopant in the emission layer may be a phosphorescent dopant, and the phosphorescent dopant may include an organometallic compound represented by Formula 81 below:

Formula 81
$$M(L_{81})_{n81}(L_{82})_{n82}$$

Formula 81A

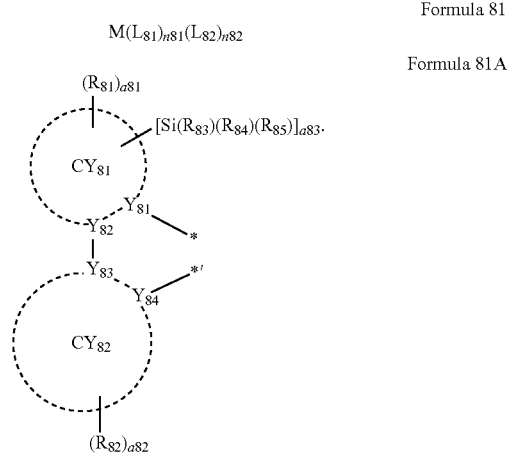

In Formulae 81 and 81A,

M may be selected from iridium (Ir), platinum (Pt), osmium (Os), titanium (Ti), zirconium (Zr), hafnium (Hf), europium (Eu), terbium (Tb), thulium (Tm), and rhodium (Rh), $L_{81}$ may be a ligand represented by Formula 81A, and n81 may be an integer from 1 to 3, wherein, when n81 is 2 or more, 2 or more groups $L_{81}$ may be identical to or different from each other, $L_{82}$ may be an organic ligand, and n82 may be an integer from 0 to 4, wherein, when n82 is 2 or more, 2 or more groups $L_{82}$ may be identical to or different from each other, $Y_{81}$ to $Y_{84}$ may each independently be carbon (C) or nitrogen (N), $Y_{81}$ and $Y_{82}$, and $Y_{83}$ and $Y_{84}$, may be each independently be linked to each other via a single bond or a double bond, $CY_{81}$ and $CY_{82}$ may each independently be selected from a $C_5$-$C_{30}$ carbocyclic group and a $C_3$-$C_{30}$ heterocarbocyclic group, $CY_{81}$ and $CY_{82}$ may optionally be linked via an organic linking group, $R_{81}$ to $R_{85}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_8$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_{81})(Q_{82})(Q_{83})$, —$N(Q_{84})(Q_{85})$, —$B(Q_{86})(Q_{87})$, and —$P(=O)(Q_{88})(Q_{89})$, a81 to a83 may each independently be an integer from 0 to 5, when a81 is two or more, two or more groups $R_{81}$ may be identical to or different from each other, a82 is two or more, and two or more groups $R_{82}$ may be identical to or different from each other, a81 is two or more, and neighboring groups $R_{81}$ may optionally be linked to form a saturated or unsaturated ring, a82 is two or more, and neighboring groups $R_{82}$ may optionally be linked to form a saturated or unsaturated ring,

* and *' in Formula 81A each indicate a binding site to M in Formula 81, at least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_8$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycycdic group, and —Si($Q_{91}$)($Q_{92}$)($Q_{93}$), wherein $Q_{81}$ to $Q_{89}$ and $Q_{91}$ to $Q_{93}$ may each independently be selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In one or more exemplary embodiments, in Formula 81A, a83 may be 1 or 2, $R_{83}$ to $R_{85}$ may each independently be selected from: —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group, but exemplary embodiments are not limited thereto.

In one or more exemplary embodiments, in Formula 81A, $Y_{81}$ may be nitrogen, $Y_{82}$ and $Y_{83}$ may each be carbon, $Y_{84}$ may be nitrogen or carbon, $CY_{81}$ and $CY_{82}$ may each independently be selected from a cyclopentadiene group, a benzene group, a heptalene group, an indene group, a naphthalene group, azulene group, a heptalene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentacene group, a hexacene group, a rubicene group, a corozene group, an ovalene group, a pyrrole group, an iso-indole group, an indole group, an indazole group, a pyrazole group, an imidazole group, a triazole group, an oxazole group, an isoxazole group, an oxadiazole group, a thiazole group, an isothiazole group, thiadiazol group, a purine group, a furan group, a thiophene group, a pyridine group, a pyrimidine group, a quinoline group, an isoquinoline group, a benzoquinoline group, a phthalazine group, naphthyridine group, a quinoxaline group, a quinazoline group, a cinnoline group, a phenanthridine group, an acridine group, phenanthroline group, phenazine group, a benzimidazole group, a benzofuran group, a benzothiophene group, an iso-benzothiazole group, a benzoxazole group, an isobenzoxazole group, benzocarbazole group, dibenzocarbazole group, an imidazopyridine group, an imidazopyrimidine group, a dibenzofuran group, a dibenzothiophene group, a dibenzothiophene sulfone group, a carbazole group, a dibenzosilole group, and a 2,3-dihydro-1H-imidazole.

In one or more exemplary embodiments, in Formula 81A, $Y_{81}$ may be nitrogen, $Y_{82}$ to $Y_{84}$ may be carbon, $CY_{81}$ may be a five-membered ring having two nitrogen atoms as a ring-forming atom, and $CY_{82}$ may be selected from a benzene group, a naphthalene group, a fluorene group, a dibenzofuran group, and a dibenzothiophene group, but exemplary embodiments of the present disclosure are not limited thereto.

In one or more exemplary embodiments, in Formula 81A, $Y_{81}$ may be nitrogen, $Y_{82}$ to $Y_{84}$ may each be carbon, $CY_{81}$ may be an imidazole or a 2,3-dihydro-1H-imidazole, and $CY_{82}$ may be selected from a benzene group, a naphthalene group, a fluorene group, a dibenzofuran group, and a dibenzothiophene group, but exemplary embodiments of the present disclosure are not limited thereto.

In one or more exemplary embodiments, in Formula 81A, $Y_{81}$ may be nitrogen, and $Y_{82}$ to $Y_{84}$ may be carbon, $CY_{81}$ may be selected from a pyrrole group, a pyrazole group, an imidazole group, a triazole group, an oxazole group, an isoxazole group, an oxadiazole group, a thiazole group, an isothiazole group, thiadiazol group, a pyridine group, a pyrimidine group, a quinoline group, an isoquinoline group, a benzoquinoline group, a phthalazine group, naphthyridine group, a quinoxaline group, a quinazoline group, a cinnoline group, a benzimidazole group, an isobenzothiazole group, a benzoxazole group, and an isobenzoxazole group, $CY_{82}$ may be selected from cyclopentadiene group, a benzene group, a naphthalene group, a fluorene group, a benzofluorene group, a dibenzofluorene group, a phenanthrene group, an anthracene group, a triphenylene group, a pyrene group, a chrysene group, a perylene group, a benzofuran group, a benzothiophene group, benzocarbazole group, dibenzocarbazole group, a dibenzofuran group, a dibenzothiophene group, a dibenzothiophene sulfone group, a carbazole group, and a dibenzosilole.

In one or more exemplary embodiments, in Formula 81A, $R_{81}$ and $R_{82}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —$B(Q_{86})(Q_{87})$ and —$P(=O)(Q_{88})(Q_{89})$, wherein $Q_{86}$ to $Q_{89}$ may each independently be selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

In one or more exemplary embodiments, $R_{81}$ and $R_{82}$ in Formula 81A may each independently be selected from:

hydrogen, deuterium, —F, a cyano group, a nitro group, —$SF_5$, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group; and —$B(Q_{86})(Q_{87})$ and —$P(=O)(Q_{88})(Q_{89})$, wherein $Q_{86}$ to $Q_{89}$ may each independently be selected from:

—CH₃, —CD₃, —CD₂H, —CDH₂, —CH₂CH₃, —CH₂CD₃, —CH₂CD₂H, —CH₂CDH₂, —CHDCH₃, —CHDCD₂H, —CHDCDH₂, —CHDCD₃, —CD₂CD₃, —CD₂CD₂H, and —CD₂CDH₂;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

In one or more exemplary embodiments, $R_{81}$ and $R_{82}$ in Formula 81A may each independently be selected from hydrogen, deuterium, —F, a cyano group, a nitro group, —SF₅, —CH₃, —CD₃, —CD₂H, —CDH₂, —CF₃, —CF₂H, —CFH₂, a group represented by one of Formulae 9-1 to 9-19, and a group represented by one of Formulae 10-1 to 10-30, but exemplary embodiments of the present disclosure are not limited thereto:

Formula 9-1

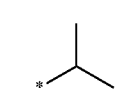
Formula 9-2

Formula 9-3

Formula 9-4

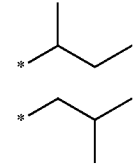
Formula 9-5

Formula 9-6

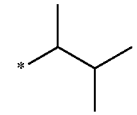
Formula 9-7

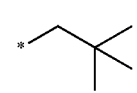
Formula 9-8

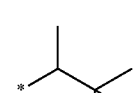
Formula 9-9

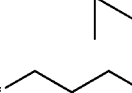
Formula 9-10

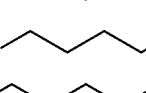
Formula 9-11

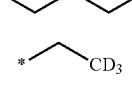
Formula 9-12

Formula 9-13

-continued

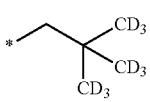
Formula 9-14

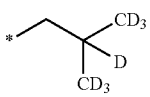
Formula 9-15

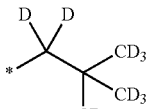
Formula 9-16

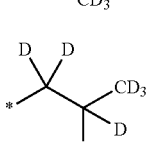
Formula 9-17

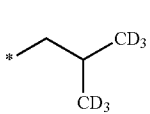
Formula 9-18

Formula 9-19

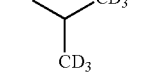
Formula 10-1

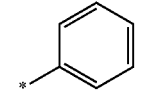
Formula 10-2

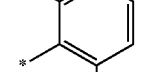
Formula 10-3

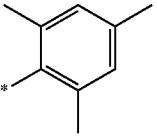
Formula 10-4

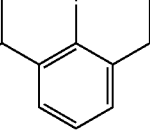
Formula 10-5

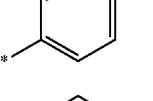
Formula 10-6

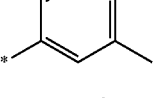
Formula 10-7

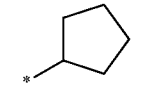

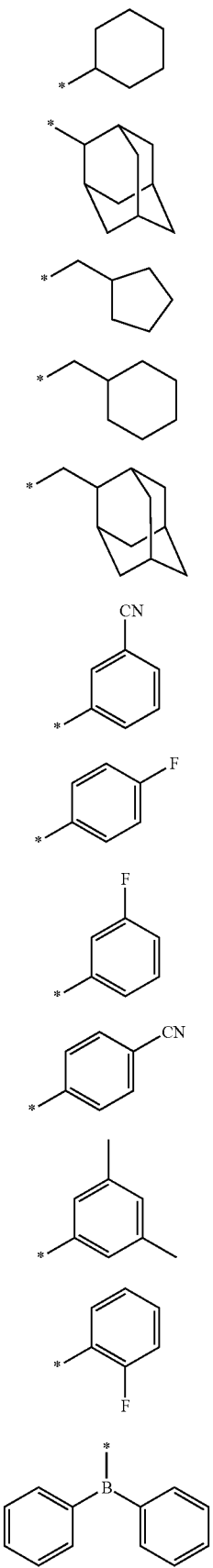

Formula 10-30

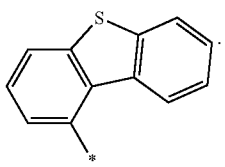

In Formulae 9-1 to 9-17 and 10-1 to 10-30, * indicates a binding site to a neighboring atom.

In one or more exemplary embodiments, in Formula 81A, the sum of a81 and a82 may be 1 or more, and at least one selected from groups $R_{81}$ in the number of a81 and $R_{82}$ in the number of a82 may be a cyano group.

In one or more exemplary embodiments, a82 may be 1 or more, and at least one of groups $R_{82}$ in the number of a82 may be a cyano group.

In one or more exemplary embodiments, at least one selected from groups $R_{81}$ in the number of a81 and groups $R_{82}$ in the number of a82 in Formula 81A may be deuterium. In one or more exemplary embodiments, $L_{82}$ in Formula 81 may be selected from ligands represented by Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114):

Formula 3-1(1)

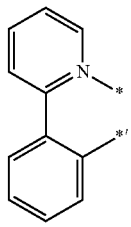

Formula 3-1(2)

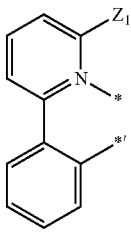

Formula 3-1(3)

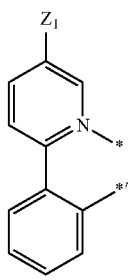

Formula 3-1(4)

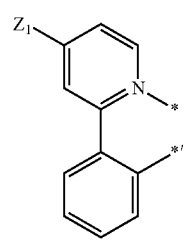

Formula 3-1(5)

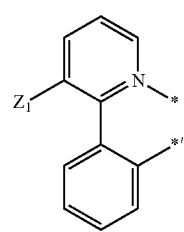

Formula 3-1(6)

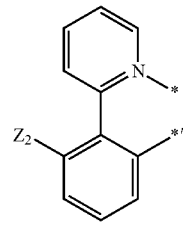

Formula 3-1(7)

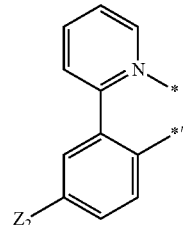

Formula 3-1(8)

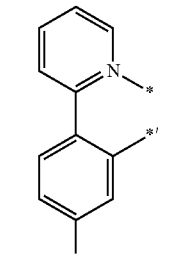

Formula 3-1(9)

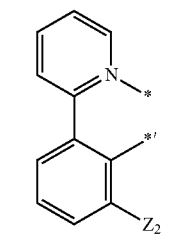

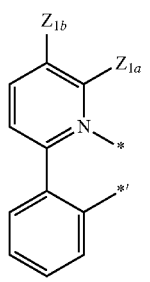 Formula 3-1(10)
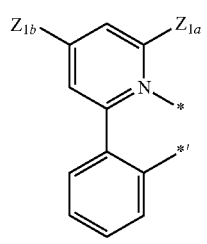 Formula 3-1(11)
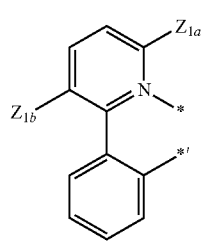 Formula 3-1(12)
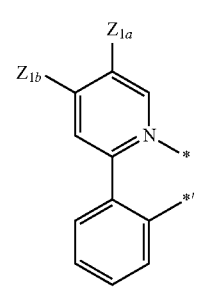 Formula 3-1(13)
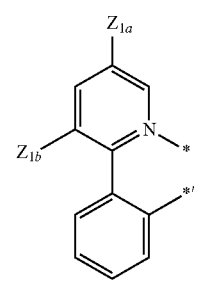 Formula 3-1(14)
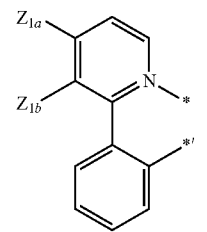 Formula 3-1(15)
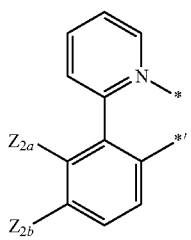 Formula 3-1(16)
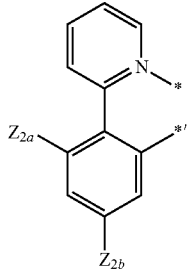 Formula 3-1(17)
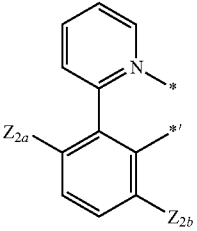 Formula 3-1(18)
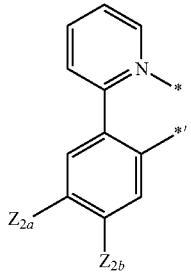 Formula 3-1(19)
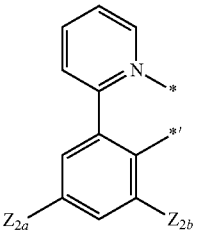 Formula 3-1(20)
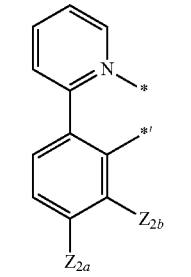 Formula 3-1(21)

-continued
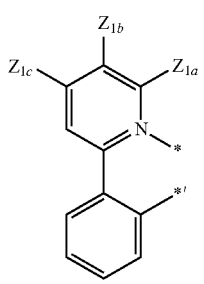
Formula 3-1(22)
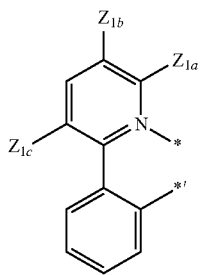
Formula 3-1(23)
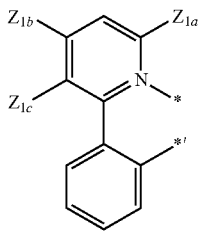
Formula 3-1(24)
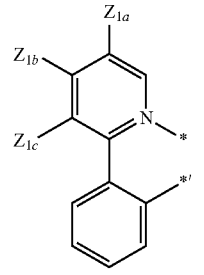
Formula 3-1(25)
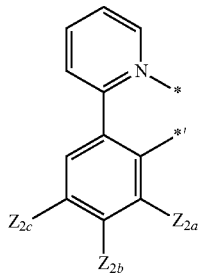
Formula 3-1(26)
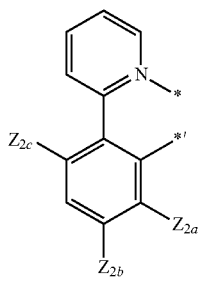
Formula 3-1(27)
-continued
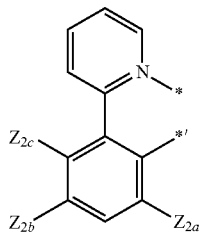
Formula 3-1(28)
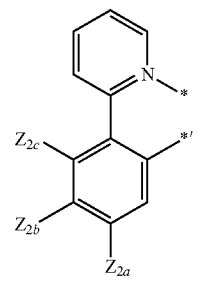
Formula 3-1(29)
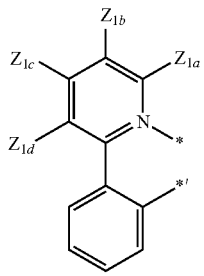
Formula 3-1(30)
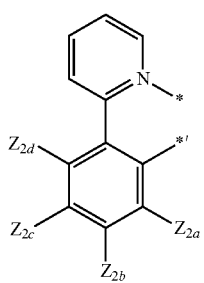
Formula 3-1(31)
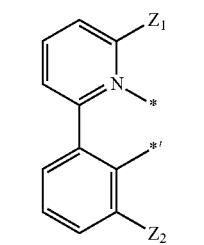
Formula 3-1(32)
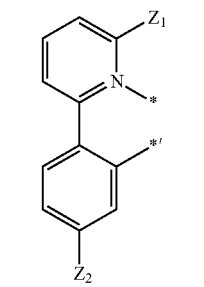
Formula 3-1(33)

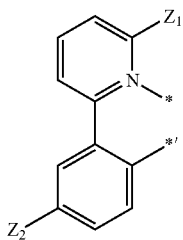
Formula 3-1(34)
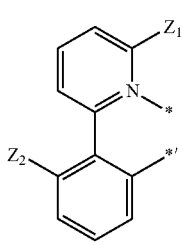
Formula 3-1(35)
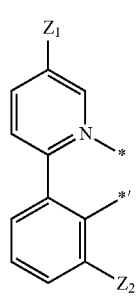
Formula 3-1(36)
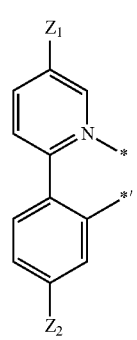
Formula 3-1(37)
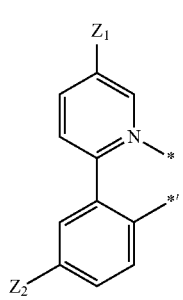
Formula 3-1(38)
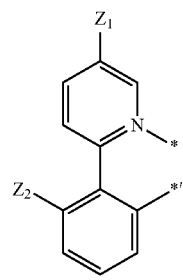
Formula 3-1(39)
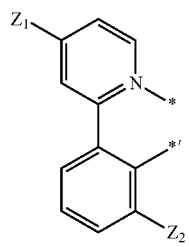
Formula 3-1(40)
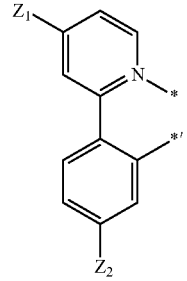
Formula 3-1(41)
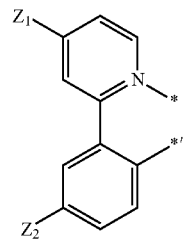
Formula 3-1(42)
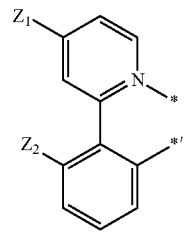
Formula 3-1(43)
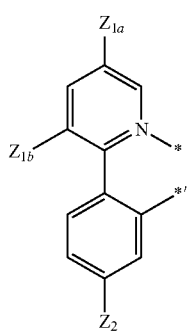
Formula 3-1(44)

Formula 3-1(45)
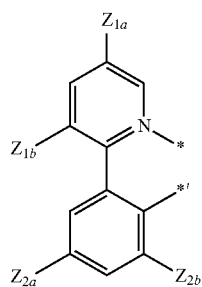
Formula 3-1(46)
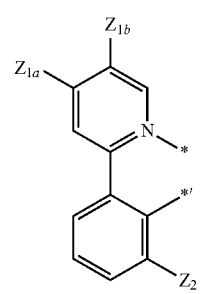
Formula 3-1(47)
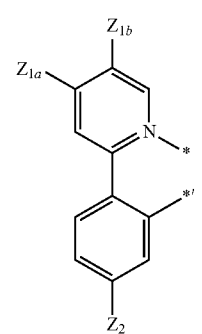
Formula 3-1(48)
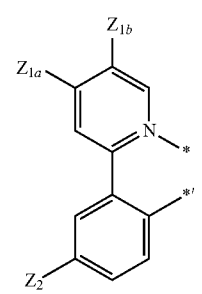
Formula 3-1(49)
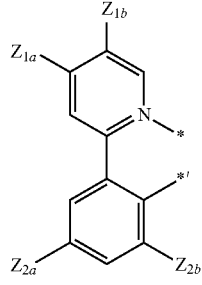
Formula 3-1(50)
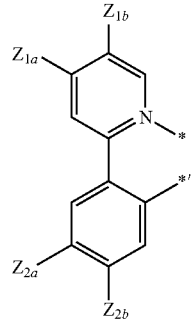
Formula 3-1(51)
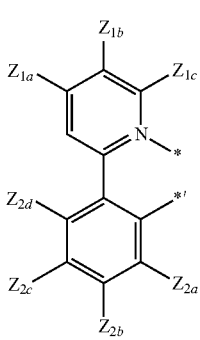
Formula 3-1(52)
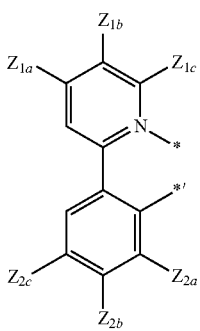
Formula 3-1(53)
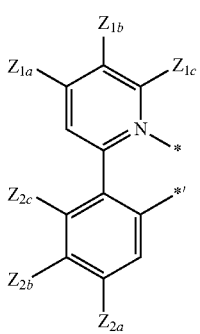
Formula 3-1(54)
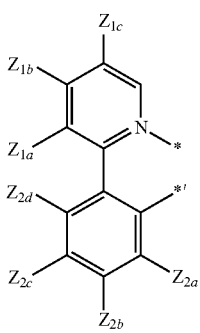

205
-continued
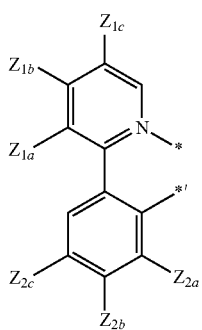
Formula 3-1(55)
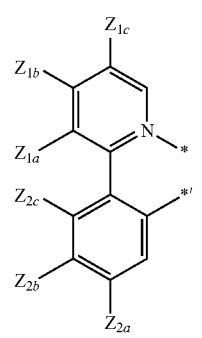
Formula 3-1(56)
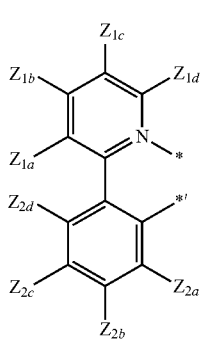
Formula 3-1(57)
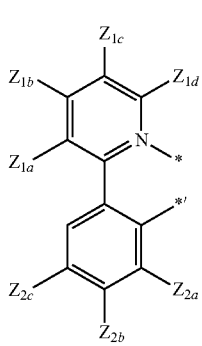
Formula 3-1(58)
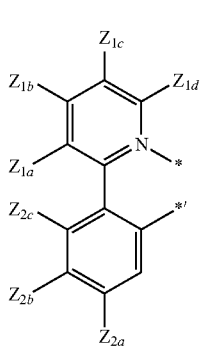
Formula 3-1(59)
206
-continued
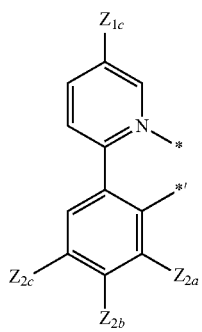
Formula 3-1(60)
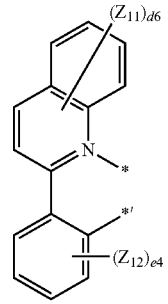
Formula 3-1(61)
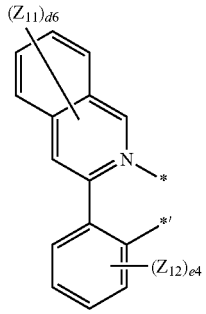
Formula 3-1(62)
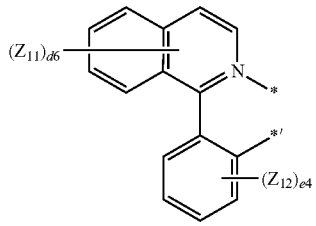
Formula 3-1(63)
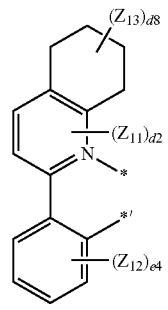
Formula 3-1(64)

Formula 3-1(65) 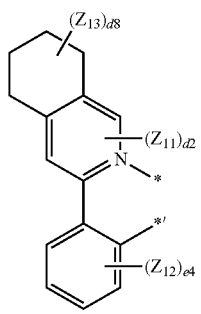
Formula 3-1(66) 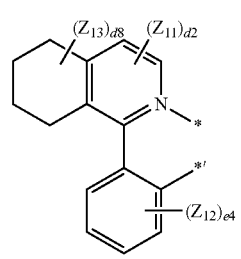
Formula 3-1(67) 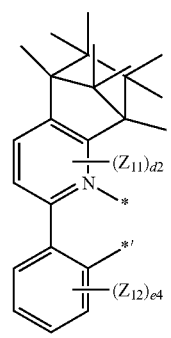
Formula 3-1(68) 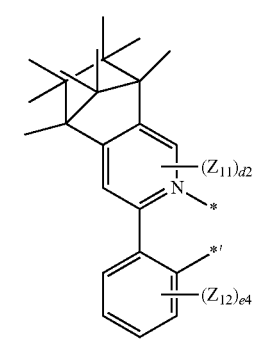
Formula 3-1(69) 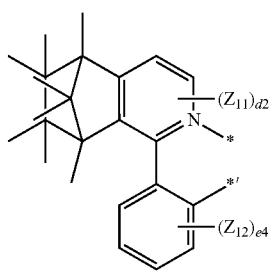
Formula 3-1(71) 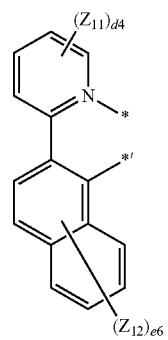
Formula 3-1(72) 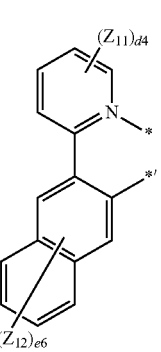
Formula 3-1(73) 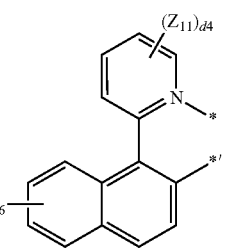
Formula 3-1(74) 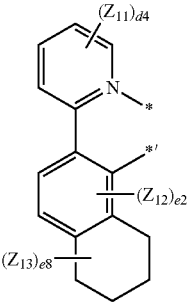
Formula 3-1(75) 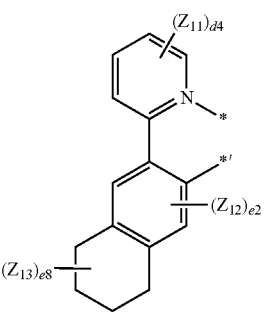

Formula 3-1(76)
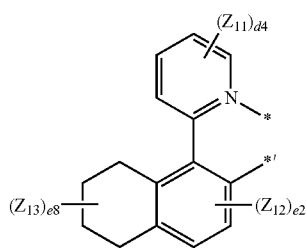
Formula 3-1(77)
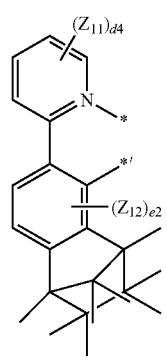
Formula 3-1(78)
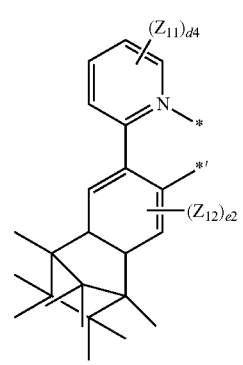
Formula 3-1(79)
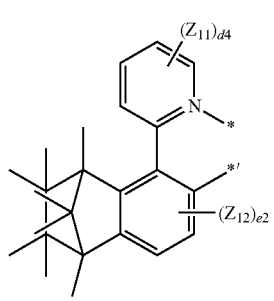
Formula 3-1(81)
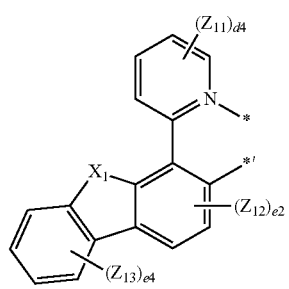
Formula 3-1(82)
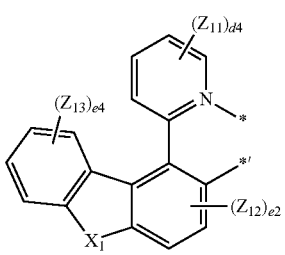
Formula 3-1(83)
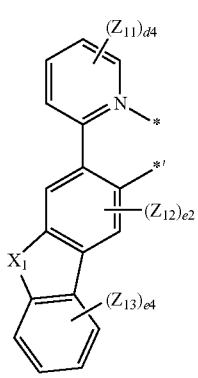
Formula 3-1(84)
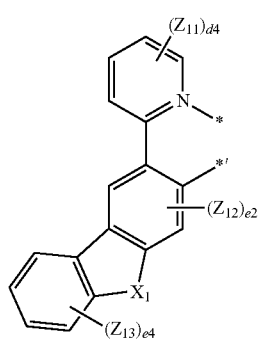
Formula 3-1(85)
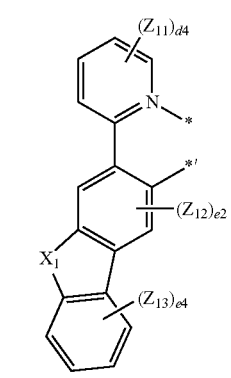

-continued
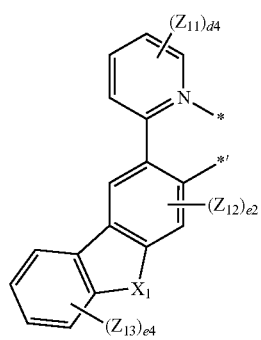
Formula 3-1(86)
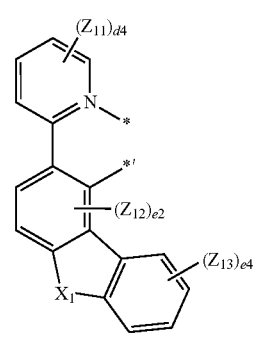
Formula 3-1(87)
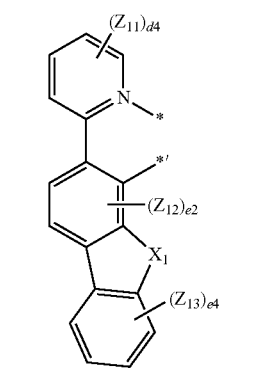
Formula 3-1(88)
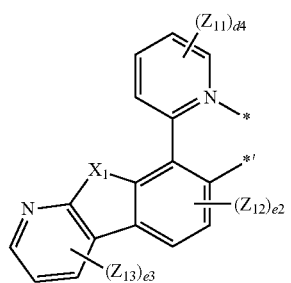
Formula 3-1(91)
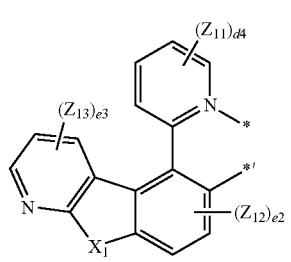
Formula 3-1(92)
-continued
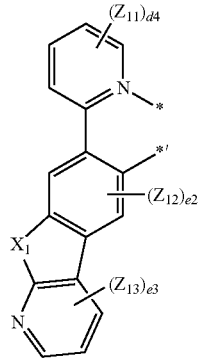
Formula 3-1(93)
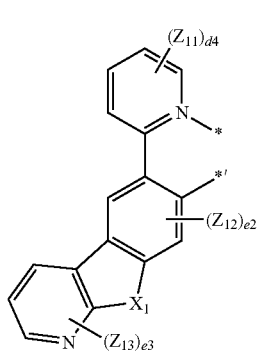
Formula 3-1(94)
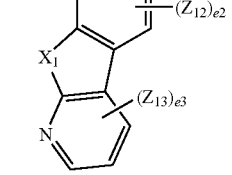
Formula 3-1(95)
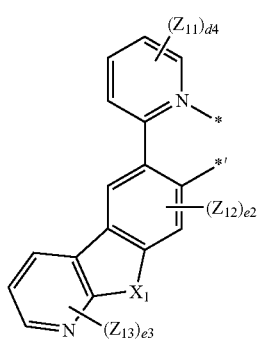
Formula 3-1(96)

-continued

Formula 3-1(97)

Formula 3-1(98)

Formula 3-1(101)

Formula 3-1(102)

Formula 3-1(103)

Formula 3-1(104)

Formula 3-1(105)

-continued

Formula 3-1(106)

Formula 3-1(107)

Formula 3-1(108)

Formula 3-1(109)

Formula 3-1(110)

Formula 3-1(111)

Formula 3-1(112)

Formula 3-1(113)

Formula 3-1(114)

In Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114), $X_1$ may be O, S, $C(Z_{21})(Z_{22})$, or $N(Z_{23})$, $X_{31}$ may be N or $C(Z_{1a})$, and $X_{32}$ may be N or $C(Z_{1b})$, $X_{41}$ may be O, S, $N(Z_{1a})$ or $C(Z_{1a})(Z_{1b})$, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B($Q_{86}$)($Q_{87}$) and —P(=O)($Q_{88}$)($Q_{89}$), wherein $Q_{86}$ to $Q_{89}$ may each independently be selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a C$_1$-C$_{10}$ alkyl group, and a phenyl group, d2 and e2 may each independently be 0 or 2, e3 may be an integer from 0 to 3, d4 and e4 may each independently be an integer from 0 to 4, d6 and e6 may each independently be an integer from 0 to 6, d8 and e8 may each independently be an integer from 0 to 8, and

* and *' each indicate a binding site to M in Formula 1.

For example, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ may each independently be selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, a group represented by one of Formulae 9-1 to 9-19, and a group represented by one of Formulae 10-1 to 10-30, but exemplary embodiments of the present disclosure are not limited thereto.

In one or more exemplary embodiments, M in Formula 81 may be Ir, and the sum of n81 and n82 may be 3; or M may be Pt, and the sum of n81 and n82 may be 2.

In one or more exemplary embodiments, the organometallic compound represented by Formula 81 may not be a salt consisting of a cation and an anion, but may be neutral.

The phosphorescent dopant may include at least one selected from Compounds PD1 to PD78 and FIr6, but exemplary embodiments of the present disclosure are not limited thereto:

PD1
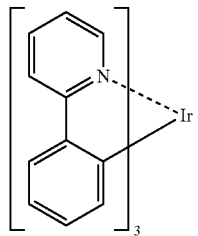

PD2
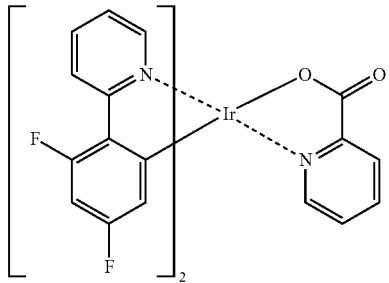

PD3
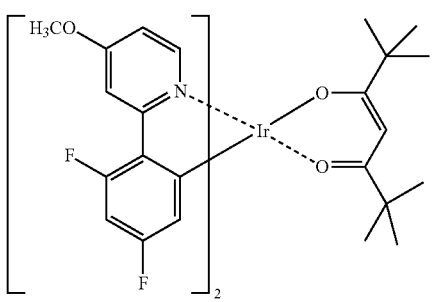

PD4
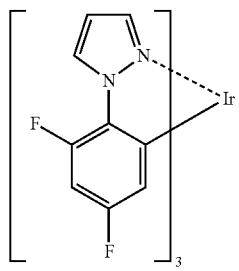

PD5
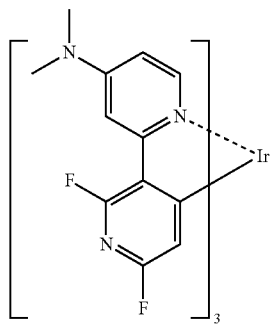

PD6
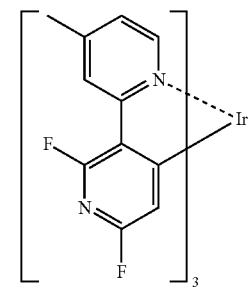

PD7
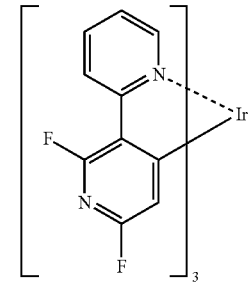

PD8
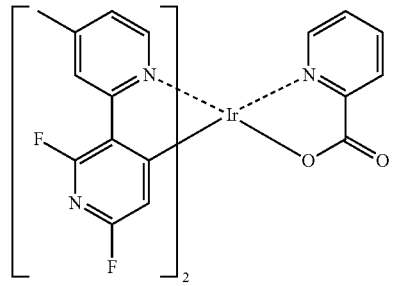

PD9
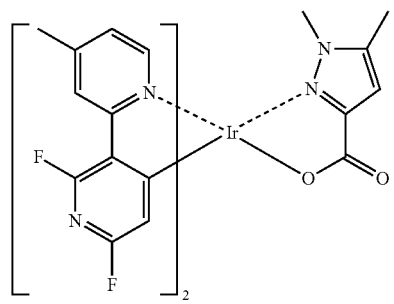

PD10
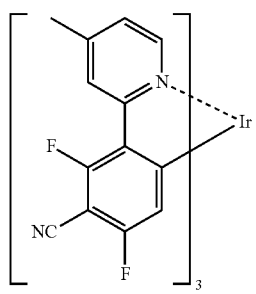
PD11
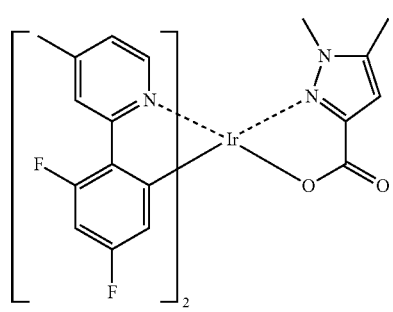
PD12
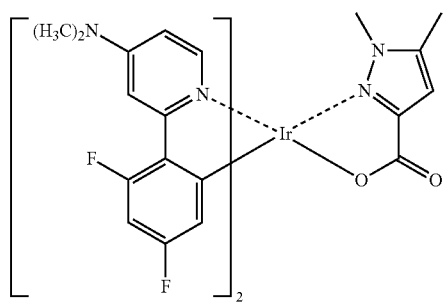
PD13
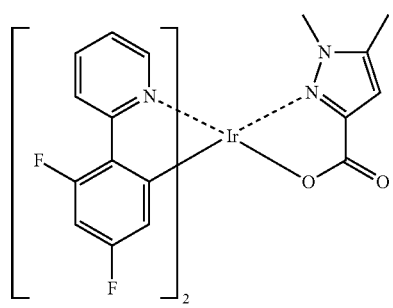
PD14
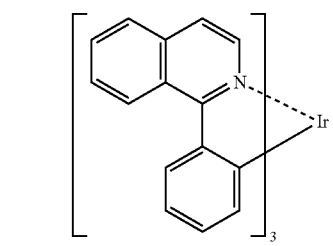
PD15
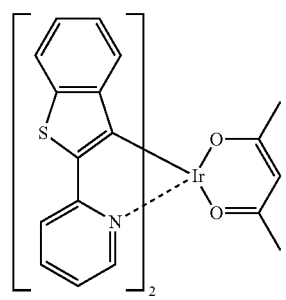
PD16
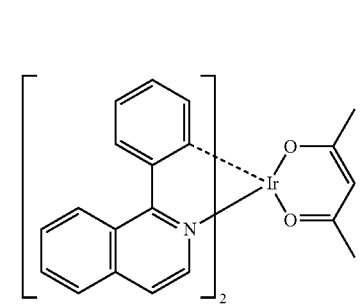
PD17
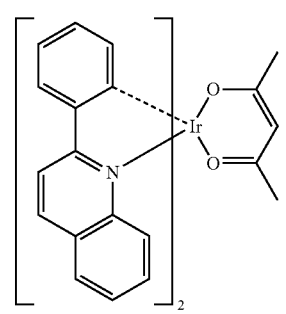
PD18
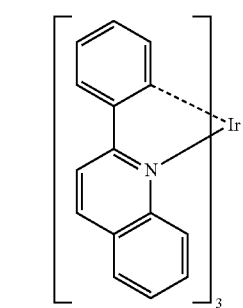
PD19
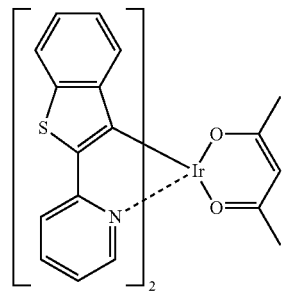

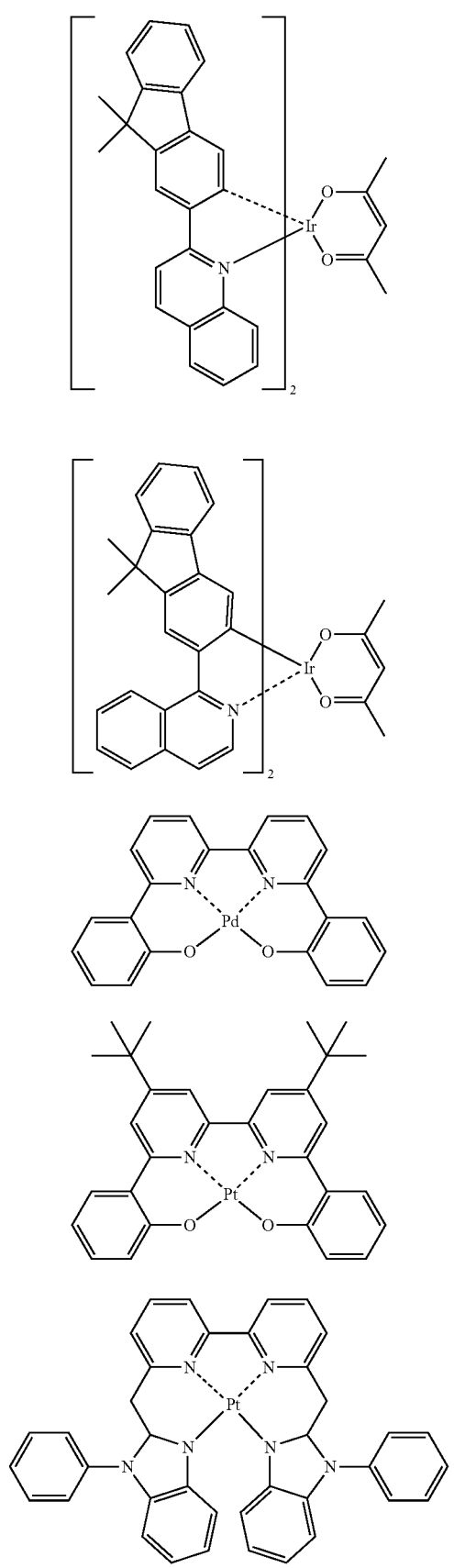
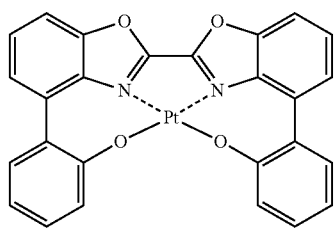
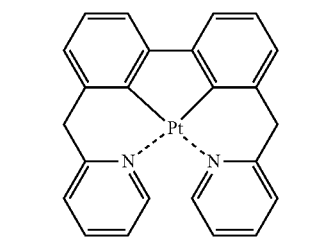
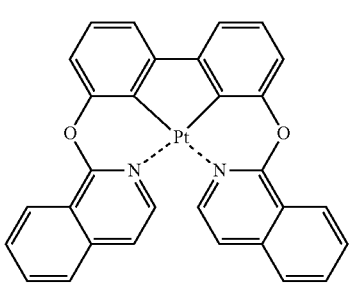
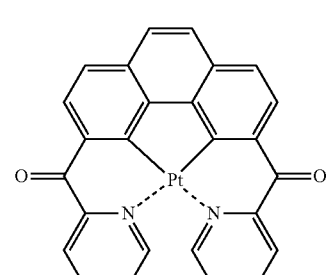
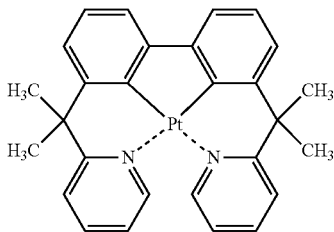
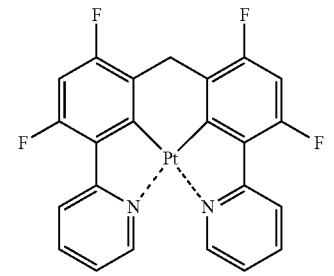

PD31 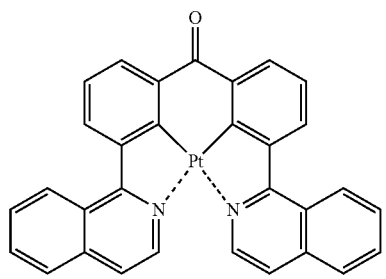
PD36 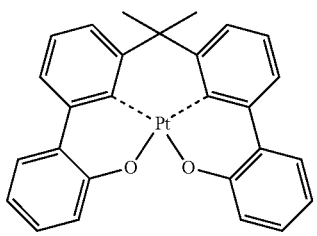
PD32 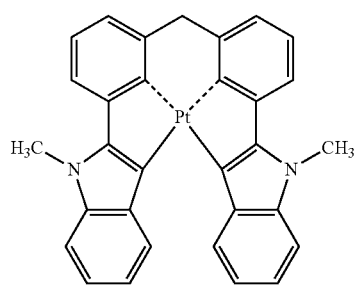
PD37 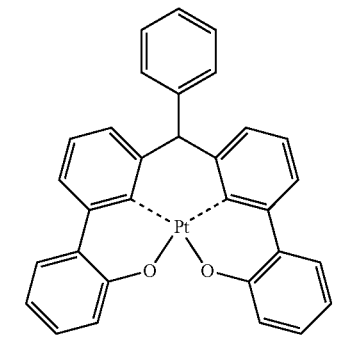
PD33 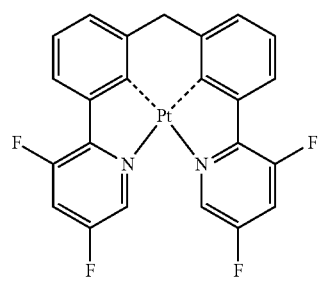
PD38 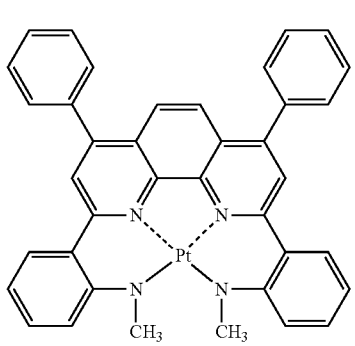
PD34 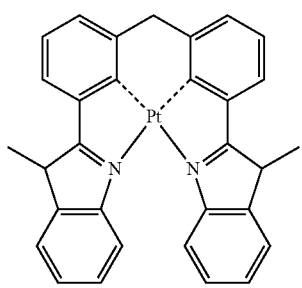
PD39 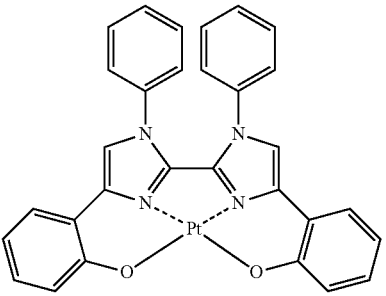
PD35 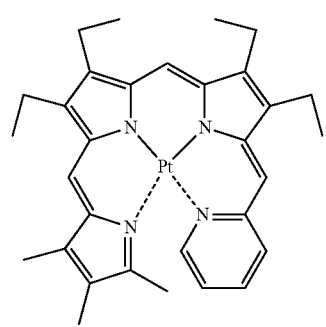
PD40 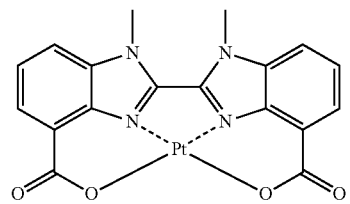
PD41 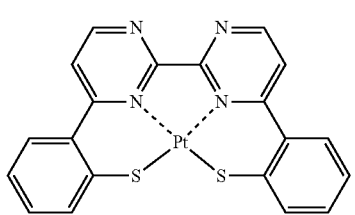

PD42 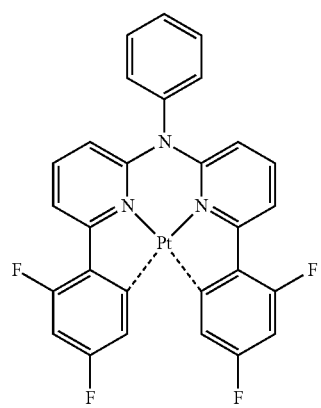
PD43 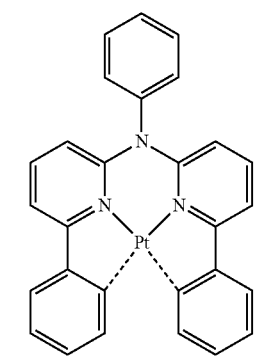
PD44 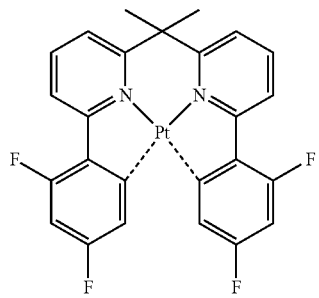
PD45 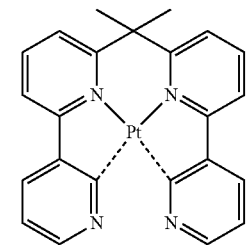
PD46 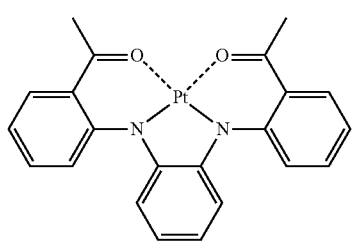
PD47 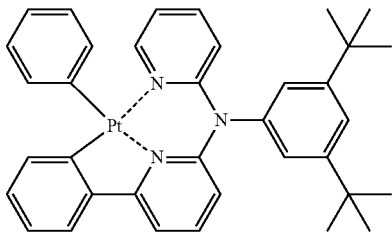
PD48 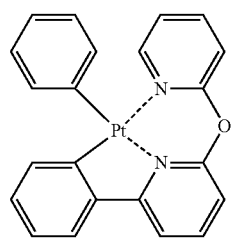
PD49 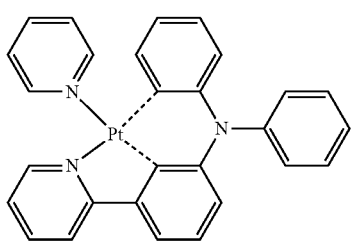
PD50 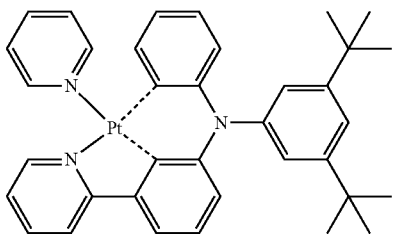
PD51 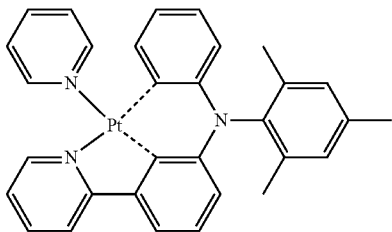
PD52 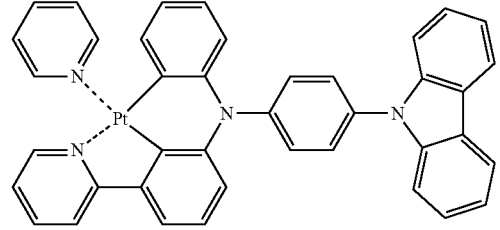

PD53
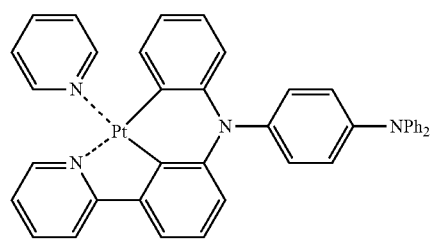
PD54
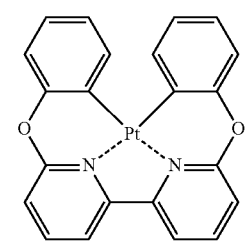
PD55
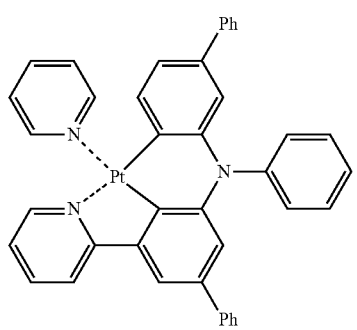
PD56
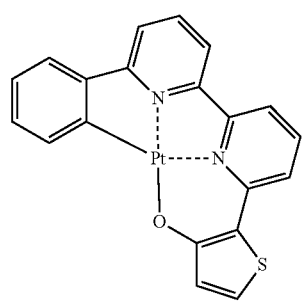
PD57
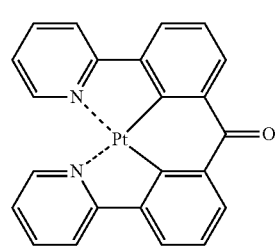
PD58
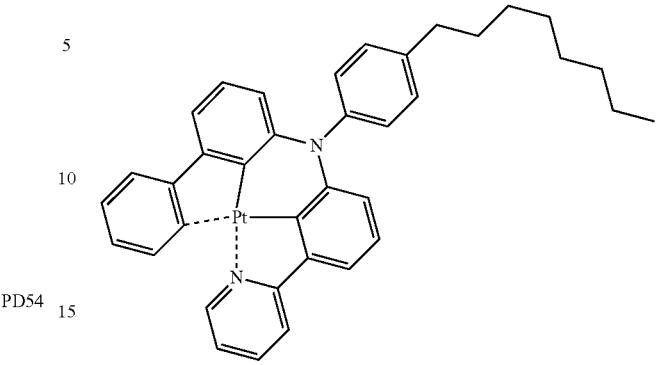
PD59
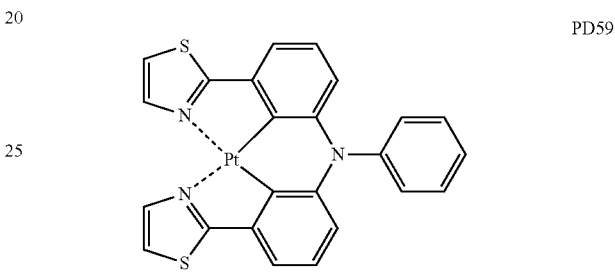
PD60
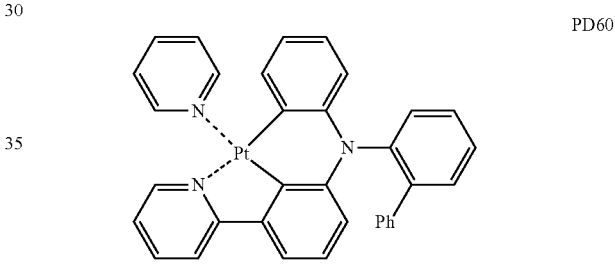
PD61
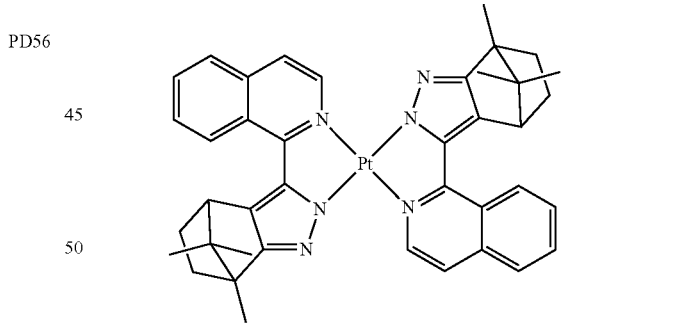
PD62
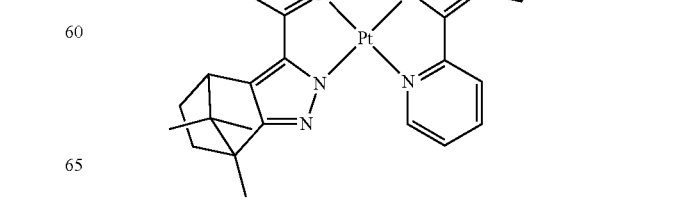

PD63 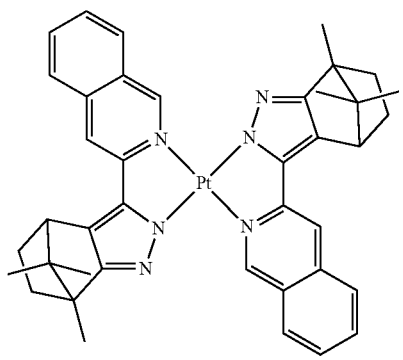
PD64 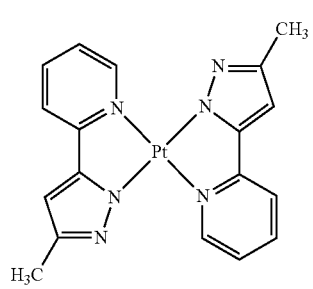
PD65 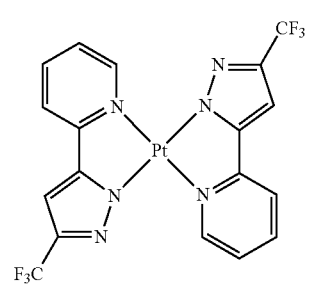
PD66 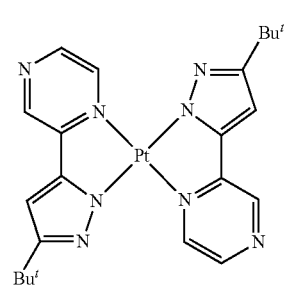
PD67 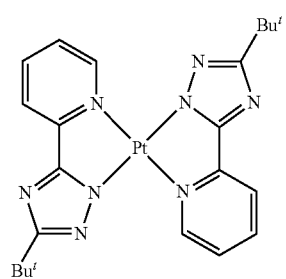
PD68 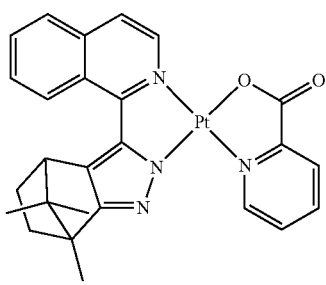
PD69 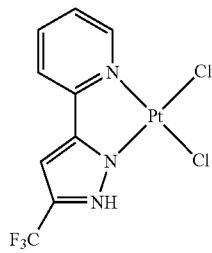
PD70 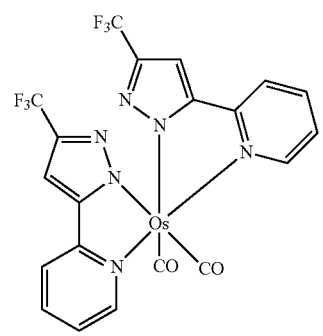
PD71 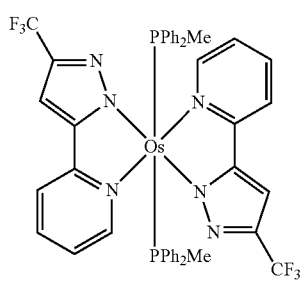
PD72 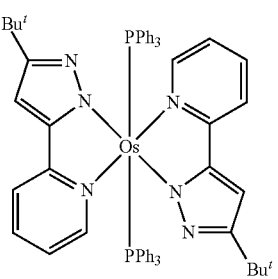

-continued

PD73 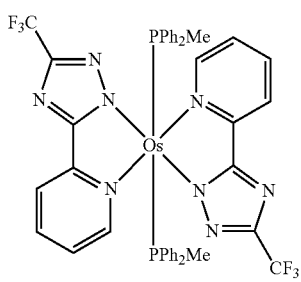

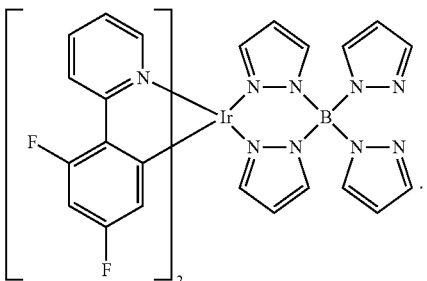 Flr6

PD74

In one or more exemplary embodiments, the phosphorescent dopant may include PtOEP:

PD75 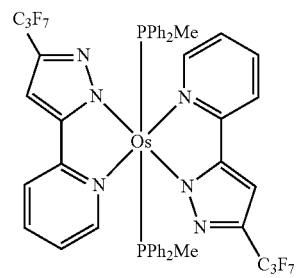

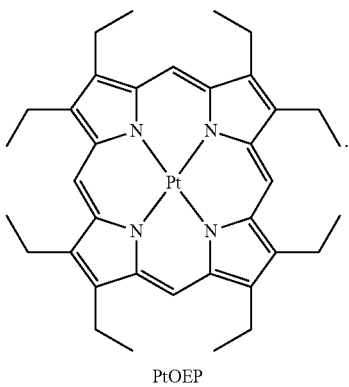

PtOEP

PD76 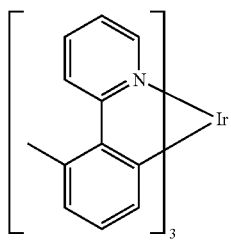

When the emission layer includes a host and a dopant, an amount of the dopant may be in a range of about 0.01 parts to about 20 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light emission characteristics may be obtained without a substantial increase in driving voltage.

PD77 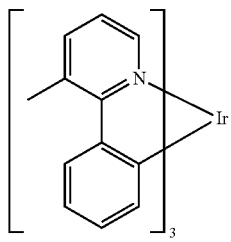

Then, an electron transport region may be disposed on the emission layer.

The electron transport region may include at least one selected from a hole blocking layer, an electron transport layer, and an electron injection layer.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

PD78 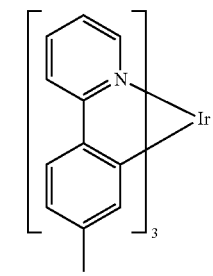

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but may also include other materials.

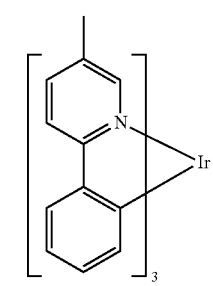

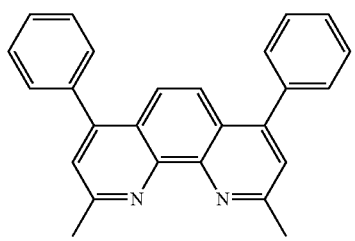

BCP

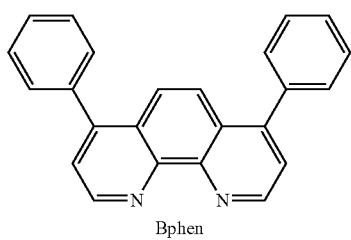

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, Alq$_3$, BAlq, TAZ, and NTAZ.

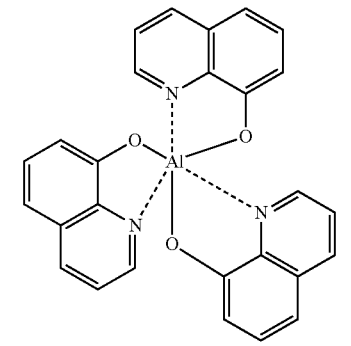

Alq$_3$

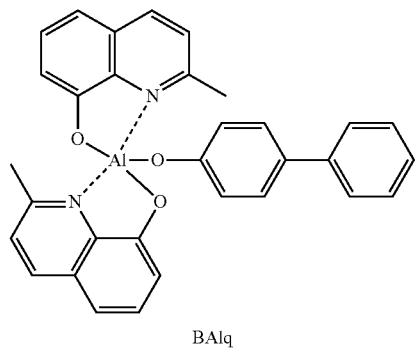

BAlq

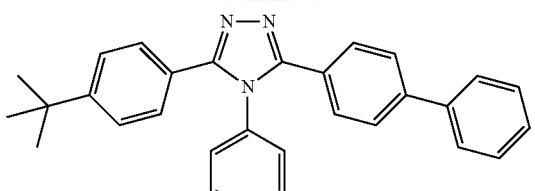

TAZ

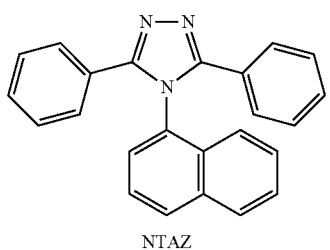

NTAZ

In one or more exemplary embodiments, the electron transport layer may include at least one of ET1 to ET19, but is not limited thereto:

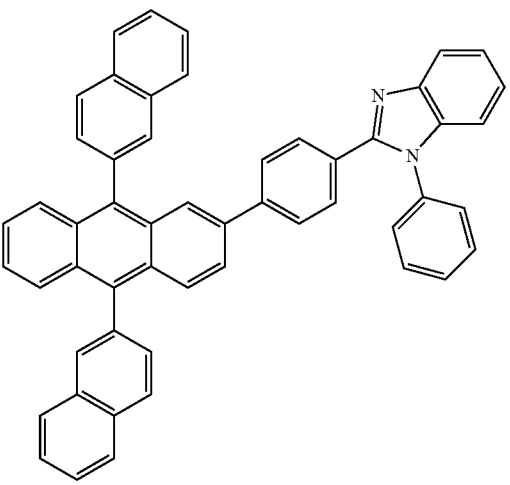

ET1

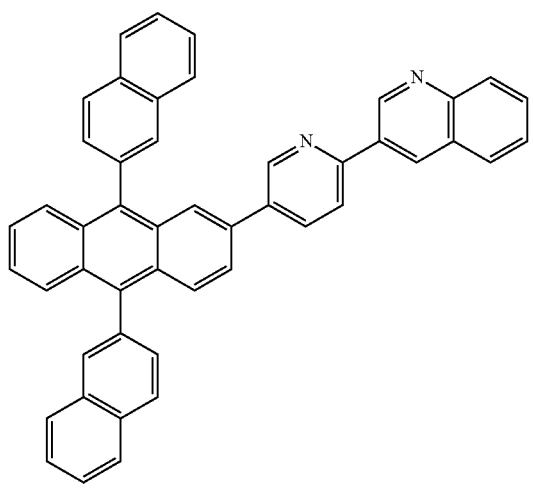

ET2

235
-continued
ET3
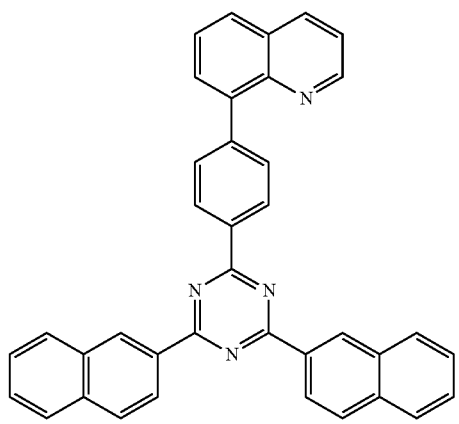
ET4
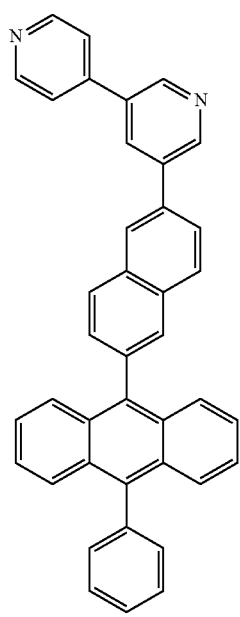
ET5
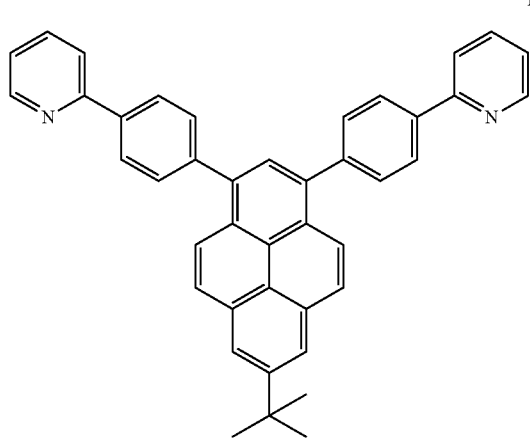
236
-continued
ET6
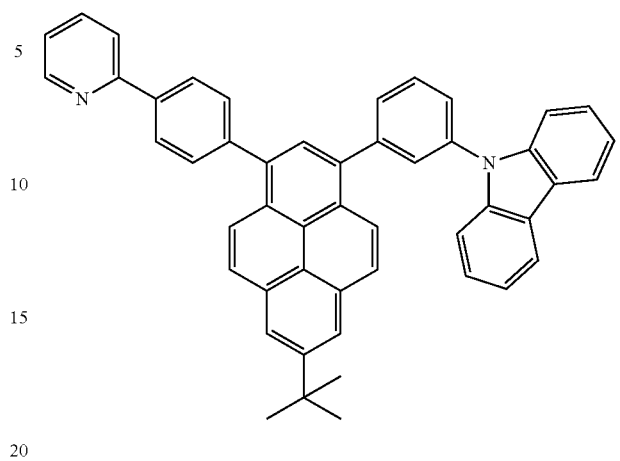
ET7
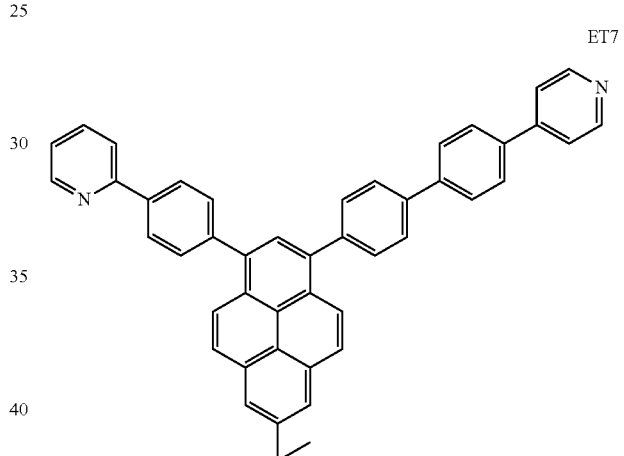
ET8
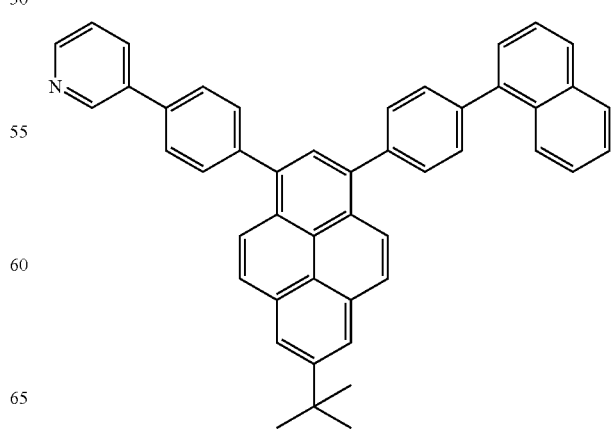

ET9
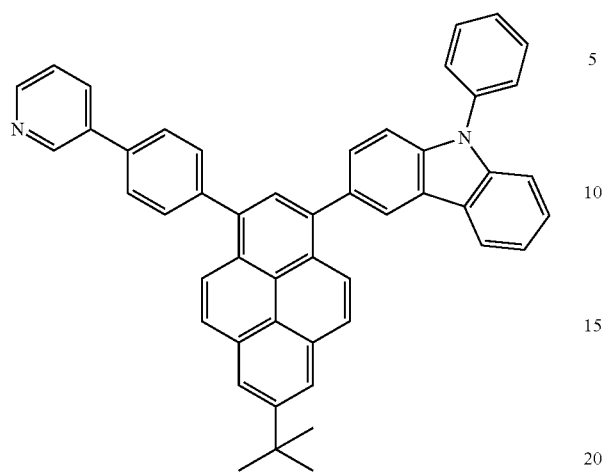
ET10
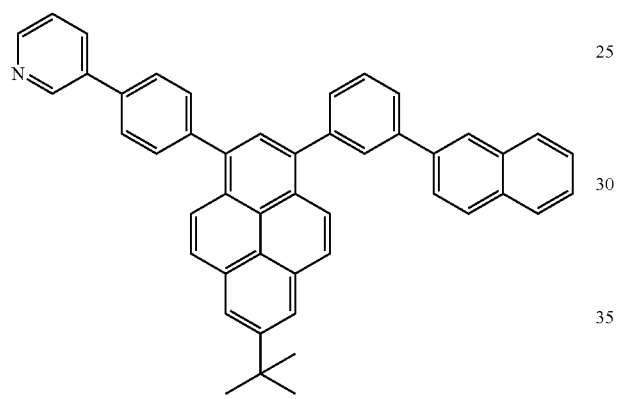
ET11
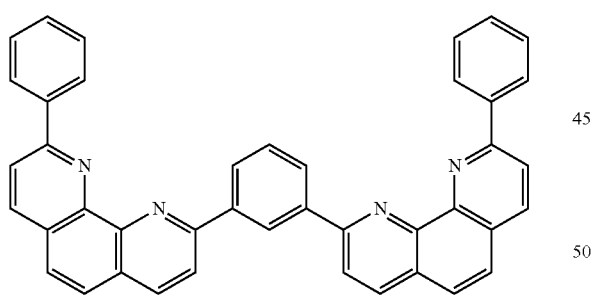
ET12
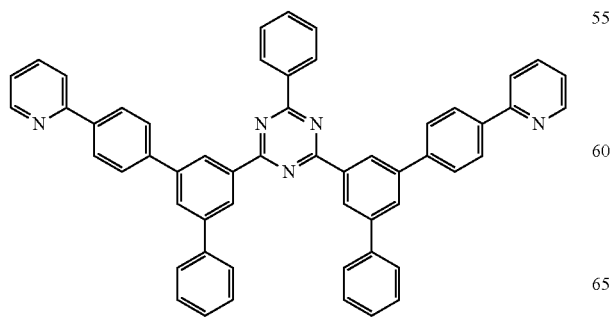
ET13
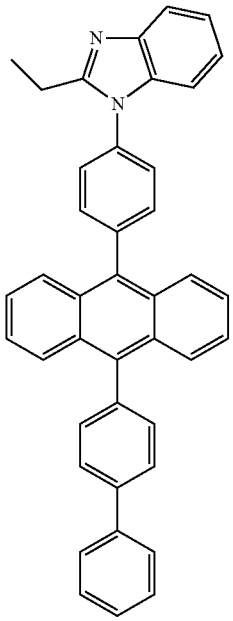
ET14
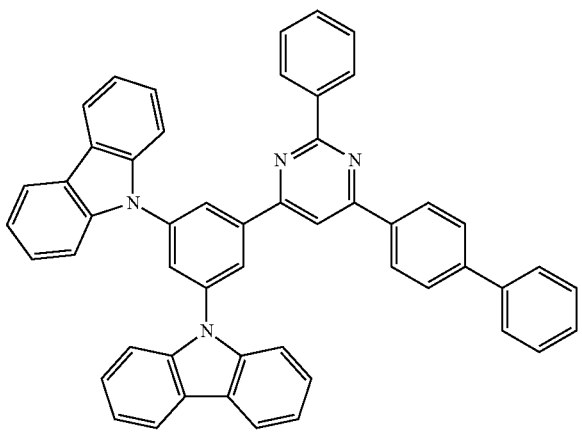
ET15
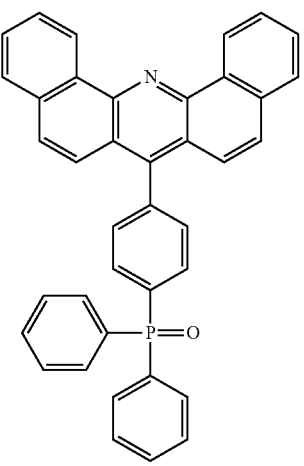

ET16

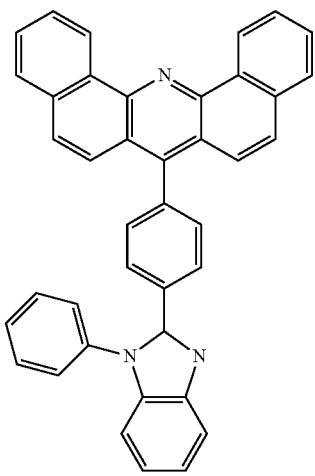

ET17

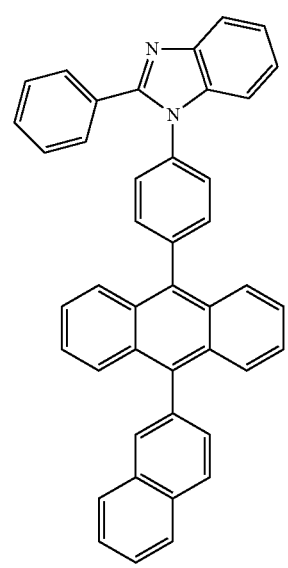

ET18

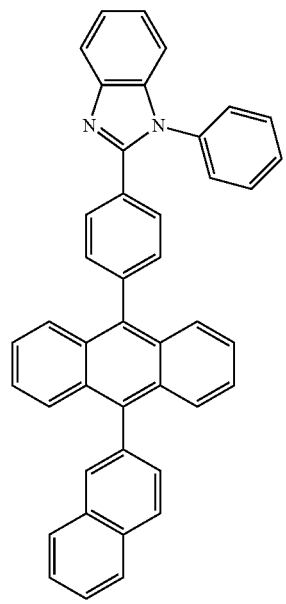

ET19

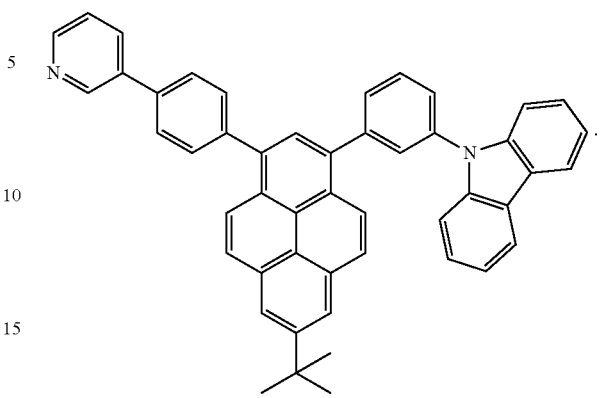

A thickness of the electron transport layer may be in a range of about 100 Å to about 1,000 Å, for example, about 150 Å to about 500 Å. While not wishing to be bound by theory, it is understood that when the thickness of the electron transport layer is within these ranges, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

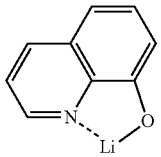

ET-D2

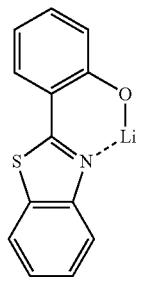

The electron transport region may include an electron injection layer (EIL) that promotes flow of electrons from the second electrode 19 thereinto.

The electron injection layer may include at least one selected from LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, or a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top-emission type light-emitting device, a transmissive electrode formed using ITO or IZO may be used as the second electrode 19.

Hereinbefore, the organic light-emitting device has been described with reference to FIG. 1, but is not limited thereto.

The term "$C_1$-$C_{60}$ alkyl group" as used herein refers to a linear or branched saturated aliphatic hydrocarbon monovalent group having 1 to 60 carbon atoms. Examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group). Examples thereof include a methoxy group, an ethoxy group, and an isopropyloxy group.

The term "$C_2$-$C_{60}$ alkenyl group" as used herein refers to a hydrocarbon group having at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group. Examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent hydrocarbon monocyclic group having 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms. Examples thereof include a tetrahydrofuranyl group and a tetrahydrothiophenyl group. The term "$C_1$-$C_{10}$ heterocycloalkylene group," as used herein, refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof, and which is not aromatic. Examples thereof include a cyclopentenyl group, a cyclohexenyl group, and a cycloheptenyl group. The term "$C_3$-$C_{10}$ cycloalkenylene group," as used herein, refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Examples of the $C_2$-$C_{10}$ heterocycloalkenyl group include a 2,3-dihydrofuranyl group and a 2,3-dihydrothiophenyl group. The term "$C_1$-$C_{10}$ heterocycloalkenylene group," as used herein, refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a carbocyclic aromatic system that has at least one heteroatom selected from N, O, P, Si, and S as a ring-forming atom, in addition to 1 to 60 carbon atoms. The term "$C_1$-$C_{60}$ heteroarylene group" as used herein refers to a divalent group having a carbocyclic aromatic system that has at least one heteroatom selected from N, O, P, Si, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group," as used herein, indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "monovalent non-aromatic condensed polycyclic group" as used herein refers to a monovalent group that has two or more rings condensed to each other, that includes only carbon atoms (for example, the number of carbon atoms may be in a range of 8 to 60) as ring-forming atoms, and that is non-aromatic in the entire molecular structure. Examples of the monovalent non-aromatic condensed polycyclic group include a fluorenyl group. The term "divalent non-aromatic condensed polycyclic group," as used herein, refers to a divalent group having the same structure as the monovalent non-aromatic condensed polycyclic group.

The term "monovalent non-aromatic condensed heteropolycyclic group" as used herein refers to a monovalent group that has two or more rings condensed to each other, has a heteroatom selected from N, O, P, Si, and S, other than carbon atoms (for example, the number of carbon atoms may be in a range of 2 to 60), as a ring-forming atom, and which is non-aromaticity in the entire molecular structure. Examples of the monovalent non-aromatic condensed heteropolycyclic group include a carbazolyl group. The term "divalent non-aromatic condensed heteropolycyclic group," as used herein, refers to a divalent group having the same structure as the monovalent non-aromatic condensed heteropolycyclic group.

The term "biphenyl group" refers to a monovalent group in which two benzene groups are linked via a single bond.

The term "terphenyl group" refers to a monovalent group in which three benzene groups are linked via a single bond.

At least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_0$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, and —$B(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{60}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, and —$B(Q_{21})(Q_{22})$; and —$Si(Q_{31})(Q_{32})(Q_{33})$, —$N(Q_{31})(Q_{32})$ and —$B(Q_{31})(Q_{32})$, wherein $Q_{11}$ to $Q_{13}$, $Q_{21}$ to $Q_{23}$, and $Q_{31}$ to $Q_{33}$ may each independently be selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

Hereinafter, a compound and an organic light-emitting device according to exemplary embodiments are described in detail with reference to Synthesis Examples and Examples. However, the compound and the organic light-emitting device are not limited thereto. The wording "B was used instead of A" used in describing Synthesis Examples means that an amount in molar equivalents of A used was identical to an amount in molar equivalents of B used.

EXAMPLES

Synthesis Example 1: Synthesis of Compound 1

Compound 1 was synthesized according to the Reaction Scheme below:

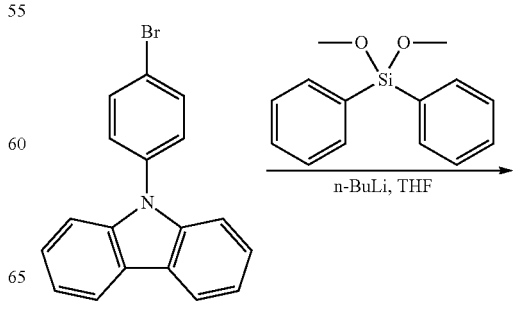

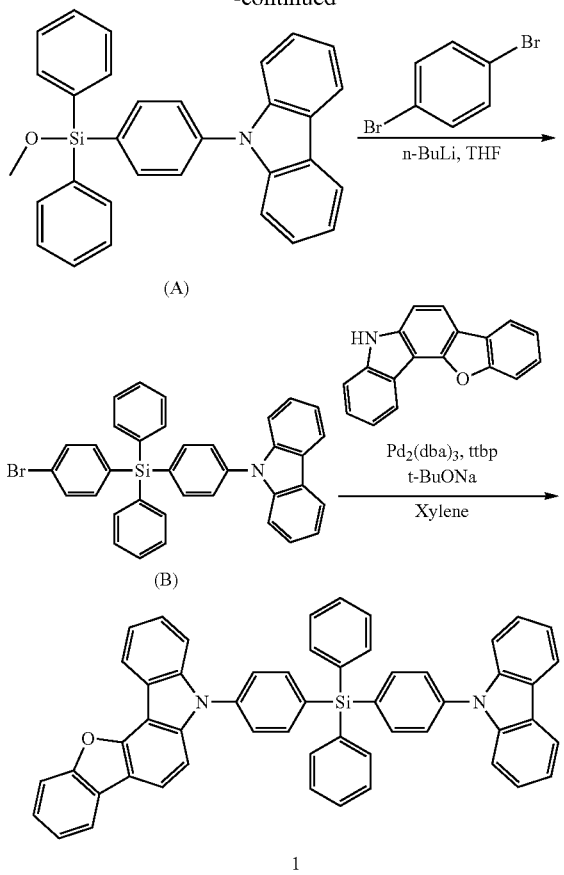

(3) Synthesis of Compound 1

10.0 g (17.2 mmol) of Intermediate (B), 4.88 g (19.0 mmol) of 5H-benzofuro[3,2-c]carbazole, 0.99 g (1.72 mmol) of Pd(dba)$_2$, 1.72 mL (50% in xylene, 3.44 mmol) of tri-tert-butylphosphine (ttbp), and 3.31 g (34.5 mmol) of sodium tert-butoxide were added to 60 mL of xylene, and the resultant mixture was heated and stirred at a temperature of 120° C. When the reaction was complete, the reaction product was cooled to room temperature and filtered through a plug of silica gel under reduced pressure. The filtered solution was concentrated under vacuum. The product was purified by silica gel column chromatography, thereby completing the preparation of 9.91 g (76%) of Compound 1.

LC-Mass (cal.: 756.26 g/mol, found: [M+H]$^+$=757 g/mol)

Synthesis Example 2: Synthesis of Compound 2

Compound 2 was synthesized according to the Reaction Scheme below:

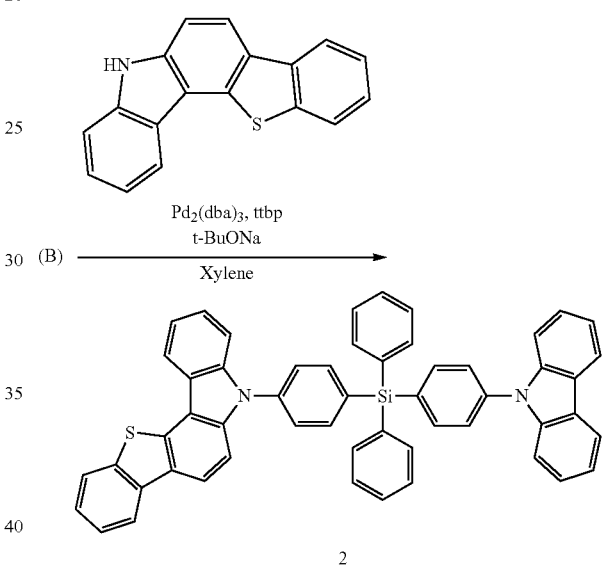

(1) Synthesis of Intermediate (A)

50.0 grams (g) (155 millimoles, mmol) of 9-(4-bromophenyl)-9H-carbazole was dissolved in 500 milliliters (mL) of tetrahydrofuran (THF) and the solution was cooled to a temperature of −78° C. Then, 97.0 mL (155.0 mmol, 1.6 molar (M) solution in n-hexane) of n-butyllithium was slowly added thereto for 30 minutes and the resultant mixture was stirred at a temperature of −78° C. for 1 hour. To the resultant mixture, 45.5 g (186 mmol) of dimethoxydiphenylsilane dissolved in 250 mL of THF was slowly added for 30 minutes. The reaction temperature was raised slowly to room temperature for 1 hour, and the reaction was additionally stirred at room temperature for 15 hours. After the reaction was complete, a saturated ammonium chloride (NH$_4$Cl) aqueous solution was added thereto. The reaction mixture was extracted and the organic layer was separated. Water was removed from the separated organic layer by using anhydrous magnesium sulfate (MgSO$_4$) as a drying agent, and the dried solution was filtered and concentrated. The product was purified by silica gel column chromatography, thereby completing the preparation of 45.2 g (64%) of Intermediate (A).

LC-Mass (cal.: 455.17 g/mol, found: [M+H]$^+$=456 g/mol)

(2) Synthesis of Intermediate (B)

22.2 g (45%) of Intermediate (B) was synthesized in the same manner as in Synthesis of Intermediate (A), except that, in synthesizing Intermediate (B), 20.0 g (84.8 mmol) of 1,4-dibromobenzene was used instead of 9-(4-bromophenyl)-9H-carbazole, and 38.6 g (84.8 mmol) of Intermediate (A) was used instead of dimethoxydiphenylsilane.

LC-Mass (cal.: 579.10 grams per mole (g/mol), found: [M+H]$^+$=580 g/mol)

9.05 g (68%) of Compound 2 was synthesized in the same manner as in Synthesis of Compound 1, except that 5.18 g (19.0 mmol) of 5H-benzo[4,5]thieno[3,2-c]carbazole) was used instead of 5H-benzofuro[3,2-c]carbazole in synthesizing Compound 2.

LC-Mass (cal.: 772.24 g/mol, found: [M+H]$^+$=773 g/mol)

Synthesis Example 3: Synthesis of Compound 17

Compound 17 was synthesized according to the Reaction Scheme below:

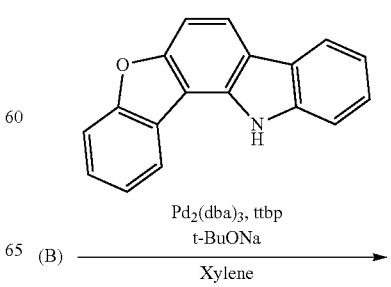

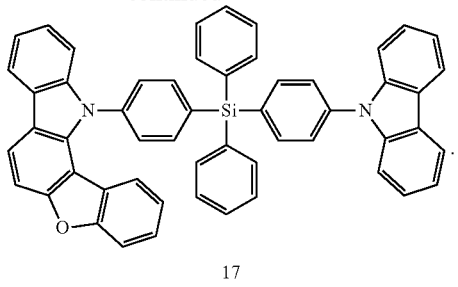

17

7.95 g (61%) of Compound 17 was synthesized in the same manner as in Synthesis of Compound 1, except that 4.88 g (19.0 mmol) of 12H-benzofuro[3,2-a]carbazole) was used instead of 5H-benzofuro[3,2-c]carbazole in synthesizing Compound 17.

LC-Mass (cal.: 756.26 g/mol, found: [M+H]$^+$=757 g/mol)

Synthesis Example 4: Synthesis of Compound 19

Compound 19 was synthesized according to the Reaction Scheme below:

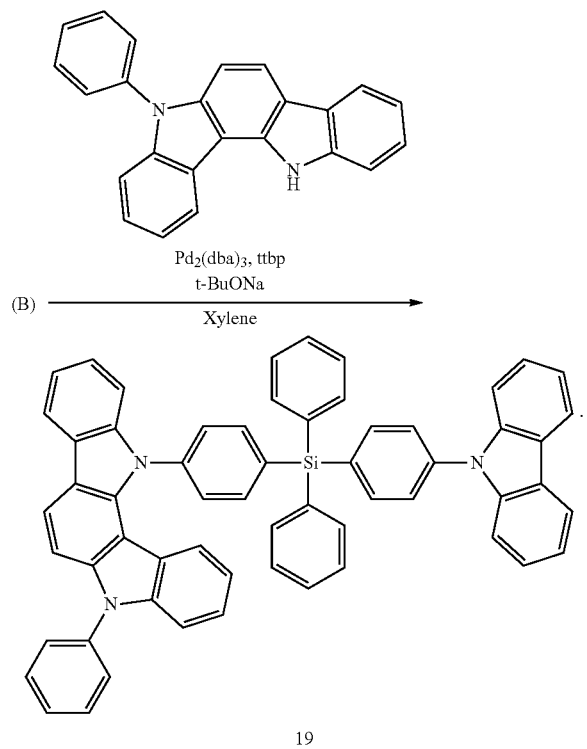

19

6.16 g (43%) of Compound 19 was synthesized in the same manner as in Synthesis of Compound 1, except that 6.30 g (19.0 mmol) of 5-phenyl-5,12-dihydroindolo[3,2-a]carbazole was used instead of 5H-benzofuro[3,2-c]carbazole.

LC-Mass (cal.: 831.31 g/mol, found: [M+H]$^+$=832 g/mol)

Synthesis Example 5: Synthesis of Compound 21

Compound 21 was synthesized according to the Reaction Scheme below:

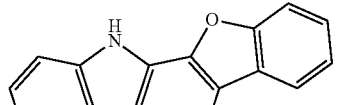

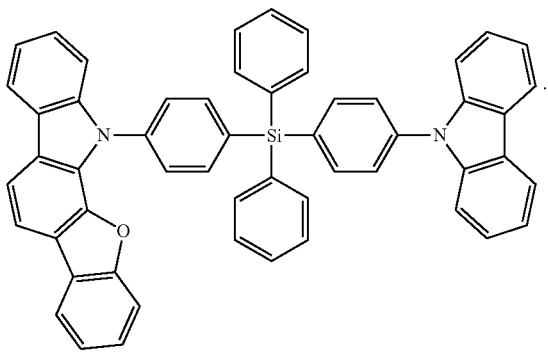

21

6.13 g (47%) of Compound 21 was synthesized in the same manner as in Synthesis of Compound 1, except that 4.88 g (19.0 mmol) of 12H-benzofuro[2,3-a]carbazole was used instead of 5H-benzofuro[3,2-c]carbazole in synthesizing Compound 21.

LC-Mass (cal.: 756.26 g/mol, found: [M+H]$^+$=757 g/mol)

Synthesis Example 6: Synthesis of Compound 25

Compound 25 was synthesized according to the Reaction Scheme below:

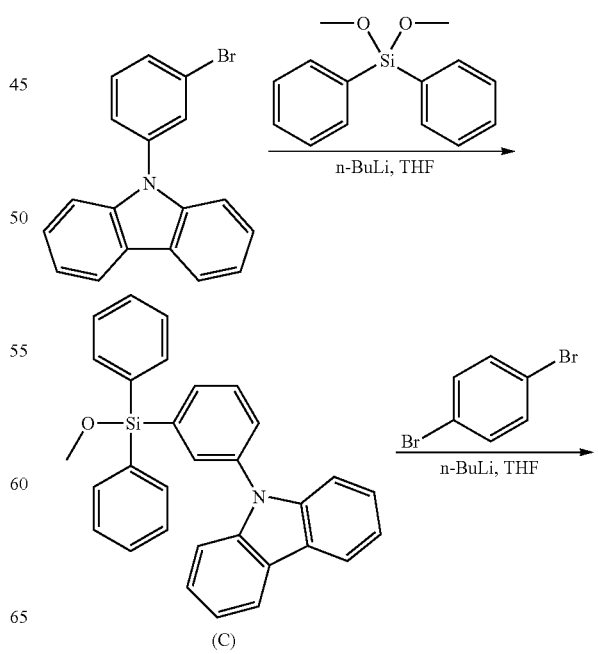

(C)

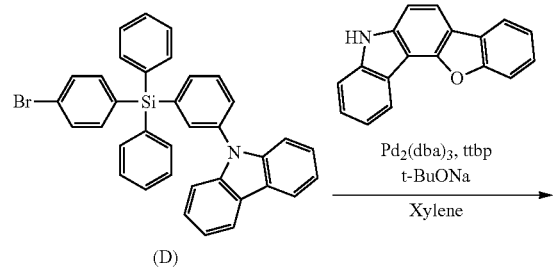

(D)

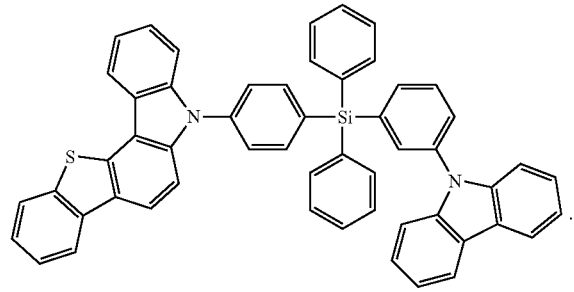

26

9.32 g (70%) of Compound 26 was synthesized in the same manner as in Synthesis of Compound 25, except that 5.18 g (19.0 mmol) of 5H-benzo[4,5]thieno[3,2-c]carbazole was used instead of 5H-benzofuro[3,2-c]carbazole in synthesizing Compound 26.

LC-Mass (cal.: 772.24 g/mol, found: $[M+H]^+$=773 g/mol)

Synthesis Example 8: Synthesis of Compound 41

Compound 41 was synthesized according to the Reaction Scheme below:

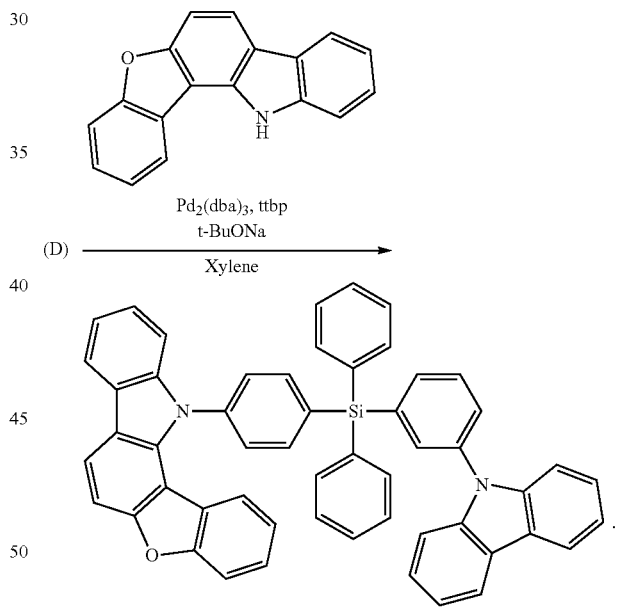

41

(1) Synthesis of Intermediate (C)

43.1 g (61%) of Intermediate (C) was synthesized in the same manner as in Synthesis of Intermediate (A), except that 50.0 g (155 mmol) of 9-(3-bromophenyl)-9H-carbazole was used instead of 9-(4-bromophenyl)-9H-carbazole in synthesizing Intermediate (C).

LC-Mass (cal.: 455.17 g/mol, found: $[M+H]^+$=456 g/mol)

(2) Synthesis of Intermediate (D)

26.1 g (53%) of Intermediate (D) was synthesized in the same manner as in Synthesis of Intermediate (B), except that 38.6 g (84.8 mmol) of Intermediate (C) was used instead of Intermediate (A) in synthesizing Intermediate (D).

LC-Mass (cal.: 579.10 g/mol, found: $[M+H]^+$=580 g/mol)

(3) Synthesis of Compound 25

9.39 g (72%) of Compound 25 was synthesized in the same manner as in Synthesis of Compound 1, except that 10.0 g (17.2 mmol) of Intermediate (D) was used instead of Intermediate (B) in synthesizing Compound 25.

LC-Mass (cal.: 756.26 g/mol, found: $[M+H]^+$=757 g/mol)

Synthesis Example 7: Synthesis of Compound 26

Compound 26 was synthesized according to the Reaction Scheme below:

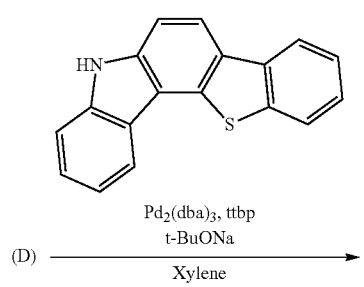

7.56 g (58%) of Compound 41 was synthesized in the same manner as in Synthesis of Compound 25, except that 4.88 g (19.0 mmol) of 12H-benzofuro[3,2-a]carbazole was used instead of 5H-benzofuro[3,2-c]carbazole in synthesizing Compound 41.

LC-Mass (cal.: 756.26 g/mol, found: $[M+H]^+$=757 g/mol)

Synthesis Example 9: Synthesis of Compound 43

Compound 43 was synthesized according to the Reaction Scheme below:

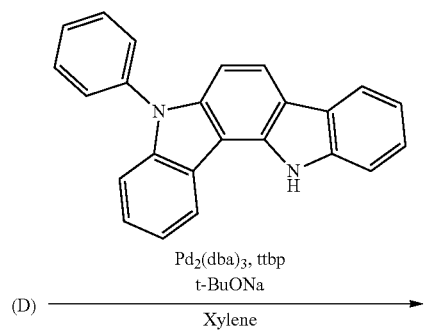

(D) Pd₂(dba)₃, ttbp
t-BuONa
Xylene
→

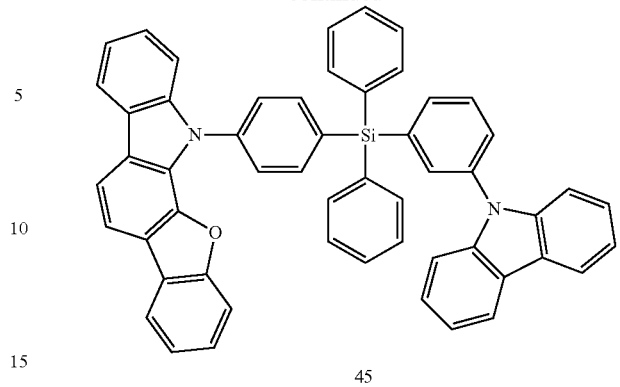

45

5.48 g (42%) of Compound 45 was synthesized in the same manner as in Synthesis of Compound 25, except that 4.88 g (19.0 mmol) of 12H-benzofuro[2,3-a]carbazole was used instead of 5H-benzofuro[3,2-c]carbazole in synthesizing Compound 45.

LC-Mass (cal.: 756.26 g/mol, found: [M+H]⁺=757 g/mol)

Synthesis Example 11: Synthesis of Compound 49

Compound 4 was synthesized according to the Reaction Scheme below:

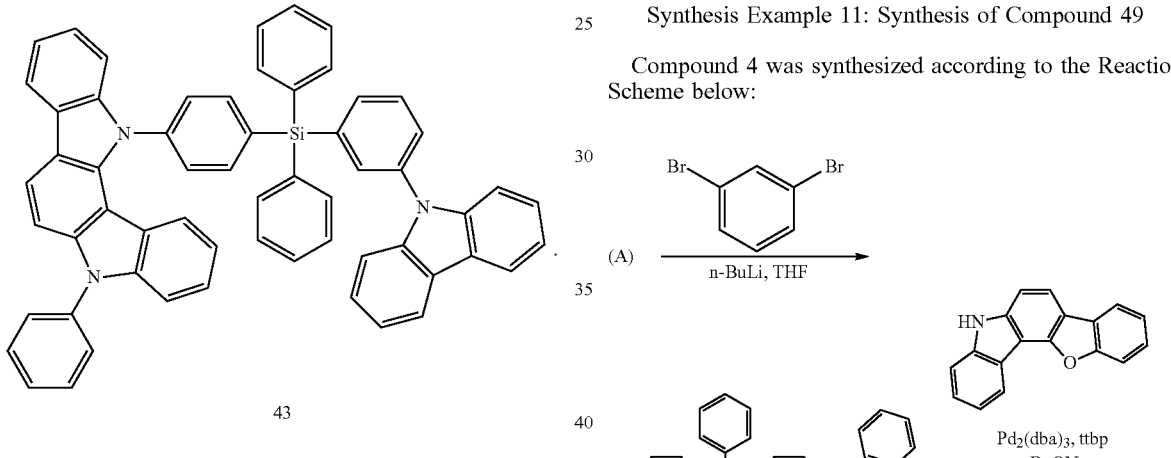

43

7.88 g (55%) of Compound 43 was synthesized in the same manner as in Synthesis of Compound 25, except that 6.30 g (19.0 mmol) of 5-phenyl-5,12-dihydroindolo[3,2-a]carbazole was used instead of 5H-benzofuro[3,2-c]carbazole in synthesizing Compound 43.

LC-Mass (cal.: 831.31 g/mol, found: [M+H]⁺=832 g/mol)

Synthesis Example 10: Synthesis of Compound 45

Compound 45 was synthesized according to the Reaction Scheme below:

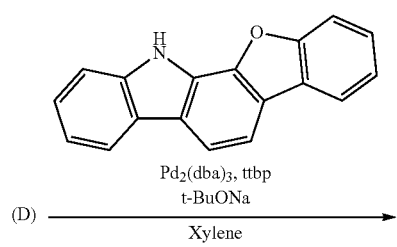

(D) Pd₂(dba)₃, ttbp
t-BuONa
Xylene
→

(1) Synthesis of Intermediate (E)

24.7 g (50%) of Intermediate (E) was synthesized in the same manner as in Synthesis of Intermediate (B), except that 20.0 g (84.8 mmol) of 1,3-dibromobenzene was used instead of Intermediate 1,4-dibromobenzene in synthesizing Intermediate (E).

LC-Mass (cal.: 579.10 g/mol, found: [M+H]⁺=580 g/mol)

(2) Synthesis of Compound 49

8.22 g (63%) of Compound 49 was synthesized in the same manner as in Synthesis of Compound 1, except that 10.0 g (17.2 mmol) of Intermediate (E) was used instead of Intermediate (B) in synthesizing Compound 49.

LC-Mass (cal.: 756.26 g/mol, found: [M+H]$^+$=757 g/mol)

Synthesis Example 12: Synthesis of Compound 65

Compound 65 was synthesized according to the Reaction Scheme below:

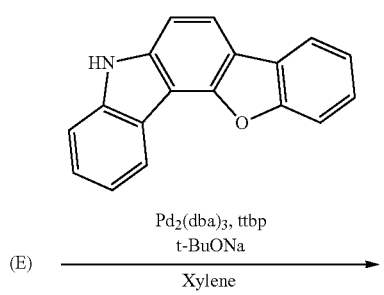

(E) $\xrightarrow[\text{Xylene}]{\text{Pd}_2(\text{dba})_3,\text{ttbp} \\ \text{t-BuONa}}$

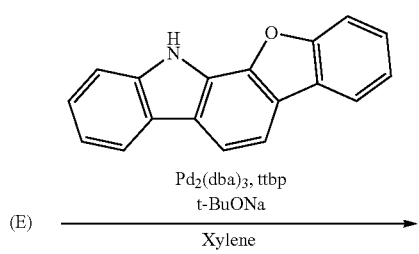

65

6.26 g (48%) of Compound 65 was synthesized in the same manner as in Synthesis of Compound 49, except that 4.88 g (19.0 mmol) of 12H-benzofuro[3,2-a]carbazole was used instead of 5H-benzofuro[3,2-c]carbazole in synthesizing Compound 65.

LC-Mass (cal.: 756.26 g/mol, found: [M+H]$^+$=757 g/mol)

Synthesis Example 13: Synthesis of Compound 69

Compound 69 was synthesized according to the Reaction Scheme below:

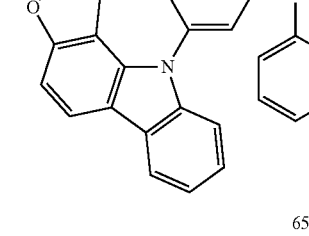

(E) $\xrightarrow[\text{Xylene}]{\text{Pd}_2(\text{dba})_3,\text{ttbp} \\ \text{t-BuONa}}$

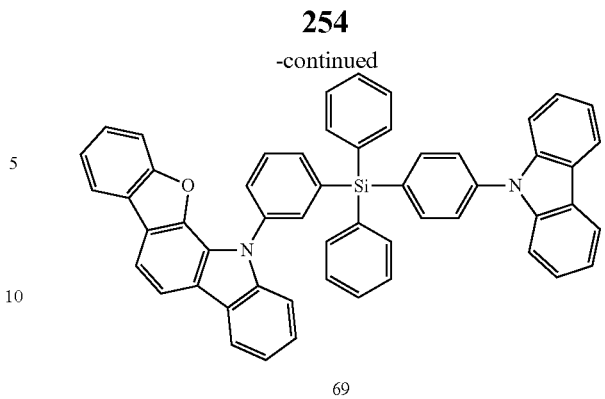

69

5.61 g (43%) of Compound 69 was synthesized in the same manner as in Synthesis of Compound 49, except that 4.88 g (19.0 mmol) of 12H-benzofuro[2,3-a]carbazole was used instead of 5H-benzofuro[3,2-c]carbazole in synthesizing Compound 69.

LC-Mass (cal.: 756.26 g/mol, found: [M+H]$^+$=757 g/mol)

Synthesis Example 14: Synthesis of Compound 73

Compound 73 was synthesized according to the Reaction Scheme below:

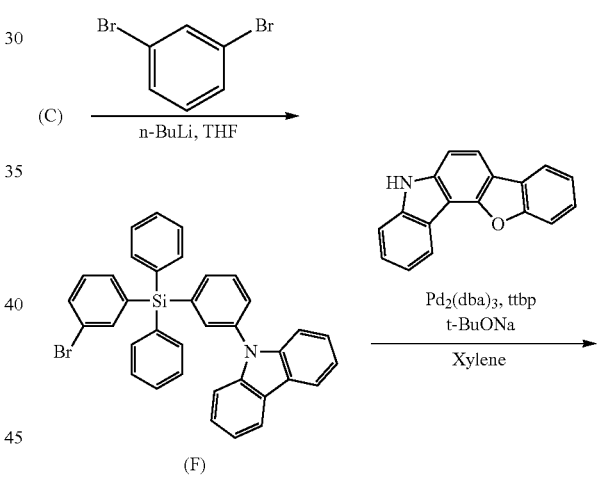

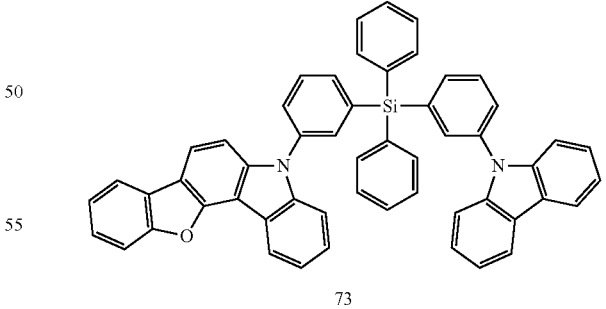

73

(1) Synthesis of Intermediate (F)

20.3 g (41%) of Intermediate (F) was synthesized in the same manner as in Synthesis of Intermediate (D), except that 20.0 g (84.8 mmol) of 1,3-dibromobenzene was used instead of Intermediate 1,4-dibromobenzene in synthesizing Intermediate (F).

LC-Mass (cal.: 579.10 g/mol, found: [M+H]$^+$=580 g/mol)

(2) Synthesis of Compound 73

8.35 g (64%) of Compound 73 was synthesized in the same manner as in Synthesis of Compound 1, except that 10.0 g (17.2 mmol) of Intermediate (F) was used instead of Intermediate (B) in synthesizing Compound 73.

LC-Mass (cal.: 756.26 g/mol, found: [M+H]$^+$=757 g/mol)

Synthesis Example 15: Synthesis of Compound 97

Compound 97 was synthesized according to the Reaction Scheme below:

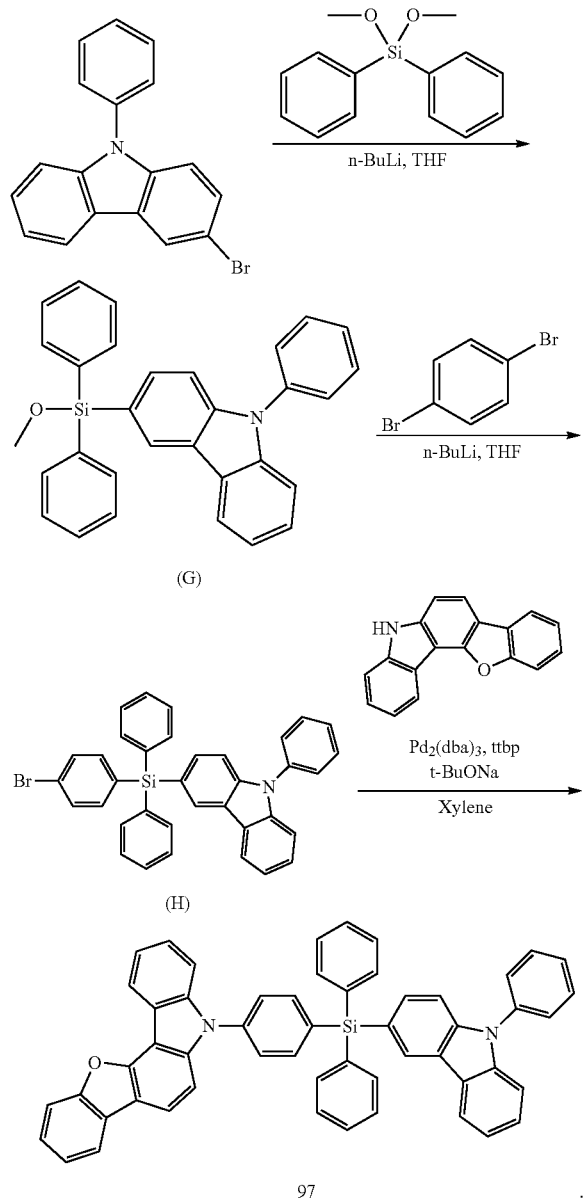

(1) Synthesis of Intermediate (G)

45.9 g (65%) of Intermediate (G) was synthesized in the same manner as in Synthesis of Intermediate (A), except that 50.0 g (155 mmol) of 3-bromo-9-phenyl-9H-carbazole was used instead of 9-(4-bromophenyl)-9H-carbazole in synthesizing Intermediate (G).

LC-Mass (cal.: 455.17 g/mol, found: [M+H]$^+$=456 g/mol)

(2) Synthesis of Intermediate (H)

27.1 g (55%) of Intermediate (H) was synthesized in the same manner as in Synthesis of Intermediate (B), except that 38.6 g (84.8 mmol) of Intermediate (G) was used instead of Intermediate (A) in synthesizing Intermediate (H).

LC-Mass (cal.: 579.10 g/mol, found: [M+H]$^+$=580 g/mol)

(3) Synthesis of Compound 97

7.96 g (61%) of Compound 97 was synthesized in the same manner as in Synthesis of Compound 1, except that 10.0 g (17.2 mmol) of Intermediate (H) was used instead of Intermediate (B) in synthesizing Compound 97.

LC-Mass (cal.: 756.26 g/mol, found: [M+H]$^+$=757 g/mol)

Synthesis Example 16: Synthesis of Compound 98

Compound 98 was synthesized according to the Reaction Scheme below:

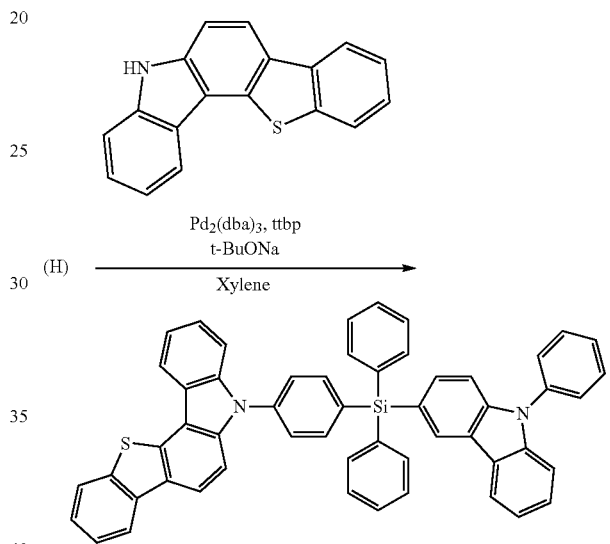

8.39 g (63%) of Compound 98 was synthesized in the same manner as in Synthesis of Compound 97, except that 5.18 g (19.0 mmol) of 5H-benzo[4,5]thieno[3,2-c]carbazole was used instead of 5H-benzofuro[3,2-c]carbazole in synthesizing Compound 98.

LC-Mass (cal.: 772.24 g/mol, found: [M+H]$^+$=773 g/mol)

Synthesis Example 17: Synthesis of Compound 113

Compound 113 was synthesized according to the Reaction Scheme below:

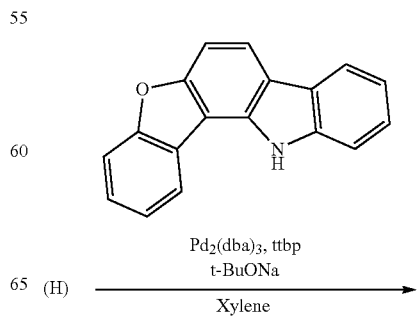

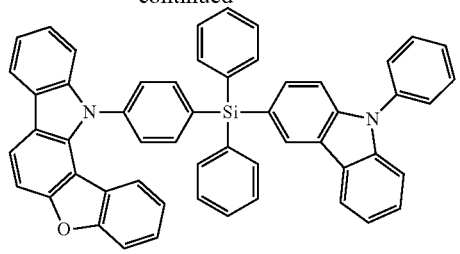

113

8.21 g (63%) of Compound 113 was synthesized in the same manner as in Synthesis of Compound 97, except that 4.88 g (19.0 mmol) of 12H-benzofuro[3,2-a]carbazole was used instead of 5H-benzofuro[3,2-c]carbazole in synthesizing Compound 113.

LC-Mass (cal.: 756.26 g/mol, found: [M+H]⁺=757 g/mol)

Synthesis Example 18: Synthesis of Compound 115

Compound 115 was synthesized according to the Reaction Scheme below:

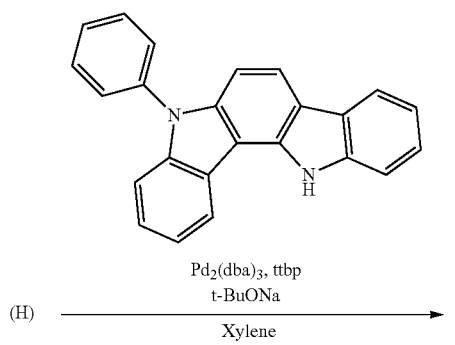

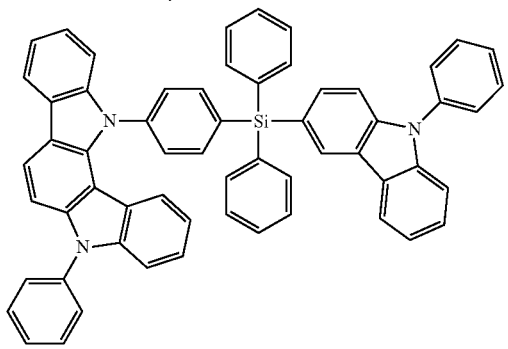

115

5.87 g (41%) of Compound 115 was synthesized in the same manner as in Compound 97, except that 6.30 g (19.0 mmol) of 5-phenyl-5,12-dihydroindolo[3,2-a]carbazole was used instead of 5H-benzofuro[3,2-c]carbazole in synthesizing Compound 115.

LC-Mass (cal.: 831.31 g/mol, found: [M+H]⁺=832 g/mol)

Synthesis Example 19: Synthesis of Compound 117

Compound 117 was synthesized according to the Reaction Scheme below:

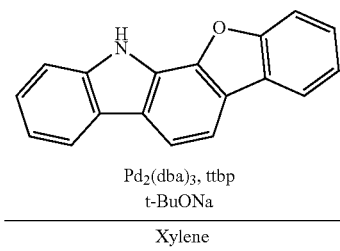

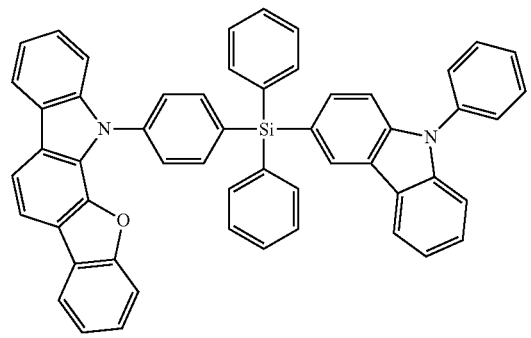

117

5.87 g (45%) of Compound 117 was synthesized in the same manner as in Synthesis of Compound 97, except that 4.88 g (19.0 mmol) of 12H-benzofuro[2,3-a]carbazole was used instead of 5H-benzofuro[3,2-c]carbazole in synthesizing Compound 117.

LC-Mass (cal.: 756.26 g/mol, found: [M+H]⁺=757 g/mol)

Synthesis Example 20: Synthesis of Compound 121

Compound 121 was synthesized according to the Reaction Scheme below:

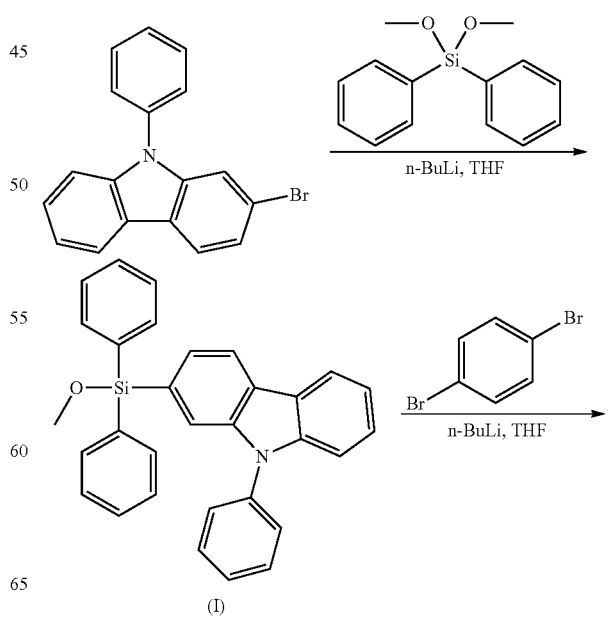

(I)

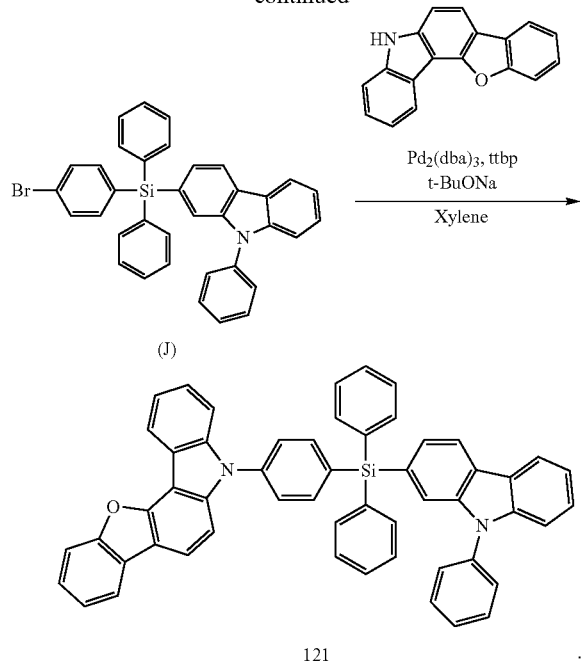

(1) Synthesis of Intermediate (I)

42.4 g (60%) of Intermediate (I) was synthesized in the same manner as in Synthesis of Intermediate (A), except that 50.0 g (155 mmol) of 2-bromo-9-phenyl-9H-carbazole was used instead of 9-(4-bromophenyl)-9H-carbazole in synthesizing Intermediate (I).

LC-Mass (cal.: 455.17 g/mol, found: [M+H]$^+$=456 g/mol)

(2) Synthesis of Intermediate (J)

23.7 g (48%) of Intermediate (J) was synthesized in the same manner as in Synthesis of Intermediate (B), except that 38.6 g (84.8 mmol) of Intermediate (I) was used instead of Intermediate (A) in synthesizing Intermediate (J).

LC-Mass (cal.: 579.10 g/mol, found: [M+H]$^+$=580 g/mol)

(3) Synthesis of Compound 121

5.74 g (44%) of Compound 121 was synthesized in the same manner as in Synthesis of Compound 1, except that 10.0 g (17.2 mmol) of Intermediate (J) was used instead of Intermediate (B) in synthesizing Compound 121.

LC-Mass (cal.: 756.26 g/mol, found: [M+H]$^+$=757 g/mol)

Synthesis Example 21: Synthesis of Compound 338

Compound 338 was synthesized according to the Reaction Scheme below:

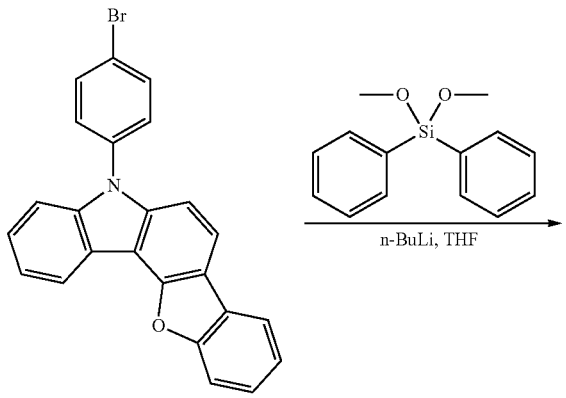

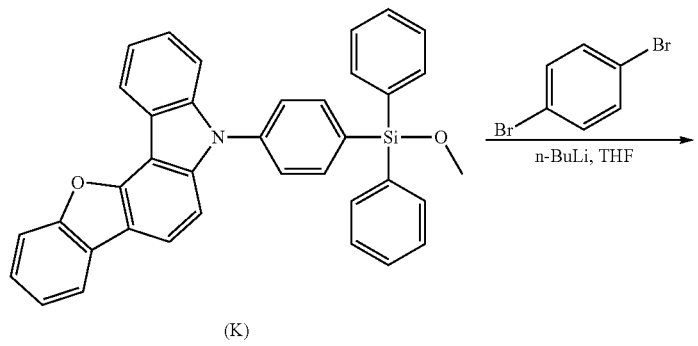

-continued

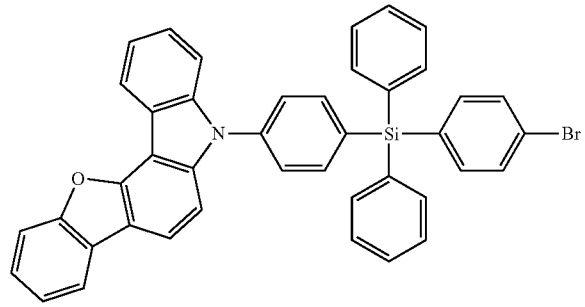

(L)

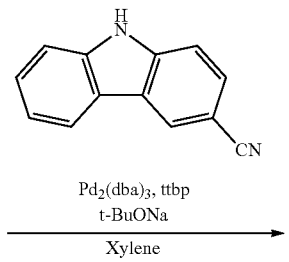

Pd₂(dba)₃, ttbp
t-BuONa
───────────→
Xylene

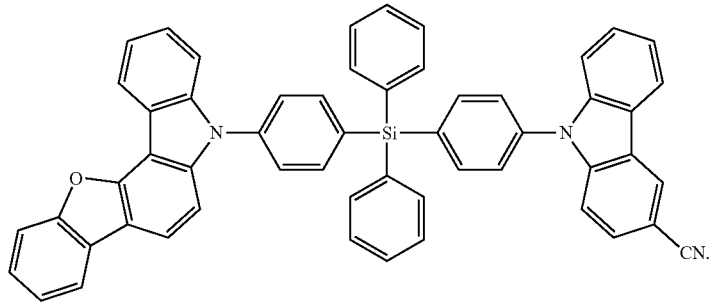

338

(1) Synthesis of Intermediate (K)

37.7 g (57%) of Intermediate (K) was synthesized in the same manner as in Synthesis of Intermediate (A), except that 50.0 g (121 mmol) of 5-(4-bromophenyl)-5H-benzofuro[3,2-c]carbazole was used instead of 9-(4-bromophenyl)-9H-carbazole in synthesizing Intermediate (K).

LC-Mass (cal.: 545.18 g/mol, found: [M+H]⁺=546 g/mol)

(2) Synthesis of Intermediate (L)

19.2 g (45%) of Intermediate (L) was synthesized in the same manner as in Synthesis of Intermediate (B), except that 34.7 g (63.6 mmol) of Intermediate (K) was used instead of Intermediate (A) in synthesizing Intermediate (L).

LC-Mass (cal.: 669.11 g/mol, found: [M+H]⁺=670 g/mol)

(3) Synthesis of Compound 338

5.25 g (45%) of Compound 338 was synthesized in the same manner as in Synthesis of Compound 1, except that, in synthesizing Compound 338, 10.0 g (14.9 mmol) of Intermediate (L) was used instead of Intermediate (B), and 3.15 g (16.4 mmol) of 9H-carbazole-3-carbonitrile was used instead of 5H-benzofuro[3,2-c]carbazole.

LC-Mass (cal.: 781.25 g/mol, found: [M+H]⁺=782 g/mol)

Synthesis Example 22: Synthesis of Compound 362

Compound 362 was synthesized according to the Reaction Scheme below:

(K) 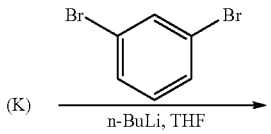 ───────────→
n-BuLi, THF

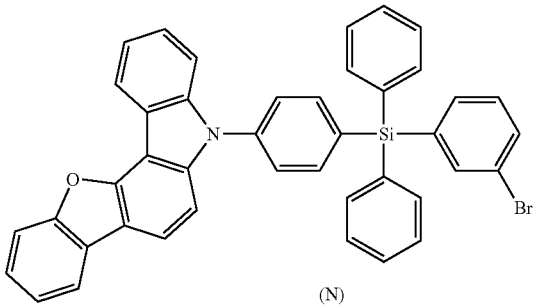

(N)

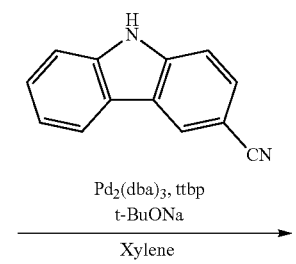

Pd₂(dba)₃, ttbp
t-BuONa
───────────→
Xylene

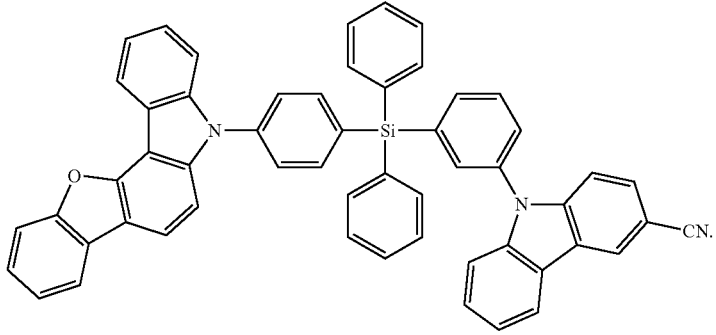

362

(1) Synthesis of Intermediate (N)

17.5 g (41%) of Intermediate (N) was synthesized in the same manner as in Synthesis of Intermediate (L), except that 15.0 g (63.6 mmol) of 1,3-dibromobenzene was used instead of Intermediate 1,4-dibromobenzene in synthesizing Intermediate (N).

LC-Mass (cal.: 669.11 g/mol, found: [M+H]$^+$=670 g/mol)

(2) Synthesis of Compound 362

4.43 g (38%) of Compound 362 was synthesized in the same manner as in Synthesis of Compound 338, except that 10.0 g (14.9 mmol) of Intermediate (N) was used instead of Intermediate (L) in synthesizing Compound 362.

LC-Mass (cal.: 781.25 g/mol, found: [M+H]$^+$=782 g/mol)

Synthesis Example 23: Synthesis of Compound 386

Compound 386 was synthesized according to the Reaction Scheme below:

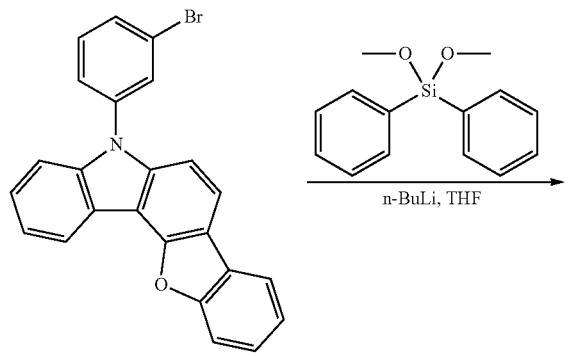

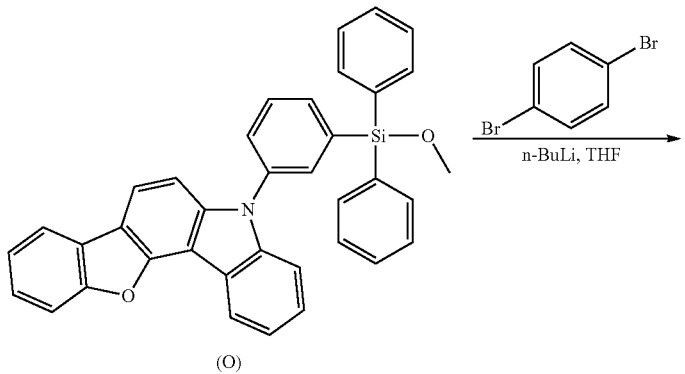

(O)

-continued

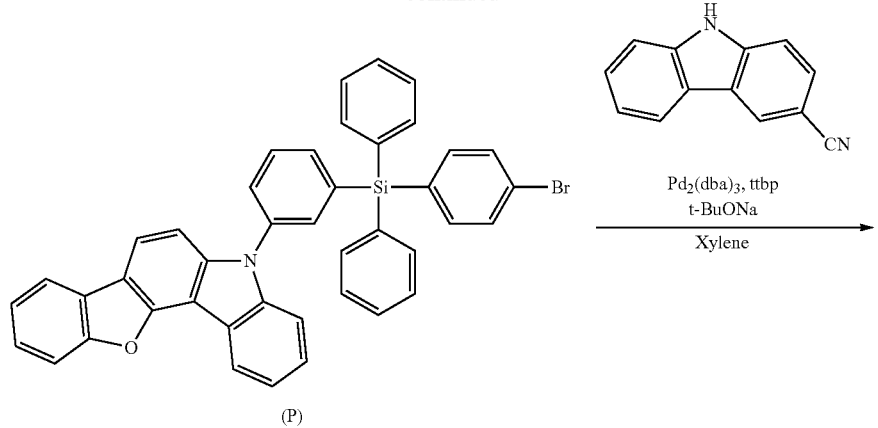
(P)

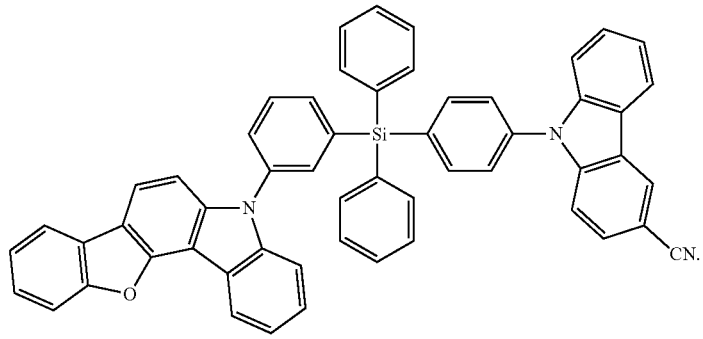
386

(1) Synthesis of Intermediate (O)

38.4 g (58%) of Intermediate (O) was synthesized in the same manner as in Synthesis of Intermediate (A), except that 50.0 g (121 mmol) of 5-(3-bromophenyl)-5H-benzofuro[3,2-c]carbazole was used instead of 9-(4-bromophenyl)-9H-carbazole in synthesizing Intermediate (O).

LC-Mass (cal.: 545.18 g/mol, found: [M+H]$^+$=546 g/mol)

(2) Synthesis of Intermediate (P)

18.8 g (44%) of Intermediate (P) was synthesized in the same manner as in Synthesis of Intermediate (B), except that 34.7 g (63.6 mmol) of Intermediate (O) was used instead of Intermediate (A) in synthesizing Intermediate (P).

LC-Mass (cal.: 669.11 g/mol, found: [M+H]$^+$=670 g/mol)

(3) Synthesis of Compound 386

4.66 g (40%) of Compound 386 was synthesized in the same manner as in Synthesis of Compound 338, except that 10.0 g (14.9 mmol) of Intermediate (P) was used instead of Intermediate (L) in synthesizing Compound 386.

LC-Mass (cal.: 781.25 g/mol, found: [M+H]$^+$=782 g/mol)

Synthesis Example 24: Synthesis of Compound A

Compound A was synthesized according to the Reaction Scheme below.

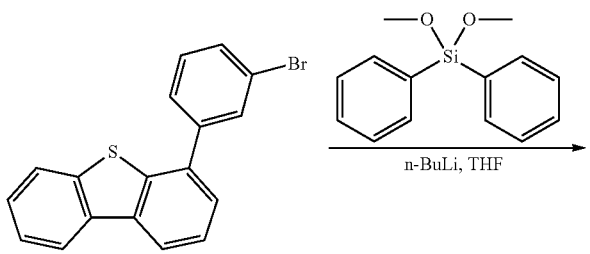

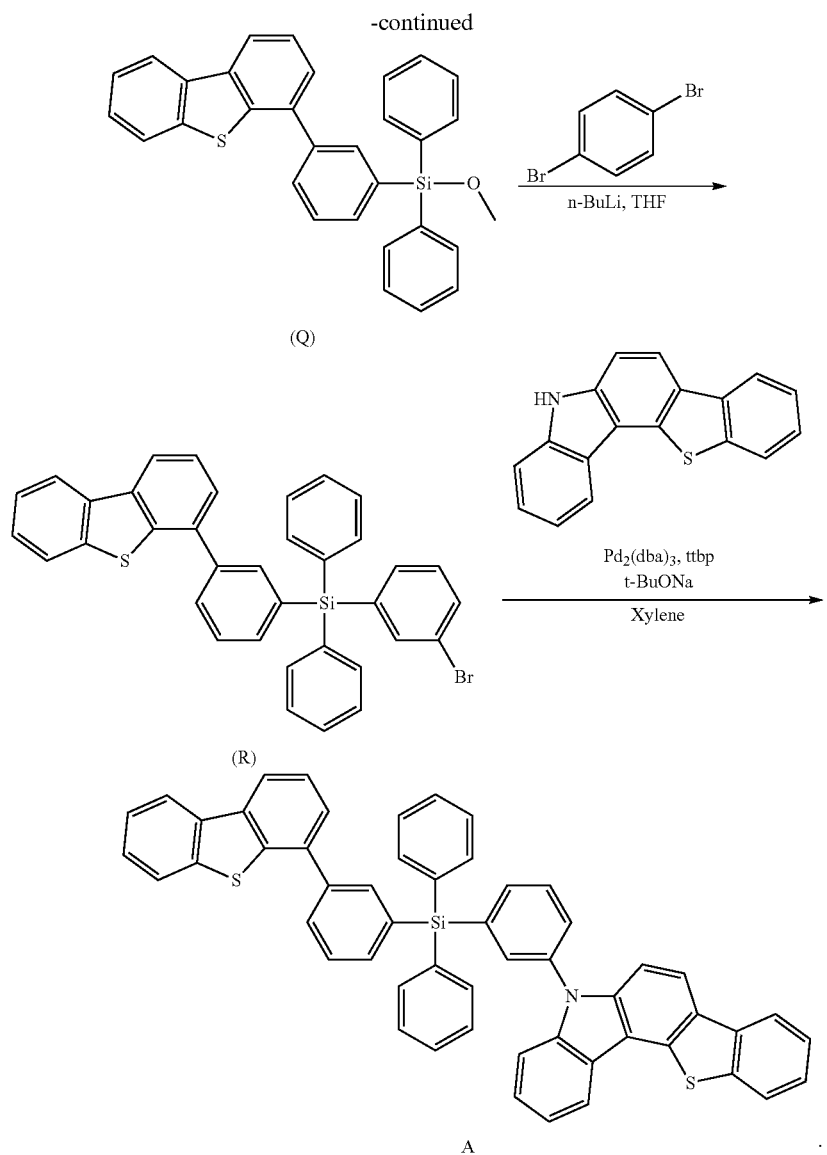

(1) Synthesis of Intermediate (Q)

39.7 g (57%) of Intermediate (Q) was synthesized in the same manner as in Synthesis of Intermediate (A), except that 50.0 g (147 mmol) of 4-(3-bromophenyl)dibenzo[b,d]thiophene was used instead of 9-(4-bromophenyl)-9H-carbazole in synthesizing Intermediate (Q).

LC-Mass (cal.: 472.13 g/mol, found: [M+H]$^+$=473 g/mol)

(2) Synthesis of Intermediate (R)

21.0 g (46%) of Intermediate (R) was synthesized in the same manner as in Intermediate (B), except that 36.1 g (76.3 mmol) of Intermediate (Q) was used instead of Intermediate (A) in synthesizing Intermediate (R).

LC-Mass (cal.: 596.06 g/mol, found: [M+H]$^+$=597 g/mol)

(3) Synthesis of Compound A 7.01 g (53%) of Compound A was synthesized in the same manner as in Synthesis of Compound 2, except that 10.0 g (16.7 mmol) of Intermediate (R) was used instead of Intermediate (B) in synthesizing Compound A.

LC-Mass (cal.: 789.20 g/mol, found: [M+H]$^+$=790 g/mol)

Synthesis Example 25: Synthesis of Compound B

Compound B was synthesized according to the Reaction Scheme below:

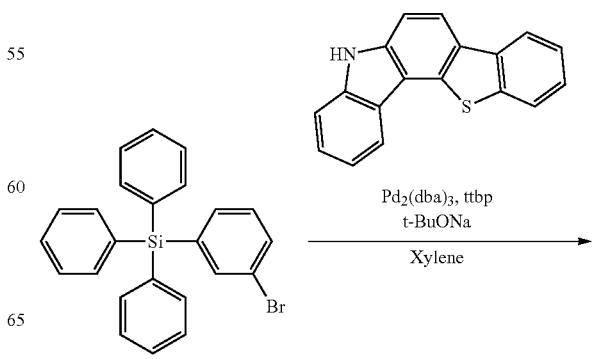

-continued

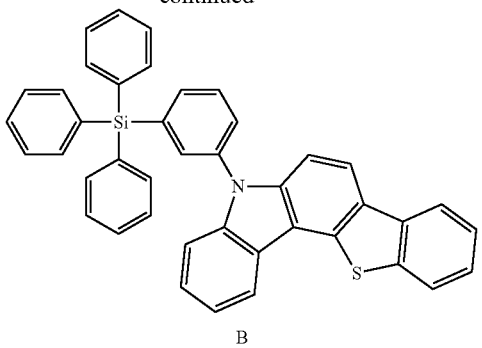

B 5.27 g (72%) of Compound B was synthesized in the same manner as in Synthesis of Compound 2, except that 5.00 g (12.0 mmol) of (3-bromophenyl)triphenylsilane was used instead of Intermediate (B) in synthesizing Compound B.

LC-Mass (cal.: 607.18 g/mol, found: [M+H]$^+$=608 g/mol)

Example 1

A glass substrate with an 1,500 Angstrom-thick (Å-thick) ITO electrode (first electrode, anode) formed thereon was washed by using distilled water and ultrasonic waves. When the washing with distilled water was completed, sonification washing was performed using a solvent, such as iso-propyl alcohol, acetone, or methanol. The resultant washed substrate was dried and transferred to a plasma washer where the substrate was washed with oxygen plasma for 5 minutes and transferred to a vacuum deposition apparatus.

Compound HT3 and Compound HP-1 were co-deposited on the ITO electrode of the glass substrate to form a hole injection layer having a thickness of 100 Angstroms (Å), Compound HT3 was deposited on the hole injection layer to form a hole transport layer having a thickness of 1,300 Å, and mCP was deposited on the hole transport layer to form an electron blocking layer having a thickness of 100 Å, thereby forming a hole transport region.

Compound 1 (host) and FIr6 (dopant, 10 percent by weight, wt %) were co-deposited on the hole transport region to form an emission layer having a thickness of 400 Å.

Compound BCP was vacuum-deposited on the emission layer to form a hole blocking layer having a thickness of 100 Å, Compound ET3 and LiQ were vacuum-deposited on the hole blocking layer to form an electron transport layer having a thickness of 300 Å, LiQ was deposited on the electron transport layer to form an electron injection layer having a thickness of 10 Å, and Al was deposited on the electron injection layer to form a second electrode (cathode) having a thickness of 1,200 Å, thereby completing the manufacture of an organic light-emitting device.

Examples 2 to 23

Organic light-emitting devices of Examples 2 to 23 were manufactured in the same manner as in Example 1, except that Compounds shown in Table 2 were each used instead of Compound 1 as a host in forming an emission layer.

Comparative Examples 1 and 2

Organic light-emitting devices of Comparative Examples 1 and 2 were manufactured in the same manner as in Example 1, except that Compound A and Compound B were used instead of Compound 1 as a host in forming an emission layer.

Evaluation Example 1: Evaluation of Characteristics of Organic Light-Emitting Devices The change in current density based on a voltage, the change in luminance according to a voltage, and the luminescent efficiency of the organic light-emitting devices manufactured according to Examples 1 to 23 and Comparative Examples 1 and 2 were measured. Specific measuring methods are as follows, and results thereof are shown in Table 2.

(1) Change in Current Density According to Voltage

A value of current flowing through a unit element of the manufactured organic light-emitting device was measured by using an ammeter-voltmeter (Keithley 2400), while increasing a voltage from 0 volts (V) to 10 V, and the result was obtained by dividing the measured value of current by an area of the unit element.

(2) Change in Brightness According to Voltage

Luminance of the manufactured organic light-emitting device was measured by using a luminance meter (Minolta Cs-1000A), while increasing a voltage from 0 V to 10 V, and the result was obtained.

(3) Measurement of Luminescent Efficiency

The current efficiency (candelas per ampere, cd/A) at the same current density (10 milliamperes per square centimeter, mA/cm$^2$) was calculated by using the luminance, the current density, and the voltage, which were measured in (1) and (2).

(4) Measurement of Durability

An amount of time that lapsed when luminance was 95% of initial luminance (100%) was evaluated.

The driving voltage, current efficiency, and durability in Table 2 are relative values when the driving voltage, current efficiency, and durability of the organic light-emitting device manufactured according to Comparative Example 1 are at 100%.

TABLE 2

| | Host | Driving voltage (%) | Current efficiency (%) | Durability (%) | Color |
|---|---|---|---|---|---|
| Example 1 | Compound 1 | 84 | 124 | 135 | Blue |
| Example 2 | Compound 2 | 95 | 110 | 108 | Blue |
| Example 3 | Compound 17 | 87 | 120 | 114 | Blue |
| Example 4 | Compound 19 | 81 | 108 | 109 | Blue |
| Example 5 | Compound 21 | 87 | 114 | 120 | Blue |
| Example 6 | Compound 25 | 78 | 135 | 140 | Blue |
| Example 7 | Compound 26 | 91 | 115 | 110 | Blue |
| Example 8 | Compound 41 | 82 | 120 | 118 | Blue |
| Example 9 | Compound 43 | 78 | 125 | 114 | Blue |
| Example 10 | Compound 45 | 88 | 128 | 130 | Blue |
| Example 11 | Compound 49 | 80 | 130 | 138 | Blue |
| Example 12 | Compound 65 | 84 | 114 | 120 | Blue |
| Example 13 | Compound 69 | 84 | 105 | 131 | Blue |
| Example 14 | Compound 73 | 80 | 121 | 133 | Blue |
| Example 15 | Compound 97 | 84 | 134 | 145 | Blue |
| Example 16 | Compound 98 | 94 | 108 | 105 | Blue |
| Example 17 | Compound 113 | 84 | 106 | 124 | Blue |
| Example 18 | Compound 115 | 77 | 131 | 111 | Blue |
| Example 19 | Compound 117 | 81 | 124 | 130 | Blue |
| Example 20 | Compound 121 | 94 | 104 | 122 | Blue |
| Example 21 | Compound 338 | 64 | 158 | 245 | Blue |
| Example 22 | Compound 362 | 70 | 160 | 210 | Blue |
| Example 23 | Compound 386 | 68 | 155 | 234 | Blue |

TABLE 2-continued
| | Host | Driving voltage (%) | Current efficiency (%) | Durability (%) | Color |
|---|---|---|---|---|---|
| Comparative Example 1 | Compound A | 100 | 100 | 100 | Blue |
| Comparative Example 2 | Compound B | 135 | 76 | 42 | Blue |
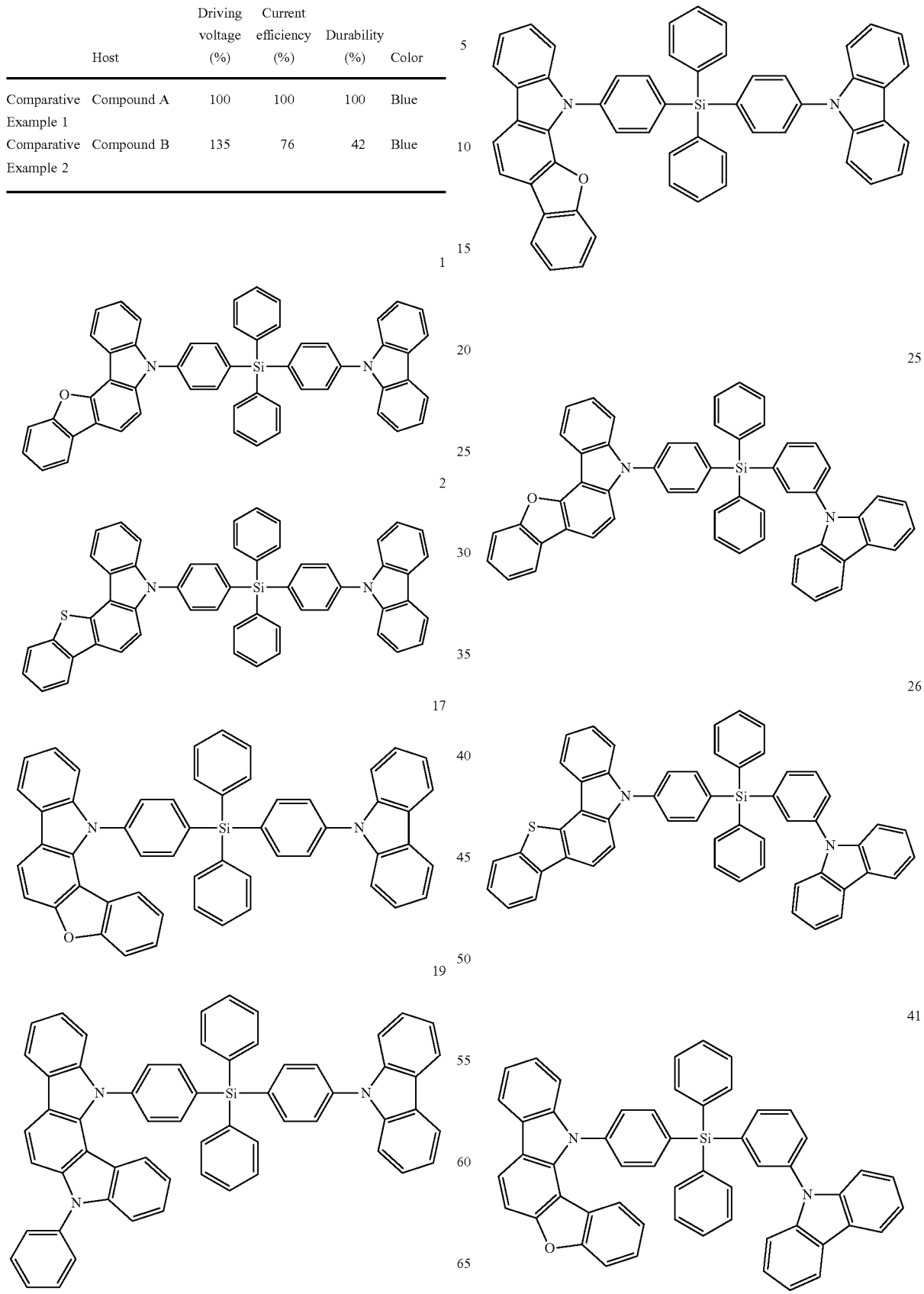

43
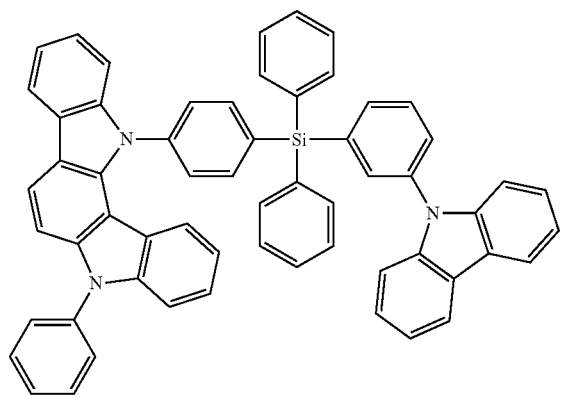
45
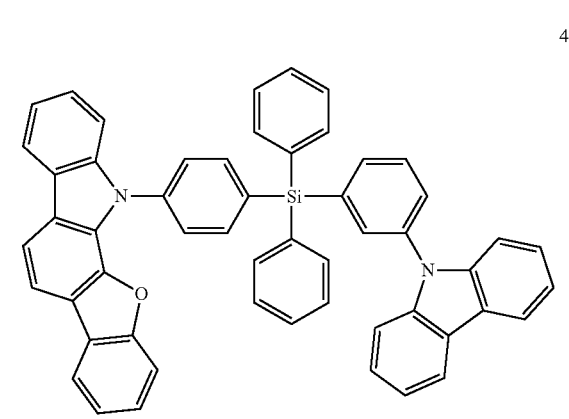
49
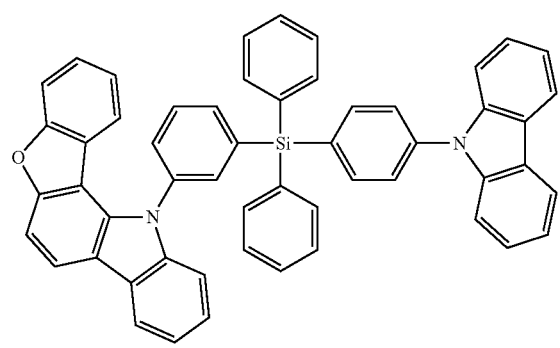
69
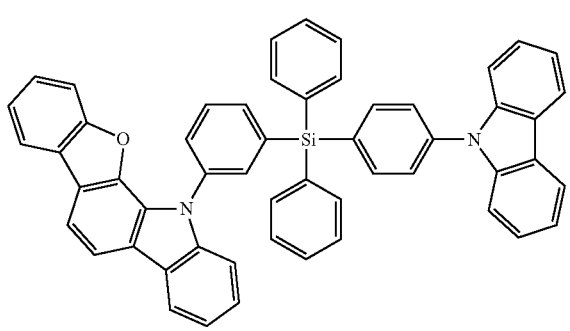
73
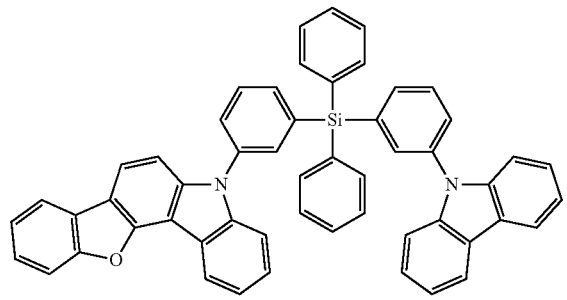
97
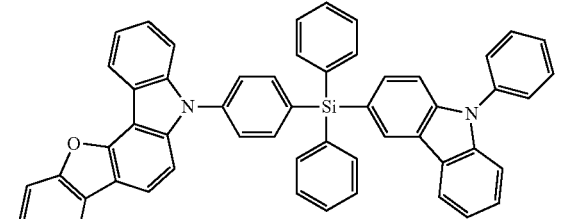
98
113
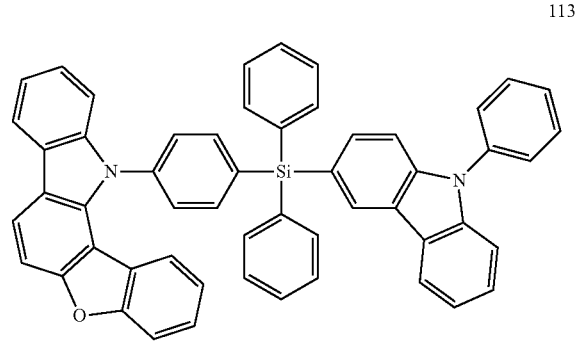

115

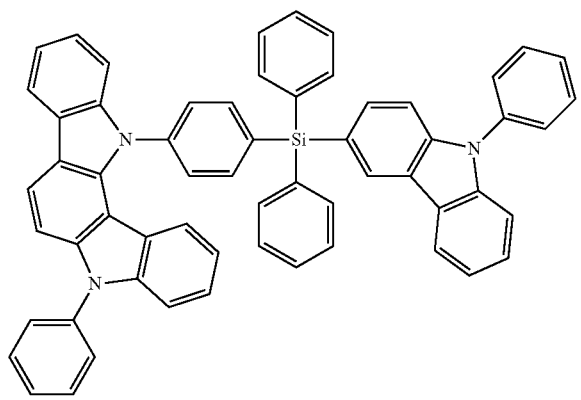

117

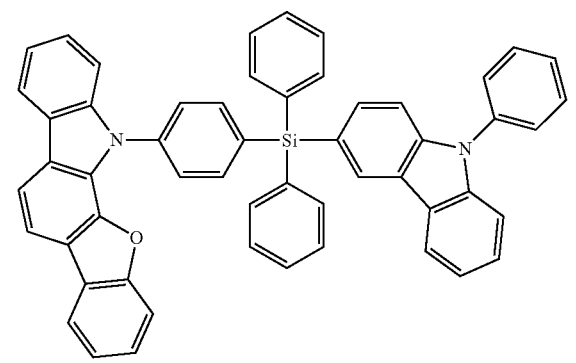

121

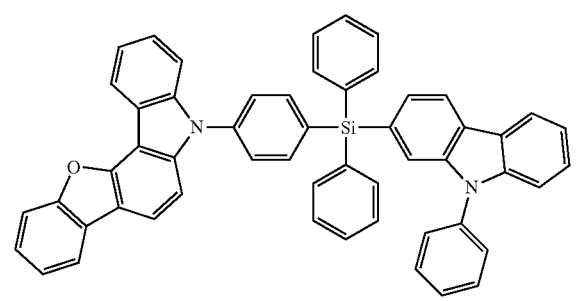

338

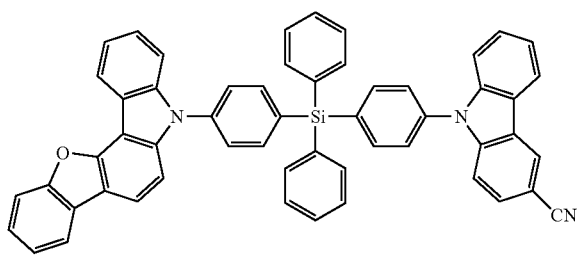

362

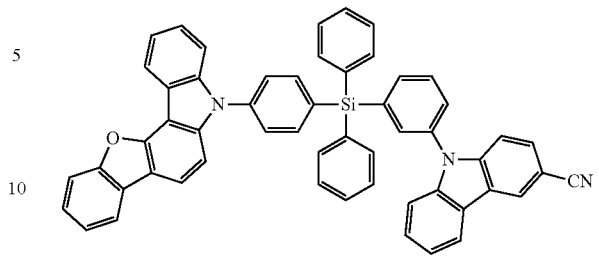

386

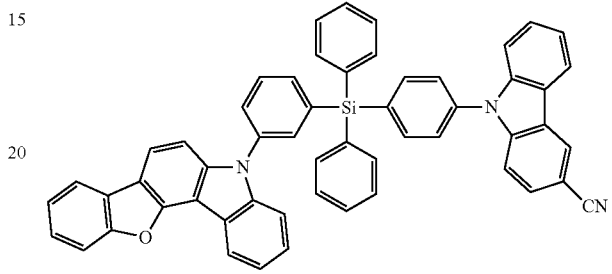

A

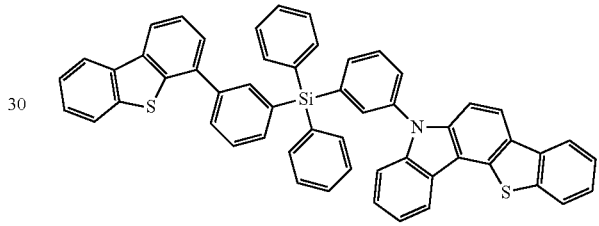

B

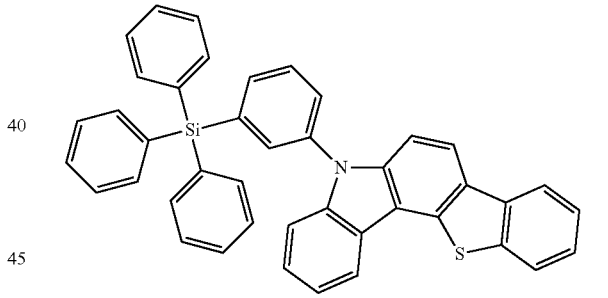

Referring to Table 2, it was found that the organic light-emitting devices of Examples 1 to 23 had a low driving voltage, high efficiency, and high durability, compared to those of Comparative Examples 1 and 2.

According to one or more exemplary embodiments, since the silyl group-containing compound has excellent electric characteristics and thermal stability, an organic light-emitting device including the silyl group-containing compound may have low driving voltage, high efficiency, high power, high quantum emission efficiency, and long lifespan characteristics.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present disclosure as defined by the following claims.

What is claimed is:

1. A silyl group-containing compound represented by Formula 1:

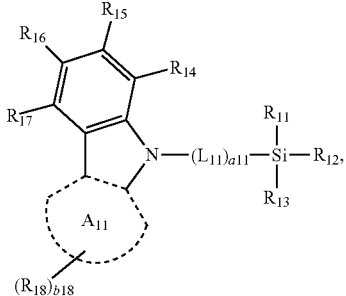

Formula 1 wherein, in Formula 1, $A_{11}$ is selected from a carbazole group, a fluorene group, a dibenzofuran group, and a dibenzothiophene group, $R_{11}$ to $R_{13}$ are each independently selected from groups represented by Formulae 2-1 to 2-6, provided that at least one selected from $R_{11}$ to $R_{13}$ is selected from groups represented by Formulae 2-1 to 2-5, and provided that at least one selected from $R_{11}$ to $R_{13}$ is represented by Formula 2-6:

2-1

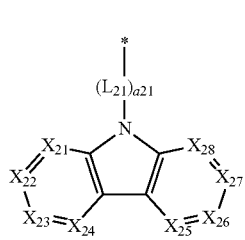

2-2

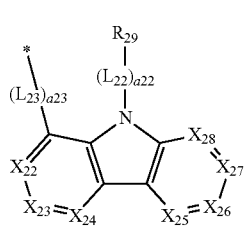

2-3

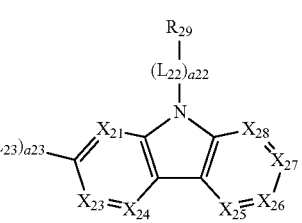

2-4

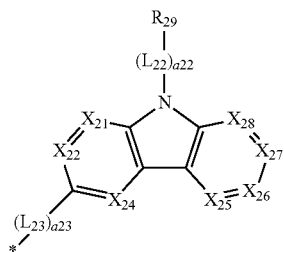

2-5

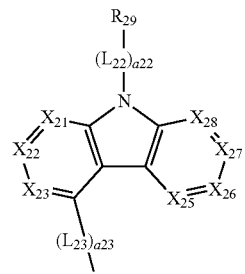

2-6

$*-(L_{24})_{a24}-R_{30}$, wherein, in Formulae 2-1 to 2-6, $X_{21}$ is selected from N and $CR_{21}$, $X_{22}$ is selected from N and $CR_{22}$, $X_{23}$ is selected from N and $CR_{23}$, $X_{24}$ is selected from N and $CR_{24}$, $X_{25}$ is selected from N and $CR_{25}$, $X_{26}$ is selected from N and $CR_{26}$, $X_{27}$ is selected from N and $CR_{27}$, and $X_{28}$ is selected from N and $CR_{28}$, $L_{11}$ and $L_{21}$ to $L_{24}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 and a21 are each independently an integer selected from 1, 2, 3, and 4, a22 to a24 are each independently an integer selected from 0, 1, 2, 3, and 4, $R_{14}$ to $R_{18}$ and $R_{21}$ to $R_{29}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), and —B($Q_1$)($Q_2$), $R_{30}$ is selected from:

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a dibenzosilolyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a carbazolyl group, a benzocarbazolyl group, a dibenzocarbazolyl group, an imidazopyridimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group; and a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a dibenzosilolyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a carbazolyl group, a benzocarbazolyl group, a dibenzocarbazolyl group, an imidazopyridimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{31}$)($Q_{32}$), and —B($Q_{31}$)($Q_{32}$), wherein $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, b18 is an integer selected from 1, 2, 3, 4, 5, 6, 7, 8, 9, and 10, $Q_1$ to $Q_3$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

2. The silyl group-containing compound of claim 1, wherein the silyl group-containing compound represented by Formula 1 is represented by one of Formulae 1-1 to 1-6:

1-1
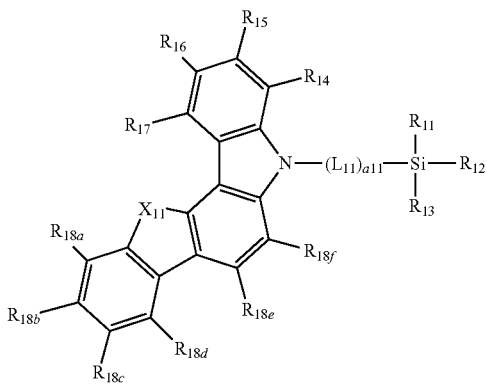

1-2
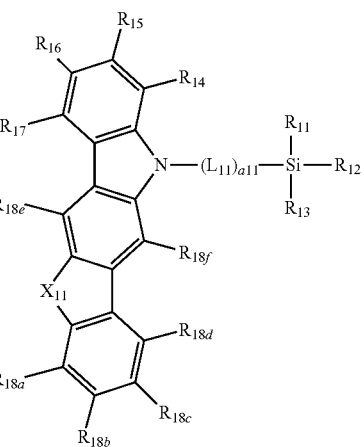

1-3
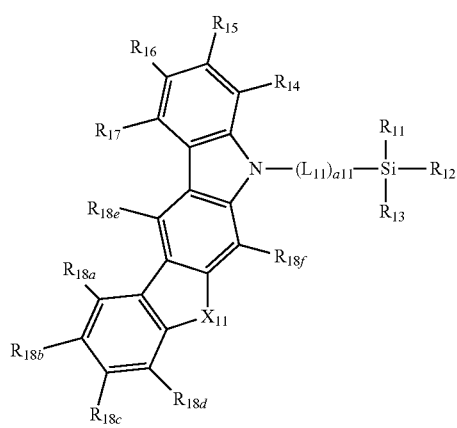

1-4

1-5
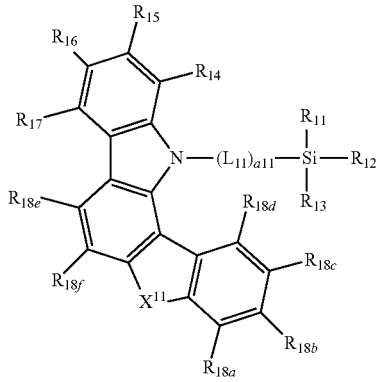

1-6
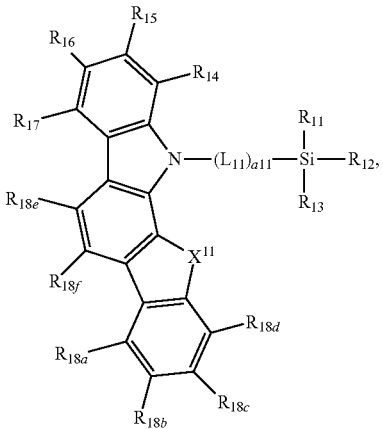

wherein, in Formulae 1-1 to 1-6,
$X_{11}$ is selected from O, S, $N(R_{18g})$, and $C(R_{18g})(R_{18h})$,
$R_{11}$ to $R_{17}$, $L_{11}$, and a11 are the same as described in connection with Formula 1, and
$R_{18a}$ to $R_{18h}$ are each independently the same as described in connection with $R_{18}$ in Formula 1.

3. The silyl group-containing compound of claim 1, wherein
$R_{11} \neq R_{12} \neq R_{13}$;
$R_{11} = R_{12}$, $R_{12} \neq R_{13}$;
$R_{12} = R_{13}$, $R_{11} \neq R_{12}$;
$R_{13} = R_{11}$, $R_{12} \neq R_{13}$; or
$R_{11} = R_{12} = R_{13}$.

4. The silyl group-containing compound of claim 1, wherein
$X_{21}$ is $CR_{21}$, $X_{22}$ is $CR_{22}$, $X_{23}$ is $CR_{23}$, $X_{24}$ is $CR_{24}$, $X_{25}$ is $CR_{25}$, $X_{26}$ is $CR_{26}$, $X_{27}$ is $CR_{27}$, and $X_{28}$ is $CR_{28}$;
$X_{21}$ is N, $X_{22}$ is $CR_{22}$, $X_{23}$ is $CR_{23}$, $X_{24}$ is $CR_{24}$, $X_{25}$ is $CR_{25}$, $X_{26}$ is $CR_{26}$, $X_{27}$ is $CR_{27}$, and $X_{28}$ is $CR_{28}$;
$X_{21}$ is $CR_{21}$, $X_{22}$ is N, $X_{23}$ is $CR_{23}$, $X_{24}$ is $CR_{24}$, $X_{25}$ is $CR_{25}$, $X_{26}$ is $CR_{26}$, $X_{27}$ is $CR_{27}$, and $X_{28}$ is $CR_{28}$;
$X_{21}$ is $CR_{21}$, $X_{22}$ is $CR_{22}$, $X_{23}$ is N, $X_{24}$ is $CR_{24}$, $X_{25}$ is $CR_{25}$, $X_{26}$ is $CR_{26}$, $X_{27}$ is $CR_{27}$, and $X_{28}$ is $CR_{28}$;
$X_{21}$ is $CR_{21}$, $X_{22}$ is $CR_{22}$, $X_{23}$ is $CR_{23}$, $X_{24}$ is N, $X_{25}$ is $CR_{25}$, $X_{26}$ is $CR_{26}$, $X_{27}$ is $CR_{27}$, and $X_{28}$ is $CR_{28}$;
$X_{21}$ is $CR_{21}$, $X_{22}$ is $CR_{22}$, $X_{23}$ is $CR_{23}$, $X_{24}$ is $CR_{24}$, $X_{25}$ is N, $X_{26}$ is $CR_{26}$, $X_{27}$ is $CR_{27}$, and $X_{28}$ is $CR_{28}$;
$X_{21}$ is $CR_{21}$, $X_{22}$ is $CR_{22}$, $X_{23}$ is $CR_{23}$, $X_{24}$ is $CR_{24}$, $X_{25}$ is $CR_{25}$, $X_{26}$ is N, $X_{27}$ is $CR_{27}$, and $X_{28}$ is $CR_{28}$;
$X_{21}$ is $CR_{21}$, $X_{22}$ is $CR_{22}$, $X_{23}$ is $CR_{23}$, $X_{24}$ is $CR_{24}$, $X_{25}$ is $CR_{25}$, $X_{26}$ is $CR_{26}$, $X_{27}$ is N, and $X_{28}$ is $CR_{28}$;
$X_{21}$ is $CR_{21}$, $X_{22}$ is $CR_{22}$, $X_{23}$ is $CR_{23}$, $X_{24}$ is $CR_{24}$, $X_{25}$ is $CR_{25}$, $X_{26}$ is $CR_{26}$, $X_{27}$ is and $CR_{27}$, $X_{28}$ is N;

$X_{21}$ is N, $X_{22}$ is $CR_{22}$, $X_{23}$ is N, $X_{24}$ is $CR_{24}$, $X_{25}$ is $CR_{25}$, $X_{26}$ is $CR_{26}$, $X_{27}$ is $CR_{27}$, and $X_{28}$ is $CR_{28}$;

$X_{21}$ is $CR_{21}$, $X_{22}$ is N, $X_{23}$ is $CR_{23}$, $X_{24}$ is N, $X_{25}$ is $CR_{25}$, $X_{26}$ is $CR_{26}$, $X_{27}$ is $CR_{27}$, and $X_{28}$ is $CR_{28}$;

$X_{21}$ is $CR_{21}$, $X_{22}$ is $CR_{22}$, $X_{23}$ is $CR_{23}$, $X_{24}$ is $CR_{24}$, $X_{25}$ is N, $X_{26}$ is $CR_{26}$, $X_{27}$ is N, and $X_{28}$ is $CR_{28}$;

$X_{21}$ is $CR_{21}$, $X_{22}$ is $CR_{22}$, $X_{23}$ is $CR_{23}$, $X_{24}$ is $CR_{24}$, $X_{25}$ is $CR_{25}$, $X_{26}$ is N, $X_{27}$ is $CR_{27}$, and $X_{28}$ is N;

$X_{21}$ is N, $X_{22}$ is $CR_{22}$, $X_{23}$ is $CR_{23}$, $X_{24}$ is $CR_{24}$, $X_{25}$ is $CR_{25}$, $X_{26}$ is $CR_{26}$, $X_{27}$ is $CR_{27}$, and $X_{28}$ is N;

$X_{21}$ is $CR_{21}$, $X_{22}$ is N, $X_{23}$ is $CR_{23}$, $X_{24}$ is $CR_{24}$, $X_{25}$ is $CR_{25}$, $X_{26}$ is $CR_{26}$, $X_{27}$ is N, and $X_{28}$ is $CR_{28}$;

$X_{21}$ is $CR_{21}$, $X_{22}$ is $CR_{22}$, $X_{23}$ is N, $X_{24}$ is $CR_{24}$, $X_{25}$ is $CR_{25}$, $X_{26}$ is N, $X_{27}$ is $CR_{27}$, and $X_{28}$ is $CR_{28}$; or $X_{21}$ is $CR_{21}$, $X_{22}$ is $CR_{22}$, $X_{23}$ is $CR_{23}$, $X_{24}$ is N, $X_{25}$ is N, $X_{26}$ is $CR_{26}$, $X_{27}$ is $CR_{27}$, and $X_{28}$ is $CR_{28}$.

5. The silyl group-containing compound of claim 1, wherein $L_{11}$ and $L_{21}$ to $L_{24}$ are each independently selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

6. The silyl group-containing compound of claim 1, wherein $L_{11}$ and $L_{21}$ to $L_{24}$ are each independently selected from:

a phenylene group, a naphthylene group, a pyridinylene group, a pyrazinylene group, a pyrimidinylene group, and a triazinylene group; and a phenylene group, a naphthylene group, a pyridinylene group, a pyrazinylene group, a pyrimidinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group.

7. The silyl group-containing compound of claim 1, wherein $R_{14}$ to $R_{18}$ and $R_{21}$ to $R_{29}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a pyridinyl group, a pyrimidinyl group, and a triazinyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, a dibenzothiophenyl group, —Si($Q_{31}$)($Q_{32}$)($Q_{33}$), —N($Q_{31}$)($Q_{32}$), and —B($Q_{31}$)($Q_{32}$); and —Si($Q_1$)($Q_2$)($Q_3$), —N($Q_1$)($Q_2$), and —B($Q_1$)($Q_2$), wherein $Q_1$ to $Q_3$ and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group.

8. The silyl group-containing compound of claim 1, wherein $R_{14}$ to $R_{18}$ and $R_{21}$ to $R_{29}$ are each independently selected from hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a pyridinyl group, and a pyrimidinyl group.

9. The silyl group-containing compound of claim 1, wherein $R_{30}$ is selected from:

a cyclohexyl group, a piperidinyl group, a tetrahydro-2H-pyranyl group, a tetrahydro-2H-thiopyranyl group, a phenyl group, a biphenyl group, a terphenyl group, a naphthyl group, a fluorenyl group, a dibenzosilolyl group, a pyrrolyl group, a pyridinyl group, a pyrazinyl group, a pyrimidinyl group, a pyridazinyl group, a furanyl group, a thiophenyl group, a triazinyl group, a carbazolyl group, a dibenzofuranyl group, and a dibenzothiophenyl group; and a cyclohexyl group, a piperidinyl group, a tetrahydro-2H-pyranyl group, a tetrahydro-2H-thiopyranyl group, a phenyl group, a biphenyl group, a terphenyl group, a naphthyl group, a fluorenyl group, a dibenzosilolyl group, a pyrrolyl group, a pyridinyl group, a pyrazinyl group, a pyrimidinyl group, a pyridazinyl group, a furanyl group, a thiophenyl group, a triazinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a fluorenyl group, a carbazolyl group, a pyridinyl group, a pyrimidinyl group, a pyrazinyl group, a pyridazinyl group, and a triazinyl group.

10. The silyl group-containing compound of claim 1, wherein the silyl group-containing compound is represented by one of Formulae 1-11 to 1-40:

1-11

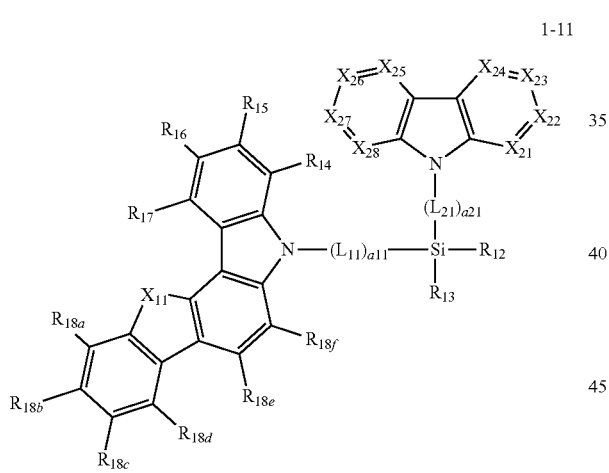

1-12

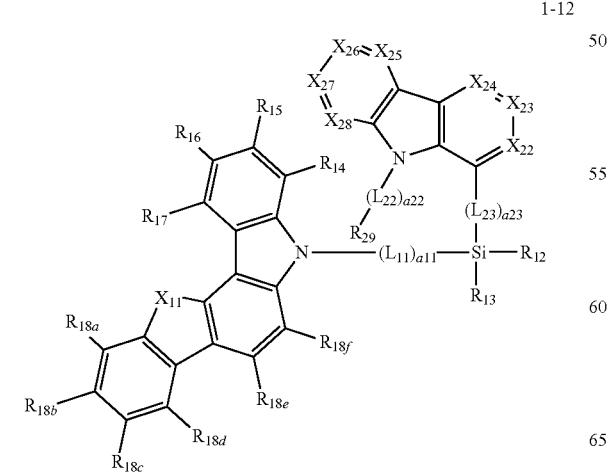

1-13

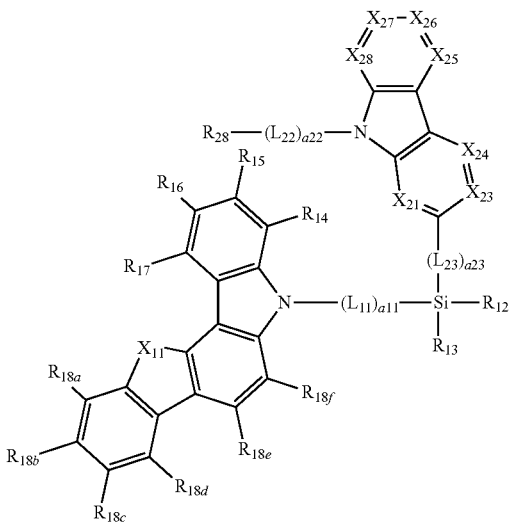

1-14

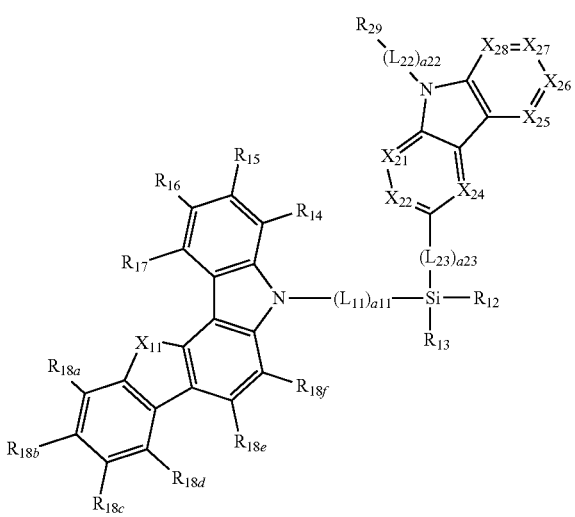

1-15

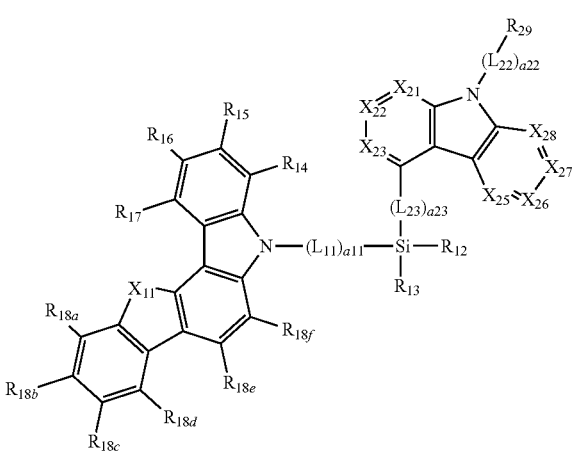

-continued
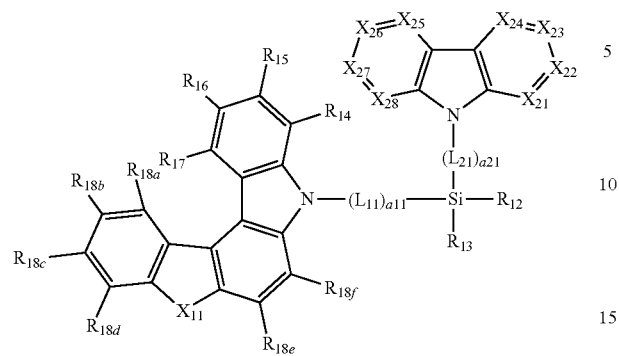
1-16
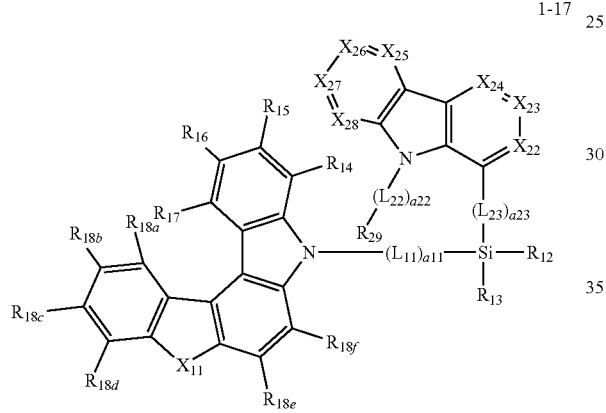
1-17
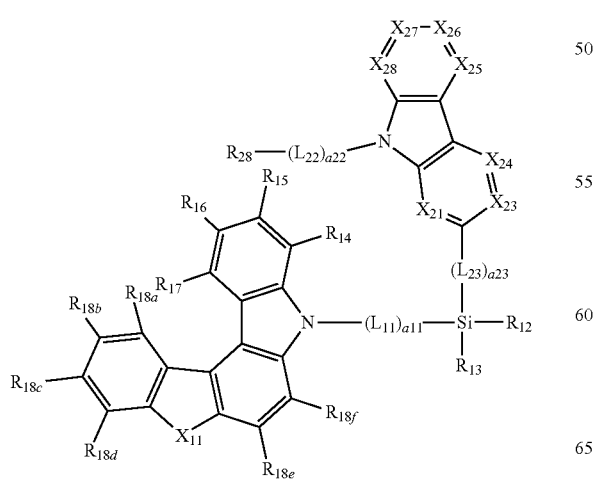
1-18
-continued
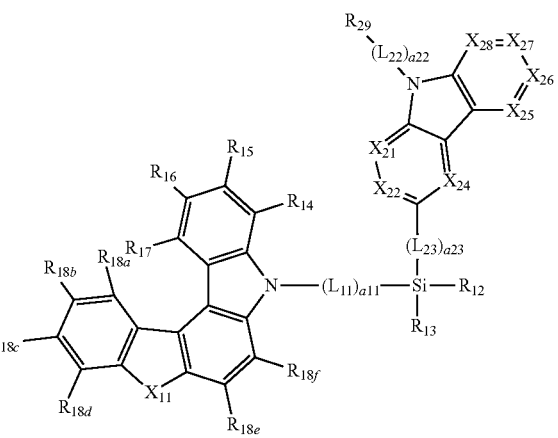
1-19
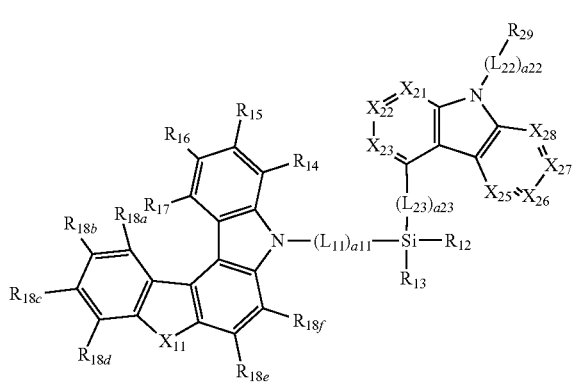
1-20
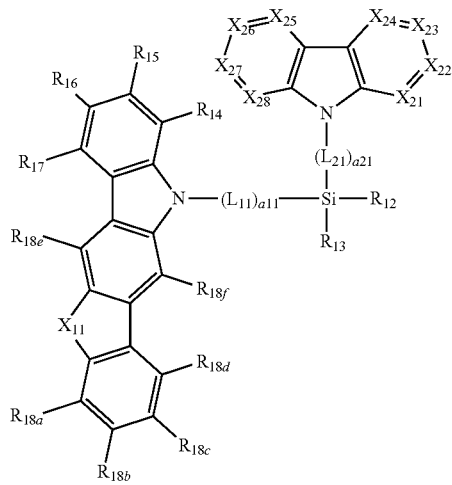
1-21

1-22
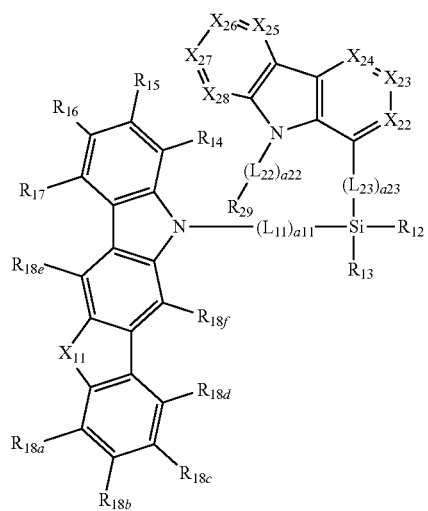
1-23
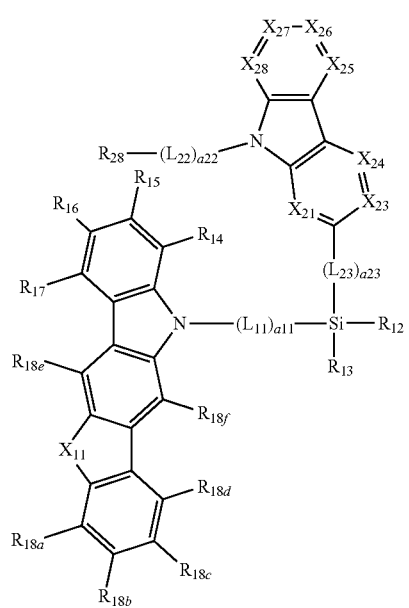
1-24
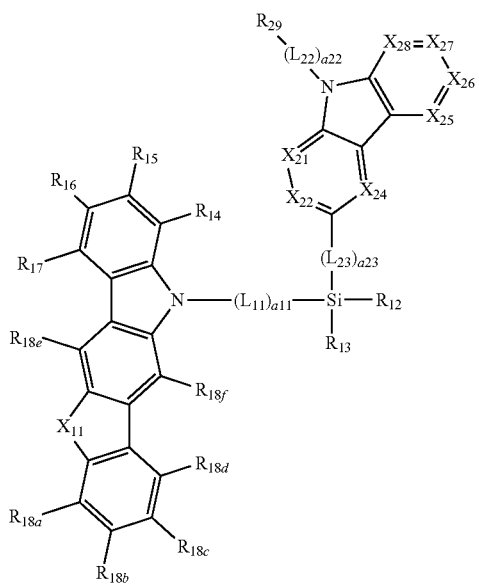
1-25
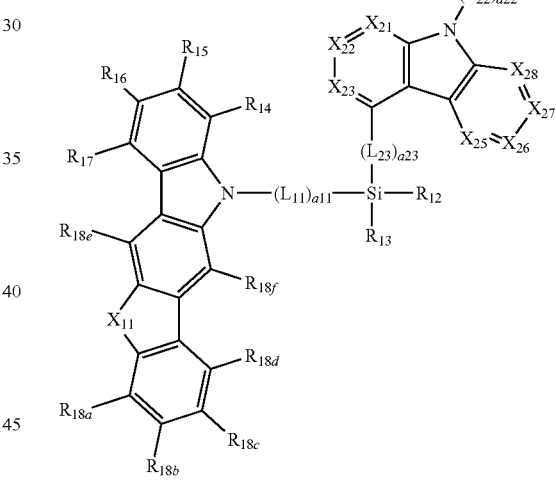
1-26
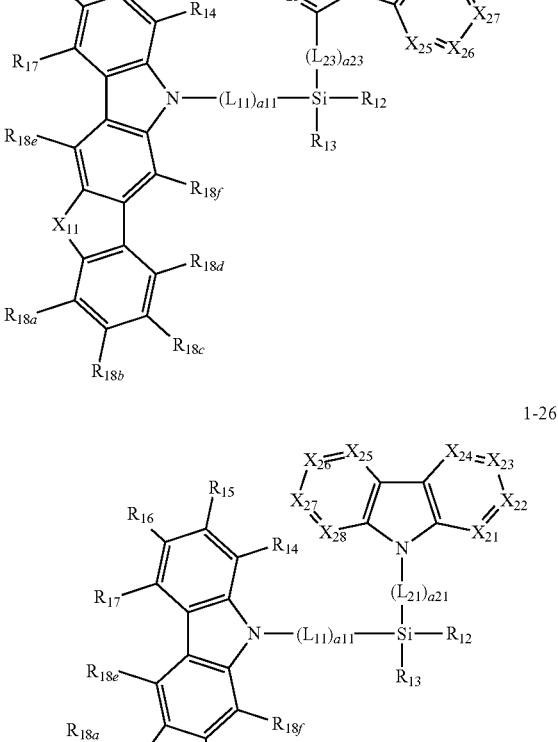

-continued
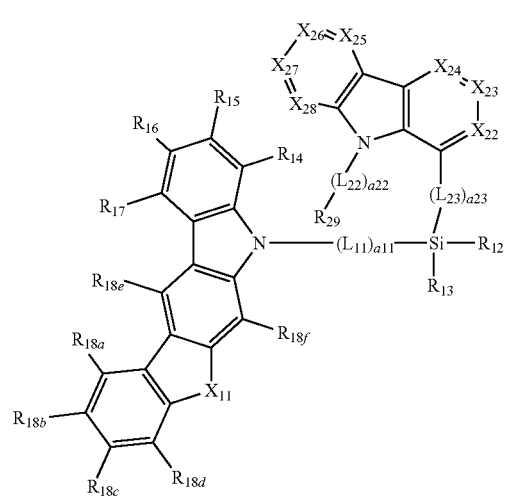
1-27
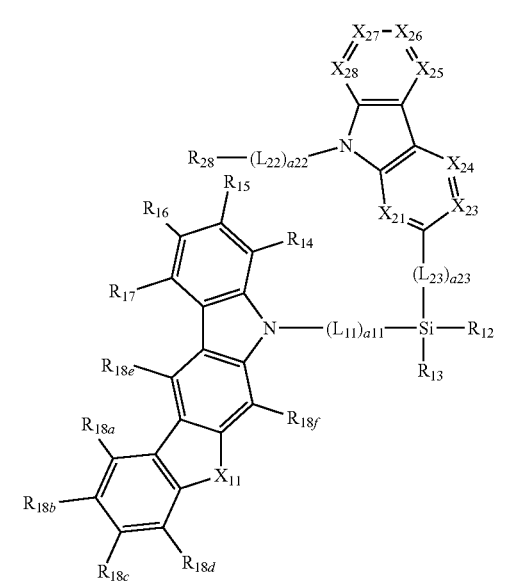
1-28
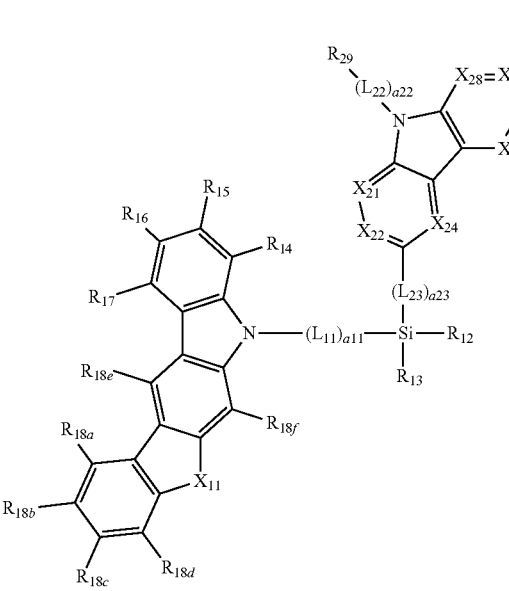
1-29
-continued
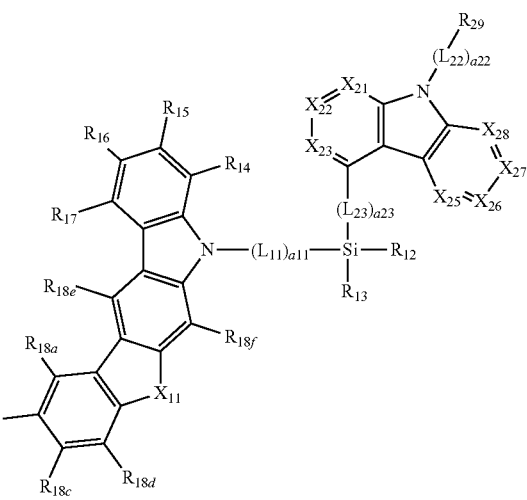
1-30
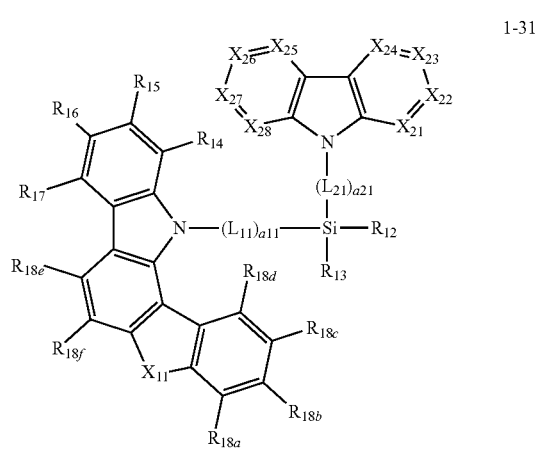
1-31
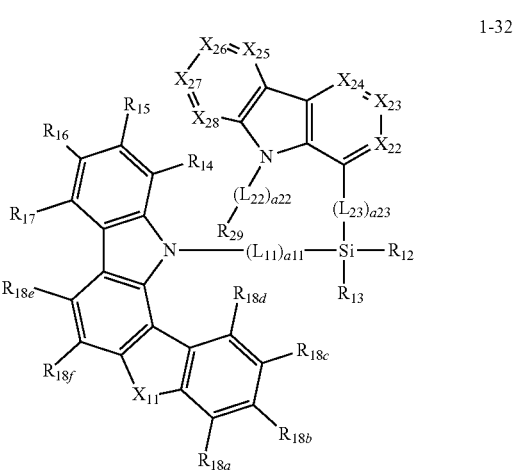
1-32

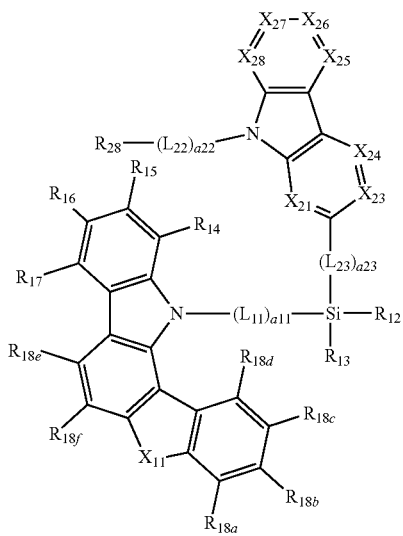
1-33
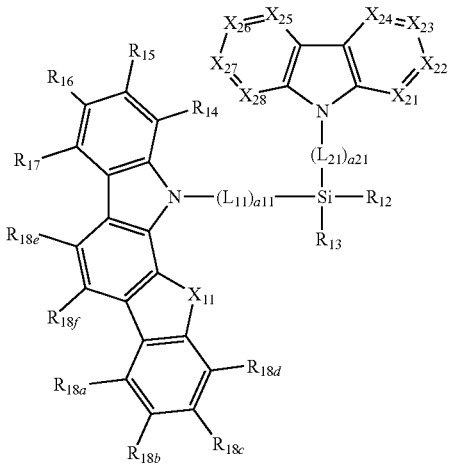
1-36
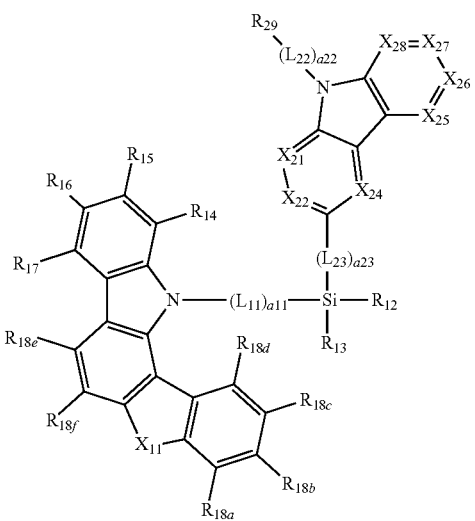
1-34
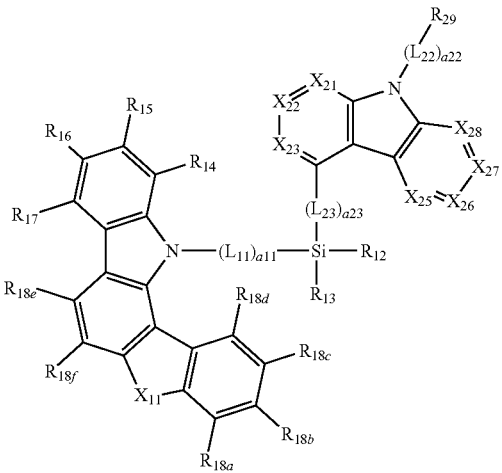
1-35
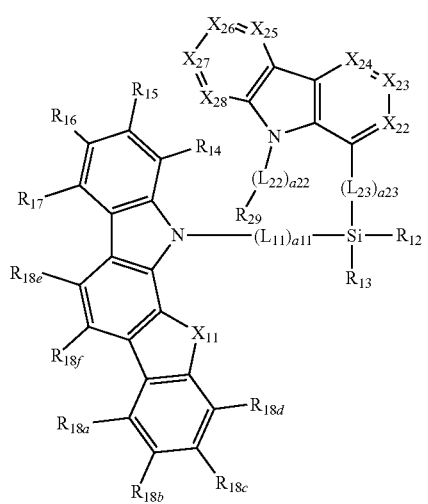
1-37

1-38

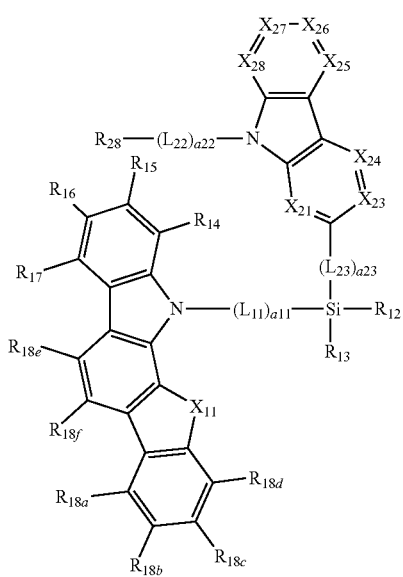

1-40

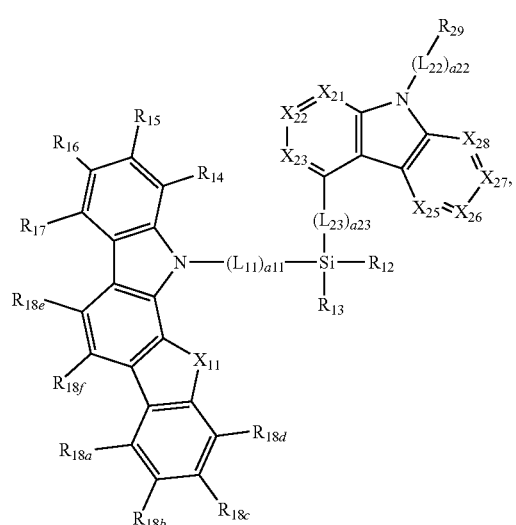

1-39

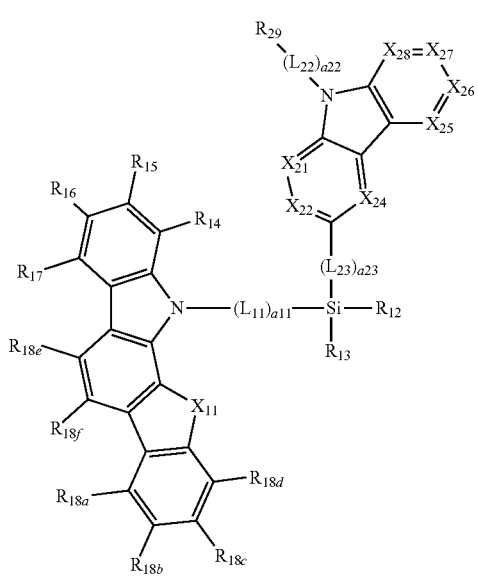

wherein, in Formulae 1-11 to 1-40, $X_{11}$ is selected from O, S, $N(R_{18g})$, and $C(R_{18g})(R_{18h})$, $R_{12}$ to $R_{17}$, $L_{11}$, and a11 are the same as described in connection with Formula 1, $X_{21}$ to $X_{28}$, $L_{21}$ to $L_{23}$, a21 to a23, and $R_{29}$ are the same as described in connection with Formulae 2-1 to 2-6, and $R_{18a}$ to $R_{18h}$ are each independently the same as described in connection with $R_{18}$ in Formula 1.

11. The silyl group-containing compound of claim 1, wherein
the silyl group-containing compound has a triplet energy level of 2.8 electron volts or higher.

12. The silyl group-containing compound of claim 1, wherein
the silyl group-containing compound represented by Formula 1 is selected from Compounds 1 to 432:

1

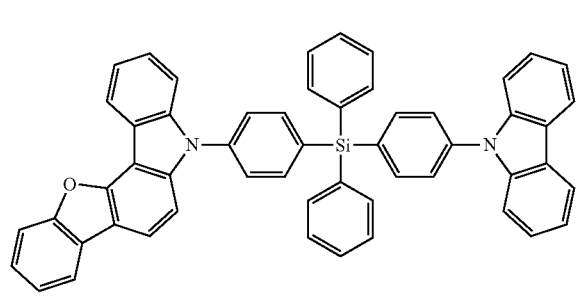

2

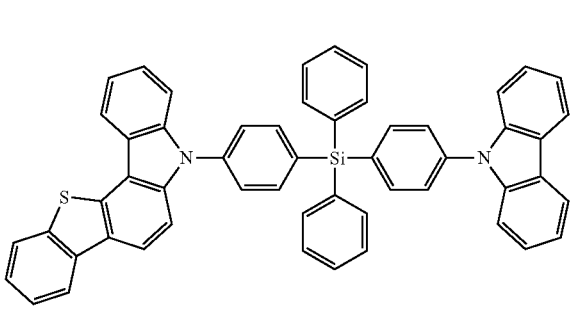

-continued
3
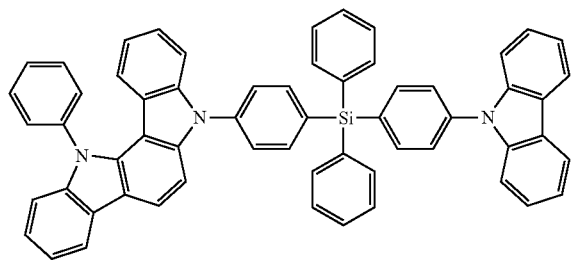
4
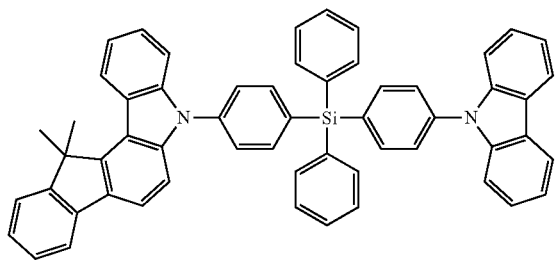
5
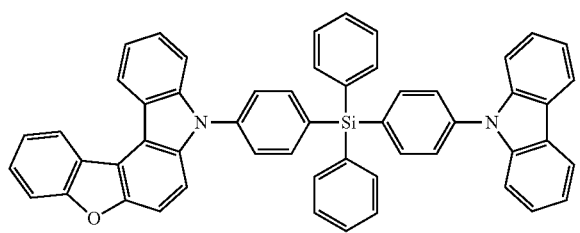
6
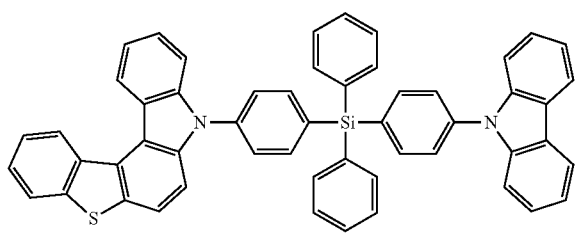
7
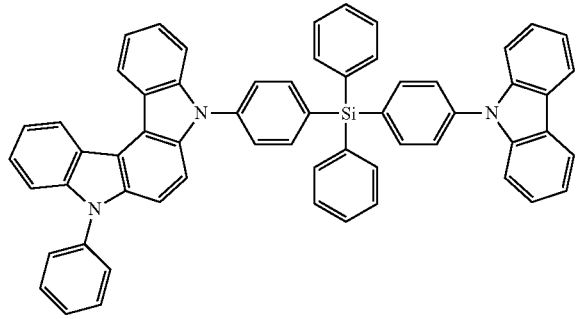
8
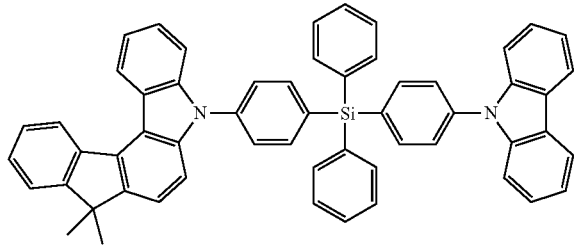
9
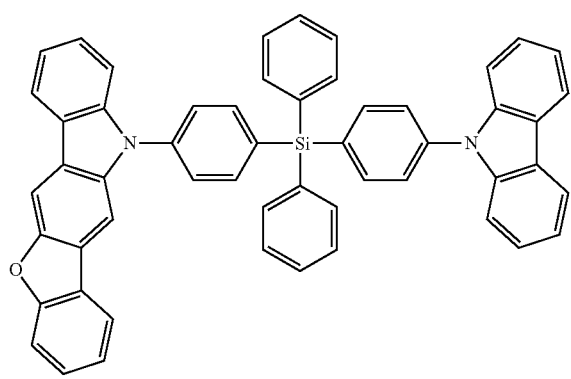
10
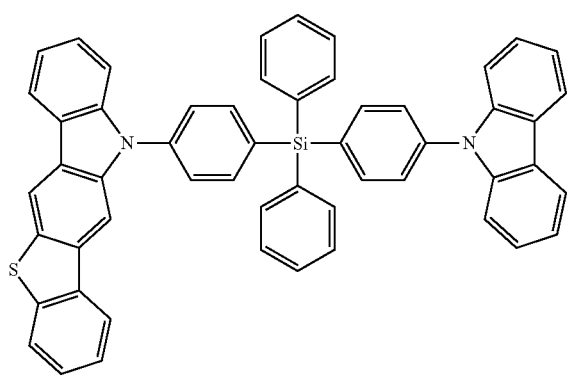
11
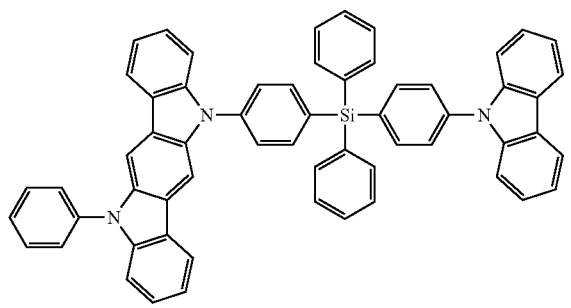
12
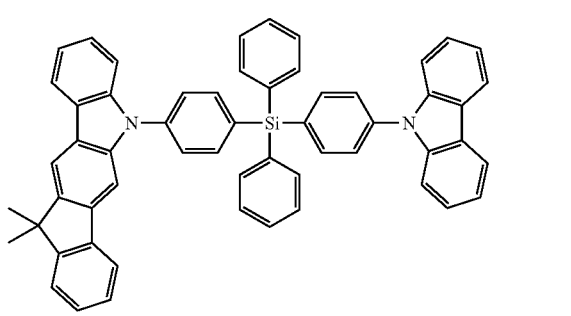

-continued
13 14
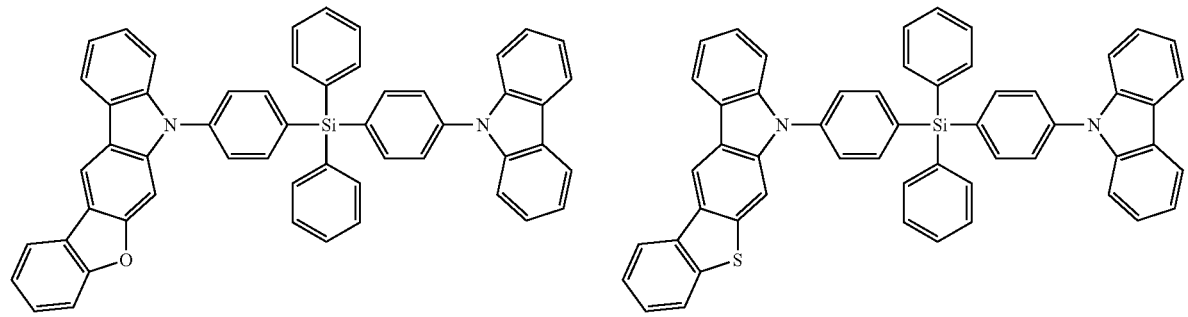
15 16
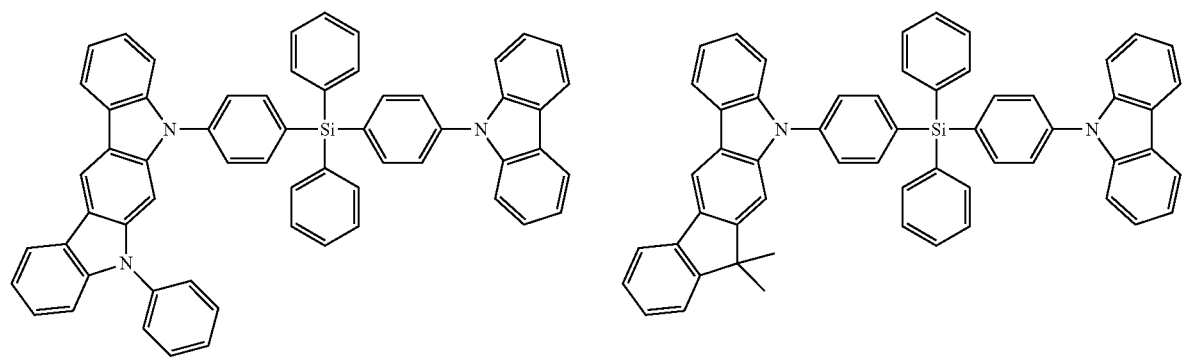
17 18
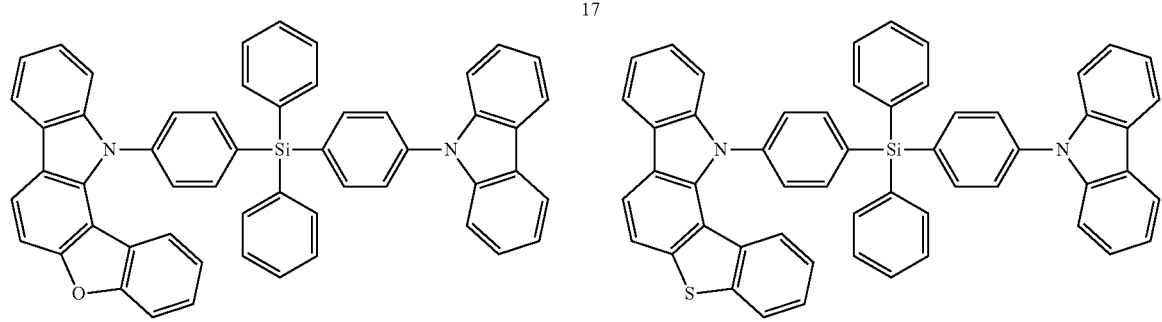
19 20
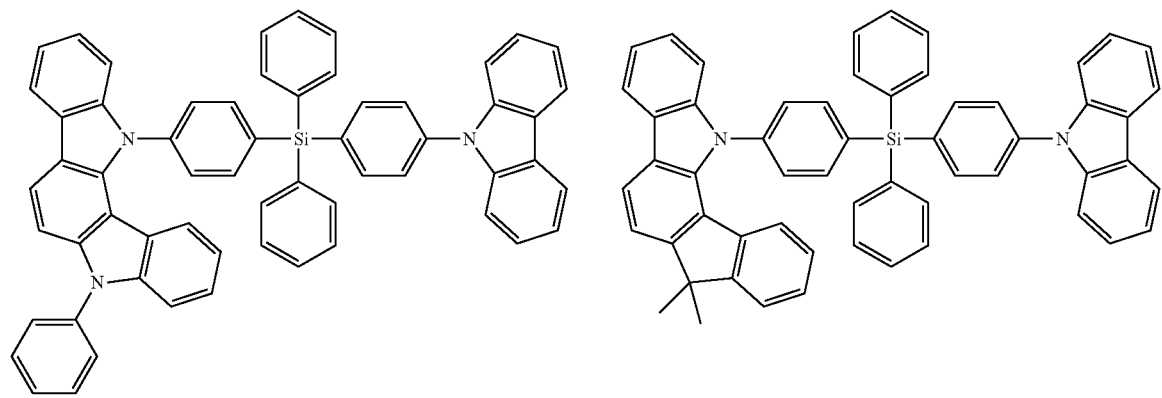

-continued
21
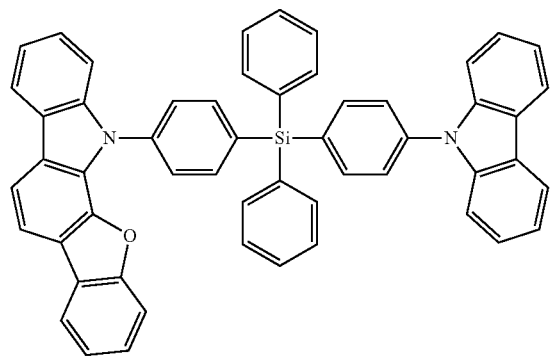
22
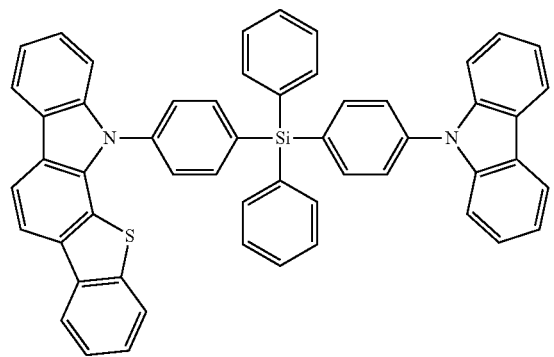
23
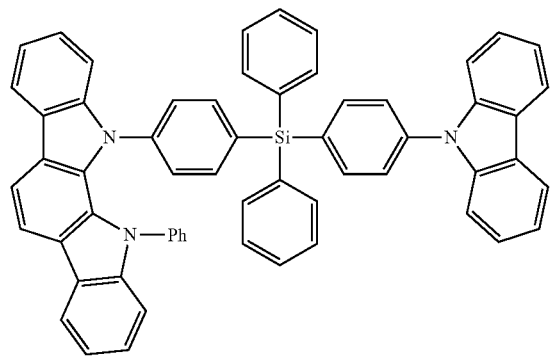
24
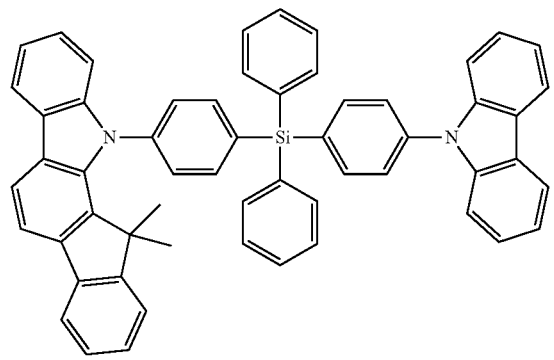
25
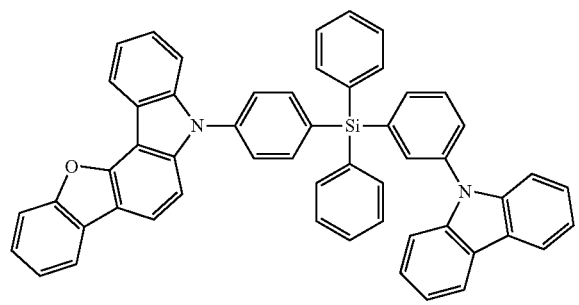
26
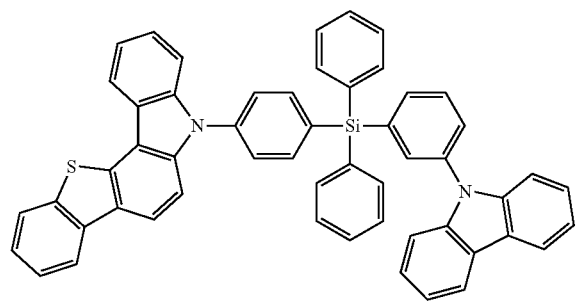
27
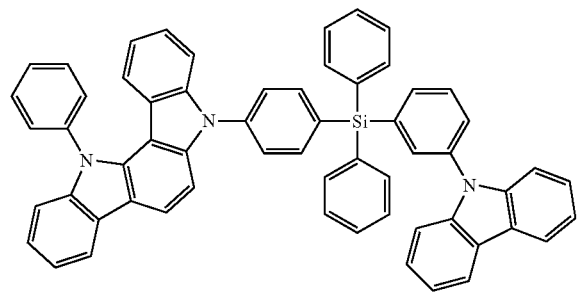
28
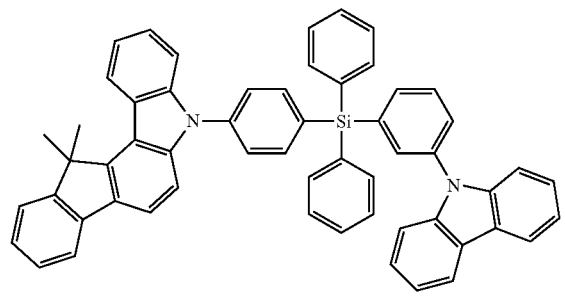

-continued
29
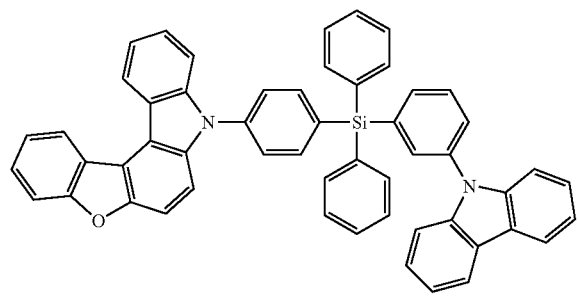
30
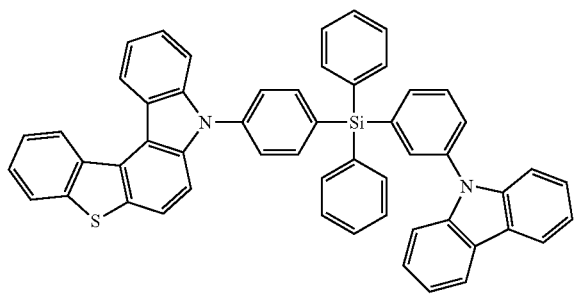
31
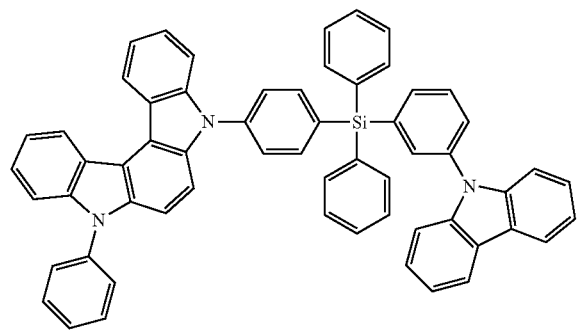
32
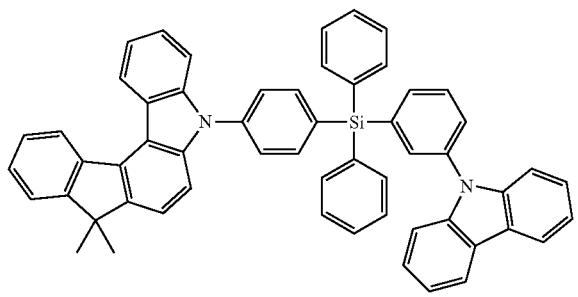
33
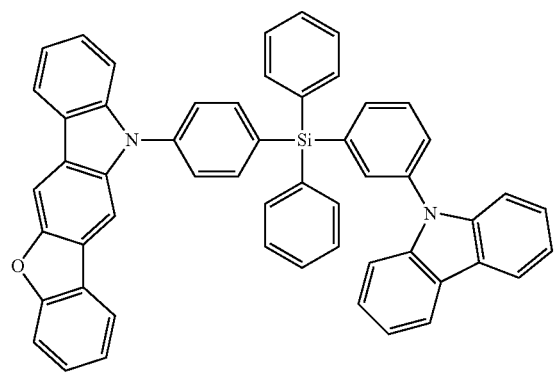
34
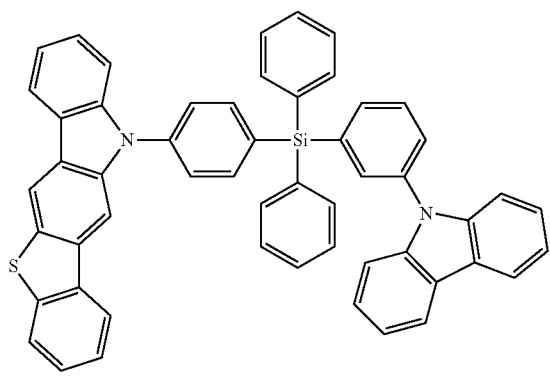
35
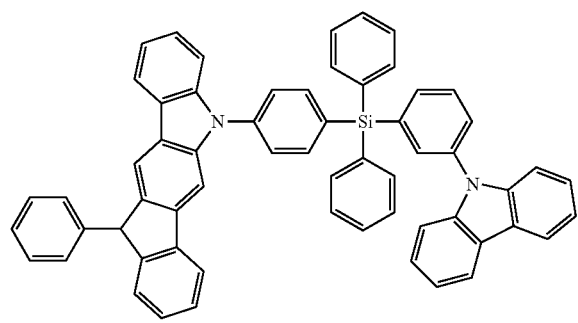
36
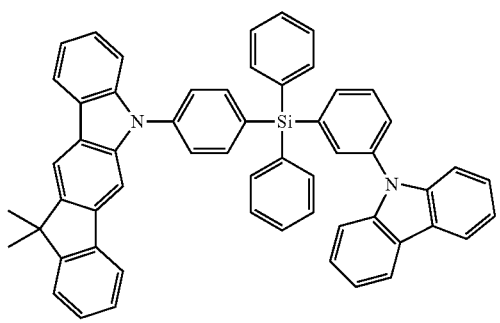

-continued
37
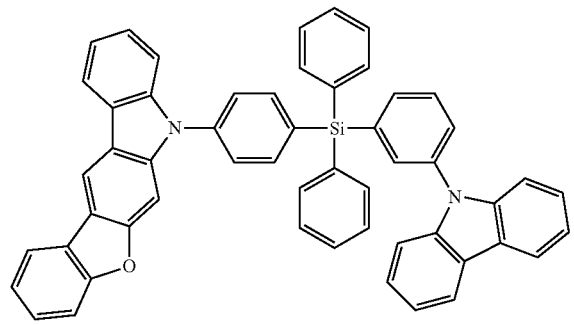
38
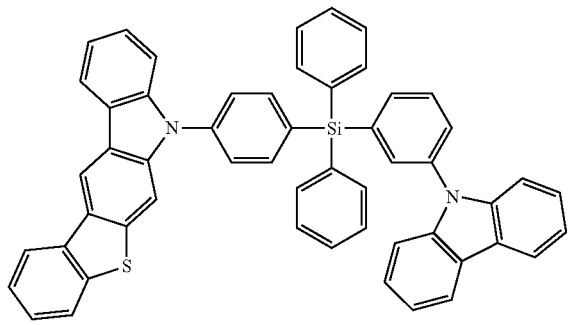
39
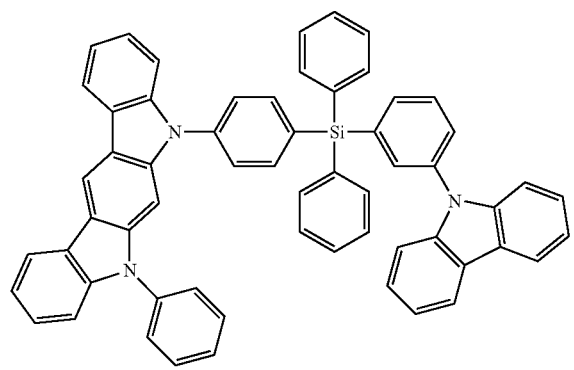
40
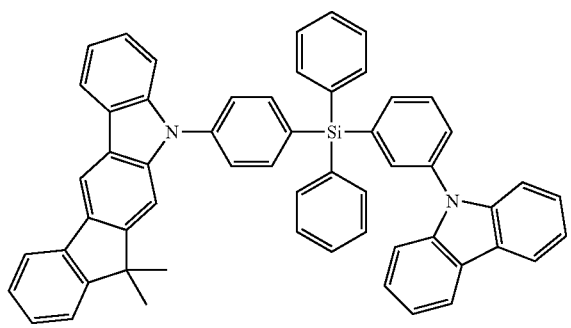
41
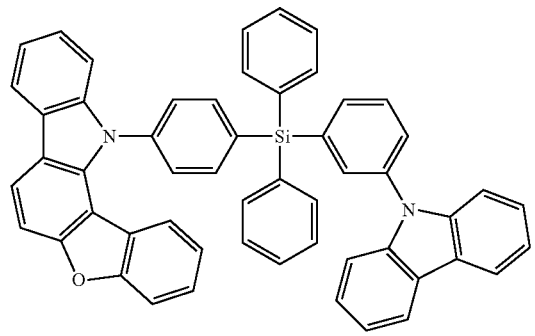
42
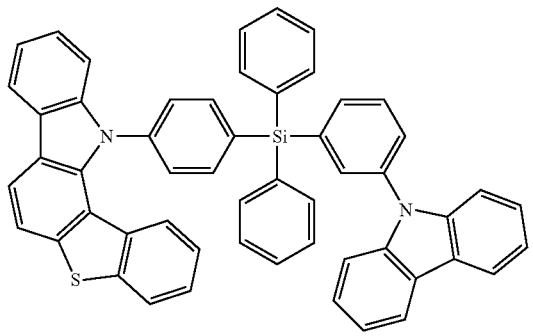
43
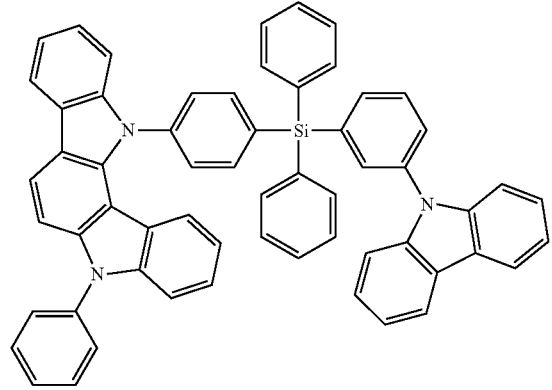
44
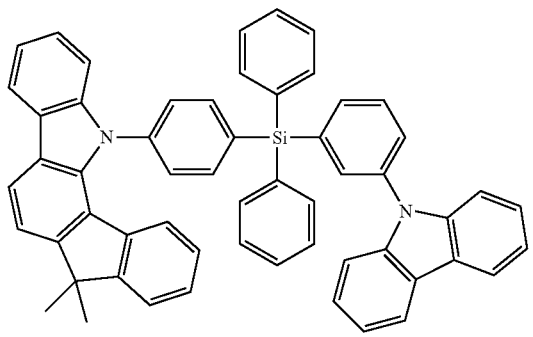

-continued
45
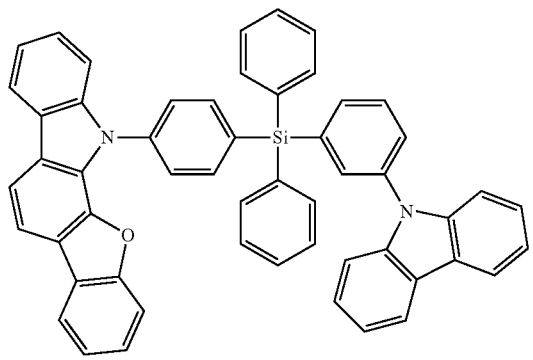
46
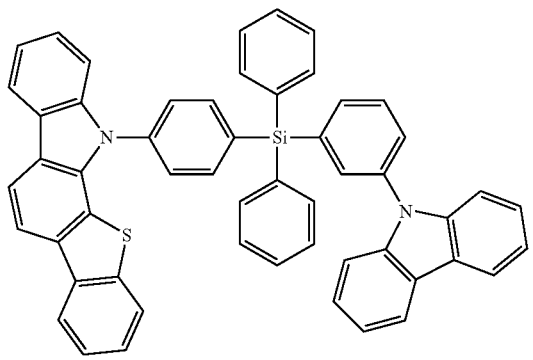
47
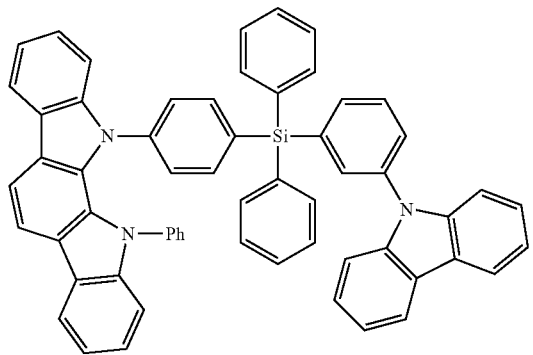
48
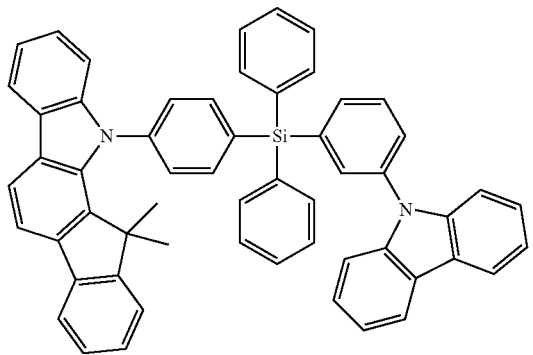
49
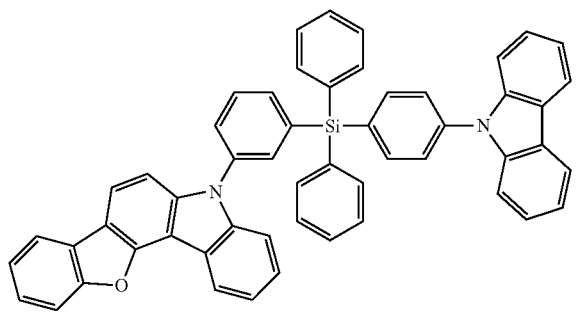
50
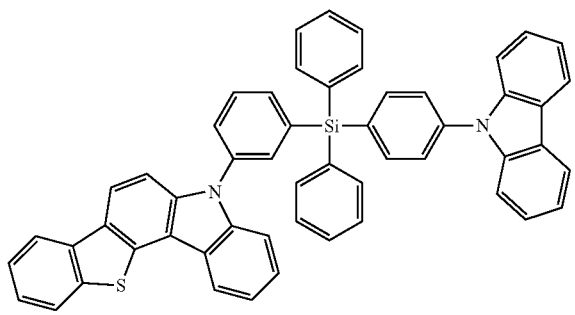
51
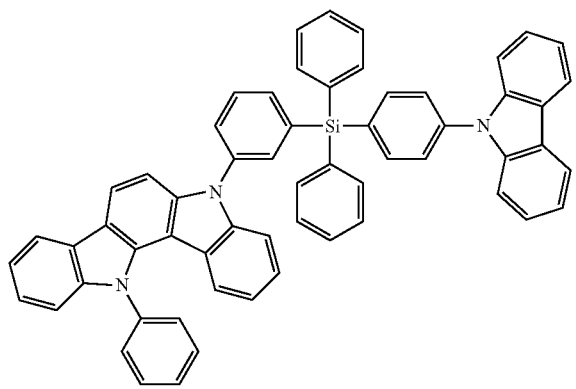
52
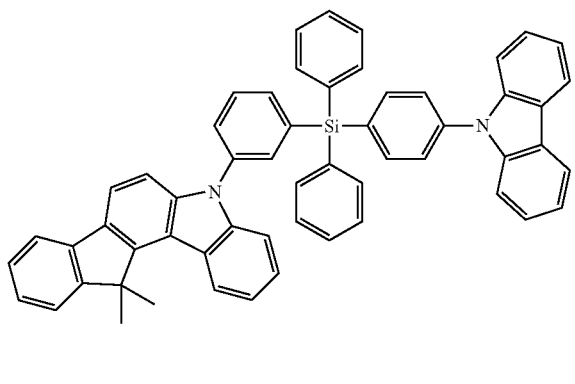

-continued
53
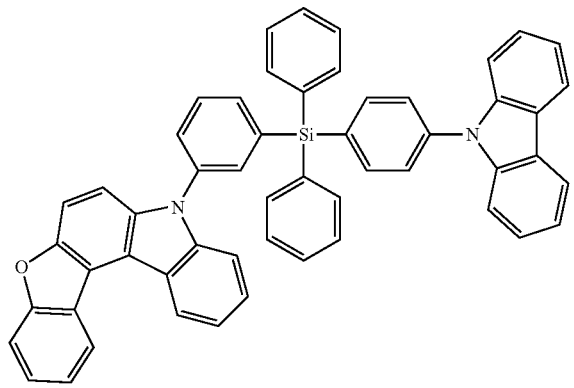
54
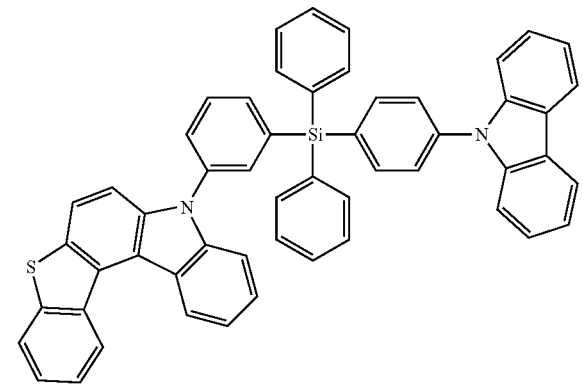
55
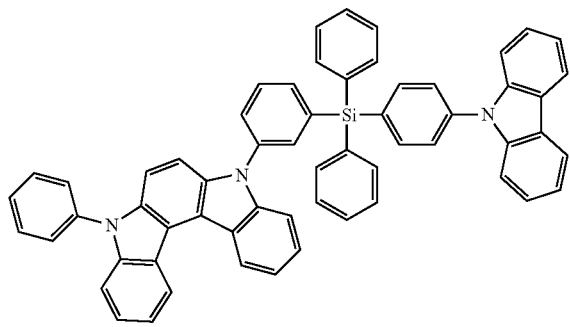
56
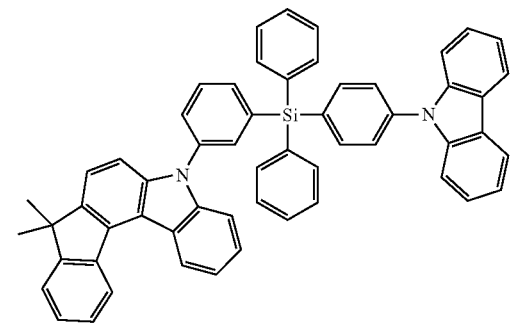
57
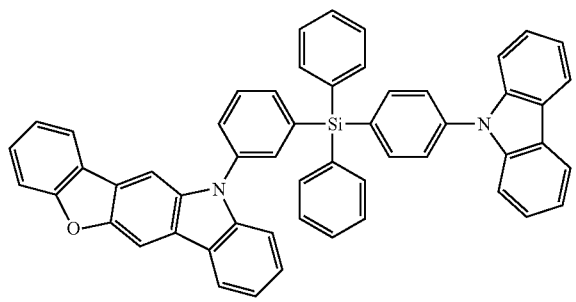
58
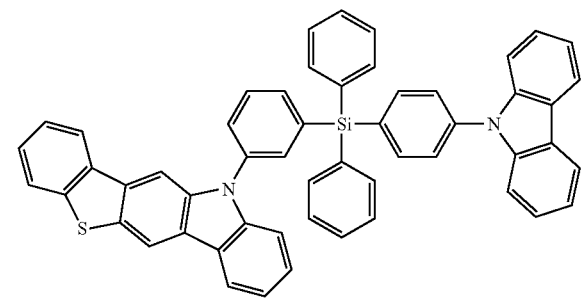
59
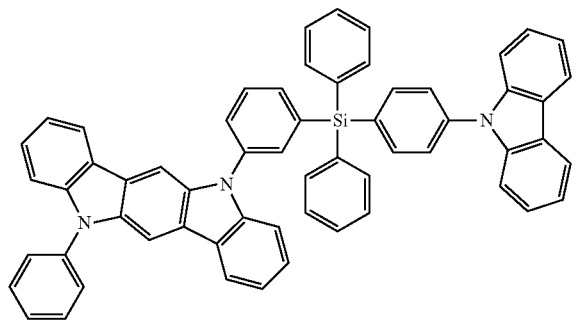
60
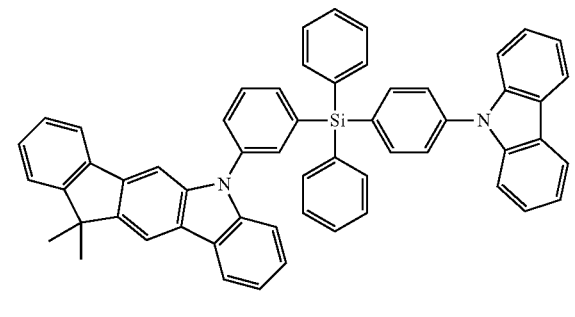

-continued
61
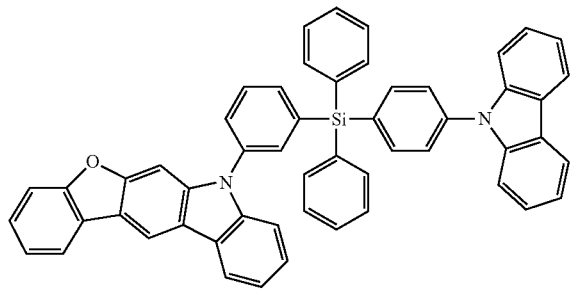
62
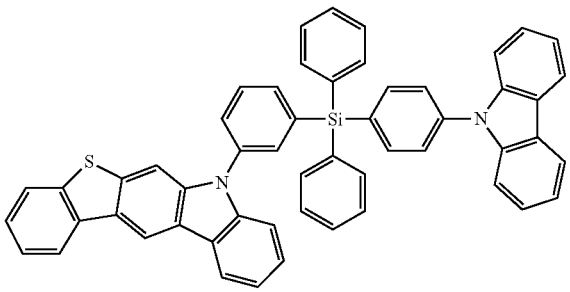
63
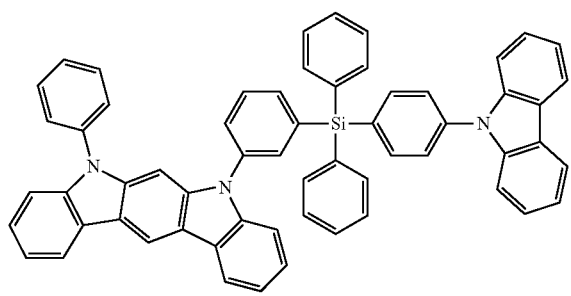
64
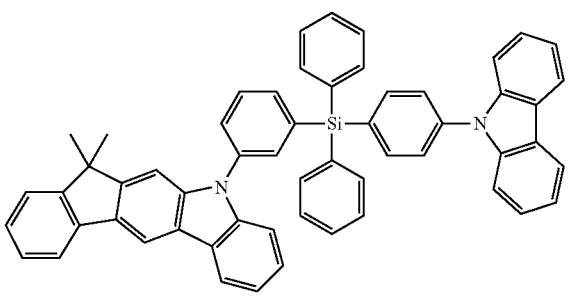
65
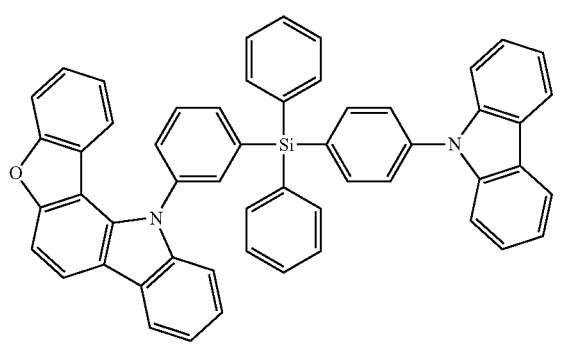
66
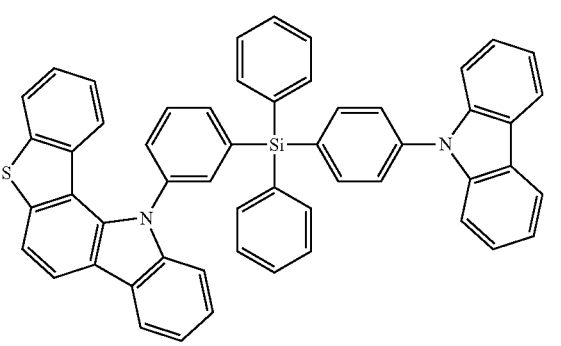
67
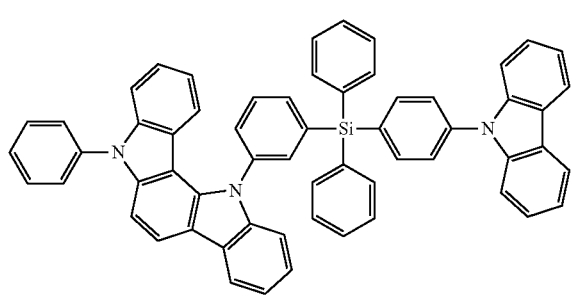
68
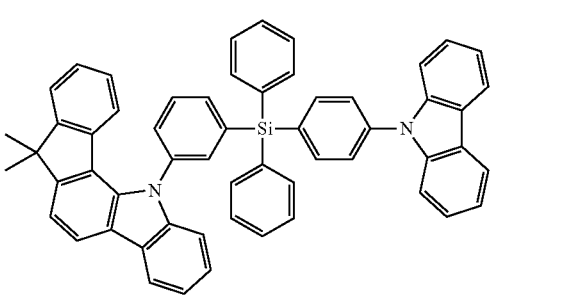
69
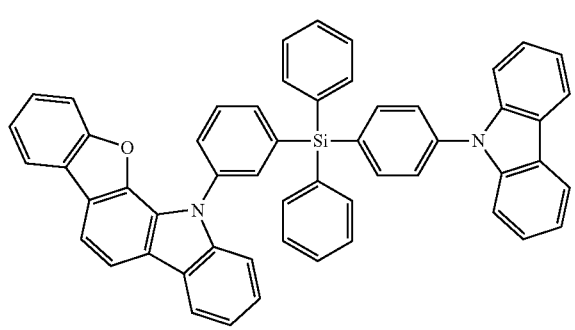
70
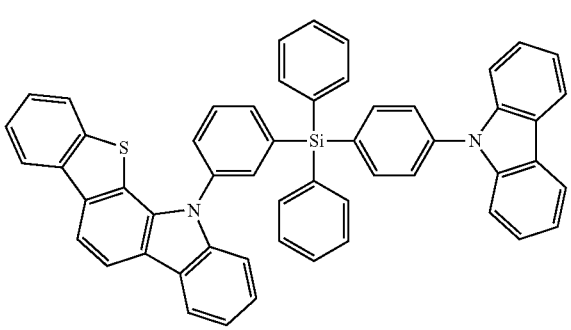

-continued
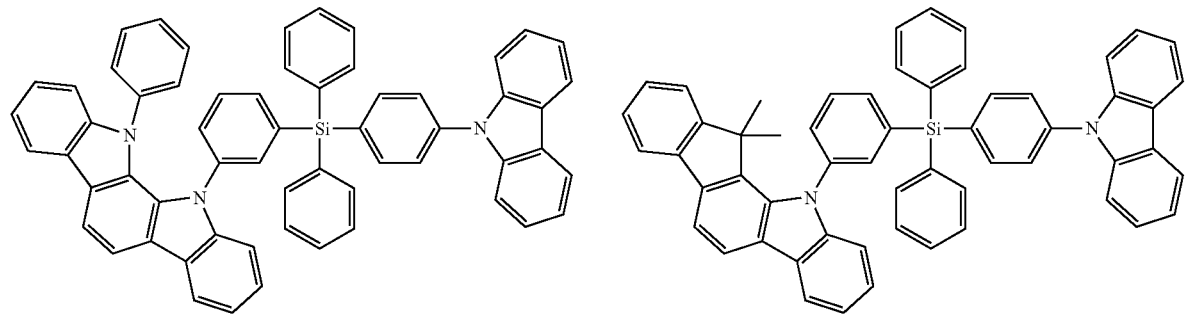
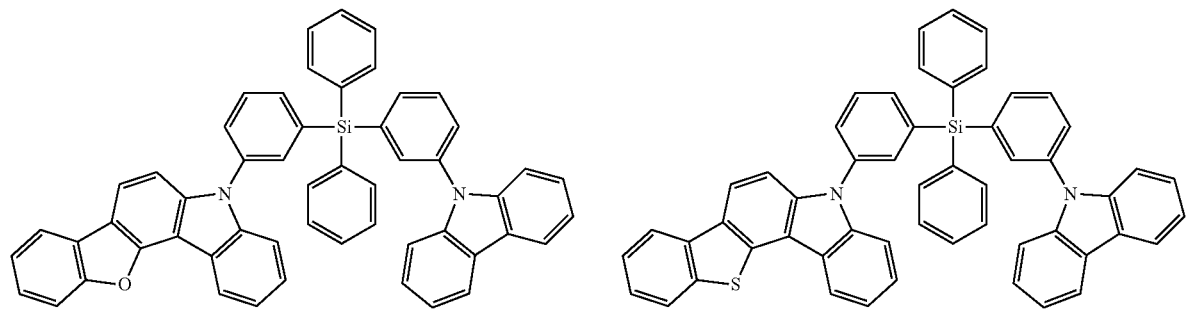
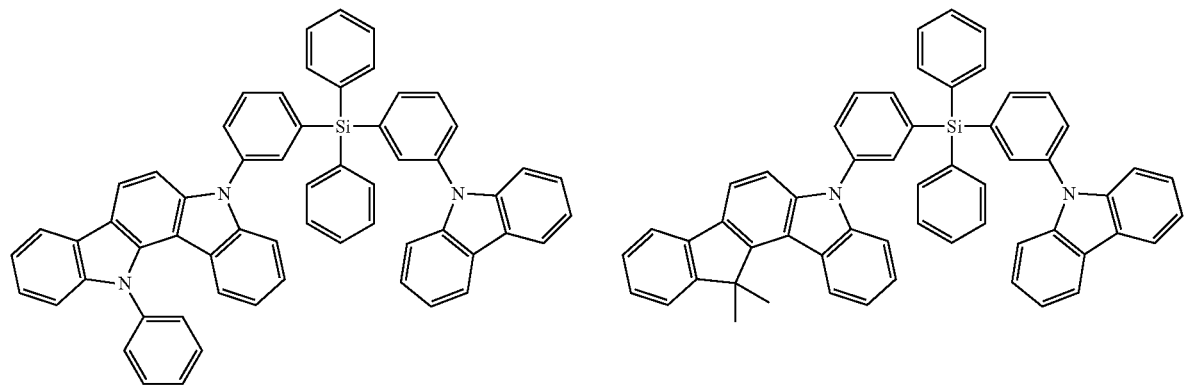
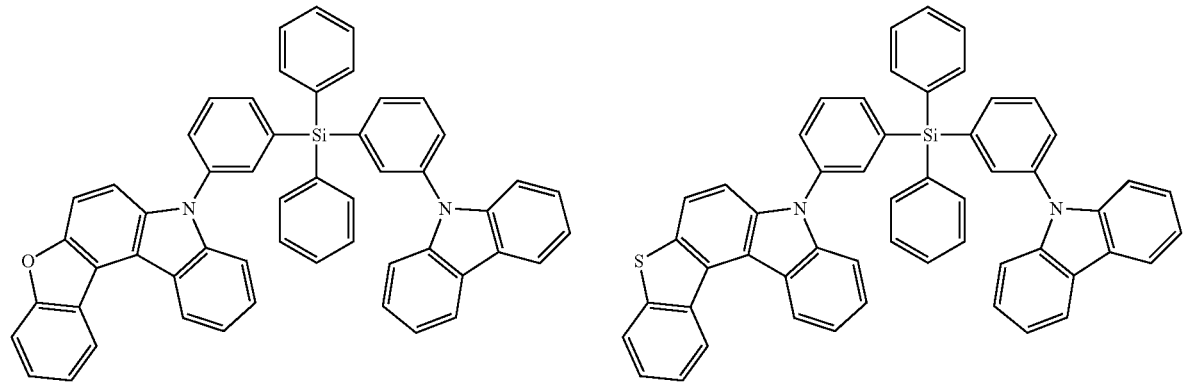

-continued
79
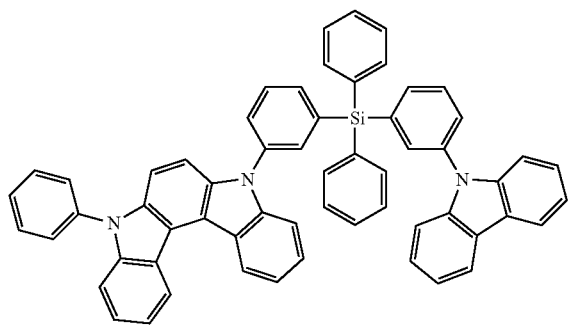
80
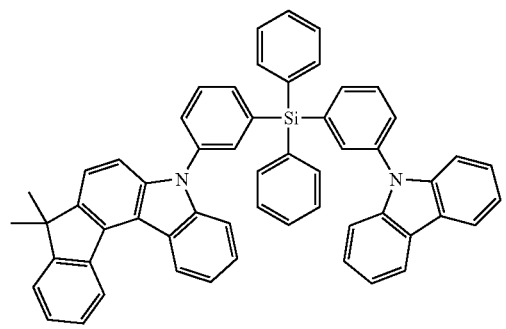
81
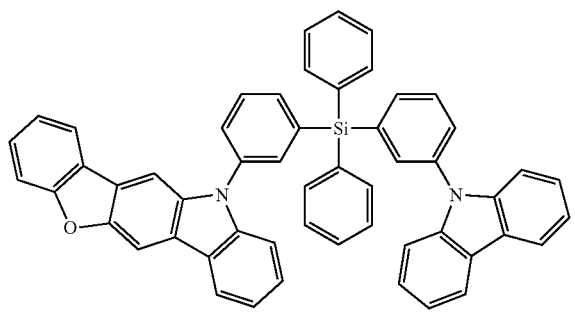
82
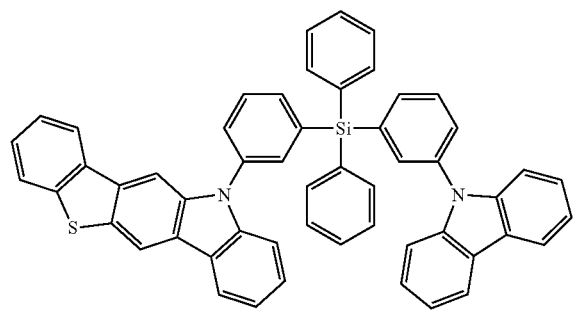
83
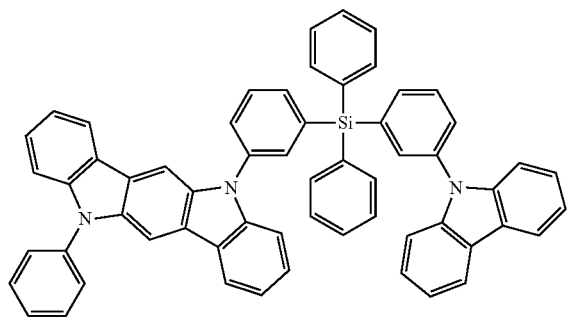
84
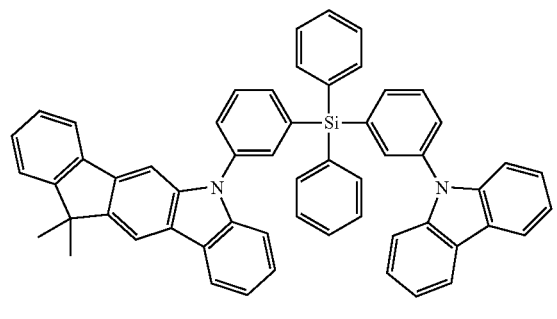
85
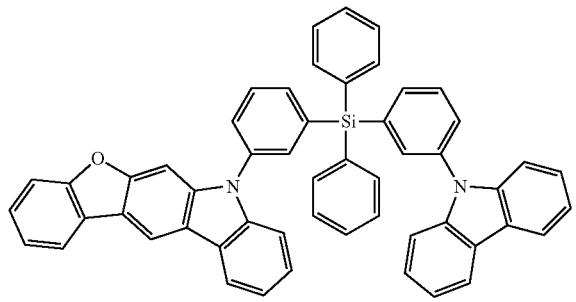
86
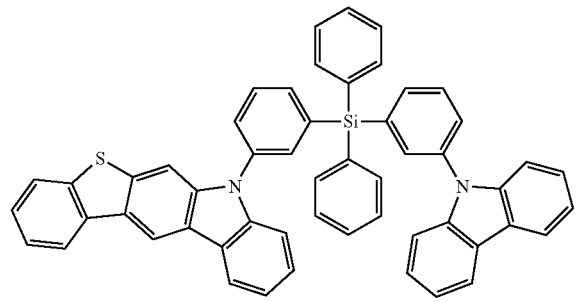

-continued
87
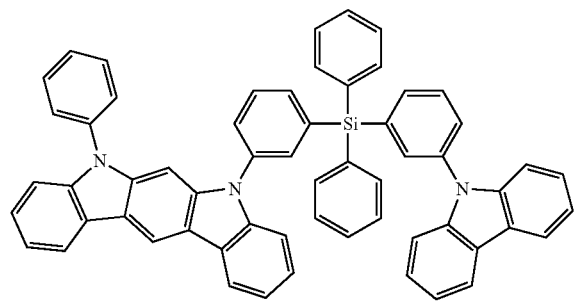
88
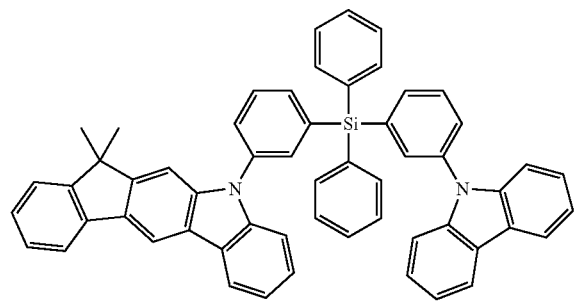
89
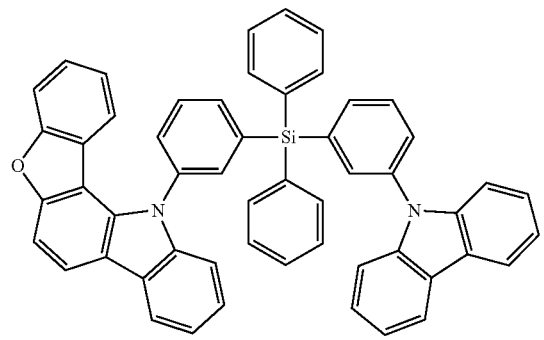
90
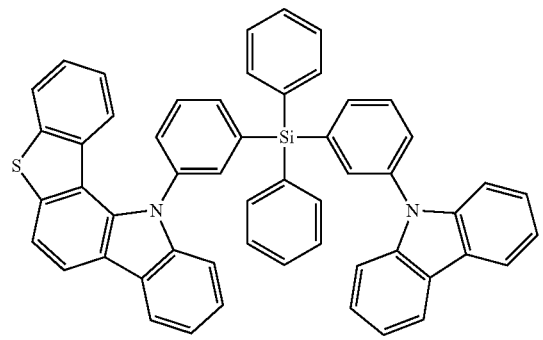
91
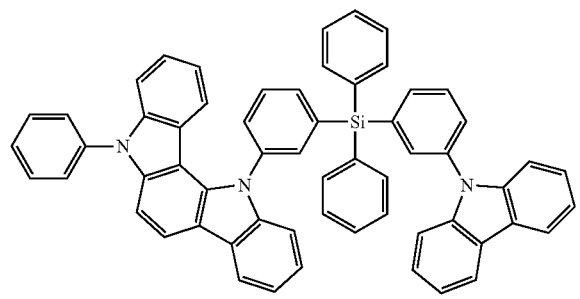
92
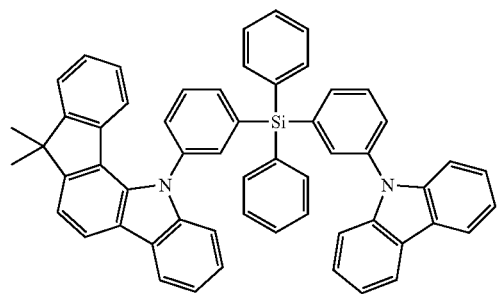
93
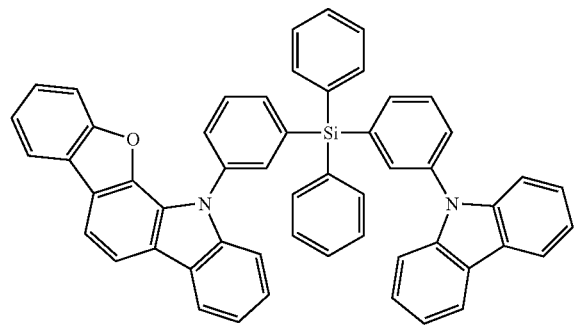
94
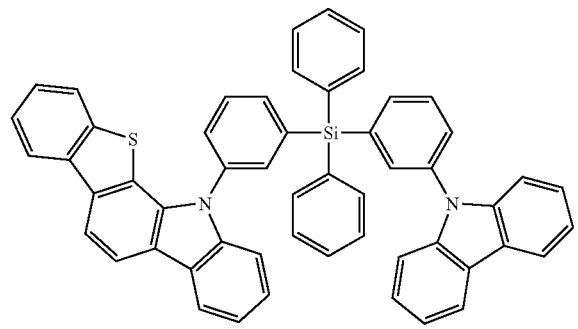

-continued
95
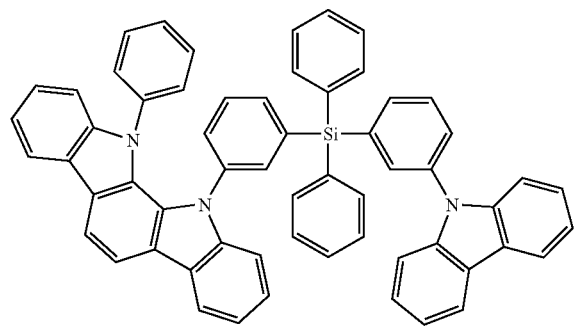
96
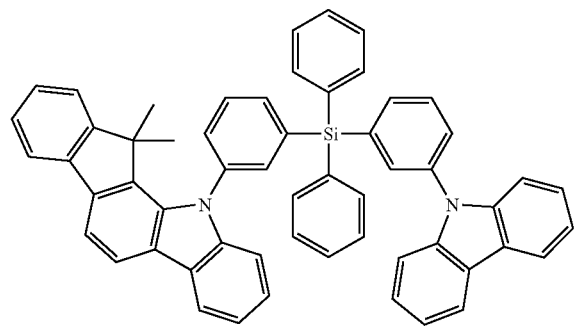
97
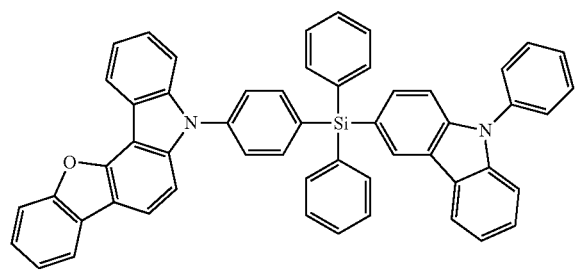
98
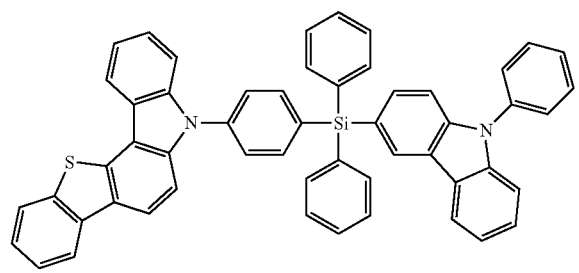
99
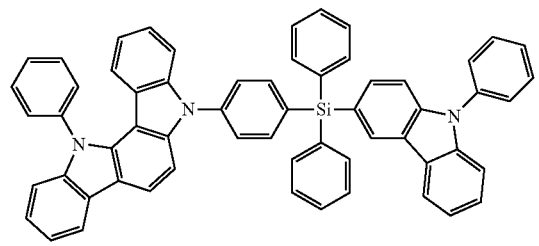
100
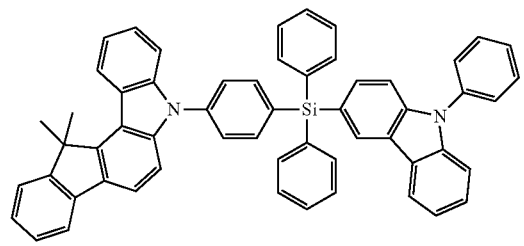
101
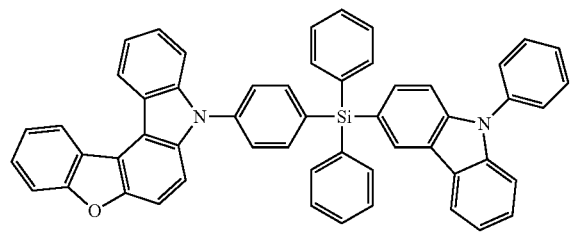
102
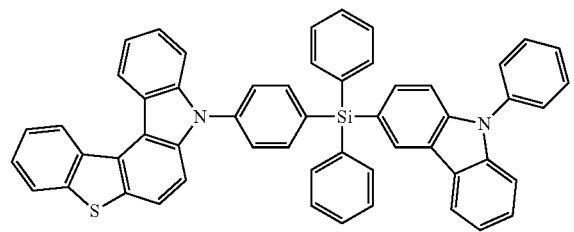
103
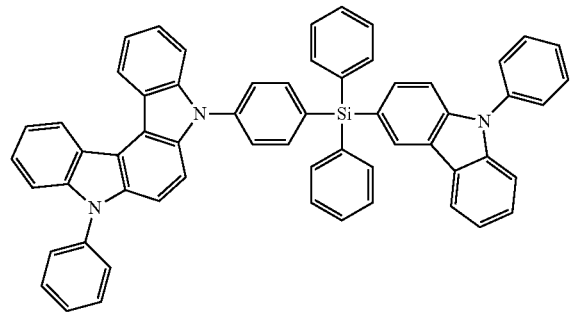
104
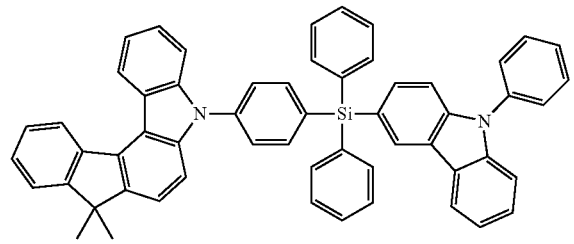

-continued
105
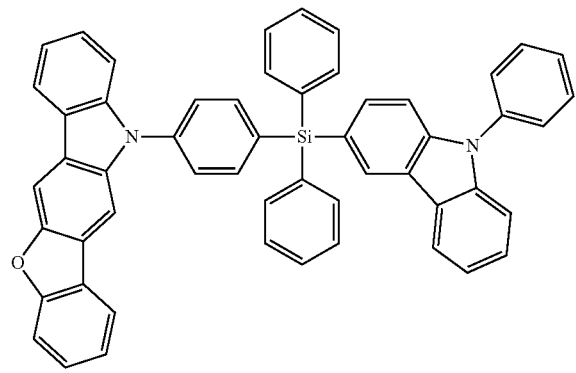
106
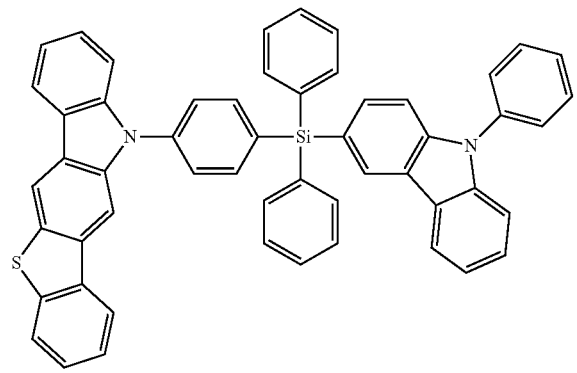
107
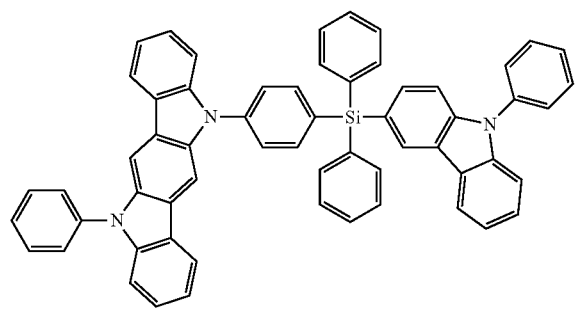
108
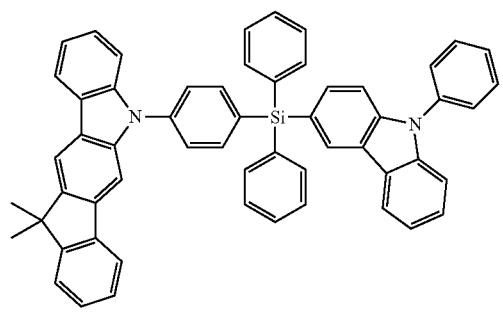
109
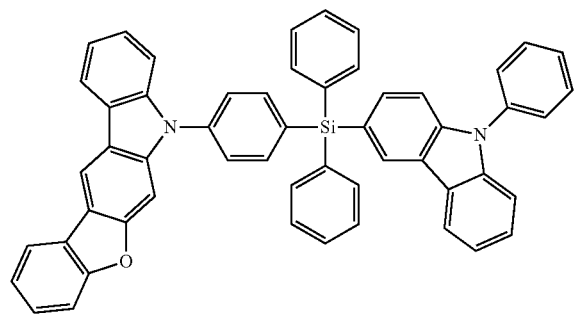
110
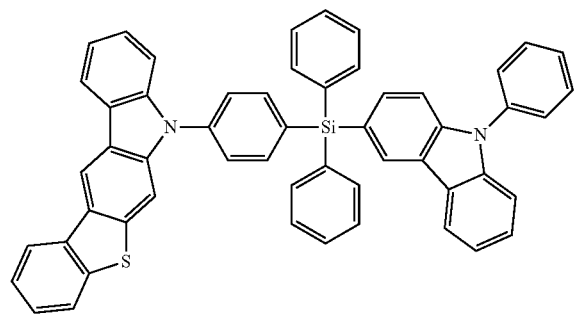
111
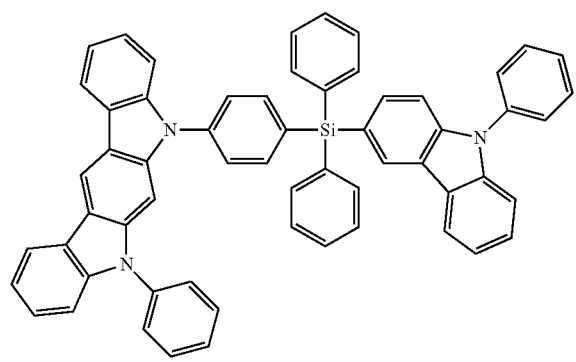
112
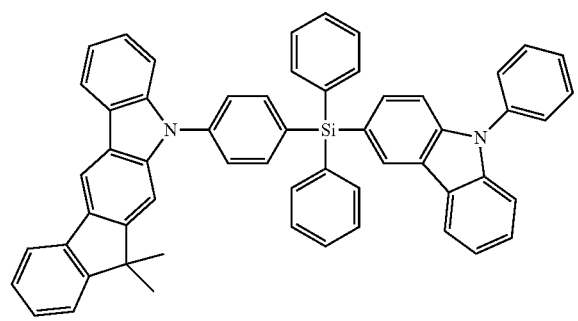

-continued
113
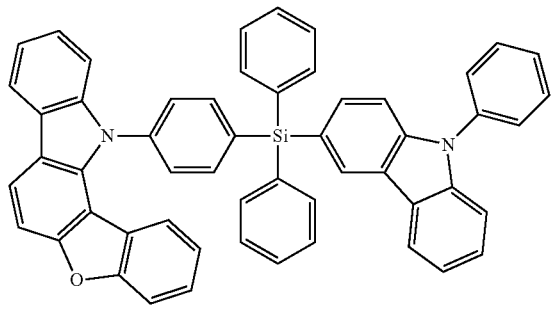
114
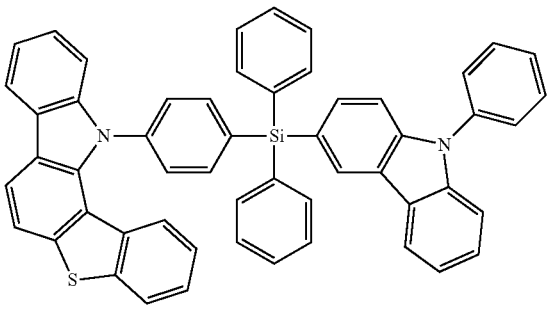
115
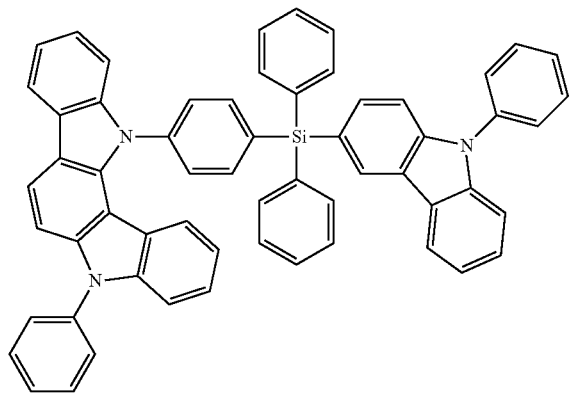
116
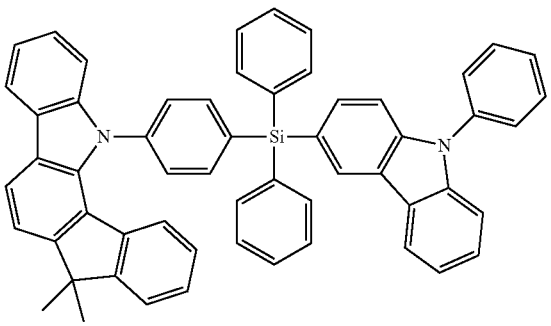
117
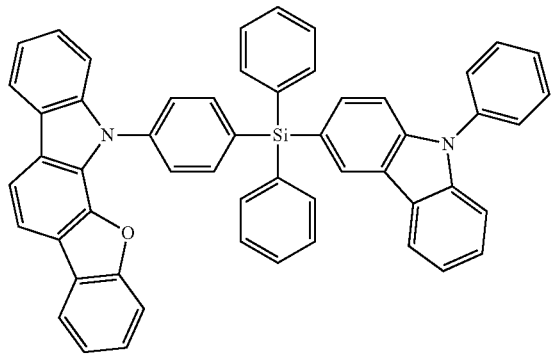
118
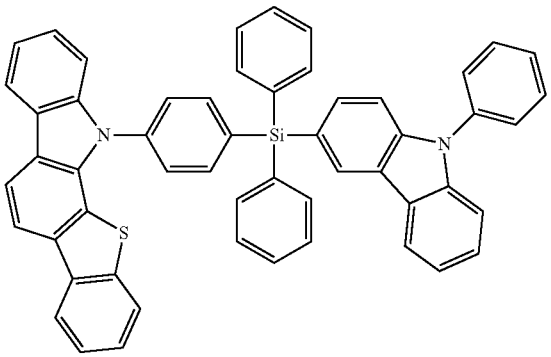
119
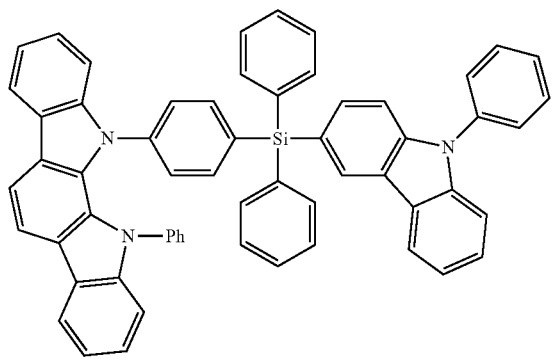
120
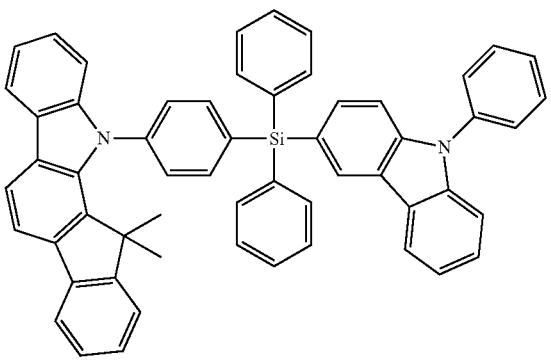

-continued
| 121 | 122 |
|---|---|
| 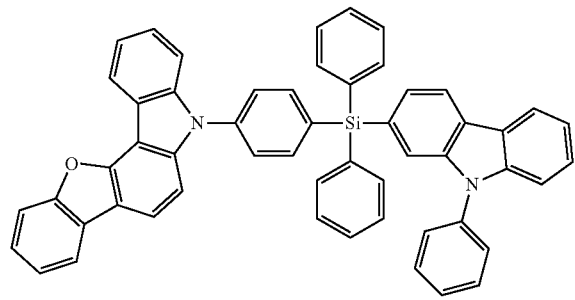 | 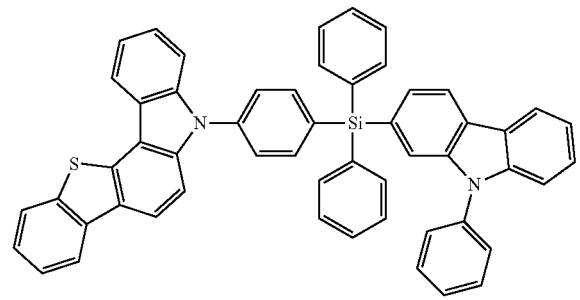 |
| 123 | 124 |
| 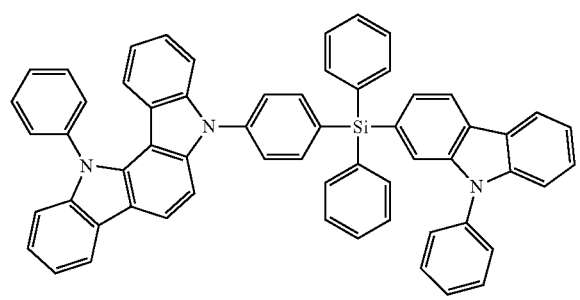 | 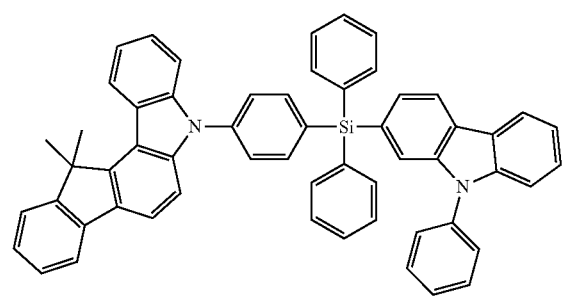 |
| 125 | 126 |
| 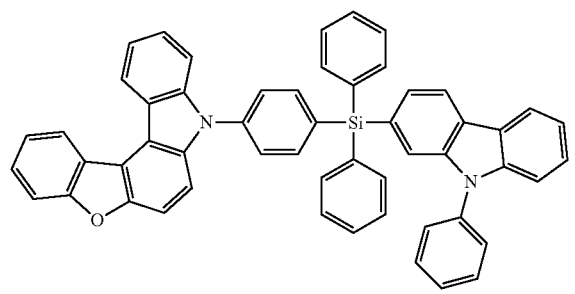 | 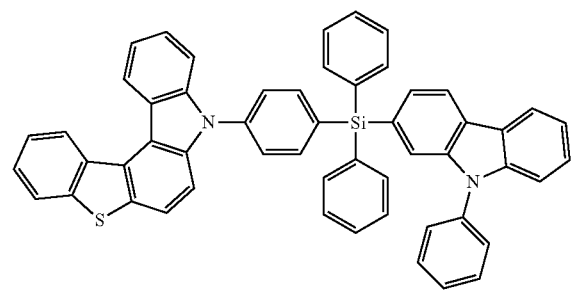 |
| 127 | 128 |
| 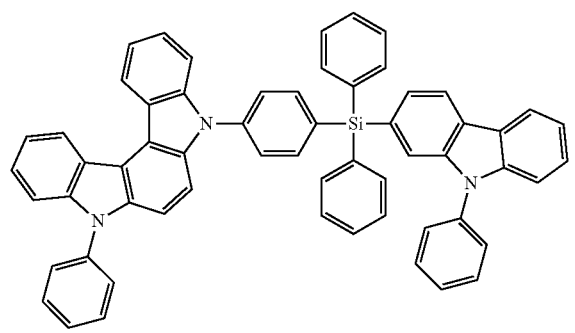 | 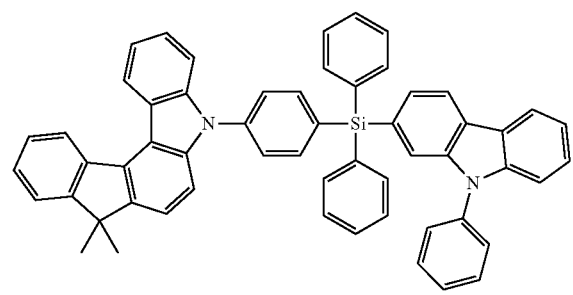 |

-continued
129
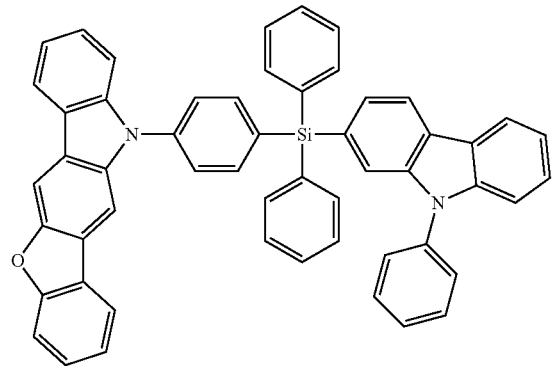
130
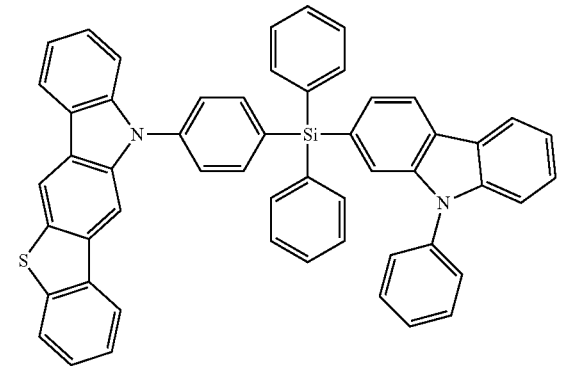
131
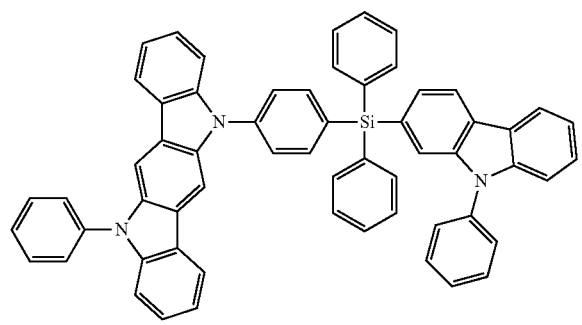
132
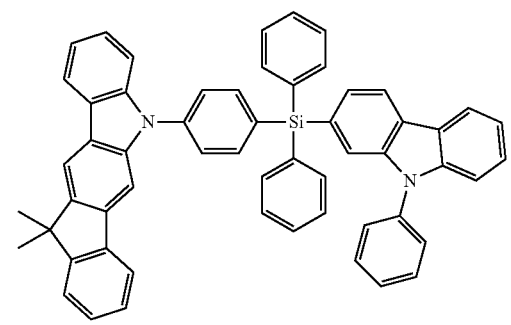
133
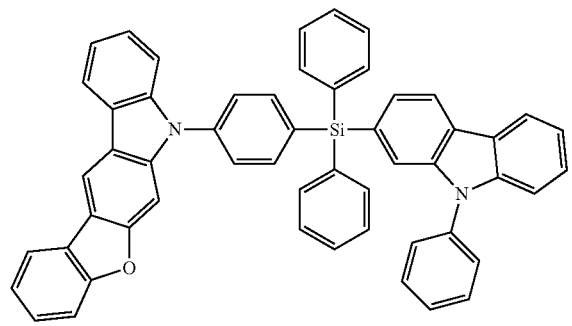
134
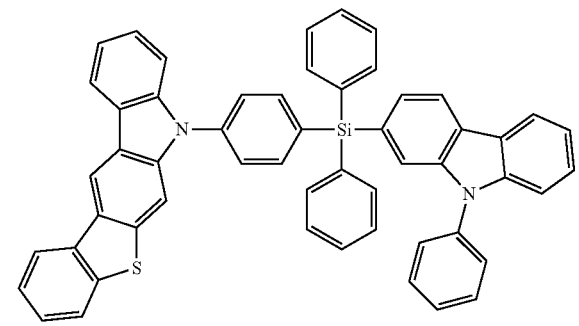
135
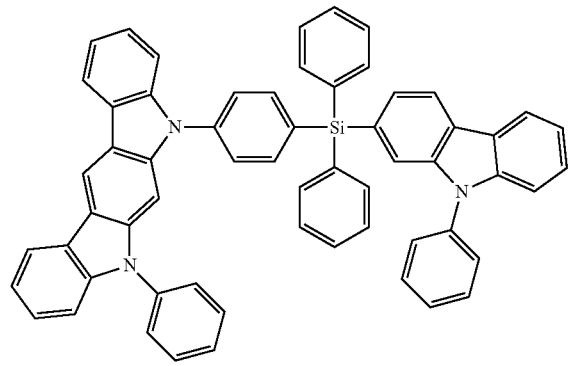
136
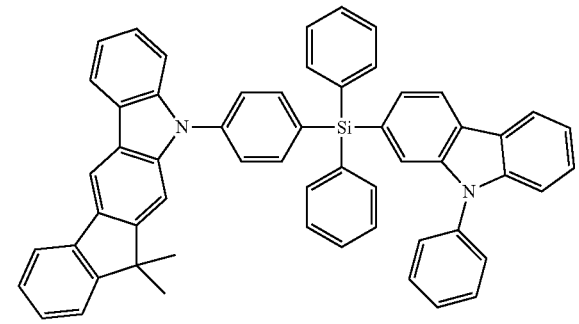

-continued
137
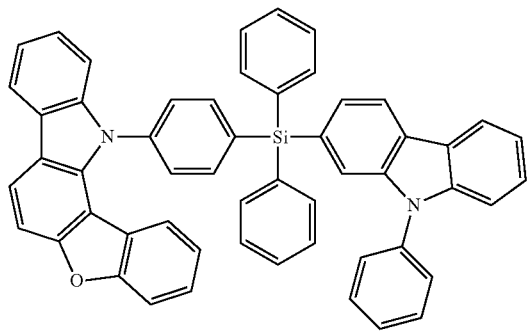
138
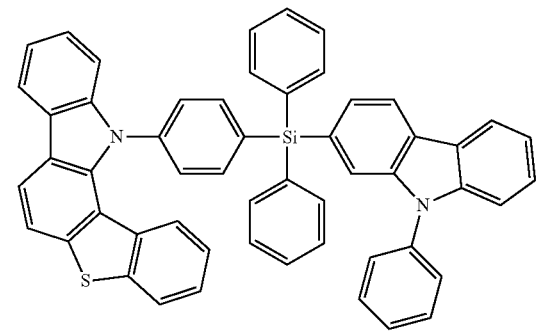
139
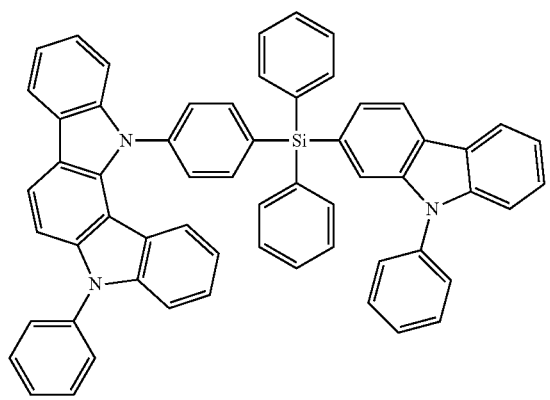
140
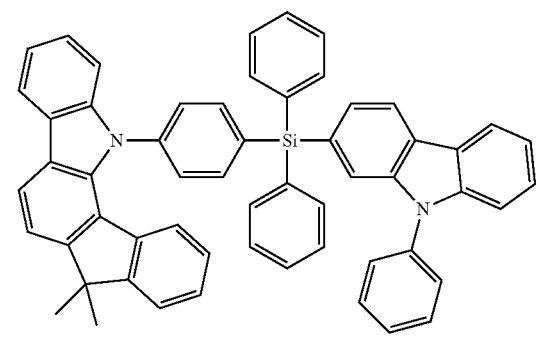
141
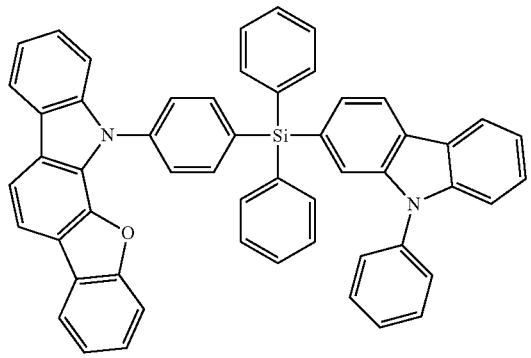
142
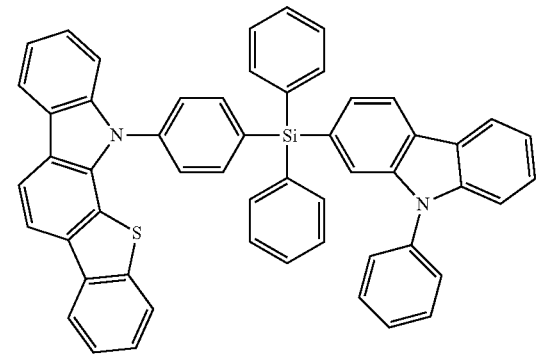
143
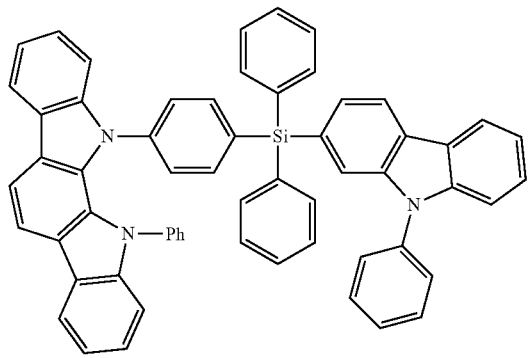
144
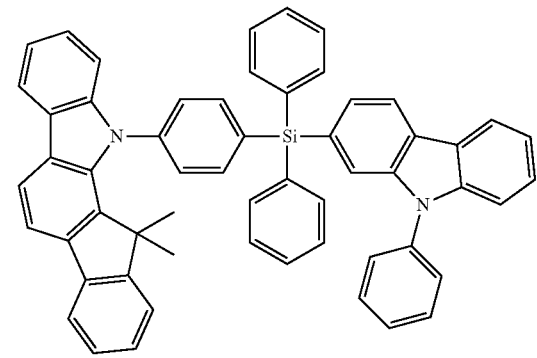

-continued
145
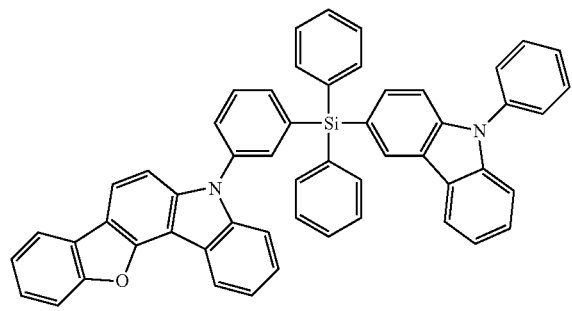
146
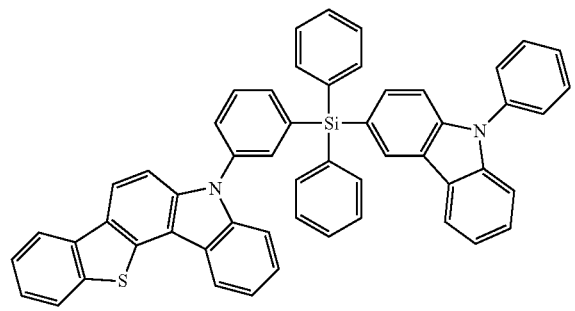
147
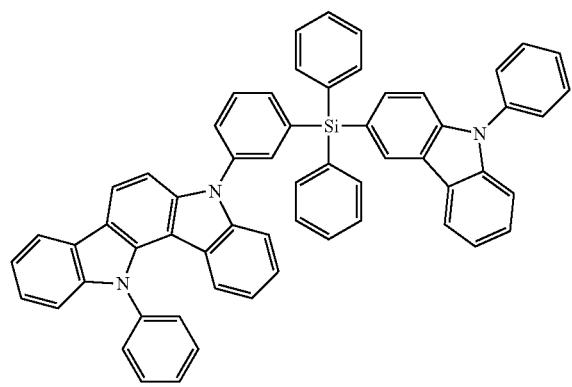
148
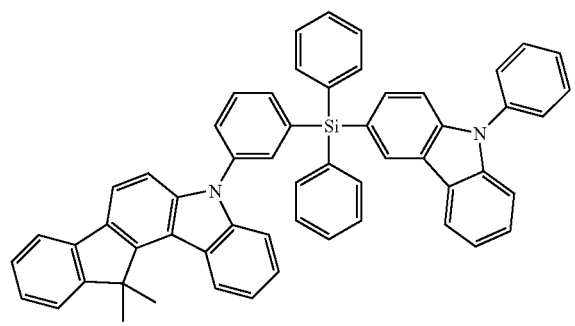
149
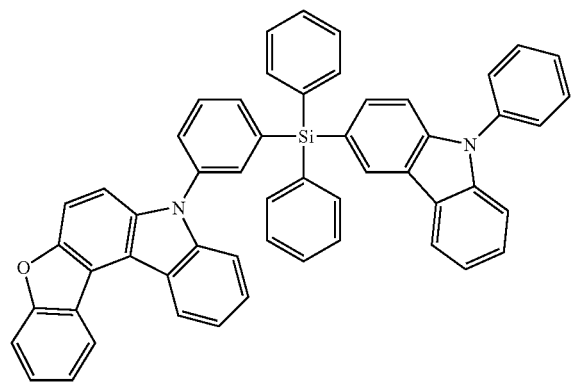
150
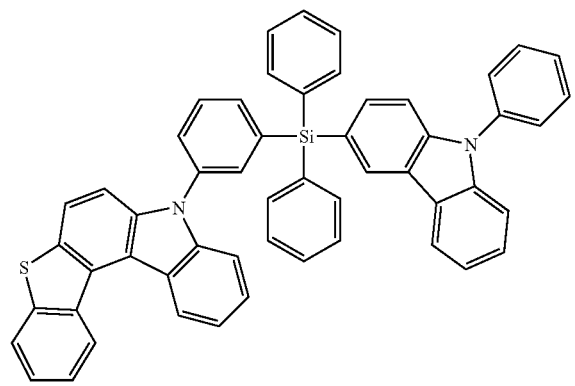
151
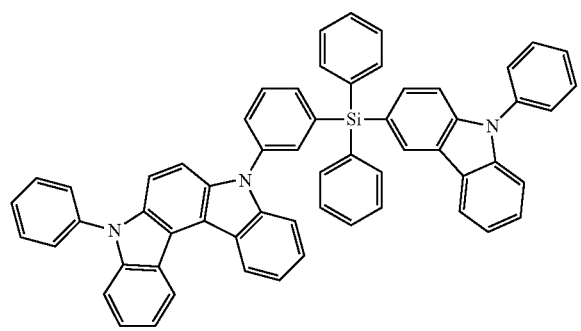
152
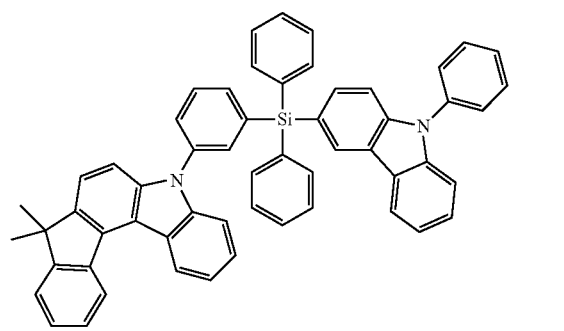

-continued
153
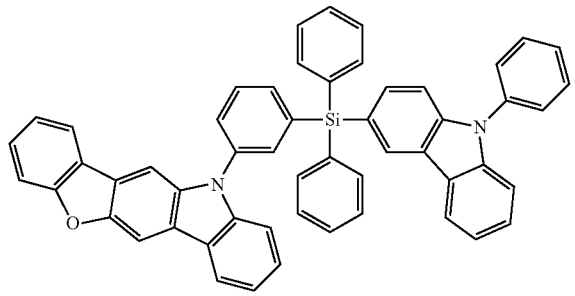
154
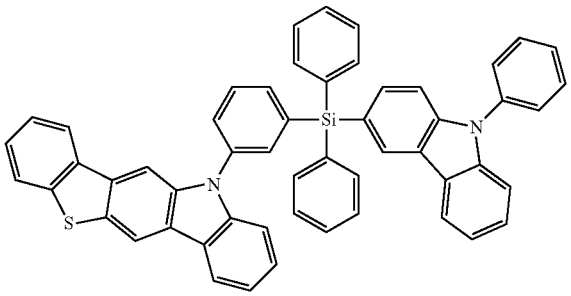
155
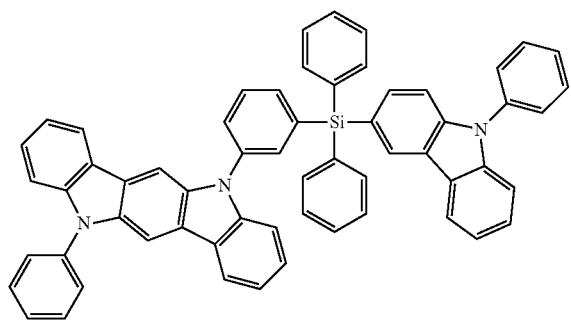
156
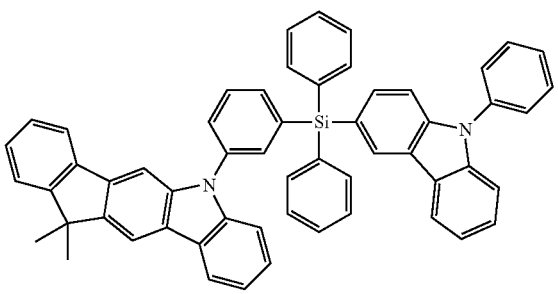
157
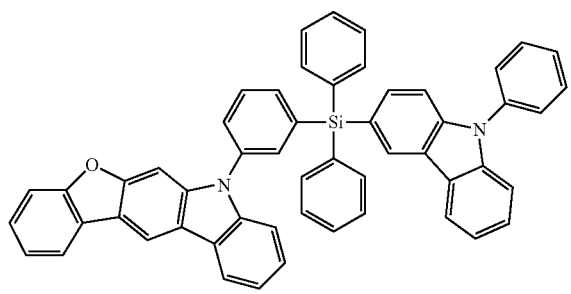
158
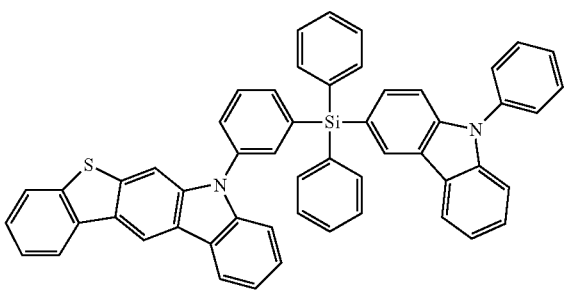
159
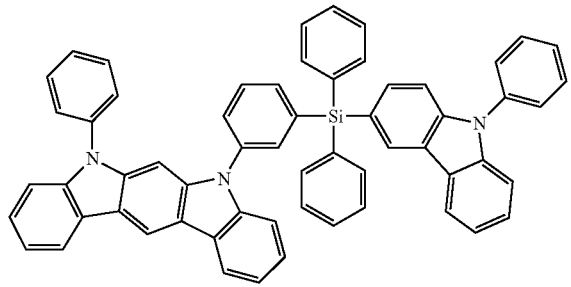
160
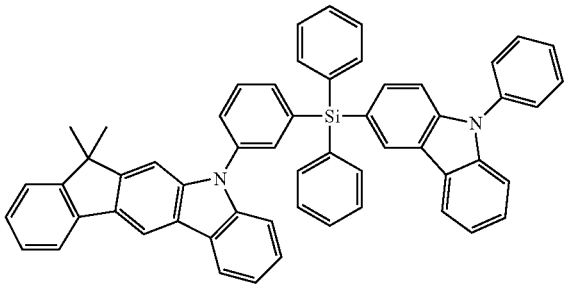
161
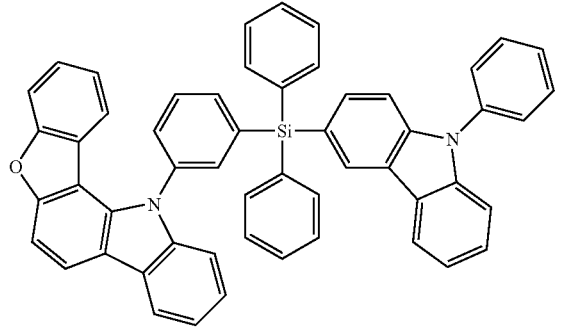
162
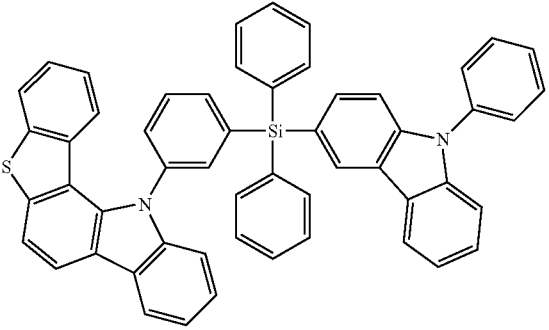

-continued
163
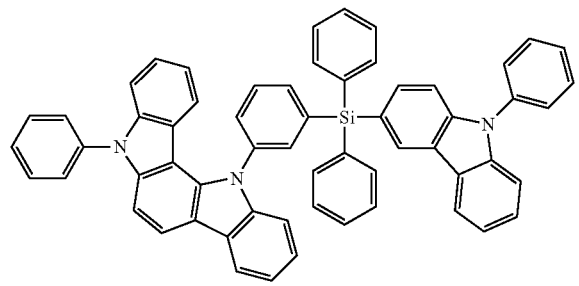
164
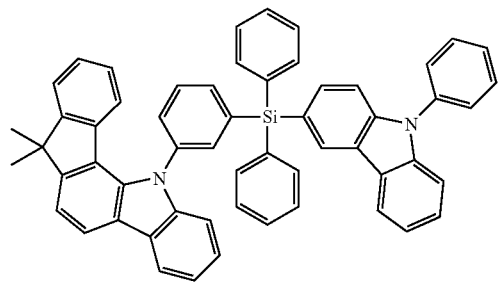
165
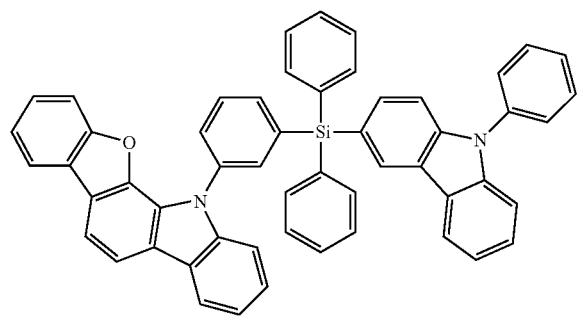
166
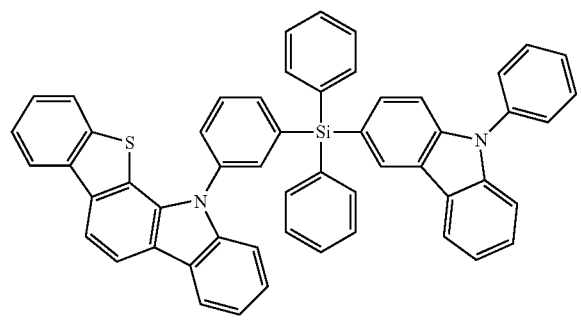
167
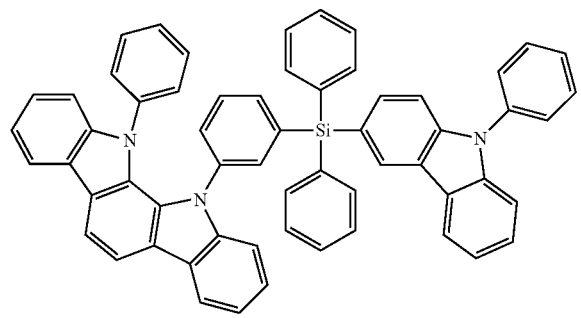
168
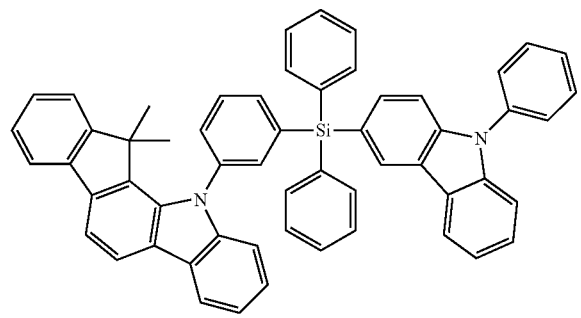
169
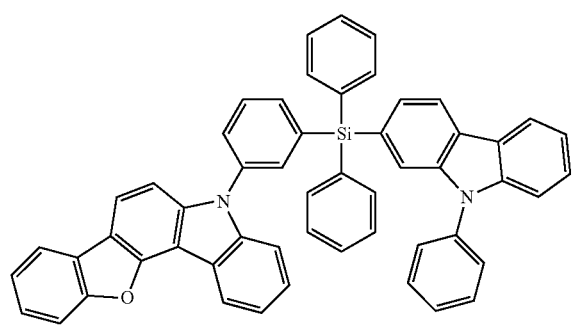
170
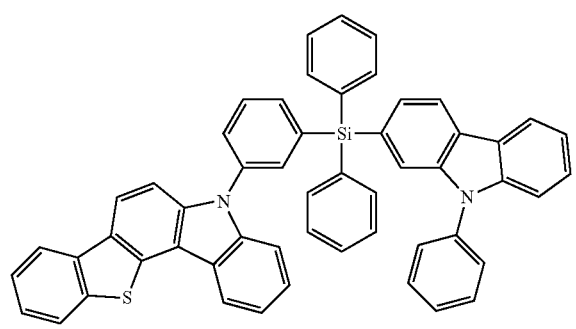

-continued
171
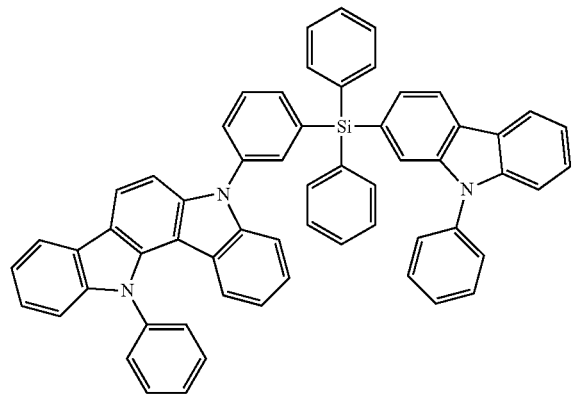
172
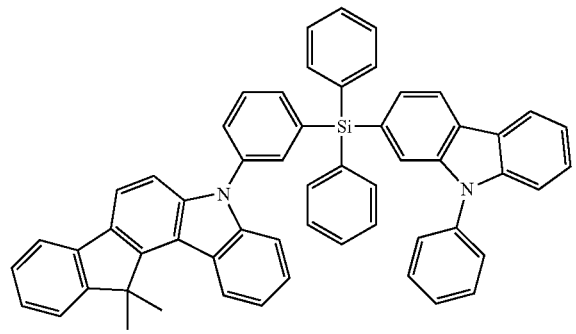
173
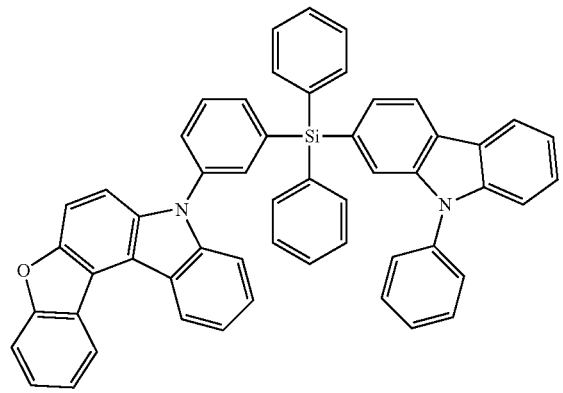
174
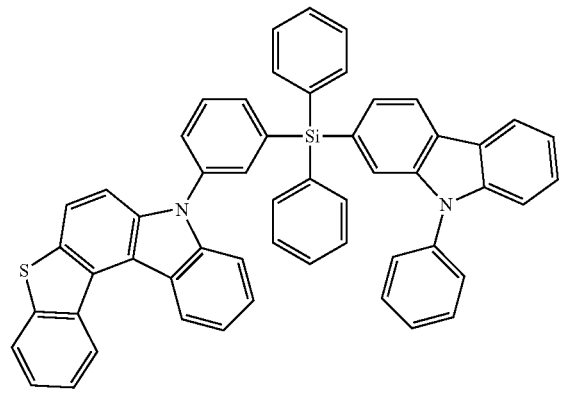
175
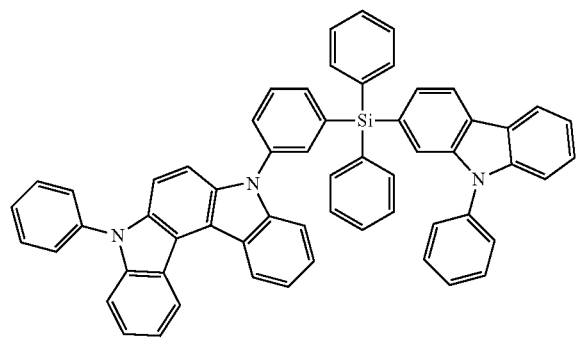
176
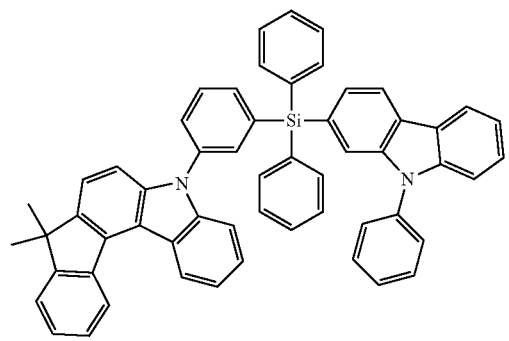
177
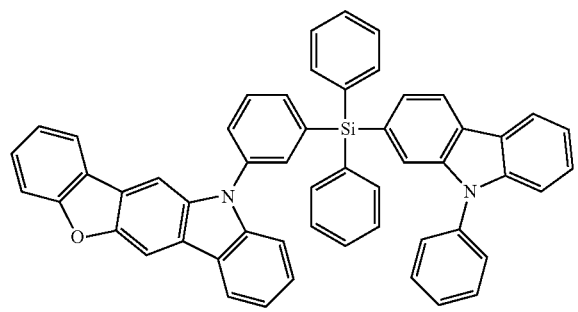
178
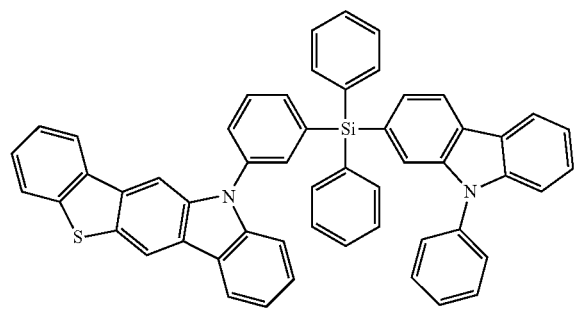

-continued
179
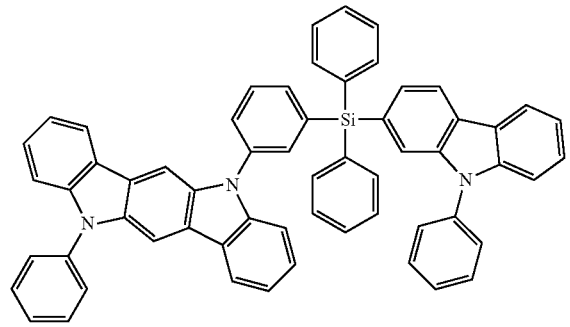
180
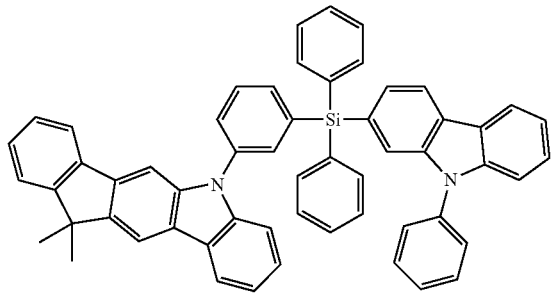
181
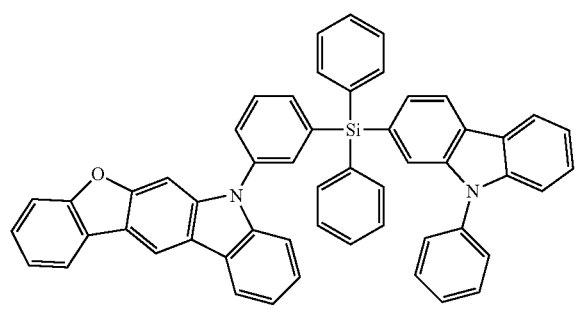
182
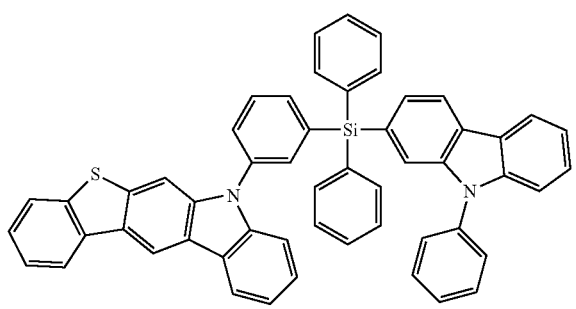
183
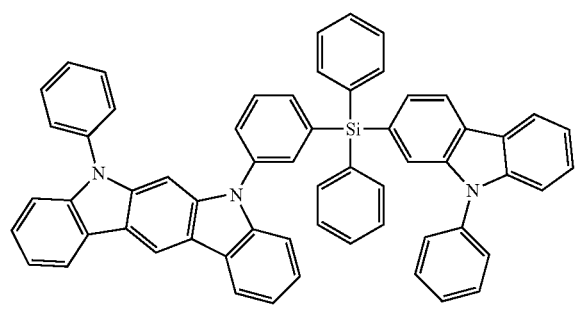
184
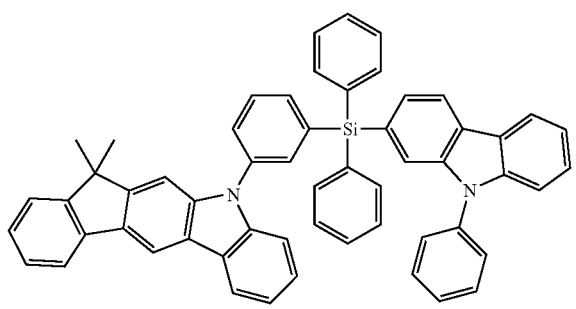
185
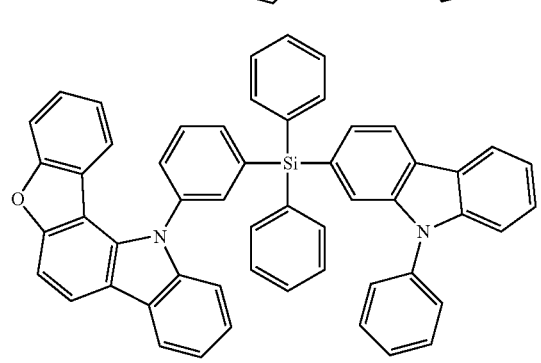
186
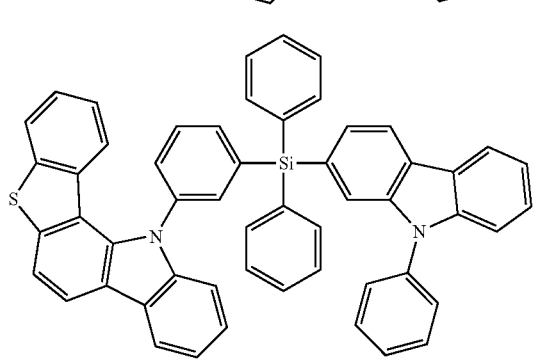
187
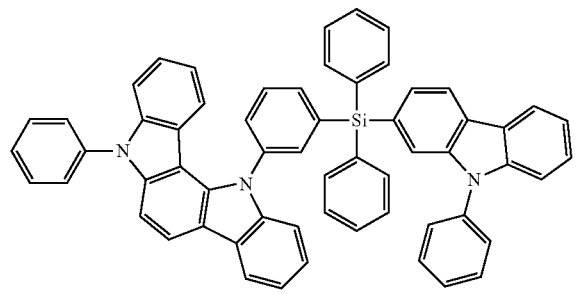
188
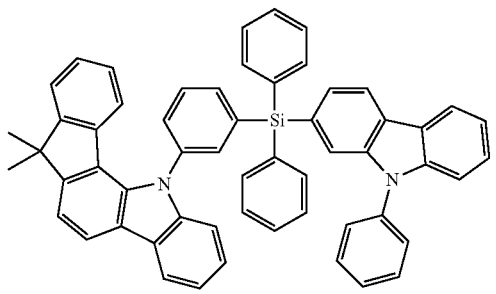

-continued
189
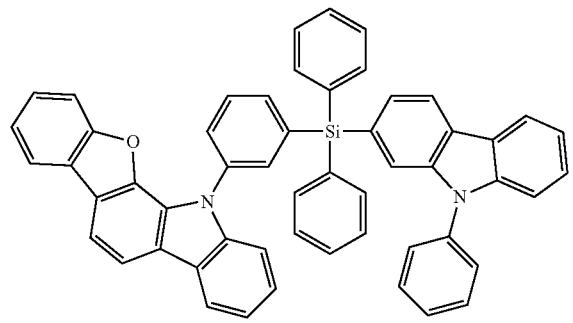
190
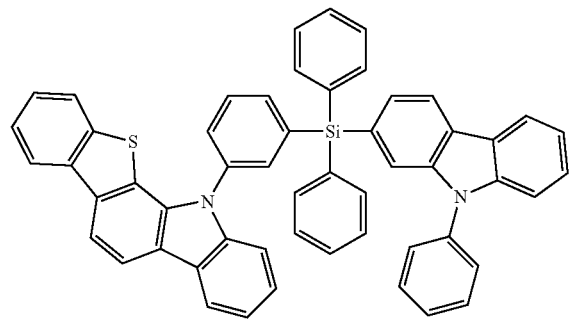
191
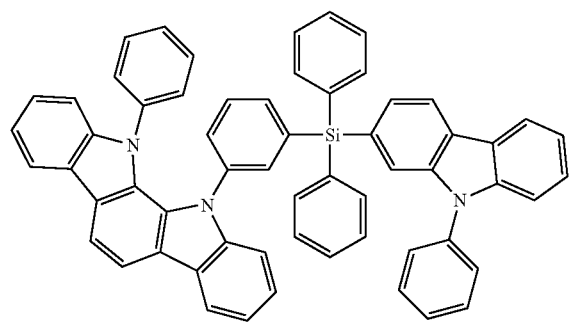
192
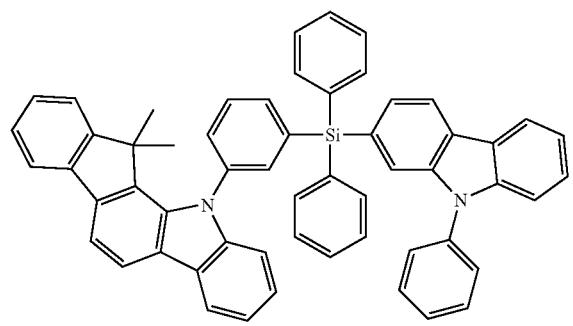
193
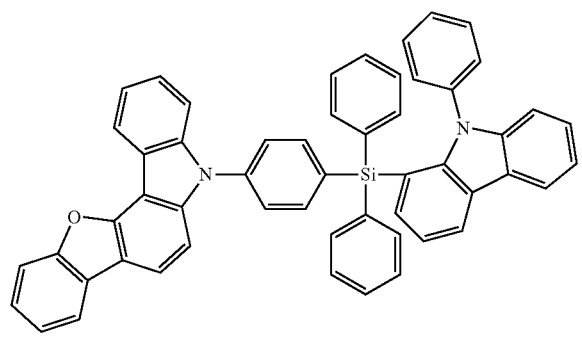
194
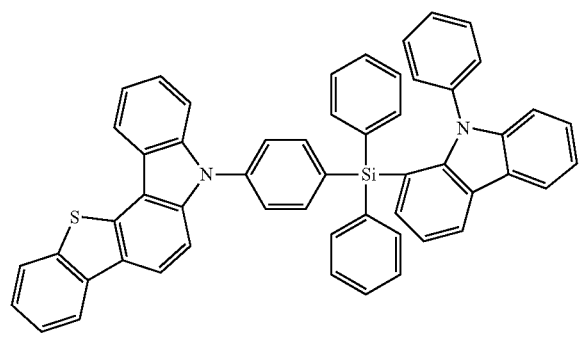
195
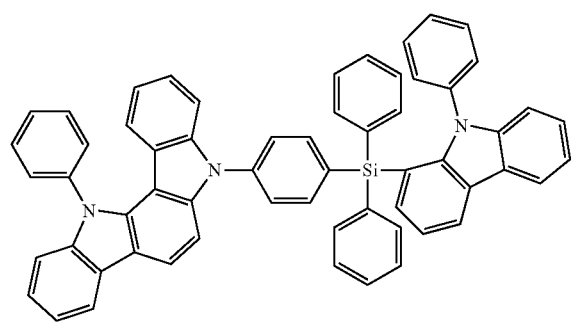
196
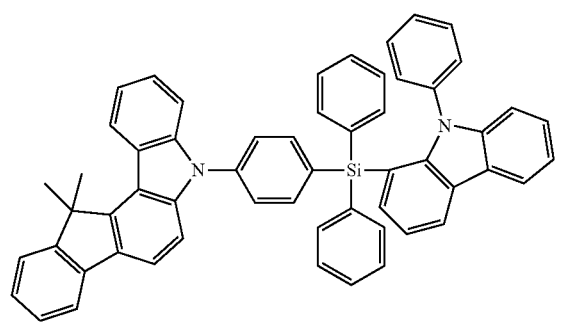

-continued
197
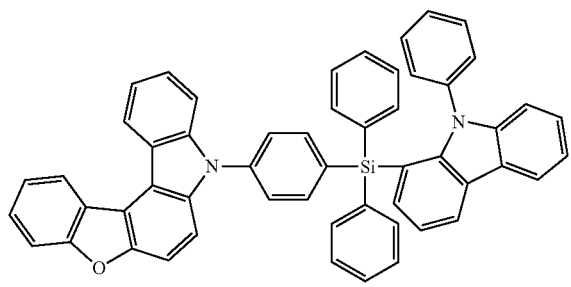
198
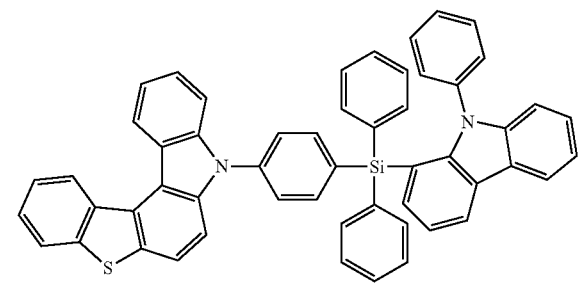
199
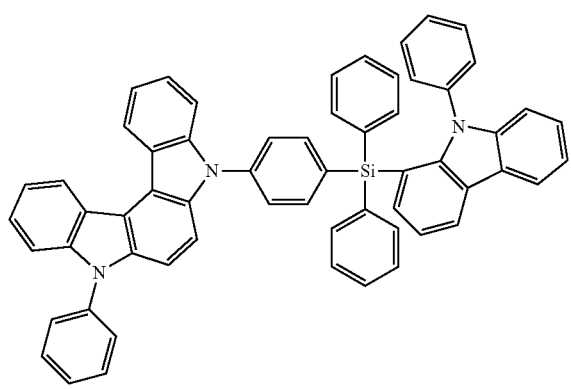
200
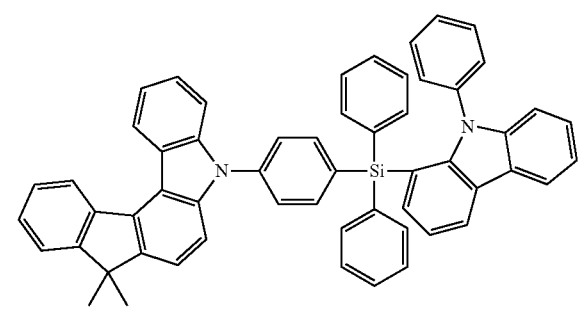
201
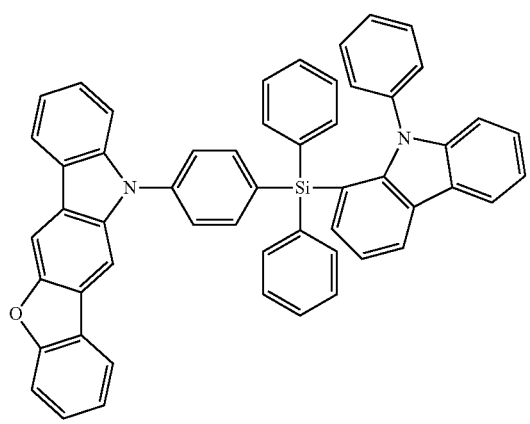
202
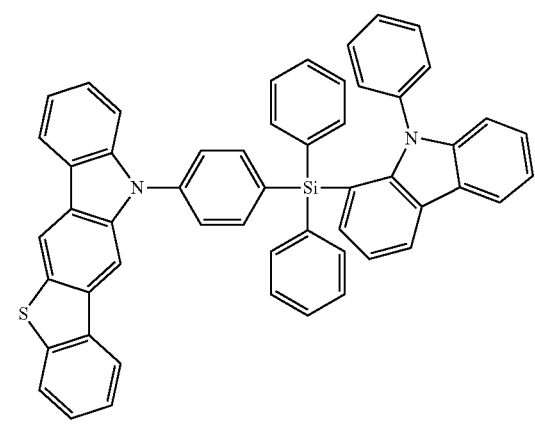
203
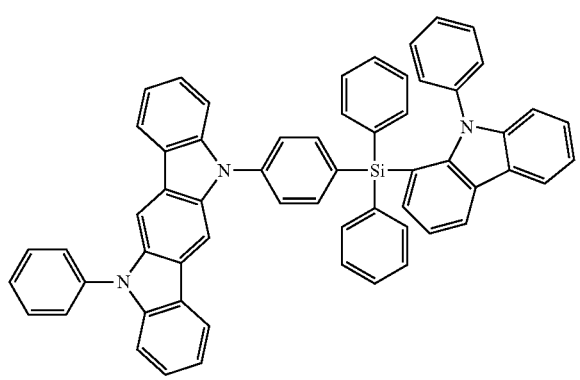
204
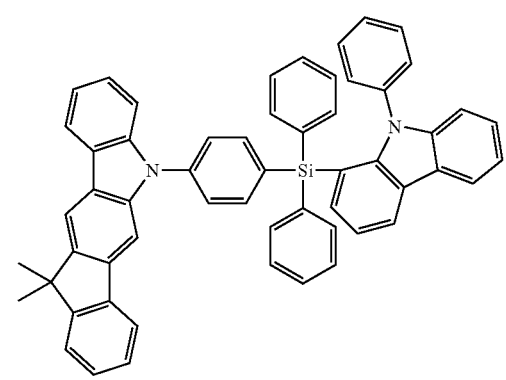

-continued
205
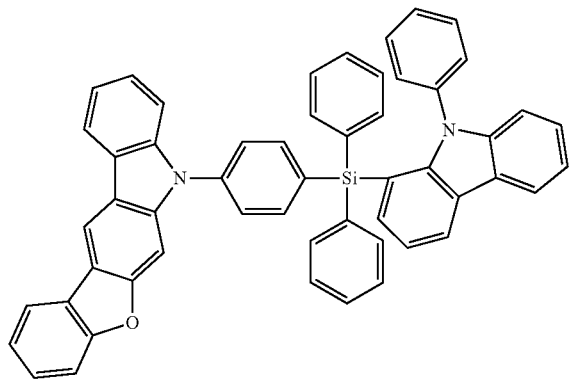
206
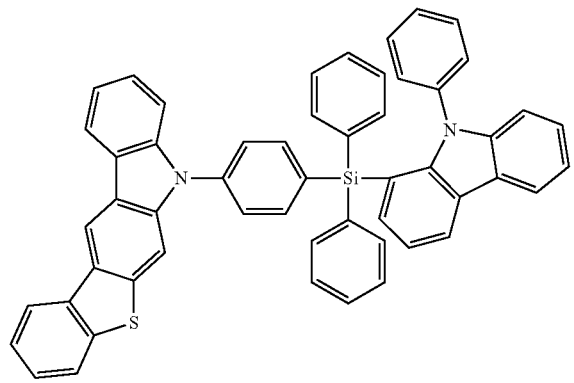
207
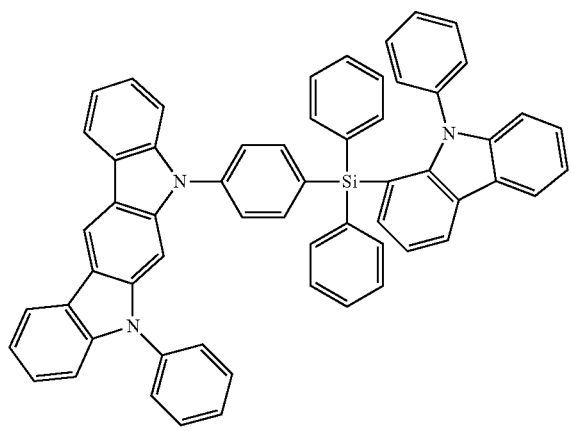
208
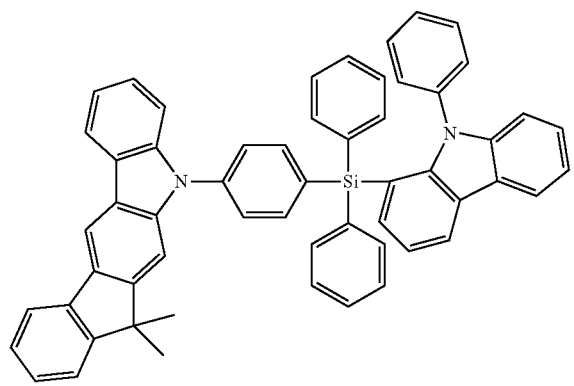
209
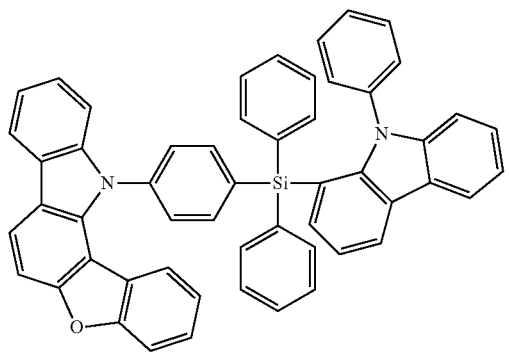
210
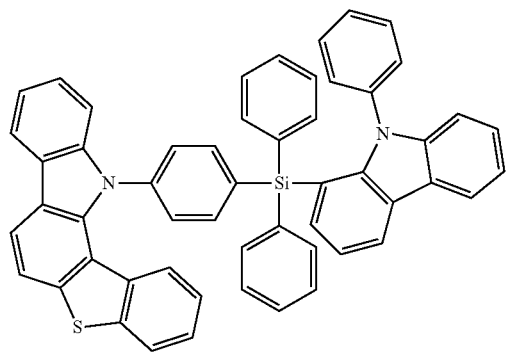

-continued
211
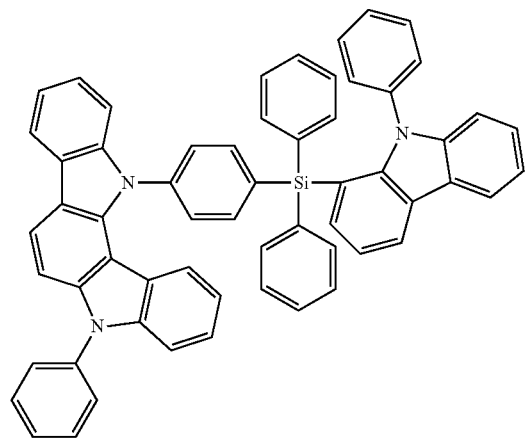
212
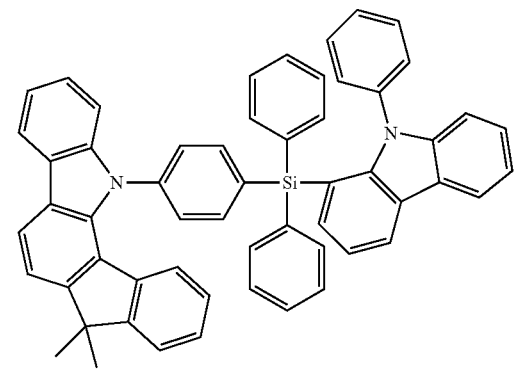
213
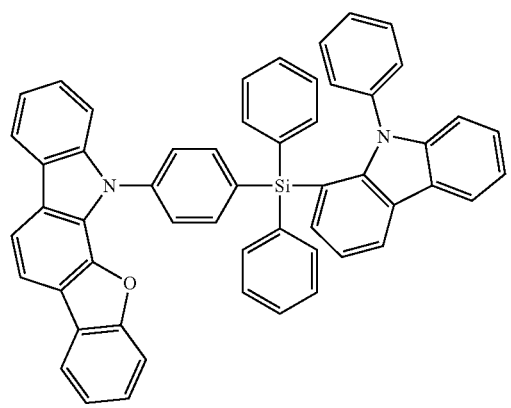
214
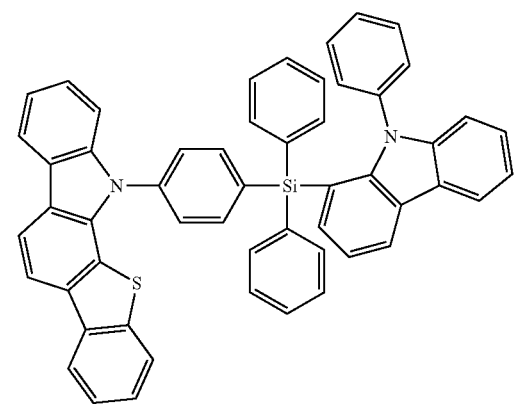
215
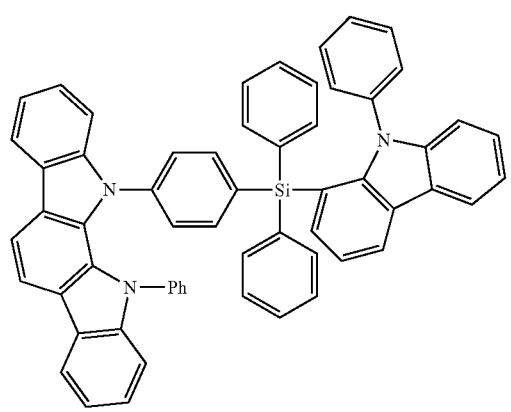
216
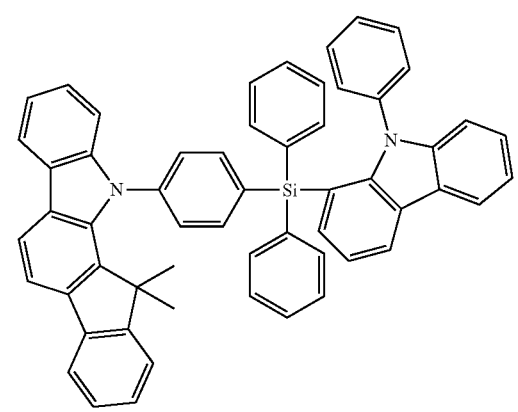
217
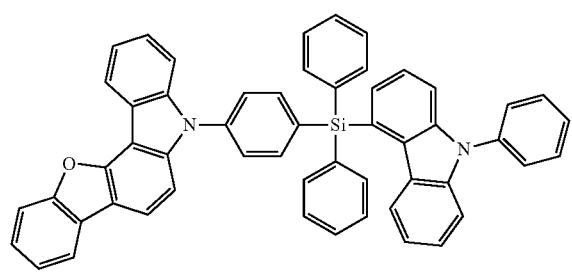
218
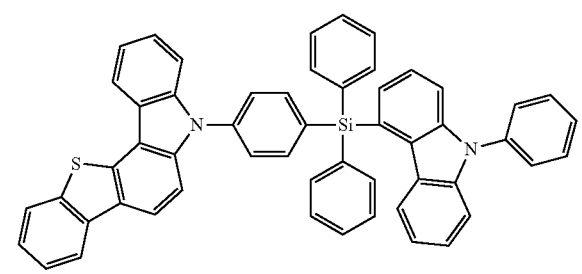

-continued
219
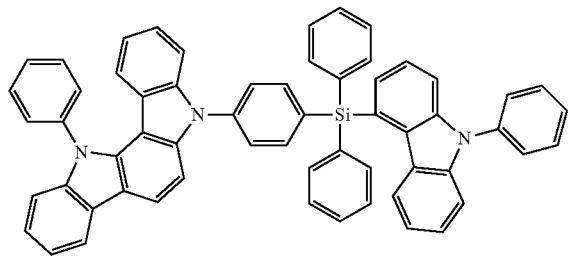
220
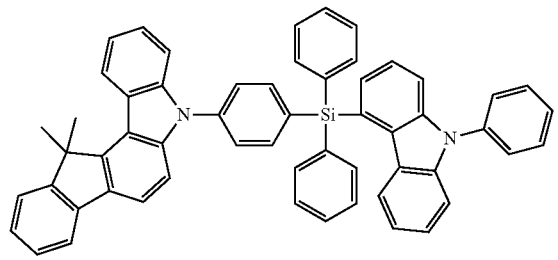
221
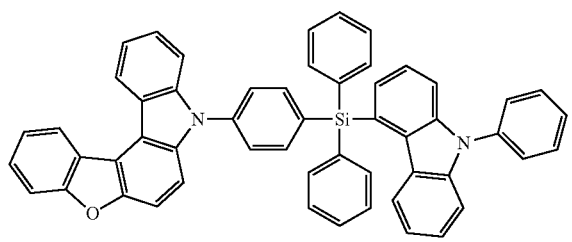
222
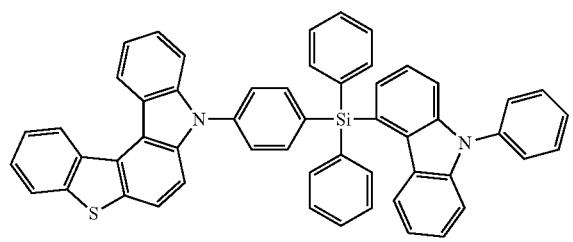
223
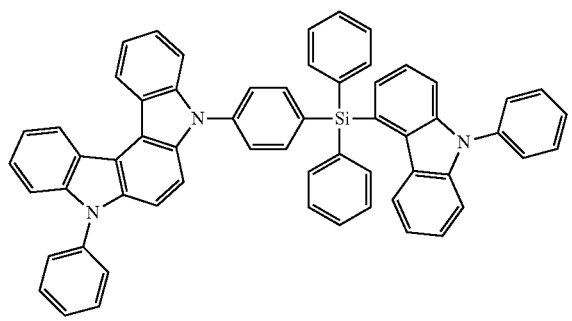
224
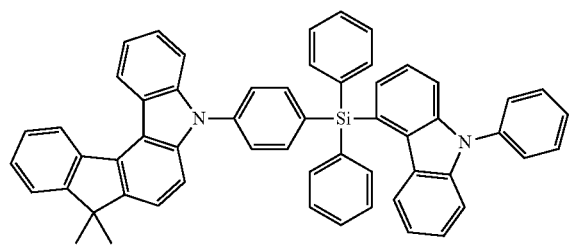
225
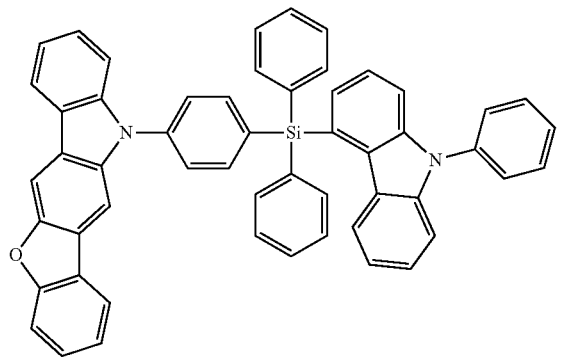
226
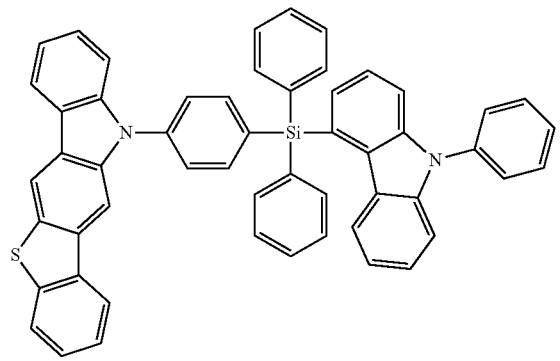

-continued
227
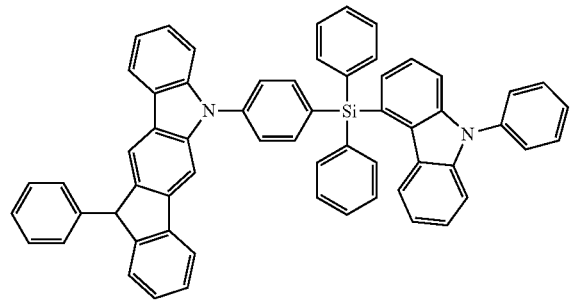
228
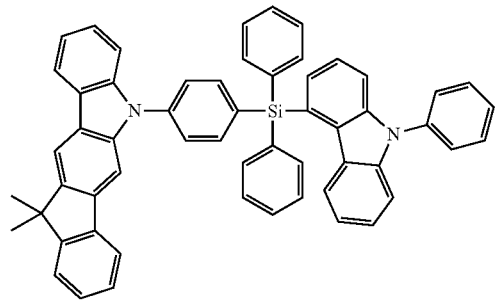
229
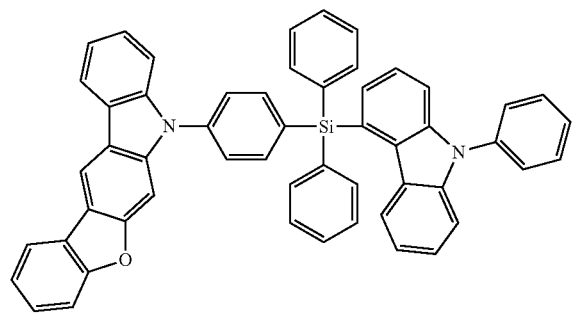
230
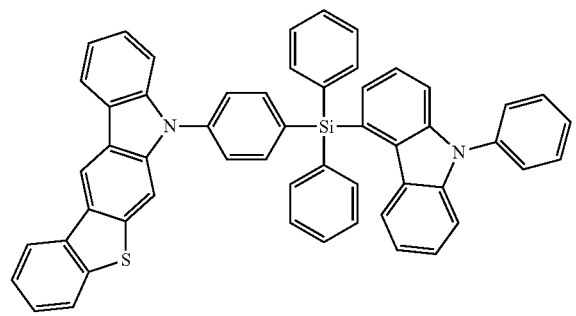
231
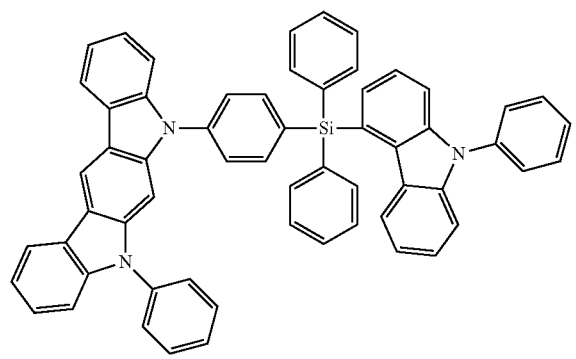
232
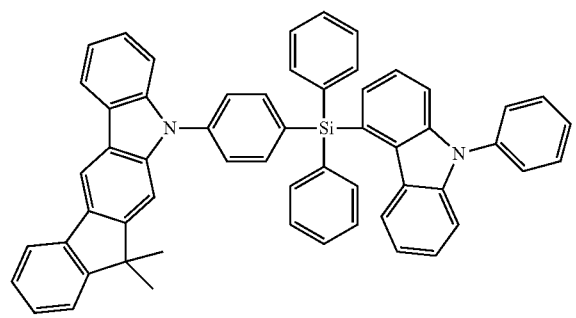
233
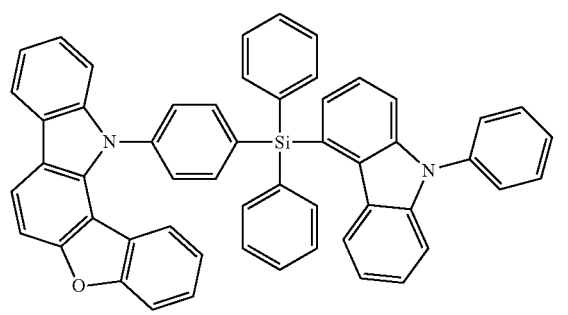
234
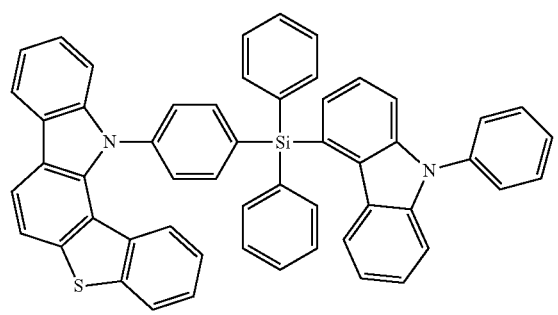

-continued
| 235 | 236 |
|---|---|
| 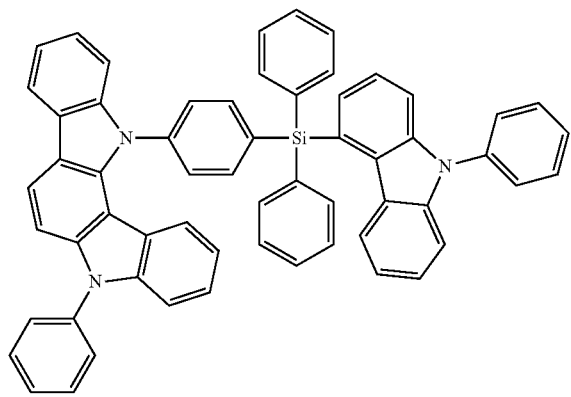 | 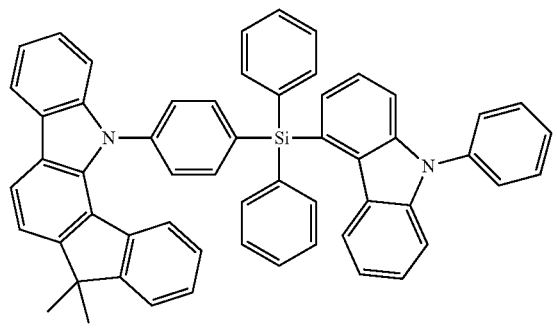 |
| 237 | 238 |
| 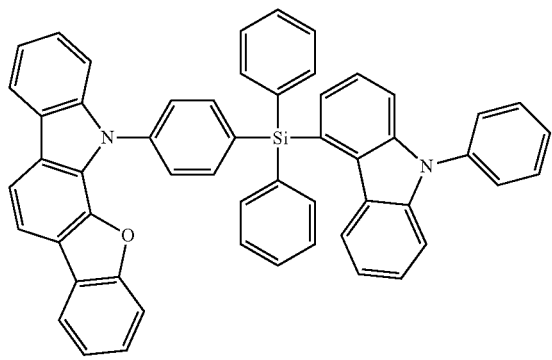 | 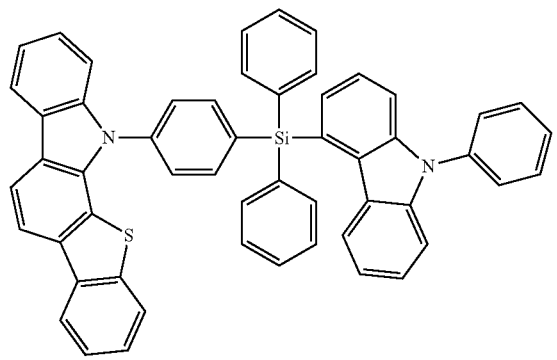 |
| 239 | 240 |
| 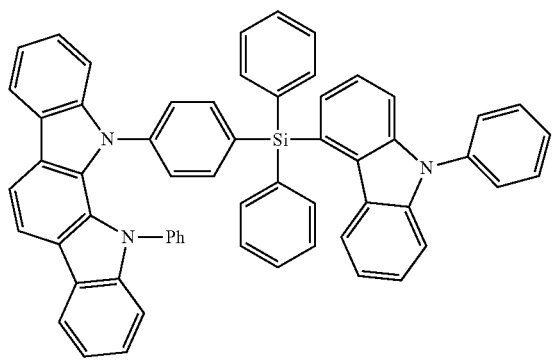 | 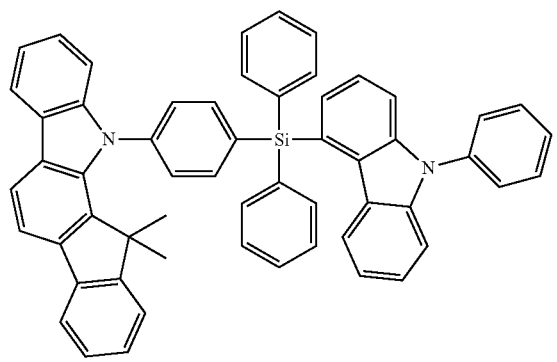 |
| 241 | 242 |
| 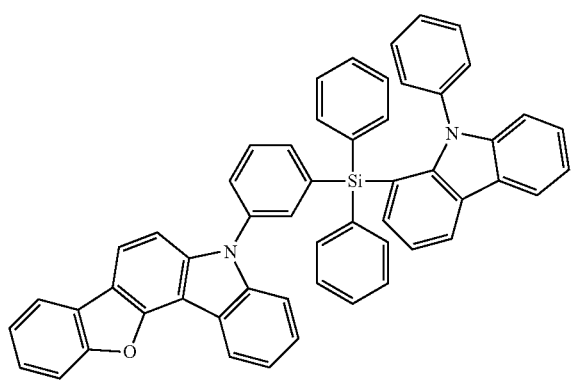 | 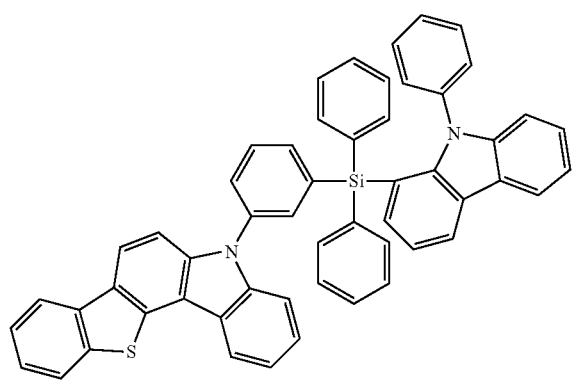 |

243
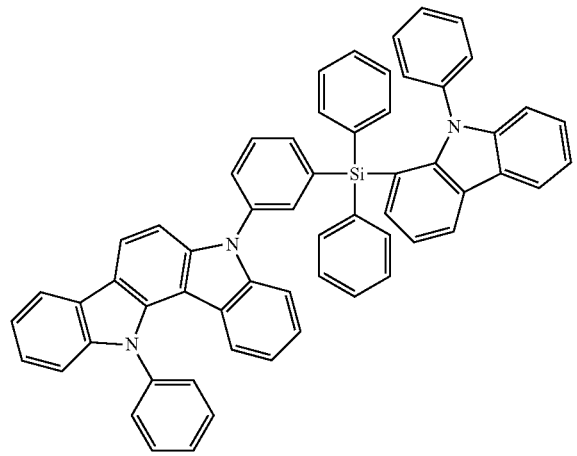
244
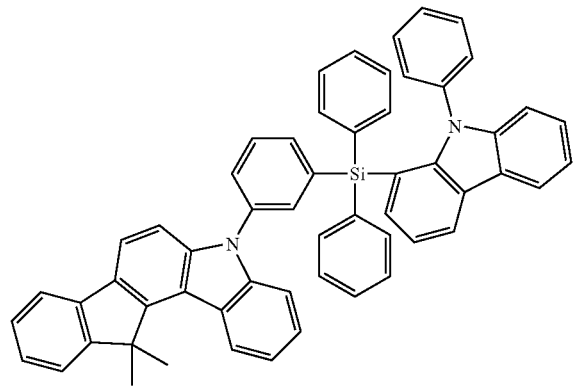
245
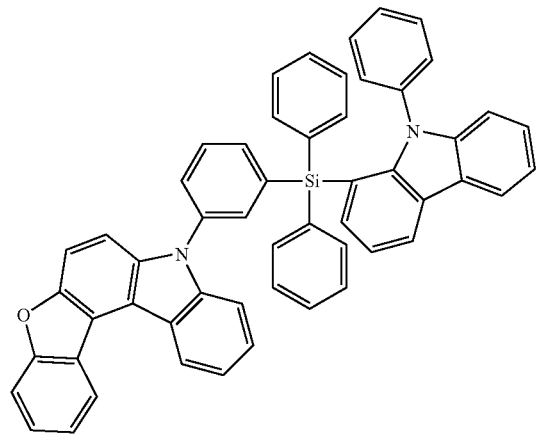
246
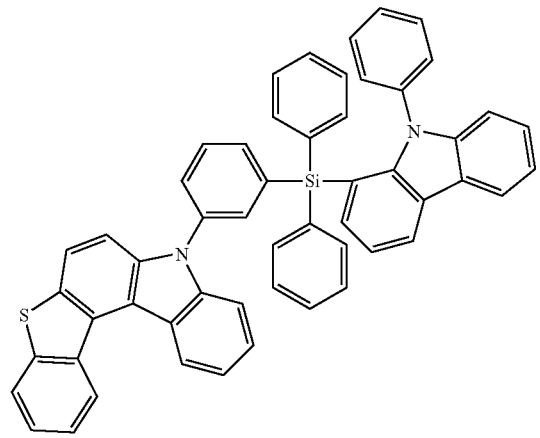
247
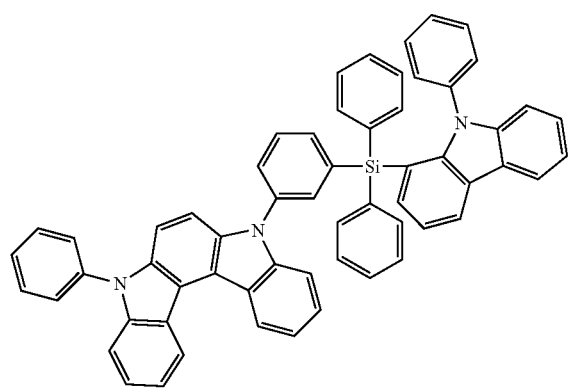
248
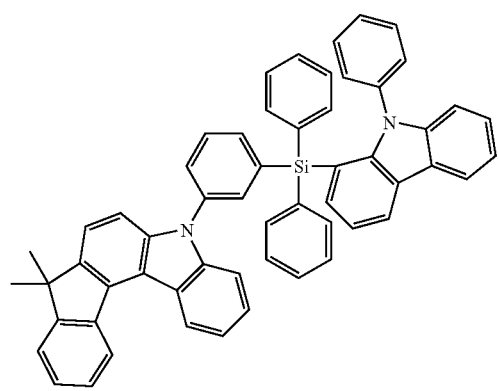

-continued
249
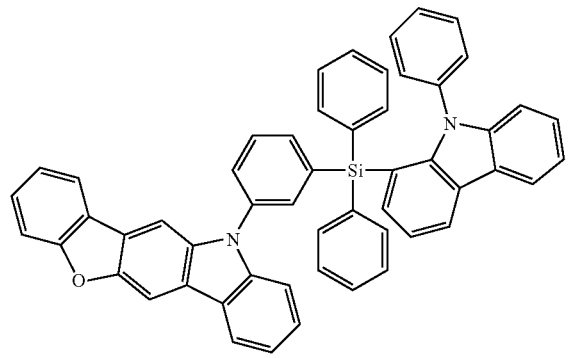
250
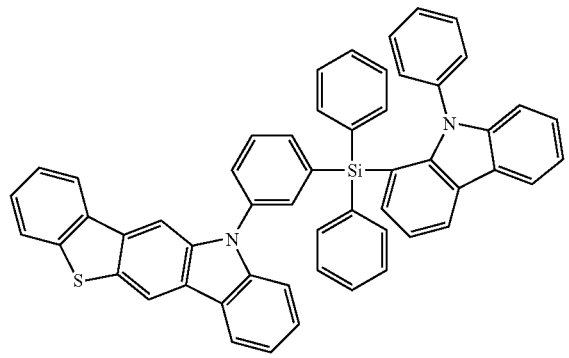
251
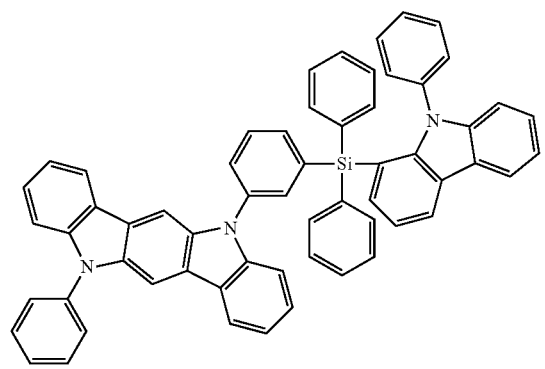
252
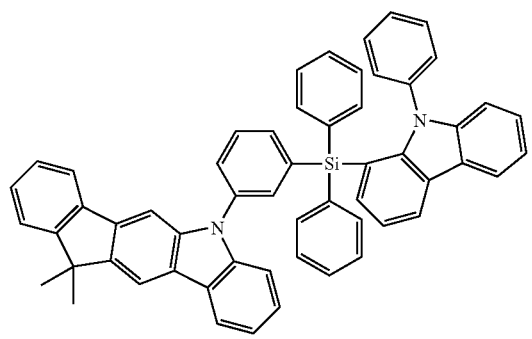
253
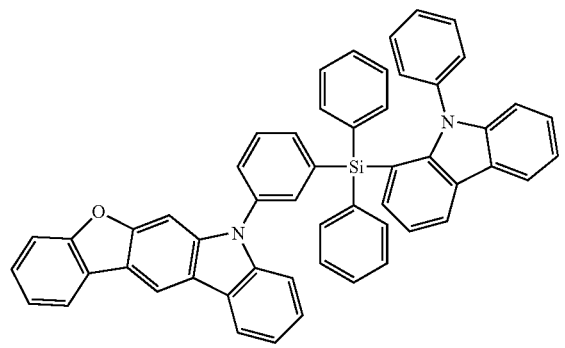
254
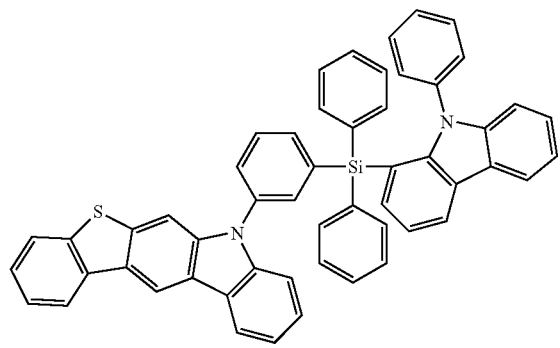
255
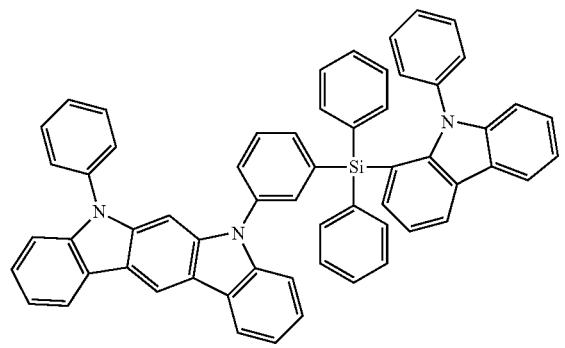
256
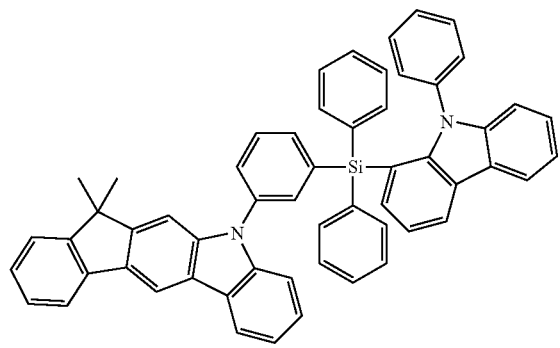

-continued
257
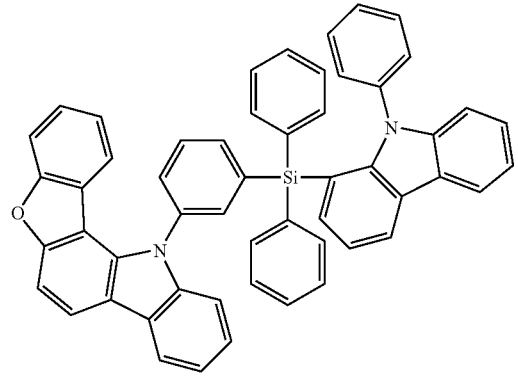
258
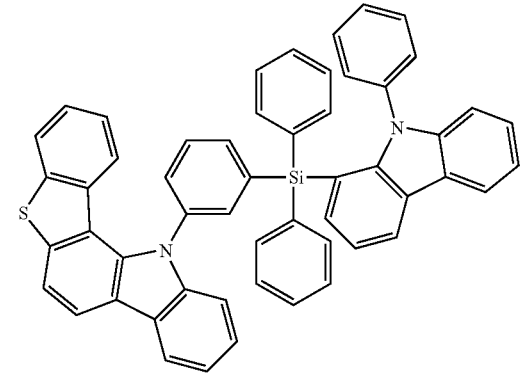
259
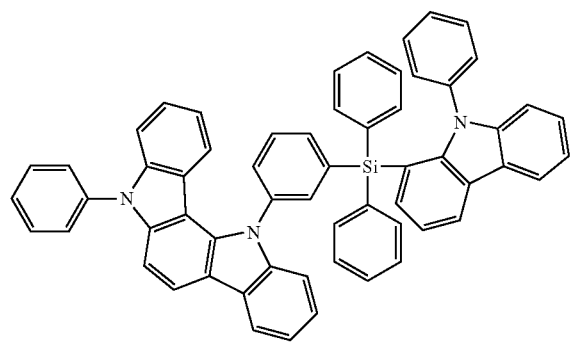
260
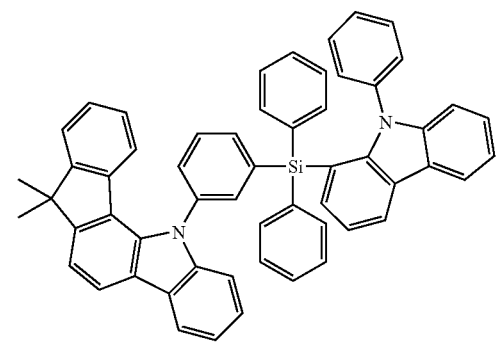
261
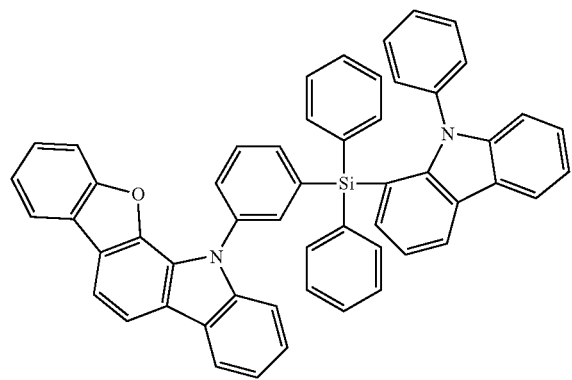
262
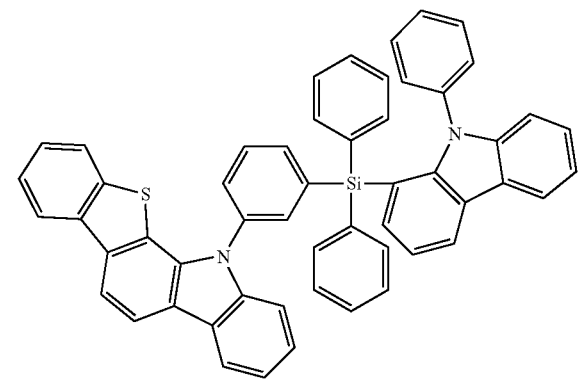
263
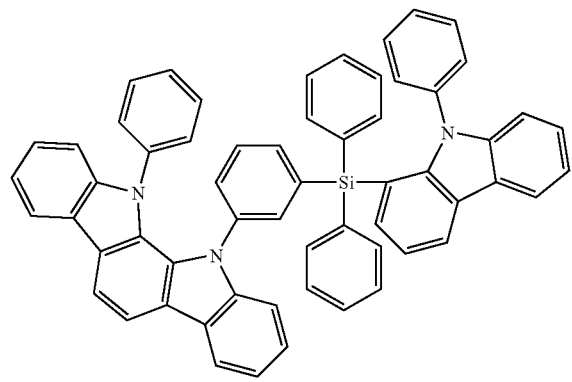
264
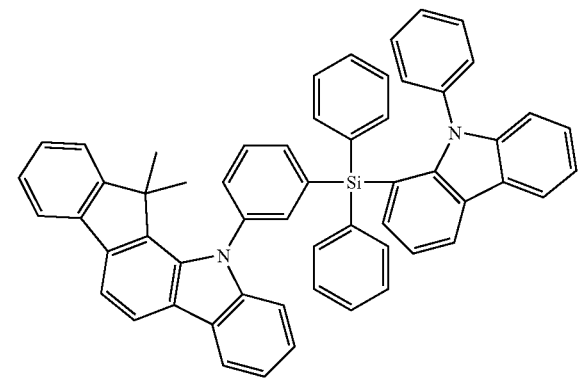

-continued
265
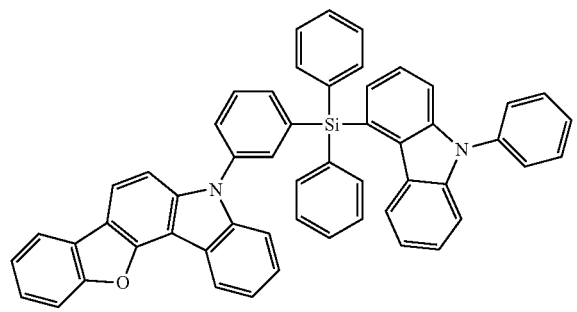
266
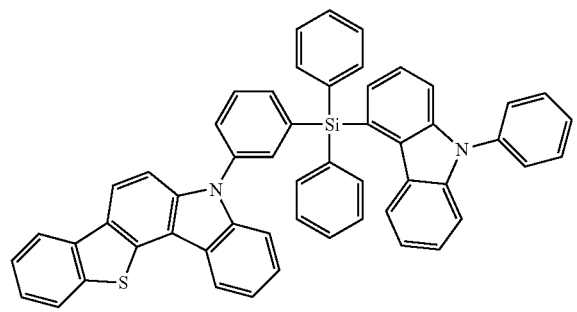
267
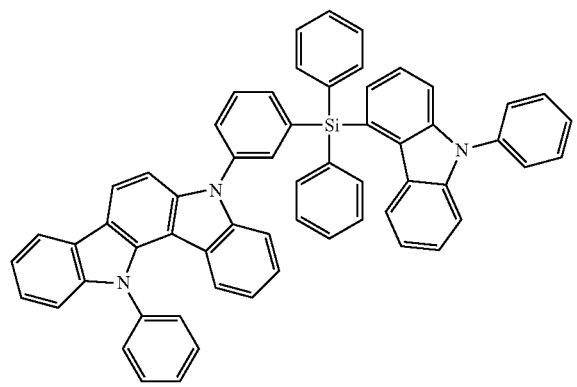
268
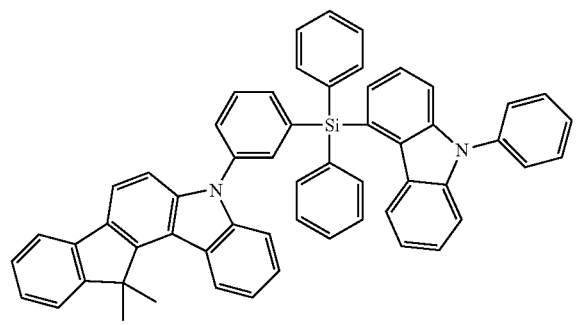
269
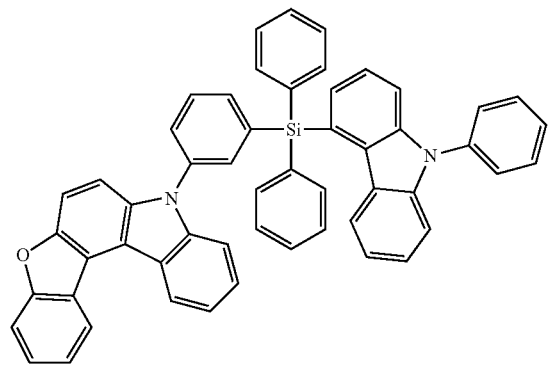
270
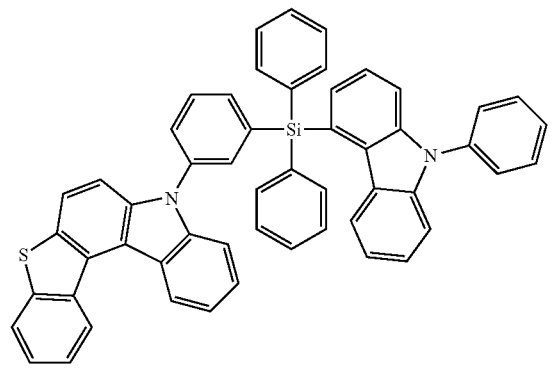
271
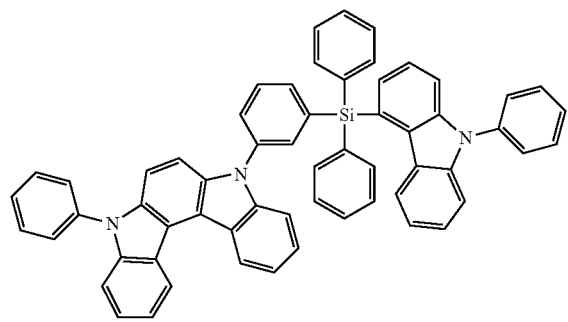
272
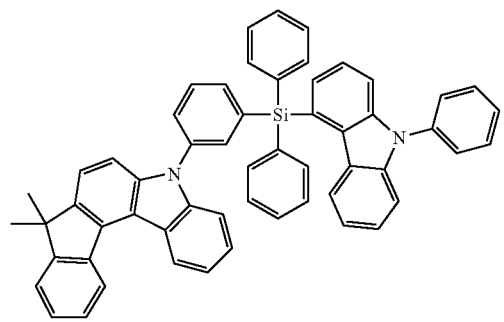

-continued
273
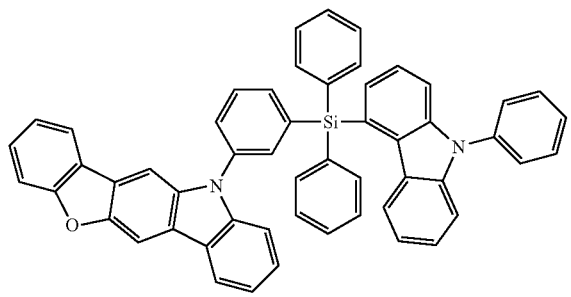
274
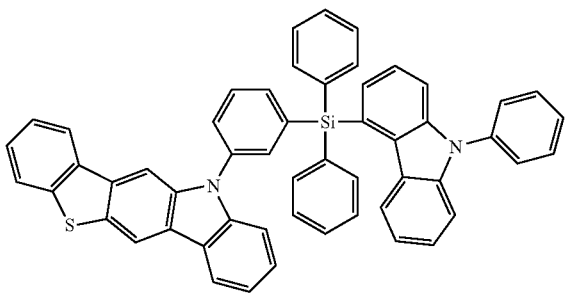
275
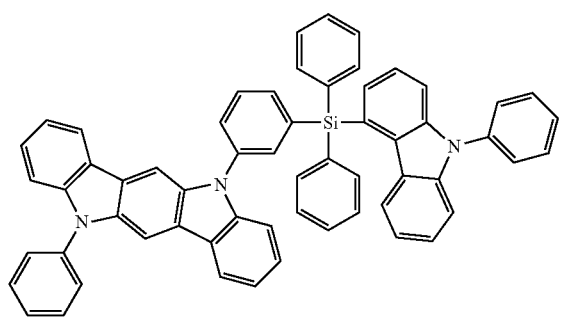
276
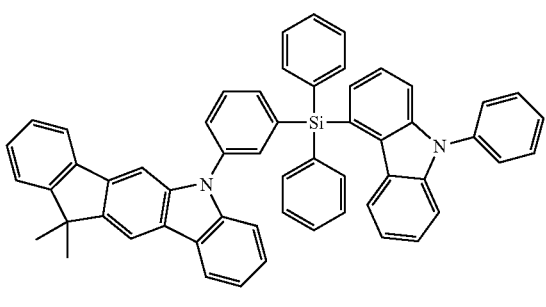
277
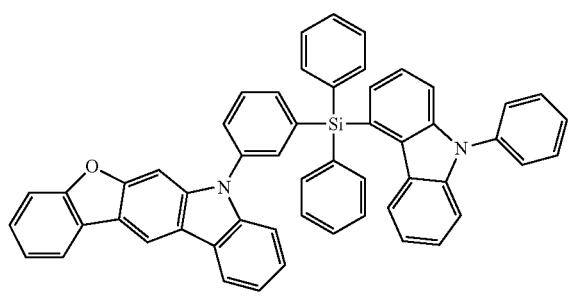
278
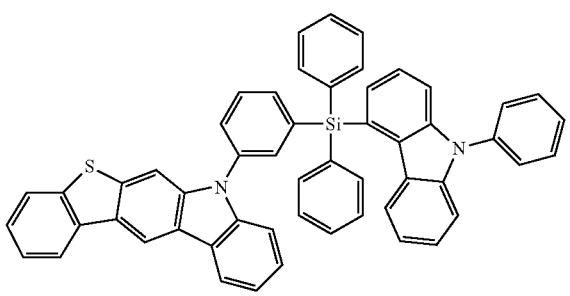
279
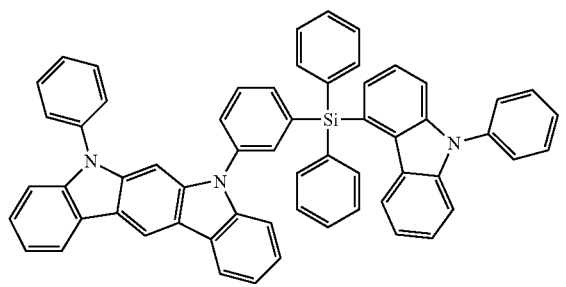
280
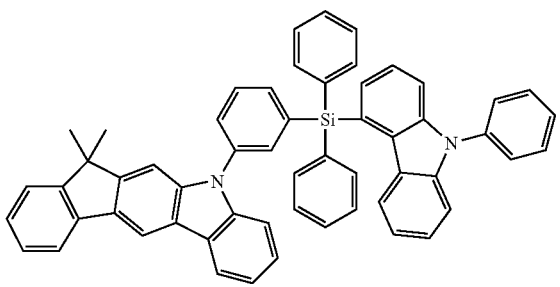
281
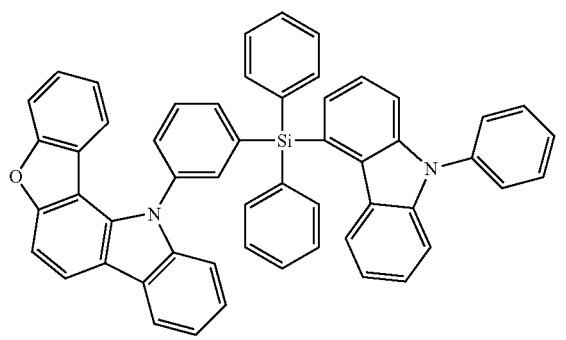
282
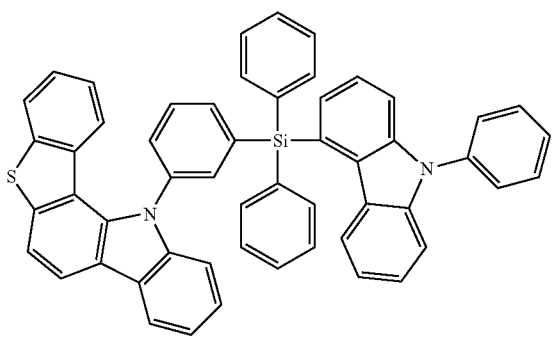

-continued
283
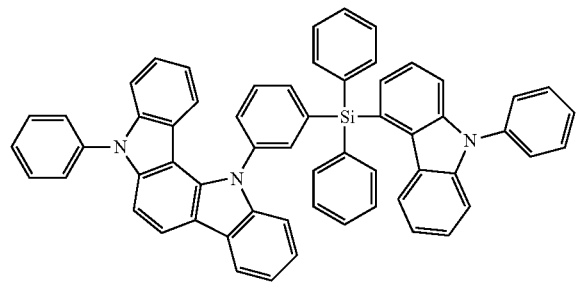
284
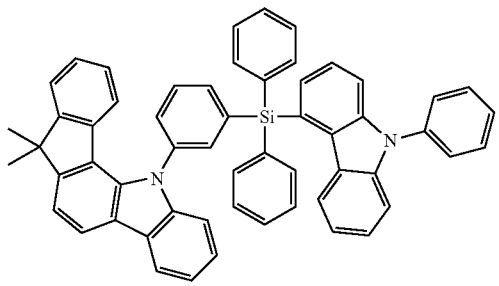
285
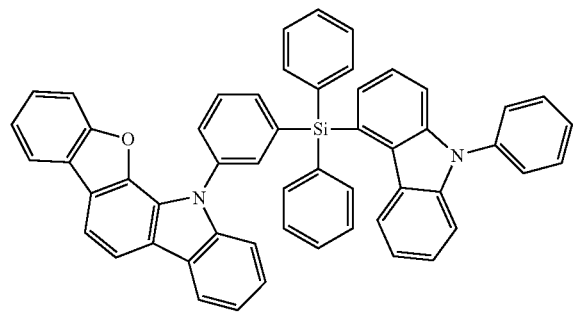
286
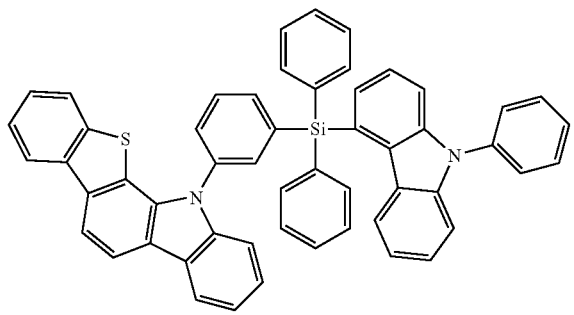
287
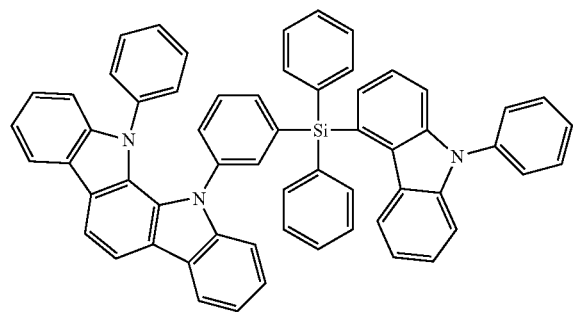
288
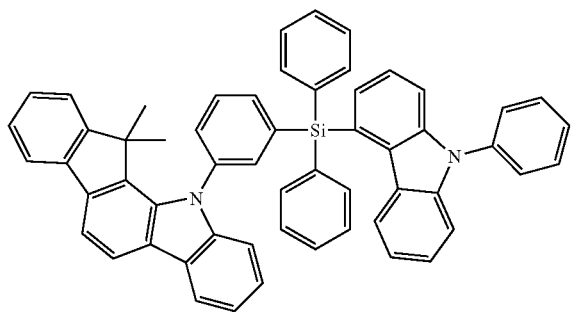
289
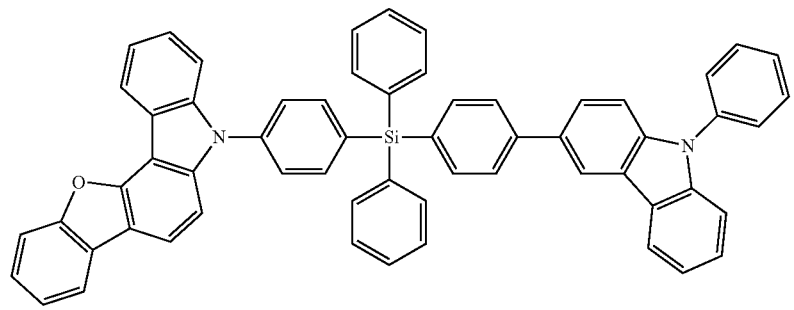

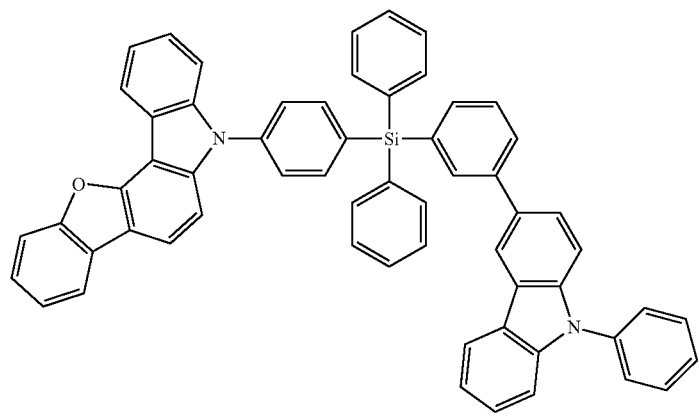
290
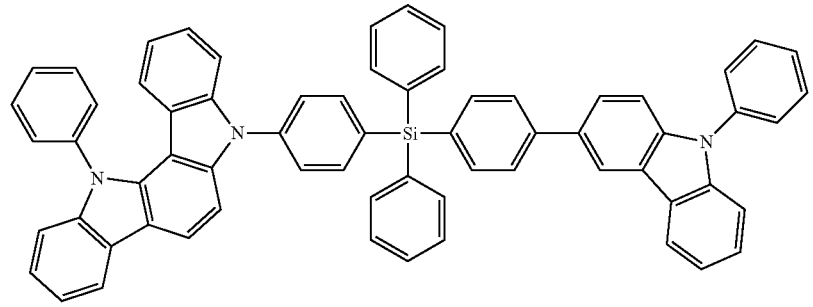
291
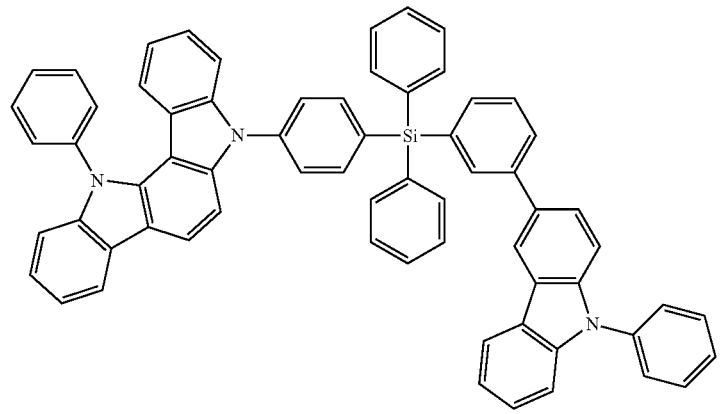
292
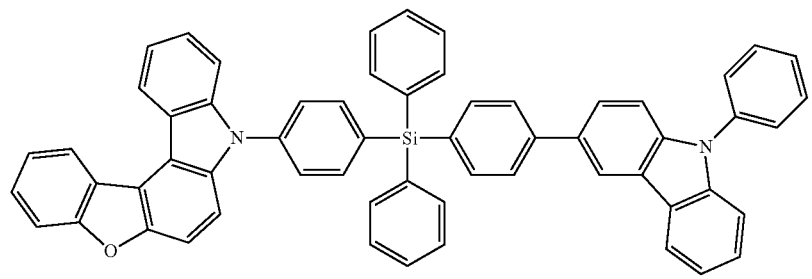
293

-continued
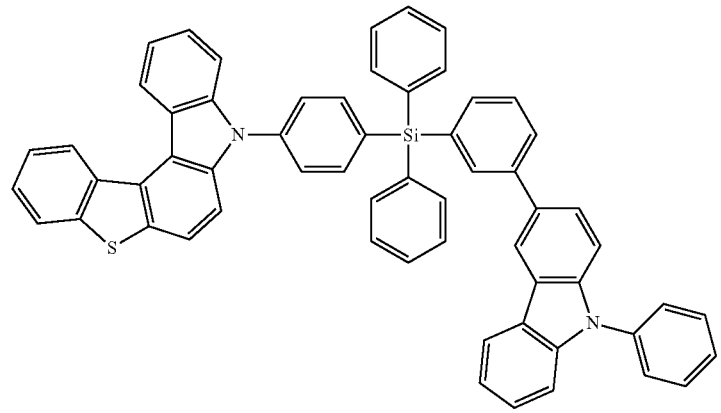
294
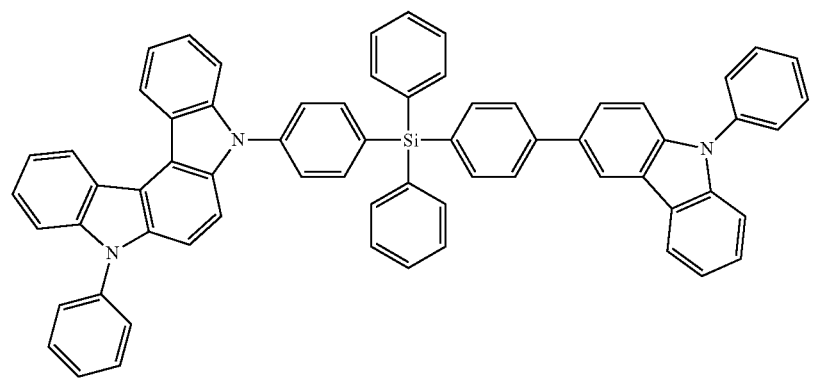
295
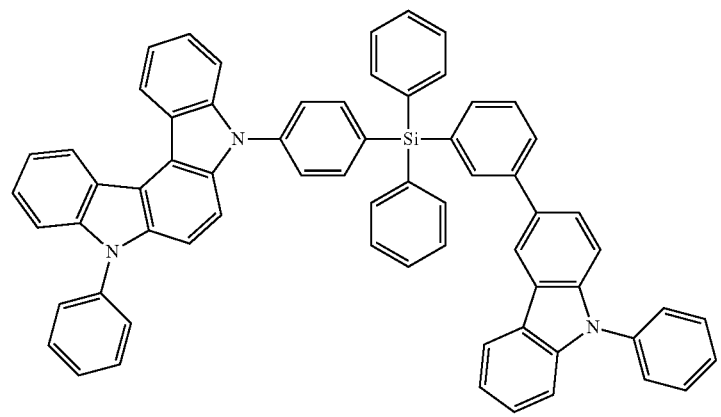
296
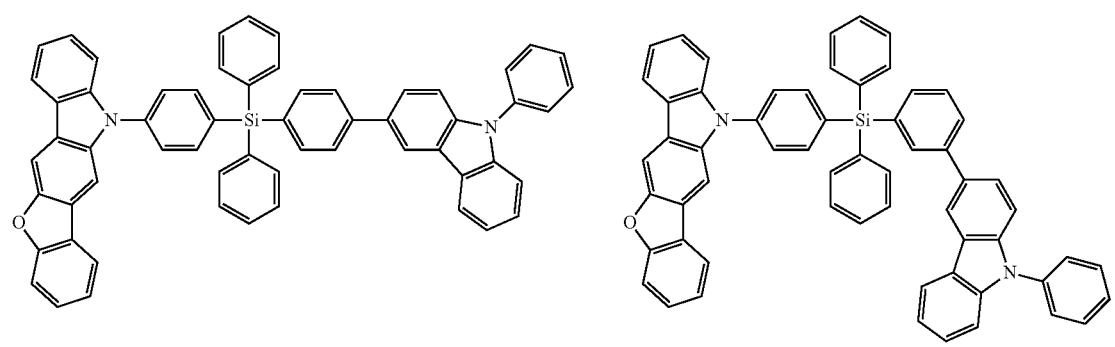
297 298

299
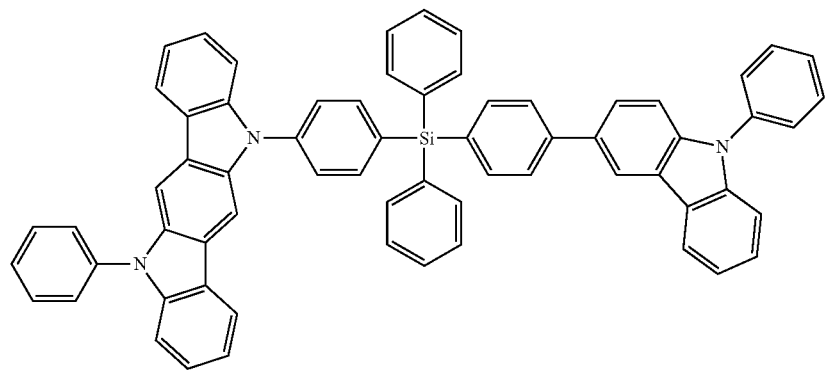
300
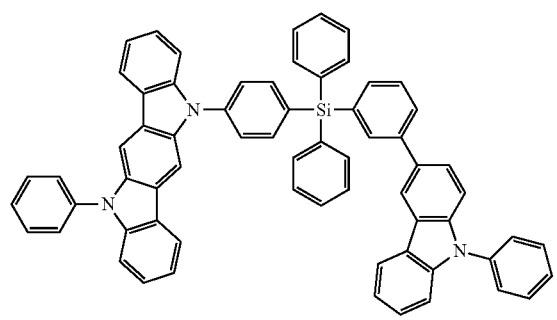
301
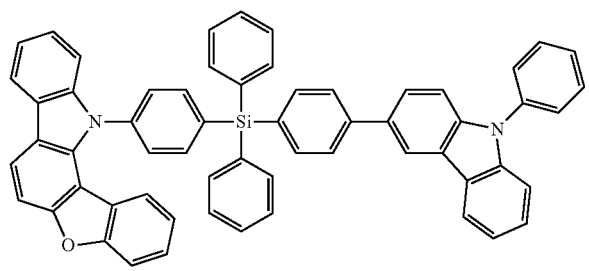
302
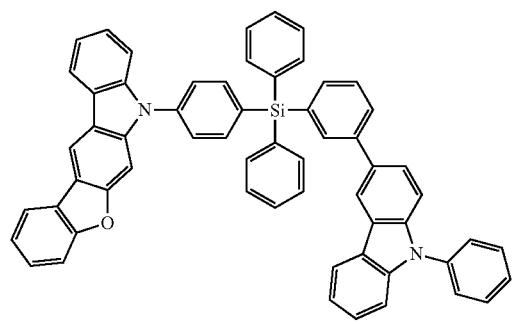
303
304
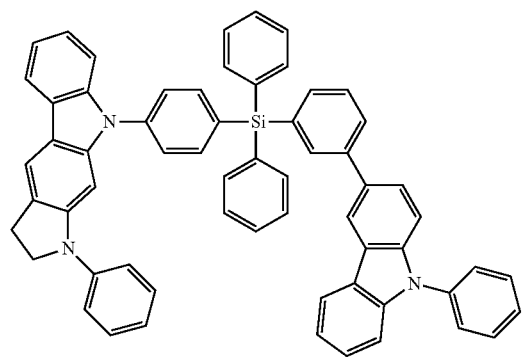
305

-continued
306
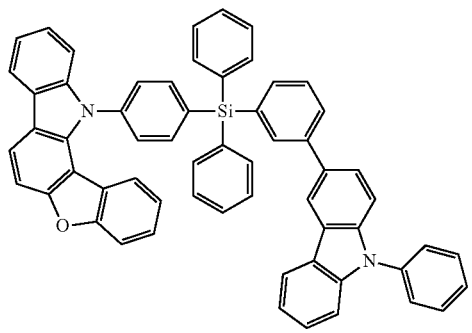
307
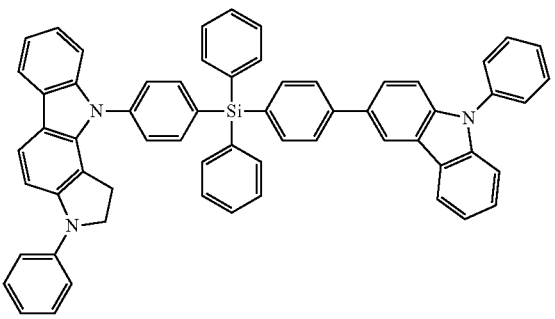
308
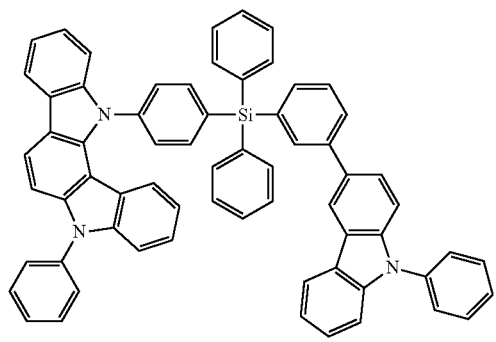
309
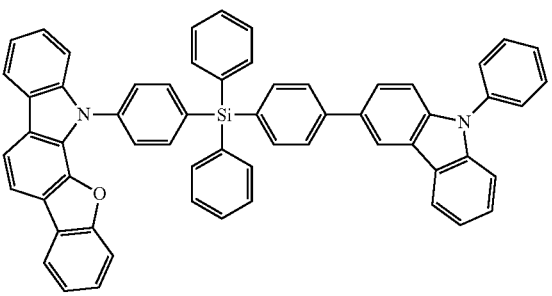
310
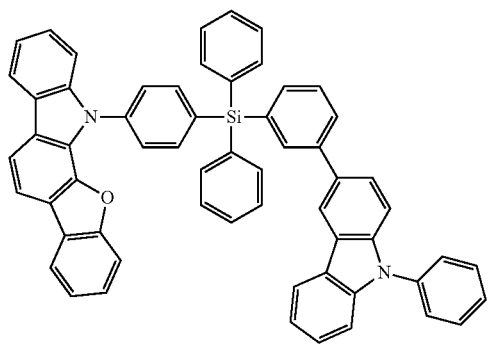
311
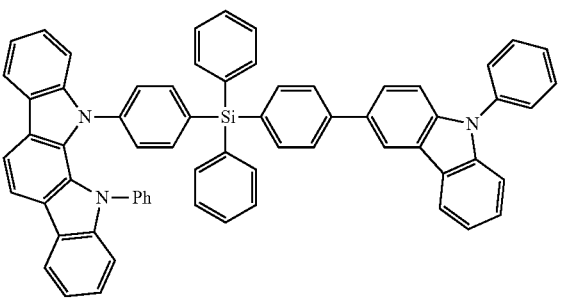
312
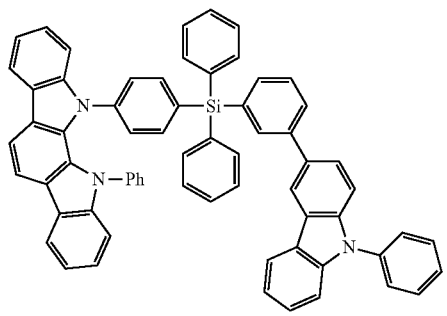
313
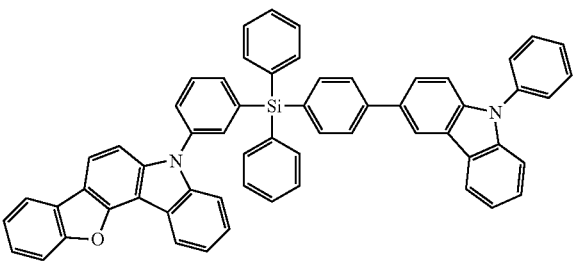

-continued
314
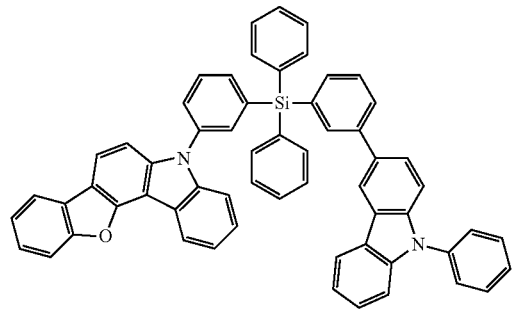
315
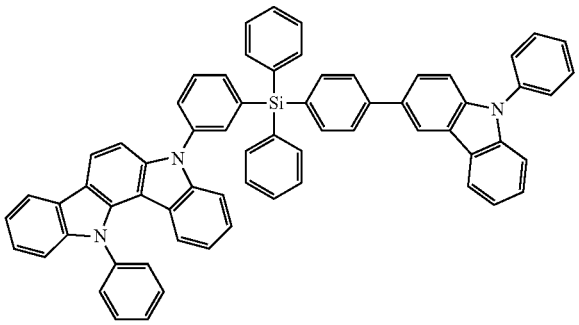
316
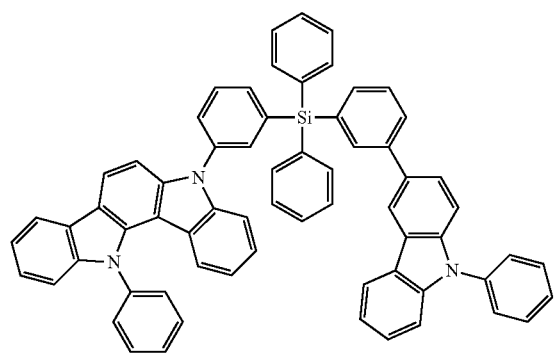
317
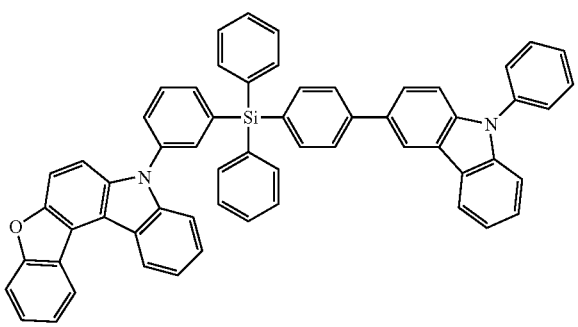
318
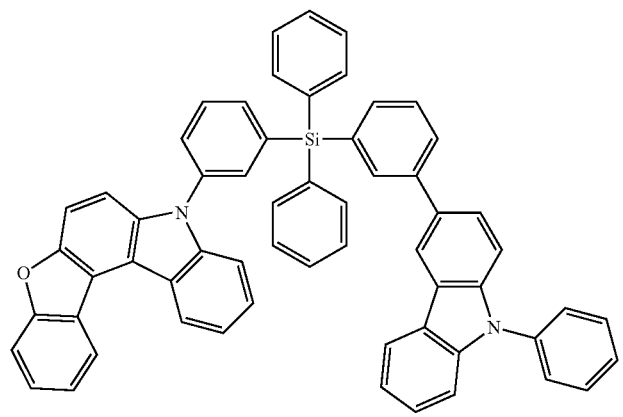
319
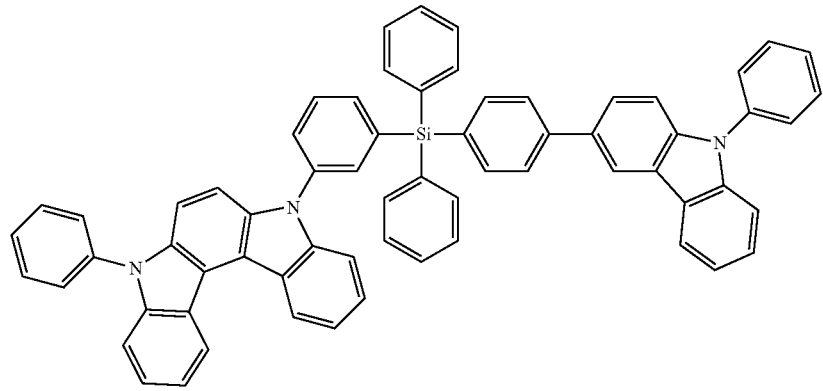

-continued
320
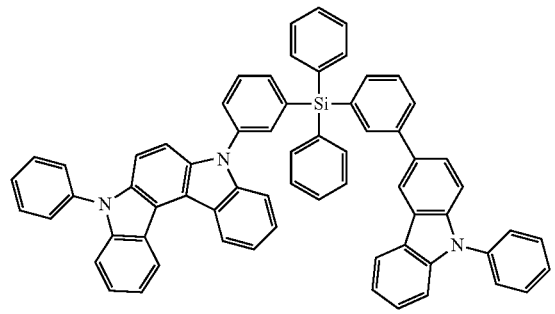
321
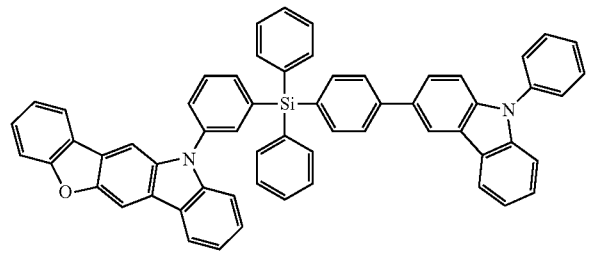
322
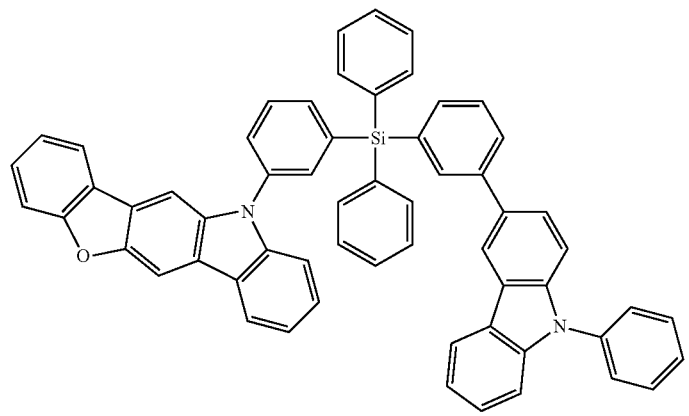
323
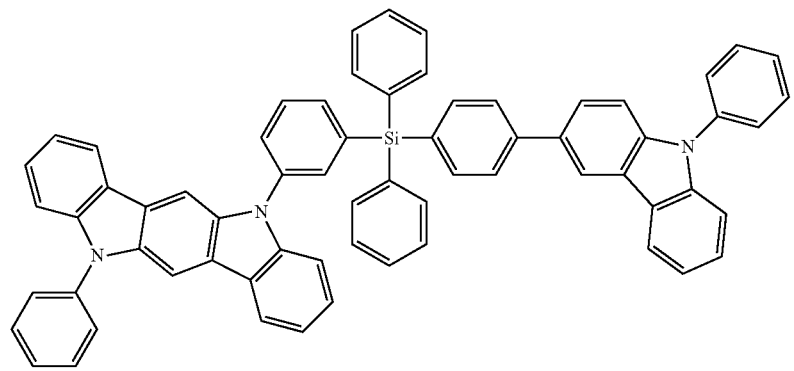
324
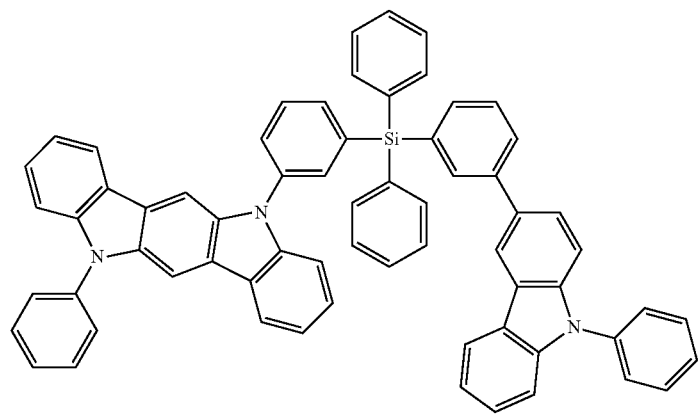

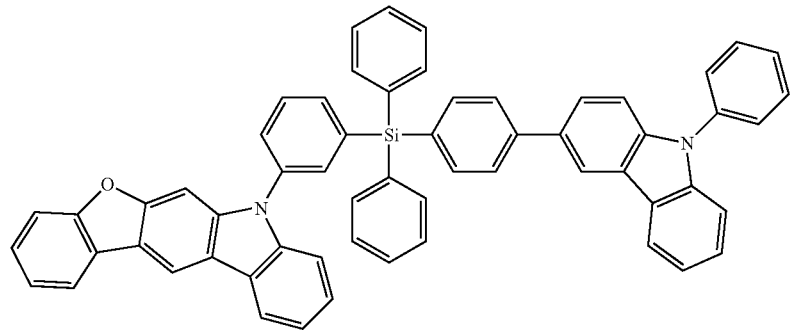
325
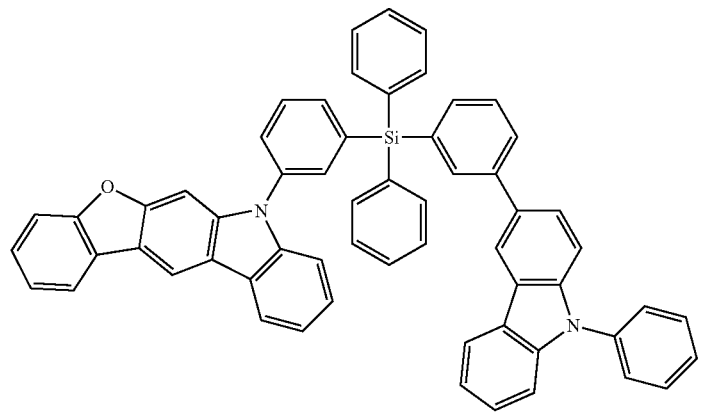
326
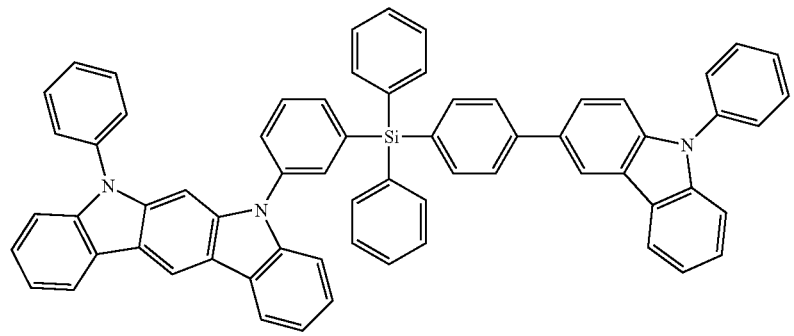
327
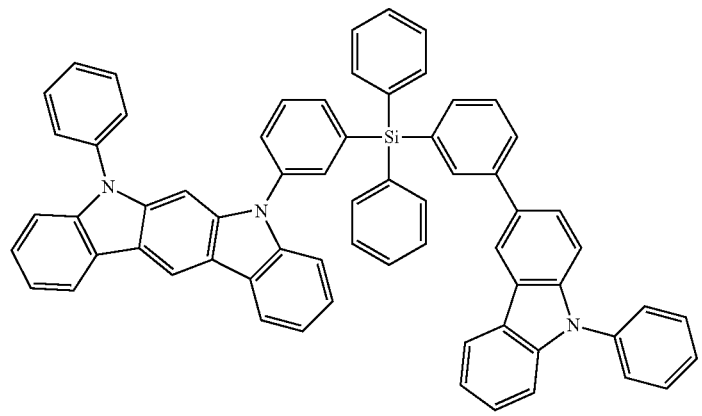
328

329
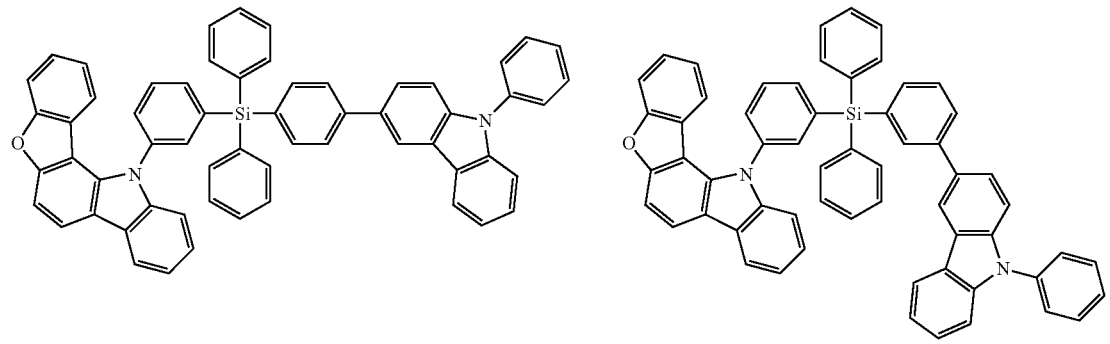
330
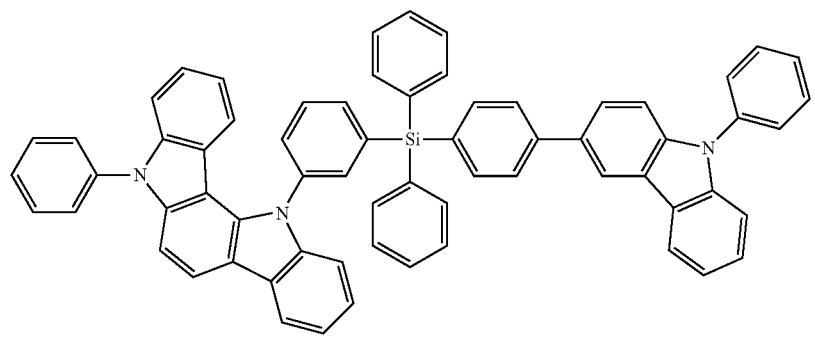
331
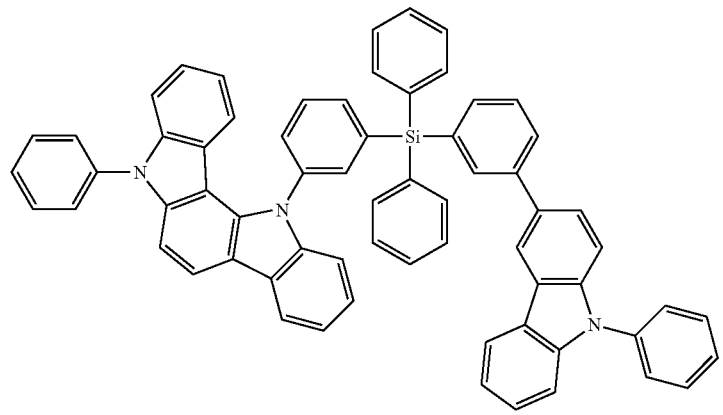
332
333
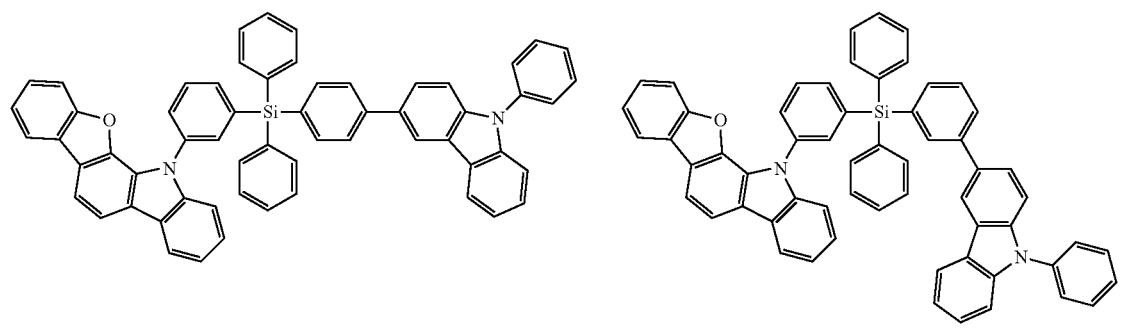
334

335
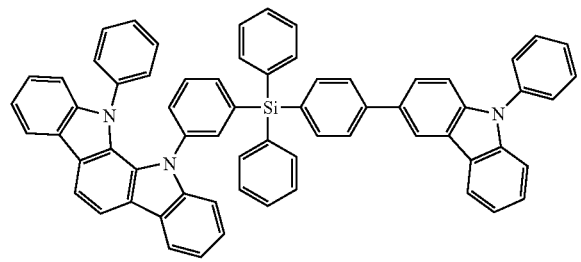
336
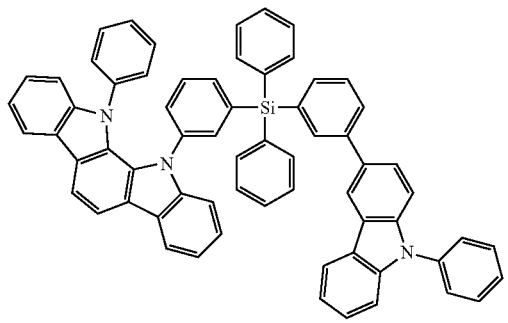
337
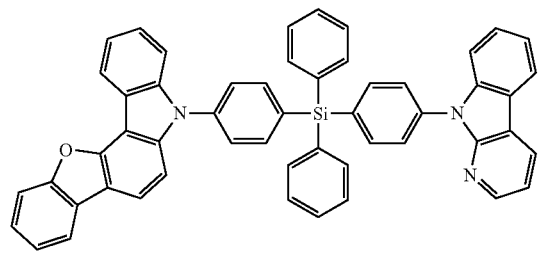
338
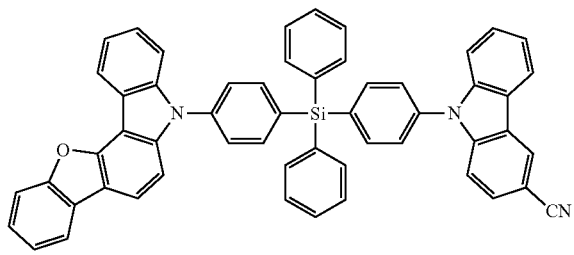
339
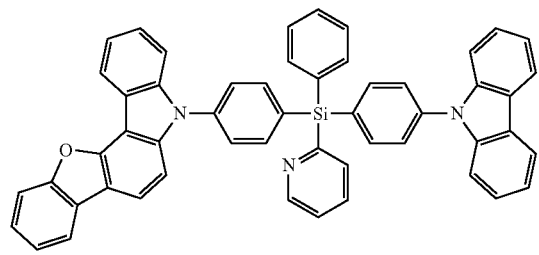
340
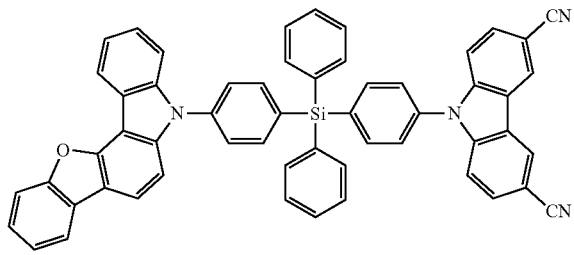
341
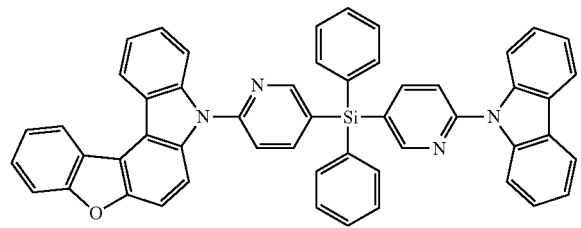
342
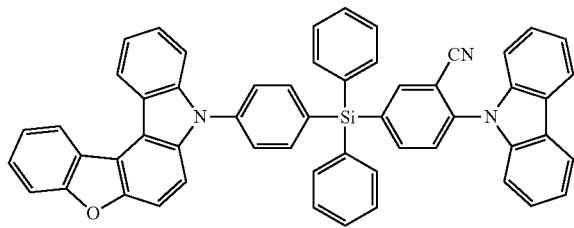
343
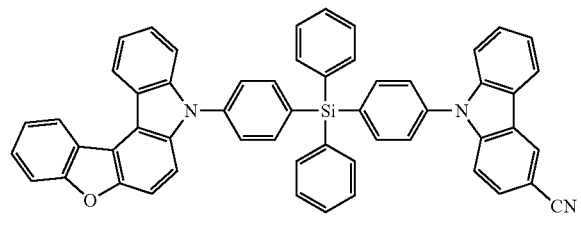
344
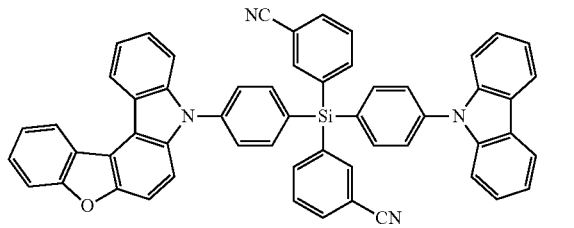

-continued
345
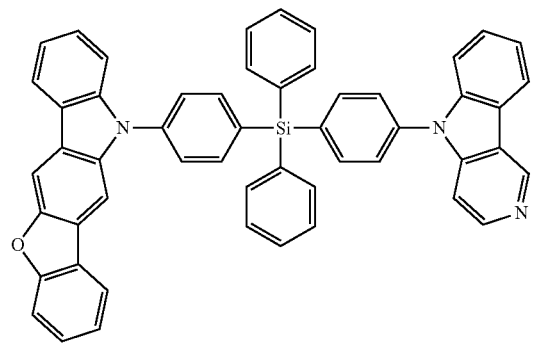
346
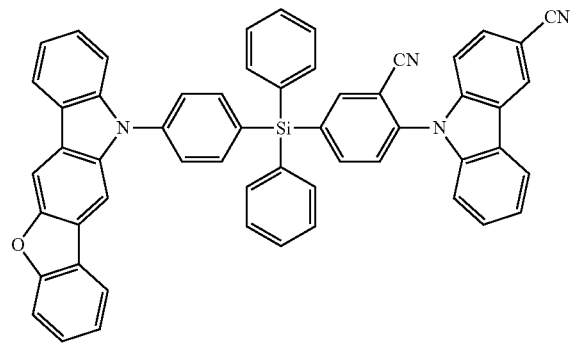
347
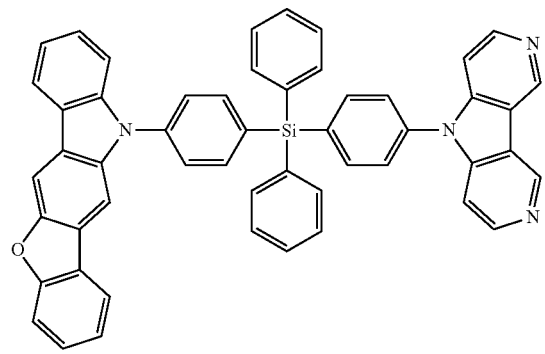
348
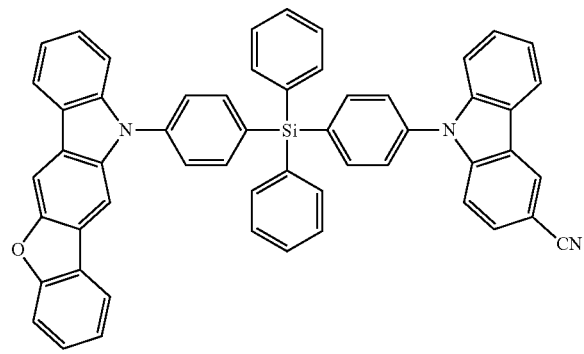
349
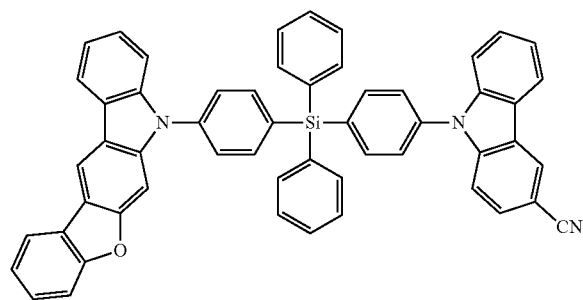
350
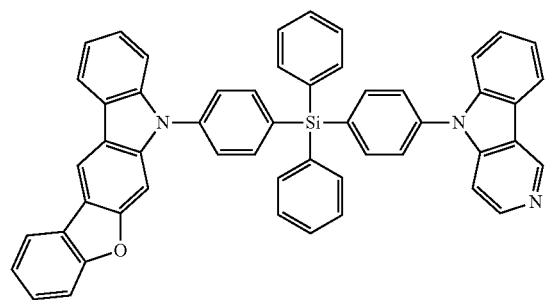
351
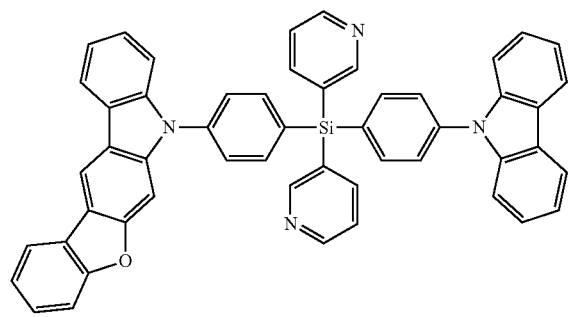
352
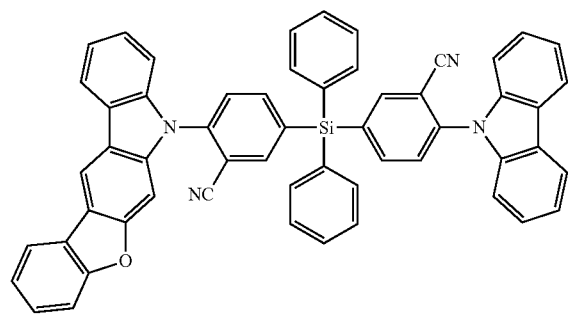

-continued
353
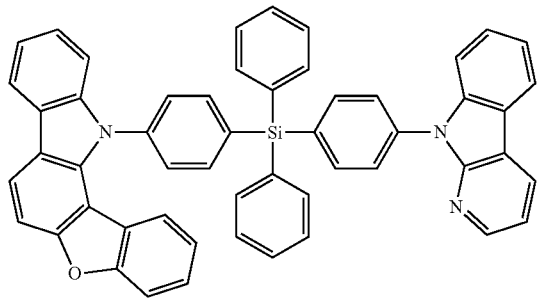
354
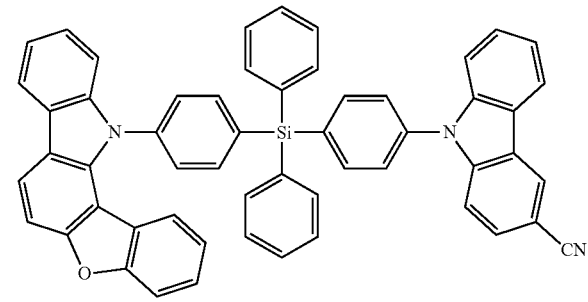
355
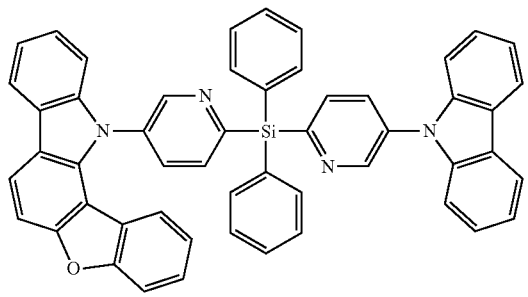
356
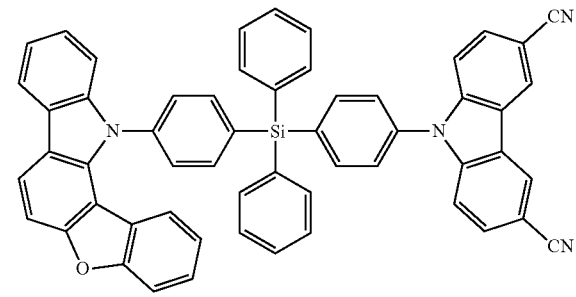
357
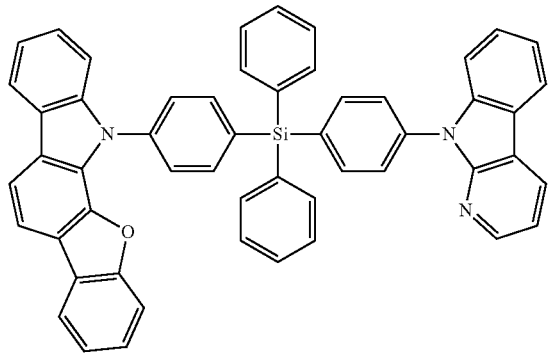
358
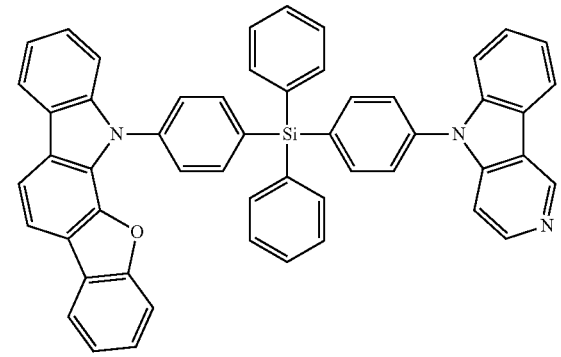
359
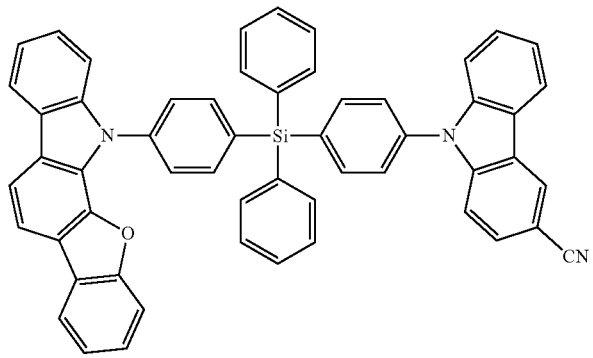
360
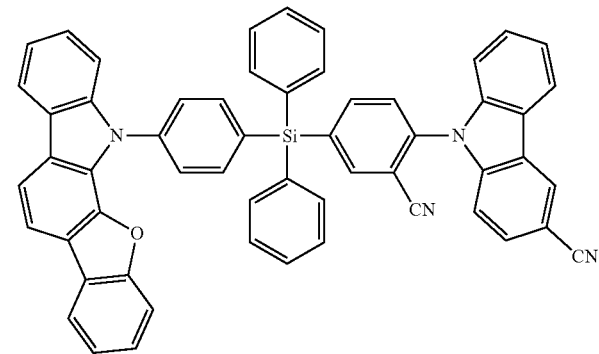

-continued
361
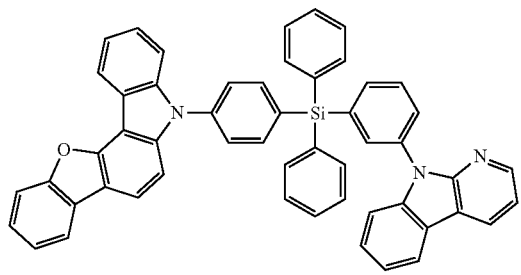
362
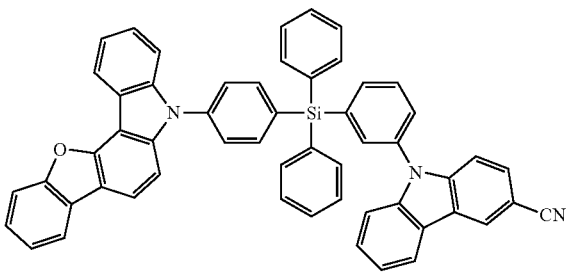
363
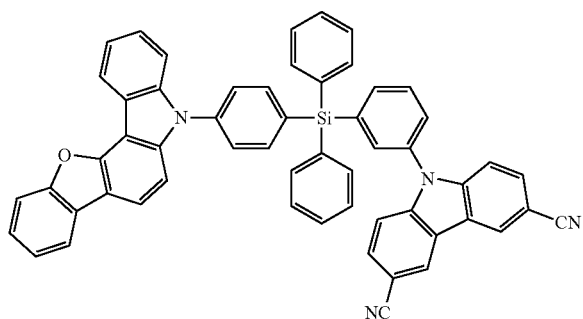
364
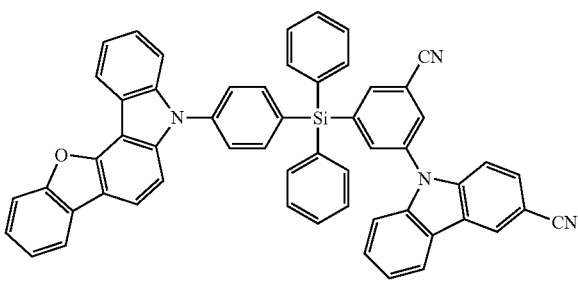
365
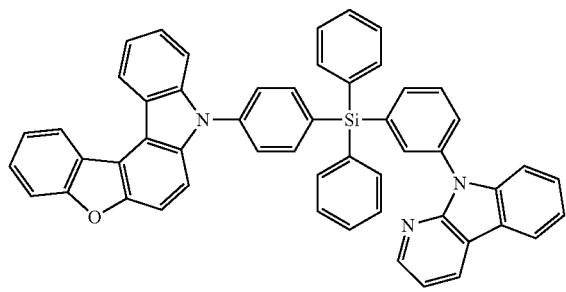
366
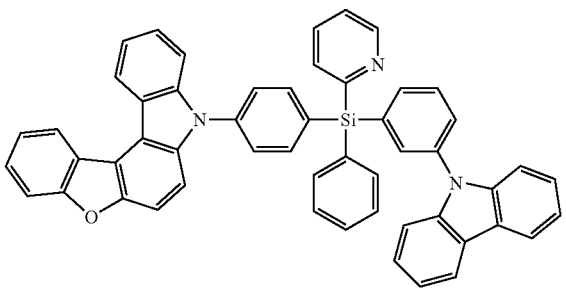
367
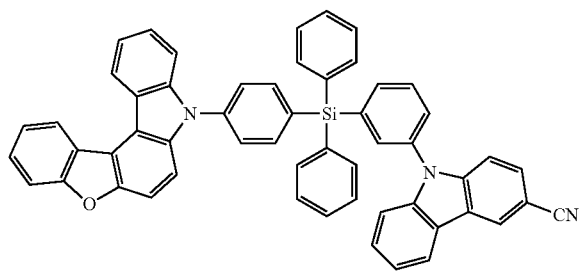
368
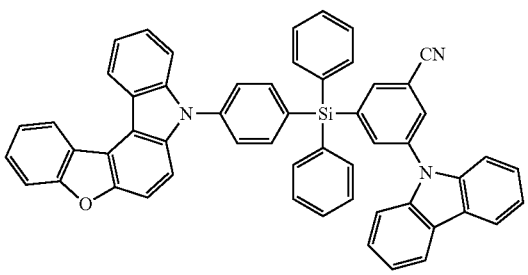
369
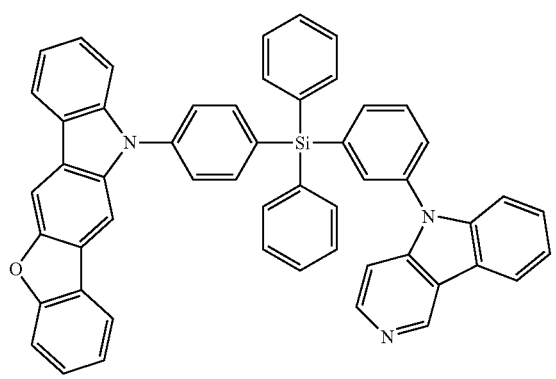
370
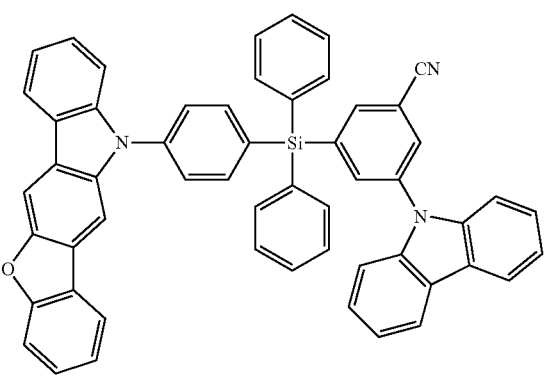

391
392
-continued
371
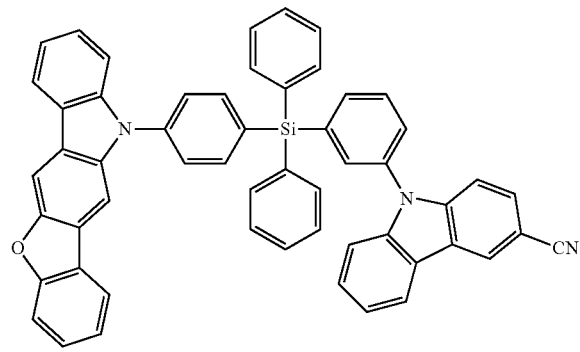
372
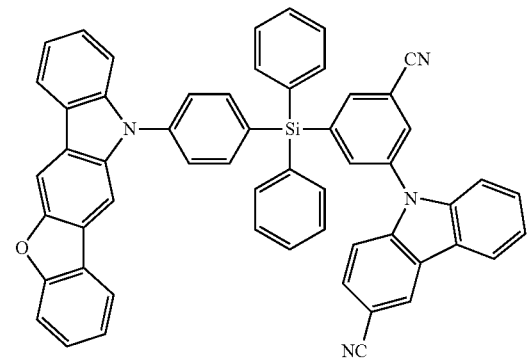
373
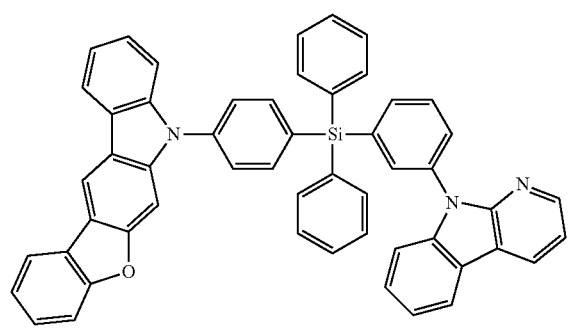
374
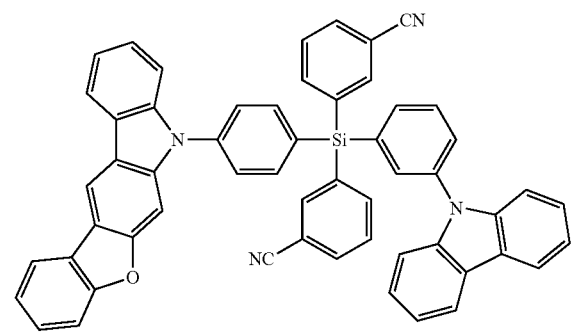
375
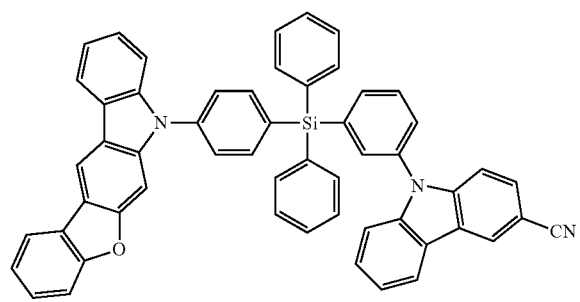
376
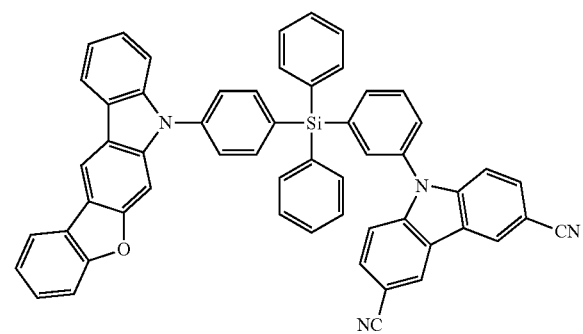
377
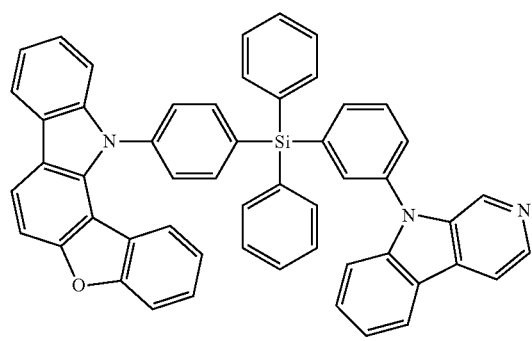
378
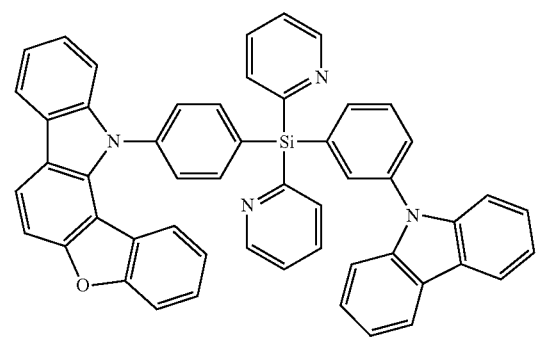

-continued
379
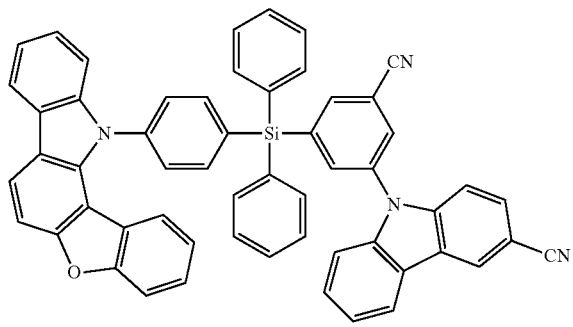
380
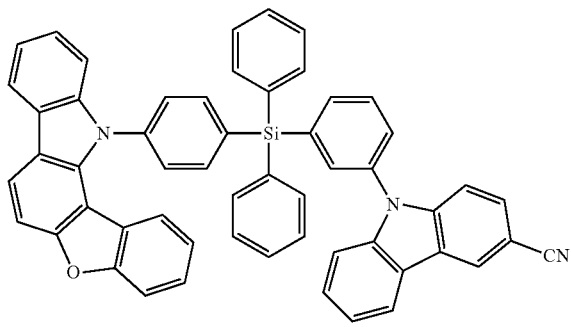
381
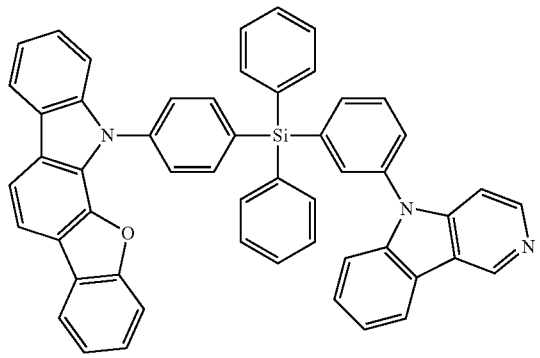
382
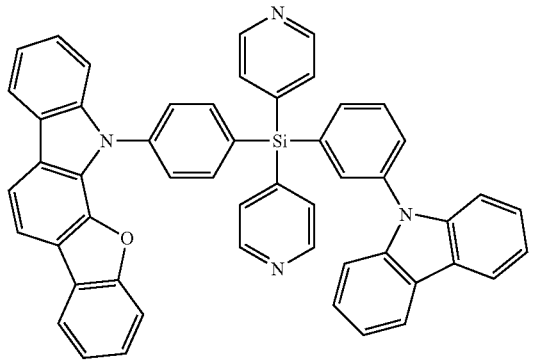
383
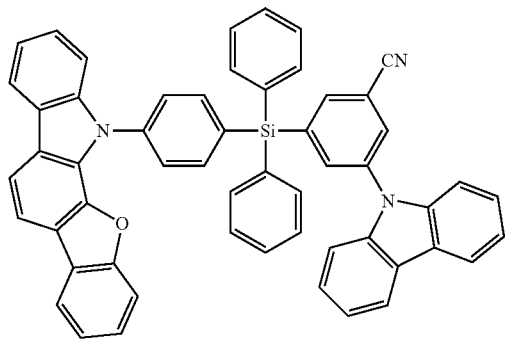
384
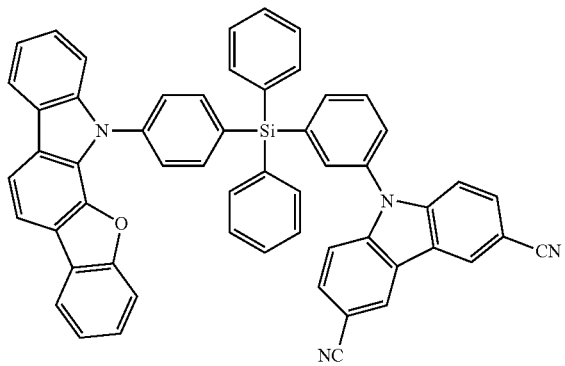
385
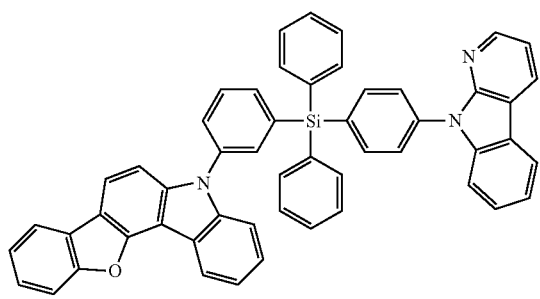
386
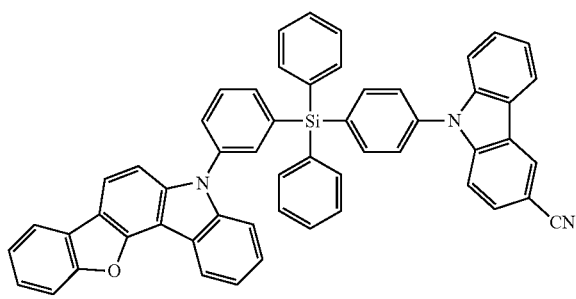

-continued
387
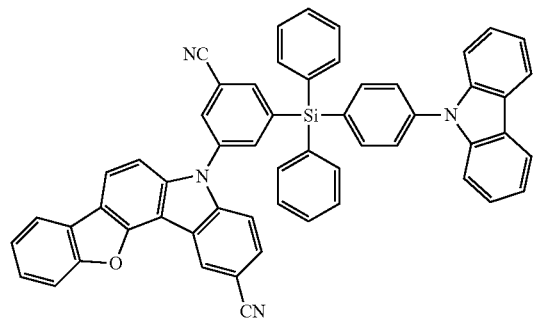
388
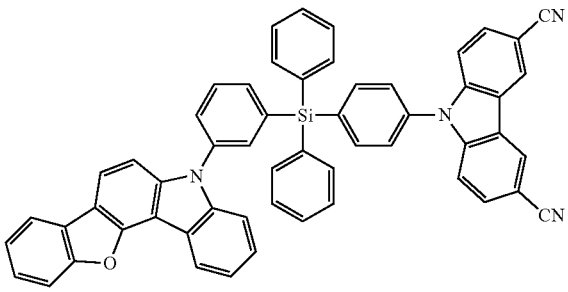
389
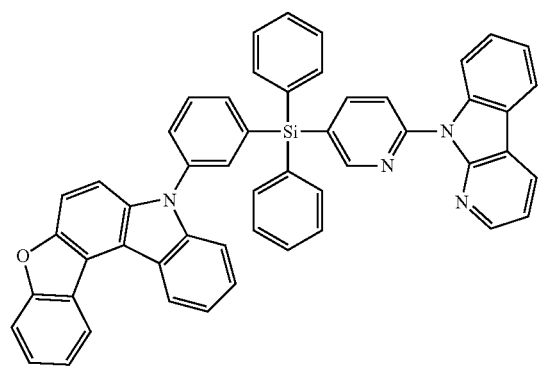
390
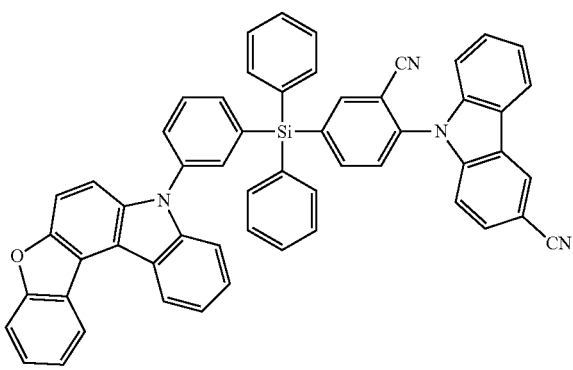
391
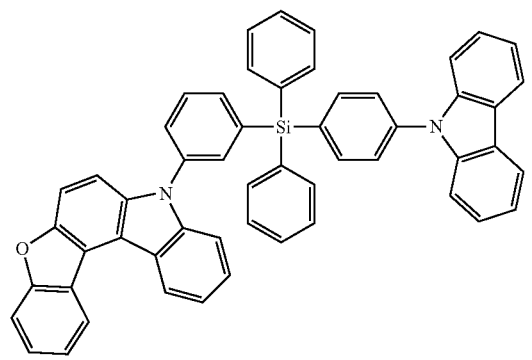
392
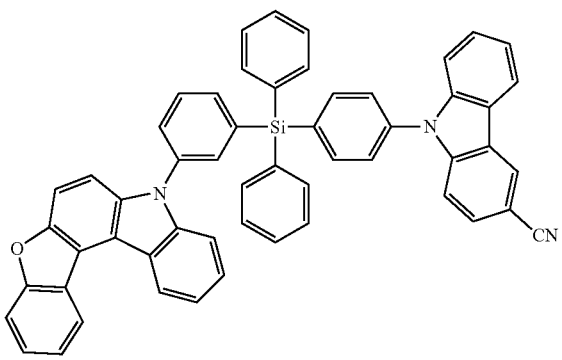
393
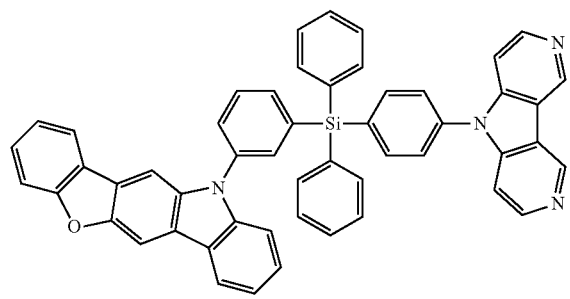
394
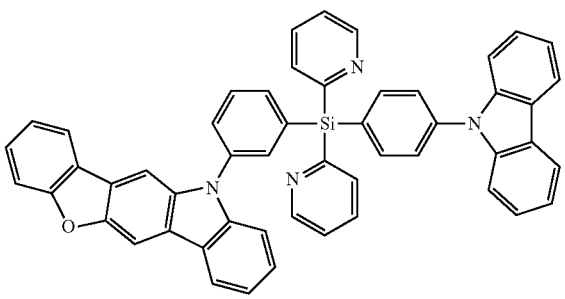

-continued
395
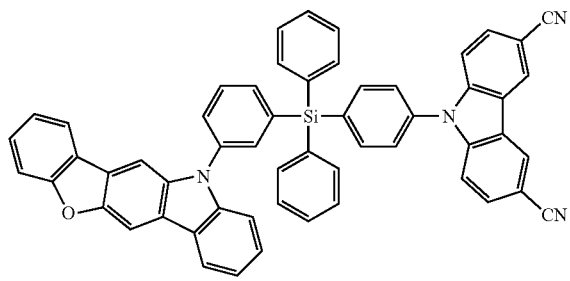
396
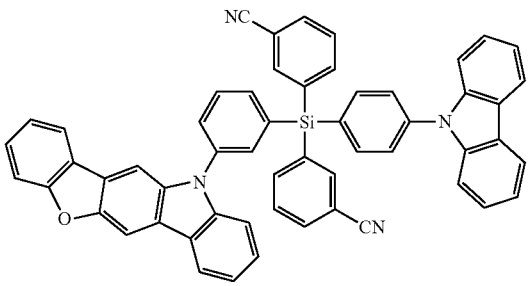
397
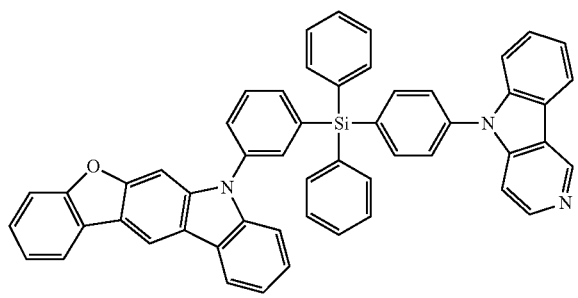
398
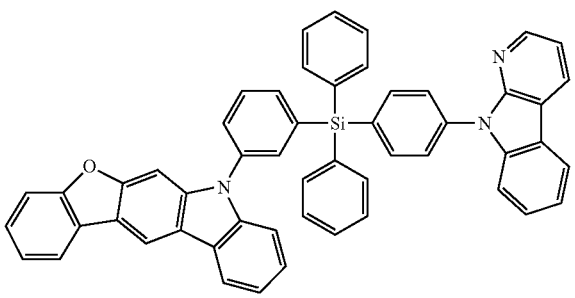
399
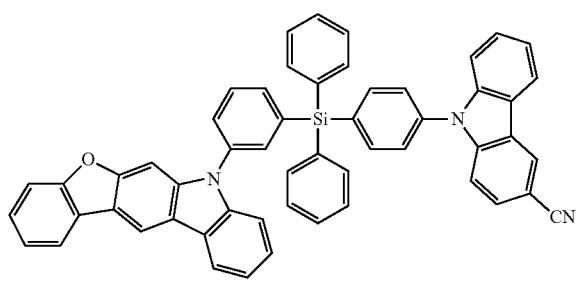
400
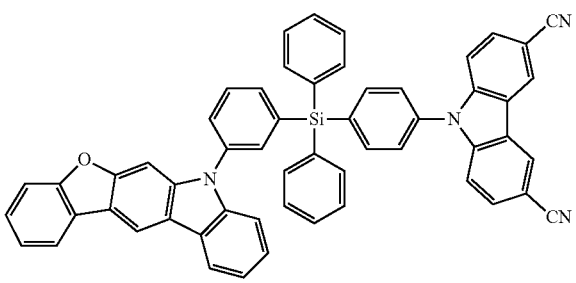
401
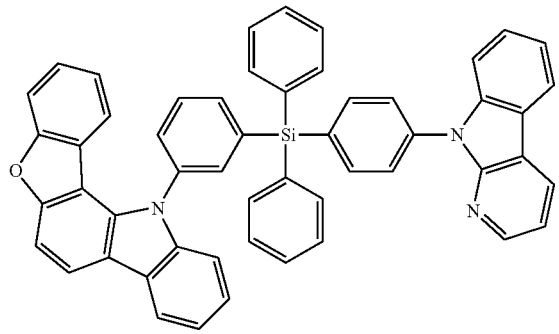
402
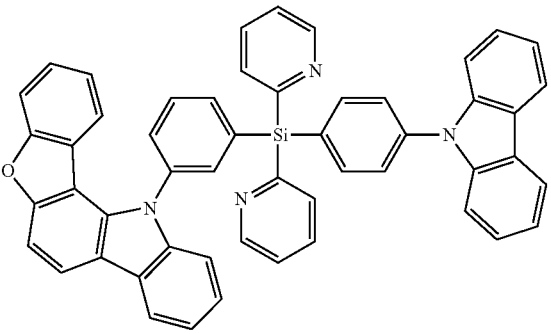
403
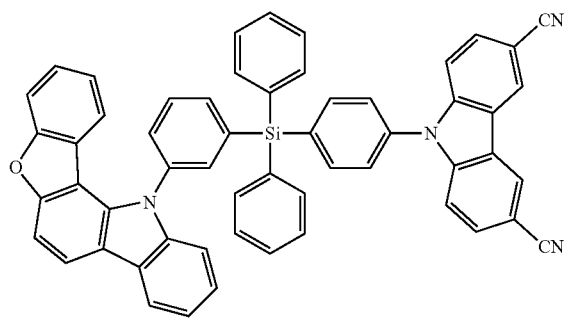
404
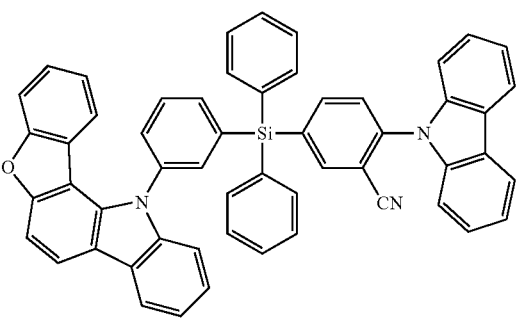

-continued
405
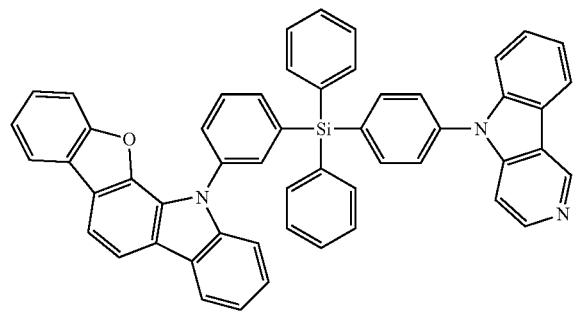
406
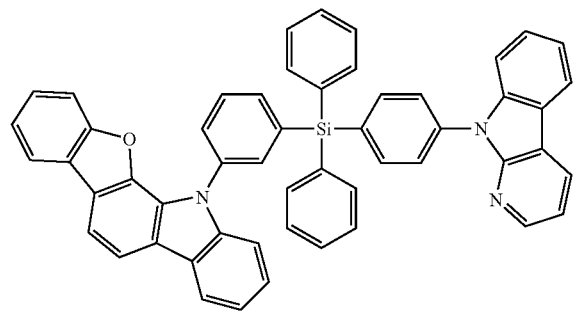
407
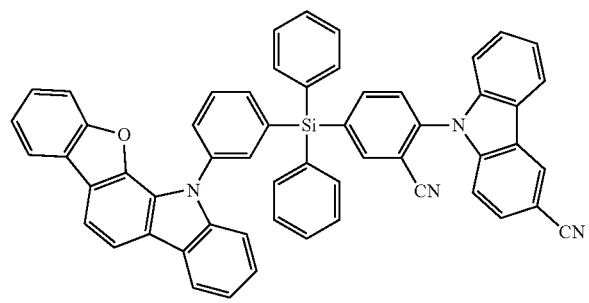
408
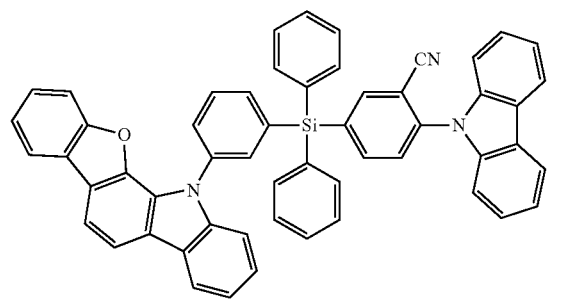
409
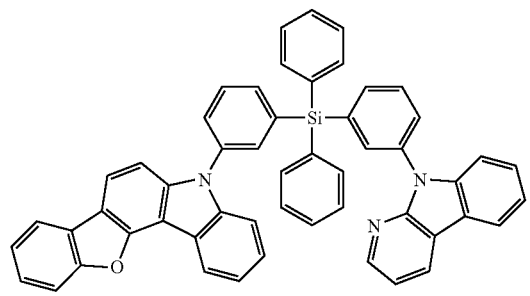
410
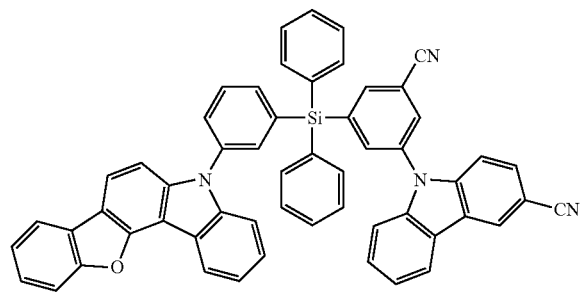
411
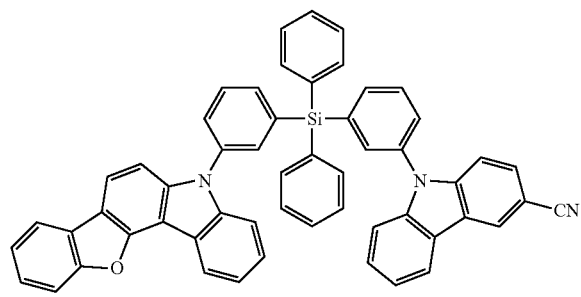
412
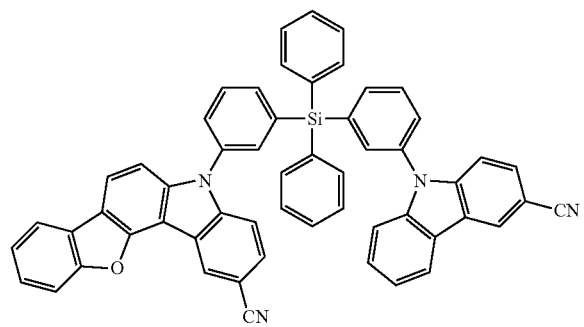

-continued
413
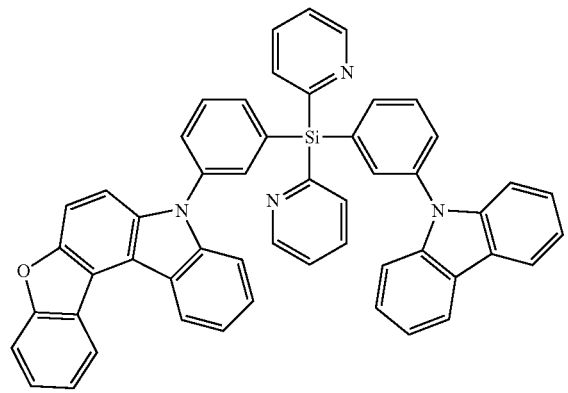
414
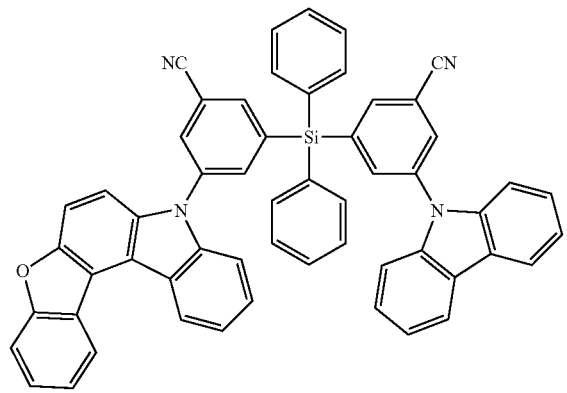
415
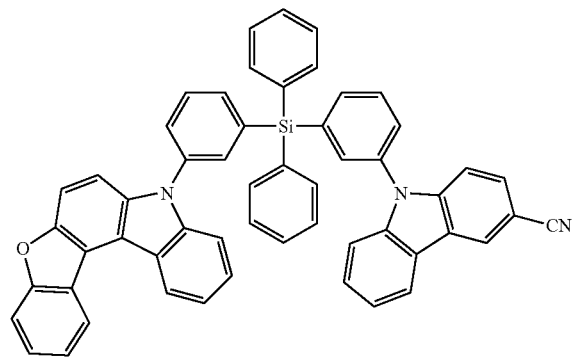
416
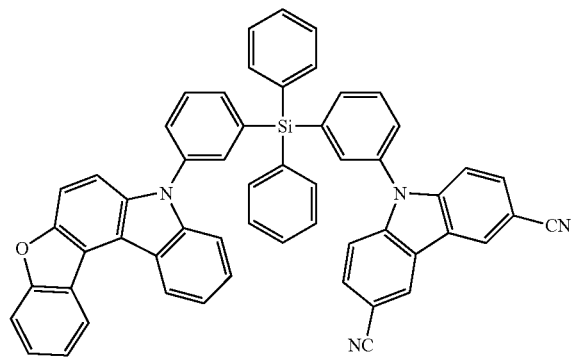
417
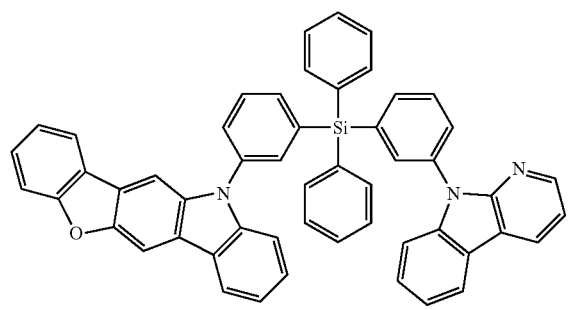
418
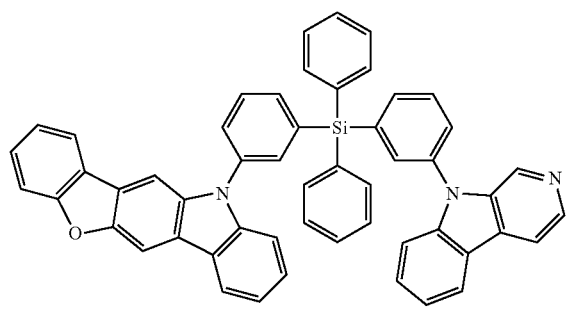
419
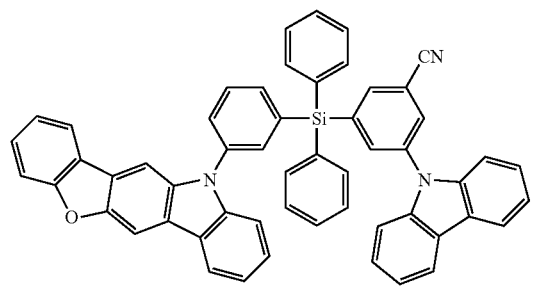
420
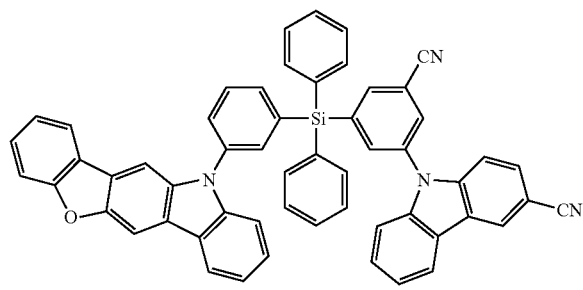

-continued
421
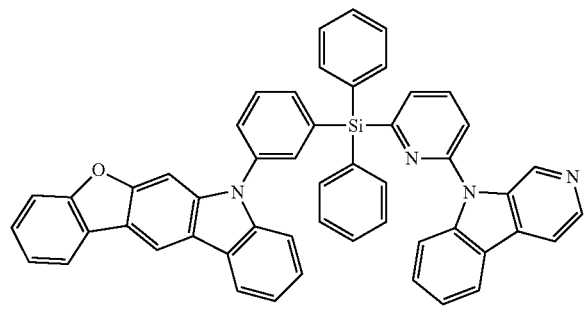
422
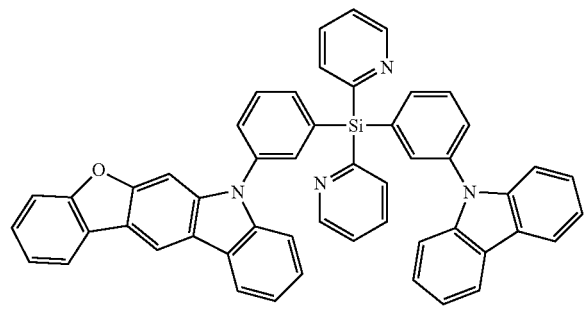
423
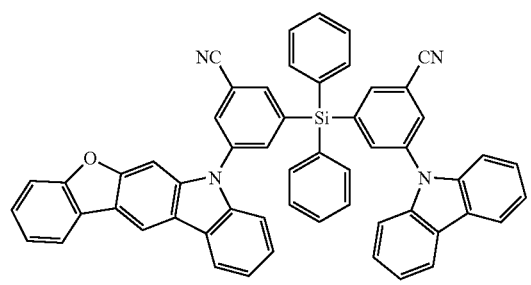
424
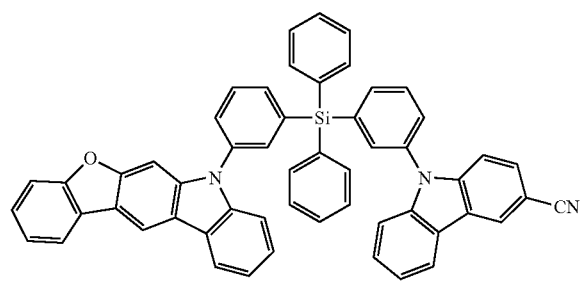
425
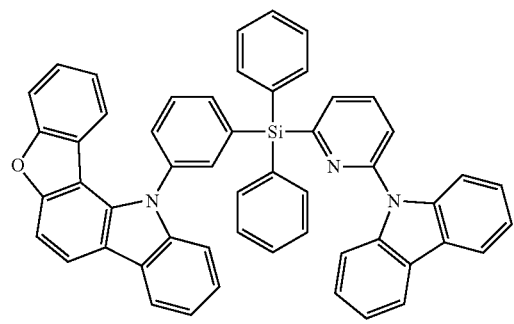
426
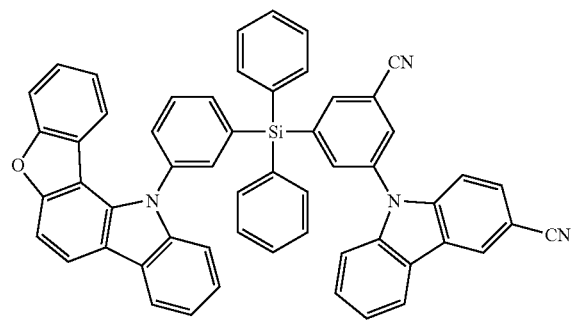
427
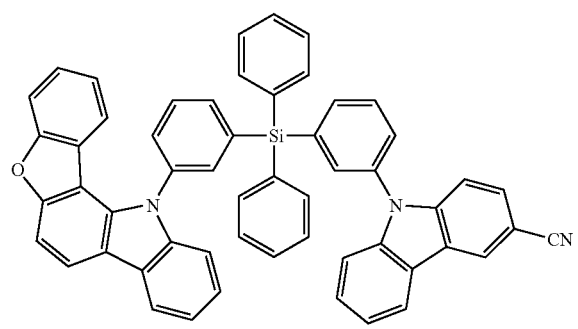
428
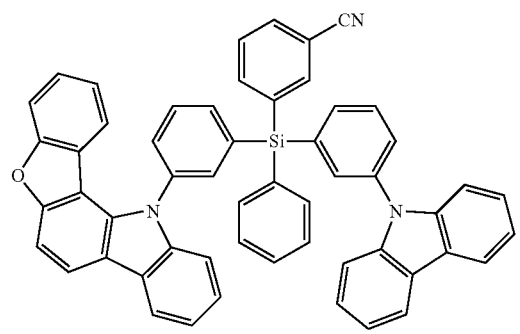

-continued

429
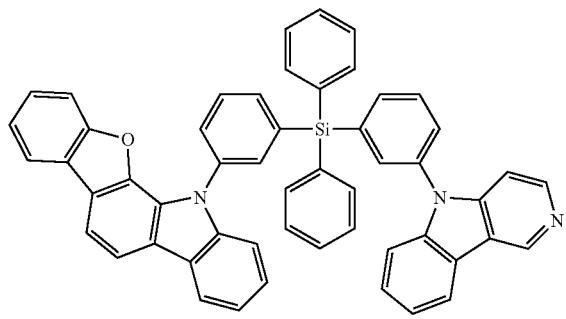

430
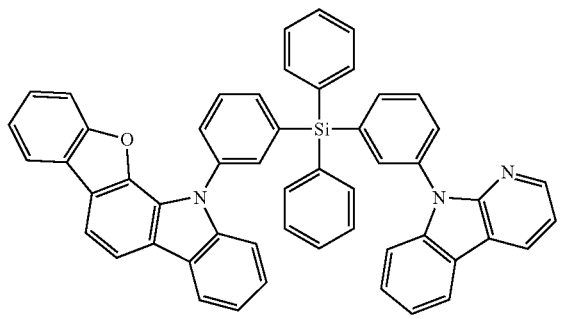

431
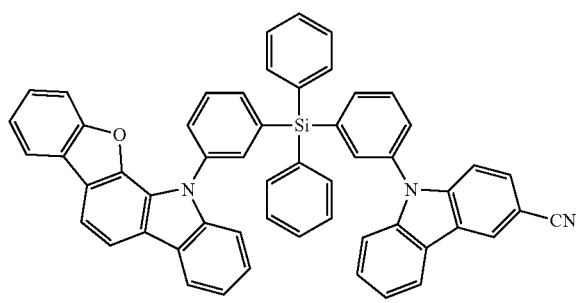

432
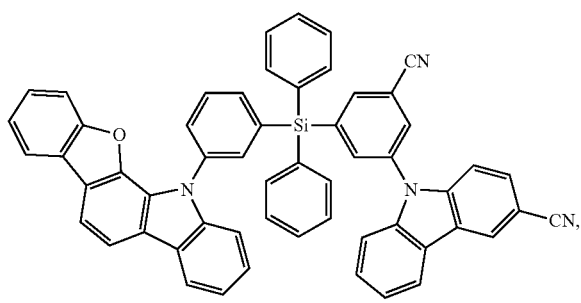

wherein, in Compounds 1 to 432,
Ph is a phenyl group.

13. An organic light-emitting device comprising:
a first electrode;
a second electrode; and
an organic layer disposed between the first electrode and the second electrode,
wherein the organic layer comprises an emission layer, and
wherein the organic layer comprises at least one of the silyl group-containing compounds represented by Formula 1 of claim 1.

14. The organic light-emitting device of claim 13, wherein
the first electrode is an anode,
the second electrode is a cathode, and
the organic layer further comprises a hole transport region disposed between the first electrode and the emission layer, and an electron transport region disposed between the emission layer and the second electrode,
wherein the hole transport region comprises a hole injection layer, a hole transport layer, an electron blocking layer, or any combination thereof, and
wherein the electron transport region comprises a hole blocking layer, an electron transport layer, an electron injection layer, or any combination thereof.

15. The organic light-emitting device of claim 13, wherein the emission layer comprises the at least one of the silyl group-containing compounds represented by Formula 1 of claim 1.

16. The organic light-emitting device of claim 15, wherein the emission layer further comprises a phosphorescent dopant represented by Formula 81:

Formula 81
$$M(L_{81})_{n81}(L_{82})_{n82}$$

Formula 81A
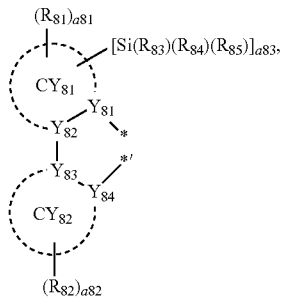

wherein, in Formulae 81 and 81A,
M is selected from iridium (Ir), platinum (Pt), osmium (Os), titanium (Ti), zirconium (Zr), hafnium (Hf), europium (Eu), terbium (Tb), thulium (Tm), and rhodium (Rh),
$L_{81}$ is a ligand represented by Formula 81A, and n81 is an integer from 1 to 3, wherein when n81 is two or more, two or more groups $L_{81}$ are identical to or different from each other,
$L_{82}$ is an organic ligand, and n82 is an integer from 0 to 4, wherein when n82 is two or more, two or more groups $L_{82}$ are identical to or different from each other,
$Y_{81}$ to $Y_{84}$ are each independently carbon (C) or nitrogen (N),
$Y_{81}$ and $Y_{82}$ are linked to each other via a single bond or a double bond, and $Y_{83}$ and $Y_{84}$ are linked to each other via a single bond or a double bond, CY$_{81}$ and CY$_{82}$ are each independently selected from a C$_5$-C$_{30}$carbocyclic group and a C$_3$-C$_{30}$heterocarbocyclic group, CY$_{81}$ and CY$_{82}$ are further optionally linked to each other via an organic linking group, R$_{81}$ to R$_{85}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —Si(Q$_{81}$)(Q$_{82}$)(Q$_{83}$), —N(Q$_{84}$)(Q$_{85}$), —B(Q$_{86}$)(Q$_{87}$), and —P(=O)(Q$_{88}$)(Q$_{89}$), a81 to a83 are each independently an integer from 0 to 5, when a81 is two or more, two or more groups R$_{81}$ are identical to or different from each other, when a82 is two or more, two or more groups R$_{82}$ are identical to or different from each other, when a81 is two or more, neighboring groups R$_{81}$ are optionally linked to each other to form a saturated or unsaturated ring, when a82 is two or more, neighboring groups R$_{82}$ are optionally linked to each other to form a saturated or unsaturated ring,

* and *' in Formula 81A each indicate a binding site to M in Formula 81, and at least one substituent selected from a substituent(s) of the substituted C$_1$-C$_{60}$ alkyl group, the substituted C$_2$-C$_{60}$ alkenyl group, the substituted C$_2$-C$_{60}$ alkynyl group, the substituted C$_1$-C$_{60}$ alkoxy group, the substituted C$_3$-C$_{10}$ cycloalkyl group, the substituted C$_1$-C$_{10}$ heterocycloalkyl group, the substituted C$_3$-C$_{10}$ cycloalkenyl group, the substituted C$_1$-C$_{10}$ heterocycloalkenyl group, the substituted C$_6$-C$_{60}$ aryl group, the substituted C$_6$-C$_{60}$ aryloxy group, the substituted C$_6$-C$_{60}$ arylthio group, the substituted C$_1$-C$_{60}$ heteroaryl group, the substituted monovalent non-aromatic condensed polycyclic group, and the substituted monovalent non-aromatic condensed heteropolycyclic group is selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, and —Si(Q$_{91}$)(Q$_{92}$)(Q$_{93}$), wherein Q$_{81}$ to Q$_{89}$ and Q$_{91}$ to Q$_{93}$ are each independently selected from hydrogen, deuterium, a C$_1$-C$_{60}$ alkyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_1$-C$_{60}$ heteroaryl group, a monovalent non-aromatic condensed polycyclic group, and a monovalent non-aromatic condensed heteropolycyclic group.

17. The organic light-emitting device of claim 16, wherein, at least one selected from groups R$_{81}$ in the number of a81 and groups R$_{82}$ in the number of a82 in Formula 81A is a cyano group or deuterium.

18. The organic light-emitting device of claim 15, wherein the emission layer emits blue light.

19. An organic light-emitting device comprising:

a first electrode as an anode;

a second electrode as a cathode; and an organic layer disposed between the first electrode and the second electrode, wherein the organic layer comprises an emission layer, wherein the organic layer further comprises a hole transport region disposed between the first electrode and the emission layer, and an electron transport region disposed between the emission layer and the second electrode, wherein the hole transport region comprises a hole injection layer, a hole transport layer, an electron blocking layer, or any combination thereof, and wherein the electron transport region comprises a hole blocking layer, an electron transport layer, an electron injection layer, or any combination thereof, wherein the hole transport region comprises an electron blocking layer, and the electron blocking layer comprises the at least one of the silyl group-containing compounds represented by Formula 1:

Formula 1 wherein, in Formula 1,

A$_{11}$ is selected from a carbazole group, a fluorene group, a dibenzofuran group, and a dibenzothiophene group, R$_{11}$ to R$_{13}$ are each independently selected from groups represented by Formulae 2-1 to 2-6, provided that at least one selected from R$_{11}$ to R$_{13}$ is selected from groups represented by Formulae 2-1 to 2-5:

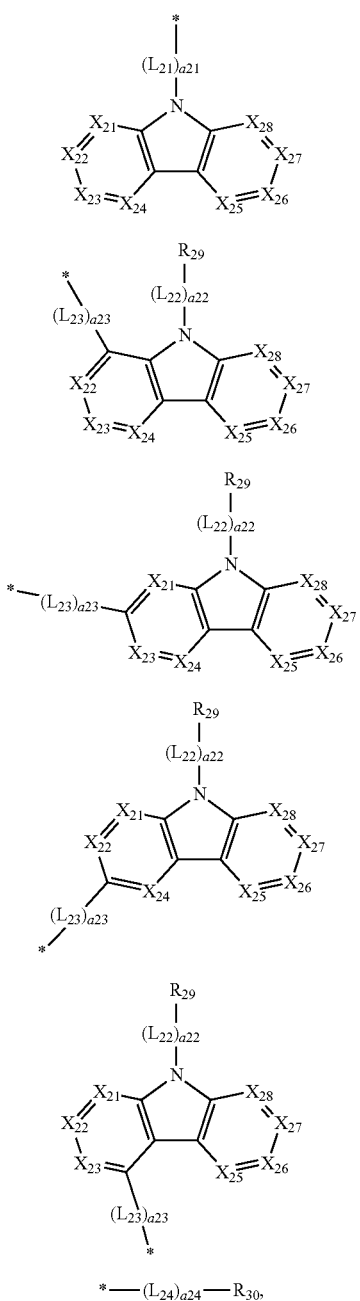

wherein, in Formulae 2-1 to 2-6, $X_{21}$ is selected from N and $CR_{21}$, $X_{22}$ is selected from N and $CR_{22}$, $X_{23}$ is selected from N and $CR_{23}$, $X_{24}$ is selected from N and $CR_{24}$, $X_{25}$ is selected from N and $CR_{25}$, $X_{26}$ is selected from N and $CR_{26}$, $X_{27}$ is selected from N and $CR_{27}$, and $X_{28}$ is selected from N and $CR_{28}$, $L_{11}$ and $L_{21}$ to $L_{24}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 and a21 are each independently an integer selected from 1, 2, 3, and 4, a22 to a24 are each independently an integer selected from 0, 1, 2, 3, and 4, $R_{14}$ to $R_{18}$ and $R_{21}$ to $R_{29}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), and —B($Q_1$)($Q_2$), $R_{30}$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b18 is an integer selected from 1, 2, 3, 4, 5, 6, 7, 8, 9, and 10, $Q_1$ to $Q_3$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and \* indicates a binding site to a neighboring atom.

\* \* \* \* \*